United States Patent
Kuntz et al.

(10) Patent No.: US 10,092,572 B2
(45) Date of Patent: *Oct. 9, 2018

(54) SUBSTITUTED BENZENE COMPOUNDS

(71) Applicant: Epizyme, Inc., Cambridge, MA (US)

(72) Inventors: Kevin Wayne Kuntz, Woburn, MA (US); John Emmerson Campbell, Cambridge, MA (US); Masashi Seki, Tsukuba (JP); Syuji Shirotori, Tsukuba (JP); Wataru Itano, Tsukuba (JP); Wanjun Zheng, Londonderry, NH (US)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/435,704

(22) PCT Filed: Oct. 15, 2013

(86) PCT No.: PCT/US2013/065127
§ 371 (c)(1),
(2) Date: Apr. 14, 2015

(87) PCT Pub. No.: WO2014/062733
PCT Pub. Date: Apr. 24, 2014

(65) Prior Publication Data
US 2015/0284370 A1    Oct. 8, 2015

Related U.S. Application Data

(60) Provisional application No. 61/714,140, filed on Oct. 15, 2012, provisional application No. 61/714,145, filed on Oct. 15, 2012, provisional application No. 61/780,703, filed on Mar. 13, 2013, provisional application No. 61/786,277, filed on Mar. 14, 2013.

(51) Int. Cl.

| | |
|---|---|
| *C07D 213/64* | (2006.01) |
| *A61K 31/5377* | (2006.01) |
| *C07D 405/14* | (2006.01) |
| *A61K 31/5375* | (2006.01) |
| *A61K 31/4412* | (2006.01) |
| *A61K 31/4545* | (2006.01) |
| *C07D 401/12* | (2006.01) |
| *C07D 405/12* | (2006.01) |

(52) U.S. Cl.
CPC ...... *A61K 31/5377* (2013.01); *A61K 31/4412* (2013.01); *A61K 31/4545* (2013.01); *A61K 31/5375* (2013.01); *C07D 213/64* (2013.01); *C07D 401/12* (2013.01); *C07D 405/12* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 5,716,993 A | 2/1998 | Ozaki et al. | |
| 5,948,803 A | 9/1999 | Maeda et al. | |
| 7,122,547 B1 | 10/2006 | Huth et al. | |
| 7,252,968 B2 | 8/2007 | Jenuwein et al. | |
| 7,442,685 B2 | 10/2008 | Zhang et al. | |
| 7,563,589 B2 | 7/2009 | Zhang et al. | |
| 7,923,219 B2 | 4/2011 | Wang et al. | |
| 8,410,088 B2 * | 4/2013 | Kuntz ............... | C07D 213/64 |
| | | | 514/211.15 |
| 8,754,230 B2 | 6/2014 | Livingston et al. | |
| 8,765,732 B2 | 7/2014 | Kuntz et al. | |
| 9,006,242 B2 | 4/2015 | Kuntz et al. | |
| 9,090,562 B2 * | 7/2015 | Kuntz ............... | C07D 213/64 |
| 9,376,422 B2 * | 6/2016 | Kuntz | |
| 9,394,283 B2 * | 7/2016 | Kuntz ............... | C07D 405/12 |
| 2002/0183324 A1 | 12/2002 | Jacobson et al. | |
| 2004/0082619 A1 | 4/2004 | Tada et al. | |
| 2005/0266473 A1 | 12/2005 | Zhang et al. | |
| 2008/0182844 A1 | 7/2008 | Bjergarde et al. | |
| 2008/0222741 A1 | 9/2008 | Chinnaiyan | |
| 2008/0269289 A1 | 10/2008 | Frank et al. | |
| 2008/0312292 A1 | 12/2008 | Yasui et al. | |
| 2009/0012031 A1 | 1/2009 | Chinnaiyan et al. | |
| 2009/0061443 A1 | 3/2009 | Zhang et al. | |
| 2009/0203057 A1 | 8/2009 | Zhang et al. | |

(Continued)

FOREIGN PATENT DOCUMENTS

| | | |
|---|---|---|
| EP | 1357111 A1 | 10/2003 |
| JP | 7033729 A | 2/1995 |
| WO | WO 1996/040100 A1 | 12/1996 |
| WO | WO 2000/018725 A1 | 4/2000 |
| WO | WO 2003/079788 A2 | 10/2003 |
| WO | WO 2005/094816 A1 | 10/2005 |
| WO | WO 2006/116713 A1 | 11/2006 |
| WO | WO 2007/045462 A2 | 4/2007 |
| WO | WO 2007/050347 A1 | 5/2007 |
| WO | WO 2007/070818 A1 | 6/2007 |
| WO | WO 2007/136592 A2 | 11/2007 |

(Continued)

OTHER PUBLICATIONS

Braña et al. "Reaction of N-(2-Pyridylmethyl)-3,5-dimethylbenzamide and N-(3-Pyridylmethyl)-3,5-dimethylbenzamide N-Oxides With Acetic Anhydride." *Journal of Heterocyclic Chemistry*, 19.6(1982):1297-1300.

(Continued)

*Primary Examiner* — Noble E Jarrell
(74) *Attorney, Agent, or Firm* — Cooley LLP; Heidi A. Erlacher; Xixi Sun

(57) ABSTRACT

The present invention relates to substituted benzene compounds. The present invention also relates to pharmaceutical compositions containing these compounds and methods of treating cancer by administering these compounds and pharmaceutical compositions to subjects in need thereof. The present invention also relates to the use of such compounds for research or other non-therapeutic purposes.

31 Claims, No Drawings

Specification includes a Sequence Listing.

(56) References Cited

U.S. PATENT DOCUMENTS

| | | | |
|---|---|---|---|
| 2010/0035912 A1 | 2/2010 | Debnath et al. | |
| 2010/0113415 A1 | 5/2010 | Rajapakse et al. | |
| 2011/0021362 A1 | 1/2011 | Trojer et al. | |
| 2012/0071418 A1 | 3/2012 | Copeland et al. | |
| 2013/0040906 A1* | 2/2013 | Kuntz .............. | C07D 473/34 514/46 |
| 2014/0142083 A1 | 5/2014 | Kuntz et al. | |
| 2014/0288041 A1 | 9/2014 | Kuntz et al. | |
| 2015/0051163 A1* | 2/2015 | Keilhack .......... | A61K 31/4412 514/34 |

FOREIGN PATENT DOCUMENTS

| | | |
|---|---|---|
| WO | WO 2008/073138 A2 | 6/2008 |
| WO | WO 2008/103277 A2 | 8/2008 |
| WO | WO 2008/104077 A1 | 9/2008 |
| WO | WO 2008/108825 A2 | 9/2008 |
| WO | WO 2008/113006 A1 | 9/2008 |
| WO | WO 2009/058298 A1 | 5/2009 |
| WO | WO 2009/077766 A1 | 6/2009 |
| WO | WO 2009/124137 A2 | 10/2009 |
| WO | WO 2010/018328 A1 | 2/2010 |
| WO | WO 2010/111653 A2 | 9/2010 |
| WO | WO 2011/082044 A1 | 7/2011 |
| WO | WO 2011/140324 A1 | 11/2011 |
| WO | WO 2011/140325 A1 | 11/2011 |
| WO | WO 2012/005805 A1 | 1/2012 |
| WO | WO 2012/034132 A2 | 3/2012 |
| WO | WO 2012/068589 A2 | 5/2012 |
| WO | WO 2012/075080 A1 | 6/2012 |
| WO | WO 2012/075500 A2 | 6/2012 |
| WO | WO 2012/118812 A2 | 9/2012 |
| WO | WO 2012/142504 A1 * | 10/2012 |
| WO | WO 2012/142513 A1 * | 10/2012 |
| WO | WO 2013/138361 A1 | 9/2013 |
| WO | WO 2013138361 * | 9/2013 |
| WO | WO 2013155317 * | 10/2013 |
| WO | WO 2013/173441 A2 | 11/2013 |
| WO | WO 2014/062720 | 4/2014 |
| WO | WO 2014/062732 | 4/2014 |
| WO | WO 2014/062733 | 4/2014 |

OTHER PUBLICATIONS

Chemical Abstracts Service Registry Nos. 1111568-29-6, 1111508-57-6, and 1111473-93-8 entered Feb. 25, 2009.
Chemical Abstracts Service Registry Nos. 1118856-92-0, 1118847-80-5, 1118847-59-8, 1118826-65-5, 1118826-02-0, 1118825-96-9, 1118825-75-4, 1118825-72-1, and 1118825-69-6 entered Mar. 11, 2009.
Chemical Abstracts Service Registry Nos. 1278089-60-3, 1277914-52-9, and 1277529-83-5, entered Apr. 10, 2011.
Chemical Abstracts Service Registry Nos. 1278854-92-4 and 127885491-3, entered Apr. 12, 2011.
Chemical Abstracts Service Registry Nos. 919939-47-2 and 919873-05-5 entered Feb. 8, 2007.
Chemical Abstracts Service Registry Nos. 923162-97-4, 923152-74-3, and 923111-85-7 entered Feb. 26, 2007.
Chemical Abstracts Service Registry Nos. 923774-47-4, 923730-10-3, and 923690-12-4 entered Feb. 28, 2007.
Chemical Abstracts Service Registry Nos. 941139-86-2 and 941091-93-6 entered Jul. 4, 2007.
Gura et al. "Systems for Identifying New Drugs are Often Faulty." *Science*, 278.5340(1997):1041-1042.
Johnson et al. "Relationships Between Drug Activity in NCI Preclinical in vitro and in vivo Models and Early Clinical Trials." *Brit. J. Cancer.* 84.10(2001):1424-1431.
Knutson et al. "A Selective Inhibitor of EZH2 Blocks H3K27 Methylation and Kills Mutant Lymphoma Cells." *Nat. Chem. Biol.* (2012):1-7. Epub: Sep. 30, 2012.
Lohr et al. "Discovery and Prioritization of Somatic Mutations in Diffuse Large B-Cell Lymphoma (DLBCL) by Whole-Exome Sequencing." *PNAS.* 109.10(2012):3879-3884. Epub Feb. 17, 2012.
Martinez-Garcia et al. "The MMSET Histone Methyl Transferase Switches Global Histone Methylation and Alters Gene Expression in t(4;14) Multiple Myeloma Cells." *Blood.* 117(2011):211-220.
McCabe et al. "EZH2 Inhibition as a Therapeutic Strategy for Lymphoma With EZH2-Activating Mutations." *Nature.* Epub: Oct. 10, 2012.
McCabe et al. "Mutation of A677 in Histone Methyltransferase EZH2 in Human B-Cell Lymphoma Promotes Hypertrimethylation of Histone H3 on Lysine 27 (H3K27)." *PNAS.*109.8(2012):2989-2994.
Miranda et al. "DZNep is a Global Histone Methylation Inhibitor That Reactivates Developmental Genes not Silenced by DNA Methylation." *Mol. Cancer Ther.* 8.6(2009):1579-1588.
Morin et al. "Somatic Mutations Altering EZH2 (Tyr641) in Follicular and Diffuse Large B-Cell Lymphomas of Germinal-Center Origin." *Nat. Genet.* 42.2(2010):181-185.
Pearce et al. "Failure Modes in Anticancer Drug Discovery and Development." *Cancer Drug Design and Discovery.* Neidle, ed. Boston: Elsevier. (2008):424-435.
Sculley et al. "Some Amide Derivatives of Certain Aminomethylpyridines." *J. Am. Chem. Soc.* 75.14(1953):3400-3403.
Simone. "Oncology: Introduction." *Cecil Textbook of Medicine.* Bennett et al., eds. Philadelphia: W. B. Saunders Co. 20th ed. 1(1996):1004-1008.
Sneeringer et al. "Coordinated Activities of Wild-Type Plus Mutant EZH2 Drive Tumor-Associated Hypertrimethylation of Lysine 27 on Histone H3 (H3K27) in Human B-Cell Lymphomas." *PNAS.* 107.49(2010):20980-20985.
Wigle et al. "The Y641 C Mutation of EZH2 Alters Substrate Specificity for Histone H3 Lysine 27 Methylation States." *FEBS Lett.* 585.19(2011):3011-3014.
Wilson et al. "Epigenetic Antagonism Between Polycomb and SWI/SNF Complexes During Oncogenic Transformation." *Cancer Cell.* 18(2010):316-328.
Yap et al. "Somatic Mutations at EZH2 Y641 Act Dominantly Through a Mechanism of Selectively Altered PRC2 Catalytic Activity, to Increase H3K27 Trimethylation." *Blood.* 117.8(2010):2451-2459.

* cited by examiner

```
                         SEQUENCE LISTING

<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 1

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (7)..(7)
<223> OTHER INFORMATION: wherein the lysine is dimethylated
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 2

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```

SUBSTITUTED BENZENE COMPOUNDS

RELATED APPLICATIONS

This application is a U.S. National Phase application of International Application No. PCT/US2013/065127, filed on Oct. 15. 2013, claims priority to, and the benefit of, U.S. provisional application Nos. 61/714,140, filed Oct. 15, 2012, 61/714,145, filed Oct. 15, 2012, 61/780,703, filed Mar. 13, 2013, and 61/786,277, filed Mar. 14, 2013. The entire contents of each of these applications are incorporated herein by reference in their entireties.

INCORPORATION-BY-REFERENCE OF SEQUENCE LISTING

The contents of the text file named "EPIZ-029N01US-ST25.txt", which was created on Apr. 14, 2015 and is 5 KB in size, are hereby incorporated by reference in their entireties.

PARTIES TO JOINT RESEARCH AGREEMENT

This invention was developed subject to a Joint Research Agreement between Epizyme, Inc. and Eisai Co., Ltd.

BACKGROUND OF THE INVENTION

There is an ongoing need for new agents as inhibitors of EZH2 activity, which can be used for treating EZH2-mediated disorder (e.g., cancer).

SUMMARY OF THE INVENTION

In one aspect, the present invention features a substituted benzene compound of the Formulae below or a pharmaceutically acceptable salt thereof.

In one aspect, the invention relates to a compound according to Formula III:

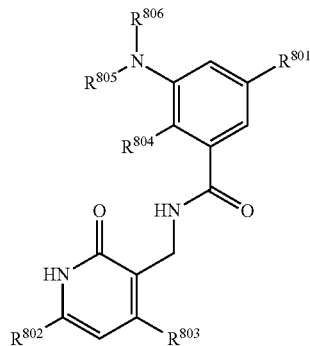

(III)

or a pharmaceutically acceptable salt, or solvate thereof, wherein $R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; and $R^{801}$ is optionally further substituted;

each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$, independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

Subsets of compounds of Formula III include those of Formula IVa or IVb and pharmaceutically acceptable salts, or solvates thereof:

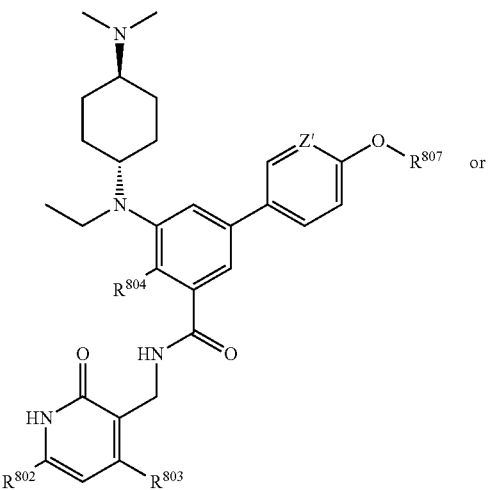

(IVa)

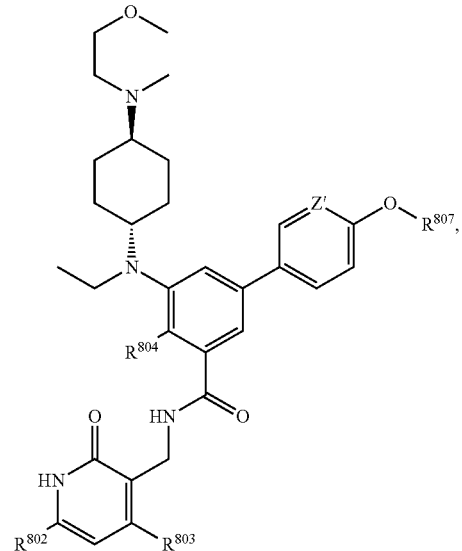

(IVb)

wherein Z' is CH or N, and $R^{807}$ is $C_{2-3}$ alkyl-$R_x$.

In another aspect, the invention relates to a compound according to Formula I:

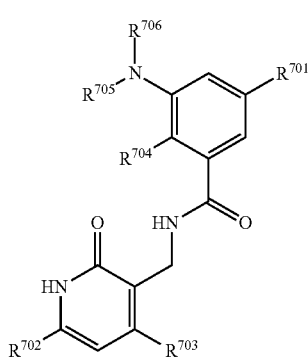
(I)

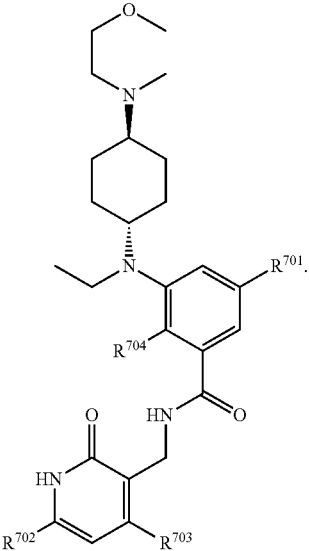
(II)

or a pharmaceutically acceptable salt or solvate thereof; wherein

R$^{701}$ is H, F, OR$^{707}$, NHR$^{707}$, —(C≡C)—(CH$_2$)$_{n7}$—R$^{708}$, phenyl, 5- or 6-membered heteroaryl, C$_{3-8}$ cycloalkyl, or 4-7 membered heterocycloalkyl containing 1-3 heteroatoms, wherein the phenyl, 5- or 6-membered heteroaryl, C$_{3-8}$ cycloalkyl or 4-7 membered heterocycloalkyl each independently is optionally substituted with one or more groups selected from halo, C$_{1-3}$ alkyl, OH, O—C$_{1-6}$ alkyl, NH—C$_{1-6}$ alkyl, and, C$_{1-3}$ alkyl substituted with C$_{3-8}$ cycloalkyl or 4-7 membered heterocycloalkyl containing 1-3 heteroatoms, wherein each of the O—C$_{1-6}$ alkyl and NH—C$_{1-6}$ alkyl is optionally substituted with hydroxyl, O—C$_{1-3}$ alkyl or NH—C$_{1-3}$ alkyl, each of the O—C$_{1-3}$ alkyl and NH—C$_{1-3}$ alkyl being optionally further substituted with O—C$_{1-3}$ alkyl or NH—C$_{1-3}$ alkyl;

each of R$^{702}$ and R$^{703}$, independently is H, halo, C$_{1-4}$ alkyl, C$_{1-6}$ alkoxyl or C$_6$-C$_{10}$ aryloxy, each optionally substituted with one or more halo;

each of R$^{704}$ and R$^{705}$, independently is C$_{1-4}$ alkyl;

R$^{706}$ is cyclohexyl substituted by N(C$_{1-4}$alkyl)$_2$ wherein one or both of the C$_{1-4}$ alkyl is substituted with C$_{1-6}$ alkoxy; or R$^{706}$ is tetrahydropyranyl;

R$^{707}$ is C$_{1-4}$ alkyl optionally substituted with one or more groups selected from hydroxyl, C$_{1-4}$ alkoxy, amino, mono- or di-C$_{1-4}$ alkylamino, C$_{3-8}$ cycloalkyl, and 4-7 membered heterocycloalkyl containing 1-3 heteroatoms, wherein the C$_{34}$ cycloalkyl or 4-7 membered heterocycloalkyl each independently is further optionally substituted with C$_{1-3}$ alkyl;

R$^{708}$ is C$_{1-4}$ alkyl optionally substituted with one or more groups selected from OH, halo, and C$_{1-4}$ alkoxy, 4-7 membered heterocycloalkyl containing 1-3 heteroatoms, or O—C$_{1-6}$ alkyl, wherein the 4-7 membered heterocycloalkyl can be optionally further substituted with OH or C$_{1-5}$ alkyl; and n$_7$ is 0, 1 or 2.

A subset of compounds of Formula I includes those of Formula II and pharmaceutically acceptable salts or solvates thereof:

In another aspect, the invention relates to compound according to formula V:

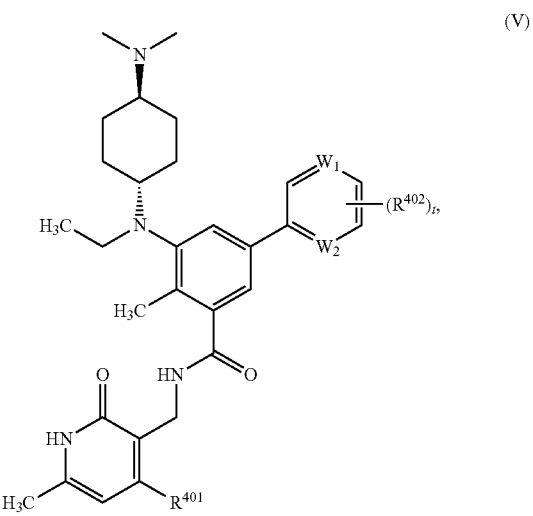
(V)

or a pharmaceutically acceptable salt or solvate thereof; wherein

W$_1$ is N or CH;

W$_2$ is N or CH;

R$^{401}$ is hydrogen, C$_1$-C$_6$ alkyl, C$_1$-C$_6$ haloalkyl;

R$^{402}$ is (a) OH, (b) (CH$_2$)—O—(C$_1$-C$_6$ alkyl), (c) O(C$_1$-C$_6$ alkyl), (d) (CH$_2$)$_j$-3-8 membered saturated, unsaturated, or aromatic carbocycle, (e) CH$_2$)$_k$-3-8 membered saturated, unsaturated, or aromatic heterocycle containing one or more heteroatoms selected from the group consisting of nitrogen, oxygen, and sulfur, (f) O—(CH$_2$)$_u$-3-8 membered saturated, unsaturated, or aromatic carbocycle, or (g) O—(CH$_2$)$_v$-3-8 membered saturated, unsaturated, or aromatic heterocycle containing one or more heteroatoms selected from the group consisting of nitrogen, oxygen, and sulfur, where (b)-(g) are optionally substituted with R$^{402a}$, R$^{402a}$ is C$_1$-C$_6$ alkyl, C$_1$-C$_6$ haloalkyl, OH, or O(C$_1$-C$_6$ alkyl);

t is 1, 2, or 3;
u is 0, 1, 2, or 3;
v is 0, 1, 2, or 3;
j is 0, 1, 2, or 3; and
k is 0, 1, 2, or 3; provided that when $R^{402}$ is piperazinyl, $W_1$ and $W_2$ are N.

In certain compounds of Formula V, $W_1$ is N and $W_2$ is CH.

In certain compounds of Formula V, $R^{401}$ is $C_1$-$C_6$ alkyl. For example, $R^{401}$ is methyl or isopropyl. For example, $R^{401}$ is methyl.

In certain compounds of Formula V, $R^{402}$ is $(CH_2)_k$-4-7 membered saturated heterocycle containing one or more nitrogen or oxygen atoms.

In certain compounds of Formula V, k is 0 or 1. For example, k is 0. For example, k is 1.

In certain compounds of Formula V, $R^{402}$ is azetidinyl, piperazinyl, or piperidinyl.

In certain compounds, $R^{402}$ is $(CH_2)$-azetidinyl, $(CH_2)$-pyrrolidinyl, $(CH_2)$-piperidinyl, $(CH_2)$-morpholinyl, or $(CH_2)$-diazepanyl.

In certain compounds of Formula V, t is 1.

In certain compounds of Formula V, $R^{402a}$ is OH, methyl, or methoxy.

In yet another aspect, the invention relates to a compound according to Formula VI:

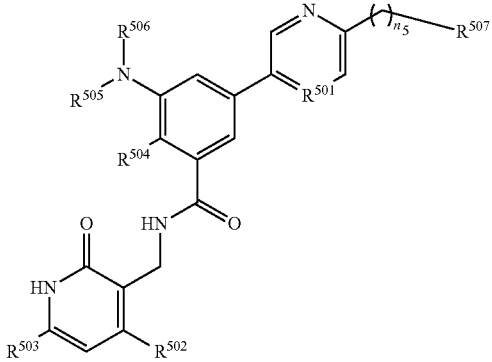

(VI)

or a pharmaceutically acceptable salt or solvate thereof, wherein
$n_5$ is 0, 1, or 2;
$R^{501}$ is C(H) or N;
$R^{502}$, $R^{503}$, $R^{504}$ and $R^{505}$ are, independently for each occurrence, $C_{1-4}$ alkyl;
$R^{506}$ is cyclohexyl substituted by $N(C_{1-4}$ alkyl$)_2$ or piperidine substituted by 1, 2, or 3 $C_{1-4}$ alkyl groups;
when $R^{501}$ is C(H), $R^{507}$ is morpholine; piperidine; diazepane; pyrrolidine; azetidine; O—$C_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, diazepane, pyrrolidine or azetidine groups can be optionally further substituted with OH, $C_{1-6}$ alkyl, or O—$C_{1-3}$ alkyl;
or when $R^{501}$ is C(H), $R^{507}$ can be piperazine optionally further substituted with $C_{1-6}$ alkyl, provided that $R^{506}$ is piperidine substituted by 1, 2, or 3 $C_{1-4}$ alkyl groups;
when $R^{501}$ is N, $R^{507}$ is morpholine; piperidine; piperazine; diazepane; pyrrolidine; azetidine; O—$C_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, piperazine, diazepane, pyrrolidine or azetidine groups can be optionally further substituted with OH, $C_{1-6}$ alkyl, or O—$C_{1-3}$ alkyl.

In still another aspect, the invention relates to a compound of Formula VII:

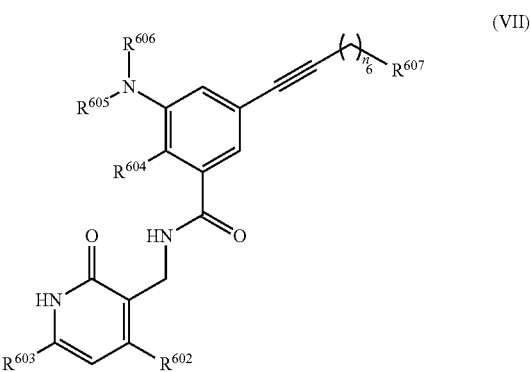

(VII)

or a pharmaceutically acceptable salt or solvate thereof, wherein
$n_6$ is 1 or 2;
$R^{602}$, $R^{603}$, $R^{604}$ and $R^{605}$ are, independently for each occurrence, $C_{1-4}$ alkyl;
$R^{606}$ is cyclohexyl substituted by N(C)_4 alkyl$)_2$ or piperidine substituted by 1, 2, or 3 $C_{1-4}$ alkyl groups; and
$R^{607}$ is morpholine, piperidine, piperazine, pyrrolidine, diazepane, azetidine or O—$C_{1-6}$ alkyl, wherein the piperidine, diazepane or azetidine groups can be optionally further substituted with OH or $C_{1-6}$ alkyl.

The present invention also provides pharmaceutical compositions comprising one or more pharmaceutically acceptable carriers and one or more compounds selected from those of any of the Formulae described herein.

Another aspect of this invention is a method of treating or preventing an EZH2-mediated disorder. The method includes administering to a subject in need thereof a therapeutically effective amount of one or more compounds selected from those of any of the Formulae described herein. The EZH2-mediated disorder is a disease, disorder, or condition that is mediated at least in part by the activity of EZH2. In one embodiment, the EZH2-mediated disorder is related to an increased EZH2 activity. In one embodiment, the EZH2-mediated disorder is a cancer. The EZH2-mediated cancer may be lymphoma, leukemia or melanoma, for example, diffuse large B-cell lymphoma (DLBCL), non-Hodgkin's lymphoma (NHL), follicular lymphoma, chronic myelogenous leukemia (CML), acute myeloid leukemia, acute lymphocytic leukemia, mixed lineage leukemia, or myelodysplastic syndromes (MDS). In one embodiment the EZH2-mediated cancer may be a malignant rhabdoid tumor or INI1-deficient tumor. The histologic diagnosis of malignant rhabdoid tumor depends on identification of characteristic rhabdoid cells (large cells with eccentrically located nuclei and abundant, eosinophilic cytoplasm) and immunohistochemistry with antibodies to vimentin, keratin and epithelial membrane antigen. In most malignant rhabdoid tumors, the SMARCB1/INI1 gene, located in chromosome band 22q 11.2, is inactivated by deletions and/or mutations. In one embodiment, the malignant rhabdoid tumors may be INI1-deficient tumor.

Unless otherwise stated, any description of a method of treatment includes uses of the compounds to provide such treatment or prophylaxis as is described in the specification, as well as uses of the compounds to prepare a medicament to treat or prevent such condition. The treatment includes treatment of human or non-human animals including rodents and other disease models. Methods described herein may be used to identify suitable candidates for treating or preventing EZH2-mediated disorders. For example, the invention also provides methods of identifying an inhibitor of a wild-type EZH2, a mutant EZH2 (e.g., a Y641, A677, and/or A687 mutant EZH2), or both.

For example, the method comprises the step of administering to a subject having a cancer with aberrant H3-K27 methylation an effective amount of one or more compounds of Formulae described herein, wherein the compound(s) inhibits histone methyltransferase activity of EZH2, thereby treating the cancer. Examples of aberrant H3-K27 methylation may include a global increase in and/or altered distribution of H3-K27 di or tri-methylation within the cancer cell chromatin.

For example, the cancer is selected from the group consisting of cancers that overexpress EZH2 or other PRC2 subunits, contain loss-of-function mutations in H3-K27 demethylases such as UTX, or overexpress accessory proteins such as PHF19/PCL3 capable of increasing and or mislocalizing EZH2 activity (see references in Sneeringer et al. *Proc Natl Acad Sci USA* 107(49):20980-5, 2010).

For example, the method comprises the step of administering to a subject having a cancer overexpressing EZH2 a therapeutically effective amount of one or more compounds of Formulae described herein, wherein the compound(s) inhibits histone methyltransferase activity of EZH2, thereby treating the cancer.

For example, the method comprises the step of administering to a subject having a cancer with a loss-of-function mutation in the H3-K27 demethylase UTX a therapeutically effective amount of one or more compounds of Formulae described herein, wherein the compound(s) inhibits histone methyltransferase activity of EZH2, thereby treating the cancer For example, the method comprises the step of administering to a subject having a cancer overexpressing an accessory component(s) of the PRC2, such as PHF19/PCL3, a therapeutically effective amount of one or more compounds of Formulae described herein, wherein the compound(s) inhibits histone methyltransferase activity of EZH2, thereby treating the cancer In still another aspect, this invention relates to a method of modulating the activity of the wild-type EZH2, the catalytic subunit of the PRC2 complex which catalyzes the mono- through tri-methylation of lysine 27 on histone H3 (H3-K27). For example, the present invention relates to a method of inhibiting the activity of EZH2 in a cell. This method can be conducted either in vitro or in vivo.

In yet another aspect, this invention features to a method of inhibiting in a subject conversion of H3-K27 to trimethylated H3-K27. The method comprises administering to a subject a therapeutically effective amount of one or more of the compounds of Formulae described herein to inhibit histone methyltransferase activity of EZH2, thereby inhibiting conversion of H3-K27 to trimethylated H3-K27 in the subject.

For example, the method comprises the step of administering to a subject having a cancer expressing a mutant EZH2 a therapeutically effective amount of one or more compounds of Formulae described herein, wherein the compound(s) inhibits historic methyltransferase activity of EZH2, thereby treating the cancer.

For example, the cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin's lymphoma (NHL), follicular lymphoma or diffuse large B-cell lymphoma. Alternatively, the leukemia is chronic myelogenous leukemia (CML), acute myeloid leukemia, acute lymphocytic leukemia or mixed lineage leukemia.

For example, the precancerous condition is myelodysplastic syndromes (MDS, formerly known as preleukemia).

For example, the cancer is a hematological cancer.

For example, the cancer is selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, a subject in need thereof is one who had, is having or is predisposed to developing brain and CNS cancer, kidney cancer, ovarian cancer, pancreatic cancer, leukemia, lymphoma, myeloma, and/or sarcoma. Exemplary brain and central CNS cancer includes medulloblastoma, oligodendroglioma, atypical teratoid/rhabdoid tumor, choroid plexus carcinoma, choroid plexus papilloma, ependymoma, glioblastoma, meningioma, neuroglial tumor, oligoastrocytoma, oligodendroglioma, and pineoblastoma. Exemplary ovarian cancer includes ovarian clear cell adenocarcinoma, ovarian endomethrioid adenocarcinoma, and ovarian serous adenocarcinoma. Exemplary pancreatic cancer includes pancreatic ductal adenocarcinoma and pancreatic endocrine tumor. Exemplary sarcoma includes chondrosarcoma, clear cell sarcoma of soft tissue, ewing sarcoma, gastrointestinal stromal tumor, osteosarcoma, rhabdomyosarcoma, and not otherwise specified (NOS) sarcoma. Alternatively, cancers to be treated by the compounds of the present invention are non NHL cancers.

For example, the cancer is selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid/rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, and not otherwise specified (NOS) sarcoma. Preferably, the cancer is medulloblastoma, ovarian clear cell adenocarcinoma, ovarian endomethrioid adenocarcinoma, pancreatic ductal adenocarcinoma, malignant rhabdoid tumor, atypical teratoid/rhabdoid tumor, choroid plexus carcinoma, choroid plexus papilloma, glioblastoma, meningioma, pineoblastoma, carcinosarcoma, extrarenal rhabdoid tumor, schwannoma, skin squamous cell carcinoma, chondrosarcoma, ewing sarcoma, epitheloid sarcoma, renal medullo carcinoma, diffuse large B-cell lymphoma, follicular lymphoma and/or NOS sarcoma. More preferably, the cancer is malignant rhabdoid tumor, medulloblastoma and/or atypical teratoid/rhabdoid tumor.

For example, the method comprises the step of administering to a subject having a cancer expressing a mutant EZH2 a therapeutically effective amount of one or more compounds of Formulae described herein, wherein the compound(s) inhibits activity (e.g., histone methyltransferase activity) of the mutant EZH2, the wild-type EZH2, or both, thereby treating the cancer.

For example, the method further comprises the steps of performing an assay to detect a mutant EZH2 in a sample comprising cancer cells from a subject in need thereof.

In another aspect, the invention features a method of selecting a therapy for a patient having a disease associated with EZH2-mediated protein methylation. The method includes the steps of determining the presence of gene mutation in the EZH2 gene of the subject; and selecting, based on the presence of a gene mutation in the EZH2 gene a therapy for treating the disease. In one embodiment, the therapy includes the administration of one or more of the compounds of the invention. In one embodiment, the method further includes administrating one or more of the compounds of the invention to the subject. In one embodiment, the disease is cancer and the mutation is a Y641 mutation.

In yet another aspect, a method of treatment is provided for a patient in need thereof, the method comprising the steps of determining the presence of gene mutation in the EZH2 gene and treating the patient in need thereof, based on the presence of a gene mutation in the EZH2 gene, with a therapy that includes the administration of the compounds of the invention. In one embodiment, the patient is a cancer patient and the mutation is a Y641 mutation.

In still another aspect, this invention relates to a method of modulating the activity of the wild-type and mutant histone methyltransferase EZH2, the catalytic subunit of the PRC2 complex which catalyzes the mono- through tri-methylation of lysine 27 on histone H3 (H3-K27). For example, the present invention relates to a method of inhibiting the activity of certain mutant forms of EZH2 in a cell. The mutant forms of EZH2 include a substitution of another amino acid residue for tyrosine 641 (Y641, also Tyr641) of wild-type EZH2. The method includes contacting the cell with an effective amount of one or more of the compounds of any Formula described herein. This method can be conducted either in vitro or in vivo.

In yet another aspect, this invention features to a method of inhibiting in a subject conversion of H3-K27 to trimethylated H3-K27. The method comprises administering to a subject expressing a mutant EZH2 a therapeutically effective amount of one or more of the compounds of any Formula described herein to inhibit histone methyltransferase activity of EZH2, thereby inhibiting conversion of H3-K27 to trimethylated H3-K27 in the subject. For example, the histone methyltransferase activity inhibited is that of the Y641 mutant of EZH2. For example, the compound of this invention selectively inhibits histone methyltransferase activity of the Y641 mutant of EZH2. For example, the Y641 mutant of EZH2 is selected from the group consisting of Y641C, Y641F, Y641H, Y641N, and Y641S.

The method of inhibiting in a subject conversion of H3-K27 to trimethylated H3-K27 may also comprise performing an assay to detect a mutant EZH2 in a sample from a subject before administering to the subject expressing a mutant EZH2 a therapeutically effective amount of one or more of the compounds of any Formula described herein. For example, performing the assay to detect the mutant EZH2 includes whole-genome resequencing or target region resequencing that detects a nucleic acid encoding the mutant EZH2. For example, performing the assay to detect the mutant EZH2 includes contacting the sample with an antibody that binds specifically to a polypeptide or fragment thereof characteristic of the mutant EZH2. For example, performing the assay to detect the mutant EZH2 includes contacting the sample under highly stringent conditions with a nucleic acid probe that hybridizes to a nucleic acid encoding a polypeptide or fragment thereof characteristic of the mutant EZH2.

Further, the invention also relates to a method of identifying an inhibitor of a mutant EZH2, wild-type EZH2, or both. The method comprises the steps of combining an isolated EZH2 with a histone substrate, a methyl group donor, and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 (e.g., formation of trimethylated H3-K27) in the histone substrate, thereby identifying the test compound as an inhibitor of the EZH2 when methylation of H3-K27 (e.g., formation of trimethylated H3-K27) in the presence of the test compound is less than methylation of H3-K27 (e.g., formation of trimethylated H3-K27) in the absence of the test compound.

In one embodiment, performing the assay to detect methylation of H3-K27 in the histone substrate comprises measuring incorporation of labeled methyl groups.

In one embodiment, the labeled methyl groups are isotopically labeled methyl groups.

In one embodiment, performing the assay to detect methylation of H3-K27 in the histone substrate comprises contacting the histone substrate with an antibody that binds specifically to trimethylated H3-K27.

Also within the scope of the invention is a method of identifying a selective inhibitor of a mutant EZH2. The method comprises the steps of combining an isolated mutant EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the mutant EZH2 and the test compound (M+) to (b) trimethylation with the mutant EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the mutant EZH2 when the ratio (a)/(b) is less than the ratio (c)/(d).

The present invention further provides a method of identifying a subject as a candidate for treatment with one or more compounds of the invention. The method comprises the steps of performing an assay to detect a mutant EZH2 in a sample from a subject; and identifying a subject expressing a mutant EZH2 as a candidate for treatment with one or more compounds of the invention, wherein the compound(s) inhibits histone methyltransferase activity of EZH2.

Still another aspect of the invention is a method of inhibiting conversion of H3-K27 to trimethylated H3-K27. The method comprises the step of contacting wild-type EZH2, a mutant EZH2, or both with a histone substrate comprising H3-K27 and an effective amount of a compound of the present invention, wherein the compound inhibits histone methyltransferase activity of EZH2, thereby inhibiting conversion of H3-K27 to trimethylated H3-K27.

Further, the compounds or methods described herein can be used for research (e.g., studying epigenetic enzymes) and other non-therapeutic purposes.

In certain embodiments, the preferred compounds disclosed herein have improved pharmacological and/or pharmacokinetic properties, e.g., lower clearance rates, reduced risk of adverse drug-drug interactions in combination therapy through reduction of time-dependent and reversible inhibition of cytochrome P-450 enzymes.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

The present invention provides novel substituted benzene compounds, synthetic methods for making the compounds, pharmaceutical compositions containing them and various uses of the compounds.

In one aspect, the invention relates to a compound according to Formula I:

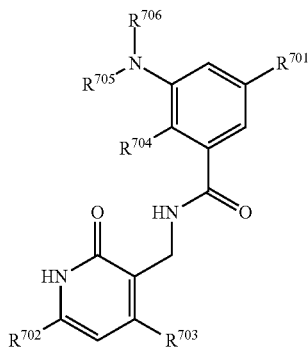

(I)

or a pharmaceutically acceptable salt thereof; wherein
$R^{701}$ is H, F, $OR^{707}$, $NHR^{707}$, $-(C\equiv C)-(CH_2)_{n_7}-R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NE-$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-2}$ alkyl being optionally further substituted with O—$C_{1-3}$ alkyl or NH—$C_{1-3}$ alkyl;

each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$, independently is $C_{1-4}$ alkyl;

$R^{706}$ is cyclohexyl substituted by $N(C_{1-4}$ alkyl$)_2$ wherein one or both of the $C_{1-4}$ alkyl is substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

For example, $R^{706}$ is cyclohexyl substituted by $N(C_{1-4}$ alkyl$)_2$ wherein one of the $C_{1-4}$ alkyl is unsubstituted and the other is substituted with methoxy.

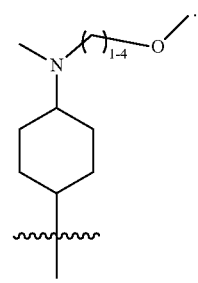

For example, wherein $R^{706}$ is

A subset of compounds of Formula I includes those of Formula II and pharmaceutically acceptable salts thereof:

(II)

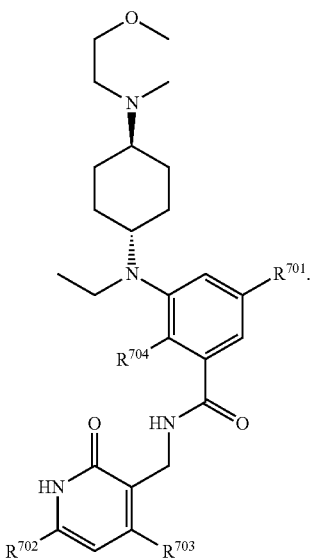

The compounds of Formula I or II can include one or more of the following features:

For example, $R^{702}$ is methyl or isopropyl.

For example, $R^{703}$ is methyl or methoxyl.

For example, $R^{704}$ is methyl.

For example, $R^{701}$ is $OR^{707}$.

For example, $R^{707}$ is $C_{1-3}$ alkyl optionally substituted with $OCH_3$ or morpholine.

For example, $R^{701}$ is H or F.

For example, $R^{701}$ is tetrahydropyranyl optionally substituted with methyl, methoxy, ethyl substituted with morpholine, or —$OCH_2CH_2OCH_3$.

For example, $R^{701}$ is phenyl optionally substituted with methyl, methoxy, ethyl substituted with morpholine, or —$OCH_2CH_2OCH_3$.

For example, $R^{701}$ is 5-membered heteroaryl (e.g., pyrrolyl, furyl, thiophenyl, thiazolyl, isothiazolyl, imidazolyl, triazolyl, tetrazolyl, pyrazolyl, oxazolyl, or isoxazolyl) optionally substituted with methyl, methoxy, ethyl substituted with morpholine, or —$OCH_2CH_2OCH_3$.

For example, $R^{701}$ is 6-membered heteroaryl (e.g., pyridyl, pyrazinyl, pyridazinyl, or pyrimidyl) optionally substituted with methyl, methoxy, ethyl substituted with morpholine, or —$OCH_2CH_2OCH_3$.

For example, $R^{701}$ is pyridyl, pyrimidyl, pyrazinyl, imidazolyl, or pyrazolyl, each of which is optionally substituted with methyl, methoxy, ethyl substituted with morpholine, or —$OCH_2CH_2OCH_3$.

For example, $R^{708}$ is morpholine, piperidine, piperazine, pyrrolidine, diazepane, or azetidine, each of which is optionally substituted with OH or $C_{1-6}$ alkyl.

For example, $R^{708}$ is morpholine

For example, $R^{708}$ is piperazine substituted with $C_{1-6}$ alkyl.

For example, $R^{708}$ is t-butyl or $C(CH_3)_2OH$.

For example, the compounds of Formula I or II do not comprise N-((4,6-dimethyl-2-oxo-1,2-dihydropyridin-3-yl)methyl)-3-(ethyl(tetrahydro-2H-pyran-4-yl)amino)-2-methyl-5-((1-methylpiperidin-4-yl)ethynyl)benzamide (i.e., Compound 105).

For example, the compounds of Formula I or II do not comprise N-((4,6-dimethyl-2-oxo-1,2-dihydropyridin-3-yl) methyl)-3-(ethyl(4-((2-methoxyethyl)(methyl)amino)cyclohexyl)amino)-2-methyl-5-(3-morpholinoprop-1-yn-1-yl) benzamide or N-((4,6-dimethyl-2-oxo-1,2-dihydropyridin-3-yl)methyl)-3-(ethyl(1r,4r)-4-((2-methoxyethyl)(methyl) amino)cyclohexyl)amino)-2-methyl-5-(3-morpholinoprop-1-yn-1-yl)benzamide (i.e., Compound 2).

For example, the compounds of Formula I or II comprise N-((4,6-dimethyl-2-oxo-1,2-dihydropyridin-3-yl)methyl)-3-(ethyl(tetrahydro-2H-pyran-4-yl)amino)-2-methyl-5-((1-methylpiperidin-4-yl)ethynyl)benzamide (i.e., Compound 105) or N-((4,6-dimethyl-2-oxo-1,2-dihydropyridin-3-yl) methyl)-3-(ethyl(4-((2-methoxyethyl)(methyl)amino)cyclohexyl)amino)-2-methyl-5-(3-morpholinoprop-1-yn-1-yl) benzamide, e.g., N-((4,6-dimethyl-2-oxo-1,2-dihydropyridin-3-yl)methyl)-3-(ethyl((1r,4r)-4-((2-methoxyethyl)(methyl)amino)cyclohexyl)amino)-2-methyl-5-(3-morpholinoprop-1-yn-1-yl)benzamide (i.e., Compound 2).

In another aspect, the invention relates to a compound according to Formula III:

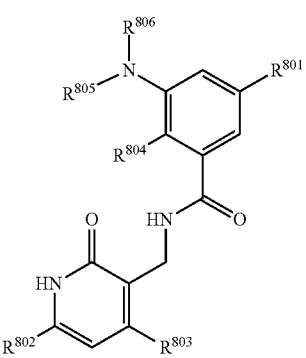

(III)

or a pharmaceutically acceptable salt thereof; wherein $R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; and $R^{801}$ is optionally further substituted;

each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$, independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

The compounds of Formula III can include one or more of the following features:

For example, $Q_x$ is a bond or methyl linker.

For example, $T_x$ is tetrahydropyranyl.

For example, $T_x$ is piperidinyl substituted by 1, 2, or 3 $C_{1-4}$ alkyl groups.

For example, T$_x$ is cyclohexyl substituted by N(C$_{1-4}$ alkyl)$_2$ wherein one or both of the C$_{1-4}$ alkyl is optionally substituted with C$_{1-6}$ alkoxy.

For example, R$^{806}$ is cyclohexyl substituted by N(C$_{1-4}$ alkyl)$_2$, e.g.,

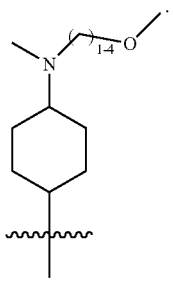

For example, R$^{801}$ is phenyl substituted with O—C$_{1-6}$ alkyl-R$_x$.

For example, R$^{801}$ is 5-membered heteroaryl substituted (e.g., pyrrolyl, furyl, thiophenyl, thiazolyl, isothiazolyl, imidazolyl, triazolyl, tetrazolyl, pyrazolyl, oxazolyl, isoxazolyl) with O—C$_{1-6}$ alkyl-R$_x$.

For example, R$^{801}$ is 6-membered heteroaryl (e.g., pyridyl, pyrazinyl, pyridazinyl, or pyrimidinyl) substituted with O—C$_{1-6}$ alkyl-R$_x$.

For example, R$^{801}$ is pyridyl, pyrimidyl, pyrazinyl, imidazolyl, or pyrazolyl, each of which is substituted with O—C$_{1-6}$ alkyl-R$_x$.

For example, subsets of compounds of Formula III include those of Formula IVa or IVb and pharmaceutically acceptable salts thereof:

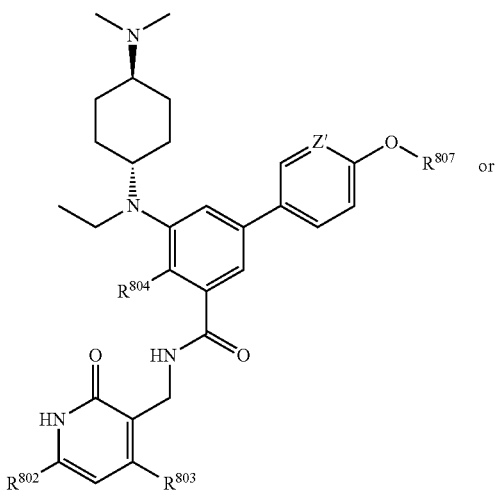

(IVa)

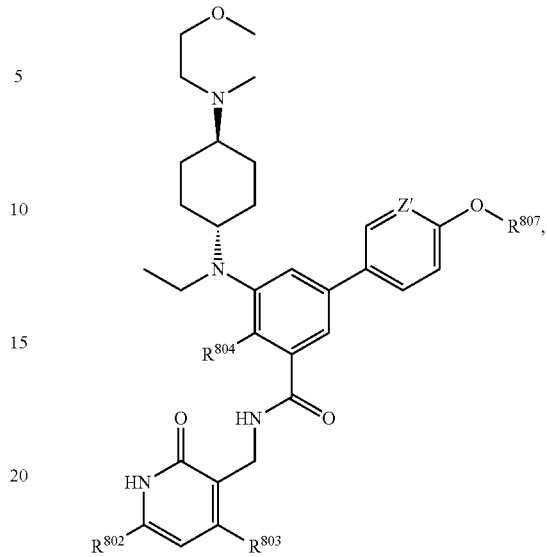

(IVb)

wherein Z' is CH or N, and R$^{807}$ is C$_{2-3}$ alkyl-R$_x$.

For example, R$^{807}$ is —CH$_2$CH$_2$OH, —CH$_2$CH$_2$OCH$_3$, or —CH$_2$CH$_2$OCH$_2$CH$_2$OCH$_3$.

For example, R$^{802}$ is methyl or isopropyl.

For example, R$^{803}$ is methyl or methoxyl.

For example, R$^{804}$ is methyl.

For example, the compounds of Formula III do not comprise N-((4,6-dimethyl-2-oxo-1,2-dihydropyridin-3-yl)methyl)-5-((4-(dimethylamino)cyclohexyl)(ethyl)amino)-4'-(2-methoxyethoxy)-4-methyl-[1,1'-biphenyl]-3-carboxamide or N-((4,6-dimethyl-2-oxo-1,2-dihydropyridin-3-yl)methyl)-5-(((1r,4r)-4-(dimethylamino)cyclohexyl)(ethyl)amino)-4'-(2-methoxyethoxy)-4-methyl-[1,1'-biphenyl]-3-carboxamide (i.e., Compound 1).

For example, the compounds of Formula III comprise N-((4,6-dimethyl-2-oxo-1,2-dihydropyridin-3-yl)methyl)-5-((4-(dimethylamino)cyclohexyl)(ethyl)amino)-4'-(2-methoxyethoxy)-4-methyl-[1,1'-biphenyl]-3-carboxamide.

For example, the compounds of Formula III comprise N-((4,6-dimethyl-2-oxo-1,2-dihydropyridin-3-yl)methyl)-5-(((1r,4r)-4-(dimethylamino)cyclohexyl)(ethyl)amino)-4'-(2-methoxyethoxy)-4-methyl-[1,1'-biphenyl]-3-carboxamide (i.e., Compound 1).

In yet another aspect, the invention relates to a compound according to Formula IA:

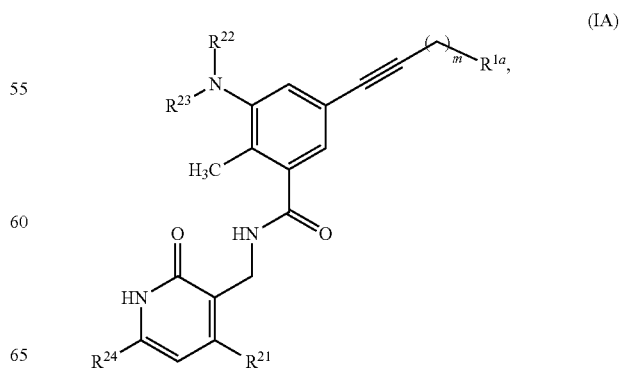

(IA)

or a pharmaceutically acceptable salt or solvate thereof, wherein $R^{21}$ is hydrogen or $C_1$-$C_6$ alkyl, $R^{22}$ is (a) 3-8 membered saturated, unsaturated, or aromatic carbocycle, or (b) 3-8 membered saturated, unsaturated, or aromatic heterocycle containing one or more heteroatoms selected from the group consisting of nitrogen, oxygen, and sulfur, where (a)-(b) are optionally substituted with one or more $R^{2a}$;

each of $R^{23}$ and $R^{24}$ independently is $C_1$-$C_6$ alkyl, $R^{1a}$ is (a) 3-8 membered saturated, unsaturated, or aromatic carbocycle, or (b) 3-8 membered saturated, unsaturated, or aromatic heterocycle containing one or more heteroatoms selected from the group consisting of nitrogen, oxygen, and sulfur, where (a)-(b) are optionally substituted with one or more $R^{3a}$;

each $R^{2a}$ independently is $C_1$-$C_6$ alkyl, $NH_2$, $NH(C_1$-$C_6$ alkyl), or $N(C_1$-$C_6$ alkyl$)_2$;

each $R^{3a}$ independently is (a) OH, (b) $C_1$-$C_6$ alkyl, or (c) $O(C_1$-$C_6$ alkyl), where (b)-(c) are optionally substituted with one or more OH, and m is 0, 1, 2, or 3;

provided that (i) when $R^{22}$ is tetrahydropyranyl, $R^{1a}$ is not morpholinyl; or (ii) when $R^{1a}$ is piperazinyl or cyclopropyl, $R^{21}$ is not methyl or (iii) the compound is not N-((4,6-dimethyl-2-oxo-1,2-dihydropyridin-3-yl)methyl)-3-((4-(dimethylamino) cyclohexyl)(ethyl)amino)-2-methyl-5-(3-(4-methyl-piperazin-1-yl)prop-1-yn-1-yl)benzamide or 5-(cyclopropylethynyl)-N-((4,6-dimethyl-2-oxo-1,2-dihydropyridin-3-yl)methyl)-3-((4-(dimethylamino) cyclohexyl)(ethyl)amino)-2-methylbenzamide.

For example, in certain compounds of Formula IA, $R^{21}$ is $C_1$-$C_6$ alkyl. Such as, for example, $R^1$ is methyl or isopropyl.

For example, in certain compounds of Formula IA, $R^{22}$ is a 6-membered saturated carbocycle or a 6-membered saturated heterocycle. Such as, for example, $R^{22}$ is cyclohexyl or tetrahydropyranyl. In some compounds, the cyclohexyl is substituted with $N(C_1$-$C_6$ alkyl$)_2$, such as, e.g., $N(CH_3)_2$.

For example, in certain compounds of Formula IA, $R^{22}$ is tetrahydropyranyl.

For example, in certain compounds of Formula IA, $R^{1a}$ is 4-7 membered saturated heterocycle. For example, $R^{1a}$ is azetidinyl, pyrrolidinyl, piperidinyl, morpholinyl, piperazinyl, or diazepanyl.

For example, $R^{23}$ is ethyl.

For example, $R^{24}$ is methyl.

For example, m is 0 or 1.

In another aspect, the invention relates to compound according to Formula IIIa:

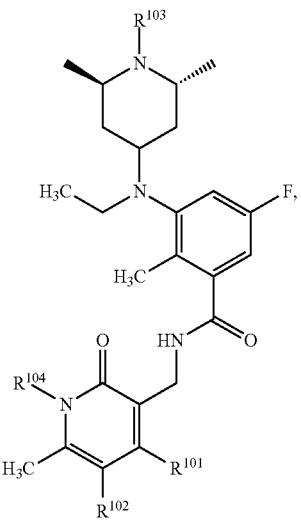

or a pharmaceutically acceptable salt or solvate thereof, wherein $R^{101}$ is hydrogen, $C_1$-$C_6$ alkyl, or $C_1$-$C_6$ haloalkyl;

$R^{102}$ is hydrogen or halogen;

$R^{103}$ is hydrogen or $C_1$-$C_6$ alkyl; and $R^{104}$ is hydrogen or $C_1$-$C_6$ alkyl; provided that when $R^{101}$ is methyl, and when $R^{102}$ and $R^{103}$ are hydrogen, $R^{104}$ is not hydrogen.

For example, in certain compounds of Formula IIIa, $R^{101}$ is $C_1$-$C_6$ alkyl. Such as, for example, $R^{101}$ is methyl, n-propyl, or isopropyl.

In certain compounds of Formula IIIa, $R^{101}$ is $C_1$-$C_6$ haloalkyl. For example, $R^{101}$ is $CF_3$, $CF_2H$, or $CFH_2$. In certain compounds of Formula IIIa, $R^{101}$ is $CF_3$.

For example, in certain compounds of Formula IIIa, $R^{102}$ is halogen. For example, $R^{102}$ is fluoro.

In another aspect, the invention relates to compound according to Formula IIIb:

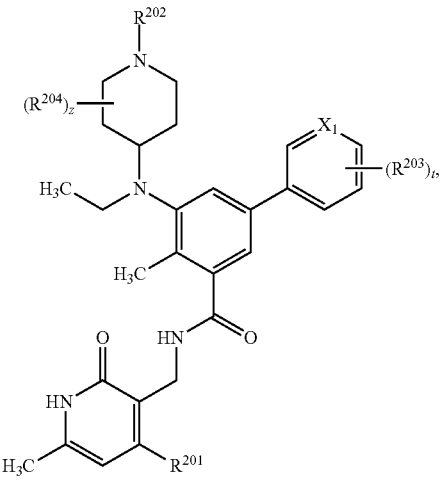

or a pharmaceutically acceptable salt or solvate thereof, wherein $X_1$ is N or CH;

$R^{201}$ is hydrogen, $C_1$-$C_6$ alkyl, $C_1$-$C_6$ haloalkyl;

$R^{202}$ is hydrogen or $C_1$-$C_6$ alkyl;

$R^{203}$ is (a) OH, (b) $C_1$-$C_6$ alkyl, (c) O($C_1$-$C_6$ alkyl), (d) $(CH_2)_j$-3-8 membered saturated, unsaturated, or aromatic carbocycle, (e) $(CH_2)_k$-3-8 membered saturated, unsaturated, or aromatic heterocycle containing one or more heteroatoms selected from the group consisting of nitrogen, oxygen, and sulfur, (f) O—$(CH_2)_u$-3-8 membered saturated, unsaturated, or aromatic carbocycle, or (g) O—$(CH_2)_v$-3-8 membered saturated, unsaturated, or aromatic heterocycle containing one or more heteroatoms selected from the group consisting of nitrogen, oxygen, and sulfur, where (b)-(g) are optionally substituted with $R^{203a}$ $R^{203a}$ is $C_1$-$C_6$ alkyl, $C_1$-$C_6$ haloalkyl, OH, or O($C_1$-$C_6$ alkyl);

$R^{204}$ is $C_1$-$C_6$ alkyl;

t is 1, 2, or 3;

u is 0, 1, 2, or 3;

v is 0, 1, 2, or 3;

z is 0, 1, 2, or 3;

j is 0, 1, 2, or 3; and k is 0, 1, 2, or 3.

For example, in certain compounds of Formula IIIb, $X_1$ is N and $X_2$ is CH. For example, in certain compounds of Formula III, $R^{201}$ is $C_1$-$C_6$ alkyl. For example, $R^{201}$ is methyl.

For example, in certain compounds of Formula IIIb, $R^{202}$ is hydrogen. In certain other compounds of Formula III, $R^{202}$ is $C_1$-$C_6$ alkyl. For example, $R^{202}$ is methyl.

For example, in certain compounds of Formula IIIb, $R^{203}$ is $(CH_2)_k$-6 membered saturated heterocycle. For example, k is 1.

For example, in certain other compounds of Formula IIIb, $R^{203}$ is $(CH_2)$-piperazinyl or $(CH_2)$-morpholinyl. For example, t is 1.

In certain compounds of Formula IIIb, $R^{204}$ is methyl.

In certain compounds of Formula IIIb, z is 2.

In another aspect, the invention relates to compound according to Formula IV:

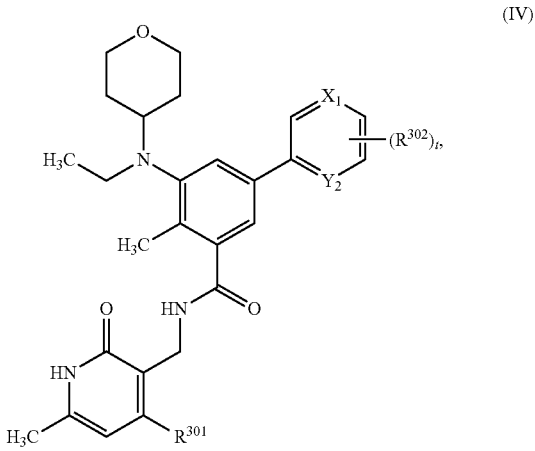

(IV)

or a pharmaceutically acceptable salt or solvate thereof, wherein $Y_1$ is N or CH;

$Y_2$ is N or CH;

$R^{301}$ is hydrogen, $C_1$-$C_6$ alkyl, $C_1$-$C_6$ haloalkyl;

$R^{302}$ is (a) $C_1$-$C_6$ alkyl (b) $C_1$-$C_6$ haloalkyl, (c) O($C_1$-$C_6$ alkyl), (d) $(CH_2)_j$-3-8 membered saturated, unsaturated, or aromatic carbocycle, (e) $(CH_2)_k$-3-8 membered saturated, unsaturated, or aromatic heterocycle containing one or more heteroatoms selected from the group consisting of nitrogen, oxygen, and sulfur, (f) O—$(CH_2)_u$-3-8 membered saturated, unsaturated, or aromatic carbocycle, or (g) O—$(CH_2)_v$-3-8 membered saturated, unsaturated, or aromatic heterocycle containing one or more heteroatoms selected from the group consisting of nitrogen, oxygen, and sulfur, where (a)-(g) are optionally substituted with $R^{302a}$ $R^{302a}$ is $C_1$-$C_6$ alkyl, $C_1$-$C_6$ haloalkyl, OH, or O($C_1$-$C_6$ alkyl);

t is 1, 2, or 3;

u is 0, 1, 2, or 3;

v is 0, 1, 2, or 3;

j is 0, 1, 2, or 3; and k is 0, 1, 2, or 3; provided that (i) when $R^{302}$ is $(CH_2)$-morpholinyl, $R^{301}$ is not methyl, isopropyl or n-propyl; or (ii) $R^{302}$ is not piperazinyl or $(CH_2)$-piperazinyl.

For example, in certain compounds of Formula IV, Y1 is N and Y2 is CH.

For example, in certain compounds of Formula IV, $R^{301}$ is $C_1$-$C_6$ alky. For example, $R^{301}$ is methyl or isopropyl. In certain compounds, $R^{301}$ is methyl. In other compounds $R^{301}$ is $C_1$-$C_6$ haloalkyl. For example, $R^{301}$ is $CF_3$, $CF_2H$, or $CFH_2$. In some compounds, $R^{301}$ is $CF_3$.

For example, in certain compounds of Formula IV, $R^{302}$ is O($C_1$-$C_6$ alkyl). For example, $R^{302}$ is methoxy or isopropoxy. In certain other compounds, $R^{302}$ is O-4-6 membered saturated heterocycle. For example, the heterocycle is azetidinyl or piperidinyl. In certain compounds, of Formula IV, $R^{302}$ is $(CH_2)$-4-7 membered saturated heterocycle. For example, the heterocycle is azetidinyl, pyrrolidinyl, piperidinyl, morpholinyl, or diazepanyl.

In another aspect, the invention relates to compound according to formula V:

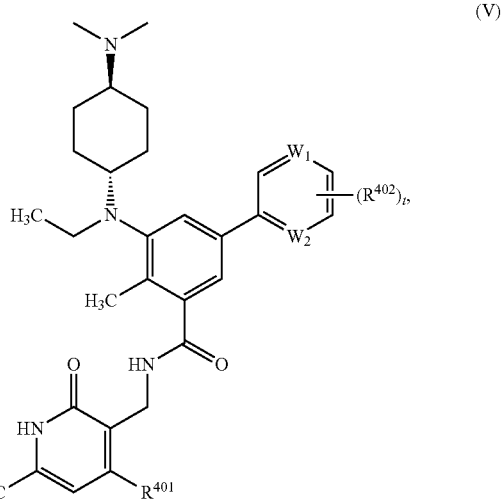

(V)

or a pharmaceutically acceptable salt or solvate thereof, wherein $W_1$ is N or CH;

$W_2$ is N or CH;

$R^{401}$ is hydrogen, $C_1$-$C_6$ alkyl, $C_1$-$C_6$ haloalkyl;

$R^{402}$ is (a) OH, (b) $(CH_2)$—O—($C_1$-$C_6$ alkyl), (c) O($C_1$-$C_6$ alkyl), (d) $(CH_2)_j$-3-8 membered saturated, unsaturated, or aromatic carbocycle, (e) $CH_2)_k$-3-8 membered saturated, unsaturated, or aromatic heterocycle containing one or more heteroatoms selected from the group consisting of nitrogen, oxygen, and sulfur, (f) O—$(CH_2)_u$-3-8 membered saturated, unsaturated, or aromatic carbocycle, or (g) O—$(CH_2)_v$-3-8 membered saturated, unsaturated, or aromatic heterocycle containing one or more heteroatoms selected from the group consisting of nitrogen, oxygen, and sulfur, where (b)-(g) are optionally substituted with $R^{402a}$, $R^{402a}$ is $C_1$-$C_6$ alkyl, $C_1$-$C_6$ haloalkyl, OH, or O($C_1$-$C_6$ alkyl);

t is 1, 2, or 3;
u is 0, 1, 2, or 3;
v is 0, 1, 2, or 3;
j is 0, 1, 2, or 3; and
k is 0, 1, 2, or 3; provided that when $R^{402}$ is piperazinyl, $W_1$ and $W_2$ are N.

In certain compounds of Formula V, $W_1$ is N and $W_2$ is CH.

In certain compounds of Formula V, $R^{401}$ is $C_1$-$C_6$ alkyl. For example, $R^{401}$ is methyl or isopropyl. For example, $R^{401}$ is methyl.

In certain compounds of Formula V, $R^{402}$ is $(CH_2)_k$-4-7 membered saturated heterocycle containing one or more nitrogen or oxygen atoms.

In certain compounds of Formula V, k is 0 or 1. For example, k is 0. For example, k is 1.

In certain compounds of Formula V, $R^{402}$ is azetidinyl, piperazinyl, or piperidinyl.

In certain compounds, $R^{402}$ is $(CH_2)$-azetidinyl, $(CH_2)$-pyrrolidinyl, $(CH_2)$-piperidinyl, $(CH_2)$-morpholinyl, or $(CH_2)$-diazepanyl.

In certain compounds of Formula V, t is 1.

In certain compounds of Formula V, $R^{402a}$ is OH, methyl, or methoxy.

In another aspect, the invention relates to a compound of Formula VI:

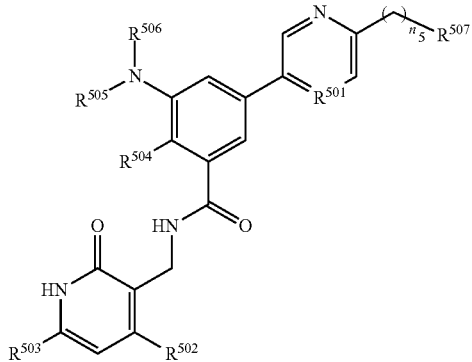

(VI)

or a pharmaceutically acceptable salt or solvate thereof, wherein $n^5$ is 0, 1, or 2;
$R^{501}$ is C(H) or N;
$R^{502}$, $R^{503}$, $R^{504}$ and $R^{505}$ are, independently for each occurrence, $C_{1-4}$ alkyl;
$R^{506}$ is cyclohexyl substituted by N($C_{1-4}$ alkyl)$_2$ or piperidine substituted by 1, 2, or 3 $C_{1-4}$ alkyl groups;
when $R^{501}$ is C(H), $R^{507}$ is morpholine; piperidine; diazepane; pyrrolidine; azetidine; O—$C_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, diazepane, pyrrolidine or azetidine groups can be optionally further substituted with OH, $C_{1-6}$ alkyl, or O—$C_{1-3}$ alkyl;

or when $R^{501}$ is C(H), $R^{507}$ can be piperazine optionally further substituted with $C_{1-6}$ alkyl, provided that $R^{506}$ is piperidine substituted by 1, 2, or 3 $C_{1-4}$ alkyl groups;

when $R^{501}$ is N, $R^{507}$ is morpholine; piperidine; piperazine; diazepane; pyrrolidine; azetidine; O—$C_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, piperazine, diazepane, pyrrolidine or azetidine groups can be optionally further substituted with OH, $C_{1-6}$ alkyl, or O—$C_{1-3}$ alkyl.

In certain compounds of Formula VI, $R^{501}$ is C(H), and $R^{507}$ is piperidine; diazepane; pyrrolidine; azetidine; O—$C_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, diazepane, pyrrolidine or azetidine groups can be optionally further substituted with OH, $C_{1-6}$ alkyl, or O—$C_{1-3}$ alkyl.

In certain compounds of Formula VI, $R^{501}$ is C(H) and $R^{507}$ is piperidine, diazepane, pyrrolidine, azetidine or O—$C_{1-6}$ alkyl, wherein the piperidine, diazepane, pyrrolidine or azetidine groups can be optionally further substituted with OH or $C_{1-6}$ alkyl.

In certain compounds of Formula VI, $R^{501}$ is C(H), $R^{507}$ is piperazine optionally further substituted with $C_{1-6}$ alkyl, and $R^{506}$ is piperidine substituted by 1, 2, or 3 $C_{1-4}$ alkyl groups.

In certain compounds of Formula VI, $R^{501}$ is N, and $R^{507}$ is morpholine, piperidine, piperazine, diazepane, pyrrolidine, azetidine or O—$C_{1-6}$ alkyl, wherein the piperidine, piperazine, diazepane, pyrrolidine or azetidine groups can be optionally further substituted with OH or $C_{1-6}$ alkyl.

In certain compounds of Formula VI, $R^{502}$ is methyl or isopropyl, and $R^{503}$ is methyl.

In certain compounds of Formula VI, wherein $R^{504}$ is methyl.

In certain compounds of Formula VI, $R^{505}$ is ethyl.

In certain compounds of Formula VI, $R^{506}$ is

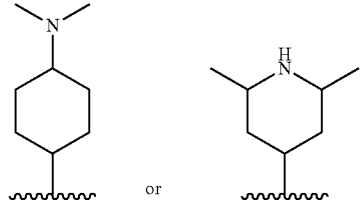

In certain compounds of Formula VI, $R^{506}$ is

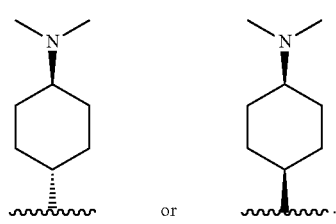

In certain compounds of Formula VI, when $R^{501}$ is C(H), $R^{507}$ is piperidine or diazepane, which are substituted with OH or $C_{1-6}$ alkyl, or when $R^{501}$ is N, $R^{507}$ is piperidine, piperazine, or diazepane, which are optionally further substituted with OH or $C_{1-6}$ alkyl.

In certain compounds of Formula VI, when $R^{501}$ is C(H), $R^{507}$ is piperidine substituted with $C_{1-6}$ alkyl, or when $R^{501}$ is N, $R^{507}$ is piperidine substituted with OH or piperazine substituted with $C_{1-6}$ alkyl.

In certain compounds of Formula VI, when $R^{501}$ is N, $R^{507}$ is unsubstituted piperazine.

In certain compounds of Formula VI, $n_5$ is 0 or 1.

In certain compounds of Formula VI, when $R^{501}$ is C(H) or N, $R^{507}$ is O—$C_{1-6}$ alkyl or O-heterocycle, and $n_5$ is 1.

In certain compounds of Formula VI, when $R^{501}$ is C(H), $R^{507}$ is unsubstituted piperazine and $R^{506}$ is piperidine substituted by 1, 2, or 3 $C_{1-4}$ alkyl groups.

In yet another aspect, the invention relates to a compound of Formula VII:

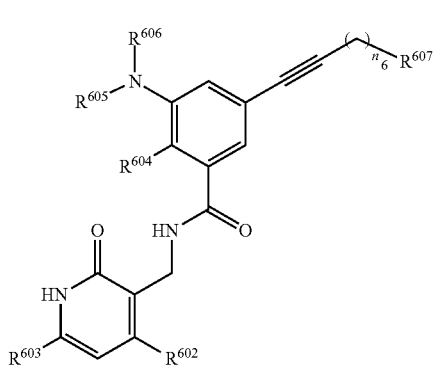

(VII)

or a pharmaceutically acceptable salt or solvate thereof; wherein $n_6$ is 0, 1 or 2;

$R^{602}$, $R^{603}$, $R^{604}$ and $R^{605}$ are, independently for each occurrence, $C_{1-4}$ alkyl; or each of $R^{602}$ and $R^{603}$, independently is $C_{1-4}$ alkoxyl;

$R^{606}$ is tetrahydropyran, cyclohexyl substituted by $N(C_{1-4}$ alkyl$)_2$ or piperidine substituted by 1, 2, or 3 $C_{1-4}$ alkyl groups; and $R^{607}$ is morpholine, piperidine, piperazine, pyrrolidine, diazepane, azetidine or O—$C_{1-6}$ alkyl, wherein the piperidine, diazepane or azetidine groups can be optionally further substituted with OH; $C_{1-6}$ alkyl optionally substituted with one or more halo; $C_{3-6}$ cycloalkyl; C(O)$C_{1-6}$ alkyl; or 4- to 7-membered heterocycloalkyl optionally substituted with $C_{1-4}$ alkyl;

provided that when $R^{606}$ is tetrahydropyran, $n_6$ is 0 or 2.

In certain compounds of Formula VII, $R^{602}$ is methyl or isopropyl and $R^{603}$ is methyl.

In certain compounds of Formula VII, $R^{604}$ is methyl and $R^{605}$ is ethyl.

In certain compounds of Formula VII, $R^{606}$ is

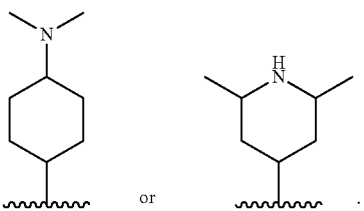

In certain compounds of Formula VII, $R^{606}$ is

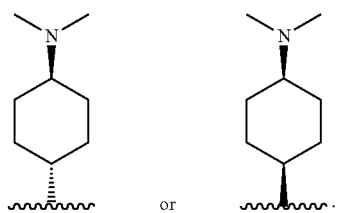

In certain compounds of Formula VII, $R^{607}$ is piperidine or diazepane, each of which is substituted with OH or $C_{1-6}$ alkyl.

In certain compounds of Formula VII, $R^{607}$ is piperidine substituted with OH.

In certain compounds of Formula VII, $R^{607}$ is piperidine substituted with $C_{1-6}$ alkyl optionally substituted with one or more halo; $C_{3-6}$ cycloalkyl; C(O)$C_{1-6}$ alkyl; or 4- to 7-membered heterocycloalkyl.

In certain compounds of Formula VII, $R^{607}$ is piperidine substituted with substituted with $C_{1-6}$ alkyl optionally substituted with one or more halo; $C_{3-6}$ cycloalkyl; C(O)$C_{1-6}$ alkyl; or 4- to 7-membered heterocycloalkyl; and n6 is 0.

In certain compounds of Formula VII, $n_6$ is 2.

In yet another aspect, the invention relates to a compound of Formula VIIa

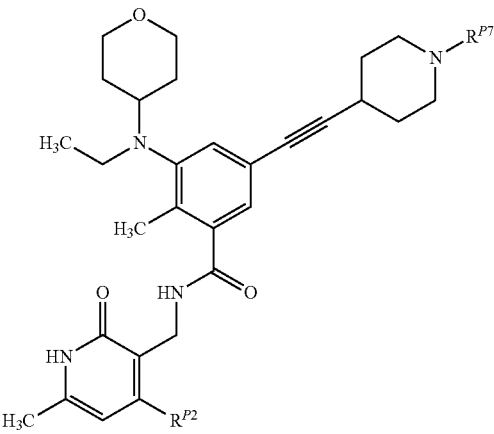

(VIIa)

or a pharmaceutically acceptable salt or solvate thereof; wherein $R^{P2}$ is $CH_3$ or $OCH_3$, and $R^{P7}$ is $C_{1-4}$ alkyl; $C_{3-6}$ cycloalkyl, or 4- to 7-membered heterocycloalkyl optionally substituted with $C_{1-4}$ alkyl.

In certain compounds of Formula VIIa, $R^{P7}$ is cyclopropyl or cyclobutyl.

In certain compounds of Formula VIIa, $R^{P7}$ is azetidinyl or piperidinyl, each optionally substituted with $CH_3$.

In certain compounds of Formula VIIa, $R^{P7}$ is oxetanyl.

In yet another aspect, the invention relates to a compound of Formula VIIb

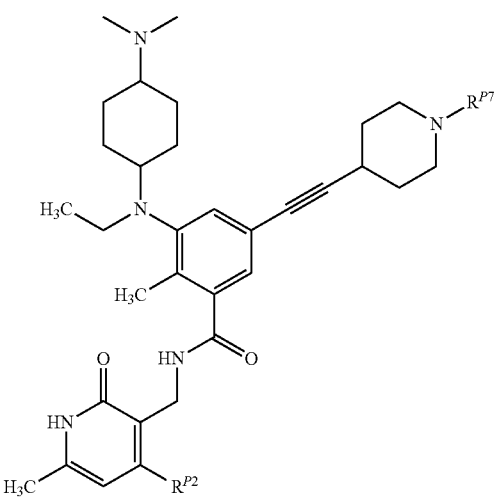

(VIIb)

or a pharmaceutically acceptable salt or solvate thereof; wherein $R^{P2}$ is $CH_3$ or $OCH_3$, and $R^{P7}$ is $C(O)C_{1-4}$ alkyl or $C_{1-4}$ haloalkyl.

In certain compounds of Formula VIIb, $R^{P7}$ is $C(O)CH_3$.

In certain compounds of Formula VIIb, $R^{P7}$ is $CH_2CF_3$.

The present invention provides the compounds of Formula (I'):

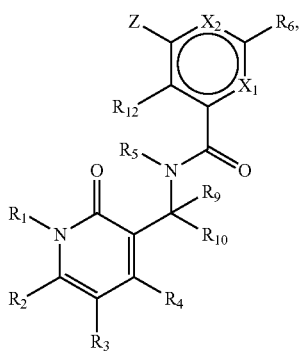

(I')

or a pharmaceutically acceptable salt thereof. In this formula, $X_1$ is N or $CR_{11}$;

$X_2$ is N or $CR_{13}$;

Z is $NR_7R_8$, $OR_7$, $S(O)_nR_7$, or $CR_7R_8R_{14}$, in which n is 0, 1, or 2;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$, is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl optionally substituted with OH, O—$C_1$-$C_6$ alkyl, or NH—$C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_kC(O)$, $NR_k$, $S(O)_2$, $NR_kS(O)_2$, or $C_1$-$C_3$ alkyl linker, $R_k$ being H or $C_1$-$C_6$ alkyl, and $T_5$ is H, halo, $C_1$-$C_6$ alkyl, $C_2$-$C_6$ alkenyl, $C_2$-$C_6$ alkynyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, $R_{11}$, $R_{12}$, and $R_{13}$, independently, is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, or $R_7$ and $R_8$, together with the C atom to which they are attached, form $C_3$-$C_8$ cycloalkyl or a 4 to 11-membered heterocycloalkyl ring having 1 to 3 heteroatoms, and each of the 4 to 11-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

One subset of the compounds of Formula (I') includes those of Formula (Ia):

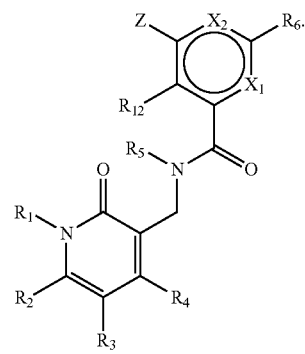

(Ia)

Another subset of the compounds of Formula (I') includes those of Formula (Ib), (Ic), or (Id):

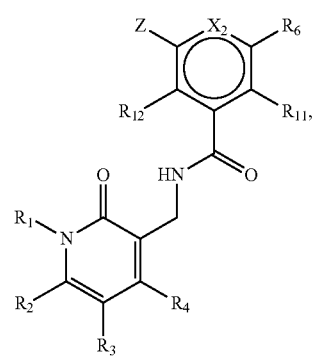

(Ib)

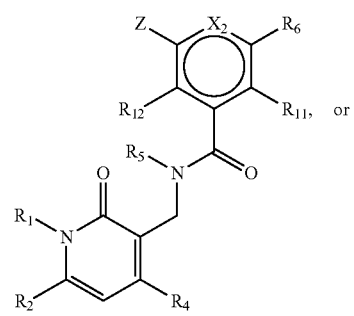

(Ic)

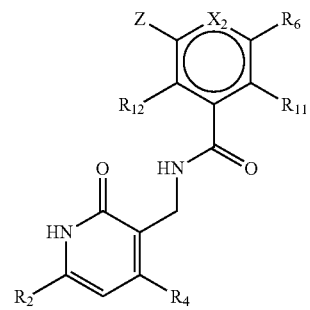

(Id)

The compounds of Formula (I'), (Ia), (Ib), (Ic), and (Id) can include one or more of the following features when applicable:

For example, $X_1$ is $CR_{11}$ and $X_2$ is $CR_{13}$.
For example, $X_1$ is $CR_{11}$ and $X_2$ is N.
For example, $X_1$ is N and $X_2$ is $CR_{13}$.
For example, $X_1$ is N and $X_2$ is N.

For example, Z is $NR_7R_8$.

For example, Z is $CR_7R_8R_{14}$.

For example, Z is $OR_7$.

For example, Z is $S(O)_nR_7$, in which n is 0, 1, or 2.

For example, Z is $SR_7$.

For example, $R_6$ is unsubstituted $C_6$-$C_{10}$ aryl or unsubstituted 5- or 6-membered heteroaryl.

For example, $R_6$ is $C_6$-$C_{10}$ aryl substituted with one or more -$Q_2$-$T_2$ or 5- or 6-membered heteroaryl substituted with one or more -$Q_2$-$T_2$.

For example, $R_6$ is unsubstituted phenyl.

For example, $R_6$ is phenyl substituted with one or more -$Q_2$-$T_2$.

For example, $R_6$ is 5 to 6-membered heteroaryl containing 1-3 additional heteroatoms selected from N, O, and S and optionally substituted with one or more -$Q_2$-$T_2$.

For example, $R_6$ is pyridinyl, pyrazolyl, pyrimidinyl, quinolinyl, tetrazolyl, oxazolyl, isoxazolyl, thiazolyl, isothiazolyl, furyl, or thienyl, each of which is optionally substituted with one or more -$Q_2$-$T_2$.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like) optionally substituted with one or more -$Q_3$-$T_3$.

For example, $T_2$ is —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, or —$S(O)_2NR_aR_b$.

For example, $T_2$ is —$NR_aR_b$ or —$C(O)NR_aR_b$, in which each of $R_a$ and $R_b$, independently is H or $C_1$-$C_6$ alkyl, or $R_a$ and $R_b$, together with the N atom to which they are attached, form a 4 to 7-membered heterocycloalkyl ring having 0 or 1 additional heteroatom, the $C_1$-$C_6$ alkyl and the 4 to 7-membered heterocycloalkyl ring being optionally substituted with one or more -$Q_3$-$T_3$.

For example, $Q_2$ is $C_1$-$C_3$ alkyl linker optionally substituted with halo or hydroxyl.

For example, $Q_2$ is a bond or methyl linker and $T_2$ is H, halo, —$OR_a$, —$NR_aR_b$, —$(NR_aR_bR_c)^+A^-$, or —$S(O)_2NR_aR_b$.

For example, each of $R_a$, $R_b$, and $R_c$, independently is H or $C_1$-$C_6$ alkyl optionally substituted with one or more -$Q_3$-$T_3$, For example, one of $R_a$, $R_b$, and $R_c$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like) and the ring is optionally substituted with one or more -$Q_3$-$T_3$.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_d$, $COOR_d$, —$S(O)_2R_d$, or —$NR_dR_e$.

For example, one of $R_d$ and $R_e$ is H.

For example, $R_6$ is phenyl or 5- or 6-membered heteroaryl substituted with O—$C_{1-6}$ alkyl or NH—$C_{1-6}$ alkyl, each of which is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl.

For example, $R_6$ is

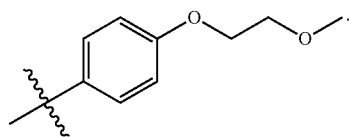 [SMILES: *c1ccc(OCCOC)cc1]

For example, $R_7$ is not H.

For example, $R_7$ is —$C(O)R_f$.

For example, $R_7$ is —$C(O)R_f$, in which $R_f$ is $C_3$-$C_8$ cycloalkyl.

For example, $R_7$ is $C_6$-$C_{10}$ aryl substituted with one or more -$Q_5$-$T_5$.

For example, $R_7$ is phenyl optionally substituted with one or more -$Q_5$-$T_5$.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like) optionally substituted with one or more -$Q_5$-$T_5$.

For example, $R_7$ is 5 to 6-membered heterocycloalkyl optionally substituted with one or more -$Q_5$-$T_5$.

For example, $R_7$ is isopropyl.

For example, $R_7$ is pyrrolidinyl, piperidinyl, tetrahydropyran, cyclopentyl, cyclohexyl, or cycloheptyl, each optionally substituted with one -$Q_5$-$T_5$.

For example, $R_7$ is cyclopentyl or cyclohexyl, each optionally substituted with one -$Q_5$-$T_5$.

For example, $R_7$ is pyrrolidinyl, piperidinyl, tetrahydropyran, tetrahydro-2H-thiopyranyl, cyclopentyl, cyclohexyl, or cycloheptyl, each optionally substituted with one or more -$Q_5$-$T_5$.

For example, $R_7$ is cyclopentyl, cyclohexyl or tetrahydro-2H-thiopyranyl, each optionally substituted with one or more -$Q_5$-$T_5$.

For example, R₇ is tetrahydropyran or

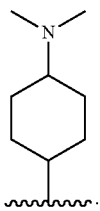 [SMILES: *C1CCC(N(C)C)CC1]

For example, R₇ is

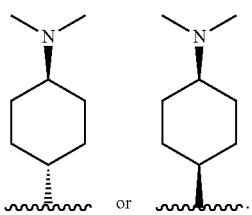 or

For example, R₇ is

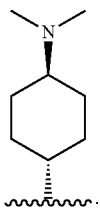

For example, R₇ is

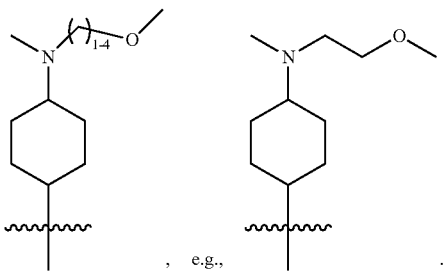, e.g.,

For example, R₇ is

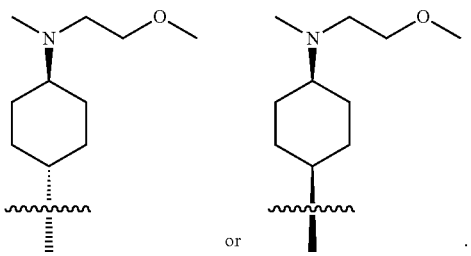 or

For example, R₇ is

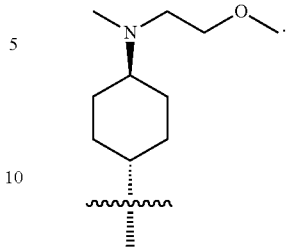

For example, one or more -Q₅-T₅ are oxo.
For example, R₇ is 1-oxide-tetrahydro-2H-thiopyranyl or 1,1-dioxide-tetrahydro-2H-thiopyranyl.
For example, Q₅ is a bond and T₅ is amino, mono-$C_1$-$C_6$ alkylamino, or di-$C_1$-$C_6$ alkylamino.
For example, Q₅ is NHC(O) and T₅ is $C_1$-$C_6$ alkyl or $C_1$-$C_6$ alkoxy.
For example, -Q₅-T₅ is oxo.
For example, T₄ is 4 to 7-membered heterocycloalkyl or $C_3$-$C_8$ cycloalkyl and one or more -Q₅-T₅ are oxo.
For example, T₅ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.
For example, Q₅ is a bond and T₅ is $C_1$-$C_6$ alkyl, $C_3$-$C_8$ cycloalkyl, or 4 to 7-membered heterocycloalkyl.
For example, Q₅ is CO, S(O)₂, or NHC(O); and T₅ is $C_1$-$C_6$ alkyl, $C_1$-$C_6$ alkoxyl, $C_3$-$C_8$ cycloalkyl, or 4 to 7-membered heterocycloalkyl.
For example, T₅ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.
For example, Q₅ is $C_1$-$C_3$ alkyl linker and T₅ is H or $C_6$-$C_{10}$ aryl.
For example, Q₅ is $C_1$-$C_3$ alkyl linker and T₅ is $C_3$-$C_8$ cycloalkyl, 4 to 7-membered heterocycloalkyl, or S(O)$_q$R$_q$.
For example, R₁₁ is H.
For example, each of R₂ and R₄, independently, is H or $C_1$-$C_6$ alkyl optionally substituted with amino, mono-$C_1$-$C_6$ alkylamino, di-$C_1$-$C_6$ allylamino, or $C_6$-$C_{10}$ aryl.
For example, each of R₂ and R₄, independently is $C_1$-$C_3$ alkyl optionally substituted with $C_1$-$C_6$ alkoxyl.
For example, each of R₂ and R₄ is methyl.
For example, R₁ is H.
For example, R₁₂ is H, methyl, ethyl, ethenyl, or halo.
For example, R₁₂ is methyl.
For example, R₁₂ is ethyl.
For example, R₁₂ is ethenyl.
For example, R₈ is H, methyl, ethyl, or ethenyl.
For example, R₈ is methyl.
For example, R₈ is ethyl.
For example, R₈ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like).
For example, R₈ is tetrahydropyran.
For example, R₈ is tetrahydropyran and R₇ is -Q₄-T₄, in which Q₄ is a bond or $C_1$-$C_4$ alkyl linker and T₄ is H, $C_1$-$C_6$ alkyl, $C_3$-$C_8$ cycloalkyl or 4 to 7-membered heterocycloalkyl.

For example, neither $R_7$ nor $R_8$ is tetrahydropyran.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, 1,4-dioxa-8-azaspiro[4.5]decanyl, and the like) or $C_3$-$C_8$ cycloalkyl, each optionally substituted with one or more $-Q_6$-$T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one $-Q_6$-$T_6$.

For example, $-Q_6$-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_6$ is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_{13}$ is H or methyl.

For example, $R_{13}$ is H.

For example, $R_3$ is H.

For example, $A^-$ is $Br^-$ or $Cl^-$.

For example, each of $R_5$, $R_9$, and $R_{10}$ is H.

Still another subset of the compounds of formula (I') includes those of Formula (Ie), or (Ig):

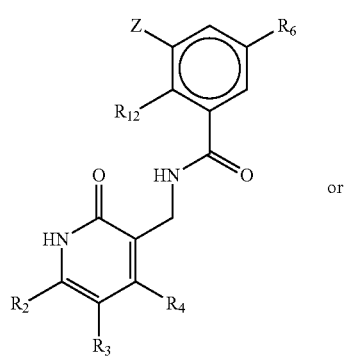

(Ie)

or

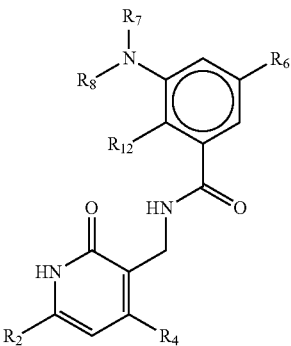

(Ig)

or a pharmaceutically acceptable salts thereof, wherein Z, $X_2$, $R_2$, $R_3$, $R_4$, $R_6$, and $R_{12}$ are defined herein.

For example, $R_2$, $R_4$ and $R_{12}$ are each, independently $C_{1-6}$ alkyl.

For example, $R_6$ is $C_6$-$C_{10}$ aryl or 5- or 6-membered heteroaryl, each of which is optionally, independently substituted with one or more $-Q_2$-$T_2$, wherein $-Q_2$ is a bond or $C_1$-$C_3$ alkyl linker, and $T_2$ is H, halo, cyano, $-OR_a$, $-NR_aR_b$, $-(NR_aR_bR_c)^+A^-$, $-C(O)NR_aR_b$, $-NR_bC(O)R_a$, $-S(O)_2R_a$, or $R_{S2}$, in which each of $R_a$ and $R_b$, independently is H or $R_{S3}$, each of $R_{S2}$ and $R_{S3}$, independently, is $C_1$-$C_6$ alkyl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally, independently substituted with one or more $-Q_3$-$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, $OR_d$, $-S(O)_2R_d$, and $-NR_dR_e$, each of $R_d$ and $R_e$ independently being H or $C_1$-$C_6$ alkyl, or $-Q_3$-$T_3$ is oxo; or any two neighboring $-Q_2$-$T_2$, together with the atoms to which they are attached form a 5- or 6-membered ring optionally containing 1-4 heteroatoms selected from N, O and S.

Another subset of the compounds of Formula (I') includes those of Formula (II'):

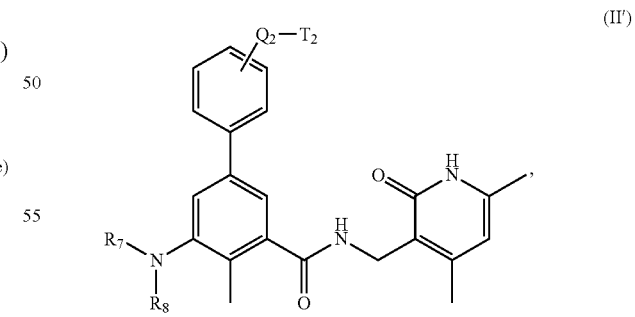

(II')

or pharmaceutically acceptable salts thereof,
wherein
$Q_2$ is a bond or methyl linker;
$T_2$ is H, halo, $-OR_a$, $-NR_aR_b$, $-(NR_aR_bR_c)^+A^-$, or $-S(O)_2NR_aR_b$;
$R_7$ is piperidinyl, tetrahydropyran, cyclopentyl, or cyclohexyl, each optionally substituted with one $-Q_5$-$T_5$;

$R_8$ is ethyl and
$R_a$, $R_b$, and $R_c$ are defined herein.
For example, $Q_2$ is a bond
For example, $Q_2$ is a methyl linker
For example, $T_2$ is $-NR_aR_b$ or $-(NR_aR_bR_c)^+A^-$.
Yet another subset of the compounds of Formula (I') includes those of Formula (IIa):

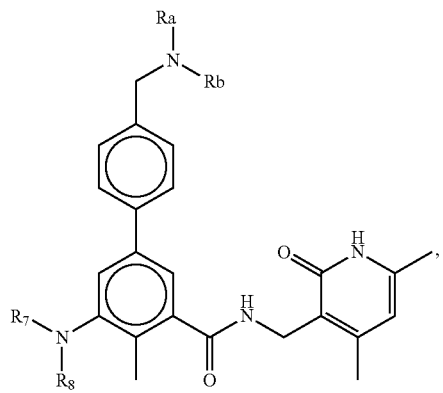

(IIa)

or pharmaceutically acceptable salts thereof, wherein $R_7$, $R_8$, $R_a$, $R_b$, and $R_c$ are defined herein.

The compounds of Formula (II') or (IIa) can include one or more of the following features when applicable:

For example, each of $R_a$ and $R_b$, independently is H or $C_1$-$C_6$ alkyl optionally substituted with one or more $-Q_3$-$T_3$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more $-Q_3$-$T_3$.

For example, $R_a$ and $R_b$, together with the N atom to which they are attached, form azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl, and the ring is optionally substituted with one or more $-Q_3$-$T_3$.

For example, one or more $-Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_d$, $COOR_d$, $-S(O)_2R_d$, or $-NR_dR_e$.

For example, one of $R_d$ and $R_e$ is H.

For example, $R_7$ is $C_3$-$C_8$ cycloalkyl or 4 to 7-membered heterocycloalkyl, each optionally substituted with one or more $-Q_5$-$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more $-Q_5$-$T_5$.

For example, $R_7$ is cyclopentyl cyclohexyl or tetrahydro-2H-thiopyranyl, each optionally substituted with one or more $-Q_5$-$T_5$.

For example, $Q_5$ is NHC(O) and $T_5$ is $C_1$-$C_6$ alkyl or $C_1$-$C_6$ alkoxy.

For example, one or more $-Q_5$-$T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1$-$C_6$ alkylamino, di-$C_1$-$C_6$ alkylamino.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $R_8$ is H or $C_1$-$C_6$ alkyl which is optionally substituted with one or more substituents selected from the group consisting of halo, hydroxyl, COOH, $C(O)O-C_1$-$C_6$ alkyl, cyano, $C_1$-$C_6$ alkoxyl, amino, mono-$C_1$-$C_6$ alkylamino, and di-$C_1$-$C_6$ alkylamino.

For example, $R_8$ is H, methyl, or ethyl.

Still another subset of compounds of Formula (I') includes those of Formula (III'):

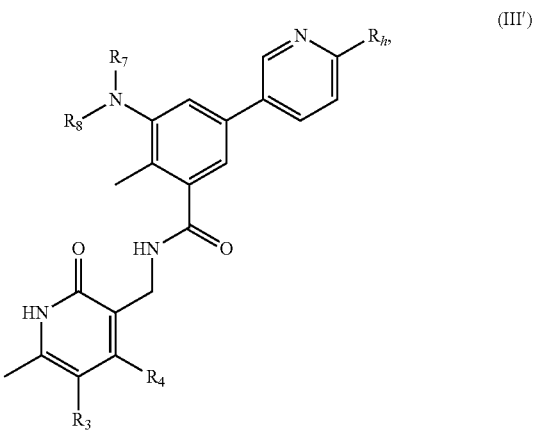

(III')

or pharmaceutically acceptable salts thereof, wherein
$R_3$ is hydrogen, $C_1$-$C_3$ alkyl or halo;
$R_4$ is $C_1$-$C_3$ alkyl,
$R_7$ is $C_1$-$C_6$ alkyl, $C_3$-$C_8$ cycloalkyl or 4 to 7-membered heterocycloalkyl, optionally substituted with one or more $R_s$;
$R_8$ is $C_1$-$C_6$ alkyl;
$R_h$ is $-Q_h$-$T_h$, wherein $Q_h$ is a bond, a $C_1$-$C_3$ alkyl linker or $N(R_N)$; $T_h$ is $OR_{h1}$ or $-NR_{h1}R_{h2}$, in which $R_{h1}$ and $R_{h2}$ are independently hydrogen or $C_1$-$C_6$ alkyl, or one of $R_{h1}$ and $R_{h2}$ is methyl and the other is a 6-membered N-containing heterocycloalkyl optionally substituted with one or two methyl, or together with the N atom to which they are attached, $R_{h1}$ and $R_{h2}$ form a 4 to 7-membered heterocycloalkyl ring having 0 or 1 additional heteroatoms selected from oxygen and nitrogen, wherein said heterocycloalkyl ring is optionally substituted with one or more $R_j$;
$R_i$ is $C_1$-$C_3$ alkyl, $-NR_{N1}R_{N2}$ or a $C_3$-$C_8$ cycloalkyl or 5 or 6 membered heterocycle each of which cycloalkyl or heterocycle is independently optionally substituted with $R_j$;
$R_N$ is hydrogen, $C_1$-$C_6$ alkyl or $C_3$-$C_8$ cycloalkyl;
$R_j$ is $C_1$-$C_3$ alkyl, $-NR_{N1}R_{N2}$, $-NC(O)R_N$;
$R_{N1}$ and $R_{N2}$ are each independently hydrogen, $C_1$-$C_6$ alkyl, $C_3$-$C_8$ cycloalkyl, 5 or 6 membered heterocycle, each of which cycloalkyl or heterocycle is independently optionally substituted with $R_j$.

For example, $R_3$ is hydrogen.

For example, $R_3$ is halogen, such as, for example, fluoro or chloro. For example, $R_3$ is fluoro.

For example $R_4$ is methyl, ethyl, propyl, or isopropyl. For example, $R_4$ is methyl. For example, $R_4$ is isopropyl.

For example, R_7 is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like).

For example, $R_7$ is a 5 or 6 membered cycloalkyl or heterocycloalkyl.

For example, $R_7$ is a 6 membered cycloalkyl or heterocycloalkyl.

In some embodiments, $R_7$ is piperidinyl, tetrahydropyranyl, cyclopentyl, or cyclohexyl.

In some embodiments, $R_j$ is methyl. In some embodiments, $R_j$ is $NH_2$.

For example, $R_8$ is $C_1$, $C_2$ or $C_3$ alkyl. For example, $R_8$ is methyl. For example, $R_8$ is ethyl.

In some embodiments, $Q_h$ is a bond. In others, $Q_h$ is methylene.

In some embodiments, $T_h$ is $N(CH_3)_2$.

In some embodiments, one of $R_{h1}$ and $R_{h2}$ is methyl and the other is a 6-membered N-containing heterocycloalkyl optionally substituted with one or two methyl. For example, the 6-membered N-containing heterocycloalkyl does not contain further heteroatoms in the ring. For example, the 6-membered N-containing heterocycloalkyl is not further substituted besides the one or two methyl groups.

In some embodiments, $R_{h1}$ and $R_{h2}$, together with the N to which they are attached form a 6 membered ring. For example, $T_h$ is selected from piperidine, morpholine, piperazine, and N-methyl piperazine.

For example, $T_h$ is morpholine.

In some embodiments, $R_i$ is methyl or $N(CH_3)_2$. In some embodiments, $R_i$ is $C_3$-$C_8$ cycloalkyl or 5 or 6 membered heterocycle. For example, $R_i$ is a 6 membered cycloalkyl or heterocycle, substituted with zero or one $R_j$.

In some embodiments, $R_N$ is H or methyl.

In certain compounds of Formula III', $R_3$ is hydrogen, $R_4$ is $CH_3$ and $Q_h$ is methylene.

In certain compounds of formula III', $R_3$ is fluoro, $R_4$ is isopropyl and $Q_h$ is a bond.

In certain compounds of formula III', $R_3$ is hydrogen, $R_4$ is propyl or isopropyl and $Q_h$ is methylene.

In certain compounds of formula III', $R_3$ is hydrogen, $R_4$ is propyl or isopropyl and $Q_h$ is a bond.

In certain compounds of formula III', compounds are of Formula (IIIe),

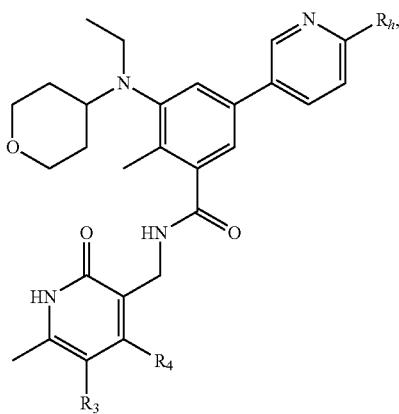

(IIIe)

wherein
$R_3$ is H or F
$R_4$ is methyl, i-propyl, or n-propyl,
$R_h$ is

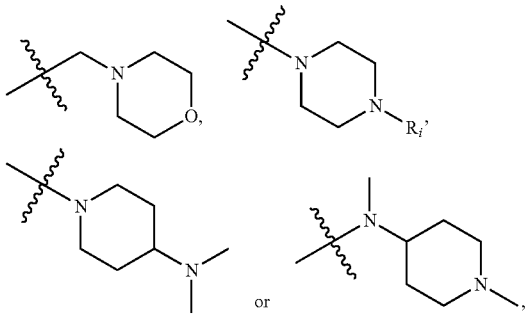

in which $R_i$ is H, methyl, or

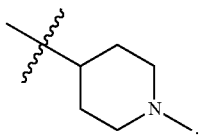 [SMILES: *C1CCN(C)CC1]

Compounds of the invention include those of Formula I", and pharmaceutically acceptable salts or solvates thereof:

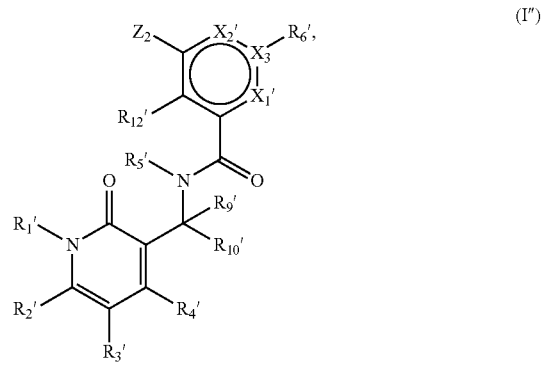

(I")

In this formula,
$X_1'$ is N or $CR_{11}'$;
$X_2'$ is N or $CR_{13}'$;
$X_3$ is N or C, and when $X_3$ is N, $R_6'$ is absent;
$Z_2$ is $NR_7'R_8'$, $OR_7'$, $S(O)_{a'}R_7'$, or $CR_7'R_8'R_{14}'$, in which a' is 0, 1, or 2;
each of $R_1'$, $R_5'$, $R_9'$, and $R_{10}'$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;
each of $R_2'$, $R_3'$, and $R_4'$, independently, is -$Q_1'$-$T_1'$, in which $Q_1'$ is a bond or $C_1$-$C_3$ alkyl linker optionally substituted with halo, cyano, hydroxyl or $C_1$-$C_6$ alkoxy, and $T_1'$ is H, halo, hydroxyl, COOH, cyano, azido, or $R_{S1}'$, in which $R_{S1}'$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-C1-$C_6$ alkylamino, di-$C_1$-$C_6$ alkylamino, 4 to 12-membered heterocycloalkyl, or 5- or 6-membered heteroaryl, and $R_{S1}'$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6'$ is H, halo, cyano, azido, $OR_a'$, —$NR_a'R_b'$, —$C(O)R_a'$, —$C(O)OR_a'$, —$C(O)NR_a'R_b'$, —$NR_b'C(O)R_a'$, —$S(O)_b R_a'$, —$S(O)_b NR_a'R_b'$, or $R_{S2}'$, in which $R_{S2}'$ is $C_1$-$C_6$ alkyl, $C_2$-$C_6$ alkenyl, $C_2$-$C_6$ alkynyl, $C_3$-$C_8$ cycloalkyl, or 4 to 12-membered heterocycloalkyl, b' is 0, 1, or 2, each of $R_a'$ and $R_b'$, independently is H or $R_{S3}'$, and $R_{S3}'$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a'$ and $R_b'$, together with the N atom to which they are attached, form a 4 to 12-membered heterocycloalkyl ring having 0 or 1 additional heteroatom; and each of $R_{S2}'$, $R_{S3}'$, and the 4 to 12-membered heterocycloalkyl ring formed by $R_a'$ and $R_b'$, is optionally substituted with one or more -$Q_2'$-$T_2'$, wherein $Q_2'$ is a bond or $C_1$-$C_3$ alkyl linker each optionally substituted with halo, cyano, hydroxyl or $C_1$-$C_6$ alkoxy, and $T_2'$ is H, halo, cyano, —$OR_c'$, —$NR_c'R_d'$, —$C(O)R_c'$, —$C(O)OR_c'$, —$C(O)NR_c'R_d'$, —$NR_d'C(O)R_c'$, —$NR_d'C(O)OR_c'$, —$S(O)_2 R_c'$, —$S(O)_2 NR_c'R_d'$, or $R_{S4}'$, in which each of $R_c'$ and $R_d'$, independently is H or $R_{S5}'$, each of $R_{S4}'$ and $R_{S5}'$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c'$ and $R_d'$, together with the N atom to which they are attached, form a 4 to 12-membered heterocycloalkyl ring having 0 or 1 additional heteroatom, and each of $R_{S4}'$, $R_{S5}'$, and the 4 to 12-membered heterocycloalkyl ring formed by $R_c'$ and $R_d'$, is optionally substituted with one or more -$Q_3'$-$T_3'$, wherein $Q_3'$ is a bond or $C_1$-$C_3$ alkyl linker each optionally substituted with halo, cyano, hydroxyl or $C_1$-$C_6$ alkoxy, and $T_3'$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e'$, $COOR_e'$, —$S(O)_2 R_e'$, —$NR_e'R_f'$, and —$C(O)NR_e'R_f'$, each of $R_e'$ and $R_f'$ independently being H or $C_1$-$C_6$ alkyl, or -$Q_3'$-$T_3'$ is oxo; or -$Q_2'$-$T_2'$ is oxo; provided that -$Q_2'$-$T_2'$ is not H;

$R_7'$ is -$Q_4'$-$T_4'$, in which $Q_4'$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4'$ is H, halo, cyano, $NR_g'R_h'$, —$C(O)R_g'$, —$C(O)OR_g'$, —$C(O)NR_g'R_h'$, —$C(O)NR_g'OR_h'$, —$NR_g'C(O)R_h'$, —$S(O)_2 R_g'$, or $R_{S6}'$, in which each of $R_g'$ and $R_h'$, independently is H or $R_{S7}'$, each of $R_{S6}'$ and $R_{S7}'$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S6}'$ and $R_{S7}'$ is optionally substituted with one or more -$Q_5'$-$T_5'$, wherein $Q_5'$ is a bond, C(O), C(O)$NR_k'$, $NR_k'C(O)$, $NR_k'$, $S(O)_2$, $NR_k'S(O)_2$, or $C_1$-$C_3$ alkyl linker, $R_k'$ being H or $C_1$-$C_6$ alkyl, and $T_5'$ is H, halo, $C_1$-$C_6$ alkyl, $C_2$-$C_6$ alkenyl, $C_2$-$C_6$ alkynyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_{q'} R_{q'}'$ in which q' is 0, 1, or 2 and $R_{q'}'$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5'$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5'$-$T_5'$ is oxo; provided that $R_7'$ is not H;

each of $R_8'$, $R_{11}'$, $R_{12}'$, and $R_{13}'$, independently, is H, halo, hydroxyl, COOH, cyano, $R_{S8}'$, $OR_{S8}'$, or $COOR_{S8}'$, in which $R_{S8}'$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}'$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7'$ and $R_8'$, together with the N atom to which they are attached, form a 4 to 12-membered heterocycloalkyl ring having 0 to 2 additional heteroatoms, or $R_7'$ and $R_8'$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7'$ and $R_8'$ is optionally substituted with one or more -$Q_6'$-$T_6'$, wherein $Q_6'$ is a bond, C(O), C(O)$NR_m'$, $NR_m'C(O)$, $S(O)_2$, or $C_1$-$C_3$ alkyl linker, $R_m'$ being H or $C_1$-$C_6$ alkyl, and $T_6'$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_p R_p'$ in which p' is 0, 1, or 2 and $R_p'$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6'$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6'$ is H, halo, hydroxyl, or cyano; or -$Q_6'$-$T_6'$ is oxo; and $R_{14}'$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

provided that the compound is not

N-(5-(((4,6-dimethyl-2-oxo-1,2-dihydropyridin-3-yl)methyl)carbamoyl)-2-methylphenyl)furan-2-carboxamide, N,N'-(5-(((4,6-dimethyl-2-oxo-1,2-dihydropyridin-3-yl)methyl)carbamoyl)-1,3-phenylene)diacetamide, N-((4,6-dimethyl-2-oxo-1,2-dihydropyridin-3-yl)methyl)-3-pivalamidobenzamide, 3-(3,4-dihydro-2H-benzo[b][1,4]dioxepine-7-sulfonamido)-N-((4,6-dimethyl-2-oxo-1,2-dihydropyridin-3-yl)methyl)benzamide, N-((4,6-dimethyl-2-oxo-1,2-dihydropyridin-3-yl)methyl)-3,5-dimethoxybenzamide, N-((4,6-dimethyl-2-oxo-1,2-dihydropyridin-3-yl)methyl)-3,4,5-trimethoxybenzamide, 3-allyl-N-((4,6-dimethyl-2-oxo-1,2-dihydropyridin-3-yl)methyl)-4,5-dimethoxybenzamide, 4-(2-amino-2-oxoethoxy)-3-chloro-N-((4,6-dimethyl-2-oxo-1,2-dihydropyridin-3-yl)methyl)-5-methoxybenzamide, 3-chloro-N-((4,6-dimethyl-2-oxo-1,2-dihydropyridin-3-yl)methyl)-4-hydroxy-5-methoxybenzamide, or 3-bromo-N-((4,6-dimethyl-2-oxo-1,2-dihydropyridin-3-yl)methyl)-5-methoxy-4-propoxybenzamide.

One subset of the compounds of Formula (I″) includes those of Formula (I″a):

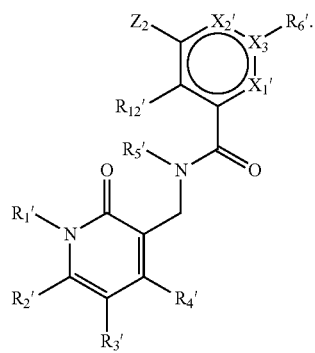

Another subset of the compounds of Formula (I″) includes those of Formula (I″b), (I″c), or (I″d):

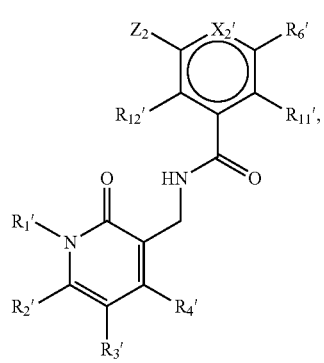

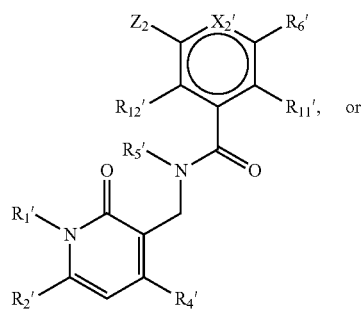

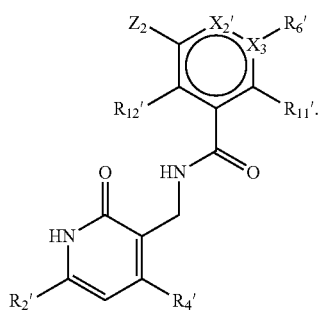

Yet another subset of the compounds of Formula (I″) includes those of Formula (IIA):

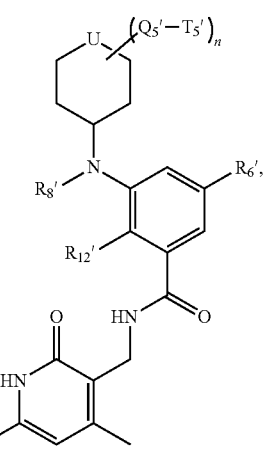

or pharmaceutically acceptable salts thereof, wherein n is 0, 1, or 2; U is O, S, N-$Q_5'$-$T_5'$, or CH-$Q_5'$-$T_5'$; $R_{12}'$ is Cl, Br, or methyl; and $R_6'$, $R_8'$, $Q_5'$, and $T_5'$ are defined herein.

Still another subset of the compounds of Formula (I″) includes those of Formula (IIB):

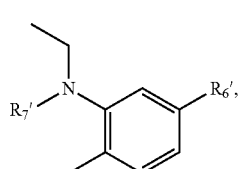

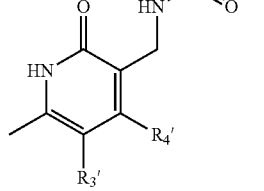

or pharmaceutically acceptable salts thereof, wherein $R_7'$ is a 4 or 6-membered heterocycloalkyl having one nitrogen atom in the ring and is substituted with one or two methyl groups or one i-propyl group; $R_3'$ is H or F; $R_4'$ is methyl, ethyl, n-propyl, isopropyl, or $CF_3$, and $R_6'$ is $CF_3$, Cl, or F, provided that when $R_4'$ is methyl, (1) $R_6'$ is $CF_3$, or (2) $R_3'$ is F, or (3) $R_6'$ is $CF_3$ and $R_3'$ is F, or (4) $R_6'$ is F or Cl and $R_7'$ is a 6-membered heterocycloalkyl having only one nitrogen and is substituted with two methyl groups.

The compounds of Formulae (I"), (I"a), (I"b), (I"c), (IIA) and (IIB) can include one or more of the following features when applicable:

For example, $X_1'$ is $CR_{11}'$ and $X_2'$ is $CR_{13}'$.

For example, $X_1'$ is $CR_{11}'$ and $X_2'$ is N.

For example, $X_1'$ is N and $X_2'$ is $CR_{13}'$.

For example, $X_1'$ is N and $X_2'$ is N.

For example, $X_3$ is C.

For example, $X_3$ is N and $R_6'$ is absent.

For example, $Z_2$ is $NR_7'R_8'$.

For example, $Z_2$ is $CR_7'R_8'R_{14}'$.

For example, $Z_2$ is $OR_7'$.

For example, $Z_2$ is $S(O)_{a'}R_7'$, in which a' is 0, 1, or 2.

For example, $R_6'$ is H.

For example, $R_6'$ is halo (e.g., fluorine, chlorine, bromine, and iodine).

For example, $R_6'$ is not fluorine.

For example, $R_6'$ is $C_1$-$C_3$ alkyl optionally substituted with one or more $-Q_2'$-$T_2'$ For example, $R_6'$ is $CF_3$.

For example, $R_6'$ is $C_2$-$C_6$ alkenyl, $C_2$-$C_6$ alkynyl, or $C_3$-$C_6$ cycloalkyl each optionally substituted with one or more $-Q_2'$-$T_2'$.

For example, $R_6'$ is ethenyl.

For example, $R_6'$ is ethynyl.

For example, $R_6'$ is ethynyl substituted with one or more $-Q_2'$-$T_2'$, in which $-Q_2'$ is a bond or $C_1$-$C_3$ alkyl linker and $T_2'$ is $C_1$-$C_6$ alkyl, $C_3$-$C_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more $-Q_3'$-$T_3'$.

For example, $R_6'$ is cyano.

For example, $R_6'$ is azido.

For example, $R_6'$ is C(O)H.

For example, $R_6'$ is $OR_a'$ or $—C(O)R_a'$.

For example, $R_a'$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like), which is optionally substituted with one or more $-Q_2'$-$T_2'$.

For example, $R_6'$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more $-Q_2'$-$T_2'$.

For example, $R_6'$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more $-Q_2'$-$T_2'$ For example, $R_6'$ is 4 to 7-membered heterocycloalkyl optionally substituted with one or more $-Q_2'$-$T_2'$, and $-Q_2'$-$T_2'$ is oxo or $-Q_2'$ is a bond and $T_2'$ is $—OR_c'$, $—NR_c'R_d'$, $—C(O)R_c'$, $—C(O)OR_c'$, $—S(O)_2R_c'$, $C_1$-$C_6$ alkyl, or 4 to 7-membered heterocycloalkyl, each of which is optionally substituted with one or more $-Q_3'$-$T_3'$ when $R_c'$ or $R_d'$ is not H.

For example, $R_6'$ is $—NR_a'R_b'$, $—C(O)R_a'$, $—C(O)OR_a'$, $—C(O)NR_a'R_b'$, $—NR_b'C(O)R_a'$, $—SR_a'$, $—S(O)_2R_a'$, or $—S(O)_2NR_a'R_b'$.

For example, each of $R_a'$ and $R_b'$, independently is H, $C_1$-$C_6$ alkyl, or $C_3$-$C_8$ cycloalkyl optionally substituted with one or more $-Q_2'$-$T_2'$.

For example, one of $R_a'$ and $R_b'$ is H.

For example, $R_a'$ and $R_b'$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) and the ring is optionally substituted with one or more $-Q_2'$-$T_2'$.

For example, $-Q_2'$-$T_2'$ is oxo.

For example, $Q_2'$ is a bond.

For example, $Q_2'$ is an unsubstituted $C_1$-$C_3$ alkyl linker.

For example, $T_2'$ is $C_1$-$C_6$ alkyl or $C_6$-$C_{10}$ aryl, each optionally substituted with one or more $-Q_3'$-$T_3'$.

For example, $T_2'$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2'$ is halo (e.g., fluorine, chlorine, bromine, and iodine).

For example, $T_2'$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more $-Q_3'$-$T_3'$.

For example, $T_2'$ is $—OR_c'$, $—NR_c'R_d'$, $—C(O)R_c'$, $—C(O)OR_c'$, or $—S(O)_2R_c'$.

For example, $R_c'$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like), which is optionally substituted with one or more $-Q_3'$-$T_3'$.

For example, each of $R_c'$ and $R_d'$, independently is H or $C_1$-$C_6$ alkyl optionally substituted with one or more $-Q_3'$-$T_3'$.

For example, $R_c'$ is H.

For example, $R_d'$ is H.

For example, $R_c'$ and $R_d'$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) and the ring is optionally substituted with one or more -$Q_3'$-$T_3'$.

For example, $Q_2'$ is a bond and $T_2'$ is —$OR_c'$, —$NR_c'R_d'$, —$C(O)R_c'$, —$C(O)OR_c'$, —$S(O)_2R_c'$, $C_1$-$C_6$ alkyl, or 4 to 7-membered heterocycloalkyl, each of which is optionally substituted with one or more -$Q_3'$-$T_3'$ when $R_c'$ or $R_d'$ is not H.

For example, -$Q_3'$-$T_3'$ is oxo.

For example, $T_2'$ is 4 to 7-membered heterocycloalkyl or $C_3$-$C_8$ cycloalkyl and one or more -$Q_3'$-$T_3'$ are oxo.

For example, $Q_3$ is a bond or unsubstituted or substituted $C_1$-$C_3$ alkyl linker.

For example, $T_3'$ is H, halo, 4 to 7-membered heterocycloalkyl, $C_1$-$C_3$ alkyl, $OR_e'$, $COOR_e'$, —$S(O)_2R_e'$, —$NR_e'R_f'$, or —$C(O)NR_e'R_f'$.

For example, one of $R_d'$ and $R_e'$ is H.

For example, $Q_3'$ is a bond or $C_1$-$C_3$ alkyl linker and $T_3'$ is selected from the group consisting of $C_1$-$C_3$ alkyl, halo, $OR_e'$, —$S(O)_2R_e'$, —$NR_e'R_f'$, and —$C(O)NR_e'R_f'$.

For example, $Q_3'$ is a bond or $C_1$-$C_3$ alkyl linker and $T_3'$ is selected from the group consisting of $C_1$-$C_3$ alkyl, $OR_e'$, —$S(O)_2R_e'$, or —$NR_e'R_f'$.

For example, $R_e'$ is H.

For example, $R_f'$ is H.

For example, $R_7'$ is —$C(O)R_g'$.

For example, $R_7'$ is —$C(O)R_g'$, in which $R_g'$ is $C_3$-$C_8$ cycloalkyl, 4 to 7-membered heterocycloalkyl, $C_3$-$C_8$ cycloalkyl.

For example, $R_7'$ is $C_6$-$C_{10}$ aryl substituted with one or more -$Q_5'$-$T_5'$.

For example, $R_7'$ is phenyl optionally substituted with one or more -$Q_5'$-$T_5'$.

For example, $R_7'$ is $C_1$-$C_6$ alkyl optionally substituted with one or more -$Q_5'$-$T_5'$.

For example, $R_7'$ is $C_3$-$C_8$ cycloalkyl optionally substituted with one or more -$Q_5'$-$T_5'$.

For example, $R_7'$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_5'$-$T_5'$.

For example, $R_7'$ is 5 to 6-membered heterocycloalkyl optionally substituted with one or more -$Q_5'$-$T_5'$.

For example, $R_7'$ is isopropyl.

For example, $R_7'$ is pyrrolidinyl, piperidinyl, tetrahydropyran, cyclopentyl, or cyclohexyl, cycloheptyl, each optionally substituted with one -$Q_5'$-$T_5'$.

For example, $R_7'$ is cyclopentyl or cyclohexyl, each optionally substituted with one -$Q_5'$-$T_5'$.

For example, $R_7'$ is tetrahydropyran or

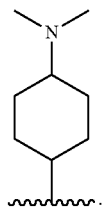 [SMILES: *C1CCC(N(C)C)CC1]

For example, $R_7'$ is

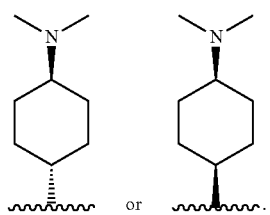

For example, $R_7'$ is

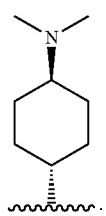

For example, $R_7'$ is

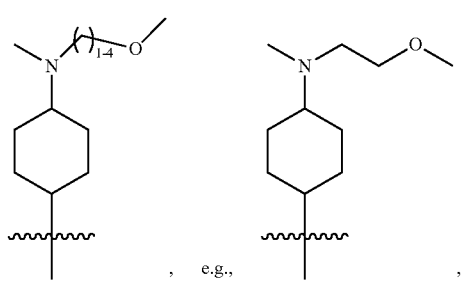

, e.g.,

For example, $R_7'$ is

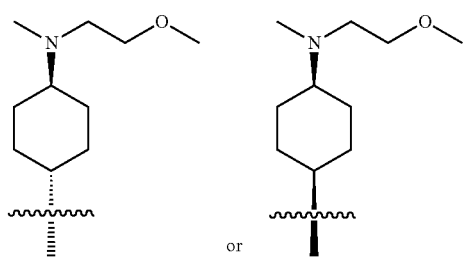

or

For example, R$_7$' is

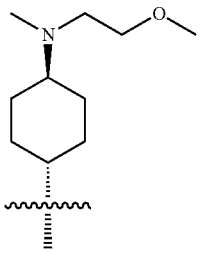

For example, Q$_5$' is NHC(O) and T$_5$' is C$_1$-C$_6$ alkyl or C$_1$-C$_6$ alkoxy.

For example, -Q$_5$'-T$_5$' is oxo.

For example, T$_4$' is 4 to 7-membered heterocycloalkyl, C$_3$-C$_8$ cycloalkyl, or C$_6$-C$_{10}$ aryl, and one or more -Q$_5$'-T$_5$' are oxo.

For example, R$_7$' is 1-oxide-tetrahydro-2H-thiopyranyl or 1,1-dioxide-tetrahydro-2H-thiopyranyl.

For example, R$_7$' is cyclohexanonyl, e.g., cyclohexanon-4-yl.

For example, T$_5$' is H, halo, C$_1$-C$_6$ alkyl, C$_1$-C$_6$ alkoxyl, C$_3$-C$_8$ cycloalkyl, C$_6$-C$_{10}$ aryl, or 4 to 7-membered heterocycloalkyl.

For example, Q$_5$' is a bond and T$_5$' is C$_1$-C$_6$ alkyl, C$_3$-C$_8$ cycloalkyl, or 4 to 7-membered heterocycloalkyl.

For example, Q$_5$' is a bond and T$_5$' is 5- or 6-membered heteroaryl, amino, mono-C$_1$-C$_6$ alkylamino, di-C$_1$-C$_6$ alkylamino, T$_5$' being optionally substituted with one or more substituents selected from the group consisting of halo, hydroxyl, C$_1$-C$_6$ alkoxyl, or C$_3$-C$_8$ cycloalkyl.

For example, Q$_5$' is CO, S(O)$_2$, or NHC(O); and T$_5$' is C$_1$-C$_6$ alkyl, C$_1$-C$_6$ alkoxyl, C$_3$-C$_8$ cycloalkyl, or 4 to 7-membered heterocycloalkyl.

For example, T$_5$' is C$_1$-C$_6$ alkyl or C$_1$-C$_6$ alkoxyl, each optionally substituted with halo, hydroxyl, cyano, C$_1$-C$_6$ alkoxyl, amino, mono-C$_1$-C$_6$ alkylamino, di-C$_1$-C$_6$ alkylamino, or C$_3$-C$_8$ cycloalkyl.

For example, Q$_5$' is C$_1$-C$_3$ alkyl linker and T$_5$' is H or C$_6$-C$_{10}$ aryl.

For example, Q$_5$' is C$_1$-C$_3$ alkyl linker and T$_5$' is C$_3$-C$_8$ cycloalkyl, 4 to 7-membered heterocycloalkyl, or S(O)$_q$R$_a$'.

For example, R$_6$' is halo (e.g., fluorine, chlorine, bromine, and iodine) and Z$_2$ is S(O)$_a$R$_7$', in which a' is 0, 1, or 2 and R$_7$' is C$_1$-C$_6$ alkyl (e.g., methyl, ethyl, n-propyl, i-propyl, butyl, or t-butyl), C$_3$-C$_8$ cycloalkyl (e.g., cyclopentyl, cyclohexyl, or cycloheptyl) or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) and R$_7$' is optionally substituted with one or more -Q$_5$'-T$_5$'.

For example, R$_6$' is halo (e.g., fluorine, chlorine, bromine, and iodine) and Z$_2$ is OR$_7$' in which R$_7$' is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxszepanyl, 2-oxa-5-azabicyclo[2.2.1]heptanyl, 2,5-diazabicyclo[2.2.1]heptanyl, and morpholinyl, and the like) and R$_7$' is optionally substituted with one or more -Q$_5$'-T$_5$'.

For example, R$_{11}$' is H.

For example, each of R$_2$' and R$_4$', independently, is H or C$_1$-C$_6$ alkyl optionally substituted with azido, halo, amino, mono-C$_1$-C$_6$ alkylamino, di-C$_1$-C$_6$ alkylamino, or C$_6$-C$_{10}$ aryl.

For example, each of R$_2$' and R$_4$', independently is C$_1$-C$_3$ alkyl optionally substituted with C$_1$-C$_6$ alkoxyl.

For example, each of R$_2$' and R$_4$' is methyl.

For example, R$_1$' is H.

For example, R$_1$' is C$_1$-C$_6$ alkyl optionally substituted with azido, halo, amino, mono-C$_1$-C$_6$ alkylamino, di-C$_1$-C$_6$ alkylamino, or C$_6$-C$_{10}$ aryl.

For example, R$_{12}$' is H, methyl, ethyl, ethenyl, or halo.

For example, R$_{12}$' is methyl.

For example, R$_{12}$' is ethyl.

For example, R$_{12}$' is ethenyl or propenyl.

For example, R$_{12}$' is methoxyl.

For example, R$_8$' is H, methyl, ethyl, or ethenyl.

For example, R$_8$' is methyl.

For example, R$_8$' is ethyl.

For example, R$_8$' is propyl.

For example, R$_8$' is ethenyl or propenyl.

For example, R$_8$' is C$_1$-C$_6$ alkyl substituted with one or more substituents selected from the group consisting of halo (e.g., F, Cl, or Br), hydroxyl, or C$_1$-C$_6$ alkoxyl.

For example, R$_8$' is 4 to 7-membered optionally substituted heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like).

For example, R$_8$' is piperidinyl.

For example, R$_8$' is 4 to 7-membered optionally substituted heterocycloalkyl and R$_7$' is Q$_4$'-T$_4$', in which Q$_4$' is a bond or C$_1$-C$_4$ alkyl linker and T$_4$' is H, C$_1$-C$_6$ alkyl, C$_3$-C$_8$ cycloalkyl or 4 to 7-membered heterocycloalkyl.

For example, neither R$_7$' nor R$_8$' is tetrahydropyran.

For example, Z$_2$ is NR$_7$'R$_8$' or CR$_7$'R$_8$'R$_{14}$' wherein R$_7$' and R$_8$', together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, and the like) or C$_3$-C$_8$ cycloalkyl, each optionally substituted with one or more -Q$_6$'-T$_6$'.

For example, the ring formed by R$_7$' and R$'' is selected from the group consisting of azetidinyl, pyrrolidinyl, piperidinyl, morpholinyl, piperazinyl, and cyclohexenyl, each optionally substituted with one -Q$_6$'-T$_6$'.

For example, -Q$_6$'-T$_6$' is oxo.

For example, T$_6$' is H, halo, C$_1$-C$_6$ alkyl, C$_1$-C$_6$ alkoxyl, C$_3$-C$_8$ cycloalkyl, C$_6$-C$_{10}$ aryl, or 4 to 7-membered heterocycloalkyl.

For example, Q$_6$' is a bond and T$_6$ is C$_1$-C$_6$ alkyl, C$_3$-C$_8$ cycloalkyl, or 4 to 7-membered heterocycloalkyl.

For example, Q$_6$' is CO, S(O)$_2$, or NHC(O); and T$_6$' is C$_1$-C$_6$ alkyl, C$_1$-C$_6$ alkoxyl, C$_3$-C$_8$ cycloalkyl, or 4 to 7-membered heterocycloalkyl.

For example, $T_6'$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_6'$ is $C_1$-$C_3$ alkyl linker and $T_6'$ is H or $C_6$-$C_{10}$ aryl.

For example, $Q_6'$ is $C_1$-$C_3$ alkyl linker and $T_6'$ is $C_3$-$C_8$ cycloalkyl, 4 to 7-membered heterocycloalkyl, or $S(O)_p R_p'$.

For example, each of $R_p'$ and $R_q'$, independently, is $C_1$-$C_6$ alkyl.

For example, $R_6'$ is —$S(O)_{b'} R_a'$ or azido, in which b' is 0, 1, or 2 and $R_a'$ is $C_1$-$C_6$ alkyl or $C_3$-$C_8$ cycloalkyl; and $Z_2$ is $NR_7'R_8'$, in which $R_7'$ is $C_3$-$C_8$ cycloalkyl (e.g., cyclopentyl, cyclohexyl, or cycloheptyl) or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like), each optionally substituted with one or more -$Q_5'$-$T_5'$ and $R_8'$ is H or $C_1$-$C_6$ alkyl (e.g., methyl, ethyl, n-propyl, i-propyl, butyl, or t-butyl).

For example, $R_6'$ is halo (e.g., fluorine, chlorine, bromine, and iodine) and $Z_2$ is $NR_7'R_8'$ or $CR_7'R_8'R_{14}'$ wherein $R_7'$ and $R_8'$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, and the like) or $C_3$-$C_8$ cycloalkyl, each optionally substituted with one or more -$Q_6'$-$T_6'$.

For example, $R_{13}'$ is H or methyl.

For example, $R_{13}'$ is H.

For example, $R_3'$ is H.

For example, each of $R_5'$, $R_9'$, and $R_{10}'$ is H.

In addition to the above-described features of the compounds of this invention where applicable, the compounds of Formula (IIA) can include one or more of the following features:

For example, $Q_5'$ is a bond and $T_5'$ is H, $C_1$-$C_6$ alkyl, $C_3$-$C_8$ cycloalkyl, 4 to 12-membered heterocycloalkyl, 5- or 6-membered heteroaryl, amino, mono-$C_1$-$C_6$ alkylamino, or di-$C_1$-$C_6$ alkylamino, $T_5'$ being optionally substituted with one or more substituents selected from the group consisting of halo, hydroxyl, $C_1$-$C_6$ alkoxyl, or $C_3$-$C_8$ cycloalkyl.

For example, $Q_5'$ is CO, $S(O)_2$, or NHC(O); and $T_5'$ is $C_1$-$C_6$ alkyl, $C_1$-$C_6$ alkoxyl, $C_3$-$C_8$ cycloalkyl, or 4 to 12-membered heterocycloalkyl.

For example, $Q_5'$ is $C_1$-$C_3$ alkyl linker and $T_5'$ is H or $C_6$-$C_{10}$ aryl.

For example, $Q_5'$ is $C_1$-$C_3$ alkyl linker and $T_5'$ is $C_3$-$C_8$ cycloalkyl, 4 to 12-membered heterocycloalkyl, or $S(O)_q R_q'$.

For example, $Q_5'$ is NHC(O) and $T_5'$ is $C_1$-$C_6$ alkyl or $C_1$-$C_6$ alkoxy.

For example, one or more -$Q_5'$-$T_5'$ are oxo.

For example, U is CH-$Q_5'$-$T_5'$ and n is 0

For example, one or more -$Q_6'$-$T_5'$ are oxo.

For example, $Q_6'$ is a bond or C(O) and $T_6'$ is $C_1$-$C_6$ alkyl or $C_1$-$C_6$ alkoxy.

Representative compounds of the present invention include compounds listed in Tables 1A and 1B.

TABLE 1A

| Compound no. | Structure |
|---|---|
| 1 | 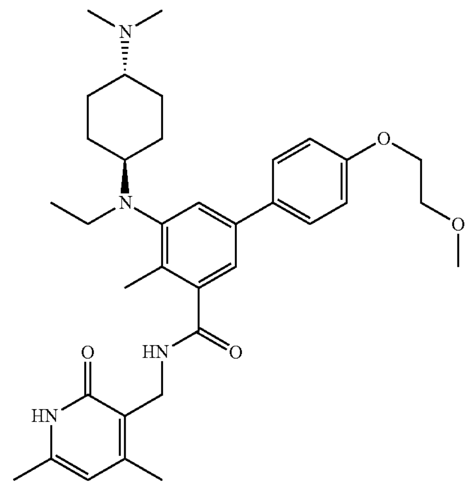 |
| 2 | 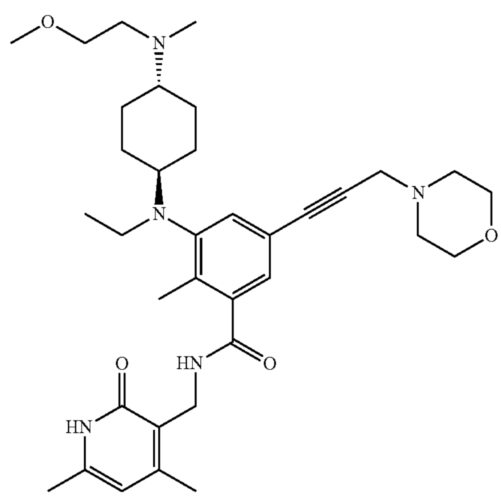 [SMILES: CCN(c1cc(C#CCN2CCOCC2)cc(C(=O)NCc2c(C)cc(C)[nH]c2=O)c1C)[C@H]1CC[C@H](N(C)CCOC)CC1] |
| 3 | 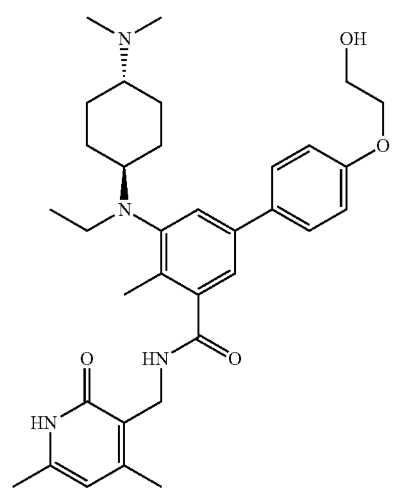 [SMILES: CCN(c1cc(-c2ccc(OCCO)cc2)cc(C(=O)NCc2c(C)cc(C)[nH]c2=O)c1C)[C@H]1CC[C@H](N(C)C)CC1] |

TABLE 1A-continued

| Compound no. | Structure |
|---|---|
| 4 | *(chemical structure)* |
| 5 | *(chemical structure)* |
| 6 | *(chemical structure)* |
| 6b | *(chemical structure)* |
| 7 | *(chemical structure)* |
| 8 | *(chemical structure)* |

TABLE 1A-continued

| Compound no. | Structure |
|---|---|
| 9 | 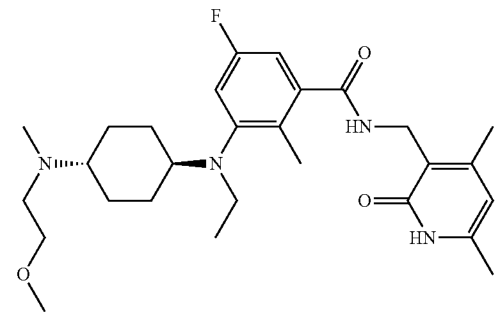 [SMILES: CCN(c1cc(F)cc(C(=O)NCc2c(C)cc(C)[nH]c2=O)c1C)[C@H]1CC[C@H](N(C)CCOC)CC1] |
| 10 | 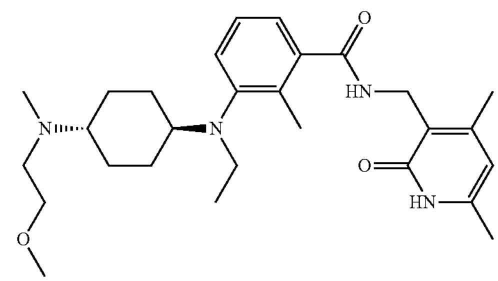 [SMILES: CCN(c1cccc(C(=O)NCc2c(C)cc(C)[nH]c2=O)c1C)[C@H]1CC[C@H](N(C)CCOC)CC1] |
| 11 | 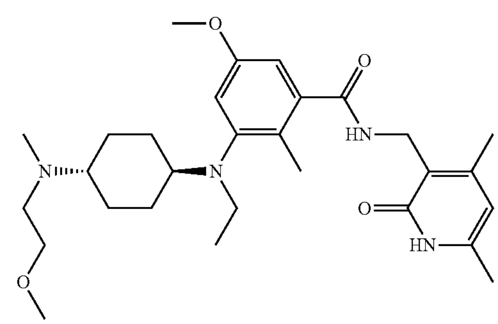 [SMILES: CCN(c1cc(OC)cc(C(=O)NCc2c(C)cc(C)[nH]c2=O)c1C)[C@H]1CC[C@H](N(C)CCOC)CC1] |
| 12 | 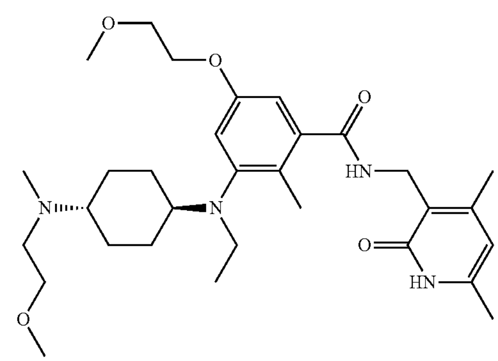 [SMILES: CCN(c1cc(OCCOC)cc(C(=O)NCc2c(C)cc(C)[nH]c2=O)c1C)[C@H]1CC[C@H](N(C)CCOC)CC1] |
| 13 | 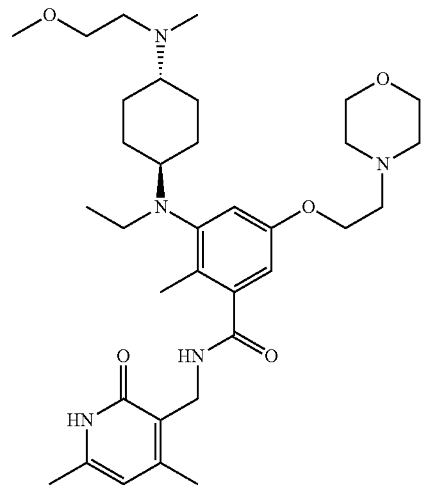 [SMILES: CCN(c1cc(OCCN2CCOCC2)cc(C(=O)NCc2c(C)cc(C)[nH]c2=O)c1C)[C@H]1CC[C@H](N(C)CCOC)CC1] |
| 14 | 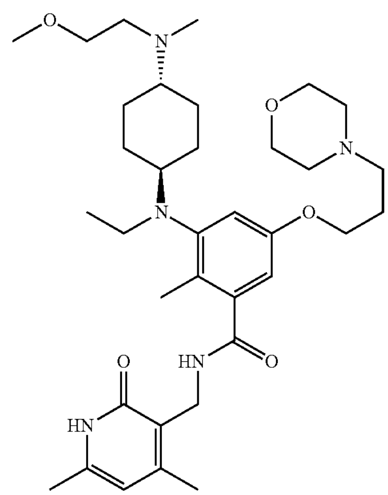 [SMILES: CCN(c1cc(OCCCN2CCOCC2)cc(C(=O)NCc2c(C)cc(C)[nH]c2=O)c1C)[C@H]1CC[C@H](N(C)CCOC)CC1] |
| 15 | 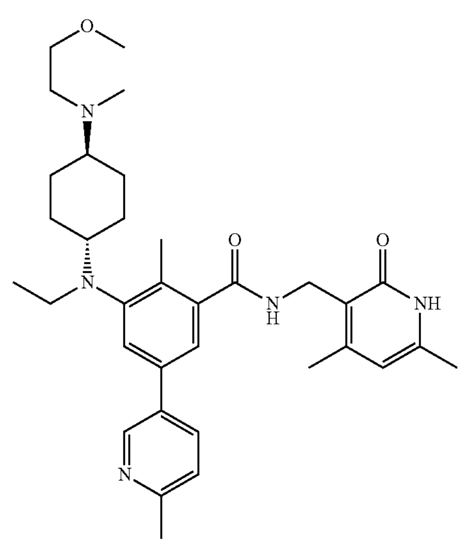 [SMILES: CCN(c1cc(-c2ccc(C)nc2)cc(C(=O)NCc2c(C)cc(C)[nH]c2=O)c1C)[C@H]1CC[C@H](N(C)CCOC)CC1] |

TABLE 1A-continued
| Compound no. | Structure |
|---|---|
| 16 | 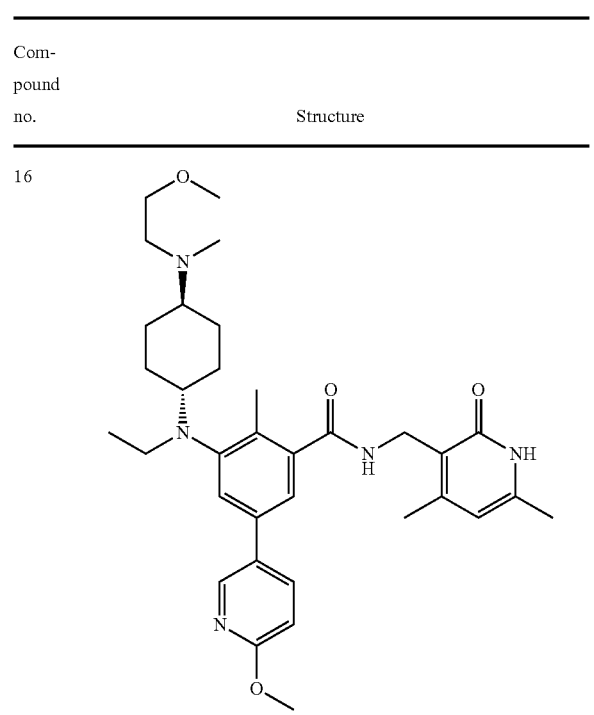 |
| 17 | 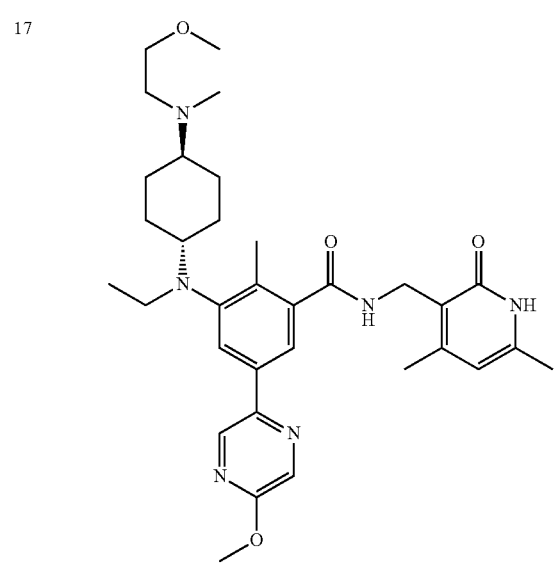 |
| 18 | 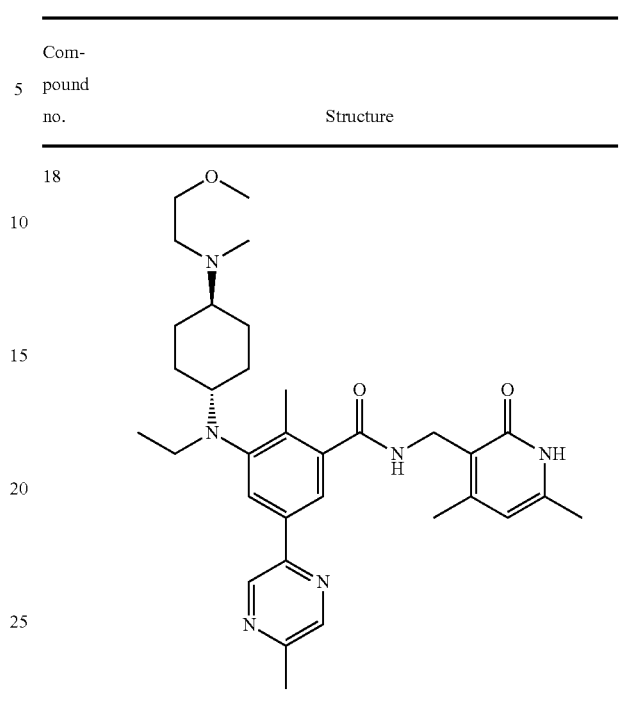 |
| 19 | 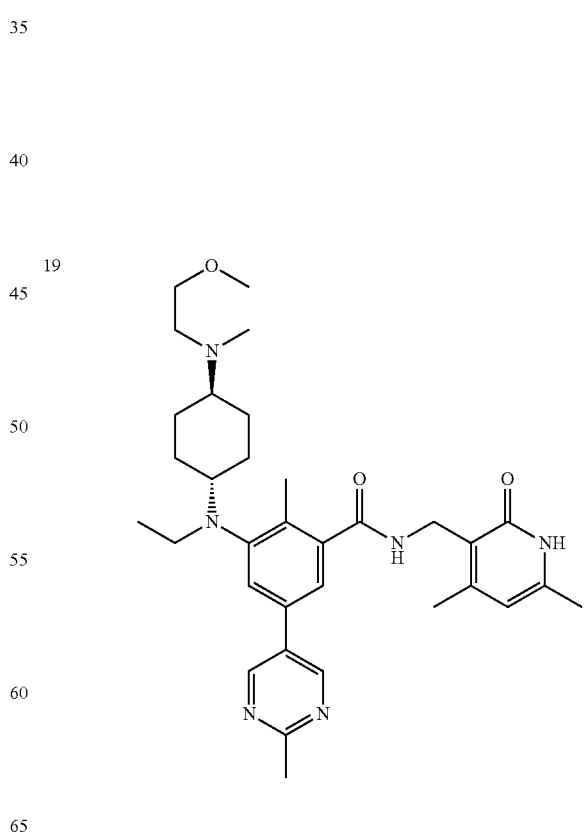 |

TABLE 1A-continued

| Compound no. | Structure |
|---|---|
| 20 | (chemical structure) |
| 21 | (chemical structure) |
| 22 | (chemical structure) |
| 23 | (chemical structure) |
| 24 | (chemical structure) |
| 25 | (chemical structure) |

TABLE 1A-continued
| Compound no. | Structure |
|---|---|
| 26 | 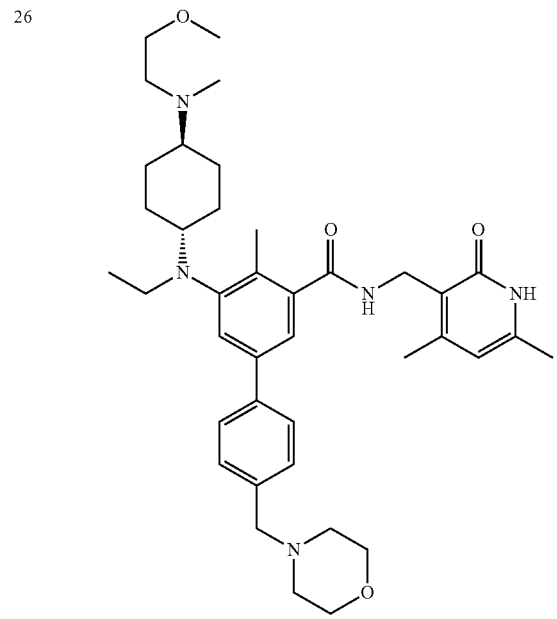 |
| 27 | 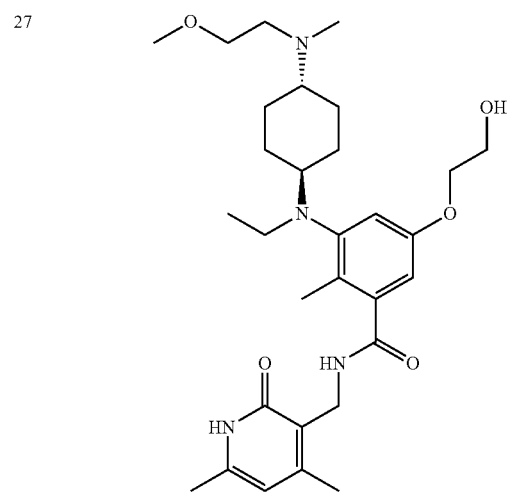 |
| 28 | 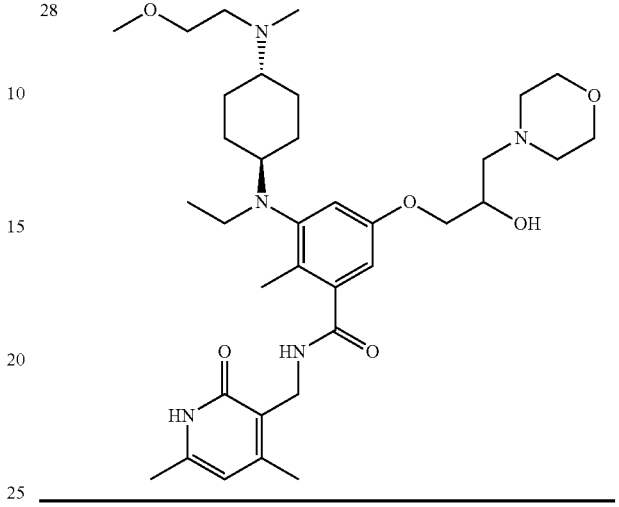 |
TABLE 1B
| Compound no. | Structure |
|---|---|
| 101 | 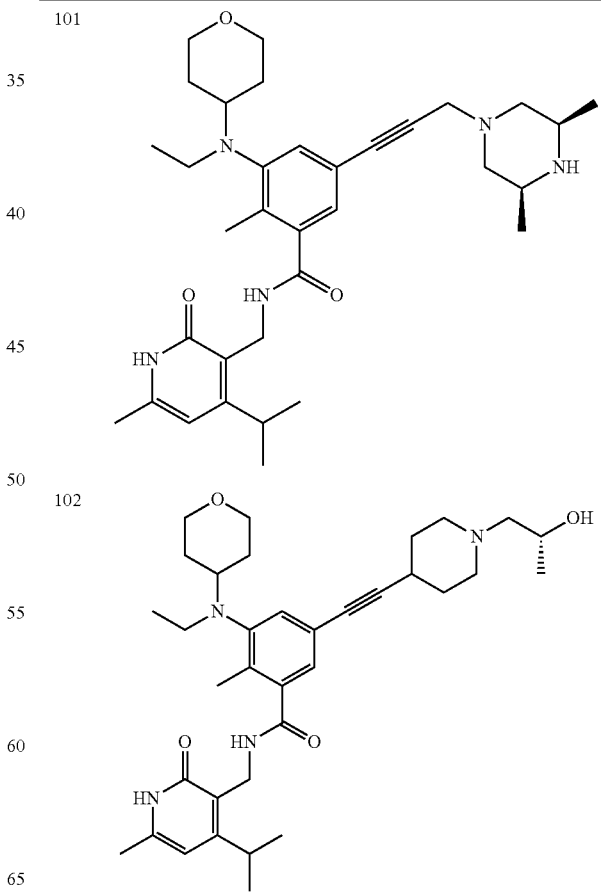 |
| 102 | 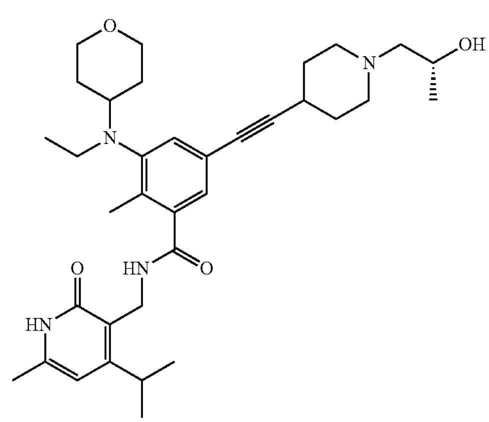 [SMILES: CCN(c1cc(C#CC2CCN(C[C@@H](C)O)CC2)cc(C(=O)NCc2c(C(C)C)cc(C)[nH]c2=O)c1C)C1CCOCC1] |

TABLE 1B-continued
| Compound no. | Structure |
|---|---|
| 103 | 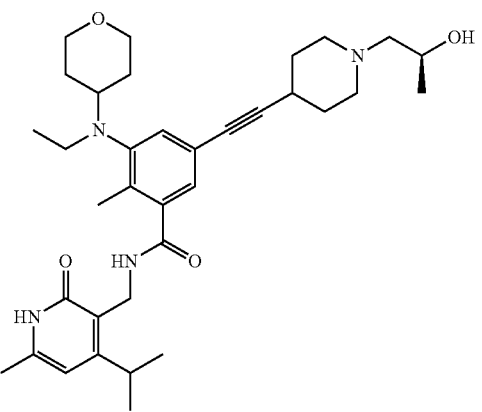 [SMILES: CCN(c1cc(C#CC2CCN(C[C@H](C)O)CC2)cc(C(=O)NCc2c(C(C)C)cc(C)[nH]c2=O)c1C)C1CCOCC1] |
| 104 | 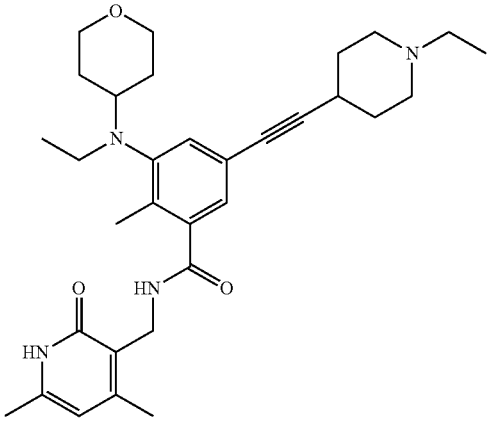 [SMILES: CCN1CCC(C#Cc2cc(C(=O)NCc3c(C)cc(C)[nH]c3=O)c(C)c(N(CC)C3CCOCC3)c2)CC1] |
| 105 | 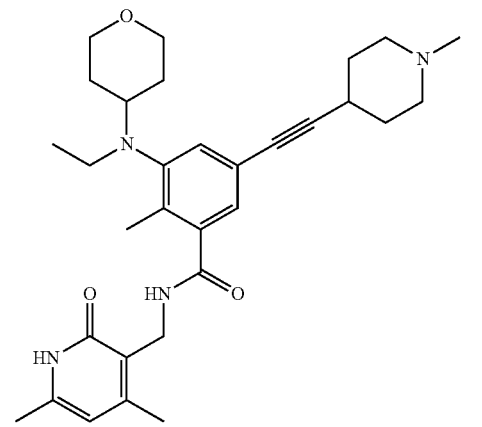 |
| 106 | 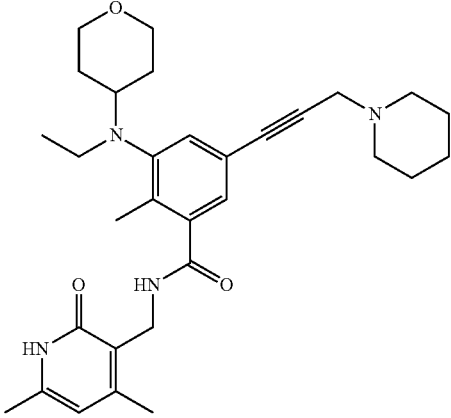 [SMILES: CCN(c1cc(C#CCN2CCCCC2)cc(C(=O)NCc2c(C)cc(C)[nH]c2=O)c1C)C1CCOCC1] |
| 107 | 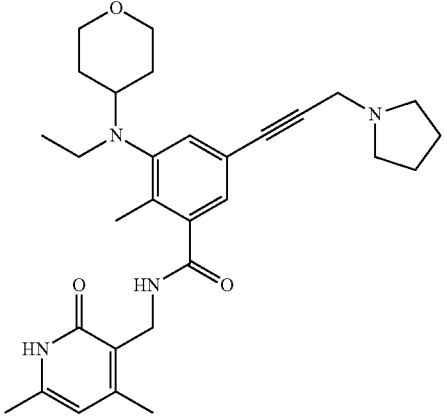 [SMILES: CCN(c1cc(C#CCN2CCCC2)cc(C(=O)NCc2c(C)cc(C)[nH]c2=O)c1C)C1CCOCC1] |
| 108 | 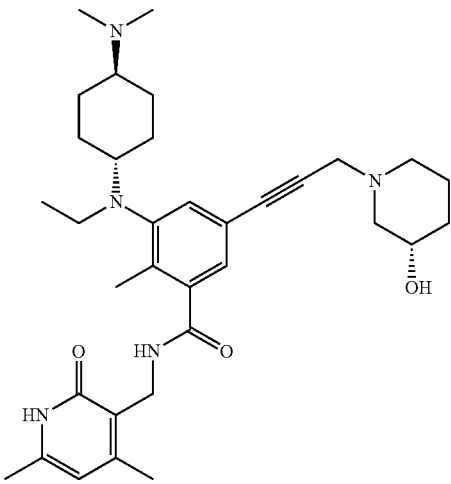 [SMILES: CCN(c1cc(C#CCN2CCC[C@H](O)C2)cc(C(=O)NCc2c(C)cc(C)[nH]c2=O)c1C)[C@H]1CC[C@H](N(C)C)CC1] |

TABLE 1B-continued
| Compound no. | Structure |
|---|---|
| 109 | 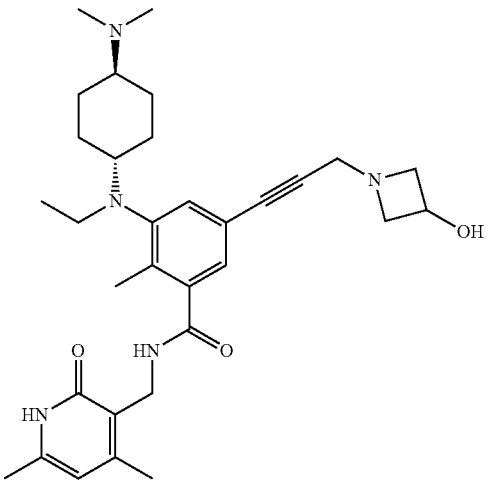 [SMILES: CCN(c1cc(C#CCN2CC(O)C2)cc(C(=O)NCc2c(C)cc(C)[nH]c2=O)c1C)[C@H]1CC[C@H](N(C)C)CC1] |
| 110 | 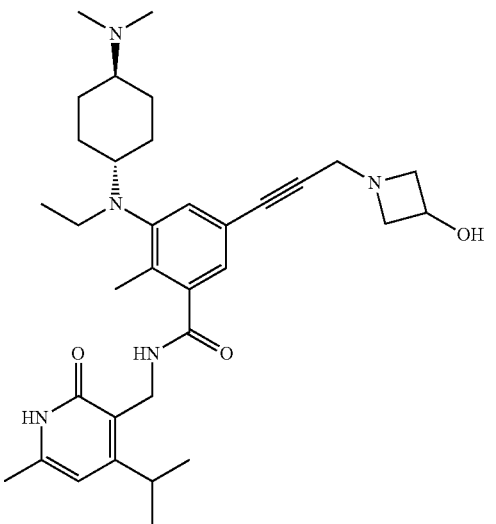 [SMILES: CCN(c1cc(C#CCN2CC(O)C2)cc(C(=O)NCc2c(C(C)C)cc(C)[nH]c2=O)c1C)[C@H]1CC[C@H](N(C)C)CC1] |
| 111 | 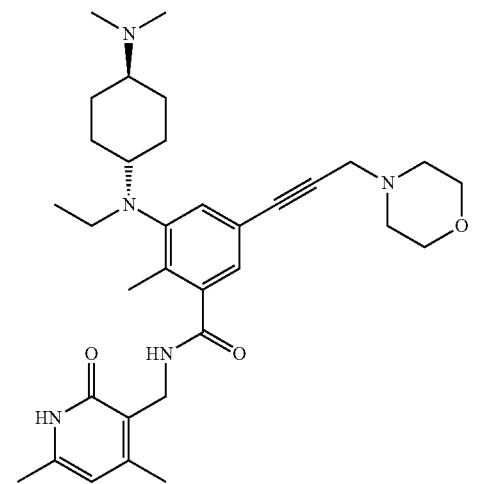 |
| 112 | 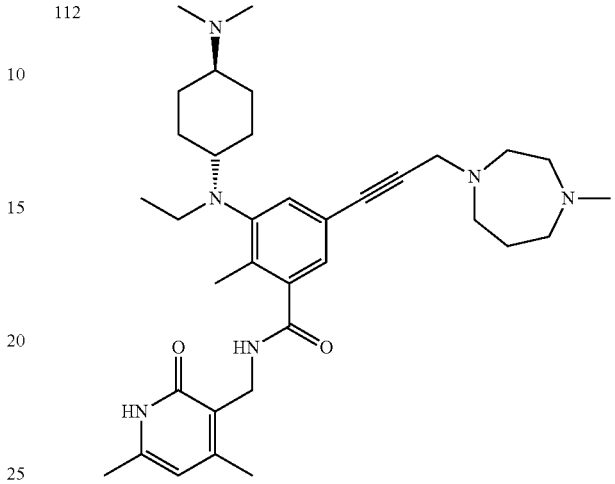 |
| 113 | 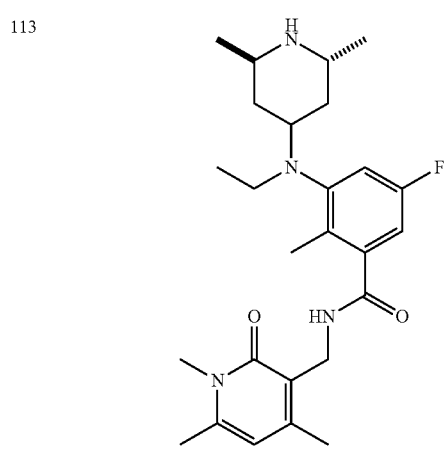 |
| 115 | 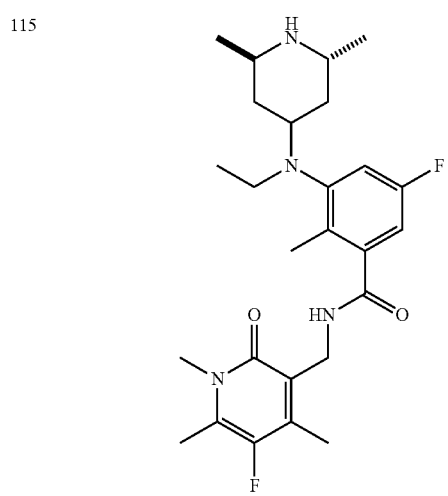 |

TABLE 1B-continued
| Compound no. | Structure |
|---|---|
| 116 | 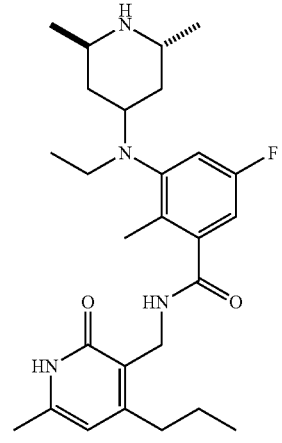 [SMILES: CCCc1cc(C)[nH]c(=O)c1CNC(=O)c1cc(F)cc(N(CC)C2C[C@@H](C)N[C@H](C)C2)c1C] |
| 117 | 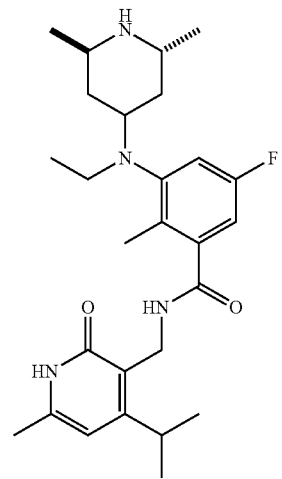 [SMILES: CCN(c1cc(F)cc(C(=O)NCc2c(C(C)C)cc(C)[nH]c2=O)c1C)C1C[C@@H](C)N[C@H](C)C1] |
| 118 | 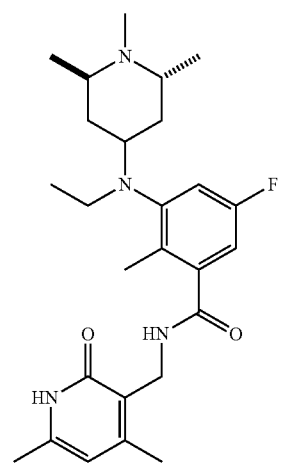 [SMILES: CCN(c1cc(F)cc(C(=O)NCc2c(C)cc(C)[nH]c2=O)c1C)C1C[C@@H](C)N(C)[C@H](C)C1] |
| 119 | 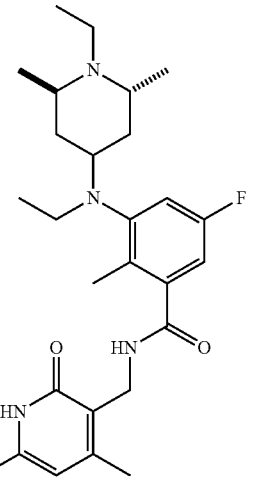 |
| 120 | 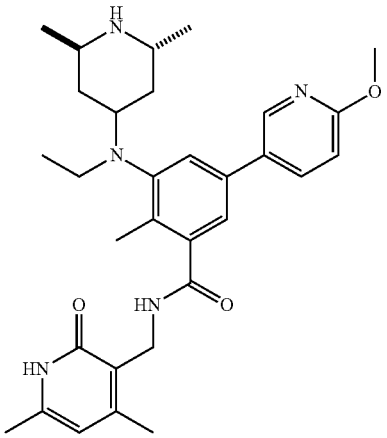 |
| 121 | 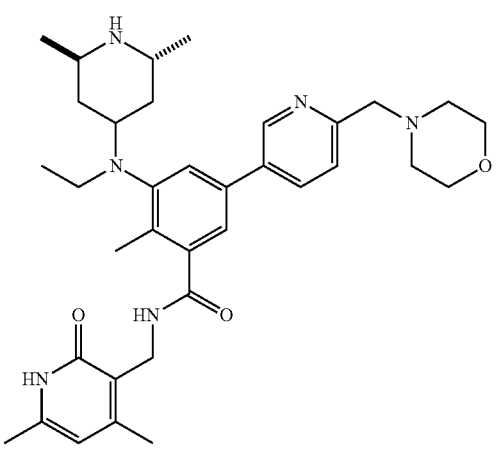 [SMILES: CCN(c1cc(-c2ccc(CN3CCOCC3)nc2)cc(C(=O)NCc2c(C)cc(C)[nH]c2=O)c1C)C1C[C@@H](C)N[C@H](C)C1] |

TABLE 1B-continued
| Compound no. | Structure |
|---|---|
| 122 | 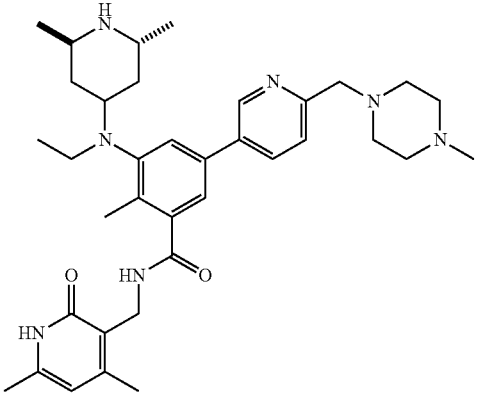 |
| 123 | 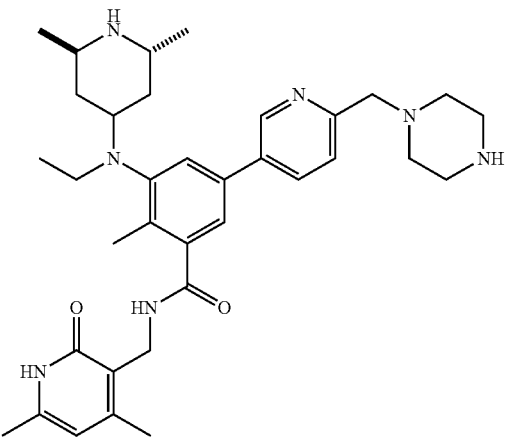 [SMILES: CCN(c1cc(-c2ccc(CN3CCNCC3)nc2)cc(C(=O)NCc2c(C)cc(C)[nH]c2=O)c1C)C1C[C@@H](C)N[C@H](C)C1] |
| 124 | 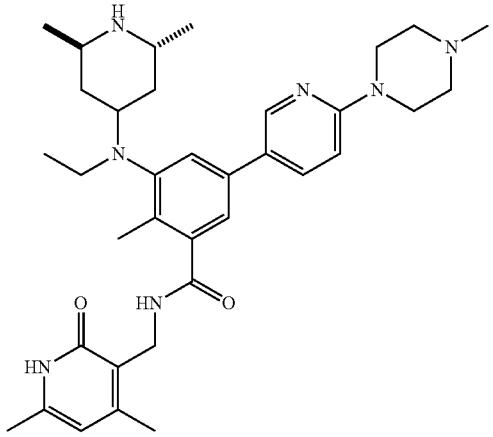 |
| 125 | 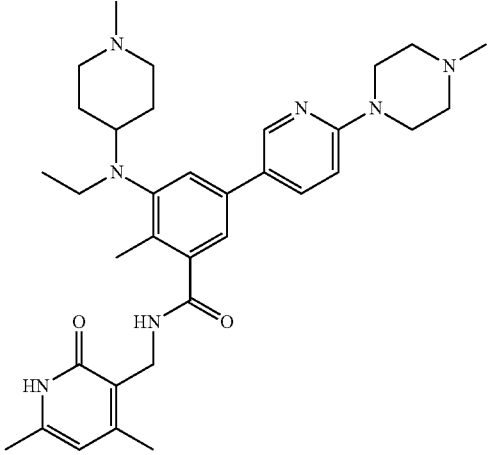 |
| 126 | 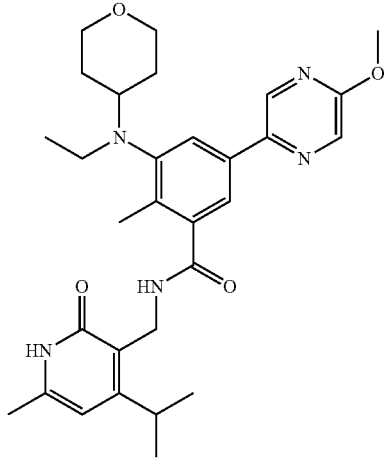 |
| 127 | 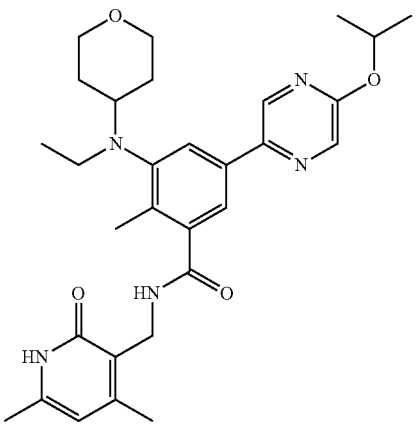 [SMILES: CCN(c1cc(-c2cnc(OC(C)C)cn2)cc(C(=O)NCc2c(C)cc(C)[nH]c2=O)c1C)C1CCOCC1] |

TABLE 1B-continued
| Compound no. | Structure |
|---|---|
| 128 | 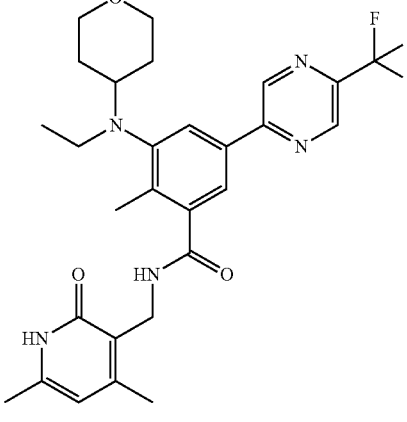 |
| 129 | 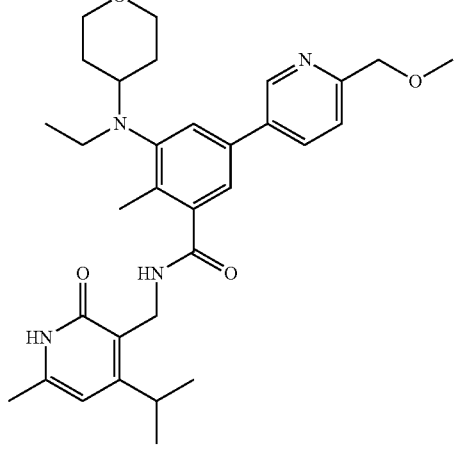 |
| 130 | 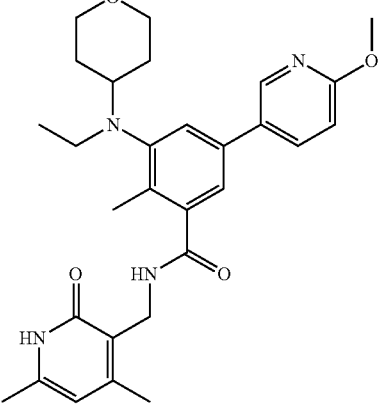 |
| 131 | 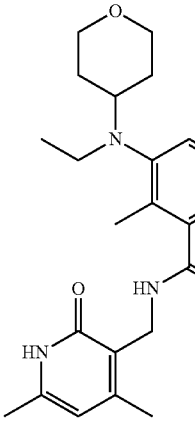 |
| 132 | 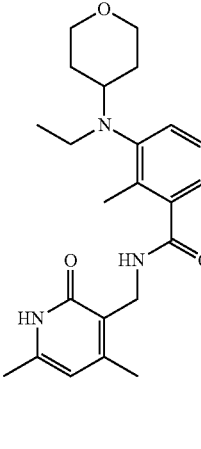 |
| 133 | 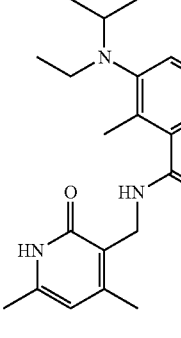 |

TABLE 1B-continued
| Compound no. | Structure |
|---|---|
| 134 | 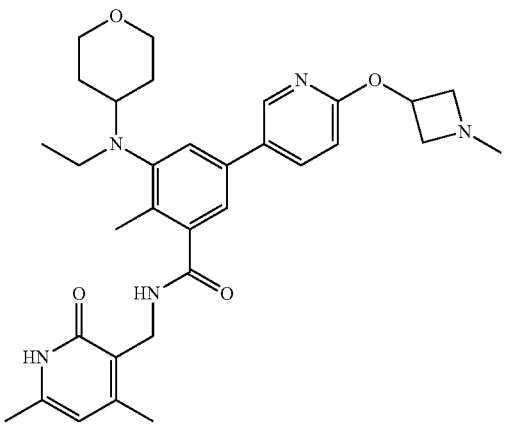 |
| 135 | 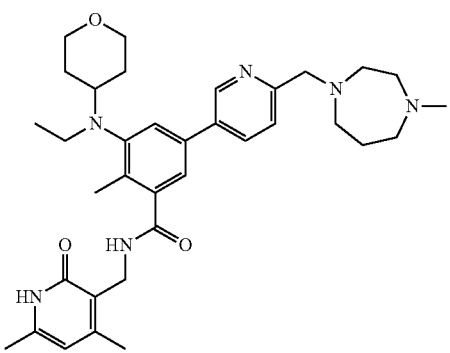 |
| 136 | 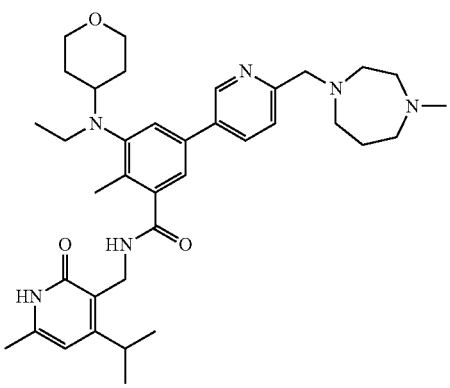 |
| 137 | 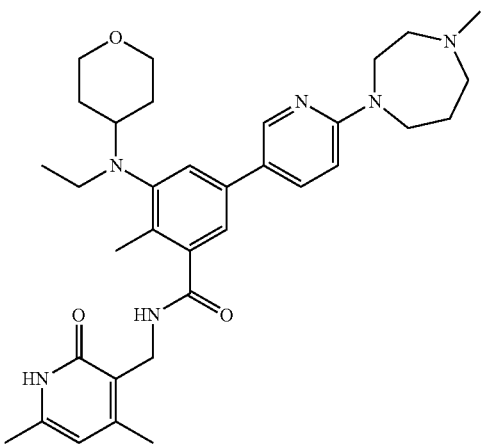 |
| 138 | 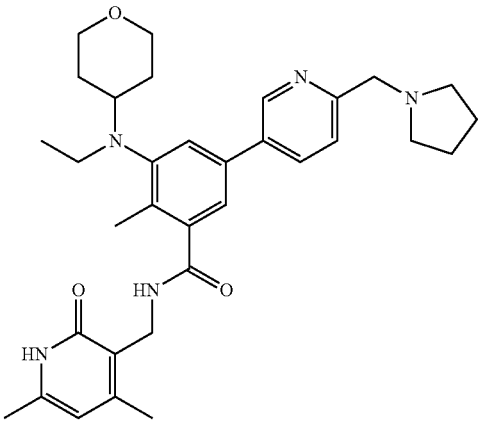 [SMILES: CCN(c1cc(-c2ccc(CN3CCCC3)nc2)cc(C(=O)NCc2c(C)cc(C)[nH]c2=O)c1C)C1CCOCC1] |
| 139 | 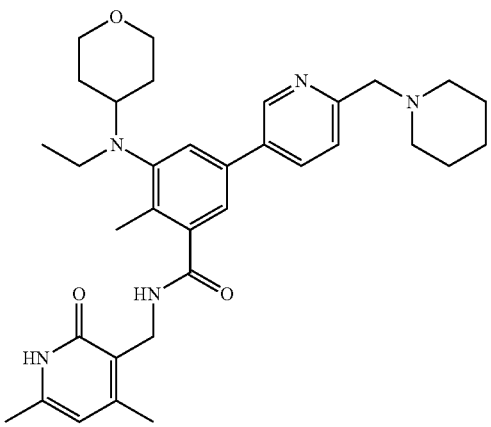 [SMILES: CCN(c1cc(-c2ccc(CN3CCCCC3)nc2)cc(C(=O)NCc2c(C)cc(C)[nH]c2=O)c1C)C1CCOCC1] |

TABLE 1B-continued

| Compound no. | Structure |
|---|---|
| 140 | 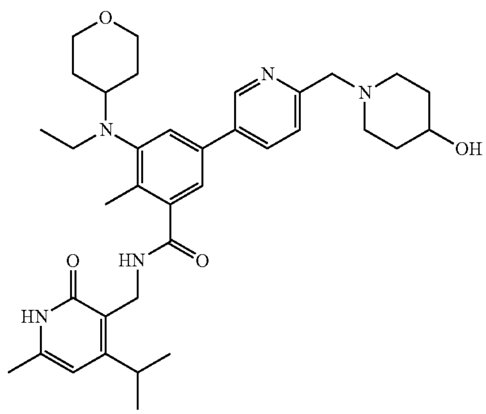 [SMILES: CCN(c1cc(-c2ccc(CN3CCC(O)CC3)nc2)cc(C(=O)NCc2c(C(C)C)cc(C)[nH]c2=O)c1C)C1CCOCC1] |
| 141 | 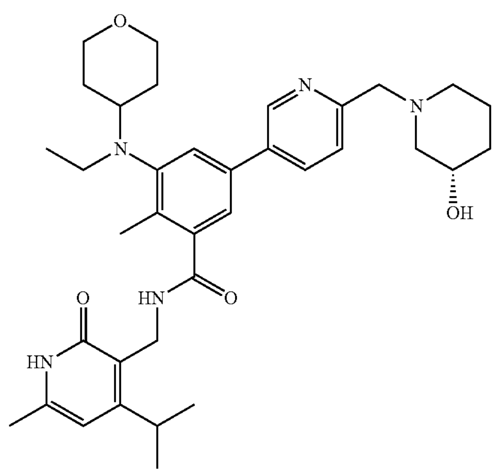 [SMILES: CCN(c1cc(-c2ccc(CN3CCC[C@H](O)C3)nc2)cc(C(=O)NCc2c(C(C)C)cc(C)[nH]c2=O)c1C)C1CCOCC1] |
| 142 | 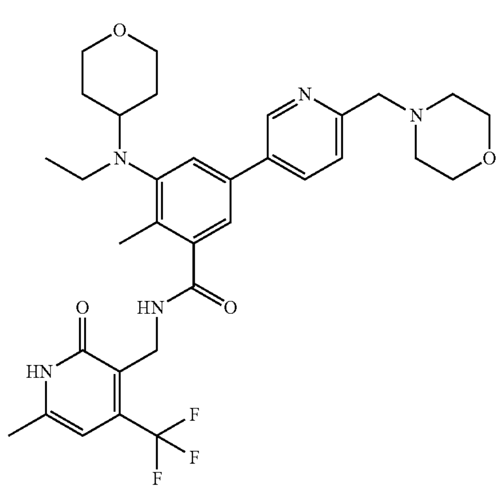 [SMILES: CCN(c1cc(-c2ccc(CN3CCOCC3)nc2)cc(C(=O)NCc2c(C(F)(F)F)cc(C)[nH]c2=O)c1C)C1CCOCC1] |
| 143 | |
| 144 | |
| 145 | |

TABLE 1B-continued

| Compound no. | Structure |
|---|---|
| 146 | (structure) |
| 147 | (structure) |
| 148 | (structure) |
| 149 | (structure) |
| 150 | (structure) |
| 151 | (structure) |

TABLE 1B-continued
| Compound no. | Structure |
|---|---|
| 152 | 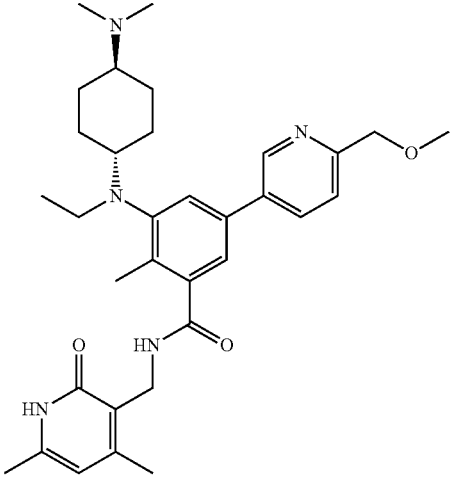 |
| 153 | 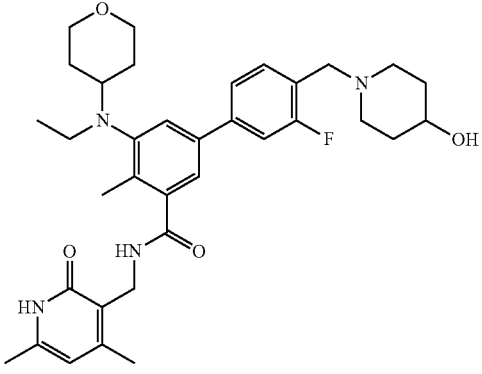 [SMILES: CCN(c1cc(-c2ccc(CN3CCC(O)CC3)c(F)c2)cc(C(=O)NCc2c(C)cc(C)[nH]c2=O)c1C)C1CCOCC1] |
| 154 | 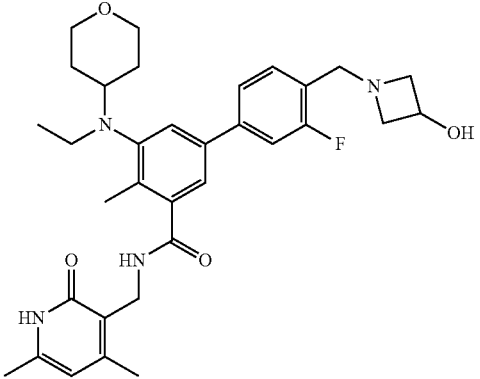 [SMILES: CCN(c1cc(-c2ccc(CN3CC(O)C3)c(F)c2)cc(C(=O)NCc2c(C)cc(C)[nH]c2=O)c1C)C1CCOCC1] |
| 155 | 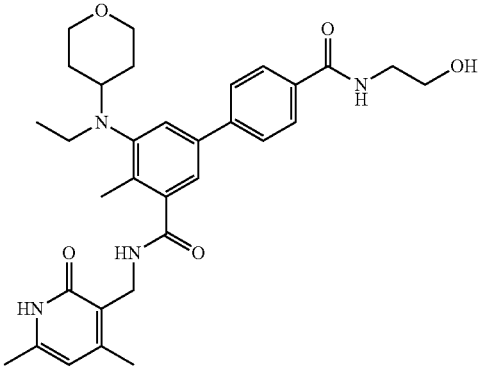 [SMILES: CCN(c1cc(-c2ccc(C(=O)NCCO)cc2)cc(C(=O)NCc2c(C)cc(C)[nH]c2=O)c1C)C1CCOCC1] |
| 156 | 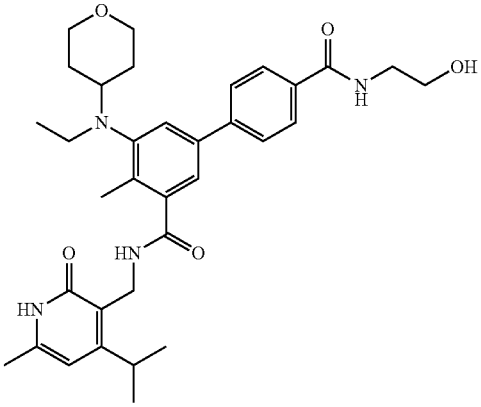 [SMILES: CCN(c1cc(-c2ccc(C(=O)NCCO)cc2)cc(C(=O)NCc2c(C(C)C)cc(C)[nH]c2=O)c1C)C1CCOCC1] |
| 157 | 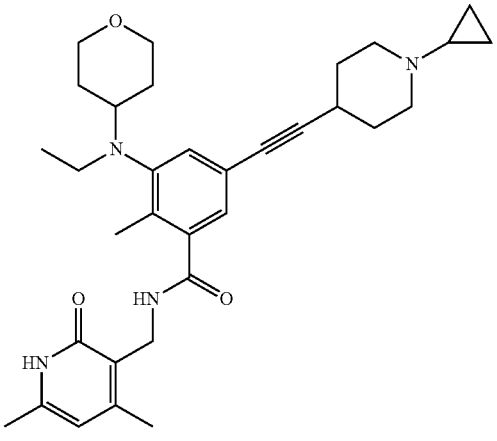 [SMILES: CCN(c1cc(C#CC2CCN(C3CC3)CC2)cc(C(=O)NCc2c(C)cc(C)[nH]c2=O)c1C)C1CCOCC1] |

TABLE 1B-continued

| Compound no. | Structure |
|---|---|
| 158 | 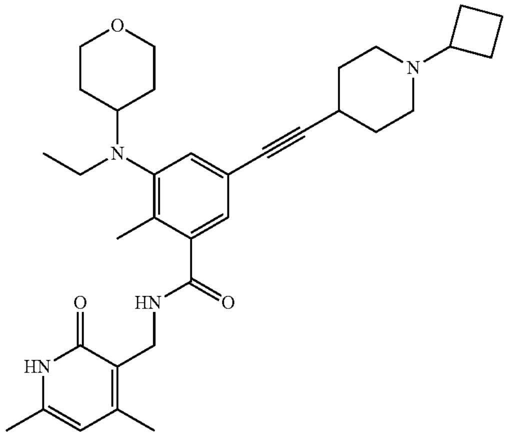 [SMILES: CCN(c1cc(C#CC2CCN(C3CCC3)CC2)cc(C(=O)NCc2c(C)cc(C)[nH]c2=O)c1C)C1CCOCC1] |
| 159 | 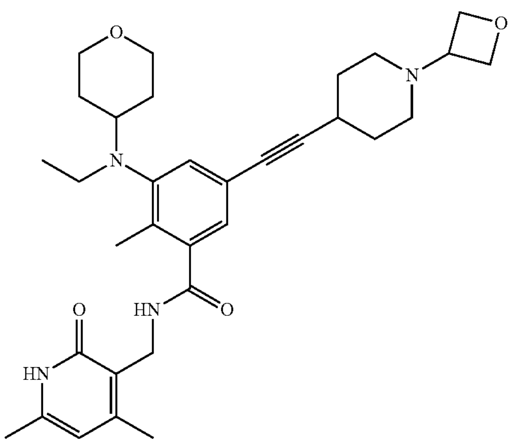 [SMILES: CCN(c1cc(C#CC2CCN(C3COC3)CC2)cc(C(=O)NCc2c(C)cc(C)[nH]c2=O)c1C)C1CCOCC1] |
| 160 | 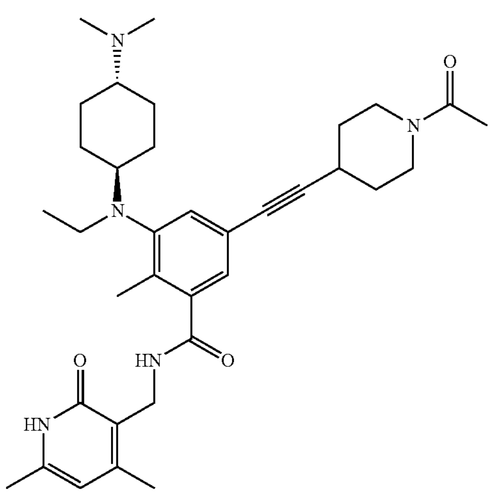 [SMILES: CCN(c1cc(C#CC2CCN(C(C)=O)CC2)cc(C(=O)NCc2c(C)cc(C)[nH]c2=O)c1C)[C@H]1CC[C@H](N(C)C)CC1] |
| 161 | 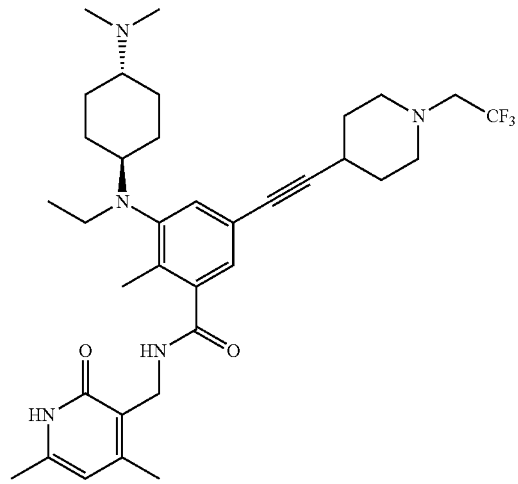 [SMILES: CCN(c1cc(C#CC2CCN(CC(F)(F)F)CC2)cc(C(=O)NCc2c(C)cc(C)[nH]c2=O)c1C)[C@H]1CC[C@H](N(C)C)CC1] |
| 162 | 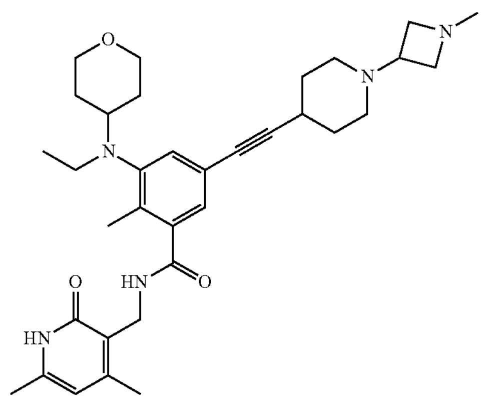 |
| 163 | 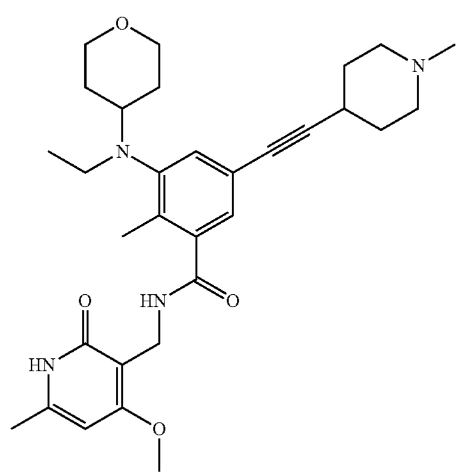 |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and Spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The tem "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention may include all isomers, such as geometrical isomers, optical isomers based on an asymmetrical carbon, stereoisomers, tautomers, enantiomers, rotamers, diastereomers, racemates and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Calm et al., *Angew. Chem.* 1966, 78, 413; Calm and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

As used herein, any occurrence of

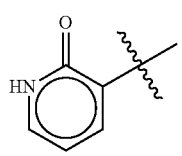

should be construed as

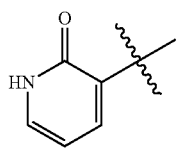

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

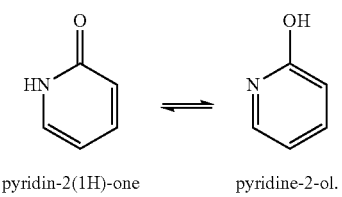 [SMILES: O=c1cccc[nH]1 ; Oc1ccccn1]

pyridin-2(1H)-one       pyridine-2-ol.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of this invention include the compounds themselves, such as any of the formulae disclosed herein. The compounds of this invention may also include their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I') are substituted benzene compounds, and have a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention provides methods for the synthesis of the compounds of any Formula disclosed herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; Greene, T. W., Wuts, P. G. M., *Protective Groups in Organic Synthesis*, $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, $3^{rd}$ edition, John Wiley & Sons: New York, 1999.

Preferred protecting groups include, but are not limited to:
For a hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
AA ammonium acetate
ACN acetonitrile
Ac acetyl
AcOH acetic acid
atm atmosphere
aq. aqueous
BID or b.i.d. bis in die (twice a day)
tBuOK potassium t-butoxide
Bn benzyl
BOC tert-butoxy carbonyl
BOP (benzotriazol-1-yloxy)tris(dimethylamino)-phosphoniumhexafluorophosphate
Cbz benzyloxy carbonyl
$CDCl_3$ deuterated chloroform
$CH_2Cl_2$ dichloromethane
COMU (1-Cyano-2-ethoxy-2-oxoethylidenaminooxy)dimethyl-amino-morpholino-carbenium hexafluorophosphate
d days
DBU 1,8-diazabicyclo[5.4.0]undec-7-ene
DCE 1,2 dichloroethane
DCM dichloromethane
DEAD Diethyl azodicarboxylate
DIAD Diisopropyl azodicarboxylate
DiBAL-H diisobutyl aluminium hydride
DIPEA N,N-diisopropylethylamine (Hunig's base)
DMA Dimethylacetamide
DMAP N, N dimethyl-4-aminopyridine
DMB 2,4 dimethoxy benzyl
DMF N,N-Dimethylformamide
DMSO Dimethyl sulfoxide
DPPA Diphenyiphosphonic azide
EA or EtOAc Ethyl acetate
EDC or EDCI N-(3-Dimethylaminopropyl)-N'-ethylcarbodiimide
$Et_2O$ diethyl ether
ELS Evaporative Light Scattering
ESI– Electrospray negative mode
ESI+ Electrospray positive mode
$Et_3N$ or TEA triethylamine
EtOH ethanol
FA formic acid
FC or FCC Flash chromatography
h hours
$H_2O$ water
HATU O-(7-Azabenzotriazol-1-yl)-N,N,N',N'-tetramethyluronium hexafluorophosphate
HOAT 1-Hydroxy-7-azabenzotriazole
HOBt 1-Hydroxybenzotriazole
HO-Su N-Hydroxysuccinimide
HCl hydrogen chloride or hydrochloric acid
HPLC High performance liquid chromatography
$K_2CO_3$ potassium carbonate
KHMDs Potassium hexamethyldisilazide
LC/MS or LC-MS Liquid chromatography mass spectrum
LDA Lithium diisopropylamide
LiHMDs Lithium hexamethyldisilazide
LG leaving group
M Molar
m/z mass/charge ratio
m-CPBA meta-chloroperbenzoic acid
MeCN Acetonitrile
MeOD d4-methanol
MeI Methyl iodide
MS3 Å 3 Å molecular sieves
$MgSO_4$ Magnesium Sulfate
min minutes
Ms Mesyl
MsCl Mesyl chloride
MsO Mesylate MS Mass Spectrum
MWI microwave irradiation
Na₂CO₃ sodium carbonate
Na₂SO₄ sodium sulfate
NaHCO₃ sodium bicarbonate
NaHMDs Sodium hexamethyldisilazide
NaOH sodium hydroxide
NaHCO₃ sodium bicarbonate
Na₂SO₄ sodium sulfate
NIS N-iodosuccinimide
NMR Nuclear Magnetic Resonance
o/n or O/N overnight
Pd/C Palladium on carbon
Pd(dppf)Cl₂.DCM [1,1'-Bis(diphenylphosphino)ferrocene]dichloropalladium(II), complex with dichloromethane
PPAA 1-Propanephosphonic acid cyclic anhydride
Pd(OH)₂ Palladium dihydroxide
PE Petroleum Ether
PG protecting group
PMB para methoxybenzyl
p.o. per os (oral administration)
ppm parts per million
prep HPLC preparative High Performance Liquid Chromatography
prep TLC preparative thin layer chromatography
p-TsOH para-toluenesulfonic acid
PYBOP (Benzotriazol-1-yloxy)tripyrrolidinophosphonium hexafluorophosphate
QD or q.d. quaque die (once a day)
RBF round bottom flask
RP-HPLC Reverse phase High Performance liquid chromatography
Rt or RT Room temperature
SEM (Trimethylsilyl)ethoxymethyl
SEMCl (Trimethylsilyl)ethoxymethyl chloride
SFC Super critical chromatography
SGC silica gel chromatography
STAB Sodium triacetoxy borohydride
TBAF tetra-n-butylammonium fluoride
TBME tert-Butyl methyl ether
TEA Triethylamine
TFA trifluoroacetic acid
TfO triflate
THF tetrahydrofuran
THP tetrahydropyran
TID or t.i.d ter in die (three times a day)
TLC thin layer chromatography
TMSCl Trimethylsilyl chloride
Ts tosyl
TsOH tosic acid
UV ultraviolet Compounds of the present invention can be conveniently prepared by a variety of methods familiar to those skilled in the art. The compounds of this invention with any Formula disclosed herein may be prepared according to the procedures illustrated in the Schemes below, from commercially available starting materials or starting materials which can be prepared using literature procedures. The Z and R groups (such as R, R₂, R₃, R₄, R₆, R₇, R₈, and R₁₂) in the Schemes are as defined as the variables in the corresponding positions in any of Formulae disclosed herein, unless otherwise specified.

One of ordinary skill in the art will note that, during the reaction sequences and synthetic schemes described herein, the order of certain steps may be changed, such as the introduction and removal of protecting groups.

Scheme A depicts a route of synthesizing various pyridone moieties:

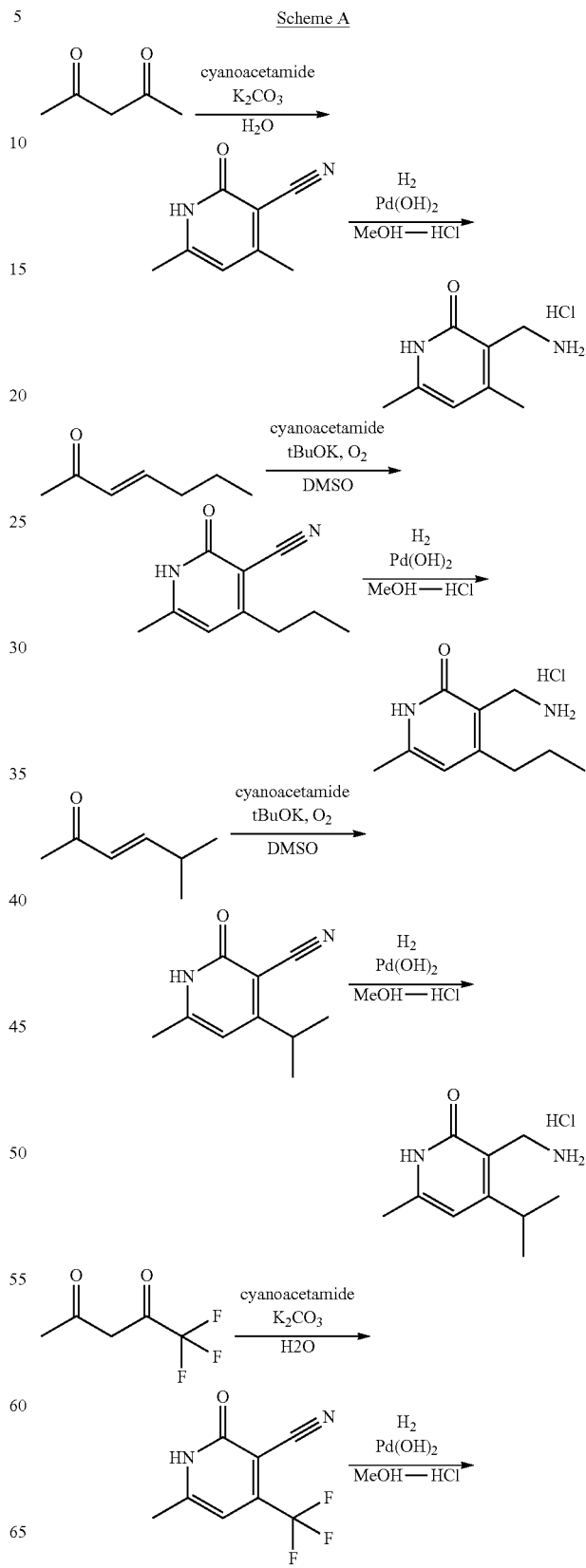

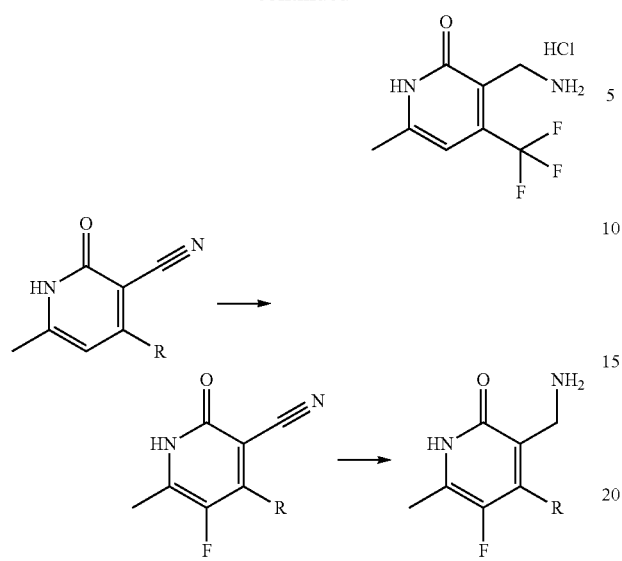
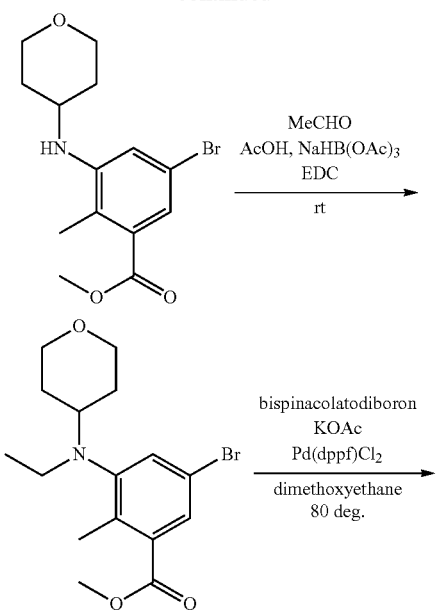
R = Me, CF₃, i-propyl, n-propyl
Scheme B depicts a route of synthesizing various benzoic acid methyl ester intermediates:
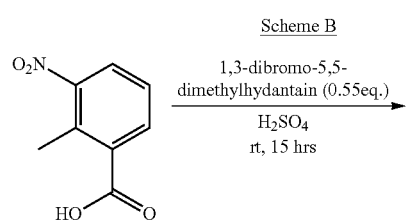
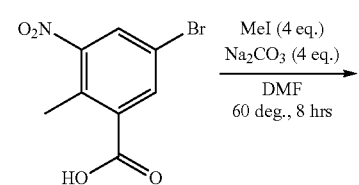
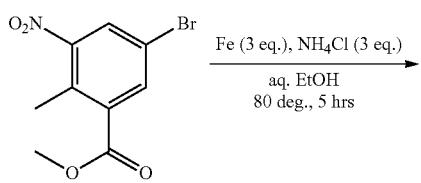
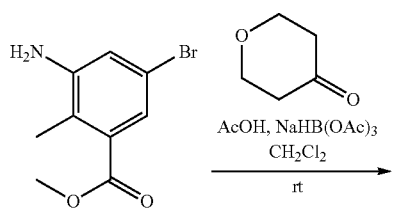
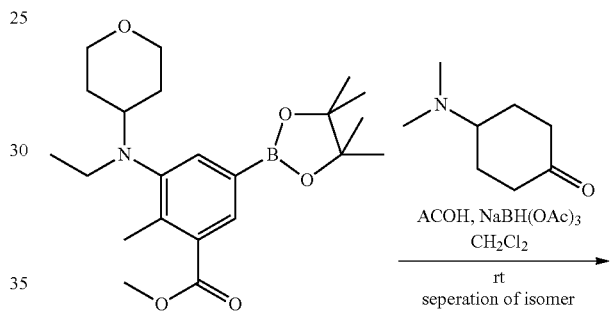
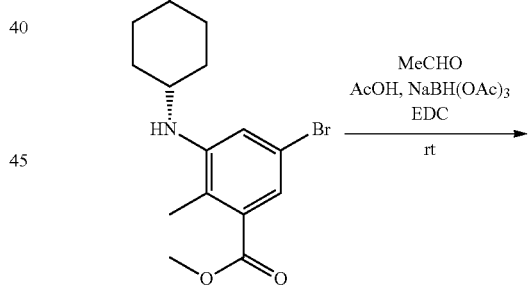
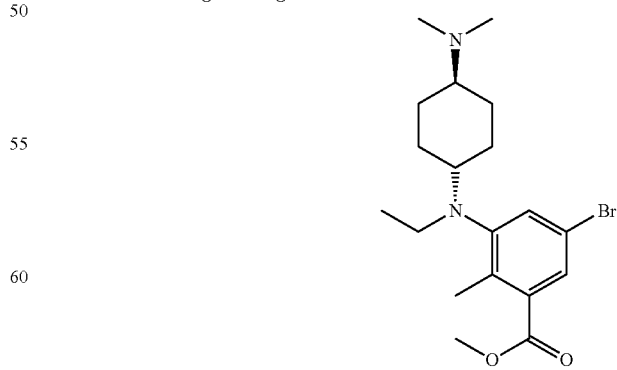
Scheme C depicts a route of synthesizing various tetrahydropyran moieties:

Scheme C
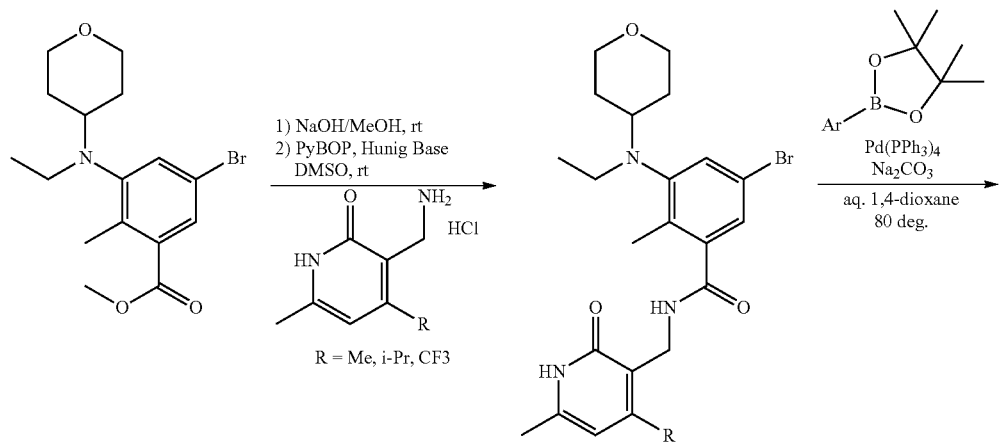
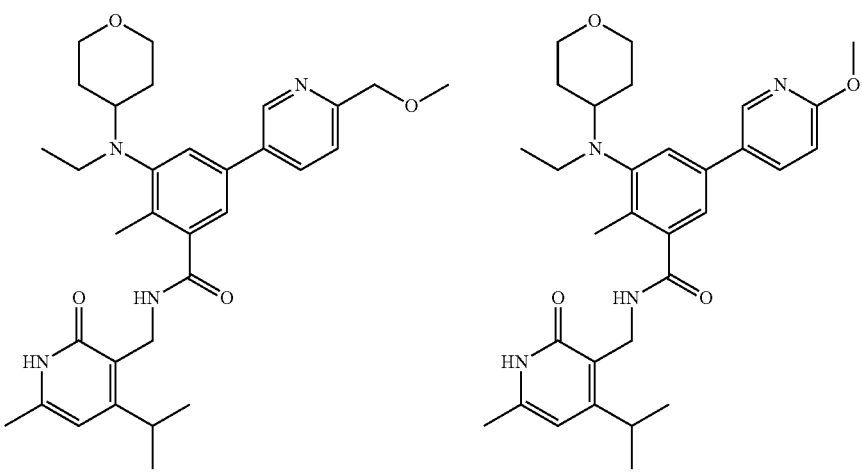
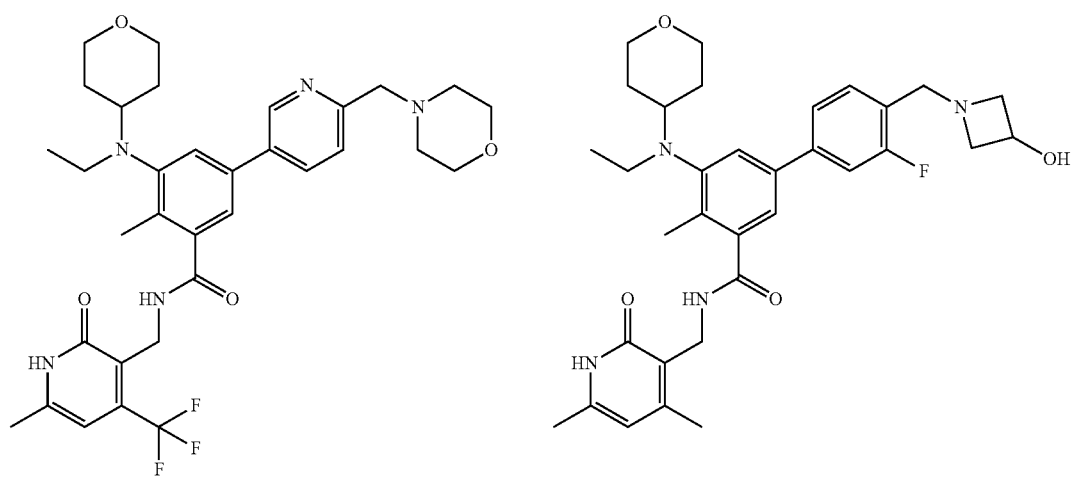

-continued
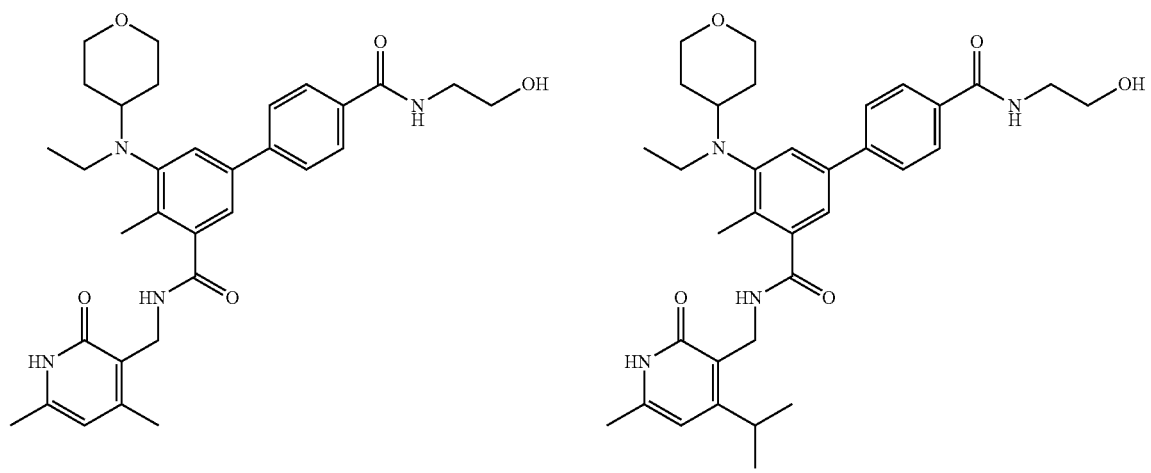
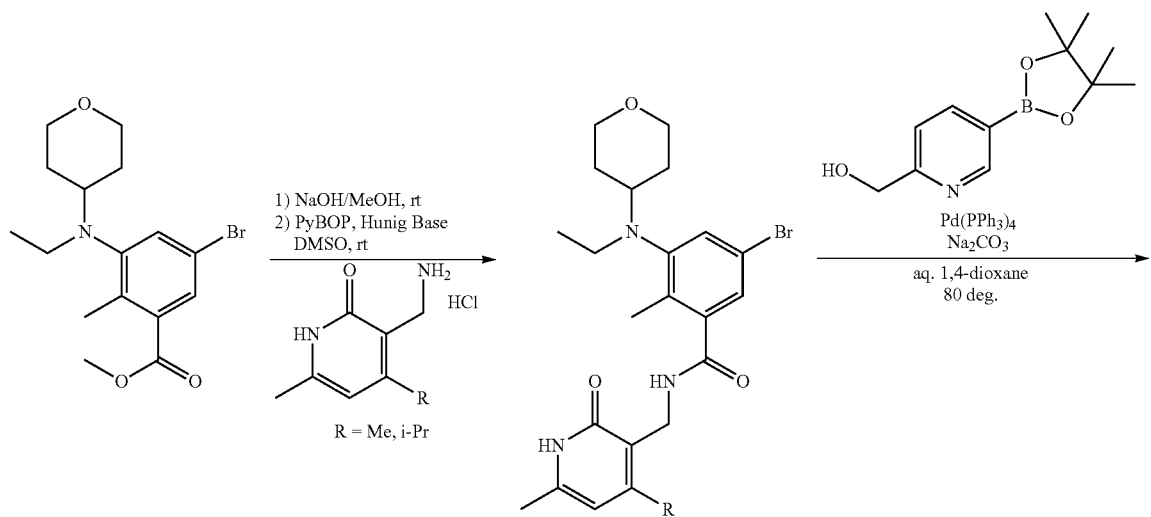
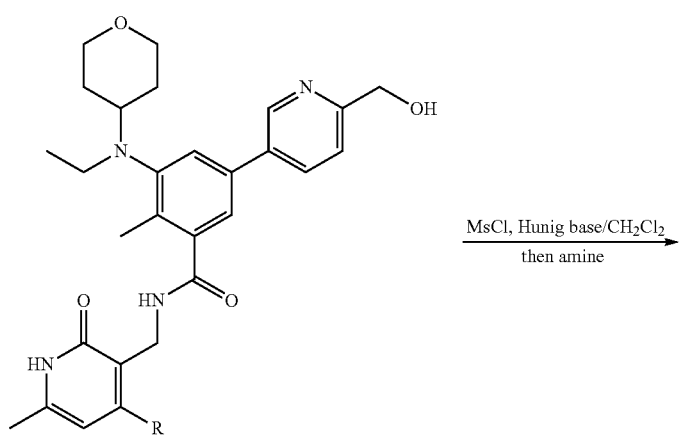

-continued
101
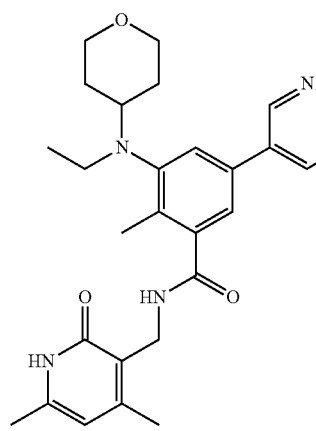
102
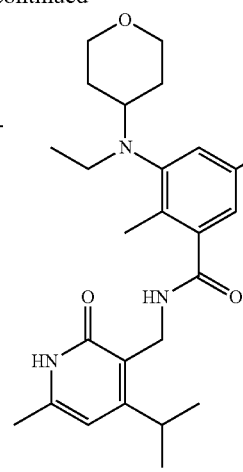
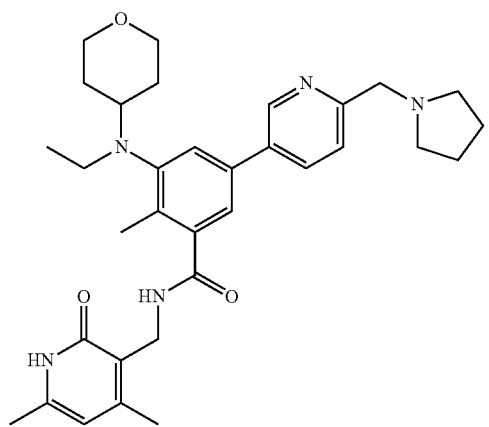
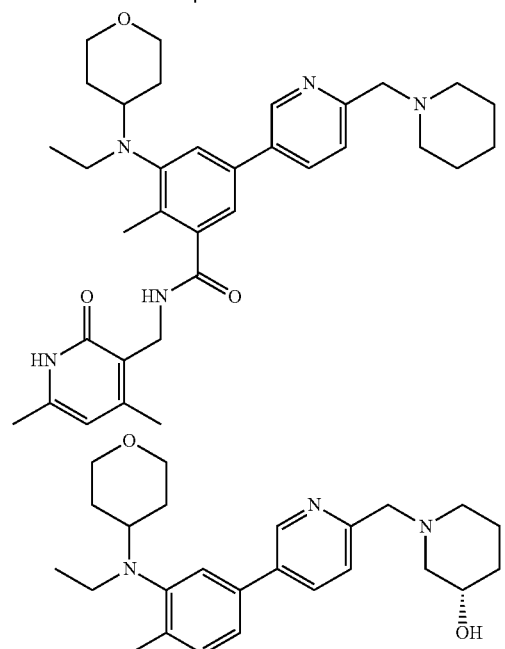
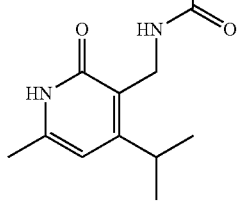
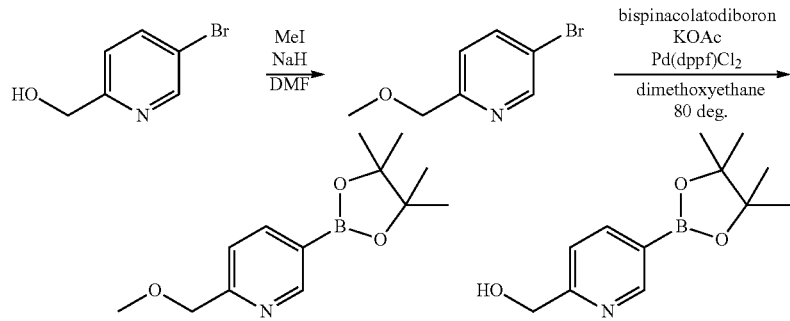
ref.) WO200974812A1

-continued
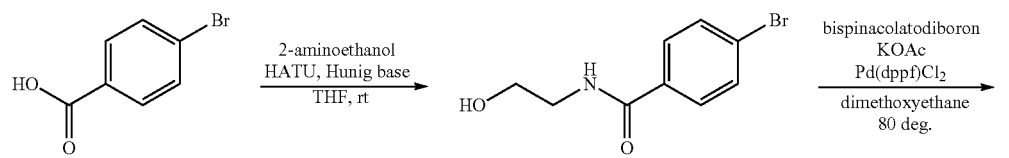
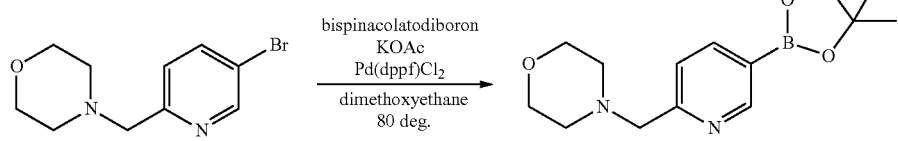
commercially available
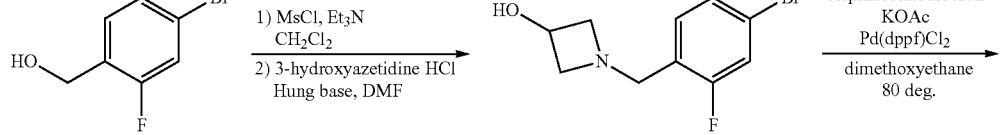
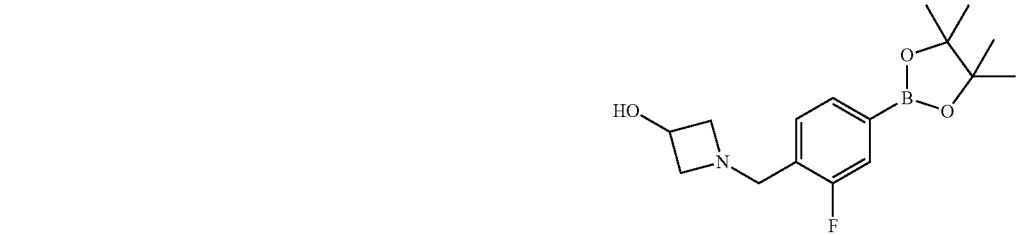
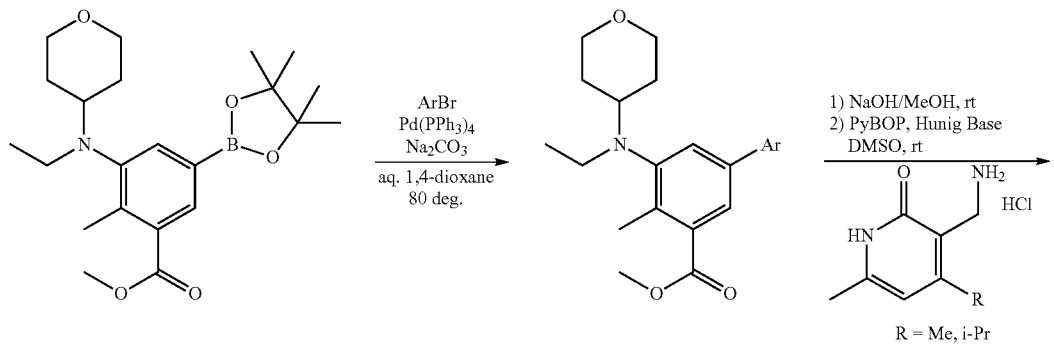

-continued
105
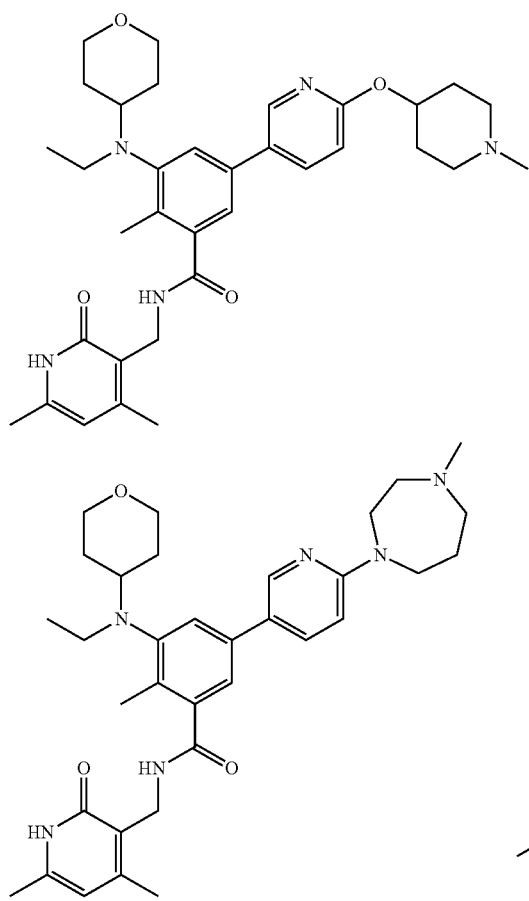
106
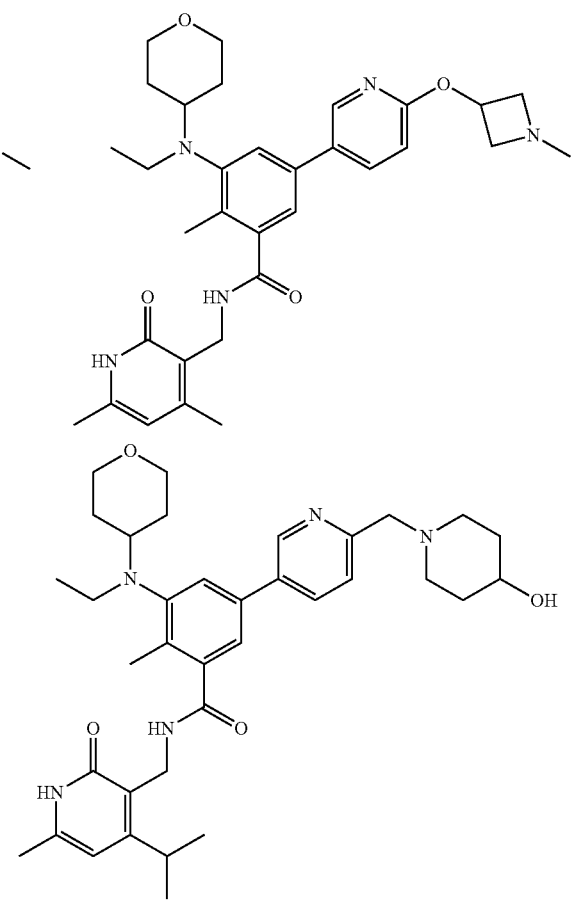
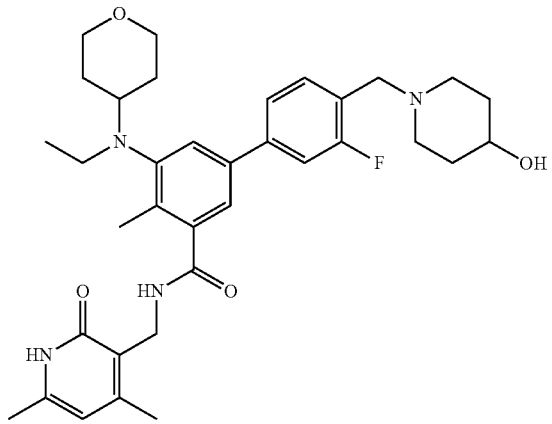
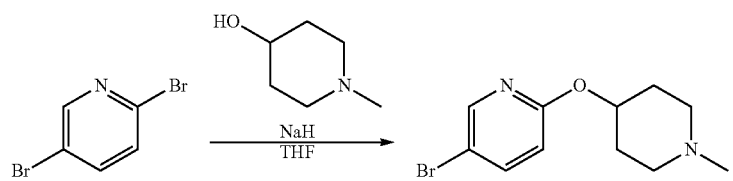
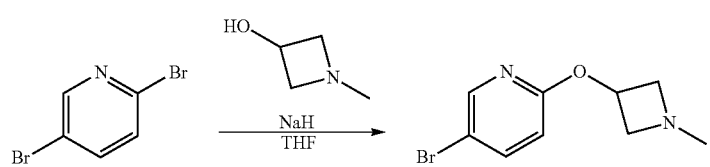

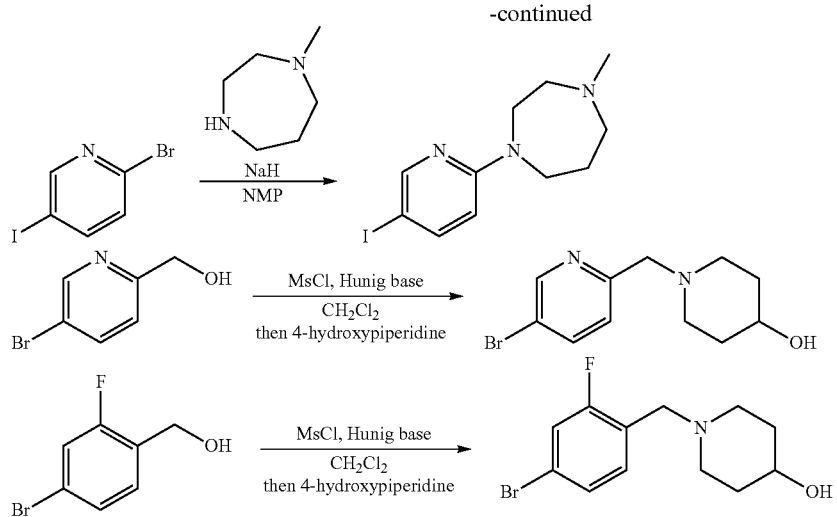
Scheme D depicts a route of synthesizing various Dimethylaminocyclohexyl analogs:
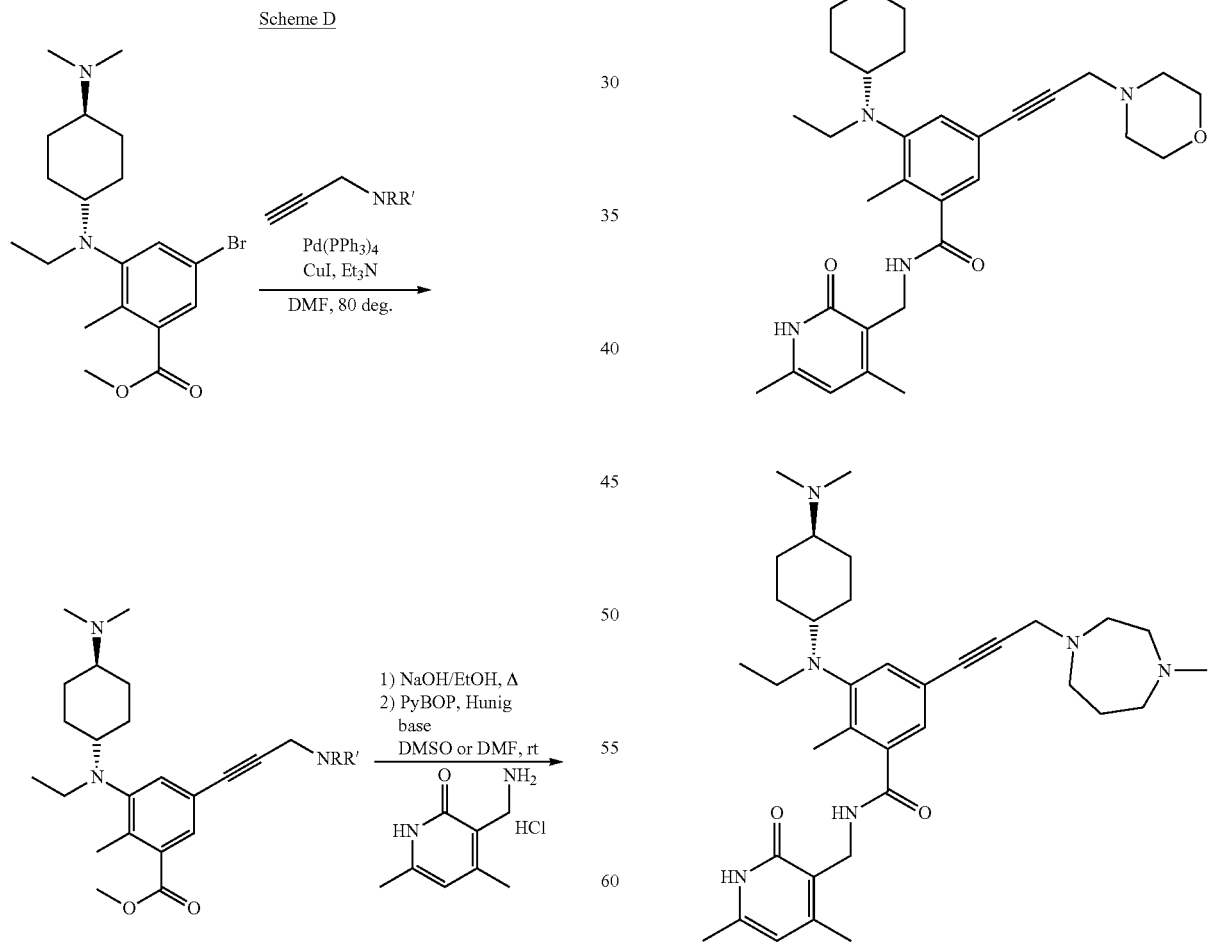
Scheme 1 shows the synthesis of modified aryl analogs following a general route that utilizes well-established chemistry.

Scheme 1

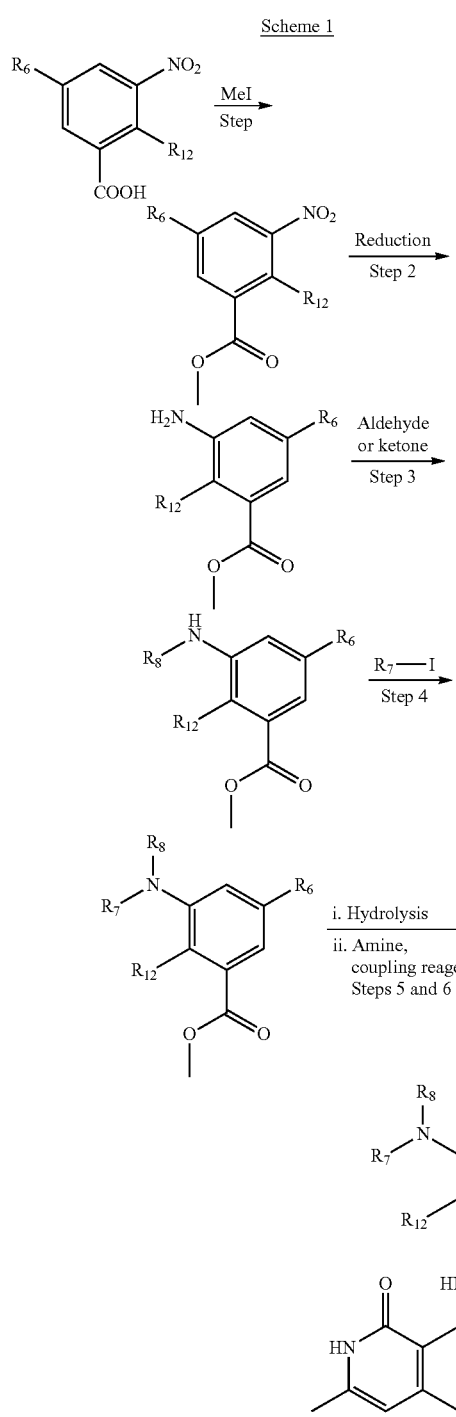

a protic solvent, such as ethanol, at an appropriate temperature, such as 80° C. (Step 2). Introduction of the $R_8$ can be done using a reductive amination with an appropriate ketone or aldehyde in the presence of an appropriate reducing agent, such as sodium cyanoborohydride, and catalytic acid, such as acetic acid, in an appropriate solvent, such as methanol. A variety of $R_7$ groups can be introduced by alkylation using $R_7$-LG, where LG is a leaving group, such as iodine, in the presence of a mild base, such as cesium carbonate, in an appropriate polar solvent, such as acetonitrile, at an appropriate temperature, such as 80° C. (Step 4). Alternatively, $R_7$ groups can be introduced by reductive amination with $R_7$-ketone or $R_7$-aldehyde in the presence of an appropriate reducing agent, such as sodium cyanoborohydride, and catalytic acid, such as acetic acid, in an appropriate solvent, such as methanol. The ester moiety can be converted to an amide using a standard two step protocol. The ester can be hydrolyzed to the corresponding acid using a suitable base, such as sodium hydroxide, in a polar solvent, such as ethanol (Step 5). The acid would then be subjecting to a standard amide coupling reaction whereupon the appropriate amine would be added along with a suitable amide coupling reagent such as PYBOP in a suitable solvent such as DMSO to give the desired amide (Step 6).

Scheme 2

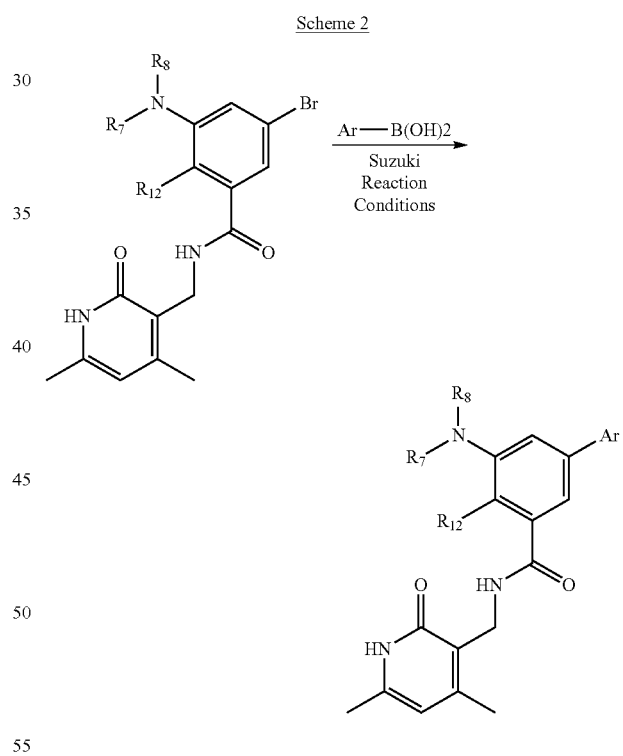

Scheme 1 shows the synthesis of modified aryl analogs following a general route that utilizes well-established chemistry. Substituted nitrobenzoic acids, many of which are commercially available or can be made by nitration of the appropriate substituted benzoic acids or other chemistry known to one skilled in the art, can be converted to their methyl esters by treatment with methyliodide in a polar solvent, such as DMF, in the presence of an appropriate base, such as sodium carbonate, at an appropriate temperature, such as 60° C. (Step 1). The nitro group can be reduced to an amine using an appropriate reducing agent, such as iron, in the presence of an acid, such as ammonium chloride, in Depending upon the nature of the $R_6$ substituent, further chemical modification could be employed to convert the $R_6$ substituent into an alternative $R_6$ substituent. A representative sampling of such modifications could include hydrogenation, protecting group removal followed by additional amide coupling reactions, palladium catalyzed coupling reactions, reductive amination reactions or alkylation reactions. For example, as depicted in Scheme 2, if $R_6$ is a bromide, alternative $R_6$ substituents could then be introduced using standard transition metal-based protocols that rely upon a leaving group such as a bromide as a connection point. The bromide would be combined with an appropriate boronic ester derivative, in the presence of a mild base and a palladium catalyst in a polar solvent such as dioxane/water, at elevated temperature to give the desired new $R_6$ substituent (i.e. Suzuki reaction). For example, as depicted in Scheme 3, if the Suzuki reaction is conducted with a boronic ester derivative bearing a formyl group further modification by reductive amination reaction with primary and secondary amines (e.g. morpholine, dimethylamine) can be conducted to introduce amine groups.

Scheme 3

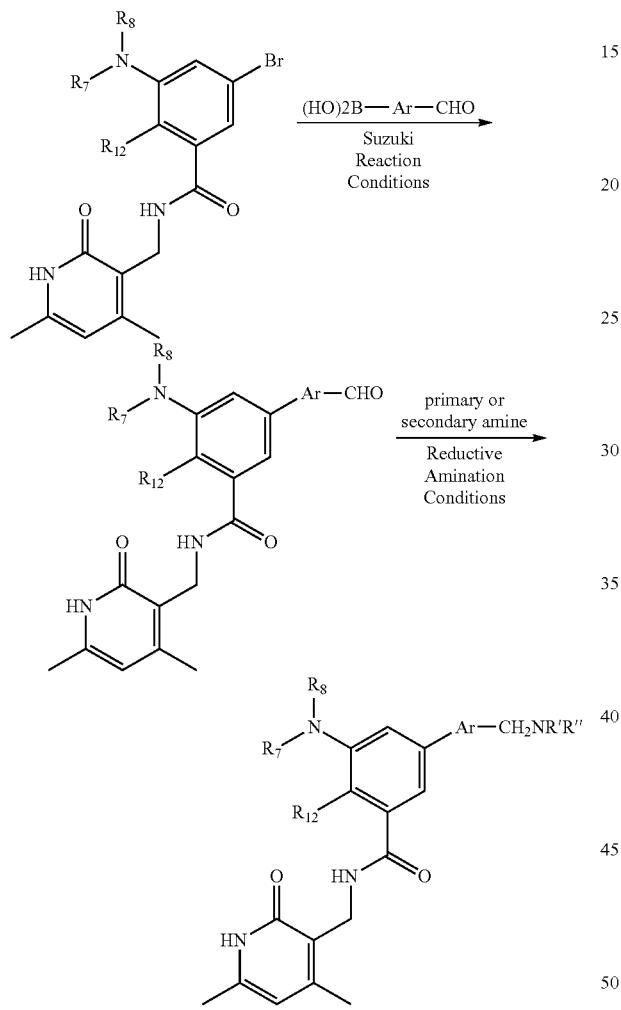

Depending upon the nature of the $R_7$ substituent, further chemical modification subsequent to Step 6 of Scheme 1 could be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 4 shows the general synthesis of 2,6-disubstituted isonicotinamide compounds. Suzuki reaction in Step 1 of an aryl boronic acid compound with methyl 2,6-dichloroisonicotinate starting material can be used to introduce an aryl group which may be substituted with a functional group X that is suitable for further transformation. Such X groups include formyl or hydroxymethyl which can readily be transformed in Step 2 to various groups Y. Such Y groups include aminomethyl, monoalkylaminomethyl and dialkylaminomethyl groups. The latter can be prepared by reductive amination in the case where X is formyl or by converting X=hydroxymethyl to bromomethyl followed by alkylation with an amine Ester hydrolysis a subsequent step gives an acid intermediate which can be coupled with appropriate 3-(aminomethyl)-pyridin-2(1H)-ones to give the penultimate 2-chloro-6-aryl-isonicotine amide intermediate. Suzuki reaction or amination reaction then gives compounds substituted in the 2-position with a Z group. In the case of an amination reaction examples of Z can be monoalkylamino or dialkylamino. In the case of a Suzuki reaction Z can be aryl, dihydroaryl or tetrahydroaryl such as cyclohexenyl.

Scheme 4

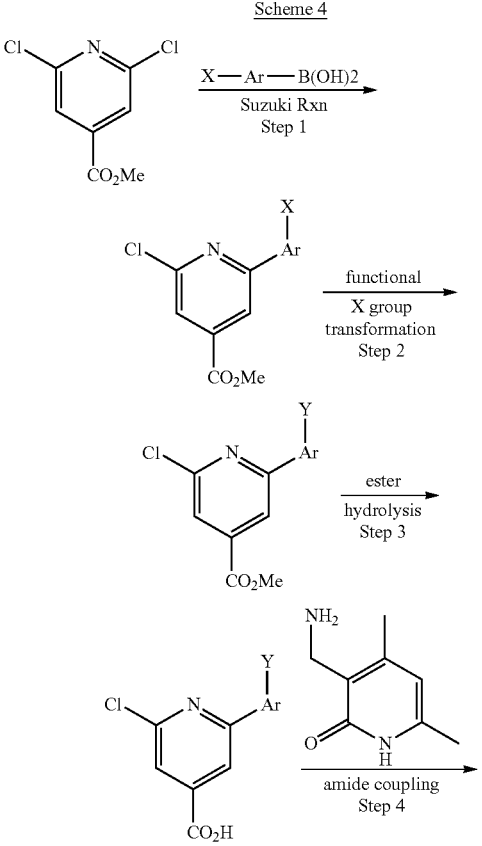

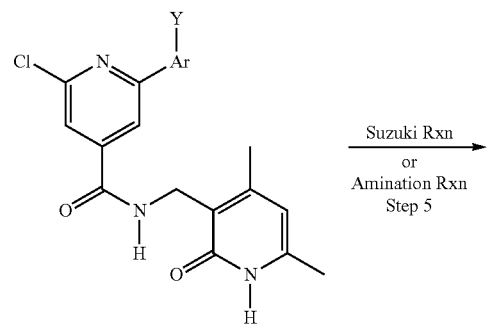

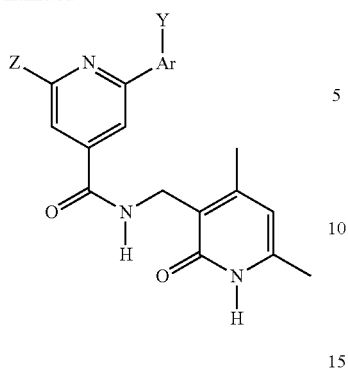

Scheme 5 shows the general synthesis of 6-aryl-3-methyl-picolinamides having monoalkylamino or dialkylamino groups in the 4-position. Starting from methyl 3-bromo-6-chloropicolinate oxidation to the N-oxide followed by chlorination with phosphorus oxychloride gives methyl 3-bromo-4,6-dichloropicolinate. The 4-chloro group can be selectively substituted with diverse mono and dialkyl amines which may also contain functional or protected functional groups that may be unmasked at a later stage. Palladium catalyzed methylation with tetramethyltin followed by ester hydrolysis and amide coupling with appropriate 3-(aminomethyl)-pyridin-2(1H)-ones yields penultimate 2-chloro pyridine intermediates. Suzuki coupling reaction group of these intermediates with aryl boronic acids results in replacement of the 2-chloro group with an aryl group. Thus, this yields 6-aryl-3-methyl-picolinamides having monoalkylamino or dialkylamino groups in the 4-position. The aryl group which may be substituted with a functional group X that remains in the final product or is converted to an another group by deprotection or functional group conversion reaction e.g. reductive amination.

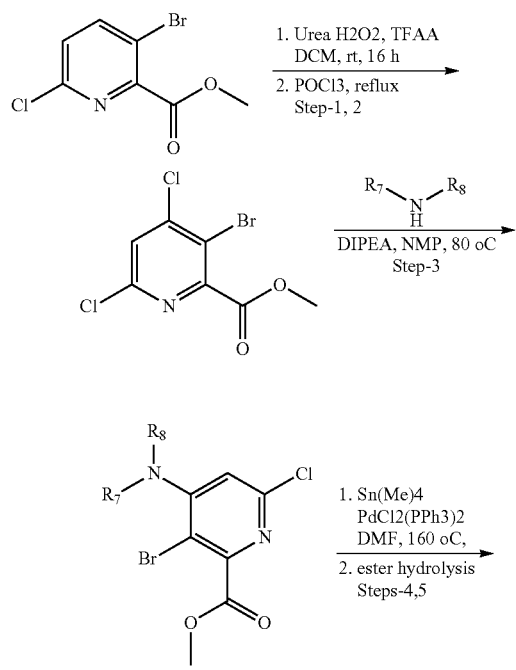

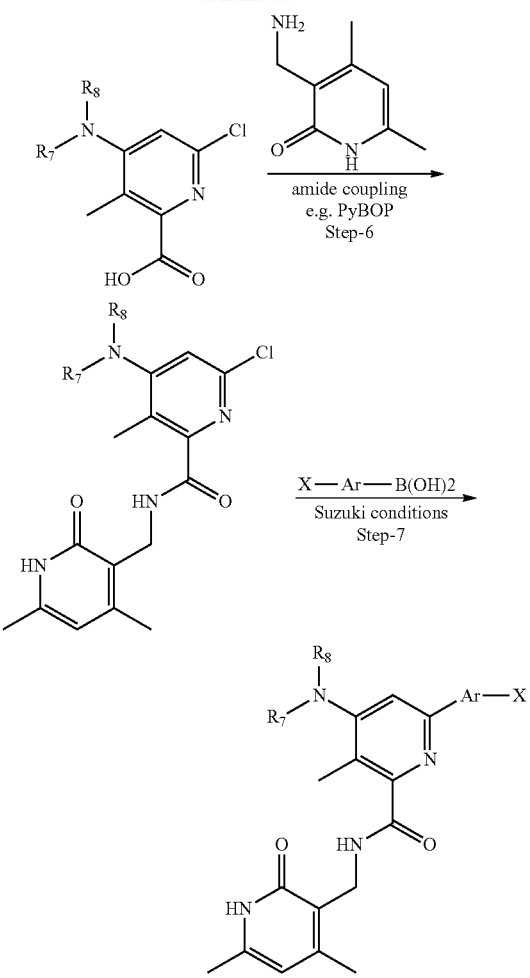

General syntheses of 3-(aminomethyl)-pyridin-2(1H)-ones intermediates for the amide coupling reaction from Scheme 1 are depicted in Scheme 6 below. In one method, a diketone can be condensed with 2-cyanoacetamide in the presence of an appropriate reagent such as piperidine acetate in a polar solvent such as ethanol to provide a cyanopyridone (Step 9). In another method, when $R_3$ is H, an appropriately substituted alkynyl ketone can be condensed with 2-cyanoacetamide in the presence of an appropriate reagent such as piperidine acetate in a polar solvent such as ethanol to provide a cyanopyridone (Step 11). The cyano group can be reduced under appropriate conditions such as hydrogenation in the presence of catalytic Raney nickel in a polar solvent such as ammonium in methanol to provide the amine (Step 10).

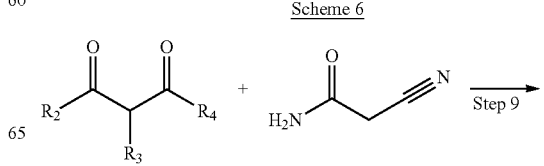

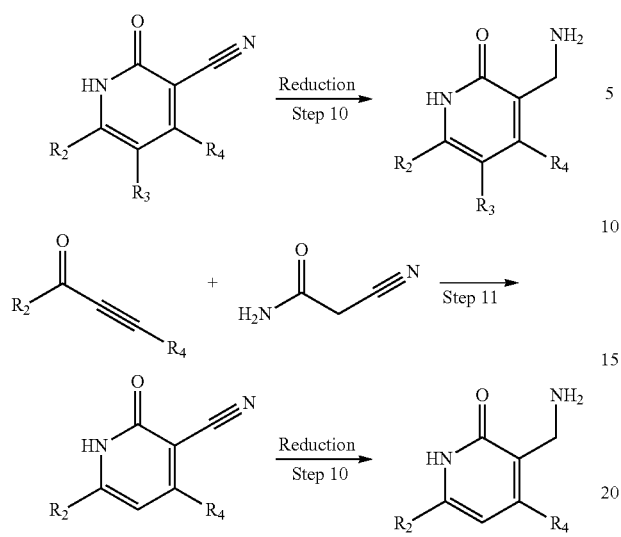

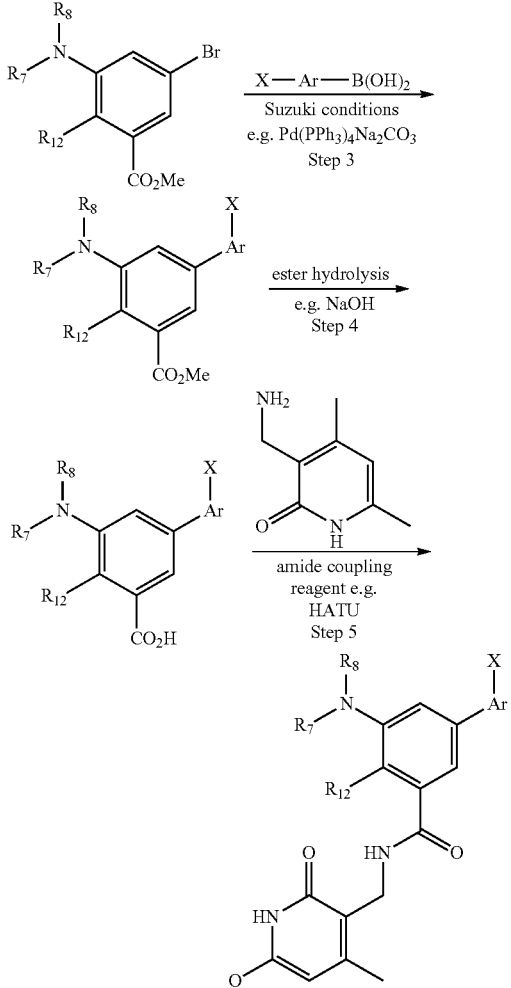

Additionally, depending upon the nature of the $R_2$, $R_3$, or $R_4$ group, further chemical modification can be employed to convert each of them independently into an alternative substituent. A representative sampling of such modifications can include hydrogenation, protecting group removal followed by additional amide coupling reactions, palladium catalyzed coupling reactions, reductive amination reactions, and alkylation reactions.

Scheme 4 depicts a variant of the general synthesis route of Scheme 1 based on 2-substituted (substituent is an $R_{12}$ group) methyl 3-amino-5-bromo-benzoate starting materials. These starting materials can in turn be prepared from 2-substituted 3-nitro-benzoic acids which are commercially available or can be prepared by nitration of 2-substituted benzoic acids. Thus, bromination of 2-substituted 3-nitro-benzoic acids with a suitable reagent such as 1,3-dibromo-5,5-dimethyl-2,4-imidazolidinedione yields the appropriate 2-substituted 3-nitro-5-bromo-benzoic acids. A variety of esterification and then nitro group reduction methods can then be sequentially implemented to prepare the 2-substituted methyl 3-amino-5-bromo-benzoate starting materials from the 2-substituted 3-nitro-5-bromo-benzoic acids.

Scheme 7

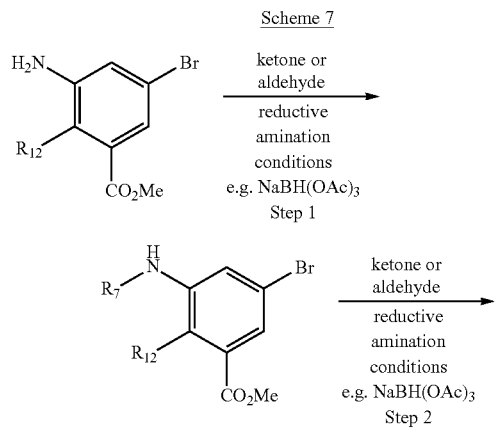

As depicted in Scheme 7 the $R_7$ group can be introduced from 2-substituted methyl 3-amino-5-bromo-benzoates in Step 1 using a reductive amination with an appropriate $R_7$-ketone or $R_7$-aldehyde in the presence of an appropriate reducing agent such as sodium cyanoborohydride and catalytic acid such as acetic acid in an appropriate solvent such as methanol. Similarly, $R_8$ groups can be introduced in Step 2 by reductive amination with $R_8$-ketone or $R_8$-aldehyde in the presence of an appropriate reducing agent such as sodium cyanoborohydride and catalytic acid such as acetic acid in an appropriate solvent such as methanol. Alternatively, a variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. In Step 3, aryl groups corresponding to $R_6$ can be introduced by Suzuki reaction of the intermediate bromide with an appropriate aryl boronic acid or ester derivative, e.g, X—Ar—B(OH)$_2$, in the presence of a mild base and a palladium catalyst in a polar solvent such as dioxane/water, at elevated temperature. The X group in X—Ar—B(OH)$_2$ may be a fully elaborated substituent on the aryl ring or may be a functional group that can be converted into another group by functional group modification. A representative sampling of such modifications could include hydrogenation, protecting group removal followed by additional amide coupling reactions, palladium catalyzed coupling reactions, reductive amination reactions or alkylation reactions. For example if the Suzuki reaction is conducted with a boronic acid derivative bearing a formyl group further modification by reductive amination reaction with primary and secondary amines (e.g. morpholine, dimethylamine) can be conducted to introduce amine groups. In Step 4 the ester moiety can be hydrolyzed to the corresponding acid using a suitable base such as sodium hydroxide in a polar solvent such as ethanol. In Step 5, the acid can be subjected to a standard amide coupling reaction whereupon the appropriate amine would be added along with a suitable amide coupling reagent such as PYBOP in a suitable solvent such as DMSO to give the desired amide. Depending upon the nature of the $R_7$ substituent, further chemical modification subsequent to Step 5 of Scheme 4 could be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 8 below depicts the general synthesis of 2-monoalkylamino and 2-dialkylmino-3-substituted-6-aryl-isonicotinamides wherein the 3-substituent corresponds to $R_{12}$ and the 6-aryl group corresponds to $R_6$, Formula I' In Step 1 the 3-substituent may be introduced by the method described by Epsztain J. et al. *Tetrahedron*, 1991, v. 47, 1697-16708, by metallation of 2-chloro-isonicotinanilide with n-butyl-lithium followed by trapping with an an alkyliodide such as methyliodide or aldehyde or other electrophilic group.

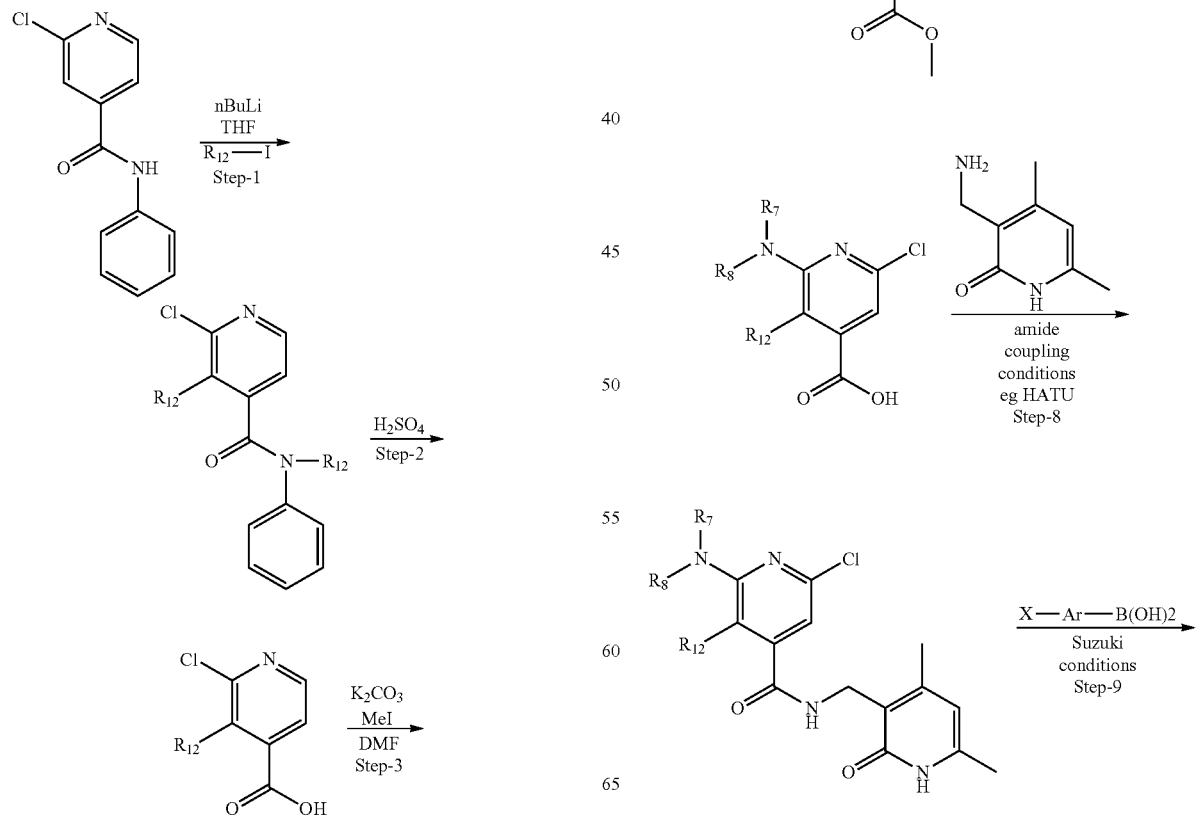

-continued

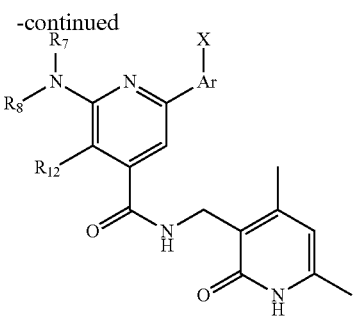

In cases where the trapping reagent yields a substituent with a functional group this group may be masked or converted into another functional group compatible with the subsequent chemical steps. In Step 2 anilide amide hydrolysis under standard acidic conditions maybe conducted followed by methyl ester synthesis under standard conditions for example as shown with methyl iodide and base gives corresponding methyl 2-chloro-3-substituted isonicotinates. In Step 4 an alkylamino group can be introduced by Buchwald coupling reaction of an $R_7NH_2$ monoalkylamine with the methyl 2-chloro-3-substituted isonicotinates. This reaction is well precedented for diverse 2-chloropyridine systems in the chemical literature. In an optional Step 5 for dialkylamino compounds $R_8$ groups can be introduced by reductive amination with $R_8$-ketone or $R_8$-aldehyde in the presence of an appropriate reducing agent such as sodium cyanoborohydride and catalytic acid such as acetic acid in an appropriate solvent such as methanol. Alternatively, a variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. In Step 6, oxidation to the N-oxide followed by chlorination with phosphorus oxychloride gives methyl 6-chloro-2-mono or dialkylamino-3-substituted isonicotinates. In Step 7 the ester moiety can be hydrolyzed to the corresponding acid using a suitable base such as sodium hydroxide in a polar solvent such as ethanol. In Step 8, the acid can be subjected to a standard amide coupling reaction whereupon the appropriate amine or substituted 3-(aminomethyl)-pyridin-2(1H)-one would be added along with a suitable amide coupling reagent such as PYBOP in a suitable solvent such as DMSO to give the desired amide. In Step 9, aryl groups corresponding to $R_6$ can be introduced by Suzuki reaction of the intermediate bromide with an appropriate aryl boronic acid or ester derivative, e,g, X—Ar—$B(OH)_2$, in the presence of a mild base and a palladium catalyst in a polar solvent such as dioxane/water, at elevated temperature. The X group in X—Ar—$B(OH)_2$ may be a fully elaborated substituent on the aryl ring or may be a functional group that can be converted into another group by functional group modification. A representative sampling of such modifications could include hydrogenation, protecting group removal followed by additional amide coupling reactions, palladium catalyzed coupling reactions, reductive amination reactions or alkylation reactions. For example if the Suzuki reaction is conducted with a boronic acid derivative bearing a formyl group further modification by reductive amination reaction with primary and secondary amines (e.g. morpholine, dimethylamine) can be conducted to introduce amine groups. Depending upon the nature of the $R_7$ substituent, further chemical modification steps may be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 9

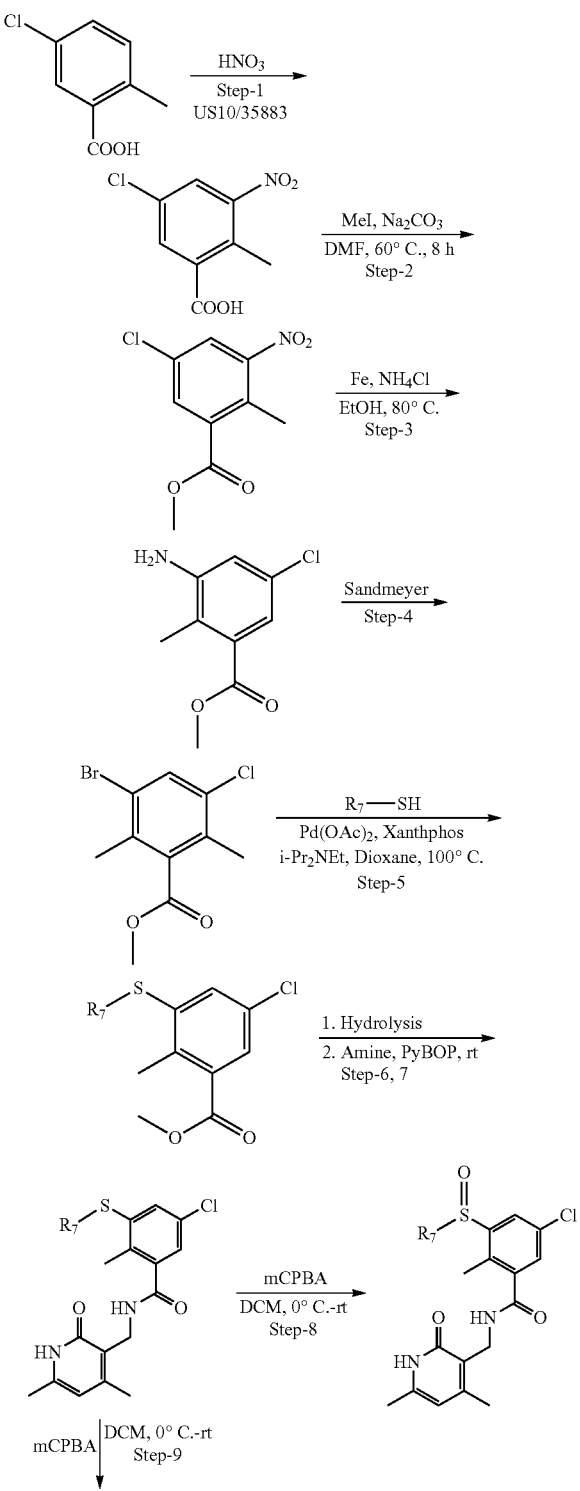

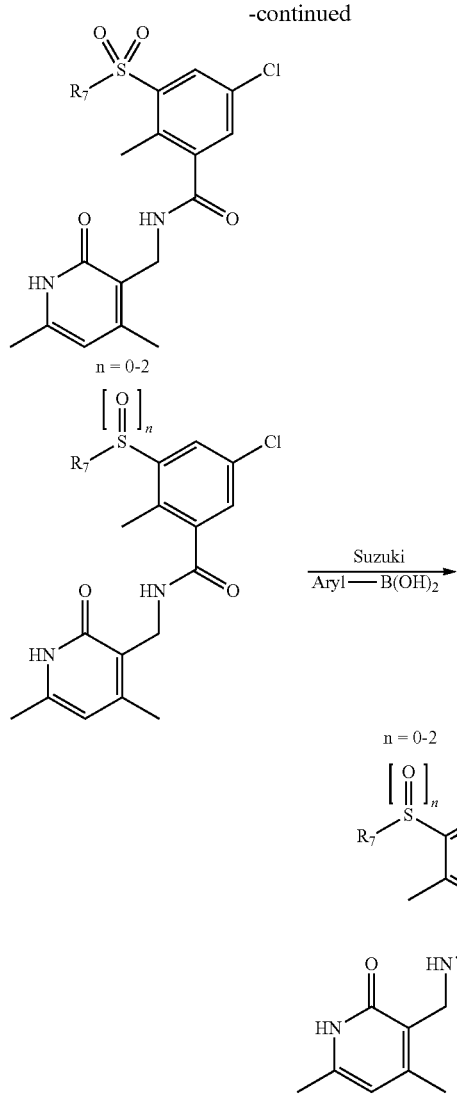

n = 0-2 n = 0-2

Scheme 9 depicts a synthesis of modified aryl analogs following a general route that utilizes well-established chemistry. Starting with a substituted benzoic acid such as 5-chloro-2-methylbenzoic acid, nitration using standard conditions such as treatment with conc. $H_2SO_4$ and conc. $HNO_3$ can provide the nitro analog. Esterification of the acid can be achieved using an alkylating agent such as methyl iodide in the presence of a base such as sodium carbonate in a polar solvent such as DMF. The nitro group can be reduced using conditions such iron and ammonium chloride in a protic solvent such as ethanol with heating to a temperature such as 80° C. The resulting aniline can be converted to a bromide using a Sandmeyer reaction such treatment with $CuBr_2$ and t-butyl nitrite in a solvent such as acetonitrile. A palladium catalyzed coupling of a thiol with the bromide can be achieved using a palladium source such as $Pd(OAc)_2$ with a ligand such as Xanthphos in the presence of a base such as N,N-diisopropyl ethylamine in a solvent such as 1,4-dioxane optionally heating to a temperature such as 100° C. The ester can be hydrolyzed with an aqueous base such as NaOH in water. The resulting acid can be coupled to the 3-(aminomethyl)-4,6-dimethylpyridin-2(1H)-one using standard amino acid coupling conditions such as PYBOP in DMSO. The resulting thioether may be oxidized to the corresponding sulfoxide or sulfone by using the appropriate equivalents of an oxidant such as m-CPBA in a solvent such as DCM. Aryl substituents can be incorporated by using palladium couplings such as a Suzuki reaction as described above.

Scheme 10

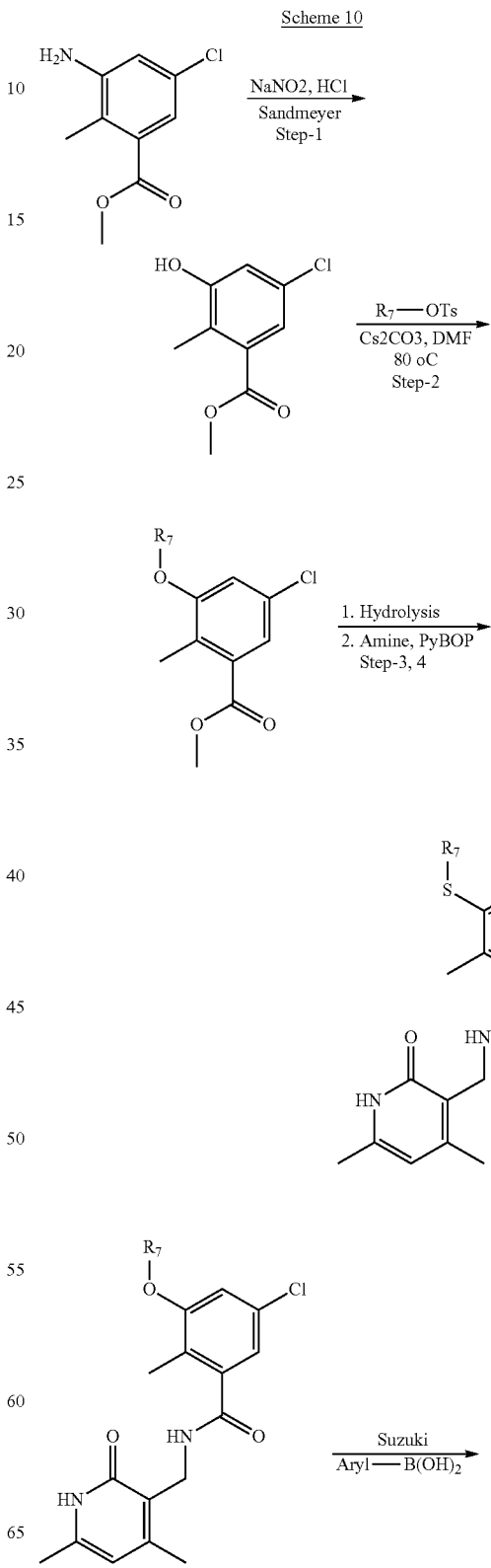

-continued

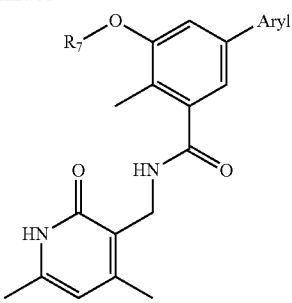

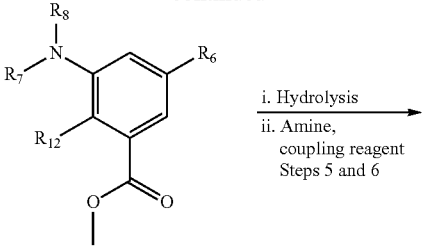

i. Hydrolysis
ii. Amine, coupling reagent
Steps 5 and 6

Scheme 10 depicts a synthesis of modified aryl analogs following a general route that utilizes well-established chemistry. Starting with a substituted aniline such as methyl 3-amino-5-chloro-2-methylbenzoate, the aniline can be converted to a phenol using a Sandmeyer reaction such as treatment with aqueous $NaNO_2$ solution in a aqueous acid such as 50% $H_2SO_4$. The phenol can be alkylated using an alkylating agent such as tetrahydro-2H-pyran-4-yl 4-methylbenzenesulfonate in the presence of an appropriate base such as cesium carbonate in as polar solvent such as DMF optionally heating to a temperature such as 80° C. The ester can be hydrolyzed with an aqueous base such as NaOH in water. The resulting acid can be coupled to the 3-(amino methyl)-4,6-dimethylpyridin-2(1H)-one using standard amino acid coupling conditions such as PYBOP in DMSO. Aryl substituents can be incorporated by using palladium couplings such as a Suzuki reaction as described above.

Scheme 1'

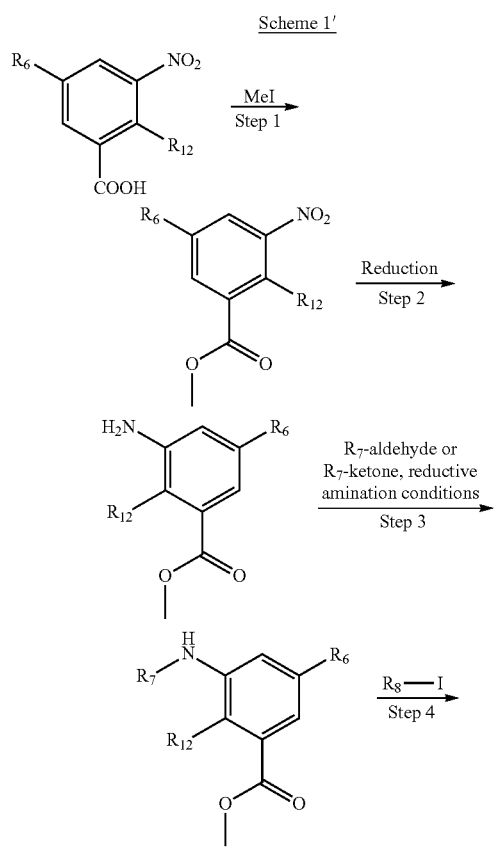

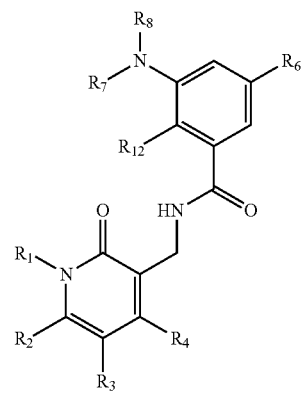

Scheme 1' shows the synthesis of benzene analogs wherein Z=—$N(R_7)(R_8)$ following a general route that utilizes well-established chemistry. Substituted nitrobenzoic acids, many of which are commercially available or can be prepared by nitrations of the appropriate substituted benzoic acids or other chemistry known to one skilled in the art, can be converted to their methyl esters by treatment with methyliodide in a polar solvent such as DMF in the presence of an appropriate base such as sodium carbonate at an appropriate temperature such as 60° C. (Step 1). The nitro group can be reduced to an amine using an appropriate reducing agent such as iron in the presence of an acid such as ammonium chloride in a protic solvent such as ethanol at an appropriate temperature such as 80° C. (Step 2). Introduction of the $R_7$ can be done using a reductive amination with an appropriate $R_7$-ketone or $R_7$-aldehyde in the presence of an appropriate reducing agent such as sodium cyanoborohydride and catalytic acid such as acetic acid in an appropriate solvent such as methanol. A variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. (Step 4). Alternatively, $R_5$ groups can be introduced by reductive amination with $R_8$-ketone or $R_8$-aldehyde in the presence of an appropriate reducing agent such as sodium cyanoborohydride and catalytic acid such as acetic acid in an appropriate solvent such as methanol. The ester moiety can be converted to an amide using a standard two step protocol. The ester can be hydrolyzed to the corresponding acid using a suitable base such as sodium hydroxide in a polar solvent such as ethanol (Step 5). The acid would then be subjecting to a standard amide coupling reaction whereupon the appropriate amine would be added along with a suitable amide coupling reagent such as PYBOP in a suitable solvent such as DMSO to give the desired amide (Step 6).

Scheme 2'

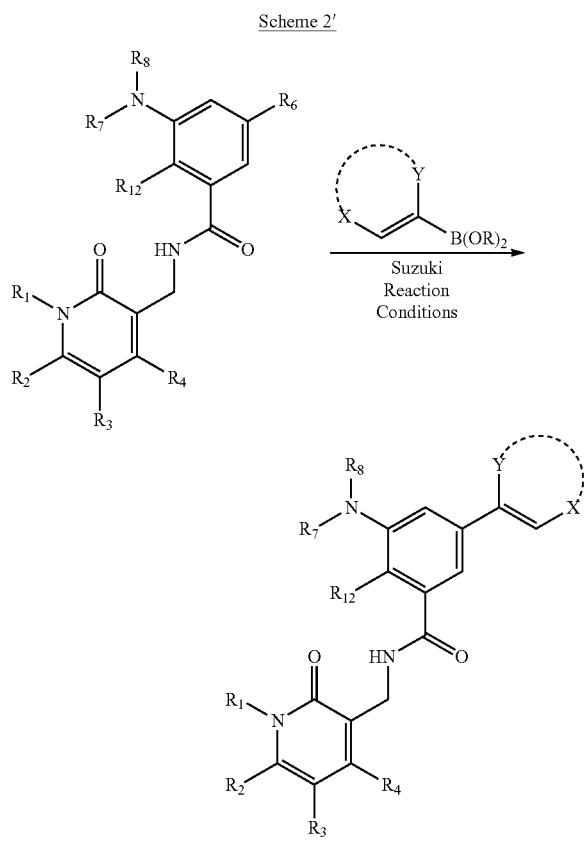

Depending upon the nature of the $R_6$ substituent, further chemical modification could be employed to convert the $R_6$ substituent into an alternative $R_6$ substituent. A representative sampling of such modifications could include hydrogenation, protecting group removal followed by additional amide coupling reactions, palladium catalyzed coupling reactions, reductive amination reactions or alkylation reactions. For example, if $R_6$ is a bromide, alternative $R_6$ substituents could then be introduced using standard transition metal-based protocols that rely upon a leaving group such as a bromide as a connection point.

In one such protocol as depicted in Scheme 2' non-aromatic $R_6$ substituents attached via a carbon-carbon bond may be introduced by Suzuki reaction of a compound where $R_6$=Br with an appropriate unsaturated non-aromatic boronic ester derivative (e.g. an olefinic boronic ester derivative such as vinyl 4,4,5,5-tetramethyl-2-vinyl-1,3,2-dioxaborolane) in the presence of a mild base and a palladium catalyst in a polar solvent such as dioxane/water, at elevated temperature to give the desired new $R_6$ substituent. Depending upon the nature of the $R_6$ substituent, further chemical modification could be employed to convert the unsaturated $R_6$ substituent into an alternative $R_6$ substituent. A representative sampling of such modifications could include hydrogenation, protecting group removal followed by additional amide coupling reactions, palladium catalyzed coupling reactions, reductive amination reactions or alkylation reactions. For example, in cases where an unsaturated non-aromatic $R_6$ group is introduced, further modification by hydrogenation can give the corresponding saturated $R_6$ group (e.g. conversion of a vinyl group to an ethyl group). In cases of where $R_6$ groups introduced have protected amine functionality further modifications include deprotection to give amines which may in subsequent steps be further modified for example by amide formation or reductive amination reactions.

In another protocol as depicted in Scheme 3', non-aromatic $R_6$ substituents attached via a carbon-carbon bond may be introduced by Sonogashira reaction of a compound where $R_6$=Br optionally followed by further modification of the introduced alkynyl group. In the Sonogashira reaction, a compound where $R_6$=Br is coupled with a terminal alkyne derivative in the presence of a mild base, a copper catalyst and a palladium catalyst in an organic solvent such as toluene at elevated temperature. This results in the replacement of the Br group with an alkynyl group. The resulting compound wherein the $R_6$ substituent is an alkynyl group may be subject to subsequent suitable modifications to give an alternative $R_6$ substituent. A representative sampling of such modifications could include hydrogenation, protecting group removal followed by additional amide coupling reactions, reductive amination reactions or alkylation reactions.

Scheme 3'

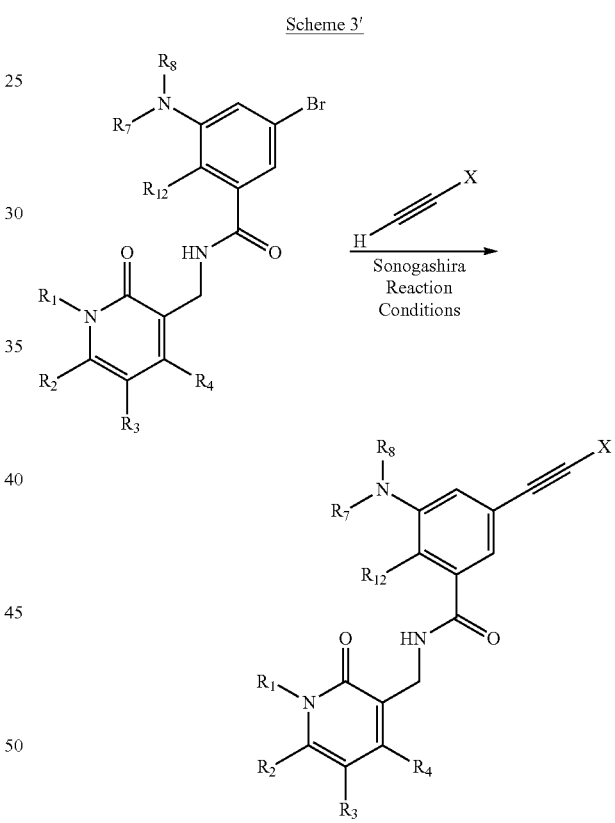

In another protocol non-aromatic $R_6$ substituents attached via a carbon-carbon bond may be prepared by other substitution reactions of the bromine atom compounds where $R_6$=Br, optionally followed by further modification of the introduced $R_6$ group. Examples of such substitution reactions include coupling reactions with zinc reagents such as cyanation and Negishi reactions. In the case of cyanation reaction, compounds where $R_6$=Br may be reacted with zinc cyanide under standard palladium catalyst mediated reaction conditions to give compounds where $R_6$=CN. The cyano group in such compounds may be subject to further modification to give other $R_6$ groups. Such cyano modifications include i. reduction to an amine which may be subsequently converted to an amide by acylation or alkylation, ii. reduction to an aldehyde which may be subjected to reductive amination reaction to give corresponding derivatives. In Negishi reactions alkylzinc reagents which may be prepared from alkyl iodides (e.g. N-Boc-3-iodoazetidine) are coupled to compounds where $R_6$=Br using palladium or nickel catalysts. In the resulting products the introduced $R_6$ group may be converted to an alternative group by further modifications of the $R_6$ group in subsequent steps such as deprotection, amide formation or alkylation.

Compounds with $R_6$ substituents which are amines attached via a nitrogen-carbon bond may be introduced by Buchwald coupling reaction of compounds where $R_6$=Br followed by optional modification of the $R_6$ group as depicted in Scheme 4'. In the Buchwald reaction compounds where $R_6$=Br are treated with a primary or secondary amine (e.g. tert-butyl piperazine-1-carboxylate) in the presence of a palladium catalyst (e.g. Pd(dba)2/BINAP) and a base (e.g. cesium carbonate) in an organic solvent (e.g. toluene) at elevated temperature. The Buchwald coupling product may be subjected to subsequent suitable modifications to give an alternative $R_6$ substituent. Such modifications are exemplified by protecting group removal, amide coupling reactions, reductive amination reactions or alkylation reactions.

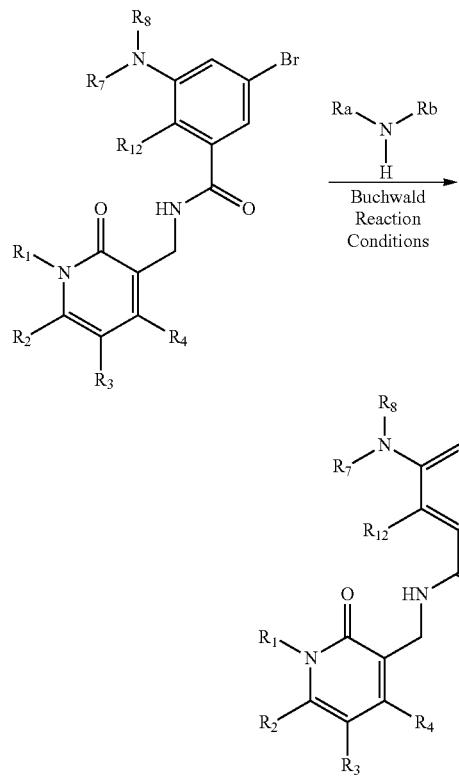

Compounds with $R_6$ substituents which are alkylthio groups attached via a sulfur-carbon bond may be prepared by coupling reaction of compounds where $R_6$=Br with thiols in the presence of a palladium catalyst and a weak base (e.g. DIPEA) in an organic solvent at elevated temperature. The coupling product sulfides may be subject to subsequent suitable modifications to give an alternative $R_6$ substituent. Such modifications include sulfur oxidation reactions to give sulfoxides and sulfones, protecting group removal, amide coupling reactions, reductive amination reactions or alkylation reactions.

In a modification of the general synthesis in Scheme 1', depending upon the nature of the $R_7$ substituent, further chemical modification subsequent to Step 6 of Scheme 1' could be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 5' shows the general synthesis of picolinamide compounds. Starting from methyl 3-bromo-6-chloropicolinate oxidation to the N-oxide followed by chlorination with phosphorus oxychloride gives methyl 3-bromo-4,6-dichloropicolinate. The 4-chloro group can be selectively substituted with diverse mono and dialkyl amines which may also contain functional or protected functional groups that may be unmasked at a later stage. The 3-bromo group may be retained or may be optionally converted into an alternative $R_{12}$ group by suitable substitution reaction and further functional group modifications. Such reactions include coupling reactions mediated with palladium catalysts. For example the 3-bromo group may be converted to an $R_{12}$=methyl group by Stine reaction with tetramethyltin. Ester hydrolysis followed by amide coupling with appropriate 3-(aminomethyl)-pyridin-2-ones yields picolinamide compounds wherein $R_6$ is a chloro group. The chloro group may optionally be converted to alternative $R_6$ groups by suitable substitution reactions either in a final step or alternatively prior to ester hydrolysis Step 6. Examples of such substitution reactions include cyanation and amination reactions either directly or mediated with palladium catalysts. Analogous compounds wherein $R_{12}$ is chloro may be prepared in analogous fashion from methyl 3,4,6-trichloropyridine-2-carboxylate.

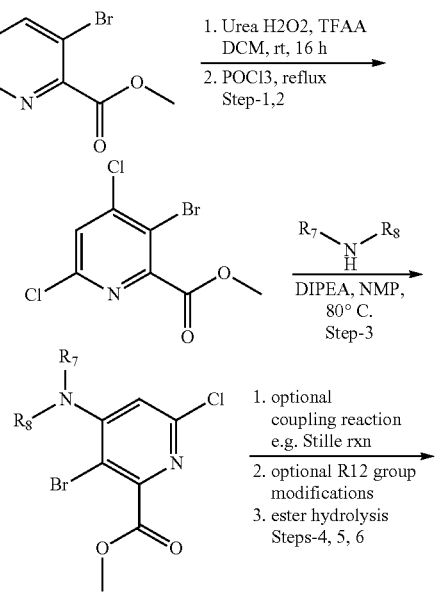

-continued

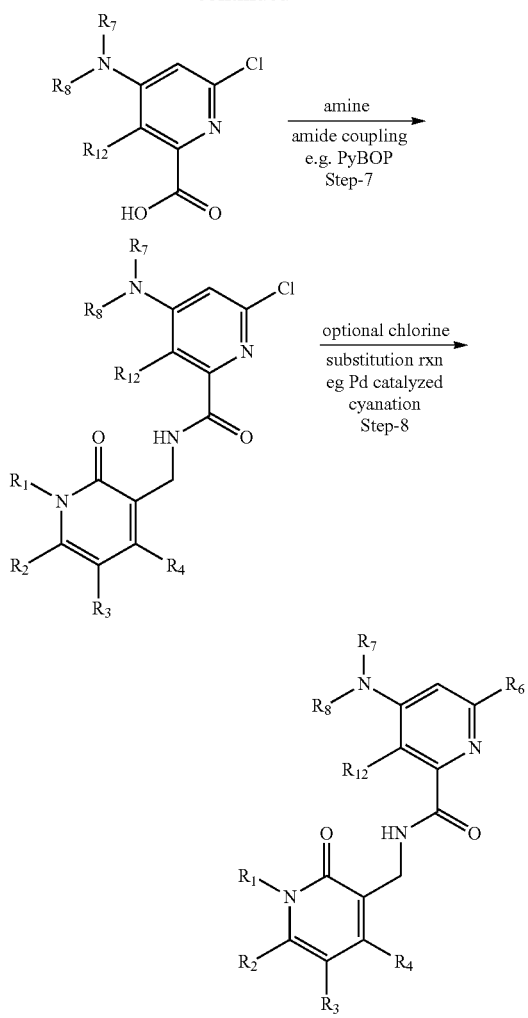

General syntheses of 3-(aminomethyl)-pyridin-2(1H)-ones intermediates for the amide coupling reaction from Scheme 1' are depicted in Scheme 6'. In one method, a diketone can be condensed with 2-cyanoacetamide in the presence of an appropriate reagent such as piperidine acetate in a polar solvent such as ethanol to provide a cyanopyridone (Step 9). In another method, when $R_3$ is H, an appropriately substituted alkynyl ketone can be condensed with 2-cyano-acetamide in the presence of an appropriate reagent such as piperidine acetate in a polar solvent such as ethanol to provide a cyanopyridone (Step 11). The cyano group can be reduced under appropriate conditions such as hydrogenation in the presence of catalytic Raney nickel in a polar solvent such as ammonium in methanol to provide the amine (Step 10).

Scheme 6'

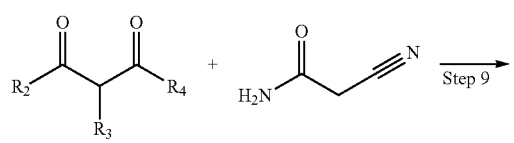

-continued

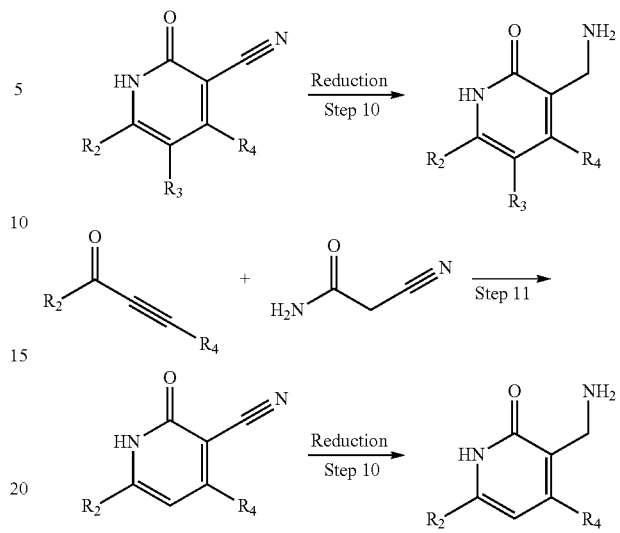

Additionally, depending upon the nature of the $R_2$, $R_3$, or $R_4$ group, further chemical modification can be employed to convert each of them independently into an alternative substituent. A representative sampling of such modifications can include hydrogenation, protecting group removal followed by additional amide coupling reactions, palladium catalyzed coupling reactions, reductive amination reactions, and alkylation reactions.

Scheme 7' depicts a variant of the general synthesis route of Scheme 1' based on 2-substituted (substituent is an $R_{12}$ group) methyl 3-amino-5-bromo-benzoate starting materials. These starting materials can in turn be prepared from 2-substituted 3-nitro-benzoic acids which are commercially available or can be prepared by nitration of 2-substituted benzoic acids. Thus, bromination of 2-substituted 3-nitro-benzoic acids with a suitable reagent such as 1,3-dibromo-5,5-dimethyl-2,4-imidazolidinedione yields the appropriate 2-substituted 3-nitro-5-bromo-benzoic acids. A variety of esterification and then nitro group reduction methods can then be sequentially implemented to prepare the 2-substituted methyl 3-amino-5-bromo-benzoate starting materials from the 2-substituted 3-nitro-5-bromo-benzoic acids.

Scheme 7'

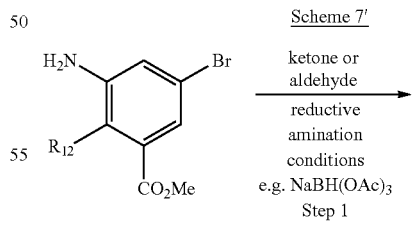

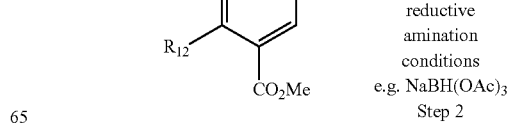

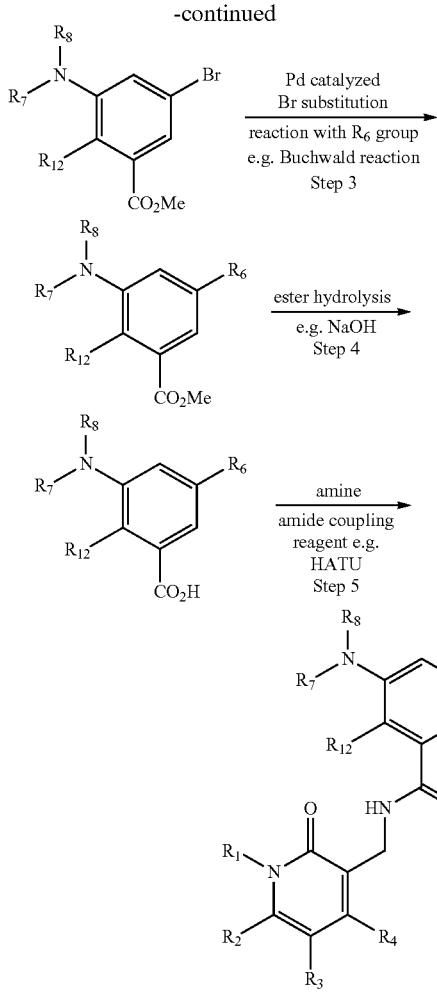

lation reactions. In Step 4 the ester moiety can be hydrolyzed to the corresponding acid using a suitable base such as sodium hydroxide in a polar solvent such as ethanol. In Step 5, the acid can be subjected to a standard amide coupling reaction whereupon the appropriate 3-(aminomethyl)-pyridin-2-one would be added along with a suitable amide coupling reagent such as PYBOP in a suitable solvent such as DMSO to give the desired amide. Depending upon the nature of the $R_7$ substituent, further chemical modification subsequent to Step 5 of Scheme 4' could be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 8' below depicts the general synthesis of 2-monoalkylamino and 2-dialkylamino-3,6-disubstituted-isonicotinamides wherein the 3-substituent corresponds to $R_{12}$ and the 6-substituent corresponds to $R_6$. In Step 1 the 3-substituent may be introduced by the method described by Epsztain J. et al. *Tetrahedron*, 1991, v. 47, 1697-16708, by metalation of 2-chloro-isonicotinanilide with n-butyllithium followed by trapping with an alkyliodide such as methyliodide or aldehyde or other electrophilic group.

Scheme 8'

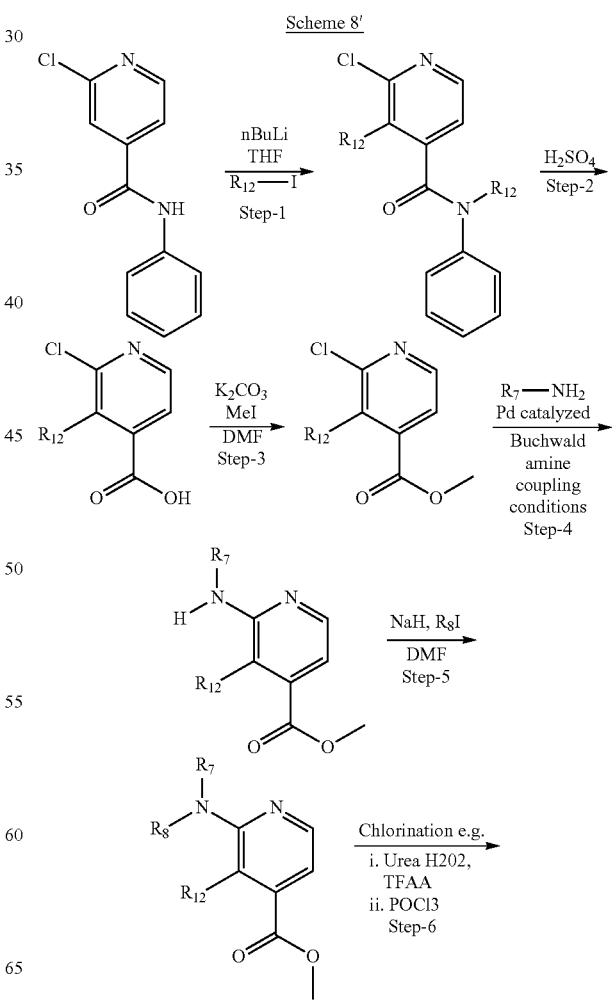

As depicted in Scheme 7' the $R_7$ group can be introduced from 2-substituted methyl 3-amino-5-bromo-benzoates in Step 1 using a reductive amination with an appropriate $R_7$-ketone or $R_7$-aldehyde in the presence of an appropriate reducing agent such as sodium cyanoborohydride and catalytic acid such as acetic acid in an appropriate solvent such as methanol. Similarly, $R_8$ groups can be introduced in Step 2 by reductive amination with $R_8$-ketone or $R_8$-aldehyde in the presence of an appropriate reducing agent such as sodium cyanoborohydride and catalytic acid such as acetic acid in an appropriate solvent such as methanol. Alternatively, a variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. In Step 3, $R_6$ groups other than bromine can be introduced via palladium catalyzed coupling reactions. Examples of such $R_6$ groups and methods have been described above. For example amines may be introduced by Buchwald reactions and unsaturated groups may be introduced by Suzuki or Sonogashiri reactions. The $R_6$ substituent may be subject to subsequent suitable modifications to give an alternative $R_6$ substituent. A representative sampling of such modifications could include hydrogenation (e.g. to saturate unsaturated groups), protecting group removal followed by additional amide coupling reactions, reductive amination reactions or alky-

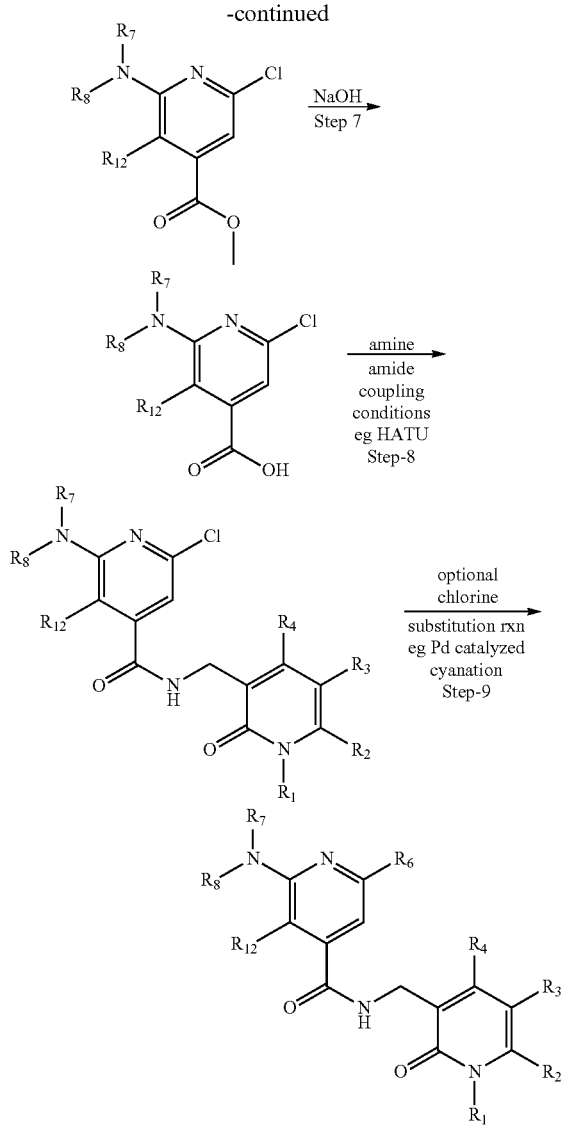

priate temperature such as 80° C. In Step 6, oxidation to the N-oxide followed by chlorination with phosphorus oxychloride gives methyl 6-chloro-2-mono or dialkylamino-3-substituted isonicotinates. In Step 7 the ester moiety can be hydrolyzed to the corresponding acid using a suitable base such as sodium hydroxide in a polar solvent such as ethanol. In Step 8, the acid can be subjected to a standard amide coupling reaction whereupon the appropriate substituted 3-(aminomethyl)-pyridin-2-one would be added along with a suitable amide coupling reagent such as PYBOP in a suitable solvent such as DMSO to give the desired amide. In Step 9, the chloro group may optionally be converted to alternative $R_6$ groups by suitable substitution reactions either in a final step or alternatively prior to ester hydrolysis Step 6. Examples of such substitution reactions include cyanation and amination reactions either directly or mediated with palladium catalysts. The $R_6$ substituent may be subject to subsequent suitable modifications to give an alternative $R_6$ substituent. A representative sampling of such modifications could include hydrogenation (e.g. to saturate unsaturated groups), protecting group removal followed by additional amide coupling reactions, reductive amination reactions or alkylation reactions. Depending upon the nature of the $R_7$ substituent, further chemical modification steps may be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

In cases where the trapping reagent yields a substituent with a functional group this group may be masked or converted into another functional group compatible with the subsequent chemical steps. In Step 2 anilide amide hydrolysis under standard acidic conditions may be conducted followed by methyl ester synthesis under standard conditions for example as shown with methyl iodide and base gives corresponding methyl 2-chloro-3-substituted isonicotinates. In Step 4 an alkylamino group can be introduced by Buchwald coupling reaction of an $R_7NH_2$ monoalkylamine with the methyl 2-chloro-3-substituted isonicotinates. This reaction is well precedented for diverse 2-chloropyridine systems in the chemical literature. In an optional Step 5 for dialkylamino compounds $R_8$ groups can be introduced by reductive amination with $R_8$-ketone or $R_8$-aldehyde in the presence of an appropriate reducing agent such as sodium cyanoborohydride and catalytic acid such as acetic acid in an appropriate solvent such as methanol. Alternatively, a variety of $R_8$ groups can be introduced by alkylation using $R_8$-LG, where LG is a leaving group such as iodine, in the presence of a mild base such as cesium carbonate in an appropriate polar solvent such as acetonitrile at an appro- Scheme 9'

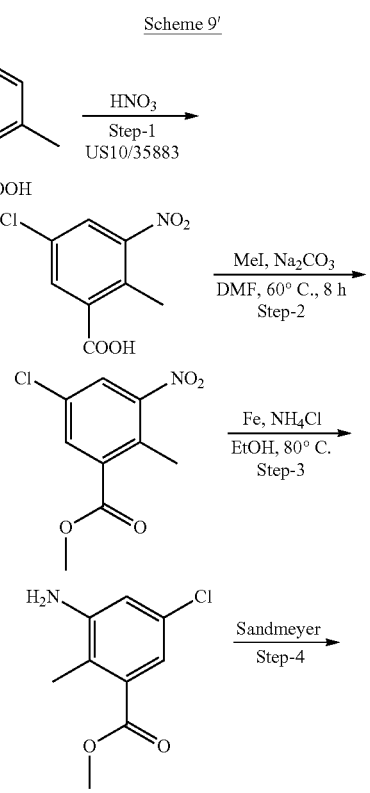

-continued

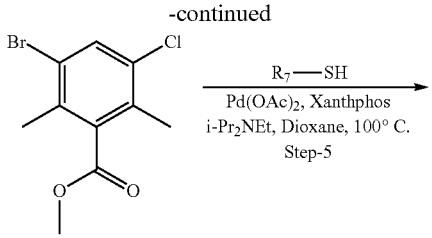

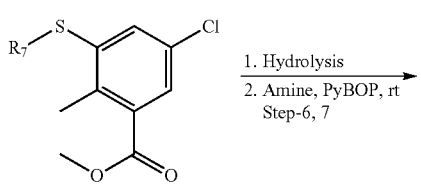

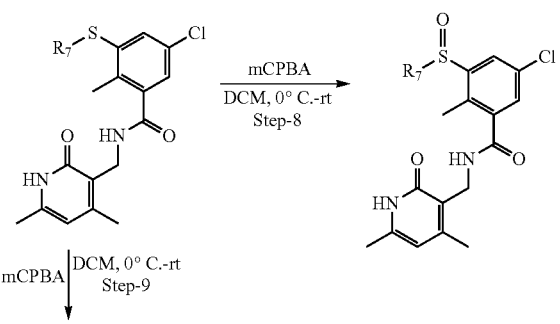

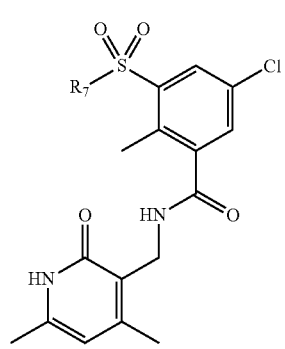

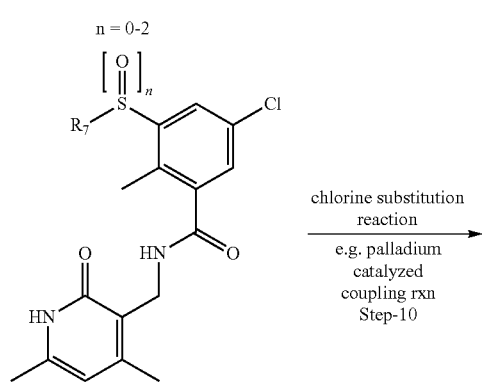

-continued

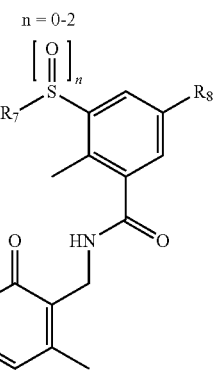

Scheme 9' depicts a synthesis of benzene analogs wherein Z is a sulfide, sulfoxide or sulfone group following a general route that utilizes well-established chemistry. Starting with a substituted benzoic acid such as 5-chloro-2-methylbenzoic acid, nitration using standard conditions such as treatment with conc. $H_2SO_4$ and conc. $HNO_3$ can provide the nitro analog. Esterification of the acid can be achieved using an alkylating agent such as methyl iodide in the presence of a base such as sodium carbonate in a polar solvent such as DMF. The nitro group can be reduced using conditions such iron and ammonium chloride in a protic solvent such as ethanol with heating to a temperature such as 80° C. The resulting aniline can be converted to a bromide using a Sandmeyer reaction such treatment with $CuBr_2$ and t-butyl nitrite in a solvent such as acetonitrile. A palladium catalyzed coupling of a thiol with the bromide can be achieved using a palladium source such as $Pd(OAc)_2$ with a ligand such as Xanthphos in the presence of a base such as N,N-diisopropyl ethylamine in a solvent such as 1,4-dioxane optionally heating to a temperature such as 100° C. The ester can be hydrolyzed with an aqueous base such as NaOH in water. The resulting acid can be coupled to the appropriate substituted 3-(aminomethyl)-pyridin-2-one (e.g. 3-(aminomethyl)-4,6-dimethylpyridin-2(1H)-one as depicted in Scheme 9') using standard amino acid coupling conditions such as PYBOP in DMSO. The resulting thioether may be oxidized to the corresponding sulfoxide or sulfone by using the appropriate equivalents of an oxidant such as m-CPBA in a solvent such as DCM. The $R_6$ chloro group may be replaced with an alternative $R_6$ group in an additional Step 10 or after Step 5 or prior to amide coupling. Examples of alternative $R_6$ groups include substituents that can be incorporated by using palladium couplings such as a Buchwald reaction to give amine groups (e.g. morpholino). The $R_6$ substituent may be subject to subsequent suitable modifications to give an alternative $R_6$ substituent. A representative sampling of such modifications includes protecting group removal followed by additional amide coupling reactions, reductive amination reactions or alkylation reactions.

Scheme 10'

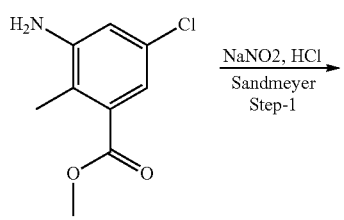

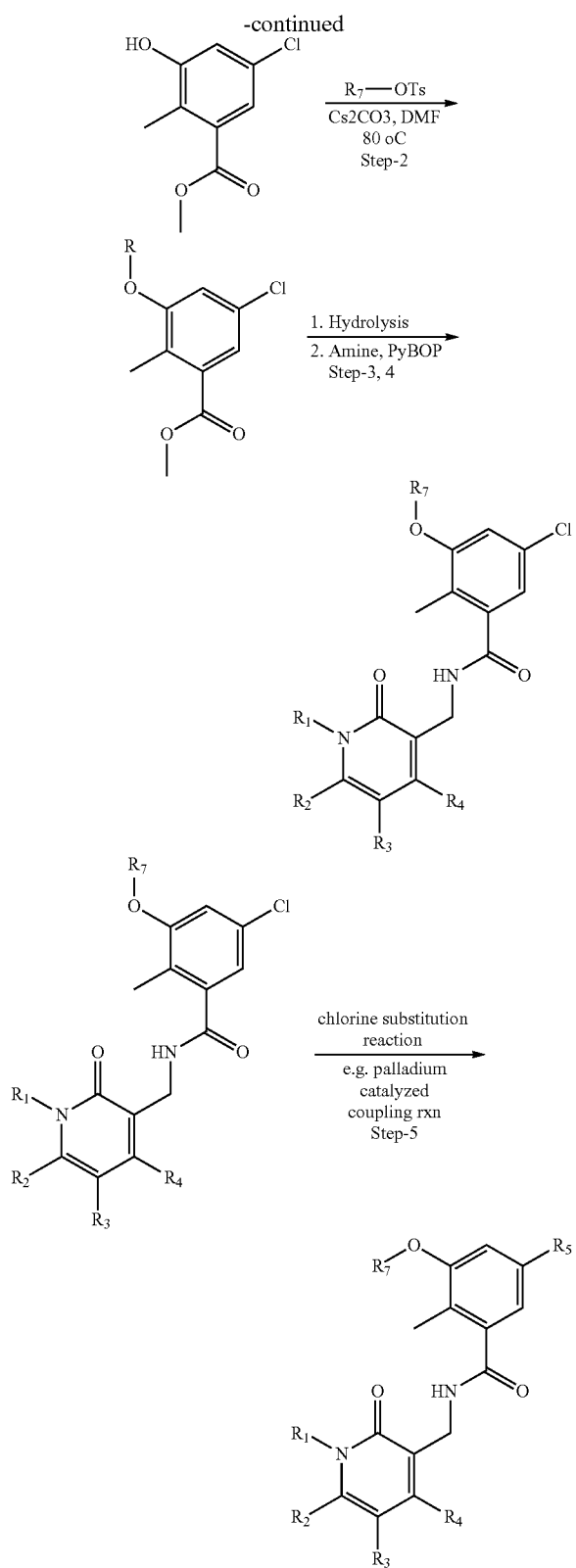

using a Sandmeyer reaction such as treatment with aqueous NaNO$_2$ solution in a aqueous acid such as 50% H$_2$SO$_4$. The phenol can be alkylated using an alkylating agent such as tetrahydro-2H-pyran-4-yl 4-methylbenzenesulfonate in the presence of an appropriate base such as cesium carbonate in as polar solvent such as DMF optionally heating to a temperature such as 80° C. The ester can be hydrolyzed with an aqueous base such as NaOH in water. The resulting acid can be coupled to the appropriate substituted 3-(aminomethyl)-pyridin-2-one using standard amino acid coupling conditions such as PYBOP in DMSO. The R$_6$ chloro group may be replaced with an alternative R$_6$ group in an additional after Step 5 or prior to amide coupling. Examples of alternative R$_6$ groups include substituents that can be incorporated by using palladium couplings such as a Buchwald reaction to give amine groups (e.g. morpholino). The R$_6$ substituent may be subject to subsequent suitable modifications to give an alternative R$_6$ substituent. A representative sampling of such modifications includes protecting group removal followed by additional amide coupling reactions, reductive amination reactions or alkylation.

Compounds of the present invention inhibit the histone methyltransferase activity of EZH2 or a mutant thereof and, accordingly, in one aspect of the invention, certain compounds disclosed herein are candidates for treating, or preventing certain conditions and diseases. The present invention provides methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, polymorph, solvate, or stereoisomeror thereof.

Unless otherwise stated, any description of a method of treatment includes uses of the compounds to provide such treatment or prophylaxis as is described in the specification, as well as uses of the compounds to prepare a medicament to treat or prevent such condition. The treatment includes treatment of human or non-human animals including rodents and other disease models.

In still another aspect, this invention relates to a method of modulating the activity of the EZH2, the catalytic subunit of the PRC2 complex which catalyzes the mono- through tri-methylation of lysine 27 on histone H3 (H3-K27) in a subject in need thereof. For example, the method comprises the step of administering to a subject having a cancer expressing a mutant EZH2 a therapeutically effective amount of a compound described herein, wherein the compound(s) inhibits histone methyltransferase activity of EZH2, thereby treating the cancer.

For example, the cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin's lymphoma (NHL), follicular lymphoma or diffuse large B-cell lymphoma. Alternatively, the leukemia is chronic myelogenous leukemia (CML), acute myeloid leukemia, acute lymphocytic leukemia or mixed lineage leukemia.

Scheme 10' depicts a synthesis of modified benzene analogs wherein L is an ether group following a general route that utilizes well-established chemistry. Starting with a substituted aniline such as methyl 3-amino-5-chloro-2-methylbenzoate, the aniline can be converted to a phenol For example, the precancerous condition is myelodysplastic syndromes (MDS, formerly known as preleukemia).

For example, the cancer is a hematological cancer.

The compound(s) of the present invention inhibit the histone methyltransferase activity of EZH2 or a mutant thereof and, accordingly, the present invention also provides methods for treating conditions and diseases the course of which can be influenced by modulating the methylation status of histones or other proteins, wherein said methylation status is mediated at least in part by the activity of EZH2. In one aspect of the invention, certain compounds disclosed herein are candidates for treating, or preventing certain conditions and diseases. Modulation of the methylation status of histones can in turn influence the level of expression of target genes activated by methylation, and/or target genes suppressed by methylation. The method includes administering to a subject in need of such treatment, a therapeutically effective amount of a compound of the present invention.

As used herein, a "subject" is interchangeable with a "subject in need thereof", both of which refer to a subject having a disorder in which EZH2-mediated protein methylation plays a part, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. A subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition. For example, the cancer is lymphoma, leukemia, melanoma, or rhabdomyosarcoma. Preferably, the lymphoma is non-Hodgkin's lymphoma, follicular lymphoma or diffuse large B-cell lymphoma. Alternatively, the leukemia is chronic myelogenous leukemia (CML). The precancerous condition is myelodysplastic syndromes (MDS, formerly known as preleukemia).

As used herein, "treating" or "treat" describes the management and care of a patient for the purpose of combating a disease, condition, or disorder and includes the administration of a compound of the present invention, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

Point mutations of the EZH2 gene at a single amino acid residue (e.g., Y641, A677, and A687) of EZH2 have been reported to be linked to lymphoma. More examples of EZH2 mutants and methods of detection of mutation and methods treatment of mutation-associated disorders are described in, e.g., U.S. Patent Application Publication No. US 20130040906, the entire content of which is incorporated herein by reference in its entirety.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., $18^{th}$ edition (1990). These texts can, of course, also be referred to in making or using an aspect of the invention.

As used herein, "combination therapy" or "co-therapy" includes the administration of a compound of the present invention, or a pharmaceutically acceptable salt, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents.

The present invention also provides pharmaceutical compositions comprising a compound of any Formula disclosed herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Syntheses of Compounds of the Invention

General Experimental
NMR
$^1$H-NMR spectra were taken using CDCl$_3$ unless otherwise stated and were recorded at 400 or 500 MHz using a Varian or Oxford instruments magnet (500 MHz) instruments. Multiplicities indicated are s=singlet, d=doublet, t=triplet, q=quartet, quint=quintet, sxt=sextet, m=multiplet, dd=doublet of doublets, dt=doublet of triplets; br indicates a broad signal.
LCMS and HPLC
Mass: Waters Acquity Ultra Performance LC. HPLC: Products were analyzed by Shimadzu SPD-20A with 150× 4.5 mm YMC ODS-M80 column or 150×4.6 mm YMC-Pack Pro C18 column at 1.0 ml/min. Mobile phase was MeCN:H$_2$O=3:2 (containing 0.3% SDS and 0.05% H$_3$PO$_4$). Products were purified by HPLC/MS (MeOH—H$_2$O con-

3-(Aminomethyl)-4,6-dimethyl-1,2-dihydropyridin-2-one HCl Salt

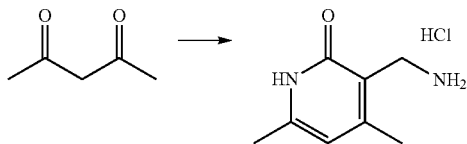

To a solution of 2-cyanoacetamide (8.40 g, 100 mmol) and acetylacetone (10.0 g, 100 mmol) in H₂O (200 mL) was added K₂CO₃ (4.00 g, 28.9 mmol). The mixture was stirred at RT for 22 hours. Then the precipitated solid was filtered with Buchner funnel, washed with ice cold H₂O, and dried under vacuum pressure to give 4,6-dimethyl-2-oxo-1,2-dihydropyridine-3-carbonitrile (13.5 g, 91% yield).

To a solution of 4,6-dimethyl-2-oxo-1,2-dihydropyridine-3-carbonitrile (10.0 g, 67.5 mmol) in MeOH (1.50 L) and conc. HCl (30 mL) was added 10% Pd(OH)$_2$ (19 g) under N$_2$ atmosphere. The N$_2$ gas was displaced by H$_2$ gas and the mixture was stirred for 26 hours at RT under hydrogen atmosphere. The H$_2$ gas was displaced by N$_2$ gas. The mixture was filtered through Celite, washed with MeOH and concentrated. The residue was triturated with EtOH, collected with Buchner funnel, and dried under vacuum pressure to give the titled compound as a white solid (11.5 g, 90%). $^1$H NMR (400 MHz, DMSO-d$_6$): δ ppm 11.86 (brs, 1H), 5.98 (s, 1H), 3.78 (m, 2H), 2.20 (s, 3H), 2.16 (s, 3H).

3-(Aminomethyl)-6-methyl-4-propyl-1,2-dihydropyridin-2-one HCl salt

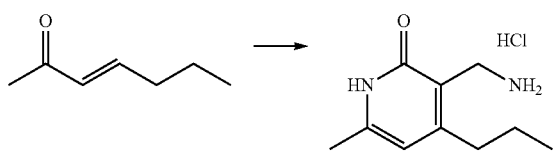

To a stirred solution of t-BuOK (20.0 g, 179 mmol) and cyanoacetamide (16.5 g, 196 mmol) in DMSO (300 mL) was added (3E)-3-hepten-2-one (20.0 g, 178 mmol). The reaction mixture was stirred at 23° C. for 30 minutes and then additional t-BuOK (60.0 g, 712 mmol) was added to the reaction mixture. The reaction mixture was placed under oxygen atmosphere and stirred for 16 h. The reaction mixture was then purged with argon and was cooled to 0° C. The mixture was diluted with aq. HCl and the resultant precipitate was collected. The solid was washed with water and dried to give 6-methyl-2-oxo-4-propyl-1,2-dihydropyridine-3-carbonitrile (15.0 g, 47%).

To a stirred solution of 6-methyl-2-oxo-4-propyl-1,2-dihydropyridine-3-carbonitrile (15.0 g, 85.1 mmol) in methanol (600 mL) and concentrated HCl (15 mL) was added Pd(OH)$_2$ (15.0 g). The mixture was stirred for 48 hours under H$_2$ atmosphere. The reaction mixture was filtered and filtrate was concentrated in vacuo. Ethanol was added to the residue, the resultant precipitate was collected and dried to give the titled compound as a white solid (13.0 g, 60%). $^1$H-NMR (400 MHz, CDCl$_3$) δ ppm; 11.86 (br. s., 1H), 6.00 (s, 1H), 3.78 (q, J=5.5 Hz, 2H), 3.61 (br. s, 2H), 2.46 (m, 2H), 2.17 (s, 3H), 1.50 (sxt, J=7.4 Hz, 2H), 0.91 (t, J=7.4 Hz, 3H).

6-Methyl-2-oxo-4-(2-propyl)-1,2-dihydropyridine-3-carbonitrile

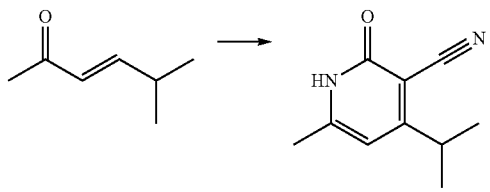

To a solution of 2-cyanoacetamide (35.1 g, 417 mmol) and t-BuOK (42.5 g, 379 mmol) in DMSO (631 mL) was added 5-methyl-3-hexen-2-one (50.0 mL, 379 mmol) under N$_2$ atmosphere. The mixture was stirred at 23° C. for 30 min and then additional t-BuOK (127 g, 1137 mmol) was added. The N$_2$ gas was displaced by O$_2$ gas and the mixture was stirred for 45 h at 23° C. under oxygen. The mixture was cooled to 0° C., diluted with H$_2$O (200 mL) and 5N HCl (227 mL, slowly added). The mixture was stirred for 15 min at 0° C. and the solid was collected with Buchner funnel. The solid was washed with H$_2$O (1500 mL) and dried with hot-air (55° C., 16 h) to give 6-methyl-2-oxo-4-(propan-2-yl)-1,2-dihydropyridine-3-carbonitrile as a white solid (26.6 g, 40%). $^1$H NMR (400 MHz, CDCl$_3$) δ ppm; 6.14 (s, 1H), 3.25-3.29 (m, 1H), 2.45 (s, 3H), 1.26 (d, J=6.8 Hz, 6H); LC-MS: ink 177.1 [M+H]$^+$, 198.9 [M+Na]$^+$.

3-(Aminomethyl)-6-methyl-4-(2-propyl)-1,2-dihydropyridin-2-one HCl salt

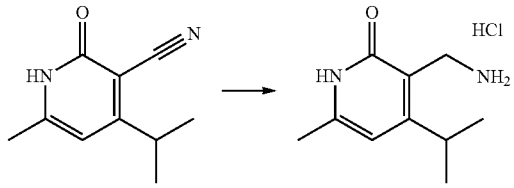

To a solution of 6-methyl-2-oxo-4-(2-propyl)-1,2-dihydropyridine-3-carbonitrile (5.00 g, 28.4 mmol) and in MeOH (400 mL) and conc. HCl (8.8 mL) was added 10% Pd(OH)$_2$ (5.17 g, 3.68 mmol) under N$_2$ atmosphere. The N$_2$ gas was displaced by H$_2$ gas and the mixture was stirred for 24 h at 23° C. under hydrogen. The H$_2$ gas was displaced by N$_2$ gas and the mixture was filtrated through celite, washed with MeOH and the filtrate was concentrated. The residue was triturated with EtOH-TBME, the solid was collected with Buchner funnel and dried in vacuo to give the titled compound as a white solid (6.15 g, 100%). $^1$H NMR (400 MHz, DMSO-d$_6$): δ ppm 11.9 (br-s, 1H), 8.03 (br-s, 2H), 6.12 (s, 1H), 3.82-3.84 (m, 2H), 3.08-3.12 (m, 1H), 2.19 (s, 3H), 1.12 (d, J=6.8 Hz, 6H).

6-Methyl-2-oxo-4-(trifluoromethyl)-1,2-dihydropyridine-3-carbonitrile

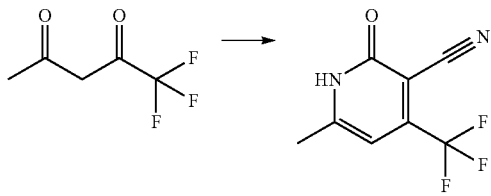

To a solution of 2-cyanoacetamide (14.0 g, 166 mmol) and trifluoroacetylacetone (20.0 mL, 166 mmol) in H$_2$O (332 mL) was added K$_2$CO$_3$ (6.60 g, 47.9 mmol). The mixture was stirred at 23° C. for 15 h. The precipitated solid was collected with Buchner funnel, washed with ice cold H$_2$O, and dried with hot air (60° C., 16 h) to give the titled compound as a white solid (17.6 g, 52%). $^1$H NMR (400 MHz, DMSO-d$_6$): δ ppm 2.38 (s, 3H), 6.66 (s, 1H).

3-(Aminomethyl)-6-methyl-4-(trifluoromethyl)-1,2-dihydropyridin-2-one hydrochloride HCl salt

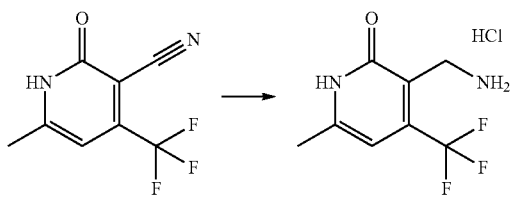

To a solution of 6-methyl-2-oxo-4-(trifluoromethyl)-1,2-dihydropyridine-3-carbonitrile (400 mg, 1.98 mmol) in MeOH (19.8 mL) and conc. HCl (436 uL) was added 10% Pd(OH)$_2$ (361 mg, 0.257 mmol) under N$_2$ atmosphere. The N$_2$ gas was displaced by H$_2$ gas and the mixture was stirred for 18 h at 23° C. under hydrogen. The H$_2$ gas was displaced by N$_2$ gas. The mixture was filtrated through Celite, washed with MeOH and the filtrate was concentrated. The residue was triturated with MeOH-Et$_2$O, collected with Buchner funnel, and dried in vacuo to give the titled compound as a white solid (433 mg, 100%). $^1$H NMR (400 MHz, DMSO-d$_6$): δ ppm 2.31 (s, 3H), 3.88 (s, 2H), 6.43 (s, 1H).

5-Fluoro-1,4,6-trimethyl-2-oxo-1,2-dihydropyridine-3-carbonitrile

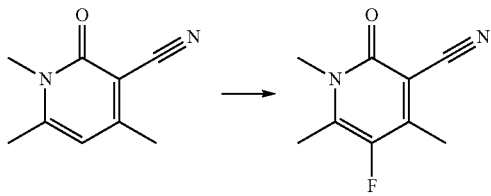

The title compound was prepared (0.430 g, 38%) following the same procedure for the preparation of 5-fluoro-4-isopropyl-6-methyl-2-oxo-1,2-dihydropyridine-3-carbonitrile and purified by silica gel chromatography (50% to 100% EtOAc-heptane). $^1$H-NMR (400 MHz): δ ppm 3.56 (s, 3H), 2.43 (d, J=2.1 Hz, 3H), 2.41 (d, J=8.4 Hz, 3H); MS (ESI) [M+H]$^+$ 181.1.

3-(Aminomethyl)-5-fluoro-1,4,6-trimethylpyridin-2(1H)-one

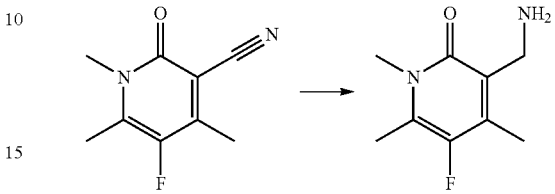

The titled compound was prepared (0.440 g, 100% yield) following the same procedure for the preparation of 3-(aminomethyl)-5-fluoro-4-isopropyl-6-methylpyridin-2(1H)-one. $^1$H NMR (400 MHz, CD$_3$OD): δ ppm 3.75 (s, 2H), 3.52 (s, 3H), 2.36 (d, J=3.2 Hz, 3H), 2.23 (d, J=2.1 Hz, 3H); MS (ESI) [M+H]$^+$ 185.1.

3-(Aminomethyl)-1,4,6-trimethylpyridin-2(1H)-one

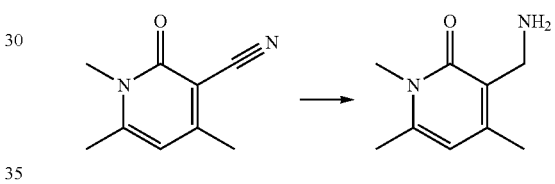

The titled compound was prepared (200 mg, 100% yield) following the same procedure for the preparation of 3-(aminomethyl)-5-fluoro-4-isopropyl-6-methylpyridin-2(1H)-one. $^1$H-NMR (400 MHz): δ ppm 5.90 (s, 1H), 3.75 (s, 2H), 3.51 (s, 3H), 2.30 (s, 3H), 2.19 (s, 3H); MS (ESI) [M+H]$^+$ 167.1.

2-((6-Methyl-2-oxo-4-(trifluoromethyl)-1,2-dihydropyridin-3-yl)methyl)isoindoline-1,3-dione

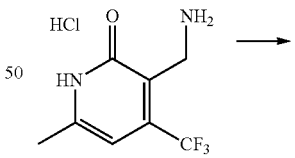

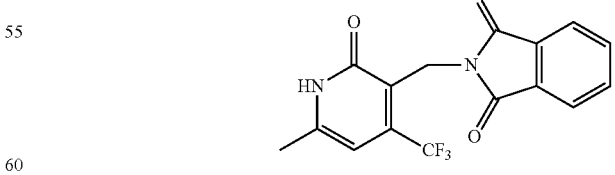

A solution of phthalic anhydride (0.140 g, 0.948 mmol), triethylamine (0.264 mL, 1.90 mmol) and 3-(aminomethyl)-6-methyl-4-(trifluoromethyl)pyridin-2(1H)-one hydrochloride (0.230 g, 0.948 mmol) in acetic acid (2.71 mL, 47.4 mol) was heated under microwave irradiation at 100° C. for 1 h. LC-MS showed a single peak corresponding to the desired product. The reaction mixture was poured into water and the precipitated solid was collected by filtration, washed with water and dried to provide the titled compound (265 mg, 83% yield). $^1$H-NMR (400 MHz, DMSO-d$_6$): δ ppm 7.83 (s, 4H), 6.29 (s, 1H), 4.74 (s, 2H), 2.24 (s, 3H); MS (ESI) [M+H]$^+$ 337.2.

2-((1,6-Dimethyl-2-oxo-4-(trifluoromethyl)-1,2-dihydropyridin-3-yl)methyl)isoindoline-1,3-dione dione

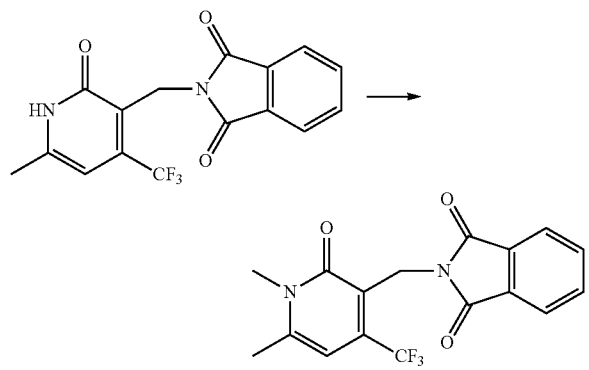

Cesium carbonate (257 mg, 0.788 mmol) was added to a suspension of 2-((6-methyl-2-oxo-4-(trifluoromethyl)-1,2-dihydropyridin-3-yl)methyl)isoindoline-1,3-dione (265 mg, 0.788 mmol) in DMSO (2.34 mL) at 23° C. The reaction mixture immediately turned to yellow. And after stirring for 16 h at 23° C., methyl iodide (49.3 μL, 0.788 mmol) was added and the yellow color turned to light yellow color. After stirring for 1 h, LCMS showed the reaction was done. The reaction mixture was poured into ice water and filtered, washed with ether and dried to give the titled compound (250 mg, 91% yield). $^1$H-NMR (400 MHz, CD$_3$OD): δ ppm 7.79 (m, 4H), 6.51 (s, 1H), 4.88 (s, 2H), 3.51 (s, 3H), 2.48 (s, 3H); MS (ESI) [M+H]$^+$ 351.2.

3-(Aminomethyl)-1,6-dimethyl-4-(trifluoromethyl)pyridin-2(1H)-one

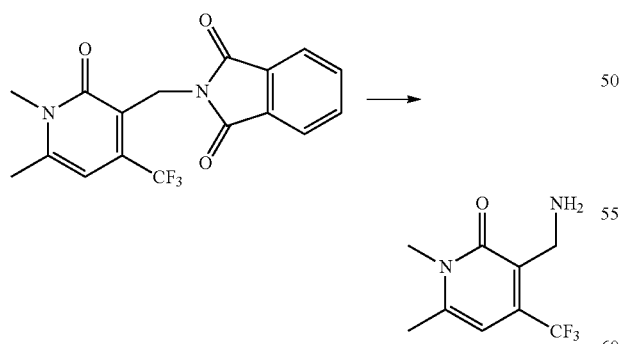

Hydrazine hydrate (106 μL, 2.14 mmol) was added to a suspension of 2-((1,6-dimethyl-2-oxo-4-(trifluoromethyl)-1,2-dihydropyridin-3-yl)methyl)isoindoline-1,3-dione (250 mg, 0.714 mmol) in ethanol (4.2 mL) and the reaction mixture was heated at 80° C. for 2 h. LC-MS showed the reaction was completed so the mixture was cooled to ambient temperature, filtered to remove the precipitated solid. The filtrate was then concentrated and azeotroped with DMF to give the crude titled compound (178 mg, 113%). The crude was used directly without further purification for next step. MS (ESI) [M+H]$^+$ 221.1.

Compound 1:

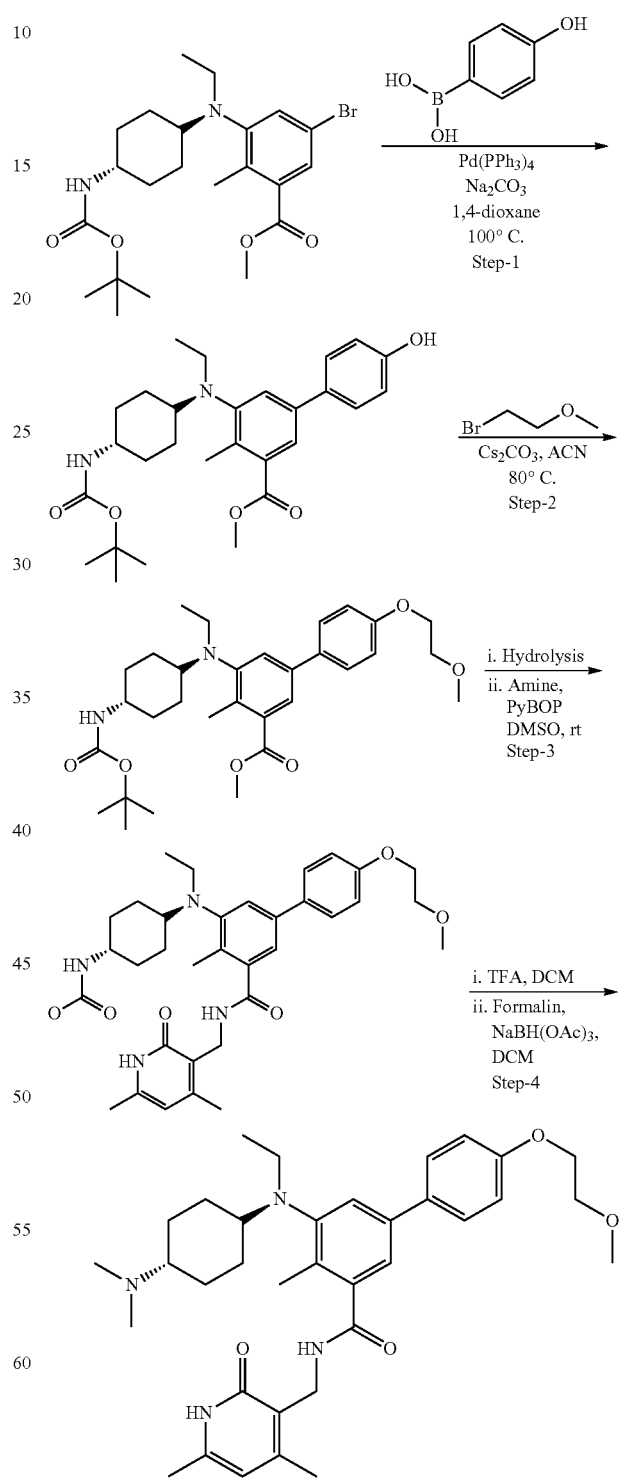

Step 1: Synthesis of methyl 5-(((trans)-4-((tert-butoxycarbonyl)amino)cyclohexyl)(ethyl)amino)-4'-hydroxy-4-methyl-[1,1'-biphenyl]-3-carboxylate To a stirred solution of methyl 5-bromo-3-(((trans)-4-((tert-butoxycarbonyl)amino)cyclohexyl)(ethyl)amino)-2-methylbenzoate (10 g, 21.3 mmol, see, e.g., WO2012142504 and (4-hydroxyphenyl)boronic acid (3.5 g, 25.3 mmol) in a mixture of dioxane (225 mL) and water (75 mL), $Na_2CO_3$ (8.01 g, 75.5 mmol) was added and the solution was purged with argon for 30 min. Then $Pd(PPh_3)_4$ (2.4 g, 2.07 mmol) was added and argon was purged again for another 15 min. Reaction mass was heated at 100° C. for 4 h. On completion, reaction mixture was diluted with water and extracted with ethyl acetate. Combined organic layer was dried over sodium sulfate. Removal of the solvent under reduced pressure followed by column chromatographic purification afforded the title compound (8.9 g, 87% yield).

Step 2: Synthesis of methyl 5-(((trans)-4-((tert-butoxycarbonyl)amino)cyclohexyl)(ethyl)amino)-4'-(2-methoxyethoxy)-4-methyl-[1,1'-biphenyl]-3-carboxylate To a stirred solution of methyl 5-(((trans)-4-((tert-butoxycarbonyl)amino)cyclohexyl)(ethyl)amino)-4'-hydroxy-4-methyl-[1,1'-biphenyl]-3-carboxylate (0.6 g, 1.24 mmol) and 1-bromo-2-methoxyethane (0.519 g, 3.73 mmol) in acetonitrile (6 mL), $Cs_2CO_3$ (0.485 g, 1.49 mmol) was added and reaction was stirred at 80° C. for 12 h. On completion, water was added to it and extracted with ethyl acetate. The combined organic layers were dried over anhydrous sodium sulfate and concentrated under reduced pressure. The crude compound was purified by column chromatography to afford the title compound (0.6 g, 76.5% yield).

Step 3: Synthesis of tert-butyl ((trans)-4-((5-(((4,6-dimethyl-2-oxo-1,2-dihydropyridin-3-yl)methyl)carbamoyl)-4'-(2-methoxyethoxy)-4-methyl-[1,1'-biphenyl]-3-yl(ethyl)-amino)-cyclohexyl)carbamate Aqueous NaOH (0.066 g, 1.66 mmol in 5 mL H2O) was added to a solution of 5-(((trans)-4-((tert-butoxycarbonyl)amino)cyclohexyl)(ethyl)amino)-4'-(2-methoxyethoxy)-4-methyl-[1,1'-biphenyl]-3-carboxylate (0.6 g, 1.11 mmol) in EtOH (10 mL) and stirred at 60° C. for 1 h. After completion of the reaction, ethanol was removed under reduced pressure and the residue was acidified using citric acid using to pH 4 was adjusted using citric acid. Extraction was carried out using 10% methanol in DCM. Combined organic layers were dried, concentrated giving respective acid (0.5 g, 85.6% yield).

The above acid (0.5 g, 0.95 mmol) was then dissolved in DMSO (5 mL) and 3-(aminomethyl)-4,6-dimethylpyridin-2(1H)-one (0.288 g, 1.90 mmol) and triethyl amine (0.096 g, 0.950 mmol) was added to it. The reaction mixture was stirred at room temperature for 15 min before PyBop (0.741 g, 1.42 mmol) was added to it and stirring was continued for overnight at room temperature. After completion of the reaction, reaction mass was poured into ice and extraction was carried out using 10% MeOH/DCM. Combined organic layers were dried over sodium sulfate and concentrated under reduced pressure to obtain crude material which then purified by column chromatography to afford the title compound (0.45 g, 71.8% yield).

Step 4: Synthesis of N-((4,6-dimethyl-2-oxo-1,2-dihydropyridin-3-yl)methyl)-5-(((trans)-4-(dimethylamino)-cyclohexyl)-(ethyl)-amino)-4'-(2-methoxyethoxy)-4-methyl-[1,1'-biphenyl]-3-carboxamide To a stirred solution of tert-butyl((trans)-4-((5-(((4,6-dimethyl-2-oxo-1,2-dihydropyridin-3-yl)methyl)carbamoyl)-4'-(2-methoxyethoxy)-4-methyl-[1,1'-biphenyl]-3-yl)(ethyl)amino)cyclohexyl)carbamate (0.45 g, 0.681 mmol) in DCM (5 mL) at 0° C., TFA (1 mL) was added and reaction was stirred for 2 h at room temperature. After completion, reaction was concentrated to dryness. The residue was then basified with $Na_2CO_3$ (aq.) to pH 8 and the aqueous layer extracted with 20% methanol in DCM. The combined organic layers were dried over $Na_2SO_4$ and the solvent removed under reduced pressure to give Boc-deprotected compound (0.3 g, 78.7% yield).

To a stirred solution of Boc-deprotected compound (0.3 g, 0.535 mmol) in dichloromethane (3 mL) was added formaldehyde solution (35-41% aq.) (0.056 g, 1.87 mmol) at 0° C. and stirred for 20 min. Then, $NaBH(OAc)_3$ (0.28 g, 1.33 mmol) was added and stirred for 2 h at 0° C. On completion of the reaction, water was added and extracted with 20% methanol in DCM. The combined organic layers were dried over $Na_2SO_4$ and the solvent was removed under reduced pressure. The crude compound was purified by prep. HPLC to afford the title compound (0.1 g, 31.7% yield).

LCMS: 589.75 (M+1)$^+$; TFA-salt: $^1$H NMR (DMSO-$d_6$, 400 MHz) δ 11.47 (brs, 1H), 9.48 (brs, 1H), 8.21 (brs, 1H), 7.57 (d, 2H, J=8.0 Hz), 7.40 (s, 1H), 7.23 (s, 1H), 7.03 (d, 2H, J=8.8 Hz), 5.87 (s, 1H), 4.29 (d, 2H, J=4.4 Hz), 4.14-4.12 (m, 2H), 3.69-3.66 (m, 2H), 3.32 (s, 3H), 3.13 (m, 4H), 2.69-2.68 (m, 6H), 2.24 (s, 3H), 2.21 (s, 3H), 2.11 (s, 3H), 1.96 (m, 4H), 1.44 (m, 4H), 0.85 (t, 3H, J=6.8 Hz).

Compound 3:

Synthesis of N-((4,6-dimethyl-2-oxo-1,2-dihydropyridin-3-yl)methyl)-5-(((trans)-4-(dimethylamino)cyclohexyl)(ethyl)amino)-4'-(2-hydroxyethoxy)-4-methyl-[1,1'-biphenyl]-3-carboxamide

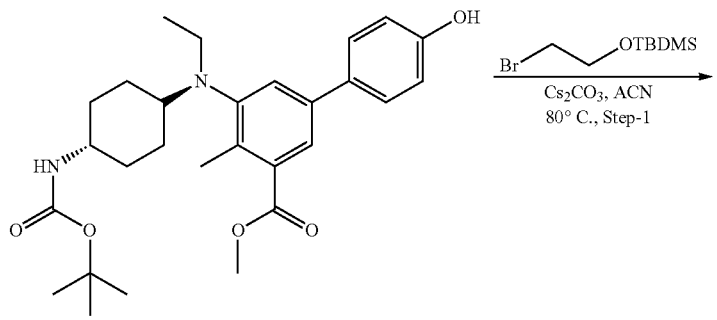

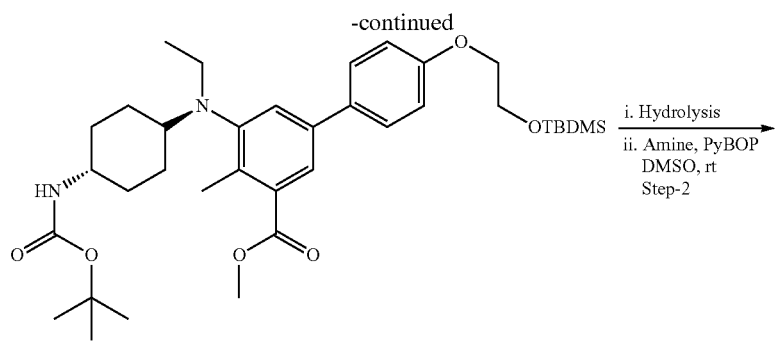

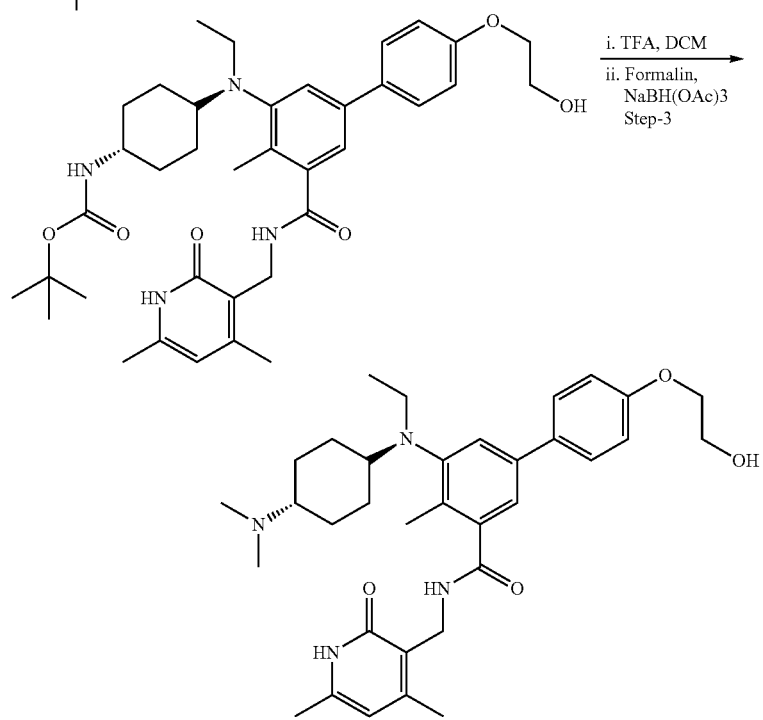

Step 1: Synthesis of methyl 5-(((trans)-4-((tert-butoxycarbonyl)amino)cyclohexyl)(ethyl)amino)-4'-2-((tert-butyldimethylsilyl)oxy)ethoxy)-4-methyl-[1,1'-biphenyl]-3-carboxylate To a stirred solution of methyl 5-(((trans)-4-((tert-butoxycarbonyl)amino)cyclohexyl)(ethyl)amino)-4'-hydroxy-4-methyl-[1,1'-biphenyl]-3-carboxylate (0.8 g, 1.65 mmol) and (2-bromoethoxy)(tert-butyl)dimethylsilane (1.97 g, 8.29 mmol) in acetonitrile (10 mL), $Cs_2CO_3$ (1.61 g, 4.97 mmol) was added and reaction was stirred at 80° C. for 12 h. On completion, reaction mass was diluted with water and extracted with ethyl acetate. The combined organic layers were dried over anhydrous $Na_2SO_4$ and concentrated under reduced pressure. The crude compound was purified by column chromatography to afford the title compound (0.7 g, 70% yield).

Step 2: Synthesis of tert-butyl ((trans)-4-((5-(((4,6-dimethyl-2-oxo-1,2-dihydropyridin-3-yl)methyl)carbamoyl)-4'-(2-hydroxyethoxy)-4-methyl-[1,1'-biphenyl]-3-yl)(ethyl)amino)cyclohexyl)carbamate Protocol as for 2, Step 3, with methyl 5-(((trans)-4-((tert-butoxycarbonyl)amino)cyclohexylyethyl)amino)-4'-(2-((tert-butyldimethylsilyl)oxy)ethoxy)-4-methyl-[1,1'-biphenyl]-3-carboxylate (0.7 g, 1.09 mmol) and 3-(amino methyl)-4,6-dimethylpyridin-2(1H)-one (0.291 g, 1.91 mmol) to afford the title compound (0.45 g, 61.8% yield).

Step 3: Synthesis of N-((4,6-dimethyl-2-oxo-1,2-dihydropyridin-3-yl)methyl)-5-(((trans)-4-(dimethylamino)cyclohexyl)(ethyl)amino)-4'-(2-hydroxyethoxy)-4-methyl-[1,1'-biphenyl]-3-carboxamide To a stirred solution of tert-butyl ((trans)-4-((5-(((4,6-dimethyl-2-oxo-1,2-dihydropyridin-3-yl)methyl)carbamoyl)-4'-(2-hydroxyethoxy)-4-methyl-[1,1'-biphenyl]-3-yl)(ethyl)amino)cyclohexyl)carbamate (0.45 g, 0.59 mmol) in DCM (5 mL) at 0° C., TFA (1 mL) was added and reaction was stirred for 2 h at room temperature. After completion, the reaction was concentrated to dryness. The residue was then basified with $Na_2CO_3$ (aq.) to pH 8 and the aqueous layer was extracted with 20% methanol in DCM. The combined organic layers were dried over $Na_2SO_4$ and the solvent was removed under reduced pressure to give Boc-deprotected compound (0.3 g, 76.9% yield).

To a stirred solution of the Boc-deprotected compound (0.3 g, 0.45 mmol) in dichloromethane (3 mL) was added formaldehyde solution (35-41% aq.) (0.05 g, 1.59 mmol) at 0° C. and stirred for 20 min. Then NaBH(OAc)₃ (0.24 g, 1.13 mmol) was added and the resulting mixture was stirred for 2 h at 0° C. On completion of the reaction, water was added and extracted with 20% methanol in DCM. The combined organic layers were dried over Na₂SO₄ and the solvent was removed under reduced pressure. The crude compound was purified by prep. HPLC to afford the title compound (0.1 g, 32.1% yield).

LCMS: 575.55 (M+1)⁺; TFA-salt: ¹H NMR (DMSO-d₆, 400 MHz) δ 11.50 (brs, 1H), 9.52 (brs, 1H), 8.23 (brs, 1H), 7.58 (d, 2H, J=8.4 Hz), 7.45 (s, 1H), 7.26 (s, 1H), 7.02 (d, 2H, J=8.4 Hz), 5.87 (s, 1H), 4.30-4.29 (m, 2H), 4.03-4.00 (m, 2H), 3.75-3.72 (m, 2H), 3.22-3.12 (m, 3H), 2.93 (m, 1H), 2.69 (m, 6H), 2.25 (s, 3H), 2.21 (s, 3H), 2.11 (s, 3H), 1.97 (m, 4H), 1.45 (m, 4H), 0.85 (t, 3H, J=6.8 Hz).

Compound 4

Synthesis of N-((4,6-dimethyl-2-oxo-1,2-dihydro-pyridin-3-yl)methyl)-3-(((trans)-4-(dimethylamino)cyclohexyl)(ethyl)amino)-5-(6-(2-hydroxyethoxy)pyridin-3-yl)-2-methylbenzamide

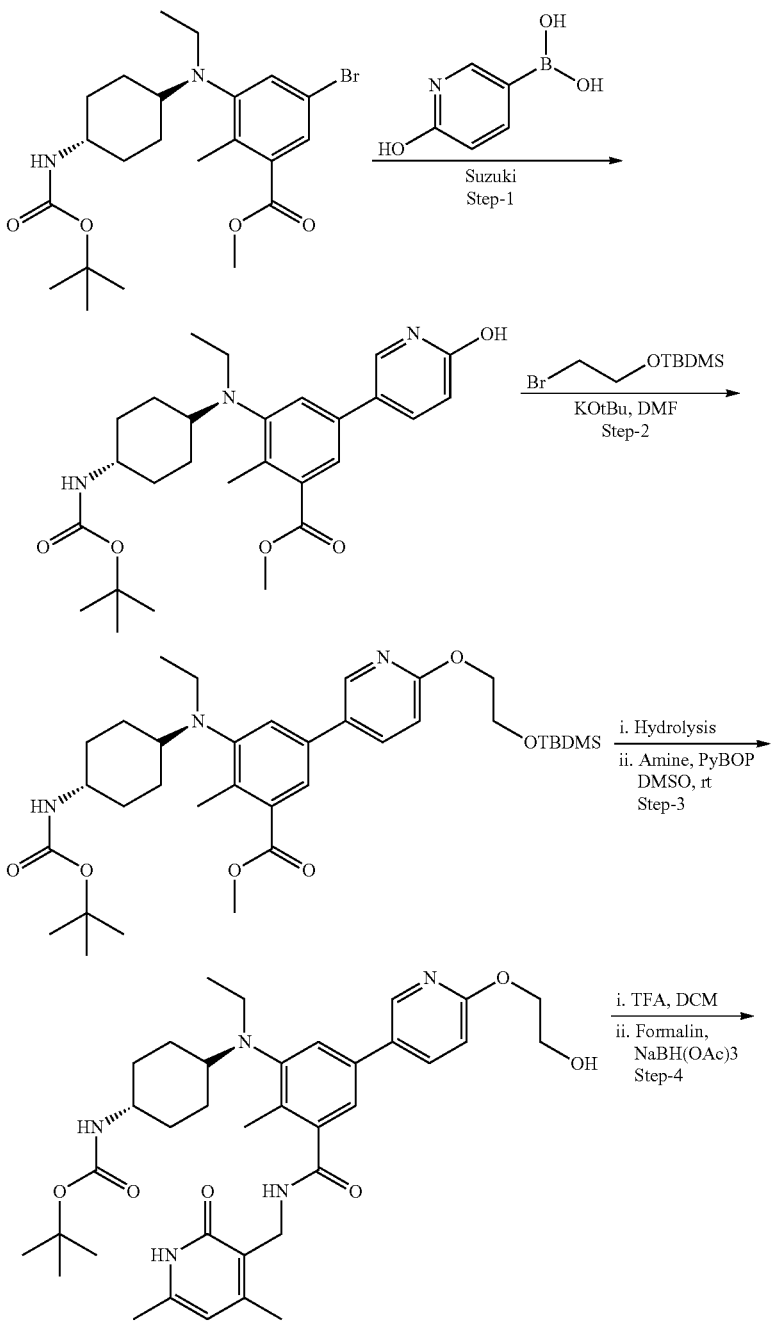

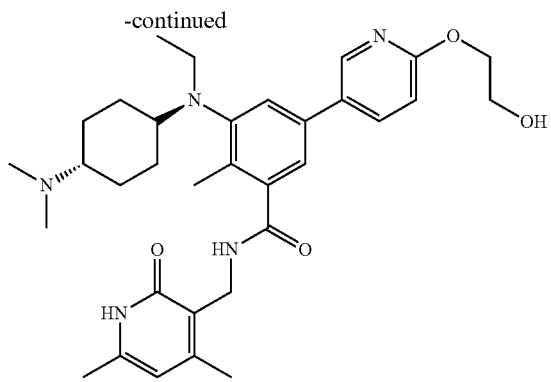

Step 1: Synthesis of methyl 3-(((trans)-4-((tert-butoxycarbonyl)amino)cyclohexyl)(ethyl)amino)-5-(6-hydroxypyridin-3-yl)-2-methylbenzoate To a stirred solution of methyl 5-bromo-3-(((trans)-4-((tert-butoxycarbonyl)amino)cyclohexyl)(ethyl)amino)-2-methylbenzoate (2 g, 4.27 mmol) and (6-hydroxypyridin-3-yl)boronic acid (1.06 g, 7.69 mmol) in dioxane/water mixture (16:4 mL), $Na_2CO_3$ (1.63 g, 15.38 mmol) was added and solution was purged with argon for 15 min. Then $Pd(PPh_3)_4$ (0.25 g, 0.21 mmol) was added and argon was purged again for 10 min. The reaction mass was heated at 100° C. for 3 h. On completion, the reaction mixture was diluted with water and extracted with 10% MeOH/DCM. The combined organic layers were dried over $Na_2SO_4$ and the solvent was removed under reduced pressure and the resulting crude material was purified by column chromatography on silica gel to afford the title compound (0.9 g, 43.6% yield).

Step 2: Synthesis of methyl 3-(((trans)-4-((tert-butoxycarbonyl)amino)cyclohexyl)(ethyl)amino)-5-(6-(2-((tert-butyldimethylsilyl)oxy)ethoxy)pyridin-3-yl)-2-methylbenzoate To a stirred solution of methyl 3-(((trans)-4-((tert-butoxycarbonyl)amino)cyclohexyl)(ethyl)amino)-5-(6-hydroxypyridin-3-yl)-2-methylbenzoate (0.9 g, 1.86 mmol) and (2-bromoethoxy)(tert-butyl)dimethylsilane (1.33 g, 5.59 mmol) in DMF (10 mL), potassium t-butoxide (0.25 g, 2.23 mmol) was added and reaction was stirred at room temperature for 12 h. On completion, water was added and extracted with ethyl acetate. The combined organic layers were dried over anhydrous $Na_2SO_4$ and concentrated under reduced pressure. The crude compound was purified by column chromatography to afford the title compound (0.7 g, 63.6% yield).

Step 3: Synthesis of tert-butyl ((trans)-4-((3-(((4,6-dimethyl-2-oxo-1,2-dihydropyridin-3-yl)methyl)carbamoyl)-5-(6-(2-hydroxyethoxy)pyridin-3-yl)-2-methylphenyl)(ethyl)amino)cyclohexyl)carbamate Protocol as for 2, Step 3, with methyl 3-(((trans)-4-((tert-butoxycarbonyl)amino)cyclohexyl)(ethyl)amino)-5-(6-(2-((tert-butyldimethylsilyl)oxy)ethoxy)pyridin-3-yl)-2-methylbenzoate (0.7 g, 1.09 mmol) and 3-(amino methyl)-4,6-dimethylpyridin-2(1H)-one (0.24 g, 1.59 mmol) to afford the title compound (0.4 g, 56.2% yield).

Step 4: Synthesis of N-((4,6-dimethyl-2-oxo-1,2-dihydropyridin-3-yl)methyl)-3-(((trans)-4-(dimethylamino)cyclohexyl)(ethyl)amino)-5-(6-(2-hydroxyethoxy)pyridin-3-yl)-2-methylbenzamide Protocol as for 3, Step 3, with tert-butyl((trans)-4-((3-(((4,6-dimethyl-2-oxo-1,2-dihydropyridin-3-yl)methyl)carbamoyl)-5-(6-(2-hydroxyethoxy)pyridin-3-yl)-2-methylphenyl)(ethyl)amino)cyclohexyl)carbamate (0.4 g, 0.62 mmol) to afford the title compound (0.11 g, 42.0% yield).

LCMS: 576.60 (M+1)+'; TFA-salt: $^1$H NMR (DMSO-$d_6$, 400 MHz) δ 11.46 (bs, 1H), 9.51 (bs, 1H), 8.16 (s, 1H), 7.97 (s, 1H), 7.80 (d, 1H, J=8.8 Hz), 7.32 (s, 1H), 7.16 (s, 1H), 6.48 (d, 1H, J=9.6 Hz), 5.87 (s, 1H), 4.28 (d, 2H, J=5.2 Hz), 4.05-4.02 (m, 2H), 3.67-3.64 (m, 2H), 3.12 (m, 3H), 2.75 (m, 1H), 2.69-2.68 (m, 6H), 2.21 (s, 3H+3H), 2.11 (s, 3H), 1.96-1.91 (m, 4H), 1.43 (m, 4H), 0.83 (t, 3H, J=6.8 Hz).

Compound 5:

Synthesis of N-((4,6-dimethyl-2-oxo-1,2-dihydropyridin-3-yl)methyl)-3-(((trans)-4-(dimethylamino)cyclohexyl)(ethyl)amino)-5-(6-(2-methoxyethoxy)pyridin-3-yl)-2-methylbenzamide

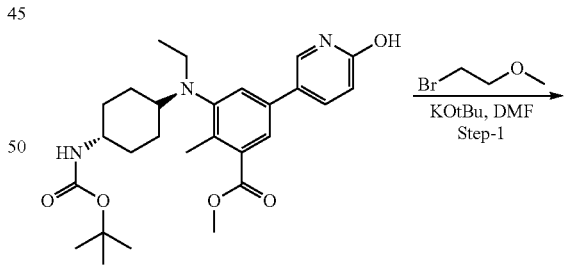

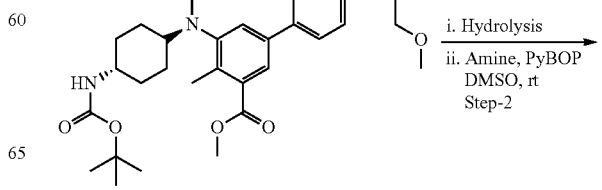

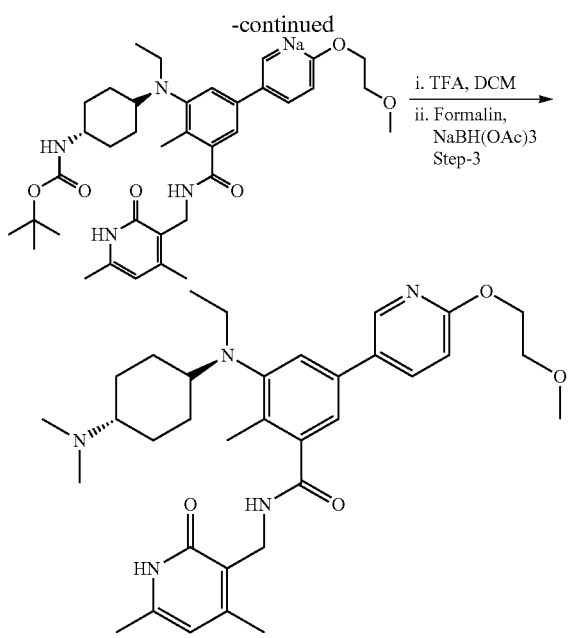

Step 1: Synthesis of methyl 3-(((trans)-4-((tert-butoxycarbonyl)amino)cyclohexyl)(ethyl)amino)-5-(6-(2-methoxyethoxy)pyridin-3-yl)-2-methylbenzoate To a stirred solution of methyl 3-(((trans)-4-((cert-butoxycarbonyl)amino)cyclohexyl)(ethyl)amino)-5-(6-hydroxypyridin-3-yl)-2-methylbenzoate (0.3 g, 0.62 mmol) and 1-bromo-2-methoxyethane (0.259 g, 1.86 mmol) in DMF (3 mL), was added KOtBu (0.083 g, 0.75 mmol) and the resulting reaction mixture was stirred at 22° C. for 2 h. On completion, water was added and extracted with ethyl acetate. The combined organic layers were dried over anhydrous $Na_2SO_4$ and concentrated in vacuo. The crude compound was purified by column chromatography over basic alumina to afford the title compound (0.3 g, 89.3% yield).

Step 2: Synthesis of tert-butyl ((trans)-4-((3-(((4,6-dimethyl-2-oxo-1,2-dihydropyridin-3-yl)methyl)carbamoyl)-5-(6-(2-methoxyethoxy)pyridin-3-yl)-2-methylphenyl)(ethyl)amino)cyclohexyl)carbamate Protocol as for 2, Step 3 with methyl 3-(((trans)-4-((tert-butoxycarbonyl)amino)cyclohexyl)(ethyl)amino)-5-(6-(2-methoxyethoxy)pyridin-3-yl)-2-methylbenzoate (0.3 g, 0.55 mmol) and 3-(amino methyl)-4,6-dimethylpyridin-2(1H)-one (0.14 g, 0.95 mmol) to afford the title compound (0.2 g, 54.7% yield).

Step 3: Synthesis of N-((4,6-dimethyl-2-oxo-1,2-dihydropyridin-3-yl)methyl)-3-(((trans)-4-(dimethylamino)cyclohexyl)(ethyl)amino)-5-(6-(2-methoxyethoxy)pyridine-3-yl)-2-methylbenzamide Protocol as for 3, Step 3 with tert-butyl ((trans)-4-((3-(((4,6-dimethyl-2-oxo-1,2-dihydropyridin-3-yl)methyl)carbamoyl)-5-(6-(2-methoxyethoxy)pyridin-3-yl)-2-methylphenyl)(ethyl)amino)cyclohexyl)carbamate to afford the title compound (0.1 g, 59.9% yield).

LCMS: 590.65 (M+1)$^+$; TFA-salt: $^1$H NMR (DMSO-$d_6$, 400 MHz) δ 11.48 (brs, 1H), 9.56 (bs, 1H), 8.17 (m, 1H), 7.99 (s, 1H), 7.80 (d, 1H, J=9.6 Hz), 7.34 (m, 1H), 7.18 (m, 1H), 6.48 (d, 1H, J=9.6 Hz), 5.87 (s, 1H), 4.28 (d, 2H, J=4.8 Hz), 4.16-4.14 (m, 2H), 3.62-3.60 (m, 2H), 3.24 (s, 3H), 3.13 (m, 4H), 2.69-2.68 (m, 6H), 2.21 (s, 6H+3H), 2.05-1.92 (m, 4H), 1.44 (m, 4H), 0.83 (t, 3H, J=6.8 Hz).

Compound 6:

Synthesis of N-((4,6-dimethyl-2-oxo-1,2-dihydropyridin-3-yl)methyl)-5-(((trans)-4-(dimethylamino)cyclohexyl)(ethyl)amino)-4'-(2-(2-methoxyethoxy)ethoxy)-4-methyl-[1,1'-biphenyl]-3-carboxamide

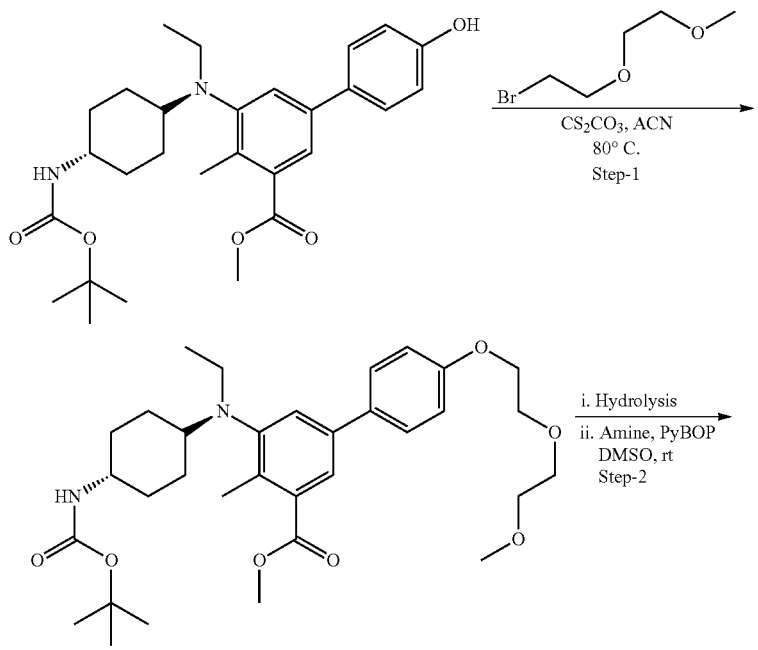

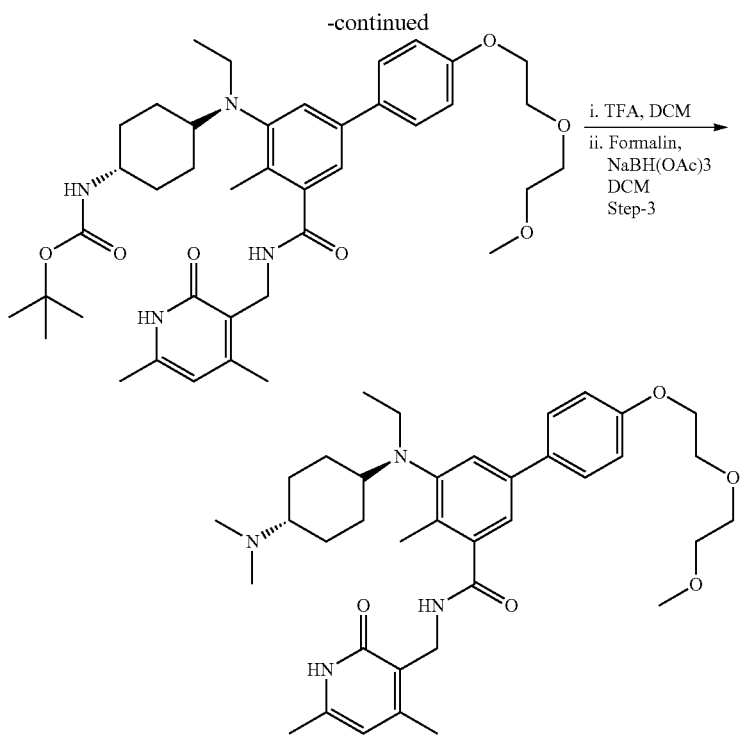

Step 1-3: Synthesis of N-((4,6-dimethyl-2-oxo-1,2-dihydropyridin-3-yl)methyl)-5-(((trans)-4-(dimethylamino)cyclohexyl)(ethyl)amino)-4'-(2-(2-methoxyethoxy)ethoxy)-4-methyl-[1,1'-biphenyl]-3-carboxamide Protocol as for 2, Steps 2-4, starting with methyl 5-(((trans)-4-((tert-butoxycarbonyl)amino)cyclohexyl)(ethyl)amino)-4'-hydroxy-4-methyl-[1,1'-biphenyl]-3-carboxylate and 1-bromo-2-(2-methoxyethoxy)ethane.

LCMS: 633.65 (M+1)+; TFA-salt: $^1$H NMR (DMSO-d$_6$, 400 MHz) δ 11.46 (brs, 1H), 8.17 (brs, 1H), 7.53 (d, 2H, J=8.0 Hz), 7.31 (s, 1H), 7.14 (s, 1H), 7.01 (d, 2H, J=8.0 Hz), 5.86 (s, 1H), 4.28 (d, 2H, J=3.6 Hz), 4.12 (s, 2H), 3.75 (s, 2H), 3.59 (d, 2H, J=4.8 Hz), 3.46 (t, 2H, J=4.0 Hz), 3.25 (s, 3H), 3.16-2.98 (m, 2H), 2.72-2.60 (m, 2H), 2.20 (s, 3H), 2.15-2.01 (brs, 12H), 1.89-1.68 (m, 5H), 1.48-1.26 (m, 2H), 1.26-1.04 (m, 2H), 0.82 (t, 3H, J=6.0 Hz).

Compound 6b

Synthesis of 5-(((trans)-4-(dimethylamino)cyclohexyl)(ethyl)amino)-N-((4-methoxy-6-methyl-2-oxo-1,2-dihydropyridin-3-yl)methyl)-4'-(2-methoxyethoxy)-4-methyl-[1,1'-biphenyl]-3-carboxamide

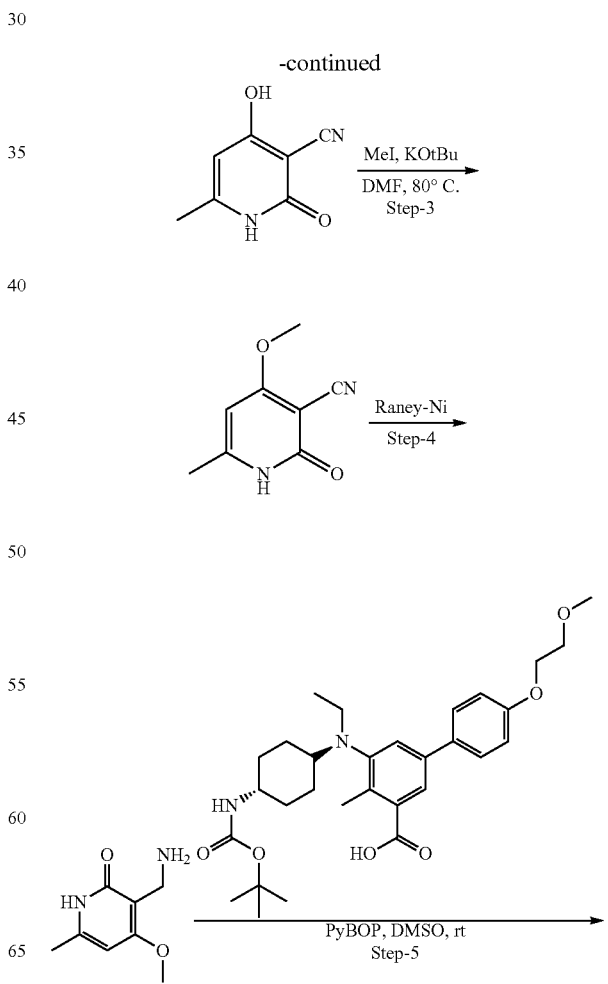

-continued

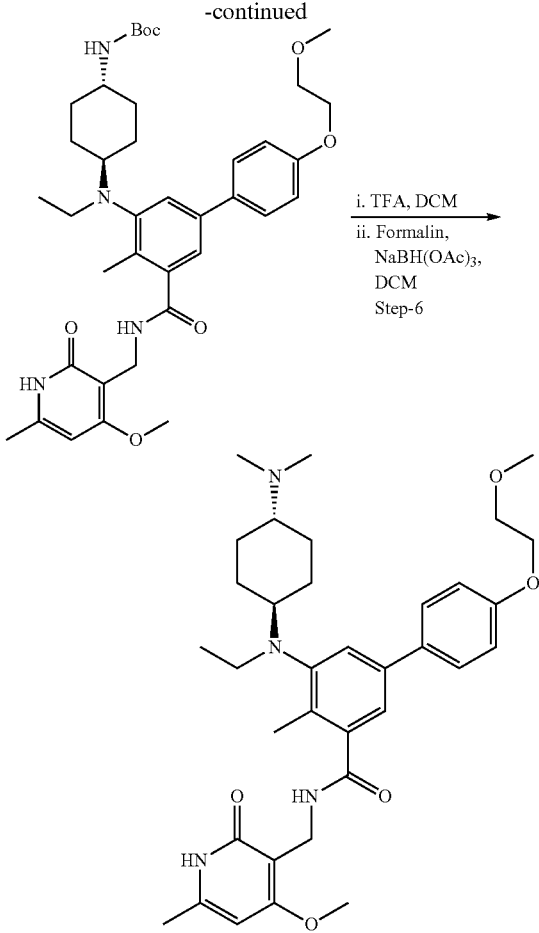

i. TFA, DCM
ii. Formalin, NaBH(OAc)₃, DCM
Step-6

Step 1: Synthesis of 2-amino-6-methyl-4-oxo-4H-pyran-3-carbonitrile

To a stirred solution of NaH (60% 19.03 g, 476 mmol) in THF (400 mL), malononitrile (31.4 g, 476 mmol) was added drop wise at −10° C. and stirred it at same temperature for 20 min. Then 4-methyleneoxetan-2-one (40 g, 476 mmol) was added at −10° C. over period of 15 min. and reaction was stirred at same temperature for 1 h. On completion, reaction was neutralized with dilute HCl (aq.) and concentrated to dryness to give the title compound (50 g, 70% yield).

Step 2: Synthesis of 4-hydroxy-6-methyl-2-oxo-1,2-dihydropyridine-3-carbonitrile A suspension of 2-amino-6-methyl-4-oxo-4H-pyran-3-carbonitrile (50 g, 333 mmol) in 10% HCl (600 mL) was heated under reflux for 4 h. The precipitate was collected by filtration and washed with water and then recrystallized from MeOH to afford the title compound (45 g, 90% yield).

Step 3: Synthesis of 4-methoxy-6-methyl-2-oxo-1,2-dihydropyridine-3-carbonitrile To a stirred solution of 4-hydroxy-6-methyl-2-oxo-1,2-dihydropyridine-3-carbonitrile (2 g, 13.24 mmol)) in DMF (10 mL) at 0° C., KOtBu (1.48 g, 13.2 mmol) and methyl iodide (1.88 g, 13.2 mmol) were added. The resulting reaction mass was stirred at room temperature for 12 h. On completion, reaction mixture was concentrated to dryness. The residue was diluted with 20% MeOH/DCM and filtered and the filtrate was washed well with 20% MeOH/DCM. The filtrate was concentrated under reduced pressure to afford crude material which was purified by silica gel column chromatography to afford the title compound (1 g, 46.1% yield).

Step 4: Synthesis of 3-(aminomethyl)-4-methoxy-6-methylpyridin-2(1H)-one

To a solution of 4-hydroxy-6-methyl-2-oxo-1,2-dihydropyridine-3-carbonitrile (0.3 g, 1.82 mmol) in methanol (5 mL), catalytic amount of Raney Nickel and ammonia solution (1 mL) were added. Reaction mass was stirred at room temperature under hydrogen pressure (balloon pressure) for 3 h. On completion of reaction, reaction mass was filtered through celite, washed with methanol and the filtrate was concentrated under reduced pressure to afford the title compound (0.3 g, 97.7%).

Step 5: Synthesis of tert-butyl ((trans)-4-(ethyl(5-(((4-methoxy-6-methyl-2-oxo-1,2-dihydropyridin-3-yl)methyl)carbamoyl)-4'-(2-methoxyethoxy)-4-methyl-[1,1'-biphenyl]-3-yl)amino)cyclohexyl) carbamate Protocol as for 2, Step 3, Part 2 with 3-(aminomethyl)-4-methoxy-6-methylpyridin-2(1H)-one (0.3 g, 0.88 mmol) and 3-(((trans)-4-((tert-butoxycarbonyl)amino)cyclohexyl)amino)-5-(2-methoxyethoxy)-2-methylbenzoic acid (0.3 g, 1.77 mmol) to afford the title compound (0.07 g, 16.1% yield).

Step 6: Synthesis of 5-(((trans)-4-(dimethylamino)cyclohexyl)(ethyl)amino)-N-((4-methoxy-6-methyl-2-oxo-1,2-dihydropyridin-3-yl)methyl)-4'-(2-methoxyethoxy)-4-methyl-[1,1'-biphenyl]-3-carboxamide Protocol as for 2, Step 4 with tert-butyl ((trans)-4-(ethyl (5-(((4-methoxy-6-methyl-2-oxo-1,2-dihydropyridin-3-yl)methyl)carbamoyl)-4'-(2-methoxyethoxy)-4-methyl-[1,1'-biphenyl]-3-yl)amino)cyclohexyl)carbamate (0.07 g, 0.14 mmol) to afford the title compound (0.02 g, 24% yield).

LCMS: 605.5 (M+1)⁺; TFA-salt: ¹H NMR (DMSO-d₆, 400 MHz) δ 11.43 (brs, 1H), 8.22 (s, 2H), 7.97 (t, 1H, J=2.0 Hz), 7.53 (d, 2H, J=8 Hz), 7.30 (s, 1H), 7.13 (s, 1H), 7.00 (d, 2H, J=8.0 Hz), 6.09 (s, 1H), 4.23 (d, 2H, J=4.0 Hz), 4.12 (t, 2H, 4.0 Hz), 3.80 (s, 3H), 3.67 (t, 2H, J=4.0 Hz), 3.32 (s, 3H), 3.09 (q, 2H, J=6.8 Hz), 2.19 (t, 12H, J=8.0 Hz), 1.81 (t, 4H, J=12.8 Hz), 1.38 (q, 2H, J=12.0 Hz), 1.17 (q, 2H, J=12.0 Hz), 0.83 (t, 3H, J=6.8 Hz). 1H merged into the solvent peak.

Compound 2:

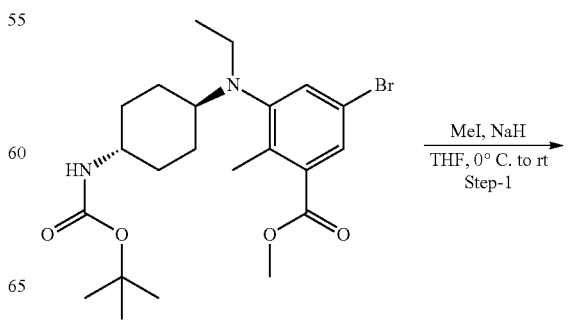

MeI, NaH
THF, 0° C. to rt
Step-1

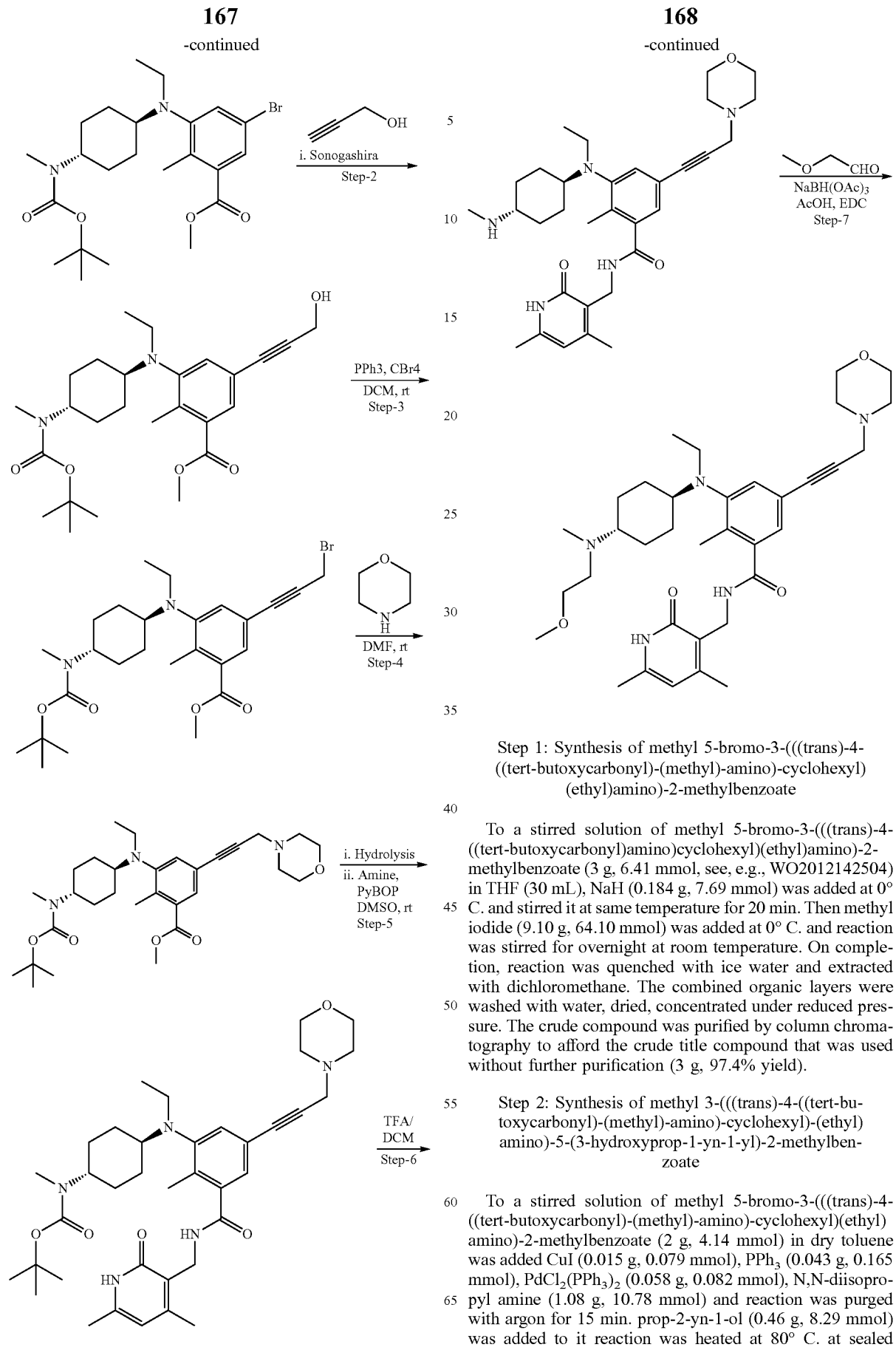

Step 1: Synthesis of methyl 5-bromo-3-(((trans)-4-((tert-butoxycarbonyl)-(methyl)-amino)-cyclohexyl)(ethyl)amino)-2-methylbenzoate To a stirred solution of methyl 5-bromo-3-(((trans)-4-((tert-butoxycarbonyl)amino)cyclohexyl)(ethyl)amino)-2-methylbenzoate (3 g, 6.41 mmol, see, e.g., WO2012142504) in THF (30 mL), NaH (0.184 g, 7.69 mmol) was added at 0° C. and stirred it at same temperature for 20 min. Then methyl iodide (9.10 g, 64.10 mmol) was added at 0° C. and reaction was stirred for overnight at room temperature. On completion, reaction was quenched with ice water and extracted with dichloromethane. The combined organic layers were washed with water, dried, concentrated under reduced pressure. The crude compound was purified by column chromatography to afford the crude title compound that was used without further purification (3 g, 97.4% yield).

Step 2: Synthesis of methyl 3-(((trans)-4-((tert-butoxycarbonyl)-(methyl)-amino)-cyclohexyl)-(ethyl)amino)-5-(3-hydroxyprop-1-yn-1-yl)-2-methylbenzoate To a stirred solution of methyl 5-bromo-3-(((trans)-4-((tert-butoxycarbonyl)-(methyl)-amino)-cyclohexyl)(ethyl)amino)-2-methylbenzoate (2 g, 4.14 mmol) in dry toluene was added CuI (0.015 g, 0.079 mmol), PPh$_3$ (0.043 g, 0.165 mmol), PdCl$_2$(PPh$_3$)$_2$ (0.058 g, 0.082 mmol), N,N-diisopropyl amine (1.08 g, 10.78 mmol) and reaction was purged with argon for 15 min. prop-2-yn-1-ol (0.46 g, 8.29 mmol) was added to it reaction was heated at 80° C. at sealed condition for 5 h. On completion, it was quenched with water and extracted with ethyl acetate. Organic layer was dried over $Na_2SO_4$. The crude compound was purified by column chromatography to afford the title compound (1.2 g, 63.2% yield).

Step 3: Synthesis of methyl 5-(3-bromoprop-1-yn-1-yl)-3-(((trans)-4-((tert-butoxy carbonyl)-(methyl) amino)cyclohexyl)(ethyl)amino)-2-methylbenzoate To a stirred solution of methyl 3-(((trans)-4-((tert-butoxycarbonyl)-(methyl)-amino)-cyclohexyl)-(ethyl)amino)-5-(3-hydroxyprop-1-yn-1-yl)-2-methylbenzoate (1.2 g, 2.62 mmol) in DCM (15 mL), $PPh_3$ (1.37 g, 5.22 mmol) and $CBr_4$ (1.7 g, 5.10 mmol) were added at 0° C. and reaction was stirred for 4 h at room temperature. On completion, reaction was quenched with ice water and extracted with dichloromethane. The combined organic layers were washed with water, dried, concentrated under reduced pressure. The crude material was purified by column chromatography to afford the title compound (0.5 g, 38.5% yield).

Step 4: Synthesis of methyl 3-(((trans)-4-((tert-butoxycarbonyl)(methyl)amino)cyclohexyl)(ethyl) amino)-2-methyl-5-(3-morpholinoprop-1-yn-1-yl) benzoate To a stirred solution of methyl 5-(3-bromoprop-1-yn-1-yl)-3-(((trans)-4-((tert-butoxy carbonyl)-(methyl)amino)cyclohexyl)(ethyl)amino)-2-methylbenzoate (1 equiv.) in DMF, morpholine (5 equiv.) was added and reaction was stirred for 12 h at room temperature. On completion, the reaction was quenched with ice water and extracted with dichloromethane. The combined organic layers were washed with water, dried, concentrated under reduced pressure to afford desired crude title compound that was used in the next step without further purification (98.7% yield)

Step 5: Synthesis of tert-butyl ((trans)-4-((3-(((4,6-dimethyl-2-oxo-1,2-dihydro pyridin-3-yl)methyl) carbamoyl)-2-methyl-5-(3-morpholinoprop-1-yn-1-yl)phenyl)(ethyl)amino)cyclohexyl)(methyl) carbamate NaOH (1.5 eq.) was added to a solution of methyl 3-(((trans)-4-((tert-butoxycarbonyl)(methyl)amino)cyclohexyl)(ethyl)amino)-2-methyl-5-(3-morpholinoprop-1-yl-1-yl)benzoate (1 equiv.) in EtOH: $H_2O$ (9:1) and stirred at 60° C. for 1 h. After completion of the reaction, ethanol was removed under reduced pressure and acidified using dilute HCl up to pH 6 and pH 4 was adjusted using citric acid. Extraction was carried out using 10% methanol in DCM. Combined organic layers were dried concentrated giving respective acid.

The above acid (1 equiv.) was then dissolved in DMSO and 3-(amino methyl)-4,6-dimethylpyridin-2(1H)-one (2 equiv.) and triethyl amine (1 equiv.) was added to it. The reaction mixture was stirred at room temperature for 15 min before PyBop (1.5 equiv.) was added to it and stirring was continued for overnight at room temperature. After completion of the reaction, the reaction mass was poured into ice and extraction was carried out using 10% MeOH/DCM. The combined organic layers were dried over $Na_2SO_4$ and concentrated under reduced pressure to obtain crude material which then purified first by water followed by acetonitrile washing to afford desired title compound (69.4% yield).

Step 6: Synthesis of N-((4,6-dimethyl-2-oxo-1,2-dihydropyridin-3-yl)methyl)-3-(ethyl((trans)-4-(methylamino)cyclohexyl)amino)-2-methyl-5-(3-morpholinoprop-1-yn-1-yl)benzamide To a stirred solution of tert-butyl((trans)-4-((3-(((4,6-dimethyl-2-oxo-1,2-dihydro pyridin-3-yl)methyl)carbamoyl)-2-methyl-5-(3-morpholinoprop-1-yn-1-yl)phenyl)(ethyl) amino)cyclohexyl)(methyl)carbamate (1 equiv.) in DCM at 0° C., TFA (3 equiv.) was added and reaction was stirred for 2 h at room temperature. After completion, reaction was concentrated to dryness. The residue was then basified with $Na_2CO_3$ (aq.) to pH 8 and the aqueous layer was extracted with 20% methanol in DCM. The combined organic layers were dried over $Na_2SO_4$ and solvent was removed under reduced pressure to afford the title compound (99% yield) which was used in the next reaction without further purification.

Step 7: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methyl-5-(3-morpholinoprop-1-yn-1-yl)benzamide To a stirred solution of N-((4,6-dimethyl-2-oxo-1,2-dihydropyridin-3-yl)methyl)-3-(ethyl((trans)-4-(methylamino) cyclohexyl)amino)-2-methyl-5-(3-morpholinoprop-1-yn-1-yl)benzamide (1 equiv.) in dichloroethane, 2-methoxyacetaldehyde (10 equiv.) and acetic acid (6 equiv.) was added at 0° C. and stirred for 20 min. Then $NaBH(OAc)_3$ (3 equiv.) was added and stirred for 2 h at 0° C. On completion of reaction, water was added and extracted with 20% methanol in DCM. Combined organic layers were dried over $Na_2SO_4$ and solvent removed under reduced pressure. The crude compound was purified by prep. HPLC to afford target molecule (0.1 g, 33.6% yield).

LCMS: 606.65 (M+1)$^+$; TFA salt: $^1$H NMR (DMSO-$d_6$, 400 MHz) δ 11.50 (brs, 1H), 9.22 (brs, 1H), 8.18 (t, 1H), 7.24 (s, 1H), 7.09 (s, 1H), 5.86 (s, 1H), 4.26-4.25 (m, 4H), 3.66-3.59 (m, 4H), 3.48-3.36 (m, 3H), 3.29-3.17 (m, 7H), 3.04-3.01 (m, 3H), 2.69-2.68 (m, 4H), 2.20 (s, 3H), 2.19 (s, 3H), 2.11 (s, 3H), 2.00-1.92 (m, 2H), 1.82-1.73 (m, 3H), 1.46 (m, 4H), 0.78 (t, 3H, J=6.4 Hz).

Alternative Synthetic Scheme for Compound 2:

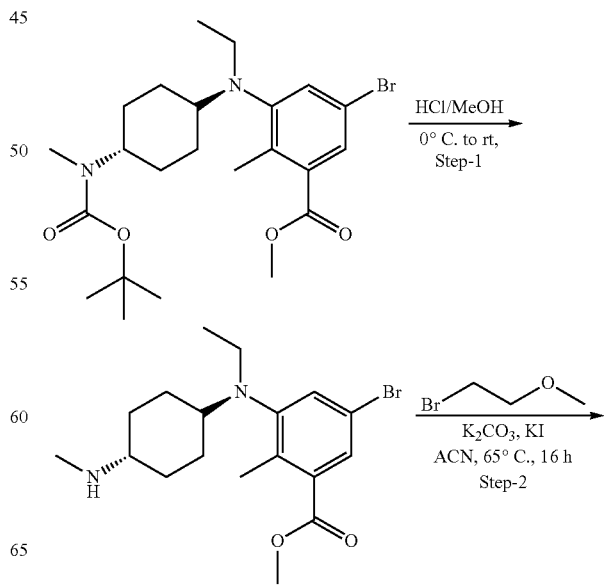

-continued

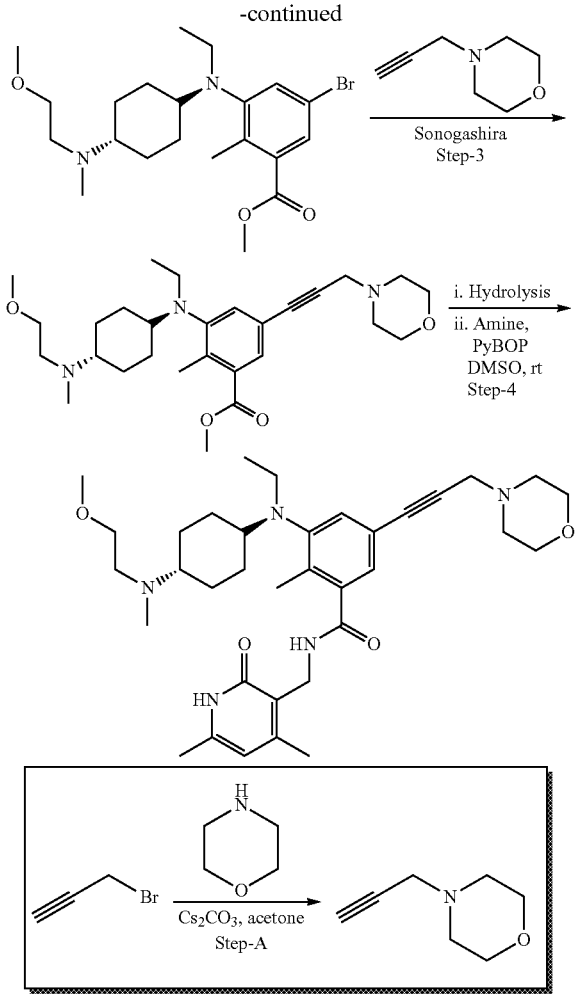

Step A: Synthesis of 4-(prop-2-yn-1-yl)morpholine

To a stirred solution of propargyl bromide (50 g, 420 mmol) in acetone (300 mL), Cs₂CO₃ (136.5 g, 420 mmol) was added at 0° C. Then morpholine (36.60 g, 420 mmol) in acetone (200 mL) was added dropwise and reaction was stirred at room temperature for 16 h. On completion, the reaction mass was filtered and the filtrate was concentrated under reduced pressure to afford the title compound (50 g, crude). The isolated compound was used directly in the subsequent coupling step without further purification.

Step 1: Synthesis of methyl 5-bromo-3-(ethyl ((trans)-4-(methylamino)cyclohexyl)amino)-2-methylbenzoate To a stirred solution of methyl 5-bromo-3-(((trans)-4-((tert-butoxycarbonyl)(methyl)amino)cyclohexyl)(ethyl) amino)-2-methylbenzoate (30 g, 62.24 mmol) in methanol (100 mL) at 0° C., methanolic HCl (500 mL) was added and reaction was stirred for 2 h at room temperature. After completion, reaction was concentrated to dryness. The residue was basified with Na₂CO₃ (aq.) to pH 8 and aqueous layer was extracted with 10% methanol in DCM (200 mL x 3). Combined organic layers were dried over Na₂SO₄ and solvent removed under reduced pressure to afford the title compound as colorless oil (25 g, crude). The isolated compound was used in the next step without further purification.

Step 2: Synthesis of methyl 5-bromo-3-(ethyl ((trans)-4-((2-methoxyethyl)-(methyl)-amino)cyclohexyl)amino)-2-methylbenzoate To a stirred solution of crude methyl 5-bromo-3-(ethyl ((trans)-4-(methylamino)cyclohexyl)amino)-2-methylbenzoate (25 g, 65.44 mmol), 1-bromo-2-methoxyethane (18.19 g, 130.8 mmol) in acetonitrile (250 mL), K₂CO₃ (18.06 g, 130.8 mmol) and KI (6.51 g, 39.21 mmol) were added. The resulting reaction mass was stirred at 65° C. for 16 h. On completion, reaction mixture was diluted with water (300 mL) and extracted with DCM (500 mL×3). The combined organic layers were washed with water, dried over Na₂SO₄ and concentrated under reduced pressure. The crude compound was purified by silica gel column chromatography to afford the title compound (20 g, 69.3% yield).

$^1$H NMR (DMSO-$d_6$, 400 MHz) δ 7.55 (s, 1H), 7.45 (s, 1H), 3.82 (s, 3H), 3.32 (m, 4H), 3.20 (s, 3H), 3.05 (q, 2H), 2.61 (m, 1H), 2.32 (s, 3H), 2.30 (m, 1H), 2.15 (s, 3H), 1.77-1.67 (m, 4H), 1.37-1.31 (m, 2H), 1.24-1.18 (m, 2H), 0.78 (t, 3H, J=6.8 Hz).

Step 3: Synthesis of methyl 3-(ethyl((trans)-4-((2-methoxyethyl)-(methyl)-amino)-cyclohexyl)-amino)-2-methyl-5-(3-morpholinoprop-1-yn-1-yl)benzoate The solution of methyl 5-bromo-3-(ethyl((trans)-4-((2-methoxyethyl)-(methyl)-amino)-cyclohexyl)-amino)-2-methylbenzoate (30 g, 68.02 mmol), 4-(prop-2-yn-1-yl) morpholine (25.51 g, 204 mmol) and triethylamine (20.61 g, 204 mmol) in DMF (300 mL) was bubbled through Argon for 20 min. Then CuI (3.87 g, 20.36 mmol) and Pd (PPh₃)₄ (7.85 g, 6.79 mmol) were added and Argon was bubbled through for further 20 min. The reaction mixture was heated at 105° C. for 4 h and then cooled to room temperature. The reaction was quenched with water (100 mL) and the aqueous phase was extracted with 10% MeOH/DCM (400 mL×3). The combined organic extracts were dried over Na₂SO₄, filtered and concentrated. The residue was purified by silica gel column chromatography to afford the title compound (21 g, 63.7% yield).

$^1$H NMR (DMSO-$d_6$, 400 MHz) δ 7.46 (s, 1H), 7.32 (s, 1H), 3.82 (s, 3H), 3.62-3.57 (m, 6H), 3.50 (s, 2H), 3.35-3.32 (m, 2H), 3.21 (s, 3H), 3.17 (m, 1H), 3.05 (q, 2H), 2.61-2.58 (m, 2H), 2.38 (s, 3H), 2.33 (m, 1H), 2.18 (m, 2H), 1.77-1.70 (m, 4H), 1.36-1.20 (m, 4H), 0.77 (t, 3H, J=6.8 Hz), 3H merged in solvent peak.

Step 4: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methyl-5-(3-morpholinoprop-1-yn-1-yl)benzamide Aqueous NaOH (2.59 g, 64.91 mmol in 10 mL H₂O) was added to a solution of methyl 3-(ethyl((trans)-4-((2-methoxyethyl)-(methyl)-amino)-cyclohexyl)-amino)-2-methyl-5-(3-morpholinoprop-1-yn-1-yl)benzoate (21 g, 43.29 mmol) in EtOH (100 mL) and stirred at 60° C. for 1 h. After completion of the reaction, ethanol was removed under reduced pressure and the residue was acidified using dilute HCl up to pH 4 using citric acid. Extraction was carried out using 10% MeOH/DCM (200 mL×3). Combined organic layers were dried concentrated giving respective acid (15.5 g, 76% yield).

To the solution of above acid (15.5 g, 32.90 mmol) in DMSO (50 mL), 3-(amino methyl)-4,6-dimethylpyridin-2 (1H)-one (10 g, 65.80 mmol) and triethyl amine (23 mL, 164.5 mmol) were added. The reaction mixture was stirred at room temperature for 15 min before PyBop (25.66 g, 49.34 mmol) was added to it at 0° C. and further stirred for overnight at room temperature. After completion, the reaction mass was poured into ice water (100 mL) and extraction was carried out using 10% MeOH/DCM (200 mL×3). Combined organic layers were dried over $Na_2SO_4$ and concentrated under reduced pressure. The crude compound was purified by column chromatography over basic alumina eluting with MeOH:DCM to afford the title compound (11 g, 55.3% yield).

LCMS: 606.50 (M+1)$^+$; $^1$H NMR (MeOD, 400 MHz) δ 7.23 (s, 1H), 7.09 (s, 1H), 6.11 (s, 1H), 4.46 (s, 2H), 3.74-3.72 (m, 4H), 3.51 (s, 2H), 3.47 (t, 2H, J=5.6 Hz), 3.32 (s, 3H), 3.07 (q, 2H, J=7.2 Hz), 2.64-2.63 (m, 7H), 2.38 (m, 1H), 2.37 (s, 3H), 2.27 (s, 3H), 2.26 (s, 3H), 2.25 (s, 3H), 1.89-1.86 (m, 4H), 1.50-1.30 (m, 4H), 0.83 (t, 3H, J=7.2 Hz).

Compound 7

Synthesis of N-((4,6-dimethyl-2-oxo-1,2-dihydro-pyridin-3-yl)methyl)-3-(ethyl((trans)-4-((2-methoxy-ethyl)(methyl)amino)cyclohexyl)amino)-2-methyl-5-(3-(4-methylpiperazin-1-yl)prop-1-yn-1-yl) benzamide

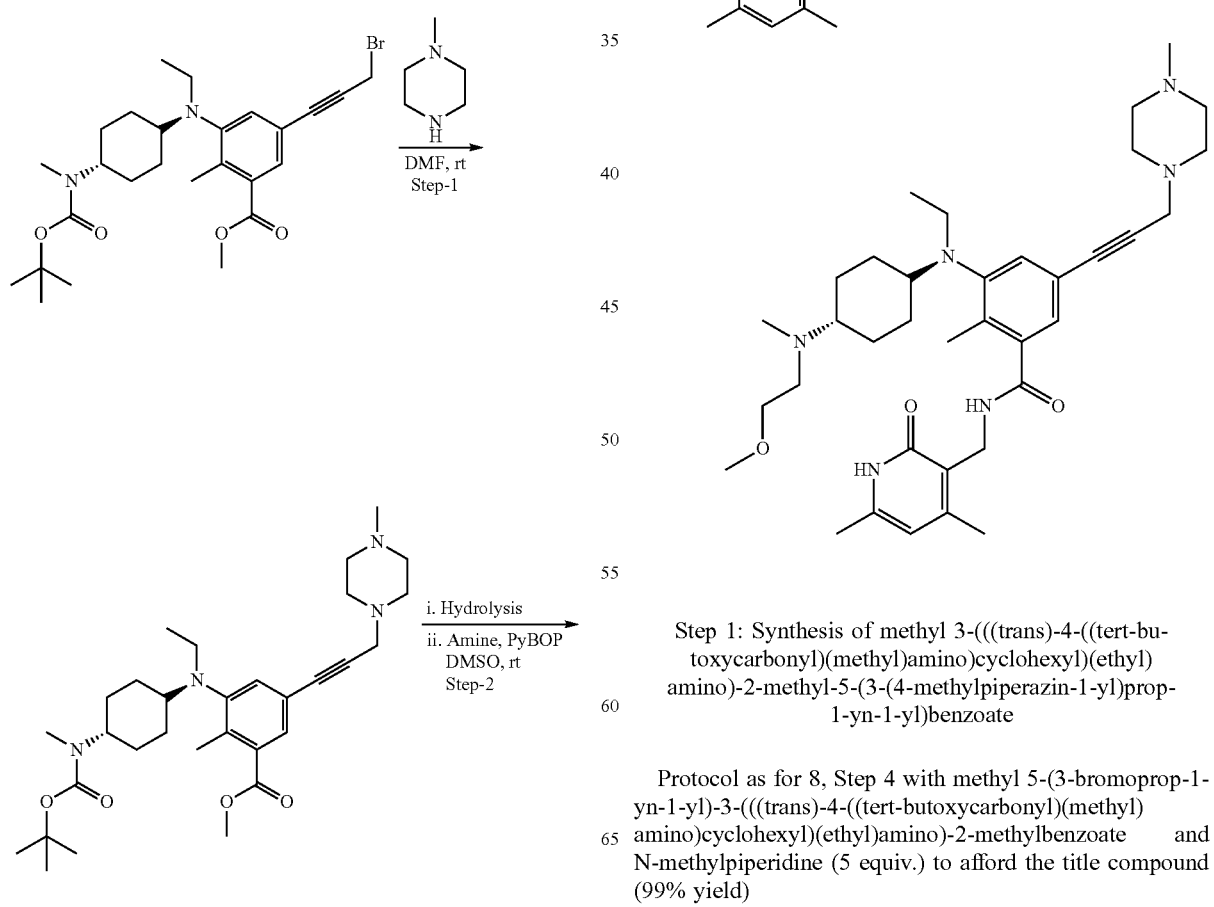

Step 1: Synthesis of methyl 3-(((trans)-4-((tert-butoxycarbonyl)(methyl)amino)cyclohexyl)(ethyl) amino)-2-methyl-5-(3-(4-methylpiperazin-1-yl)prop-1-yn-1-yl)benzoate Protocol as for 8, Step 4 with methyl 5-(3-bromoprop-1-yn-1-yl)-3-(((trans)-4-((tert-butoxycarbonyl)(methyl) amino)cyclohexyl)(ethyl)amino)-2-methylbenzoate and N-methylpiperidine (5 equiv.) to afford the title compound (99% yield)

Step 2: Synthesis of tert-butyl((trans)-4-((3-(((4,6-dimethyl-2-oxo-1,2-dihydropyridin-3-yl)methyl)carbamoyl)-2-methyl-5-(3-(4-methylpiperazin-1-yl)prop-1-yn-1-yl)phenyl)(ethyl)amino)cyclohexyl)(methyl)carbamate Protocol as for 8, Step 5 with methyl 3-(((trans)-4-((tert-butoxycarbonyl)(methyl)amino)cyclohexyl)(ethyl)amino)-2-methyl-5-(3-(4-methylpiperazin-1-yl)prop-1-yn-1-yl)benzoate and 3-(aminomethyl)-4,6-dimethylpyridin-2(1H)-one (2 equiv.) to afford the title compound (73.4% yield)

Step 3: Synthesis of N-((4,6-dimethyl-2-oxo-1,2-dihydropyridin-3-yl)methyl)-3-(ethyl((trans)-4-(methylamino)cyclohexyl)amino)-2-methyl-5-(3-(4-methylpiperazin-1-yl)prop-1-yn-1-yl)benzamide Protocol as for 8, Step 6 with tert-butyl((trans)-4-((3-(((4,6-dimethyl-2-oxo-1,2-dihydropyridin-3-yl)methyl)carbamoyl)-2-methyl-5-(3-(4-methylpiperazin-1-yl)prop-1-yn-1-yl)phenyl)(ethyl)amino)cyclohexyl)(methyl)carbamate to afford the title compound (89.7% yield)

Step 4: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methyl-5-(3-(4-methylpiperazin-1-yl)prop-1-yn-1-yl)benzamide Protocol as for 8, Step 7 with N-((4,6-dimethyl-2-oxo-1,2-dihydropyridin-3-yl)methyl)-3-(ethyl((trans)-4-(methylamino)cyclohexyl)amino)-2-methyl-5-(3-(4-methylpiperazin-1-yl)prop-1-yn-1-yl)benzamide to afford the title compound (0.07 g, 18.1% yield).

LCMS: 619.65 (M+1)$^+$; TFA-salt: $^1$H NMR (DMSO-$d_6$, 400 MHz) δ 11.50 (brs, 1H), 9.28 (brs, 1H), 8.17 (t, 1H), 7.17 (s, 1H), 7.01 (s, 1H), 5.87 (s, 1H), 4.25 (d, 2H, J=4.8 Hz), 3.66 (m, 2H), 3.62 (m, 2H), 3.44-3.36 (m, 3H), 3.31 (s, 3H), 3.17-3.02 (m, 8H), 2.79 (s, 3H), 2.69-2.68 (m, 4H), 2.61 (m, 2H), 2.19 (s, 6H), 2.11 (s, 3H), 1.96-1.92 (m, 2H), 1.83 (m, 2H), 1.46 (m, 4H), 0.78 (t, 3H, J=6.4 Hz).
Compound 8

Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-5-(3-hydroxy-3-methylbut-1-yn-1-yl)-2-methylbenzamide

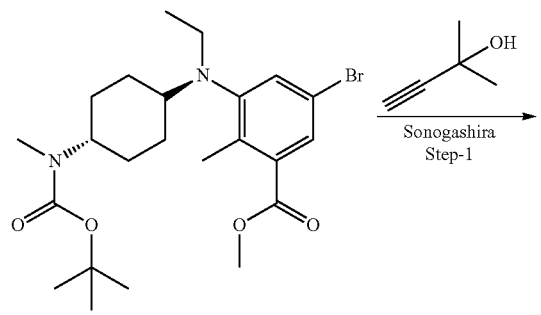

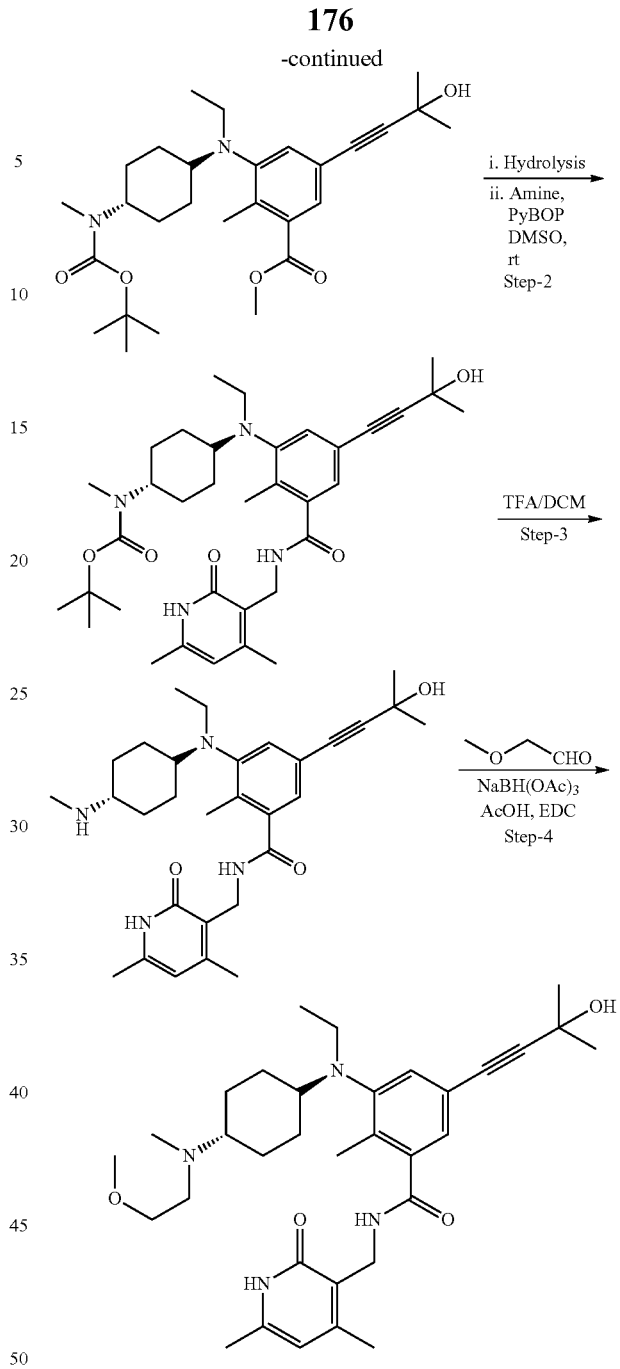

Step 1: Synthesis of methyl 3-(((trans)-4-((tert-butoxycarbonyl)(methyl)amino)cyclohexyl)(ethyl)amino)-5-(3-hydroxy-3-methylbut-1-yn-1-yl)-2-methylbenzoate To a stirred solution of methyl 5-bromo-3-(((trans)-4-((tert-butoxycarbonyl)(methyl)amino)cyclohexyl)(ethyl)amino)-2-methylbenzoate (1 g, 2.07 mmol) in DMF (10 mL), CuI (0.118 g, 0.62 mmol), Pd(PPh$_3$)$_4$ (0.239 g, 0.21 mmol), triethyl amine (0.84 mL, 6.2 mmol) were added and the reaction was purged with argon for 15 min. 2-methylbut-3-yn-2-ol (0.523 g, 6.22 mmol) was added and the reaction was heated at 100° C. in a sealed tube for 6 h. On completion, the reaction was quenched with water and extracted with ethyl acetate. The combined organic layers were dried over Na$_2$SO$_4$. The crude compound was purified by column chromatography to afford the title compound (0.8 g, 80% yield).

Steps 2-4: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-5-(3-hydroxy-3-methylbut-1-yn-1-yl)-2-methylbenzamide Protocol as for 8, Steps 5-7 starting with methyl 3-(((trans)-4-((tert-butoxycarbonyl)(methyl)amino)cyclohexyl)(ethyl)amino)-5-(3-hydroxy-3-methylbut-1-yn-1-yl)-2-methylbenzoate (0.8 g, 1.64 mmol) to afford the title compound (0.11 g, 17.5% yield).

LCMS: 565.90 (M+1)$^+$; TFA-salt: $^1$H NMR (DMSO-d$_6$, 400 MHz)δ 3, 11.45 (brs, 1H), 9.14 (brs, 1H), 8.17 (t, 1H, J=4.4 Hz), 7.11 (s, 1H), 6.94 (s, 1H), 5.86 (s, 1H), 5.08-5.05 (m, 1H), 4.96-4.93 (m, 1H), 4.25 (d, 2H, J=5.2 Hz), 3.81-3.77 (m, 3H), 3.45-3.22 (m, 6H), 3.03-3.01 (m, 3H), 2.68-2.67 (m, 4H), 2.19 (s, 3H+3H), 2.11 (s, 3H), 2.02-1.91 (m, 2H), 1.84 (m, 2H), 1.44 (s, 6H), 0.77 (t, 3H, J=6.8 Hz). 1H merged in solvent peak.

Compound 9

Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-5-fluoro-2-methylbenzamide

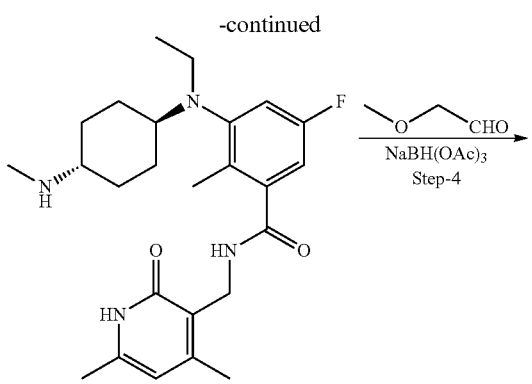

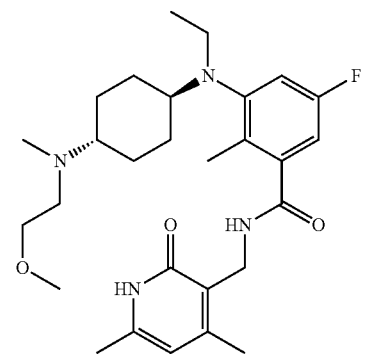

Step 1: Synthesis of methyl 3-(((trans)-4-((tert-butoxycarbonyl)(methyl)amino)cyclohexyl)(ethyl)amino)-5-fluoro-2-methylbenzoate Protocol as for 8, Step 1 with methyl 3-(((trans)-4-((tert-butoxycarbonyl)amino)cyclohexyl)(ethyl)amino)-5-fluoro-2-methylbenzoate (1 g, 2.45 mmol, see, e.g., co-owned US Provisional Application 61/714,145 filed on Oct. 15, 2012 (Attorney Docket No. 41478-514P02US)) in DMF as solvent (10 mL) to afford the title compound 0.95 g, 95% yield).

Steps 2-4: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-5-fluoro-2-methylbenzamide Protocols as for 8, Steps 5-7 starting with methyl 3-(((trans)-4-((tert-butoxycarbonyl)(methyl)amino)cyclohexyl)(ethyl)amino)-5-fluoro-2-methylbenzoate (0.95 g, 2.25 mmol) to afford the title compound (0.05 g, 4.6% yield).

LCMS: 501.40 (M+1)$^+$; TFA-salt: $^1$H NMR (DMSO-d$_6$, 400 MHz) δ 11.47 (brs, 1H), 9.25 (s, 1H), 8.17 (t, 1H), 7.02 (d, 1H, J=10.8 Hz), 6.76 (d, 1H, J=6.8 Hz), 5.86 (s, 1H), 4.25 (d, 2H, J=5.2 Hz), 3.62 (m, 2H), 3.37 (s, 3H), 3.29-3.25 (m, 3H), 3.03-3.01 (m, 2H), 2.69-2.68 (m, 4H), 2.19 (s, 3H), 2.14 (s, 3H), 2.11 (s, 3H), 1.97-1.92 (m, 2H), 1.83 (m, 2H), 1.49-1.44 (m, 4H), 0.79 (t, 3H, J=6.8 Hz).

Compound 10:

Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methylbenzamide

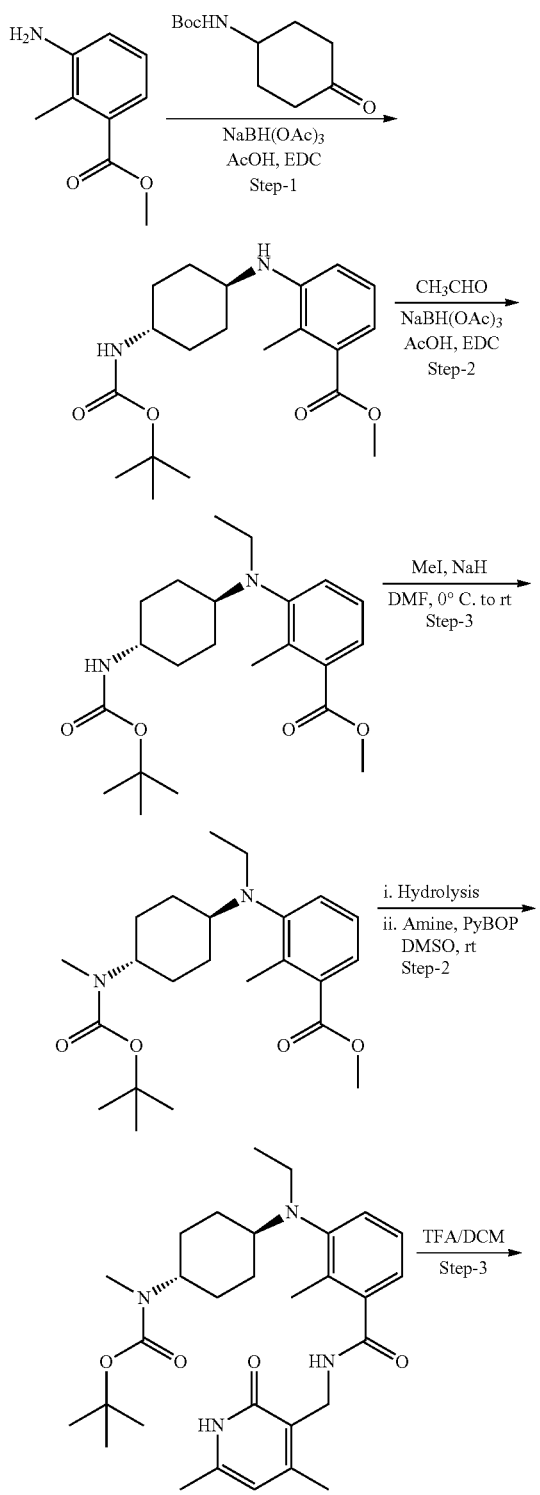

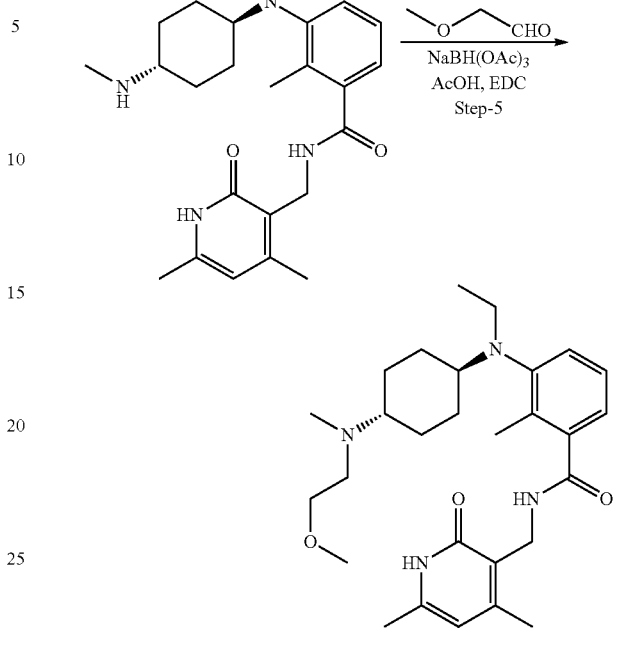

Step 1: Synthesis of methyl 3-(((trans)-4-((tert-butoxycarbonyl)amino)cyclohexyl)amino)-2-methylbenzoate To a stirred solution of methyl 3-amino-2-methylbenzoate (4.1 g, 24.82 mmol) and tert-butyl (4-oxocyclohexyl)carbamate (6.35 g, 29.80 mmol) in dichloroethane (40 mL), acetic acid (8.94 g, 149 mmol) was added and reaction stirred at room temperature for 20 minutes. Then sodium triacetoxyborohydride (15.8 g, 74.5 mmol) was added at 0° C. and reaction was stirred at room temperature for 16 h. On completion, the reaction was quenched with $Na_2CO_3$ (aq.) the organic phase was separated and the aqueous phase was extracted with DCM. The combined organic layers were washed with water, dried, concentrated under reduced pressure. The crude material obtained was purified by column chromatography to afford the title compound (3.1 g, 34.8% yield).

Step 2: Synthesis of methyl 3-(((trans)-4-((tert-butoxycarbonyl)(methyl)amino)cyclohexyl)(ethyl)amino)-2-methylbenzoate To a stirred solution of methyl 3-(((trans)-4-((tert-butoxycarbonyl)amino)cyclohexyl)amino)-2-methylbenzoate (2.9 g, 8.01 mmol) and acetaldehyde (0.53 g, 12.01 mmol) in dichloroethane (30 mL), acetic acid (2.88 g, 48.0 mmol) was added and reaction stirred at room temperature for 20 min. Then sodium triacetoxyborohydride (5.1 g, 24.05 mmol) was added at 0° C. and reaction was stirred at room temperature for 2 h. On completion, the reaction was quenched with $Na_2CO_3$ (aq.), the organic phase was separated and the aqueous phase was extracted with DCM. The combined organic layers were washed with water, dried, concentrated under reduced pressure and the crude material was purified by column chromatography to afford the title compound (2.8 g, 61% yield).

Step 3-6: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methylbenzamide Protocol as for 11, Steps 1-4 starting from methyl 3-(((trans)-4-((tert-butoxycarbonyl)-amino)-cyclohexyl)-(ethyl)-amino)-2-methylbenzoate (1.2 g, 3.08 mmol) to afford the title compound (0.1 g, 4.3% yield).

LCMS: 483.40 (M+1)$^+$; TFA-salt: $^1$H NMR (DMSO-d$_6$, 400 MHz) δ 11.45 (brs, 1H), 9.30 (brs, 1H), 8.04 (s, 1H), 7.18 (m, 2H), 6.98 (m, 1H), 5.86 (s, 1H), 4.27 (m, 2H), 3.62 (m, 2H), 3.46-3.30 (m, 6H), 3.17-3.09 (m, 2H), 2.69 (m, 4H), 2.21 (s, 3H), 2.20 (s, 3H), 2.11 (s, 3H), 1.98-1.87 (m, 4H), 1.45 (m, 4H), 0.79 (t, 3H).

Compound 11:

Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-5-methoxy-2-methylbenzamide

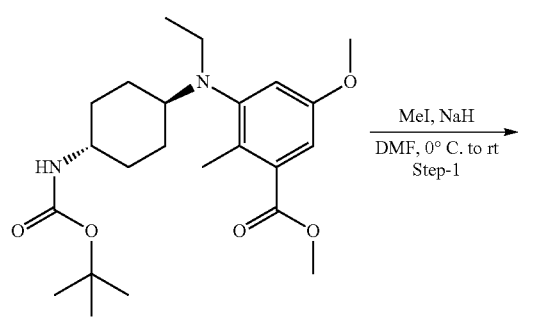

MeI, NaH
DMF, 0° C. to rt
Step-1

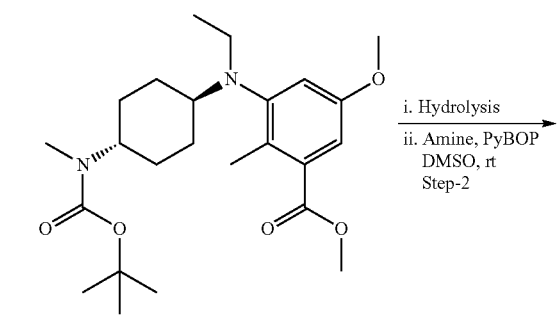

i. Hydrolysis
ii. Amine, PyBOP
DMSO, rt
Step-2

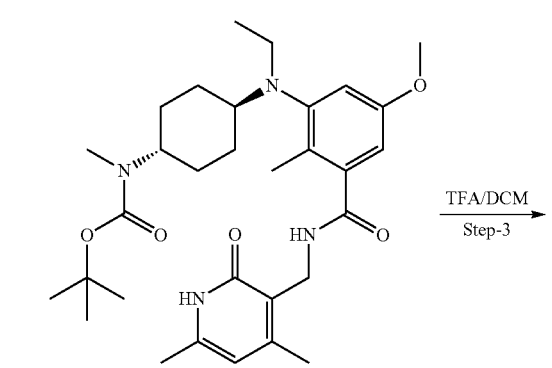

TFA/DCM
Step-3

-continued

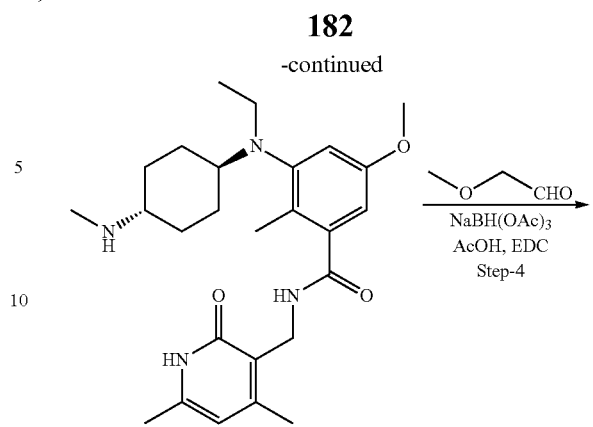

NaBH(OAc)$_3$
AcOH, EDC
Step-4

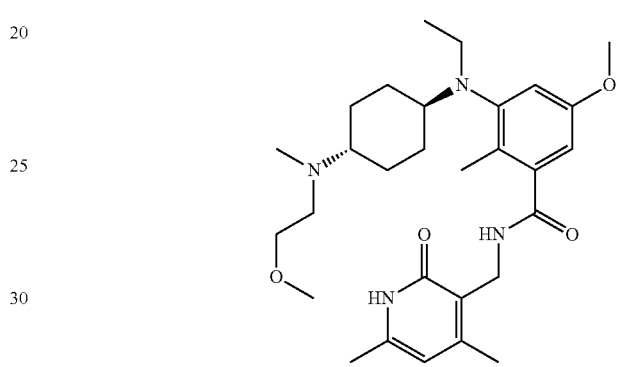

Step 1: Synthesis of methyl 3-(((trans)-4-((tert-butoxycarbonyl)(methyl)amino)cyclohexyl)(ethyl)amino)-5-methoxy-2-methylbenzoate Protocol as for 8, Step 1 with methyl 3-(((trans)-4-((tert-butoxycarbonyl)amino)cyclohexyl)(ethyl)amino)-5-methoxy-2-methylbenzoate (see, e.g., WO2012/142513 (Attorney Docket No. 41478-508001WO)).

Steps 2-4: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-5-methoxy-2-methylbenzamide Protocol as for 8, Steps 5-7 starting from methyl 3-(((trans)-4-((tert-butoxycarbonyl)(methyl)amino)cyclohexyl)(ethyl)amino)-5-methoxy-2-methylbenzoate.

LCMS: 513.55 (M+1)$^+$; TFA-salt: NMR (DMSO-d$_6$, 400 MHz) δ 11.49 (brs, 1H), 9.27 (s, 1H), 8.07 (s, 1H), 6.74 (brs, 1H), 6.58 (s, 1H), 5.87 (s, 1H), 4.26 (d, 2H, J=4.0 Hz), 3.72 (s, 3H), 3.62 (brs, 2H), 3.50-2.90 (m, 9H), 2.68 (d, 3H, J=3.6 Hz), 2.20 (s, 3H), 2.11 (s, 6H), 2.04-1.87 (m, 4H), 1.56-1.38 (m, 4H), 0.80 (brt, 3H, J=6.4 Hz).

Compound 12:

Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-5-(2-methoxyethoxy)-2-methylbenzamide

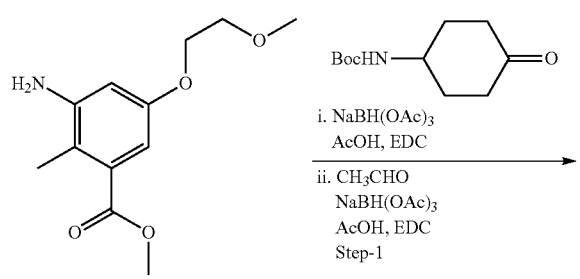

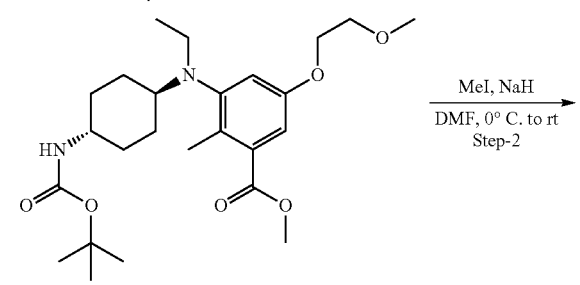

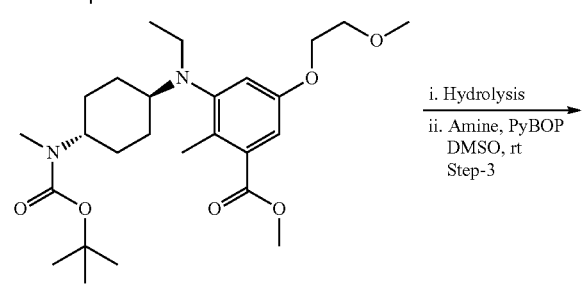

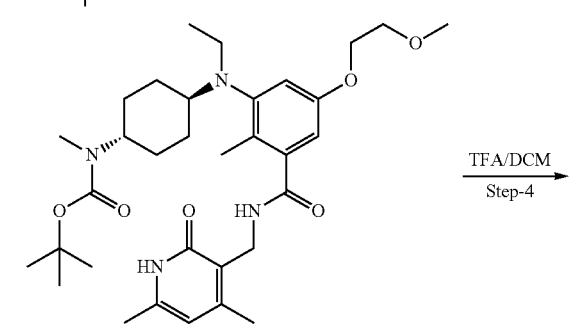

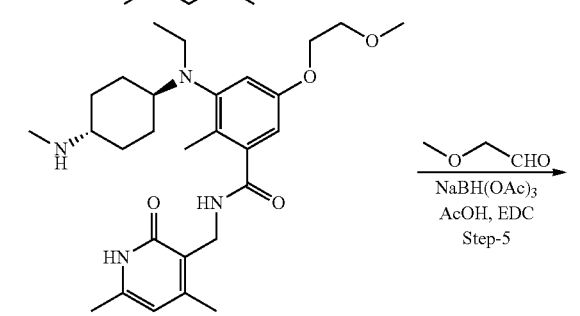

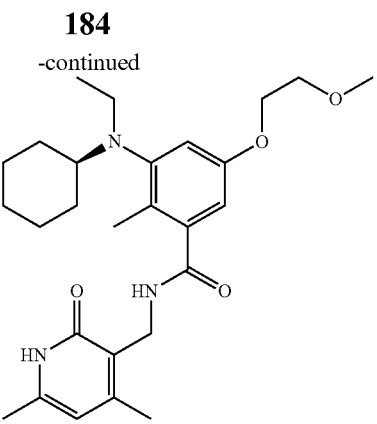

Step 1: Synthesis of methyl 3-(((trans)-4-((tert-butoxycarbonyl)amino)cyclohexyl)(ethyl)amino)-5-(2-methoxyethoxy)-2-methylbenzoate Protocol as for 10, Steps 1-2 with methyl 3-amino-5-(2-methoxyethoxy)-2-methylbenzoate.

Steps 2-5: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-5-(2-methoxyethoxy)-2-methylbenzamide Protocol as for 11, Steps 1-4 starting from methyl 3-(((trans)-4-((tert-butoxycarbonyl)amino)cyclohexyl)(ethyl)amino)-5-(2-methoxyethoxy)-2-methylbenzoate LCMS: 557.60 (M+1)$^+$; TFA-salt: NMR (DMSO-d$_6$, 400 MHz) δ 11.47 (brs, 1H), 9.19 (s, 1H), 8.05 (s, 1H), 6.73 (s, 1H), 6.56 (s, 1H), 5.86 (s, 1H), 4.25 (d, 2H, J=3.6 Hz), 4.05 (brs, 2H), 3.63 (brs, 4H), 3.30 (d, 3H, J=6.4 Hz), 3.25-2.93 (m, 3H), 2.68 (d, 4H, J=3.6 Hz), 2.19 (s, 3H), 2.11 (s, 6H), 2.03-1.69 (m, 4H), 1.53-1.38 (m, 4H), 0.80 (brt, 3H, J=6.4 Hz). 3H merged in solvent peak.

Compound 13:

Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methyl-5-(2-morpholinoethoxy)benzamide

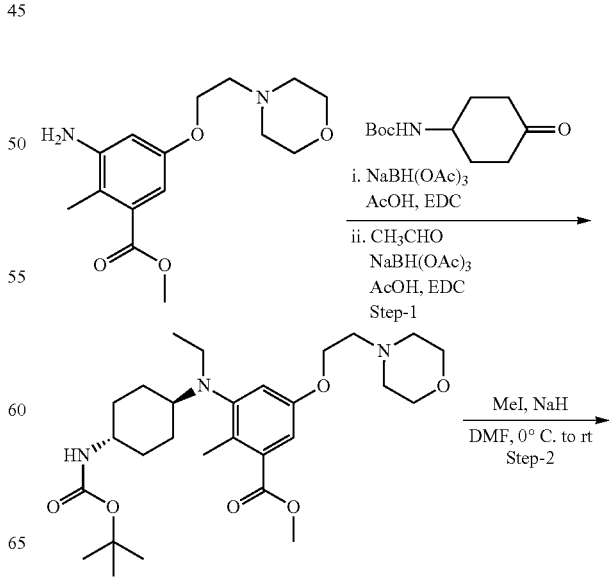

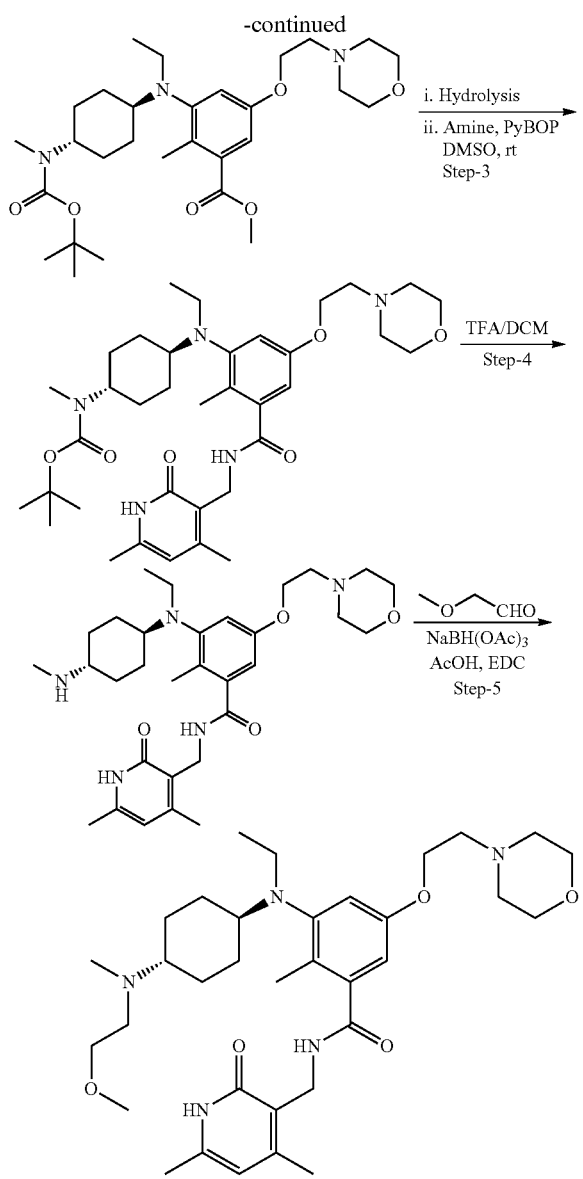

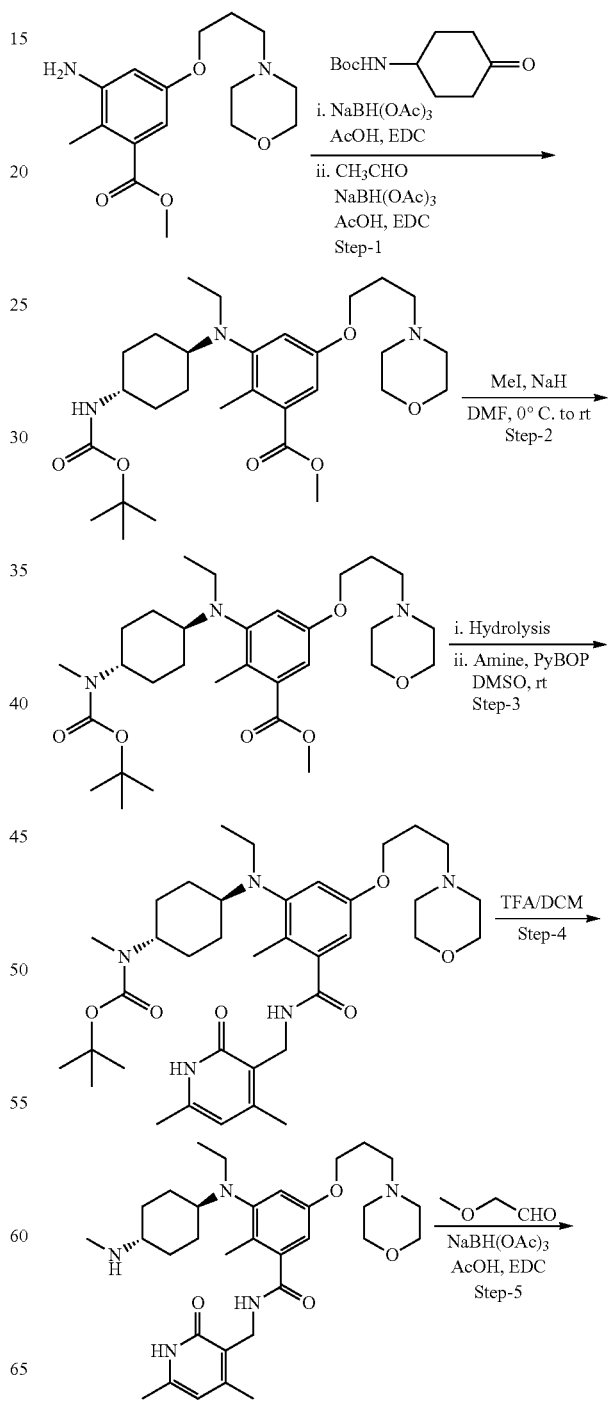

Step 1: Synthesis of methyl 3-(((trans)-4-((tert-butoxycarbonyl)amino)cyclohexyl)(ethyl)amino)-2-methyl-5-(2-morpholinoethoxy)benzoate Protocol as for 10, Steps 1-2 with methyl 3-amino-2-methyl-5-(2-morpholinoethoxy)benzoate.

Steps 2-5: Synthesis of N-((4,6-dimethyl-2-oxo-1,2-dihydropyridin-3-yl)methyl)-3-(ethyl((trans)-4-(2-methoxyethyl)(methyl)amino)cyclohexyl)amino)-2-methyl-5-(2-morpholinoethoxy)benzamide Protocol as for 11, Steps 1-4 starting from methyl 3-(((trans)-4-((tert-butoxycarbonyl)amino)cyclohexyl)(ethyl)amino)-2-methyl-5-(2-morpholinoethoxy)benzoate LCMS: 612.55 (M+1)$^+$; TFA-salt: NMR (DMSO-$d_6$, 400 MHz) δ 11.45 (brs, 1H), 9.09 (s, 1H), 8.48 (s, 1H), 8.01 (s, 1H), 6.77 (s, 1H), 6.67 (s, 1H), 5.87 (s, 1H), 4.44 (brs, 2H), 4.27 (d, 2H, J=3.2 Hz), 4.00-3.89 (m, 6H), 3.64-3.47 (m, 6H), 3.38 (q, 2H, J=6.4 Hz), 3.42-3.23 (m, 6H), 3.14-3.00 (m, 4H), 2.98-2.79 (m, 2H), 2.21 (s, 3H), 2.11 (s, 3H), 1.99 (brs, 1H), 1.90-1.78 (m, 2H), 1.70-1.59 (m, 2H), 1.53-1.37 (m, 3H), 0.81 (brt, 3H, J=6.4 Hz).

Compound 14:

Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methyl-5-(3-morpholinopropoxy)benzamide

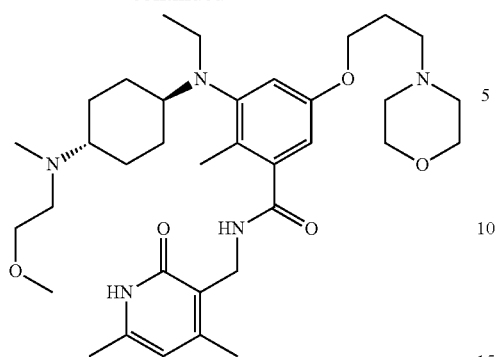

Step 1: Synthesis of methyl 3-(((trans)-4-((tert-butoxycarbonyl)amino)cyclohexyl)(ethyl)amino)-2-methyl-5-(3-morpholinopropoxy)benzoate Protocol as for 10, Steps 1-2 with methyl 3-amino-2-methyl-5-(3-morpholinopropoxy)benzoate.

Steps 2-5: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methyl-5-(3-morpholinopropoxy)benzamide Protocol as for 11, Steps 1-4 starting from methyl 3-(((trans)-4-((tert-butoxycarbonyl)amino)cyclohexyl)(ethyl)amino)-2-methyl-5-(3-morpholinopropoxy)benzoate LCMS: 626.75 (M+1)$^+$; TFA-salt: $^1$H NMR (DMSO-d$_6$, 400 MHz) δ 11.45 (brs, 1H), 8.48 (s, 2H), 8.03 (s, 1H), 6.72 (s, 1H), 6.59 (s, 1H), 5.87 (s, 1H), 4.26 (d, 2H, J=3.2 Hz), 4.03 (m, 2H), 3.93 (m, 5H), 3.65-3.57 (m, 2H), 3.55 (t, 2H, J=4.4 Hz), 3.46 (m, 4H), 3.17 (s, 3H), 3.13-3.05 (m, 3H), 3.05-2.91 (m, 3H), 2.67-2.54 (m, 1H), 2.19 (s, 3H), 2.18-2.09 (m, 3H), 2.11 (s, 3H), 2.09-1.98 (m, 4H), 1.88-1.76 (m, 2H), 1.41 (q, 2H, J=11.2 Hz), 1.35-1.20 (m, 2H), 0.79 (t, 3H, J=6.4 Hz).

Compounds 15-26:

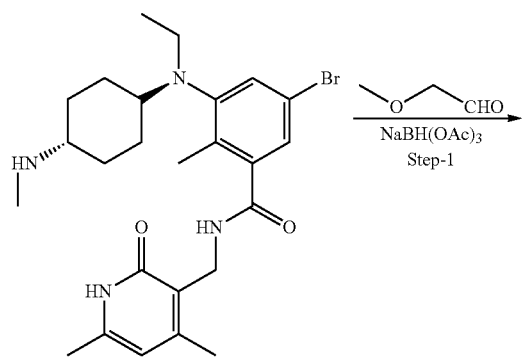

Compounds 15-26 were synthesized from common intermediate 5-bromo-N-((4,6-dimethyl-2-oxo-1,2-dihydropyridin-3-yl)methyl)-3-(ethyl((trans)-4-((2-methoxyethyl)(methyl)amino)cyclohexyl)amino)-2-methylbenzamide following standard Suzuki coupling protocols outlined above.

Step 1: Synthesis of 5-bromo-N-((4,6-dimethyl-2-oxo-1,2-dihydropyridin-3-yl)methyl)-3-(ethyl((trans)-4-((2-methoxyethyl)(methyl)amino)cyclohexyl)amino)-2-methylbenzamide Following the original protocol for making Compound 157, Step 7, 5-bromo-N-((4,6-dimethyl-2-oxo-1,2-dihydropyridin-3-yl)methyl)-3-(ethyl((trans)-4-(methylamino)cyclohexyl)amino)-2-methylbenzamide (2.5 g, 4.98 mmol) was converted to afford the desired compound (1.6 g, 57.8% yield).

Step 2: General Suzuki coupling conditions

To a stirred solution of 5-bromo-N-((4,6-dimethyl-2-oxo-1,2-dihydropyridin-3-yl)methyl)-3-(ethyl((trans)-4-((2-methoxyethyl)(methyl)amino)cyclohexyl)amino)-2-methylbenzamide (1 equiv.) and boronic acid/ester (1.2 equiv.) in dioxane/water mixture, Na$_2$CO$_3$ (3.6 equiv.) was added and solution purged with argon for 15 min. Then Pd(PPh$_3$)$_4$ (0.1 equiv.) was added and argon was purged again for 10 min. The combined reaction mixture was heated at 100° C. for 2 h. On completion, the reaction mixture was diluted with water and extracted with 10% MeOH/DCM. The combined organic layers were dried over Na$_2$SO$_4$ and the solvent removed under reduced pressure to afford crude material which was purified by column chromatography/prep. HPLC to afford the desired targets. The analytical data for Compounds 15-26 are provided in the table below.

| Compound # | Step 2 Yield | Data |
|---|---|---|
| 15 | (0.12 g, 46.7%) | LCMS: 574.45 (M + 1)+; TFA-salt: $^1$H NMR (DMSO-$d_6$, 400 MHz) δ 11.48 (brs, 1H), 9.34 (brs, 1H), 9.00 (s, 1H), 8.53 (d, 1H, J = 7.6 Hz), 8.22 (s, 1H), 7.78 (d, 1H, J = 8.0 Hz), 7.56 (s, 1H), 7.40 (s, 1H), 5.87 (s, 1H), 4.31 (d, 2H, J = 4.0 Hz), 3.62 (m, 2H), 3.48-3.42 (m, 1H), 3.25-3.15 (m, 4H), 2.76 (m, 1H), 2.68 (m, 6H), 2.26 (s, 3H), 2.22 (s, 3H), 2.11 (s, 3H), 1.99-1.90 (m, 4H), 1.48 (m, 4H), 0.84 (t, 3H, J = 6.8 Hz), 3H merged in solvent peak. |
| 16 | (0.06 g, 28.5%) | LCMS: 590.65 (M + 1)+; TFA-salt: $^1$H NMR (DMSO-$d_6$, 400 MHz) δ 11.45 (s, 1H), 8.42 (s, 1H), 8.16 (t, 1H), 7.98-7.95 (m, 1H,), 7.35 (s, 1H), 7.18 (s, 1H), 6.89 (d, 1H, J = 8.8 Hz), 5.86 (s, 1H), 4.29 (d, 2H, J = 4.8 Hz), 3.89 (s, 3H), 3.20 (s, 3H), 3.10-3.08 (m, 2H), 2.66-2.63 (m, 1H), 2.50 (m, 1H), 2.33-2.25 (m, 1H), 2.21 (m, 6H), 2.13 (s, 3H), 2.11 (s, 3H), 1.83-1.68 (m, 4H), 1.41-1.14 (m, 4H), 1.07 (s, 3H), 0.82 (t, 3H, J = 6.8 Hz). |
| 17 | (0.06 g, 22.9%) | LCMS: 591.50 (M + 1)+; TFA-salt: $^1$H NMR (DMSO-$d_6$, 400 MHz) δ 11.47 (brs, 1H), 9.13 (brs, 1H), 8.79 (s, 1H), 8.38 (s, 1H), 8.20 (s, 1H), 7.81 (s, 1H), 7.61 (s, 1H), 5.87 (s, 1H), 4.30 (d, 2H, J = 4.4 Hz), 3.95 (s, 3H), 3.61 (m, 2H), 3.37-3.31 (m, 4H), 3.27-3.12 (m, 4H), 2.80 (m, 1H), 2.69-2.68 (m, 2H), 2.25 (s, 3H), 2.22 (s, 3H), 2.11 (s, 3H), 1.98-1.91 (m, 4H), 1.48 (m, 4H), 0.83 (t, 3H, J = 6.8 Hz). |
| 18 | — | LCMS: 575.45 (M + 1)+; TFA-salt: $^1$H NMR (DMSO-$d_6$, 400 MHz) δ 11.47 (brs, 1H), 9.22 (brs, 1H), 9.11 (s, 1H), 8.59 (s, 1H), 8.24 (s, 1H), 7.89 (s, 1H), 7.70 (s, 1H), 5.88 (s, 1H), 4.31 (d, 1H, J = 4.0 Hz), 3.62 (m, 2H), 3.41-3.27 (m, 2H), 3.25-3.07 (m, 4H), 2.96 (s, 1H), 2.92-2.73 (m, 2H), 2.68 (d, 3H, J = 4.0 Hz), 2.53 (s, 3H), 2.27 (s, 3H), 2.22 (s, 3H), 2.11 (s, 3H), 2.03-1.87 (m, 4H), 1.60-1.40 (m, 4H), 0.84 (t, 3H, J = 7.6 Hz). |
| 19 | (0.07 g, 34.3%) | LCMS: 575.35 (M + 1)+; TFA-salt: $^1$H NMR (DMSO-$d_6$, 400 MHz) δ 8.97 (s, 2H), 7.56 (s, 1H), 7.38 (s, 1H), 5.92 (s, 1H), 4.29 (d, 2H), 3.59 (m, 2H), 3.28-3.06 (m, 8H), 2.89 (m, 1H), 2.66-2.65 (m, 6H), 2.24 (s, 3H), 2.22 (s, 3H), 2.11 (s, 3H), 1.91 (m, 4H), 1.46 (m, 4H), 0.82 (t, 3H, J = 6.4 Hz). |
| 20 | (0.07 g, 22.2%) | LCMS: 591.50 (M + 1)+; TFA-salt: $^1$H NMR (DMSO-$d_6$, 400 MHz) δ 11.47 (bs, 1H), 9.19 (bs, 1H), 8.92 (s, 2H), 8.18 (s, 1H), 7.49 (s, 1H), 7.32 (s, 1H), 5.87 (s, 1H), 4.29 (d, 2H, J = 4.8 Hz), 3.96 (s, 3H), 3.63-3.62 (m, 2H), 3.35 (m, 1H), 3.31 (s, 3H), 3.27-3.13 (m, 4H), 2.80 (m, 1H), 2.69-2.68 (m, 3H), 2.25 (s, 3H), 2.21 (s, 3H), 2.11 (s, 3H), 1.98-1.92 (m, 3H), 1.50-1.48 (m, 4H), 0.83 (t, 3H, J = 6.8 Hz). |
| 21 | (0.07 g, 25.5%) | LCMS: 561.45 (M + 1)+; TFA-salt: $^1$H NMR (DMSO-$d_6$, 400 MHz) δ 11.47 (brs, 1H), 9.18 (s, 1H), 9.14 (s, 2H), 8.21 (t, 1H), 7.58 (s, 1H), 7.40 (s, 1H), 5.87 (s, 1H), 4.30 (d, 2H, J = 4.4 Hz), 3.62 (m, 2H), 3.42-3.35 (m, 1H), 3.27-3.25 (m, 1H), 3.17-3.14 (m, 4H), 2.69-2.68 (m, 3H), 2.27 (s, 3H), 2.22 (s, 3H), 2.11 (s, 3H), 1.98-1.92 (m, 4H), 1.48 (m, 4H), 0.84 (t, 3H, J = 6.8 Hz), 3H merged in solvent peak. |
| 22 | — | LCMS: 561.60 (M + 1)+; TFA-salt: $^1$H NMR (DMSO-$d_6$, 400 MHz) δ 11.47 (brs, 1H), 9.26 (s, 1H), 9.14 (brs, 1H), 8.71 (s, 1H), 8.50 (s, 1H), 8.22 (s, 1H), 7.92 (s, 1H), 7.73 (s, 1H), 5.87 (s, 1H), 4.31 (d, 2H, J = 4.4 Hz), 3.62 (m, 2H), 3.40-3.28 (m, 2H), 3.25-3.07 (m, 4H), 2.80 (brs, 1H), 2.69 (d, 3H, J = 4.4 Hz), 2.52-2.40 (m, 2H), 2.28 (s, 3H), 2.22 (s, 3H), 2.1 (s, 3H), 2.03-1.86 (m, 4H), 1.58-1.43 (m, 4H), 0.84 (t, 3H0, J = 7.6 Hz). |
| 23 | — | LCMS: 563.40 (M + 1)+; $^1$H NMR (DMSO-$d_6$, 400 MHz) δ 11.45 (s, 1H), 8.12 (s, 1H), 8.08 (t, 1H, J = 4.4 Hz), 7.80 (s, 1H), 7.28 (s, 1H), 7.10 (s, 1H), 5.86 (s, 1H), 4.27 (d, 2H, J = 4.4 Hz), 3.84 (s, 3H), 3.20 (s, 3H), 3.05 (q, 2H, J = 7.6 Hz), 2.69-2.52 (m, 1H), |

-continued

| Compound # | Step 2 Yield | Data |
|---|---|---|
| | | 2.35-2.20 (m, 1H), 2.21 (s, 3H), 2.15 (s, 3H), 2.13 (s, 3H), 2.11 (s, 3H), 1.80 (d, 2H, J = 12.0 Hz), 1.69 (d, 2H, J = 12.0 Hz), 1.35 (q, 2H, J = 12.0 Hz), 1.28-1.10 (m, 2H), 0.80 (t, 3H, J = 6.8 Hz). |
| 24 | (0.07 g, 29.7%) | LCMS: 662.75 (M + 1)$^+$; TFA-salt: HPLC: $^1$H NMR (DMSO-d$_6$, 400 MHz) δ 11.47 (brs, 1H), 9.38 (brs, 1H), 8.27 (s, 1H), 8.10 (s, 1H), 7.99 (s, 1H), 7.37 (s, 1H), 7.18 (s, 1H), 5.87 (s, 1H), 5.15 (m, 2H), 4.57-4.54 (m, 2H), 4.28 (d, 2H, J = 4.8 Hz), 3.81 (m, 4H), 3.66-3.62 (m, 5H), 3.34 (m, 3H), 3.22-3.12 (m, 6H), 2.74-2.73 (m, 1H), 2.69-2.68 (m, 3H), 2.21 (s, 3H), 2.17 (s, 3H), 2.11 (s, 3H), 2.05-1.89 (m, 4H), 1.47 (m, 4H), 0.82 (t, 3H, J = 6.8 Hz). |
| 25 | (0.07 g, 29.7%) | LCMS: 567.60 (M + 1)$^+$; TFA-salt: $^1$H NMR (DMSO-d$_6$, 400 MHz) δ 11.45 (s, 1H), 8.01 (t, 1H), 6.99 (s, 1H), 6.79 (s, 1H), 5.85 (s, 1H), 4.25 (d, 2H, J = 5.2 Hz), 3.93-3.91 (m, 2H), 3.43-3.37 (m, 3H), 3.21 (s, 3H), 3.05-3.00 (m, 2H), 2.71-2.67 (m, 2H), 2.19 (s, 3H), 2.13 (s, 3H + 3H), 2.11 (s, 3H), 1.78-1.59 (m, 8H), 1.36-1.33 (m, 1H), 1.20-1.14 (m, 1H), 1.07 (s, 6H), 0.77 (t, 3H, J = 6.8 Hz). |
| 26 | (0.06 g, 20.5%) | LCMS: 658.35 (M + 1)$^+$; $^1$H NMR (DMSO-d$_6$, 400 MHz) δ 11.45 (bs, 1H), 8.18 (t, 1H), 7.57-7.55 (m, 2H), 7.38-7.34 (m, 3H), 7.18 (s, 1H), 5.86 (s, 1H), 4.29 (d, 2H, J = 4.0 Hz), 3.58 (m, 4H), 3.48 (s, 2H), 3.20 (s, 3H), 3.10-3.08 (m, 2H), 2.67-2.63 (m, 2H), 2.36 (m, 4H), 2.22 (s, 3H), 2.20 (s, 3H), 2.13 (s, 3H). 2.10 (s, 3H), 1.82-1.68 (m, 4H), 1.39-1.14 (m, 4H), 0.83 (t, 3H, J = 6.8 Hz), 4H merged in solvent peak. |

Methyl 3-((2,6-trans-dimethylpiperidin-4-yl)(ethyl)amino)-5-fluoro-2-methylbenzoate tert-Butyl 4-(ethyl(5-fluoro-3-(methoxycarbonyl)-2-methylphenyl)amino)-2,6-trans-dimethylpiperidine-1-carboxylate

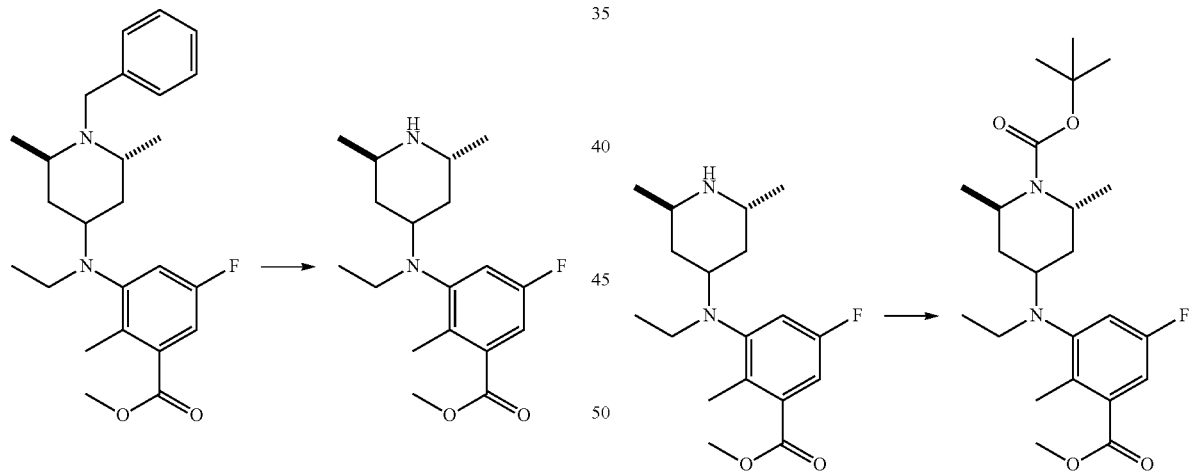

The titled compound was prepared (0.940 g, 100% yield) following the same procedure for the preparation of N-((4,6-dimethyl-2-oxo-1,2-dihydropyridin-3-yl)methyl)-3-((2,6-trans-dimethylpiperidin-4-yl)(ethyl)amino)-5-fluoro-2-methylbenzamide. $^1$H-NMR (400 MHz): δ ppm 7.27 (dt, J=8.6, 2.6 Hz, 1H), 6.98 (dt, J=9.7, 1.9 Hz, 1H), 3.90 (d, J=2.2 Hz, 3H), 3.54 (m, 1H), 3.05 (q, J=7.0 Hz, 2H), 3.06 (m, 1H), 2.96 (m, 1H), 2.42 (s. 3H), 1.85 (td, J=12.7, 4.6 Hz, 1H), 1.76 (d, J=1.8 Hz, 1H), 1.68 (m, 1H), 1.23 (q, J=12.2 Hz, 1H), 1.20 (dd, J=6.8, 1.6 Hz, 3H), 1.12 (dd, J=6.0, 1.8 Hz, 3H), 0.86 (td, J=7.0, 1.8 Hz, 3H); MS (ESI) [M+H]$^+$ 323.3.

Methyl 3-((2,6-trans-dimethylpiperidin-4-yl)(ethyl)amino)-5-fluoro-2-methylbenzoate (0.938 g, 2.91 mmol), Boc$_2$O (1.69 mL, 7.27 mmol) and TEA (2.43 mL, 17.46 mmol) was dissolved in DCM (18.7 mL, 291 mmol) at rt and the reaction mixture was stirred for overnight. MS showed reaction was done. The reaction mixture was diluted with ethylacetate and water. The separated aqueous layer was extracted once more with ethylacetate. The combined organic phase was dried over magnesium sulfate, filtered and evaporated. The residue was purified by silica gel chromatography (1%- to 20% EtOAc/heptane) to give the titled compound as a colorless oil (1.17 g, 95% yield). $^1$H NMR (400 MHz, CDCl$_3$): δ ppm 7.31 (dd, J=8.9, 2.7 Hz, 1H), 6.99 (dd, J=10.0, 2.7 Hz, 1H), 4.27 (m, 1H), 3.90 (s, 3H), 3.65 (m, 1H), 3.34 (m, 1H), 3.00 (m, 2H), 2.45 (s. 3H), 1.86 (m, 2H), 1.78 (m, 1H), 1.48 (q, J=6.6 Hz, 1H), 1.45 (s, 9H), 1.34 (d, J=6.7 Hz, 3H), 1.18 (d, J=6.8, 3H), 0.84 (t, J=7.0, 3H); MS (ESI) [M+H]⁺ 424.4.

3-((1-(tert-Butoxycarbonyl)-2,6-trans-dimethylpiperidin-4-yl)(ethyl)amino)-5-fluoro-2-methylbenzoic acid

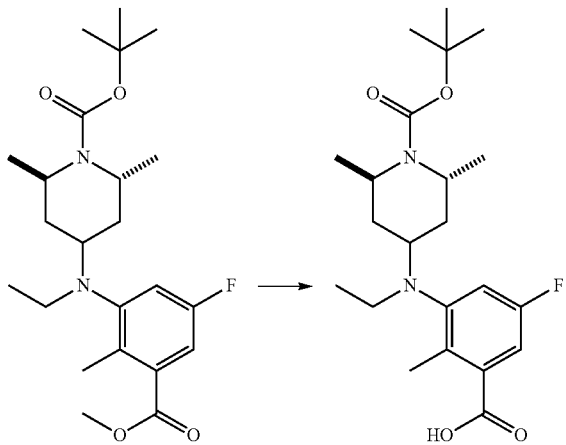 [SMILES: CCN(c1cc(F)cc(C(=O)OC)c1C)C1C[C@@H](C)N(C(=O)OC(C)(C)C)[C@H](C)C1 ; CCN(c1cc(F)cc(C(=O)O)c1C)C1C[C@@H](C)N(C(=O)OC(C)(C)C)[C@H](C)C1]

The titled compound was prepared (1.18 g, 96% yield) following the same procedure for the preparation of 3-[ethyl (1-methylpiperidin-4-yl)amino]-2-methyl-5-(trifluoromethyl)benzoic acid. ¹H NMR (400 MHz): δ ppm 7.48 (dd, J=8.9, 2.8 Hz, 1H), 7.05 (dd, J=9.8, 2.6 Hz, 1H), 4.28 (m, 1H), 3.67 (m, 1H), 3.36 (m, 1H), 3.02 (m, 2H), 2.53 (s. 3H), 1.89 (m, 2H), 1.80 (m, 1H), 1.50 (q, J=6.9 Hz, 1H), 1.47 (s, 9H), 1.36 (d, J=6.8 Hz, 3H), 1.20 (d, J=6.8 Hz, 3H), 0.84 (t, J=7.0, 3H); MS (ESI) [M+H]⁺ 410.4.

tert-Butyl 4-(ethyl(5-fluoro-3-(((5-fluoro-1,4,6-trimethyl-2-oxo-1,2-dihydropyridin-3-yl)methyl)carbamoyl)-2-methylphenyl)amino)-2,6-trans-dimethylpiperidine-1-carboxylate

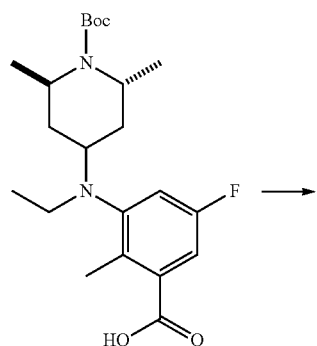

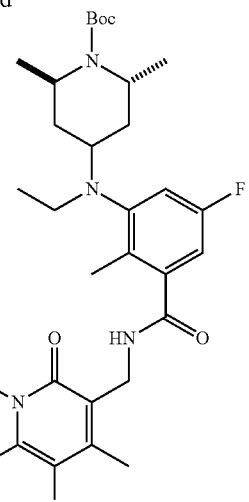

The titled compound was prepared (76.0 mg, 62% yield) following the same procedure for the preparation of N-[(4, 6-dimethyl-2-oxo-1,2-dihydropyridin-3-yl)methyl]-3-[ethyl (1-methylpiperidin-4-yl)amino]-2-methyl-5-(trifluoromethyl)benzamide. ¹H-NMR (400 MHz): δ ppm 7.06 (bt, J=6.0 Hz, 1H), 6.84 (dd, J=10.5, 2.0 Hz, 1H), 6.80 (d, J=7.2 Hz, 1H), 4.55 (d, J=5.4 Hz, 2H), 4.29 (m, 1H), 3.63 (q, J=6.4 Hz, 1H), 3.54 (s, 3H), 3.36 (m, 1H), 3.00 (m, 2H), 2.43 (d, J=5.5 Hz, 3H), 2.36 (d, J=3.2 Hz, 3H), 2.25 (s, 3H), 1.87 (m, 2H), 1.78 (m, 1H), 1.49 (m, 1H), 1.46 (s, 9H), 1.35 (d, J=2.8 Hz, 3H), 1.19 (d, J=6.8 Hz, 3H), 0.85 (t, J=6.8 Hz, 3H); MS (ESI) [M+H]⁺ 575.5.

tert-Butyl 4-(ethyl(5-fluoro-2-methyl-3-4(1,4,6-trimethyl-2-oxo-1,2-dihydropyridin-3-yl)methyl)carbamoyl)phenyl)amino)-2,6-trans-dimethylpiperidine-1-carboxylate

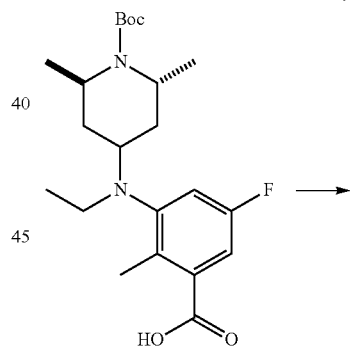

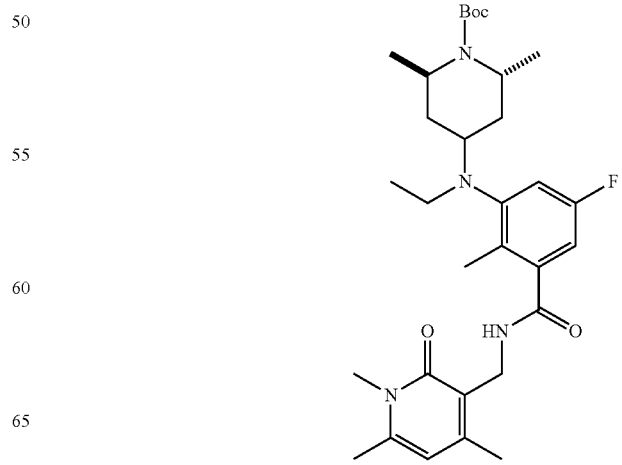

The titled compound was prepared (56.0 mg, 47% yield) following the same procedure for the preparation of N-[(4,6-Dimethyl-2-oxo-1,2-dihydropyridin-3-yl)methyl]-3-[ethyl(1-methylpiperidin-4-yl)amino]-2-methyl-5-(trifluoromethyl)benzamide. ¹H-NMR (400 MHz): δ ppm 7.12 (s, 1H), 6.85 (d, J=9.0, 2H), 6.00 (s, 1H), 4.54 (d, J=5.3 Hz, 2H), 4.31 (m, 1H), 3.63 (q, J=5.7 Hz, 1H), 3.54 (s, 3H), 3.42 (m, 1H), 3.07 (m, 2H), 2.39 (s, 3H), 2.35 (s, 3H), 2.30 (brs, 3H), 1.87 (m, 2H), 1.81 (m, 1H), 1.49 (m, 1H), 1.46 (s, 9H), 1.36 (d, J=6.3 Hz, 3H), 1.20 (d, J=6.7 Hz, 3H), 0.89 (bs, 3H); MS (ESI) [M+H]⁺ 557.5.

tert-Butyl 4-((3-((((1,6-dimethyl-2-oxo-4-(trifluoromethyl)-1,2-dihydropyridin-3-yl)methyl)carbamoyl)-5-fluoro-2-methylphenyl)(ethyl)amino)-2,6-trans-dimethylpiperidine-1-carboxylate

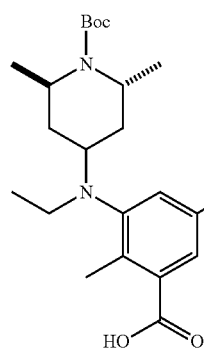

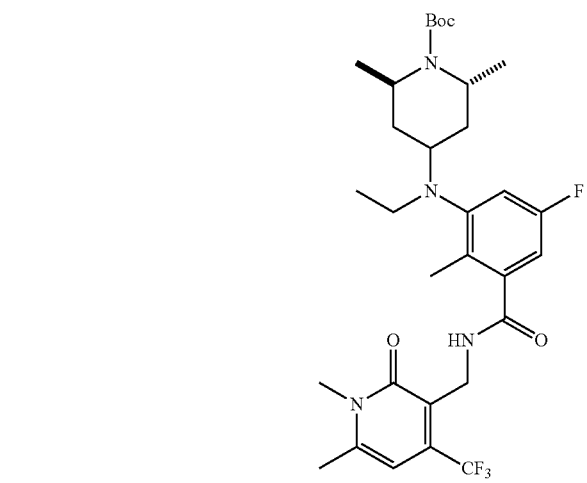

The titled compound was prepared (150 mg, 95% yield) following the same procedure for the preparation of N-[(4,6-Dimethyl-2-oxo-1,2-dihydropyridin-3-yl)methyl]-3-[ethyl(1-methylpiperidin-4-yl)amino]-2-methyl-5-(trifluoromethyl)benzamide. ¹H-NMR (400 MHz, CD₃OD): δ ppm 7.01 (dd, J=10.6, 2.5 Hz, 1H), 6.82 (dd, J=8.3, 2.8 Hz, 1H), 6.50 (s, 1H), 4.56 (s, 2H), 4.20 (m, 1H), 3.70 (q, J=4.6 Hz, 1H), 3.61 (s, 3H), 3.48 (m, 1H), 3.04 (m, 2H), 2.50 (s, 3H), 2.25 (s, 3H), 1.89 (m, 3H), 1.52 (m, 1H), 1.44 (s, 9H), 1.33 (d, J=6.6 Hz, 3H), 1.20 (d, J=7.0 Hz, 3H), 1.17 (d, J=7.0 Hz, 3H), 0.84 (t, J=7.0 Hz, 3H); MS (ESI) [M+H]⁺ 612.8.

tert-Butyl 4-(ethyl(5-fluoro-3-(((4-isopropyl-6-methyl-2-oxo-1,2-dihydropyridin-3-yl)methyl)carbamoyl)-2-methylphenyl)amino)-2,6-trans-dimethylpiperidine-1-carboxylate

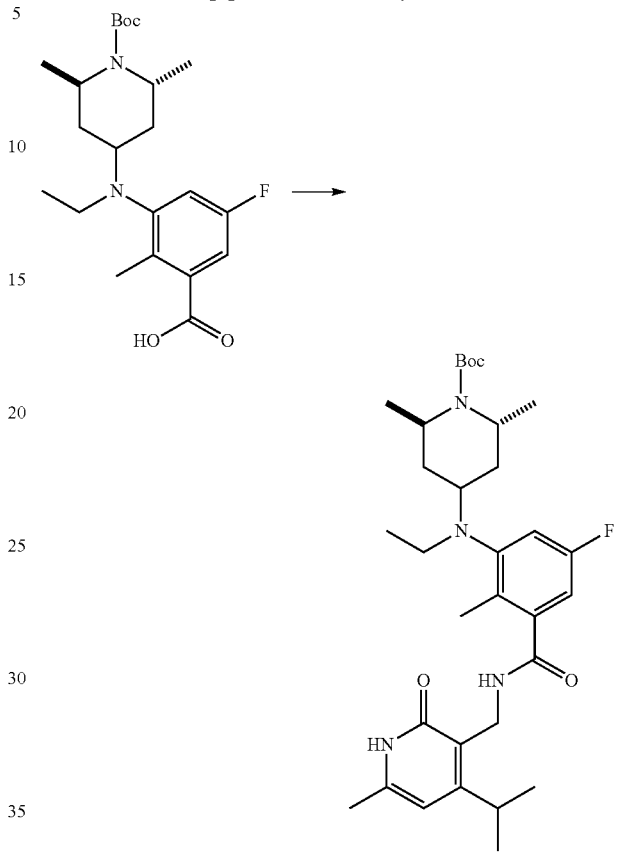

The titled compound was prepared (50.0 mg, 41% yield) following the same procedure for the preparation of N-[(4,6-Dimethyl-2-oxo-1,2-dihydropyridin-3-yl)methyl]-3-[ethyl(1-methylpiperidin-4-yl)amino]-2-methyl-5-(trifluoromethyl)benzamide. ¹H-NMR (400 MHz) δ ppm 7.10 (t, J=6.0 Hz, 1H), 6.82 (m, 2H), 6.08 (s, 1H), 4.59 (m, 2H), 4.28 (m, 1H), 3.63 (m, 1H), 3.52 (m, 2H), 3.35 (m, 1H), 2.99 (m, 2H), 2.29 (s, 3H), 2.24 (s, 3H), 1.85 (m, 2H), 1.74 (m, 1H), 1.48 (m, 1H), 1.46 (s, 9H), 1.34 (d, J=6.71 Hz, 3H), 1.22 (dd, J=6.83, 0.08 Hz, 6H), 1.18 (d, J=6.87 Hz, 3H), 0.83 (t, J=7.00 Hz, 3H); MS (ESI) [M+H]⁺ 571.5.

tert-Butyl 4-(ethyl(5-fluoro-2-methyl-3-(((6-methyl-2-oxo-4-propyl-1,2-dihydropyridin-3-yl)methyl)carbamoyl)phenyl)amino)-2,6-trans-dimethylpiperidine-1-carboxylate

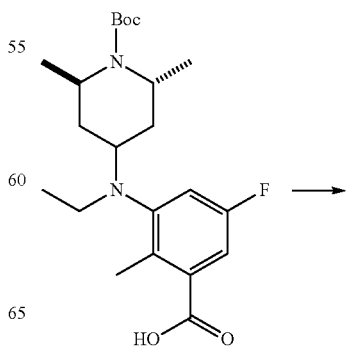

-continued

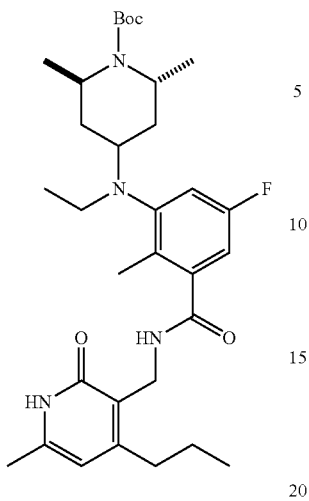

The titled compound was prepared (64.0 mg, 53% yield) following the same procedure for the preparation of N-[(4,6-Dimethyl-2-oxo-1,2-dihydropyridin-3-yl)methyl]-3-[ethyl(1-methylpiperidin-4-yl)amino]-2-methyl-5-(trifluoromethyl)benzamide. ¹H-NMR (400 MHz) δ ppm 7.19 (t, J=6.0 Hz 1H) 6.81 (m, 2H) 5.97 (s, 1H) 4.55 (m, 2H) 4.28 (m, 1H) 3.64 (m, 1H) 3.50 (m, 1H) 3.35 (m. 1H) 2.98 (m, 2H) 2.69 (m, 2H) 2.25 (s, 6H) 1.84 (m, 1H), 1.76 (m, 1H), 1.64 (m, 3H) 1.46 (m, 10H) 1.34 (d, J=6.68 Hz, 3H) 1.18 (d, J=6.87 Hz, 3H) 1.02 (t, J=7.34 Hz, 3H) 0.84 (t, J=7.1 Hz 3H); MS (ESI) [M+H]⁺ 571.5.

3-((2,6-trans-Dimethylpiperidin-4-yl)(ethyl)amino)-5-fluoro-N-((5-fluoro-1,4,6-trimethyl-2-oxo-1,2-dihydropyridin-3-yl)methyl)-2-methylbenzamide hydrochloride

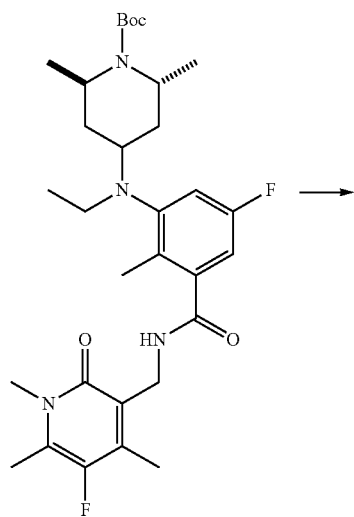

-continued

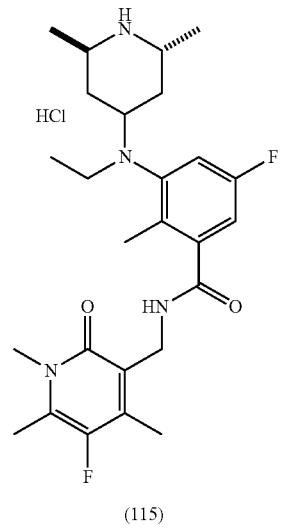

(115)

Tert-butyl 4-(ethyl(5-fluoro-3-((((5-fluoro-1,4,6-trimethyl-2-oxo-1,2-dihydropyridin-3-yl)methyl)carbamoyl)-2-methylphenyl)amino)-2,6-trans-dimethylpiperidine-1-carboxylate (75.0 mg, 0.131 mmol) was dissolved in in dichloromethane (1 mL) and 4N HCl in 1,4-dioxane (1.63 mL, 6.53 mmol) was added at rt and the mixture was stirred at room temperature for 3 h. The reaction mixture was then concentrated, azeotroped with MeOH several times to give the titled compound as a solid (67.0 mg, 100% yield). ¹H-NMR (400 MHz, DMSO-d6): δ ppm 8.80 (bs, 1H), 8.27 (t, J=4.9 Hz, 1H), 7.10 (d, J=9.3 Hz, 1H), 6.80 (d, J=9.3 Hz, 1H), 4.33 (t, J=3.9 Hz, 2H), 3.72 (m, 2H), 3.43 (s, 3H), 3.34 (m, 1H), 2.99 (m, 2H), 2.32 (d, J=3.5 Hz, 3H), 2.24 (d, J=2.2 Hz, 3H), 2.12 (s, 3H), 1.83 (m, 2H), 1.70 (m, 1H), 1.45 (m, 1H), 1.27 (d, J=7.2 Hz, 3H), 1.21 (d, J=6.2 Hz, 3H), 0.79 (t, J=6.7 Hz, 3H); MS (ESI) [M+H]⁺ 475.3.

3-((2,6-trans-Dimethylpiperidin-4-yl)(ethyl)amino)-5-fluoro-2-methyl-N-((1,4,6-trimethyl-2-oxo-1,2-dihydropyridin-3-yl)methyl)benzamide dihydrochloride

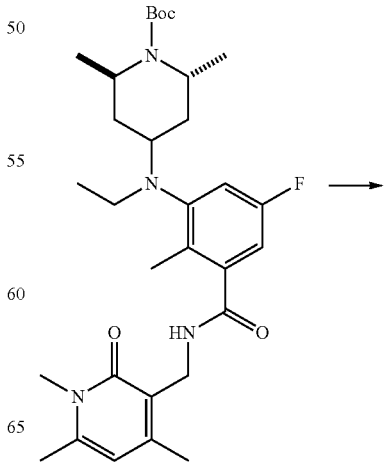

-continued

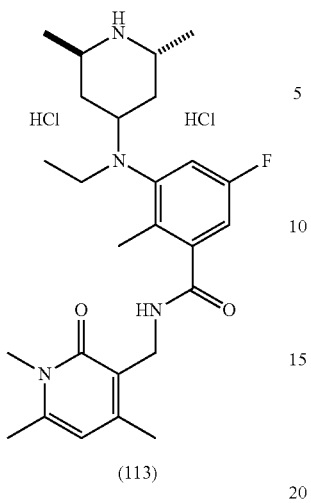

(113)

-continued

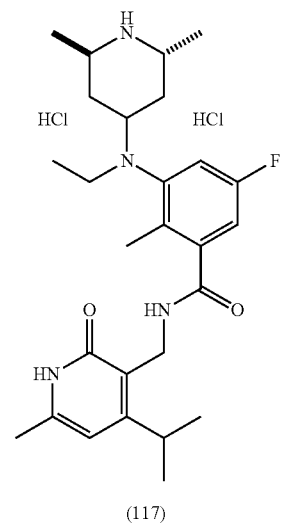

(117)

The titled compound was prepared (52.0 mg, 100% yield) following a similar procedure for the preparation of 3-((2,6-trans-dimethylpiperidin-4-yl)(ethyl)amino)-5-fluoro-N-((5-fluoro-1,4,6-trimethyl-2-oxo-1,2-dihydropyridin-3-yl)methyl)-2-methylbenzamide hydrochloride. $^1$H-NMR (400 MHz, DMSO-d6): δ ppm 8.85 (bs, 2H), 8.16 (s, 1H), 7.10 (d, J=11.1 Hz, 1H), 6.79 (d, J=7.4 Hz, 1H), 6.04 (s, 1H), 4.30 (t, J=4.6 Hz, 2H), 3.71 (m, 2H), 3.41 (s, 3H), 3.33 (m, 1H), 2.99 (m, 2H), 2.30 (s, 3H), 2.20 (s, 3H), 2.13 (s, 3H), 1.83 (m, 2H), 1.70 (m, 1H), 1.48 (m, 1H), 1.27 (d, J=6.7 Hz, 3H), 1.21 (d, J=6.1 Hz, 3H), 0.79 (t, J=6.7 Hz, 3H); MS (ESI) [M+H]$^+$ 457.4.

3-((2,6-trans-Dimethylpiperidin-4-yl)(ethyl)amino)-5-fluoro-N-((4-isopropyl-6-methyl-2-oxo-1,2-dihydropyridin-3-yl)methyl)-2-methylbenzamide dihydrochloride The titled compound was prepared (40.0 mg, 97% yield) following a similar procedure for the preparation of 3-((2,6-trans-dimethylpiperidin-4-yl)(ethyl)amino)-5-fluoro-N-((5-fluoro-1,4,6-trimethyl-2-oxo-1,2-dihydropyridin-3-yl)methyl)-2-methylbenzamide hydrochloride. $^1$H-NMR (400 MHz, DMSO-d$_6$) δ ppm 8.78 (bm, 2H), 8.14 (m, 1H), 7.05 (d, J=10.6 Hz, 1H), 6.72 (d, J=9.6 Hz, 1H), 5.97 (s, 1H), 4.26 (m, 2H), 3.65 (bm, 2H), 3.27 (bm, 1H), 3.15 (bm, 2H), 2.95 (bm, 2H), 2.09 (s, 6H), 1.80 (m, 2H), 1.65 (m, 1H), 1.41 (m, 1H), 1.22 (d, J=7.0 Hz, 3H), 1.17 (d, J=6.6 Hz, 3H), 1.07 (d, J=6.8 Hz, 6H), 0.74 (t, J=6.67 Hz, 3H); MS (ESI) [M+H]$^+$ 471.4.

3-((2,6-trans-Dimethylpiperidin-4-yl)(ethyl)amino)-5-fluoro-2-methyl-N-((6-methyl-2-oxo-4-propyl-1,2-dihydropyridin-3-yl)methyl)benzamide

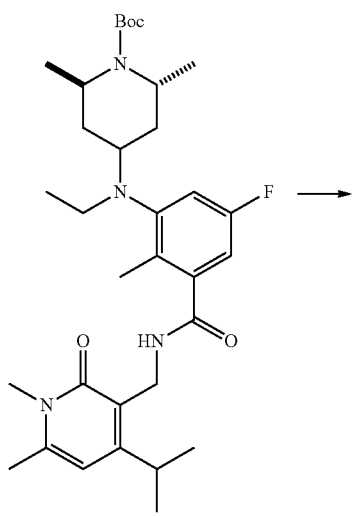

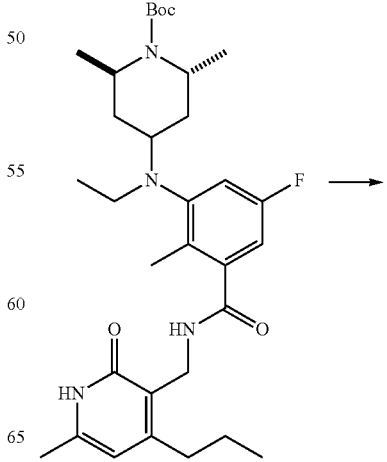

201
-continued

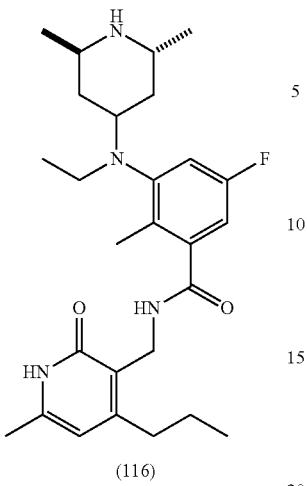

(116)

The titled compound was prepared (60.0 mg, 76% yield) following a similar procedure for the preparation of 3-((2,6-trans-dimethylpiperidin-4-yl)(ethyl)amino)-5-fluoro-N-((5-fluoro-1,4,6-trimethyl-2-oxo-1,2-dihydropyridin-3-yl)methyl)-2-methylbenzamide hydrochloride and purification by reverse phase HPLC. $^1$H-NMR (400 MHz, CD$_3$OD) δ ppm 6.96 (dd, J=10.3, 2.3 Hz, 1H), 6.76 (dd, J=8.0, 1.6 Hz, 1H), 6.10 (s, 1H), 4.43 (s, 2H), 3.48 (m, 1H), 3.16 (m, 1H), 3.04 (m, 3H), 2.64 (m, 2H), 2.22 (s, 3H), 2.19 (s, 3H), 1.81 (m, 1H), 1.73 (m, 2H), 1.61 (m, 2H), 1.24 (m, 1H), 1.19 (d, J=7.14 Hz, 3H), 1.09 (d, J=6.1 Hz, 3H), 0.99 (t, J=7.4 Hz, 3H), 0.83 (t, J=7.00 Hz, 3H); MS (ESI) [M+H]$^+$ 471.4.

tert-Butyl 4-((3-(((4,6-dimethyl-2-oxo-1,2-dihydropyridin-3-yl)methyl)carbamoyl)-5-fluoro-2-methylphenyl)(ethyl)amino)-2,6-trans-dimethylpiperidine-1-carboxylate

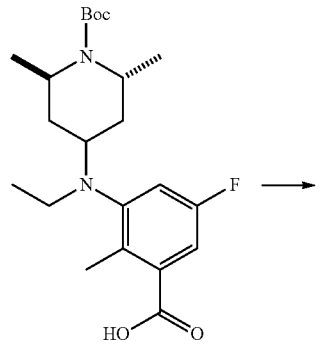

202
-continued

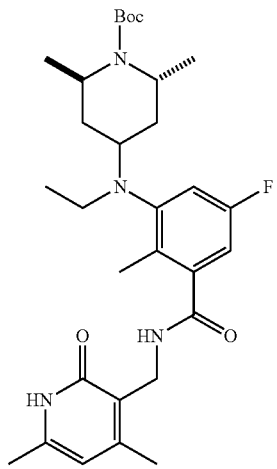

The titled compound was prepared (526 mg, 74% yield) following the same procedure for the preparation of N-[(4,6-Dimethyl-2-oxo-1,2-dihydropyridin-3-yl)methyl]-3-[ethyl(1-methylpiperidin-4-yl)amino]-2-methyl-5-(trifluoromethyl)benzamide and purification by reverse phase HPLC. $^1$H NMR (400 MHz): δ ppm 7.12 (t, J=4.7 Hz, 1H), 6.83 (dd, J=4.7, 2.4 Hz, 2H), 5.98 (s, 1H), 4.53 (d, J=5.9 Hz, 2H), 4.28 (m, 1H), 3.62 (m, 1H), 3.37 (m, 1H), 3.00 (m, 2H), 2.41 (s. 3H), 2.27 (s, 3H), 2.25 (s, 3H), 1.87 (m, 2H), 1.78 (m, 1H), 1.49 (q, J=6.7 Hz, 1H), 1.46 (s, 9H), 1.34 (d, J=6.7 Hz, 3H), 1.18 (d, J=7.2 Hz, 3H), 0.84 (t, J=7.2 Hz, 3H); MS (ESI) [M+H]$^+$ 543.5.

N-((4,6-Dimethyl-2-oxo-1,2-dihydropyridin-3-yl)methyl)-3-((2,6-trans-dimethylpiperidin-4-yl)(ethyl)amino)-5-fluoro-2-methylbenzamide dihydrochloride

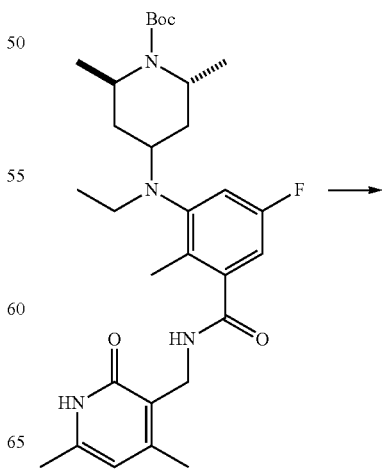

203
-continued

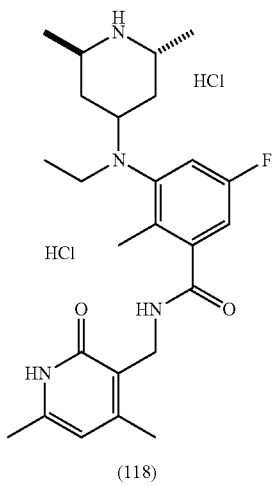

(118)

The titled compound was prepared (500 mg, 100% yield) following a similar procedure for the preparation of 3-((2,6-trans-dimethylpiperidin-4-yl)(ethyl)amino)-5-fluoro-N-((5-fluoro-1,4,6-trimethyl-2-oxo-1,2-dihydropyridin-3-yl)methyl)-2-methylbenzamide hydrochloride. This is the dihydrocloride form of the same compound made earlier, see N-[(4,6-Dimethyl-2-oxo-1,2-dihydropyridin-3-yl)methyl]-3-((2,6-trans-dimethylpiperidin-4-yl](ethyl)amino)-5-fluoro-2-methylbenzamide.

N-((4,6-Dimethyl-2-oxo-1,2-dihydropyridin-3-yl)methyl)-3-(ethyl(1-methyl-2,6-trans-dimethylpiperidin-4-yl)amino)-5-fluoro-2-methylbenzamide

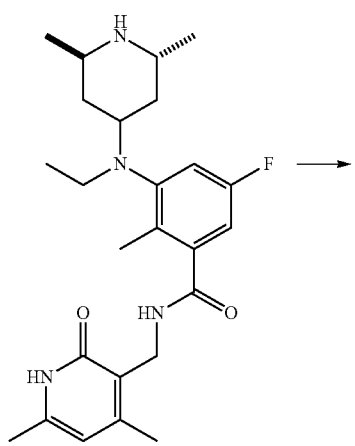

204
-continued

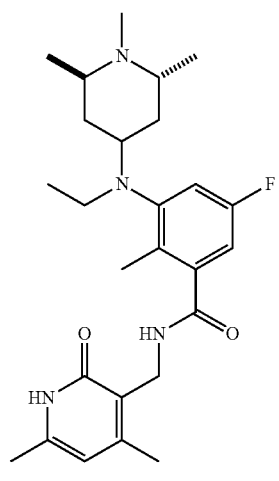

(118)

The titled compound was prepared (83.0 mg, 87% yield) following a similar procedure for the preparation of methyl 3-[ethyl(1-methylpiperidin-4-yl)amino]-2-methyl-5-(trifluoromethyl)benzoate. $^1$H-NMR (400 MHz): δ ppm 7.13 (t, J=6.1 Hz, 1H), 6.83 (dd, J=10.4, 2.8 Hz, 1H), 6.77 (dd, J=8.0, 2.4 Hz, 1H), 5.95 (s, 1H), 4.53 (d, J=6.2 Hz, 2H), 3.50 (s, 1H), 3.27 (brs, 1H), 3.08 (brs, 1H), 3.03 (q, J=6.8 Hz, 2H), 2.40 (s, 3H), 2.33 (brs, 3H), 2.24 (s, 3H), 2.23 (s, 3H), 1.72-1.62 (m, 3H), 1.09 (brs, 3H), 1.00 (brs, 3H), 0.85 (t, J=7.2, 3H); MS (ESI) [M+H]$^+$ 457.4.

N-((4,6-Dimethyl-2-oxo-1,2-dihydropyridin-3-yl)methyl)-3-(ethyl(1-ethyl-2,6-trans-dimethylpiperidin-4-yl)amino)-5-fluoro-2-methylbenzamide (119)

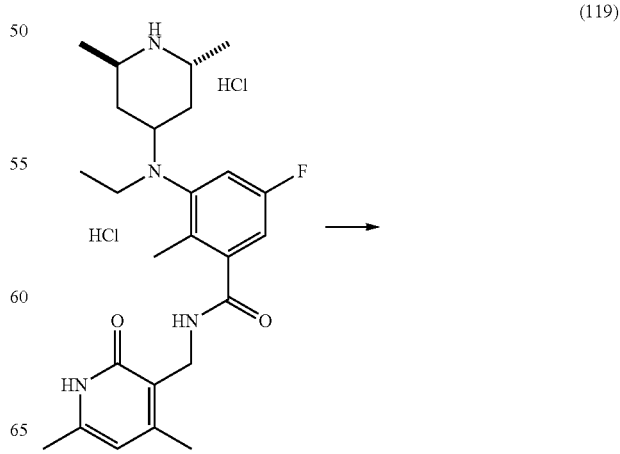

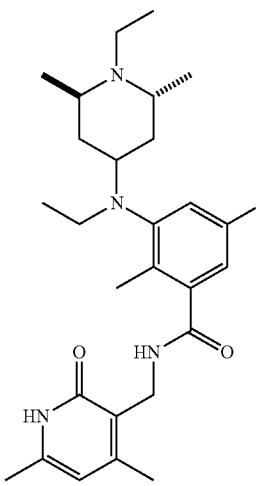

To a stirred solution of N-((4,6-dimethyl-2-oxo-1,2-dihydropyridin-3-yl)methyl)-3-((2,6-trans-dimethylpiperidin-4-yl)(ethyl)amino)-5-fluoro-2-methylbenzamide dihydrochloride (150 mg, 0.291 mmol) in MeOH (2 mL, 49.4 mmol) and acetic acid (0.017 mL, 0.291 mmol) was added acetaldehyde (0.164 mL, 2.91 mmol) and sodium triacetoxyborohydride (185 mg, 0.873 mmol) at 0° C. The reaction mixture was stirred at room temperature for 2 h. MS showed the reaction was completed. The reaction was quenched with saturated aq. NaHCO$_3$ until pH 8-9. The separated aq. Phase was extracted with DCM. The combined org. phase was concentrated to give 120 mg crude material. Purification by reverse phase HPLC/MS provided the titled compound (103 mg, 75% yield). $^1$H-NMR (400 MHz, CD$_3$OD): δ ppm 7.01 (dd, J=9.7, 2.9 Hz, 1H), 6.81 (dd, J=8.5, 2.9 Hz, 1H), 6.11 (s, 1H), 4.46 (s, 2H), 3.53 (brs, 2H), 3.21 (m, 1H), 3.07 (q, J=6.5, 2H), 2.37 (s, 3H), 2.24 (s, 3H), 2.22 (s, 3H), 1.86-1.77 (m. 4H), 1.45 (d, J=12.3 Hz, 2H), 1.14 (bs, 6H), 1.09 (brs, 3H), 0.86 (t, J=7.1, 3H); MS (ESI) [M+H]$^+$ 471.4.

5-Bromo-2-methyl-3-nitrobenzoic acid

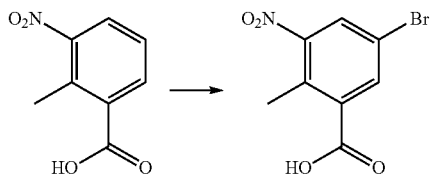

To a stirred solution of 2-methyl-3-nitrobenzoic acid (5.00 g, 27.6 mmol) in H$_2$SO$_4$ (20 mL) was added 1,3-dibromo-5,5-dimethylhydantoin (4.34 g, 15.20 mmol) at 0° C. The reaction mixture was stirred at 0° C. for 5 hours. The reaction mixture was poured onto ice cold water, the resultant precipitated solid was collected, washed with water and dried in vacuo to give the titled compound as a white solid (7.28 g, quantitative yield). $^1$H-NMR (400 MHz, DMSO-do) δ ppm; 8.31 (s, 1H), 8.17 (s, 1H), 2.43 (s, 3H).

Methyl 5-bromo-2-methyl-3-nitrobenzoate

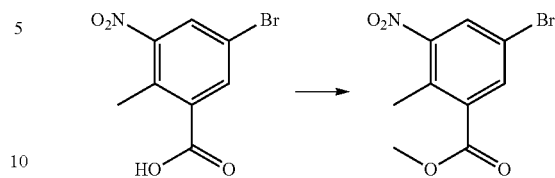

To a stirred solution of 5-bromo-2-methyl-3-nitrobenzoic acid (7.28 g, 28.0 mmol) in DMF (100 mL) was added sodium carbonate (11.9 g, 112 mmol) and methyl iodide (15.9 g, 112 mmol). The reaction mixture was stirred at 60° C. for 8 hours. After completion of the reaction, the reaction mixture was filtered and washed with ethyl acetate. The combined filtrate was washed with water and the aqueous phase was re-extracted with ethyl acetate. The combined organic layers were dried over anhydrous sodium sulfate, filtered and concentrated under reduced pressure to afford the titled compound as a solid. (7.74 g, quantitative yield). $^1$H-NMR (400 MHz, CDCl$_3$) δ (ppm); 8.17 (s, 1H), 7.91 (s, 1H), 3.96 (s, 3H), 2.59 (s, 3H).

Methyl 3-amino-5-bromo-2-methylbenzoate

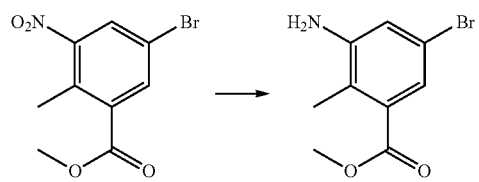

To a stirred solution of methyl 5-bromo-2-methyl-3-nitrobenzoate (7.60 g, 27.7 mmol) in aq. EtOH (100 mL of EtOH and 20 mL of H$_2$O) was added ammonium chloride (4.45 g, 83.1 mmol) and iron (4.64 g, 83.1 mmol). The reaction mixture was stirred at 80° C. for 5 hours. Then the mixture was filtered through Celite and the Celite bed was washed with ethyl acetate. The combined filtrate was concentrated in vacuo. The resultant residue was dissolved in ethyl acetate and water. The aqueous layer was extracted with ethyl acetate (twice). The combined organic layer dried over anhydrous sodium sulfate, filtered and concentrated under reduced pressure to afford the titled compound as a brown oil (6.67 g, 99%). $^1$H-NMR (400 MHz, CDCl$_3$) δ ppm; 7.37 (s, 1H), 6.92 (s, 1H), 3.94 (s, 3H), 3.80 (brs, 2H), 2.31 (s, 3H).

Methyl 5-bromo-2-methyl-3-[(oxan-4-yl)amino]benzoate

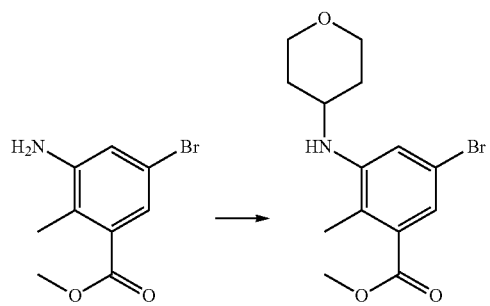 [SMILES: COC(=O)c1cc(Br)cc(N)c1C ; COC(=O)c1cc(Br)cc(NC2CCOCC2)c1C]

To a stirred solution of methyl 3-amino-5-bromo-2-methylbenzoate (40.2 g, 165 mmol) in CH$_2$Cl$_2$ (500 mL) and AcOH (60 mL) was added dihydro-2H-pyran-4-one (17.3 g, 173 mmol) and sodium triacetoxyborohydride (73.6 g, 330 mmol). The reaction mixture was stirred at RT for 20 hours. Then saturated NaHCO$_3$ aq. was added and the mixture was separated. The aqueous layer was extracted with CH$_2$Cl$_2$ and the combined organic layer was concentrated in vacuo. The residue was triturated with ethyl ether, and resultant precipitate was collected to afford the titled compound as a white solid (39.1 g, 72%). $^1$H-NMR (400 MHz, DMSO-d$_6$) δ ppm; 7.01 (s, 1H), 6.98 (s, 1H), 5.00 (d, J=7.6 Hz, 1H), 3.84-3.87 (m, 2H), 3.79 (s, 3H), 3.54-3.56 (m, 1H), 3.43 (m, 2H), 2.14 (s, 3H), 1.81-1.84 (m, 2H), 1.47-1.55 (m, 2H).

Methyl 5-bromo-3-[ethyl(oxan-4-yl)amino]-2-methylbenzoate

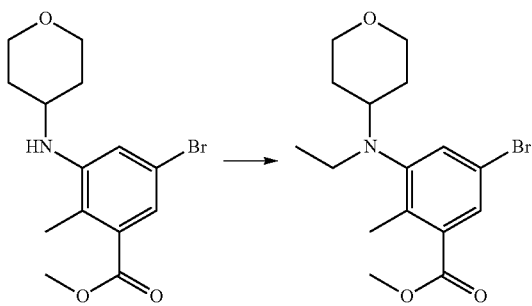 [SMILES: COC(=O)c1cc(Br)cc(NC2CCOCC2)c1C ; CCN(c1cc(Br)cc(C(=O)OC)c1C)C1CCOCC1]

To a stirred solution of methyl 5-bromo-2-methyl-3-[(oxan-4-yl)amino]benzoate (39.1 g, 119 mmol) in CH$_2$Cl$_2$ (400 mL) and AcOH (40 mL) was added acetaldehyde (24.7 g, 476 mmol) and sodium triacetoxyborohydride (79.6 g, 357 mmol). The reaction mixture was stirred at RT for 24 hours. Then saturated NaHCO$_3$ aq. was added and the mixture was separated. The aqueous layer was extracted with CH$_2$Cl$_2$ and the combined organic layer was concentrated in vacuo. The residue was purified by silica gel column chromatography (SiO$_2$ Heptane/EtOAc=3/1) to give the titled compound as a viscous oil (44.1 g, quantitative yield). $^1$H-NMR (400 MHz, DMSO-d$_6$) δ ppm; 7.62 (s, 1H), 7.52 (s, 1H), 3.80 (m, 5H), 3.31 (m, 2H), 2.97-3.05 (m, 2H), 2.87-2.96 (m, 1H), 2.38 (s, 3H), 1.52-1.61 (m, 2H), 1.37-1.50 (m, 2H), 0.87 (t, J=6.8 Hz, 3H).

Methyl 3-[ethyl(oxan-4-yl)amino]-2-methyl-5-(tetramethyl-1,3,2-dioxaborolan-2-yl)benzoate

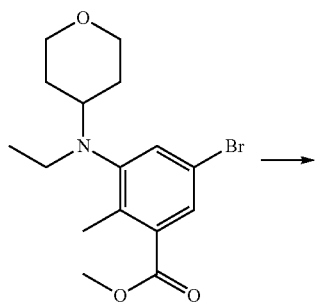

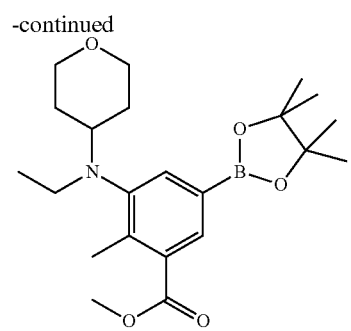

To a stirred solution of methyl 5-bromo-3-[ethyl(oxan-4-yl)amino]-2-methylbenzoate (2.93 g, 8.23 mmol) and bis(pinacolato)diboron (2.72 g, 10.7 mmol) in DMSO (40 mL) was added potassium acetate (3.07 g, 31.3 mmol) and Pd(dppf)Cl$_2$ (672 mg, 0.823 mmol). The reaction mixture was stirred at 80° C. for 2.5 hours. After cooling to RT, ethyl acetate and water were added to the mixture. The aqueous layer was extracted with ethyl acetate. The combined organic layer was washed with water (twice) and brine. The organic layer was dried over MgSO$_4$ and filtered. The filtrate was concentrated in vacuo. The residue was purified by silica gel column chromatography (SiO$_2$; Heptane/ethyl acetate=5/1 to 2/1) to give the titled compound as a yellow oil (2.92 g, 88% yield). $^1$H-NMR (400 MHz, CDCl$_3$) δ ppm; 7.99 (s, 1H), 7.66 (s, 1H), 3.90-3.98 (m, 2H), 3.89 (s, 3H), 3.25-3.37 (m, 2H), 3.09 (q, J=7.1 Hz, 2H), 2.92-3.02 (m, 1H), 2.54 (s, 3H), 1.57-1.76 (m, 4H), 1.35 ppm (s, 12H), 0.85 (t, J=7.1 Hz, 3H).

Methyl 5-bromo-3-{[trans-4-(dimethylamino)cyclohexyl]amino}-2-methylbenzoate

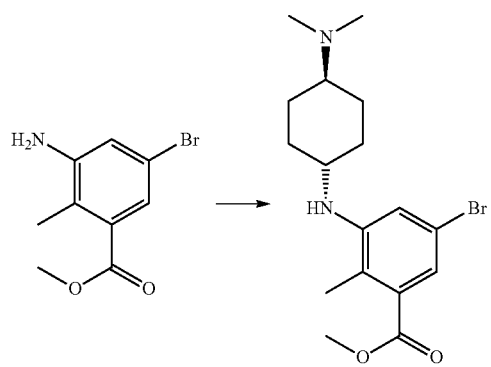

To a stirred solution of methyl 3-amino-5-bromo-2-methylbenzoate (5.00 g, 20.5 mmol) in CH$_2$Cl$_2$ (100 mL) and AcOH (5 mL) was added 4-(dimethylamino)cyclohexan-1-one (3.76 g, 26.6 mmol) and sodium triacetoxyborohydride (13.0 g, 61.5 mmol). The reaction mixture was stirred at RT for 4 hours. Then saturated NaHCO$_3$ aq. was added and the mixture was separated. The aqueous layer was extracted with CH$_2$Cl$_2$ (2×50 mL) and the combined organic layers were concentrated in vacuo. The residue was purified by silica gel column chromatography (NH—SiO$_2$ heptane/EtOAc=1/1) to give the titled compound as a brown oil (2.10 g, 28%). H-NMR (500 MHz, CDCl$_3$) δ ppm; 7.20 (d, J=1.9 Hz, 1H), 6.81 (d, J=1.9 Hz, 1H), 3.87 (s, 3H), 3.58 (d, J=7.3 Hz, 1H), 3.20 (m, 1H), 2.30 (s, 6H), 2.20 (s, 3H), 2.16-2.26

(m, 3H), 1.97 (m, 2H), 1.34-1.46 (m, 2H), 1.14-1.25 (m, 2H); MS (ESI) [M+1.1]⁺369.2, 371.2.

Methyl 5-bromo-3-{[trans-4-(dimethylamino)cyclohexyl](ethyl)amino}-2-methylbenzoate

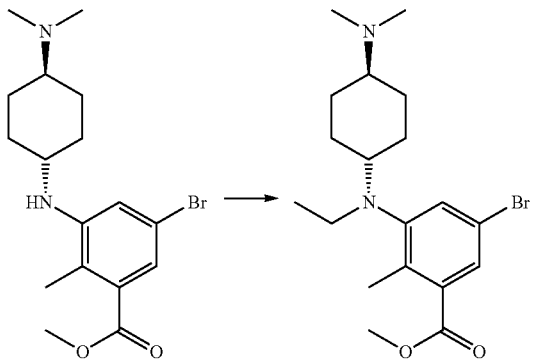

To a stirred solution of Methyl 5-bromo-3-{[trans-4-(dimethylamino)cyclohexyl]amino}-2-methylbenzoate (2.10 g, 5.69 mmol) in CH$_2$Cl$_2$ (40 mL) and AcOH (2 mL) was added acetaldehyde (626 mg, 14.2 mmol) and sodium triacetoxyborohydride (3.62 g, 17.1 mmol). The reaction mixture was stirred at RT for 3 hours and then saturated NaHCO$_3$ aq. was added and the mixture was separated. The aqueous layer was extracted with CH$_2$Cl$_2$ and the combined organic layer was concentrated in vacuo. The residue was purified by silica gel column chromatography (NH—SiO$_2$ heptane/ethylacetate=3/2) to give the titled compound as a yellow oil (824 mg, 36%). ¹HNMR (400 MHz, CDCl$_3$) δ ppm; 7.67 (d, J=2.0 Hz, 1H), 7.33 (d, J=2.0 Hz, 1H), 3.89 (s, 3H), 3.03 (q, J=7.0 Hz, 2H), 2.57-2.69 (m, 1H), 2.42 (s, 3H), 2.24 (s, 6H), 2.07-2.18 (m, 1H), 1.88 (m, 4H), 1.09-1.44 (m, 4H), 0.85 (t, J=7.0 Hz, 3H); MS (ESI) [M+H]⁺397.3, 399.3.

Methyl 3-((trans-4-aminocyclohexyl)(ethyl)amino)-5-bromo-2-methylbenzoate

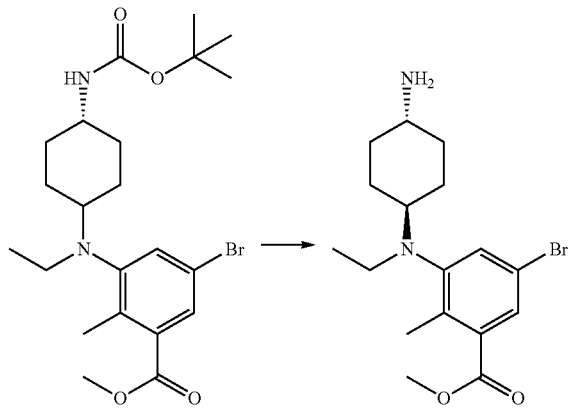

Methyl 5-bromo-3-((4-trans-((tert-butoxycarbonyl)amino)cyclohexyl)(ethyl)amino)-2-methylbenzoate (1.00 g, 2.13 mmol) was dissolved in DCM (1 mL) at rt. Then 4 M HCl in 1,4-dioxane (8 mL, 32.0 mmol) was added drop wise during 10 min at rt. After stirring additional 10 min, TLC (20% E/H) showed reaction was done, and no SM at Rf=0.55 and there is only a baseline. The mixture was then concentrated and re-dissolved in 10 mL DCM and treated with sodium bicarbonate (0.447 g, 5.33 mmol) with stirring for 15 min (bubbling was observed). The mixture was then filtered through celite washing with DCM, the filtrate was concentrated to give the titled compound (0.780 g, 100% yield). ¹H-NMR (400 MHz, CD$_3$OD): δ ppm 7.62 (d, J=2.1 Hz, 1H), 7.44 (d, J=2.1 Hz, 1H), 3.85 (s, 3H), 3.07 (q, J=7.0 Hz, 2H), 3.00 (m, 1H), 2.72 (m, 1H), 2.38 (s, 3H), 1.95 (m, 4H), 1.49 (m, 2H), 1.33 (m, 2H), 0.83 (t, J=7.0 Hz, 3H); MS (ESI) [M+H]⁺ 369.2, 371.2.

Methyl 5-bromo-3-((4-trans-(dimethylamino)cyclohexyl)(ethyl)amino)-2-methylbenzoate

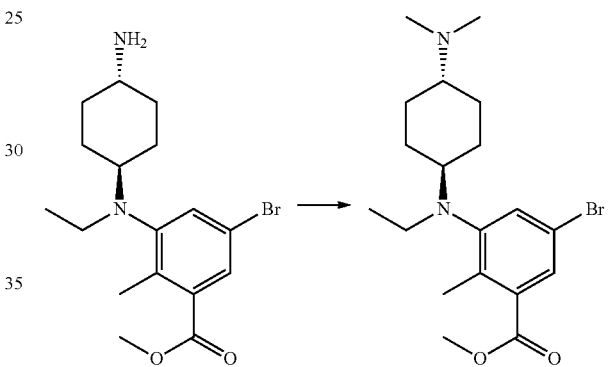

To a solution of Methyl 3-((trans-4-aminocyclohexyl)(ethyl)amino)-5-bromo-2-methylbenzoate (0.787 g, 2.13 mmol) in methanol (3 mL) and DCM (5 mL) was added formaldehyde (37% in water, 0.793 mL, 10.7 mmol) at 0° C. and stirred for 10 min. Then sodium triacetoxyborohydride (1.81 g, 8.52 mmol) was added and the mixture was stirred for 30 min at 0° C. and then at rt for 30 min. MS showed reaction is done. The reaction mixture was quenched with sat. NaHCO$_3$, extracted with 8×DCM until TLC (10% 7N NH$_3$ in MeOH/DCM) showed no product at Rf=0.35. The combined org. phase was dried (Na$_2$SO$_4$), filtered, concentrated and chromatography (25.0 g column, 5% MeOH/DCM and then 10% 7N NH$_3$ in MeOH/DCM isocratic) purification gave the titled compound (850 mg, 100% yield). ¹H-NMR (400 MHz, CD$_3$OD): δ ppm 7.60 (d, J=2.1 Hz, 1 H), 7.42 (d, J=2.1 Hz, 1 H), 3.84 (s, 3H), 3.06 (q, J=7.0 Hz, 2 H), 2.67 (m, 1H), 2.37 (s, 3H), 2.35 (m, 1H), 2.31 (s, 6H), 1.91 (m, 4H), 1.40 (m, 2H), 1.24 (m, 2H), 0.82 (t, J=7.0 Hz, 3H); MS (ESI) [M+H]⁺ 397.3, 399.3.

211

5-Bromo-3-((4-trans-(dimethylamino)cyclohexyl)(ethyl)amino)-2-methylbenzoic acid

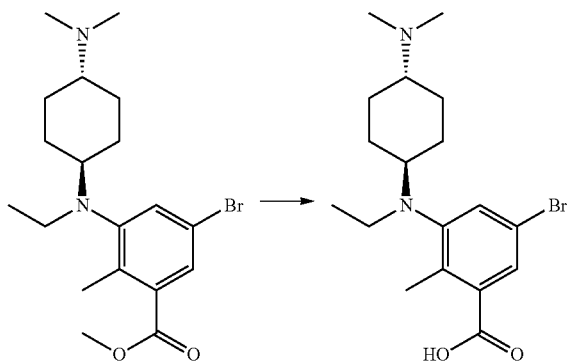 [SMILES: CCN(c1cc(Br)cc(C(=O)OC)c1C)[C@H]1CC[C@H](N(C)C)CC1 ; CCN(c1cc(Br)cc(C(=O)O)c1C)[C@H]1CC[C@H](N(C)C)CC1]

The titled compound was prepared (820 mg, 100% yield) following the same procedure for the preparation of 3-[ethyl(1-methylpiperidin-4-yl)amino]-2-methyl-5-(trifluoromethyl)benzoic acid. MS (ESI) [M+H]$^{30}$ 383.3, 385.3. The crude compound was used without further purification for the next step reaction.

5-Bromo-3-((4-trans-(dimethylamino)cyclohexyl)(ethyl)amino)-N-((4-isopropyl-6-methyl-2-oxo-1,2-dihydropyridin-3-yl)methyl)-2-methylbenzamide

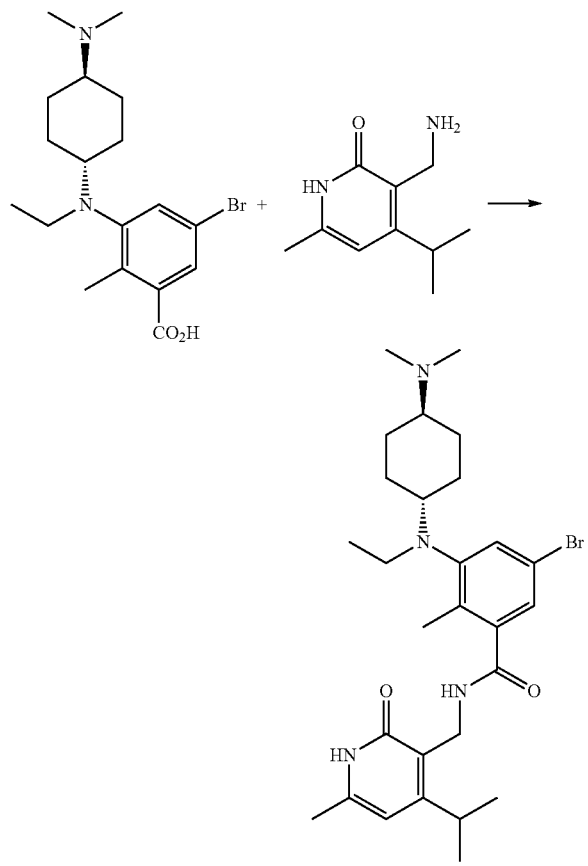

212

The titled compound was prepared (110 mg, 86% yield) following the same procedure for the preparation of N-[(4,6-dimethyl-2-oxo-1,2-dihydropyridin-3-yl)methyl]-3-[ethyl(1-methylpiperidin-4-yl)amino]-2-methyl-5-(trifluoromethyl)benzamide. $^1$H-NMR (500 MHz, CD$_3$OD) δ ppm 7.31 (d, J=2.0 Hz, 1H), 7.16 (d, J=2.0 Hz, 1H), 6.24 (s, 1H), 4.51 (s, 2H), 3.47-3.41 (m, 1H), 3.08 (q, J=7.0 Hz, 2H), 2.75-2.67 (m, 1H), 2.32 (s, 6H), 2.28 (s, 3H), 2.34-2.26 (m, 1H), 2.22 (s, 3H), 1.98-1.88 (m, 4H), 1.49-1.39 (m, 2H), 1.30-1.24 (m, 2H), 1.23 (d, J=7.0 Hz, 6H), 0.85 (t, J=7.0 Hz, 3H); MS (ESI) [M+H]$^+$ 545.4, 547.4.

5-Bromo-N-[(4,6-dimethyl-2-oxo-1,2-dihydropyridin-3-yl)methyl]-3-[ethyl(oxan-4-yl)amino]-2-methylbenzamide

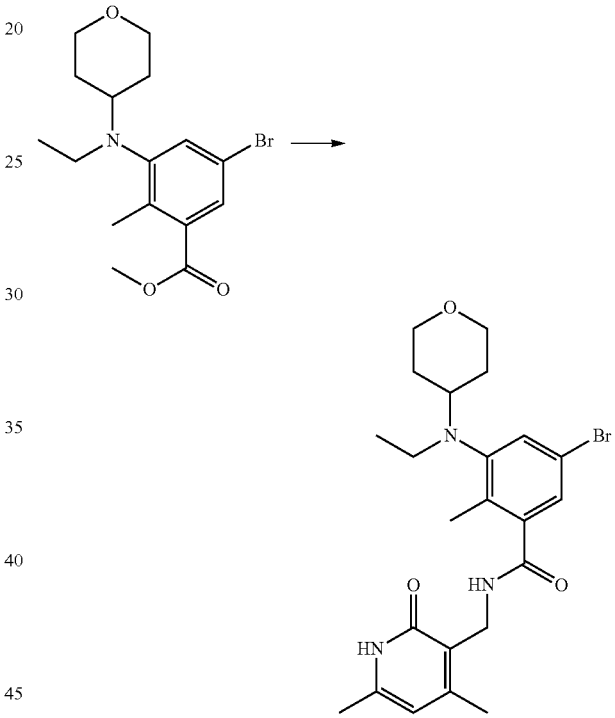

To a stirred solution of methyl 5-bromo-3-[ethyl(oxan-4-yl)amino]-2-methylbenzoate (31.0 g, 87.0 mmol) in ethanol (100 mL) was added aq. NaOH (2N, 100 mL). The reaction mixture was stirred at 60° C. for 3 hours. After cooling to rt, the reaction mixture was concentrated in vacuo, and the resultant residue was dissolved in ethyl acetate and water. The aqueous layer was acidified with aq. KHSO$_4$, extracted with ethyl acetate (300 mL, twice), concentrated in vacuo to give 5-bromo-3-[ethyl(oxan-4-yl)amino]-2-methylbenzoic acid as a crude product (28.0 g, 97%).

To a stirred solution of 5-bromo-3-[ethyl(oxan-4-yl)amino]-2-methylbenzoic acid (5.00 g, 14.6 mmol) and 3-(aminomethyl)-4,6-dimethyl-1,2-dihydropyridin-2-one HCl salt (3.31 g, 17.5 mmol) in DMSO (50 mL) was added PYBOP (11.4 g, 21.9 mmol) and Hunig's base (7.63 mL, 43.8 mmol). The reaction mixture was stirred at RT for 4 hours. The reaction mixture was quenched with water, and the resultant precipitate was collected, washed with water (2×100 mL) and ethyl ether (20 mL). The collected solid was dried under vacuum pressure to give the titled compound as a white solid (5.70 g, 82%). ¹H-NMR (400 MHz, DMSO-d₆)⁶ ppm; 11.47 (s, 1H), 8.23 (brs, 1H), 7.30 (s, 1H), 7.08 (s, 1H), 5.85 (s, 1H), 4.23 (d, J=4.4 Hz, 2H), 3.81 (d, J=10.4 Hz, 2H), 3.20-3.26 (m, 2H), 3.00-3.07 (m, 1H), 2.91-2.96 (m, 2H), 2.18 (s, 3H), 2.14 (s, 3H), 2.10 (s, 3H), 1.58-1.60 (m, 2H), 1.45-1.50 (m, 2H), 0.78 (t, J=6.8 Hz, 3H); MS (ESI) [M+H]⁺ 476.3, 478.3.

5-Bromo-3-[ethyl(oxan-4-yl)amino]-2-methyl-N-{[6-methyl-2-oxo-4-(2-propyl)-1,2-dihydropyridin-3-yl]methyl}benzamide

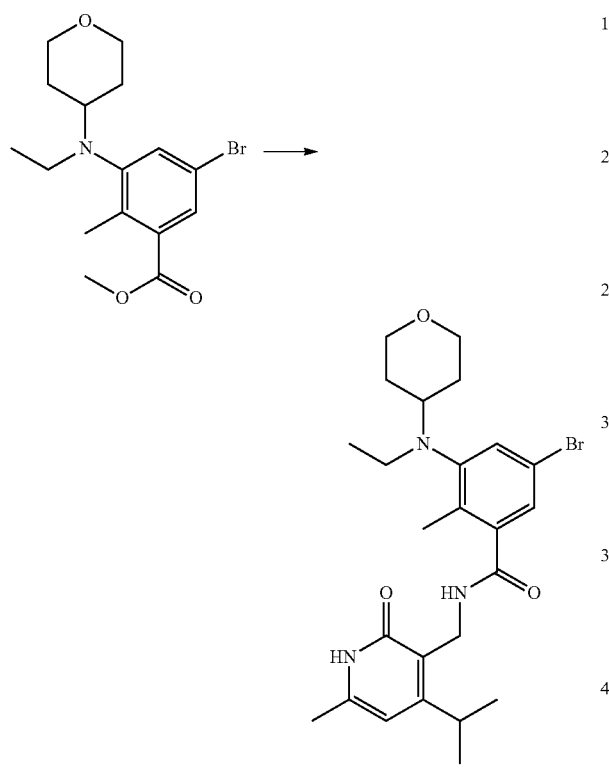

To a stirred solution of methyl 5-bromo-3-[ethyl(oxan-4-yl)amino]-2-methylbenzoate (31.0 g, 87.0 mmol) in ethanol (100 mL) was added aq. NaOH (2N, 100 mL). The reaction mixture was stirred at 60° C. for 3 hours. After cooling to rt, the reaction mixture was concentrated in vacuo, and the resultant residue was dissolved in ethyl acetate and water. The aqueous layer was acidified with aq. KHSO₄, extracted with ethyl acetate (300 mL, twice), concentrated in vacuo to give 5-bromo-3-[ethyl(oxan-4-yl)amino]-2-methylbenzoic acid as a crude product (28.0 g, 97%).

To a stirred solution of 5-bromo-3-[ethyl(oxan-4-yl) amino]-2-methylbenzoic acid (3.00 g, 8.77 mmol) and 3-(Aminomethyl)-6-methyl-4-(propan-2-yl)-1,2-dihydropyridin-2-one HCl salt (2.47 mg, 11.4 mmol) in DMSO (40 mL) was added PYBOP (6.84 mg, 13.1 mmol) and Hunig's base (7.63 mL, 43.8 mmol). The reaction mixture was stirred at RT for 17 hours. The reaction mixture was quenched with water, and the aqueous layer was extracted with ethyl acetate. The organic layer was washed with water (twice) and brine. The organic layer was dried over MgSO₄ and filtered. The filtrate was concentrated in vacuo. The residue was purified by silica gel column chromatography (SiO₂; ethylacetate/MeOH=6/1). Fractions containing target material were collected and concentrated in vacuo. The residue was re-purified by silica gel column chromatography (NH—SiO₂; Heptane/ethylacetate=1/1 to ethylacetate/methanol=10/1) to give the titled compound as a white amorphous solid (5.45 g, quantitative yield). ¹H-NMR (400 MHz, CDCl₃) δ ppm; 10.54 (brs, 1H), 7.21 (d, J=2.2 Hz, 1H), 7.17 (d, J=2.2 Hz, 1H), 7.04-7.10 (m, 1H), 6.05 (s, 1H), 4.57 (d, J=6.2 Hz, 2H), 3.91-3.99 (m, 2H), 3.47-3.56 (m, 1H), 3.27-3.36 (m, 2H), 3.02 (q, J=7.2 Hz, 2H), 2.87-2.98 (m, 1H), 2.27 (s, 3H), 2.24 (s, 3H), 1.61-1.70 (m, 4H), 1.21 (d, J=7.0 Hz, 6H), 0.85 (t, J=7.2 Hz, 3H).

5-Bromo-3-[ethyl(oxan-4-yl)amino]-2-methyl-N-{[6-methyl-2-oxo-4-(trifluoromethyl)-1,2-dihydropyridin-3-yl]methyl}benzamide

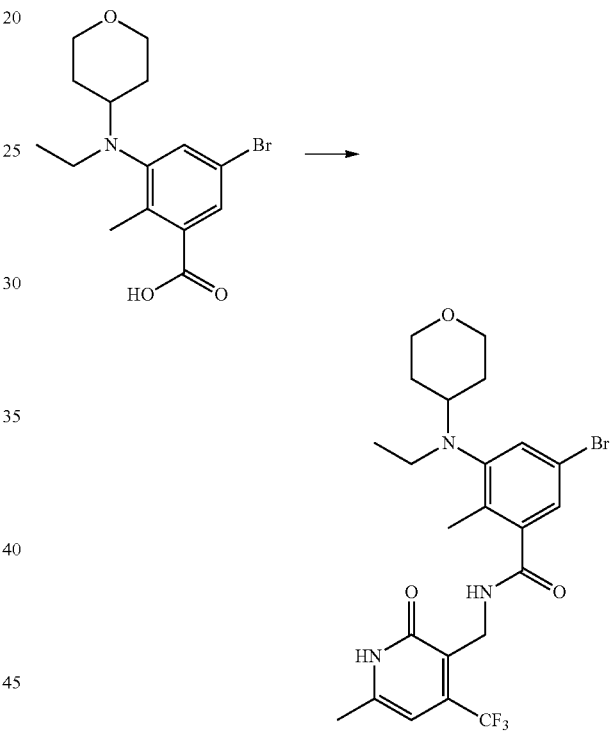

To a stirred solution of 5-bromo-3-[ethyl(oxan-4-yl) amino]-2-methylbenzoic acid (500 mg, 1.46 mmol) and 3-(Aminomethyl)-6-methyl-4-(trifluoromethyl)-1,2-dihydropyridin-2-one hydrochloride (461 mg, 1.90 mmol) in DMSO (11 mL) was added PYBOP (1.14 g, 2.19 mmol) and Hunig's base (0.763 mL, 4.38 mmol). The reaction mixture was stirred at RT for 15 hours. The reaction mixture was quenched with water, diluted with EtOAc, and partitioned. The organic layer was washed with water, brine, dried over Na₂SO₄, filtered, and concentrated. The residue was purified by silica gel column chromatography (NH—SiO₂, EtOAc/heptane=1/1 to EtOAc only) to give the titled compound (563 mg, ~89% purity, 65%). ¹H-NMR (400 MHz, DMSO-d₆) 0.5 ppm; 7.23 (d, J=2.0 Hz, 1H), 7.19 (d, J=2.0 Hz, 1H), 6.82 (t, J=6.4 Hz, 1H), 6.35 (s, 1H), 4.71 (d, J=6.4 Hz, 2H), 3.92-3.97 (m, 2H), 3.27-3.34 (m, 2H), 3.03 (q, J=7.2 Hz, 2H), 2.89-2.95 (m, 1H), 2.39 (s, 3H), 2.27 (s, 3H), 1.62-1.68 (m, 4H), 0.86 (t, J=7.2 Hz, 3H).

215

5-Bromo-2-(methoxymethyl)pyridine

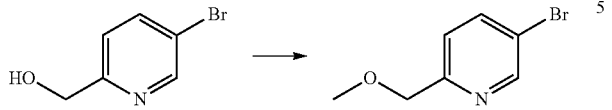

To a stirred solution of (5-bromo-2-pyridyl)methanol (1.50 g, 7.98 mmol) and MeI (600 uL, 9.58 mmol) in DMF (10 mL) was added NaH (60% in oil, 400 mg, 9.98 mmol) at 0° C. The reaction mixture was stirred at rt for 3.5 hours. The reaction mixture was quenched with water, diluted with EtOAc, and partitioned. The organic layer was washed with brine, dried over $Na_2SO_4$, filtered, and concentrated. The residue was purified by silica gel column chromatography (NH—$SiO_2$; ethyl acetate/heptane=1/8) to give the titled compound as a white solid (1.52 g, 94%). $^1$H-NMR (400 MHz, $CDCl_3$) δ ppm; 8.62 (d, J=2.4 Hz, 1H), 7.82 (dd, J=2.4, 8.4 Hz, 1H), 7.34 (d, J=8.4 Hz, 1H), 4.54 (s, 2H), 3.48 (s, 3H).

2-(Methoxymethyl)-5-(tetramethyl-1,3,2-dioxaborolan-2-yl)pyridine

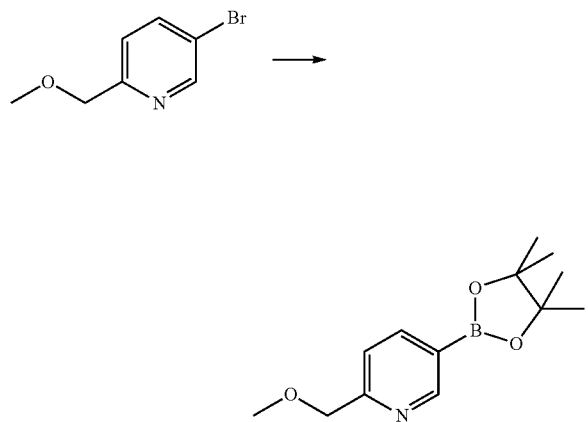

To a stirred solution of 5-bromo-2-(methoxymethyl)pyridine (700 mg, 3.46 mmol) and bis(pinacolato)diboron (968 mg, 3.81 mmol) in 1,2-dimethoxyethane (10 mL) was added potassium acetate (1.02 g, 10.4 mmol) and Pd(dppf)$Cl_2 \cdot CH_2Cl_2$ complex (595 mg, 0.692 mmol). The reaction mixture was stirred at 80° C. for 3 hours. The mixture was cooled to rt, diluted with EtOAc, and filtered through Celite pad. The filtrate was washed with water (twice), dried over $Na_2SO_4$, filtered, and concentrated to give the titled compound as a crude product (1.6 g, 50% purity (as quantitative yield)). $^1$H-NMR (400 MHz, $CDCl_3$) δ ppm; 8.88 (s, 1H), 8.07 (d, J=8.0 Hz, 1H), 7.42 (d, J=8.0 Hz, 1H), 4.61 (s, 2H), 3.48 (s, 3H), 1.25 (s, 12H).

216

3-[Ethyl(oxan-4-yl)amino]-5-[6-(methoxymethyl)pyridin-3-yl]-2-methyl-N-{[6-methyl-2-oxo-4-(2-propyl)-1,2-dihydropyridin-3-yl]methyl}benzamide

(129)

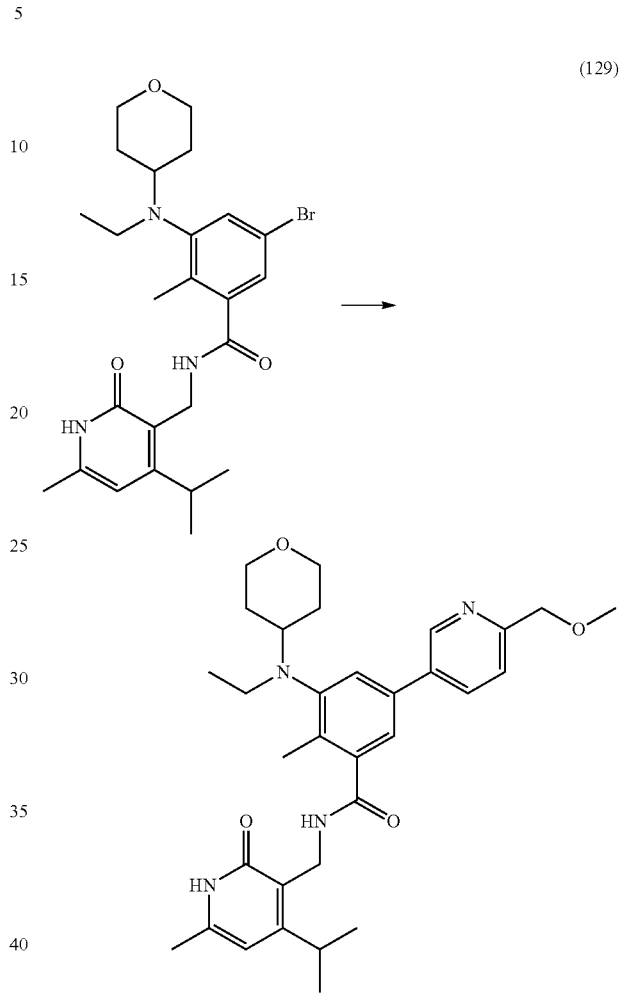

To a stirred solution of 5-bromo-3-[ethyl(oxan-4-yl)amino]-2-methyl-N-{[6-methyl-2-oxo-4-(propan-2-yl)-1,2-dihydropyridin-3-yl]methyl}benzamide (125 mg, 0.198 mmol) and a crude product of 2-(Methoxymethyl)-5-(tetramethyl-1,3,2-dioxaborolan-2-yl)pyridine (160 mg, 50% purity, 0.317 mmol) in 1,4-dixoxane (2 mL) and $H_2O$ (0.4 mL) was added $Pd(PPh_3)_4$ (23.0 mg, 0.02 mmol) and sodium carbonate (76.0 mg, 0.713 mmol). The reaction mixture was stirred at 100° C. for 3 hours. The mixture was cooled to rt, diluted with EtOAc, and filtered through Celite pad. The filtrate was washed with water (twice), dried over $Na_2SO_4$, filtered, and concentrated. The residue was purified by silica gel column chromatography (NH—$SiO_2$; heptane/ethyl acetate=1/2 to EtOAc only) and ($SiO_2$; EtOAc only to EtOAc/MeOH=5/1+5% TEA), and by PTLC ($SiO_2$; EtOAc, 6 developments). The mixture was triturated with EtOAc-hexane to give the titled compound as a white solid (33.4 mg, 31%). $^1$H-NMR (400 MHz, $CDCl_3$) δ ppm; 9.88-9.90 (m, 1H), 8.69 (d, J=2.4 Hz, 1H), 7.81 (dd, J=2.4, 8.0 Hz, 1H), 7.44 (d, J=8.0 Hz, 1H), 7.28-7.29 (m, 1H), 7.24-7.25 (m, 1H), 7.09-7.12 (m, 1H), 6.03 (s, 1H), 4.61 (s, 2H), 4.60-4.61 (m, 2H), 3.94-3.97 (m, 2H), 3.50-3.58 (m, 1H), 3.50 (s, 3H), 3.29-3.36 (m, 2H), 3.10 (q, J=6.8 Hz, 2H), 2.99-3.03 (m, 1H), 2.34 (s, 3H), 2.23 (s, 3H) 1.66-1.73 (m, 4H), 1.22 (d, J=6.8 Hz, 6H), 0.90 (t, J=6.8 Hz, 3H); MS (ESI) [M+H]+ 547.4; HPLC 98.0% purity.

N-[(4,6-Dimethyl-2-oxo-1,2-dihydropyridin-3-yl)methyl]-3-[ethyl(oxan-4-yl)amino]-5-(6-methoxypyridin-3-yl)-2-methylbenzamide

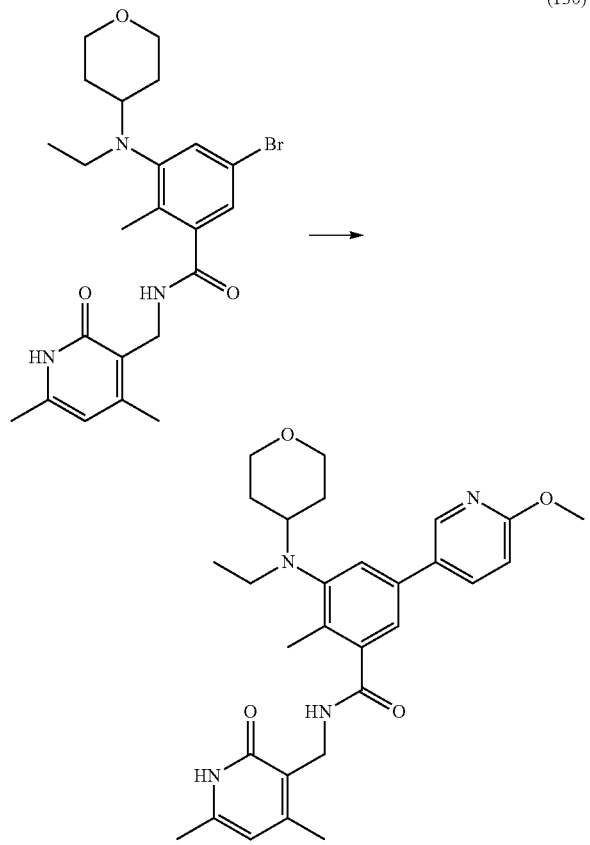

(130)

To a stirred solution of 5-bromo-N-[(4,6-dimethyl-2-oxo-1,2-dihydropyridin-3-yl)methyl]-3-[ethyl(oxan-4-yl)amino]-2-methylbenzamide (100 mg, 0.210 mmol) and 2-methoxy-5-pyridineboronic Acid (51 mg, 0.336 mmol) in 1,4-dixoxane (2 mL) and H$_2$O (0.4 mL) was added Pd(PPh$_3$)$_4$ (25 mg, 0.0216 mmol) and sodium carbonate (80 mg, 0.756 mmol). The reaction mixture was stirred at 100° C. for 4 hours. The mixture was cooled to it, diluted with EtOAc, and filtered through Celite pad. The filtrate was washed with water (twice) and brine, dried over Na$_2$SO$_4$, filtered, and concentrated. The residue was purified by silica gel column chromatography (NH—SiO$_2$; heptane/ethyl acetate=1/1~EtOAc to EtOAc/MeOH=10/1). The mixture was triturated with EtOAc-hexane to give the titled compound as a white solid (66.7 mg, 63%). $^1$H-NMR (400 MHz, CDCl$_3$) δ ppm; 10.7-10.8 (m, 1H), 8.29 (d, J=2.8 Hz, 1H), 7.70 (dd, J=2.8, 8.8 Hz, 1H), 7.25 (d, J=1.6 Hz, 1H), 7.20 (d, J=1.6 Hz, 1H), 7.13 (t, J=6.0 Hz, 1H), 6.77 (d, J=8.8 Hz, 1H), 5.91 (s, 1H), 4.55 (d, J=6.0 Hz, 2H), 3.95 (s, 3H), 3.93-3.96 (m, 2H), 3.28-3.36 (m, 2H), 3.10 (q, J=7.2 Hz, 2H), 2.96-3.03 (m, 1H), 2.41 (s, 3H), 2.34 (s, 3H), 2.17 (s, 3H) 1.68-1.72 (m, 4H), 0.89 (t, J=7.2 Hz, 3H); MS (ESI) [M+H]+ 505.5; HPLC 99.3% purity.

4-{[5-(Tetramethyl-1,3,2-dioxaborolan-2-yl)pyridin-2-yl]methyl}morpholine

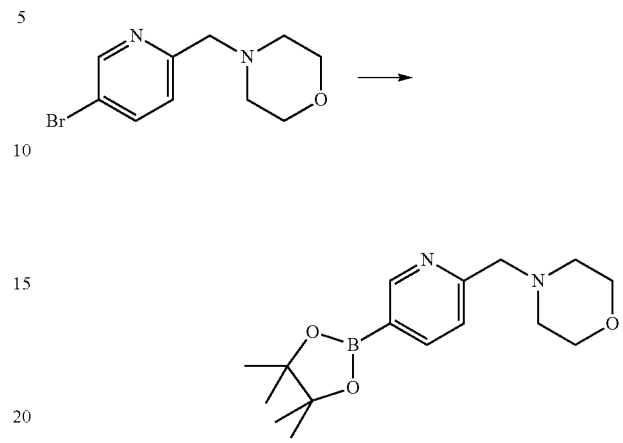

To a stirred solution of 4-[(5-bromopyridin-2-yl)methyl]morpholine (500 mg, 1.94 mmol) and bis(pinacolato)diboron (542 mg, 2.13 mmol) in 1,2-dimethoxyethane (5 mL) was added potassium acetate (571 mg, 5.82 mmol) and Pd(dppf)Cl$_2$ (400 mg, 0.235 mmol). The reaction mixture was stirred at 80° C. for 1.5 hours. The mixture was cooled to rt, evaporated, diluted with EtOAc, and filtered through Celite pad. The filtrate was washed with water (twice), brine, dried over Na$_2$SO$_4$, filtered, and concentrated to give the titled compound as a crude product (934 mg, 60% purity (as quantitative yield)). $^1$H-NMR (400 MHz, CDCl$_3$) δ ppm; 8.63 (d, J=2.4 Hz, 1H), 7.79 (dd, J=2.4, 8.4 Hz, 1H), 7.34 (d, J=8.4 Hz, 1H), 3.71-3.78 (m, 4H), 3.61 (s, 2H), 2.45-2.58 (m, 4H), 1.26 (s, 12H).

3-[Ethyl(oxan-4-yl)amino]-2-methyl-N-{[6-methyl-2-oxo-4-(trifluoromethyl)-1,2-dihydropyridin-3-yl]methyl}-5-[6-(morpholin-4-ylmethyl)pyridin-3-yl]benzamide

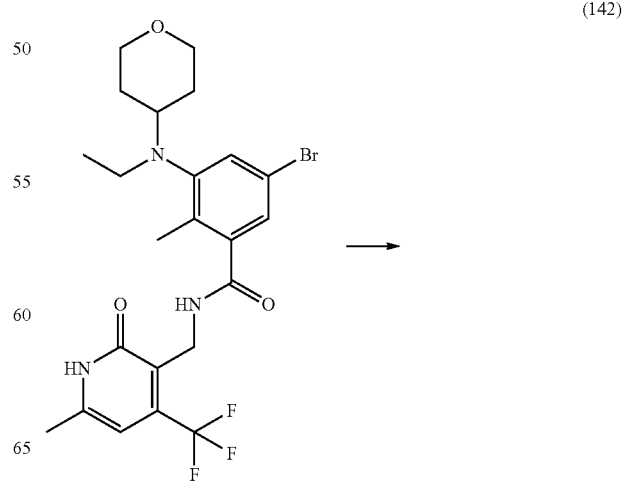

(142)

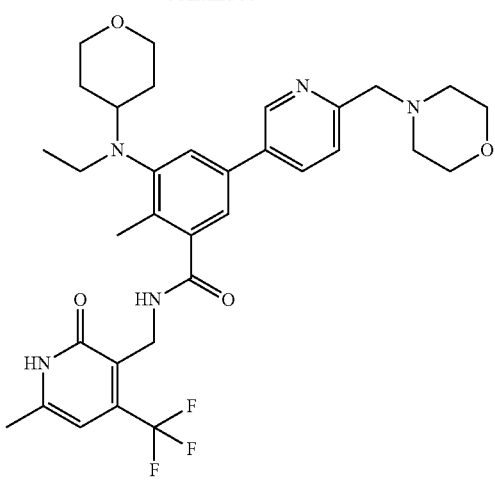

To a stirred solution of 5-bromo-3-[ethyl(oxan-4-yl)amino]-2-methyl-N-{[6-methyl-2-oxo-4-(trifluoromethyl)-1,2-dihydropyridin-3-yl]methyl}benzamide (274 mg, 89% purity, 0.46 mmol) and a crude mixture of 4-{[5-(tetramethyl-1,3,2-dioxaborolan-2-yl)pyridin-2-yl]methyl}morpholine (470 mg, ~60% purity, 0.927 mmol) in 1,4-dioxane (4.6 mL) and H$_2$O (0.92 mL) was added Pd(PPh$_3$)$_4$ (53.0 mg, 0.0459 mmol) and sodium carbonate (176 mg, 1.66 mmol). The reaction mixture was stirred at 100° C. for 3 hours. The mixture was cooled to rt, evaporated, diluted with EtOAc, and filtered through Celite pad. The filtrate was washed with water (twice), brine, dried over Na$_2$SO$_4$, filtered, and concentrated. The residue was purified by silica gel column chromatography (NH—SiO$_2$; EtOAc only to EtOAc/MeOH=5/1) and (SiO$_2$; EtOAc only to EtOAc/MeOH=5/1+5% TEA). The mixture was triturated with Et$_2$O-hexane to give the titled compound as a white solid (28.0 mg, 9.7%). $^1$H-NMR (400 MHz, CDCl$_3$) δ ppm; 8.41 (d, J=2.4 Hz, 1H), 7.64 (dd, J=2.4, 8.0 Hz, 1H), 7.30-7.40 (m, 2H), 7.22 (s, 1H), 7.18 (s, 1H), 6.26 (s, 1H), 4.77 (d, J=6.4 Hz, 2H), 3.94-3.97 (m, 2H), 3.66-3.77 (m, 4H), 3.49 (s, 2H), 3.26-3.38 (m, 2H), 3.10 (q, J=6.8 Hz, 2H), 2.94-3.05 (m, 1H), 2.42-2.49 (m, 4H), 2.39 (s, 3H), 2.31 (s, 3H) 1.66-1.73 (m, 4H), 0.90 (t, J=6.8 Hz, 3H); MS (ESI) [M+H]$^+$ 628.6; HPLC 95.4% purity.

1[(4-Bromo-2-fluorophenyl)methyl]azetidin-3-ol

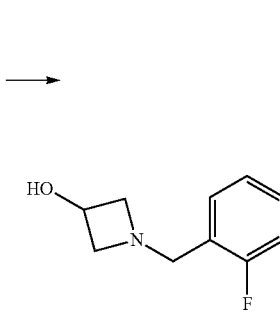

To a stirred solution of 4-bromo-2-fluorobenzyl alcohol (818 mg, 3.99 mmol) and triethylamine (0.666 mL, 4.79 mmol) in CH$_2$Cl$_2$ (6.8 mL) was added MsCl (0.340 mL, 4.39 mmol) drop wise at 0° C. The reaction mixture was stirred at 0° C. for 3 hours. The mixture was quenched with water, diluted with EtOAc, and partitioned. The organic layer was washed with brine, dried over Na$_2$SO$_4$, filtered, and concentrated.

To a stirred solution of the crude mesylate and triethylamine (2.22 mL, 16.0 mmol) in DMF (6.8 mL) was added 3-hydroxyazetidine hydrochloride (655 mg, 5.99 mmol). The reaction mixture was stirred at 23° C. for 14 hours. The reaction mixture was quenched with water, diluted with ethyl acetate, and partitioned. The organic layer was washed with water and brine, dried over Na$_2$SO$_4$, filtered and concentrated. The residue was purified by silica gel column chromatography (NH—SiO$_2$; ethyl acetate/heptane=1/1-2/1) to give the titled compound (698 mg, 67% yield). $^1$H-NMR (400 MHz, CDCl$_3$) δ ppm; 7.17-7.27 (m, 3H), 4.42-4.47 (m, 1H), 3.61-3.67 (m, 4H), 2.95-2.99 (m, 2H), 1.90-2.05 (m, 1H).

1-{[2-Fluoro-4-(tetramethyl-1,3,2-dioxaborolan-2-yl)phenyl]methyl}azetidin-3-ol

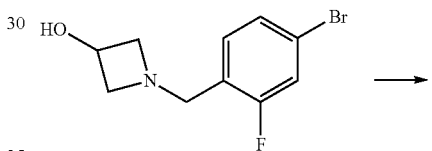

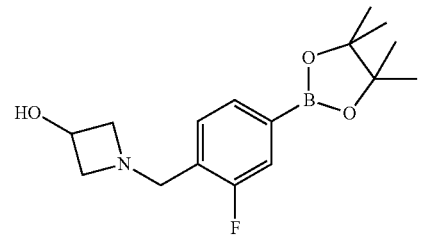

To a stirred solution of 1-[(4-bromo-2-fluorophenyl)methyl]azetidin-3-ol (348 mg, 1.34 mmol) and bis(pinacolato)diboron (374 mg, 1.47 mmol) in 1,2-dimethoxyethane (3 mL) was added potassium acetate (394 mg, 4.02 mmol) and Pd(dppf)Cl$_2$ (273 mg, 0.335 mmol). The reaction mixture was stirred at 80° C. for 2 hours. The mixture was cooled to rt, evaporated, diluted with EtOAc, and filtered through Celite pad. The filtrate was washed with water (twice), brine, dried over Na$_2$SO$_4$, filtered, and concentrated to give the titled compound as a crude product (650 mg, ~63% purity (as quantitative yield)).

221

N-[(4,6-Dimethyl-2-oxo-1,2-dihydropyridin-3-yl)methyl]-3-[ethyl(oxan-4-amino]-5-{3-fluoro-4-[(3-hydroxyazetidin-1-yl)methyl]phenyl}-2-methylbenzamide (154)

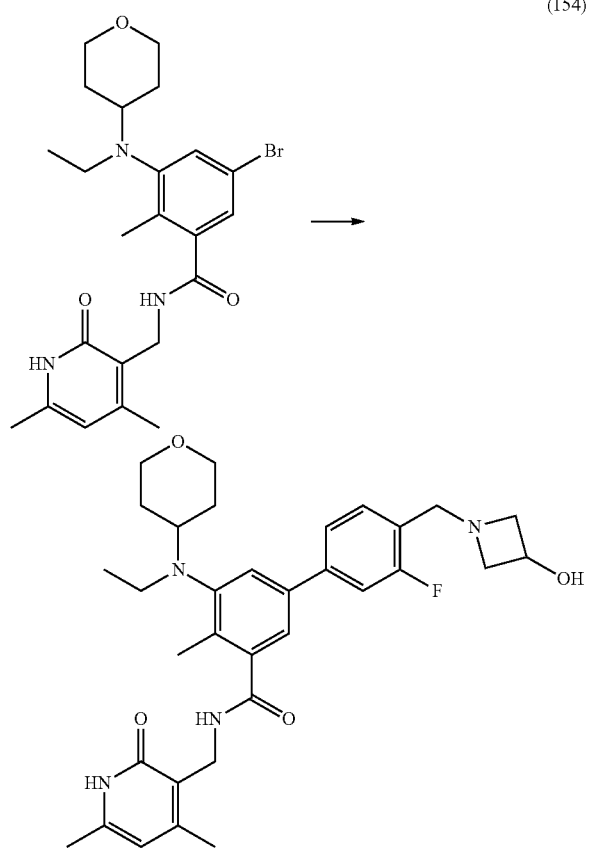

To a stirred solution of 5-bromo-N-[(4,6-dimethyl-2-oxo-1,2-dihydropyridin-3-yl)methyl]-3-[ethyl(oxan-4-yl)amino]-2-methylbenzamide (203 mg, 0.426 mmol) and a crude mixture of 1-{[2-fluoro-4-(tetramethyl-1,3,2-dioxaborolan-2-yl)phenyl]methyl}azetidin-3-ol (350 mg, 63% purity, 0.67 mmol) in 1,4-dioxane (4 mL) and H$_2$O (0.8 mL) was added Pd(PPh$_3$)$_4$ (48 mg, 0.0415 mmol) and sodium carbonate (160 mg, 1.51 mmol). The reaction mixture was stirred at 100° C. for 3 hours. The mixture was cooled to rt, evaporated, diluted with EtOAc, and filtered through Celite pad. The filtrate was washed with water (twice), brine, dried over Na$_2$SO$_4$, filtered, and concentrated. The residue was purified by silica gel column chromatography (NH—SiO$_2$; EtOAc only to EtOAc/MeOH=5/1), (SiO$_2$; EtOAc only to EtOAc/MeOH=5/1+5% TEA) and by PTLC (SiO$_2$; EtOAc/MeOH=20/1 6 developments). The mixture was triturated with EtOAc-hexane to give the titled compound as a white solid (74.1 mg, 31%). $^1$H-NMR (400 MHz, CDCl$_3$) δ ppm; 7.33 (t, J=6.0 Hz, 1H), 7.13-7.30 (m, 5H), 5.91 (s, 1H), 4.56 (d, J=6.0 Hz, 2H), 4.34-4.38 (m, 1H), 3.94-3.98 (m, 2H), 3.56-3.60 (m, 2H), 3.56 (s, 2H), 3.29-3.36 (m, 2H), 3.09 (q, J=7.2 Hz, 2H), 3.01-3.03 (m, 1H), 2.91-2.94 (m, 2H), 2.43 (s, 3H), 2.38 (s, 3H), 2.13 (s, 3H), 1.68-1.74 (m, 4H), 0.90 (t, J=7.2 Hz, 3H); MS (ESI) [M+H]$^+$ 577.6; HPLC 95.0% purity.

222

N-(2-Hydroxyethyl)-4-(tetramethyl-1,3,2-dioxaborolan-2-yl)benzamide

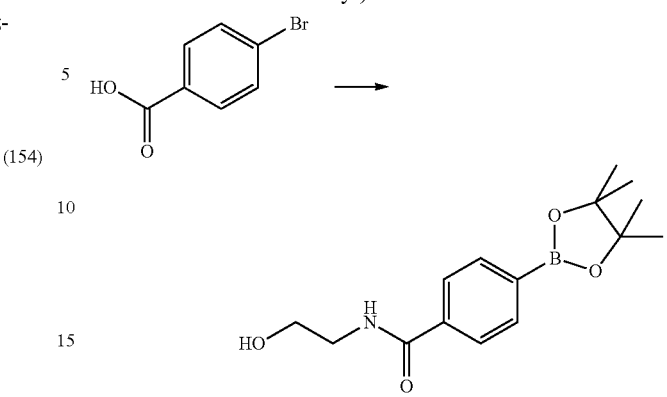

To a stirred solution of 4-bromobenzoic acid (2.00 g, 9.95 mmol) and 2-aminoethan-1-ol (912 mg, 14.9 mmol) in THF (200 mL) was added HATU (6.81 g, 17.9 mmol) and Hunig's base (5.20 mL, 29.9 mmol). The reaction mixture was stirred at RT for 2 hours. Then, the reaction mixture was quenched with water. The mixture was concentrated in vacuo, and the resultant residue was dissolved in ethyl acetate and water. The aqueous layer was extracted with ethyl acetate (twice), and the combined organic layer was concentrated in vacuo. The residue was purified by silica gel column chromatography (SiO$_2$; Heptane/ethyl acetate=1/1) to give N-(2-hydroxyethyl)benzamide as a white solid (1.70 g, 70%).

To a stirred solution of N-(2-hydroxyethyl)benzamide (1.70 g, 6.96 mmol) and bis(pinacolato)diboron (2.12 g, 8.36 mmol) in 1,2-dimethoxyethan (40 mL) was added potassium acetate (2.05 g, 20.9 mmol) and Pd(dppf)Cl$_2$ (255 mg, 0.348 mmol). The reaction mixture was stirred at 80° C. for 4 hours. After cooling to RT, the mixture was filtered through Celite pad. The filtrate was concentrated in vacuo, the resultant residue was purified by silica gel column chromatography (SiO$_2$; Heptane/ethyl acetate=1/1) to give the titled compound as a brown solid (1.20 g, 59%). $^1$H-NMR (400 MHz, CDCl$_3$) ppm; 7.87 (d, J=8.2 Hz, 2H), 7.76 (d, J=8.2 Hz, 2H), 6.71 (brs, 1H), 3.80-3.88 (m, 2H), 3.60-3.69 (m, 2H), 1.35 (s, 12H); MS (ESI) [M+H]$^+$ 292.2.

N-[(4,6-Dimethyl-2-oxo-1,2-dihydropyridin-3-371)methyl]-3-[ethyl(oxan-4-yl)amino]-5-{4-[(2-hydroxyethyl)carbamoyl]phenyl}-2-methylbenzamide (155)

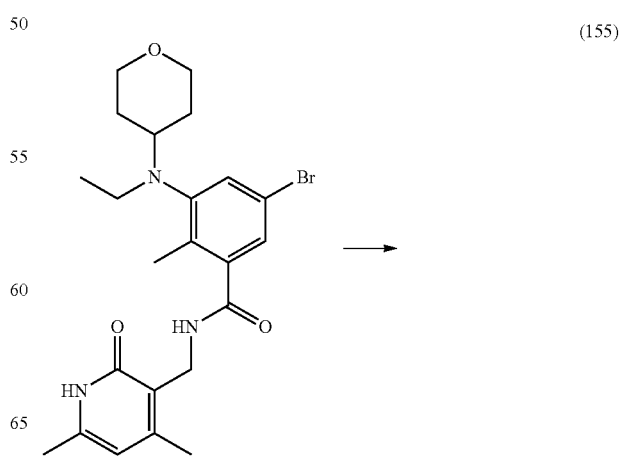

223
-continued

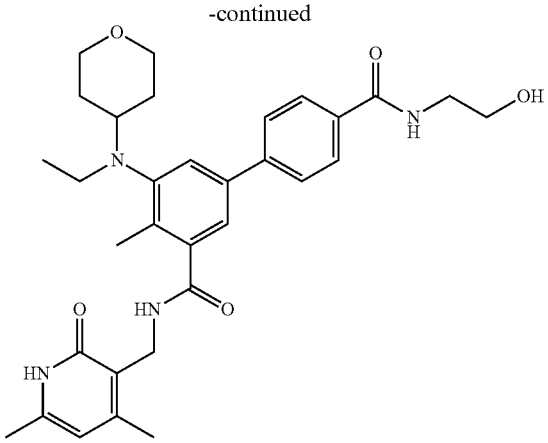

To a stirred solution of 5-bromo-N-[(4,6-dimethyl-2-oxo-1,2-dihydropyridin-3-yl)methyl]-3-[ethyl(oxan-4-yl)amino]-2-methylbenzamide (200 mg, 0.419 mmol) and N-(2-hydroxyethyl)-4-(tetramethyl-1,3,2-dioxaborolan-2-yl)benzamide (196 mg, 0.673 mmol) in 1,4-dixoxane (4.2 mL) and H$_2$O (0.8 mL) was added Pd(PPh$_3$)$_4$ (49 mg, 0.0424 mmol) and sodium carbonate (160 mg, 1.51 mmol). The reaction mixture was stirred at 100° C. for 2 hours. The mixture was cooled to rt, evaporated, and diluted with EtOAc. The mixture was washed with water (twice), brine, dried over Na$_2$SO$_4$, filtered, and concentrated. The residue was purified by silica gel column chromatography (NH—SiO$_2$; EtOAc only to EtOAc/MeOH=10/1-5/1), (SiO$_2$; EtOAc only to EtOAc/MeOH=10/1-5/1). The mixture was triturated with CH$_2$Cl$_2$-Et$_2$O-hexane to give the titled compound (122.2 mg, 52%). $^1$H-NMR (400 MHz, CDCl$_3$) δ ppm; 7.75-7.79 (m, 1H), 7.70 (br-s, 1H), 7.60 (d, J=8.4 Hz, 2H), 7.30-7.33 (m, 4H), 5.63 (s, 1H), 4.52 (d, J=6.4 Hz, 2H), 4.12-4.18 (m, 1H), 3.92-3.98 (m, 4H), 3.72-3.75 (m, 2H), 3.29 (m, 2H), 3.11 (q, J=7.2 Hz, 2H), 2.98-3.03 (m, 1H), 2.41 (s, 3H), 2.37 (s, 3H), 1.90 (s, 3H), 1.66-1.73 (m, 4H), 0.90 (t, J=7.2 Hz, 3H); MS (ESI) [M+H]$^+$ 561.5; HPLC 95.8% purity.

3-[Ethyl(oxan-4-yl)amino]-5-{4-[(2-hydroxyethyl)carbamoyl]phenyl}-2-methyl-N-{[6-methyl-2-oxo-4-(propan-2-yl)-1,2-dihydropyridin-3-yl]methyl}benzamide 224
-continued

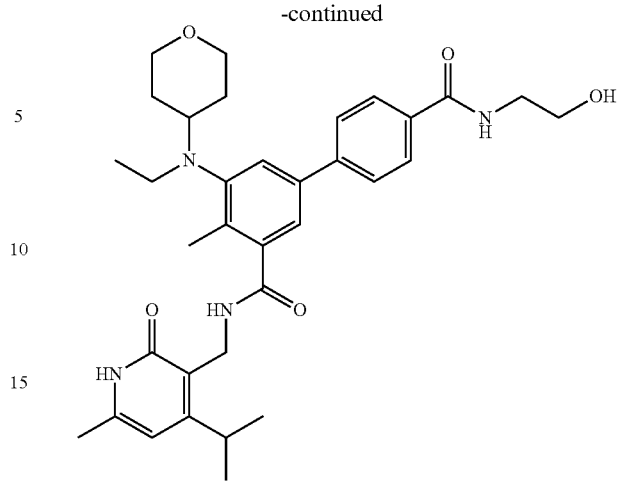

To a stirred solution of 5-bromo-3-[ethyl(oxan-4-yl)amino]-2-methyl-N-{[6-methyl-2-oxo-4-(propan-2-yl)-1,2-dihydropyridin-3-yl]methyl}benzamide (250 mg, 80% purity, 0.396 mmol) and N-(2-hydroxyethyl)-4-(tetramethyl-1,3,2-dioxaborolan-2-yl)benzamide (184 mg, 0.634 mmol) in 1,4-dioxane (4 mL) and H$_2$O (0.8 mL) was added Pd(PPh$_3$)$_4$ (40 mg, 0.0346 mmol) and sodium carbonate (151 mg, 1.43 mmol). The reaction mixture was stirred at 100° C. for 2 hours. The mixture was cooled to rt, evaporated, and diluted with EtOAc. The mixture was washed with water (twice), brine, dried over Na$_2$SO$_4$, filtered, and concentrated. The residue was purified by silica gel column chromatography (NH—SiO$_2$; EtOAc only to EtOAc/MeOH=10/1-5/1). The mixture was triturated with CH$_2$Cl$_2$-EtOAc-hexane to give the titled compound as a white solid (176 mg, 75% yield). $^1$H-NMR (400 MHz, CDCl$_3$) δ ppm; 7.85 (t, J=6.4 Hz, 1H), 7.67 (t, J=5.2 Hz, 1H), 7.52 (d, J=8.4 Hz, 2H), 7.26-7.30 (m, 4H), 5.89 (s, 1H), 4.61 (d, J=6.4 Hz, 2H), 3.91-4.02 (m, 3H), 3.84-3.89 (m, 2H), 3.64-3.68 (m, 2H), 3.51-3.56 (m, 1H), 3.29-3.36 (m, 2H), 3.09 (q, J=6.8 Hz, 2H), 2.97-3.03 (m, 1H), 2.40 (s, 3H), 2.02 (s, 3H), 1.64-1.68 (m, 4H), 1.18 (d, J=6.8 Hz, 6H), 0.88 (t, J=6.8 Hz, 3H); MS (ESI) [M+H]$^+$ 589.5; HPLC 96.7% purity.

N-[(4,6-Dimethyl-2-oxo-1,2-dihydropyridin-3-yl)methyl]-3-[ethyl(oxan-4-yl)amino]-2-methyl-5-{6-[(4-methyl-1,4-diazepan-1-yl)methyl]pyridin-3-yl}benzamide)

(156)

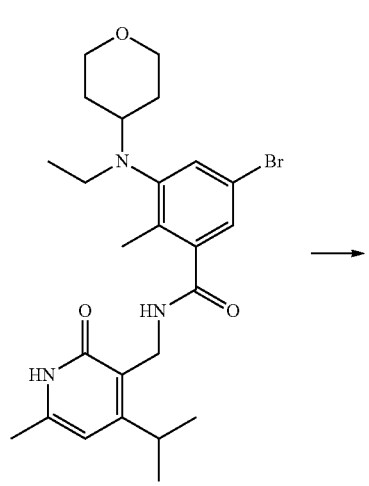

→

(135)

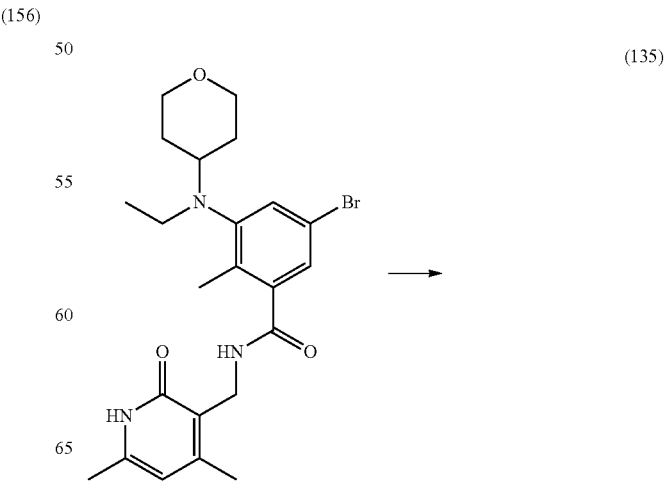

→

225
-continued

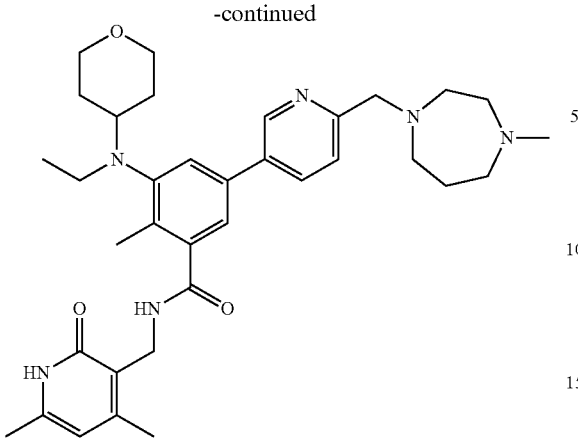

To a stirred solution of 5-bromo-N-[(4,6-dimethyl-2-oxo-1,2-dihydropyridin-3-yl)methyl]-3-[ethyl(oxan-4-yl)amino]-2-methylbenzamide (2.00 g, 4.20 mmol) and [5-(tetramethyl-1,3,2-dioxaborolan-2-yl)pyridin-2-yl]methanol (1.18 g, 5.04 mmol) in 1,4-dixoxane (40 mL) and H$_2$O (4 mL) was added Pd(PPh$_3$)$_4$ (485 mg, 0.420 mmol) and sodium carbonate (1.34 g, 12.6 mmol). The reaction mixture was stirred at 80° C. for 2 hours. Then, the reaction mixture was filtered through celite pad. The filtrate was concentrated in vacuo, the resultant residue was purified by silica gel column chromatography (NH—SiO$_2$; heptane/ethylacetate=1/5 to ethyl acetate only) to give N-[(4,6-dimethyl-2-oxo-1,2-dihydropyridin-3-yl)methyl]-3-[ethyl(oxan-4-yl)amino]-5-[6-(hydroxymethyl)pyridin-3-yl]-2-methylbenzamide as a white solid (800 mg, 37% yield).

To a stirred solution of N-[(4,6-dimethyl-2-oxo-1,2-dihydropyridin-3-yl)methyl]-3-[ethyl(oxan-4-yl)amino]-5-[6-(hydroxymethyl)pyridin-3-yl]-2-methylbenzamide (200 mg, 0.396 mmol) in CH$_2$Cl$_2$ (4 mL) was added methanesulfonyl chloride (54.4 mg, 0.475 mmol) and Hunig's base (206 uL, 1.19 mmol). The reaction mixture was stirred at RT for 30 minutes. Then 1-methyl-homopiperazine (226 mg, 1.98 mmol) was added to the reaction mixture, and the resultant mixture was stirred at RT for 1 hour. The mixture was quenched with water, and concentrated in vacuo. The residue was purified by silica gel column chromatography (NH—SiO$_2$ ethylacetate/MeOH=20/1) to give the titled compound as a white solid (25.1 mg). $^1$H-NMR (400 MHz, CDCl$_3$) δ ppm; 8.63 (dd, J=2.3, 0.8 Hz, 1H), 7.75 (dd, J=8.2, 2.3 Hz, 1H), 7.48 (d, J=8.2 Hz, 1H), 7.29 (d, J=2.0 Hz, 1H), 7.25 (d, J=2.0 Hz, 1H), 7.20 (t, J=5.9 Hz, 1H), 5.91 (s, 1H), 4.56 (d, J=5.9 Hz, 2H), 3.96 (m, 2H), 3.80 (s, 2H), 3.26-3.36 (m, 2H), 3.09 (q, J=7.0 Hz, 2H), 2.95-3.05 (m, 1H), 2.75-2.82 (m, 4H), 2.60-2.71 (m, 4H), 2.39 (s, 3H), 2.36 (s, 3H), 2.34 (s, 3H), 2.14 (s, 3H), 1.79-1.89 (m, 4H), 1.64-1.74 (m, 2H), 0.89 (t, J=7.0 Hz, 3H); MS (ESI) [M+H]$^+$ 601.6; HPLC 93.4% purity.

226
N-[(4,6-Dimethyl-2-oxo-1,2-dihydropyridin-3-yl)methyl]-3-[ethyl(oxan-4-yl)amino]-2-methyl-5-[6-(pyrrolidin-1-ylmethyl)pyridin-3-yl]benzamide (138)

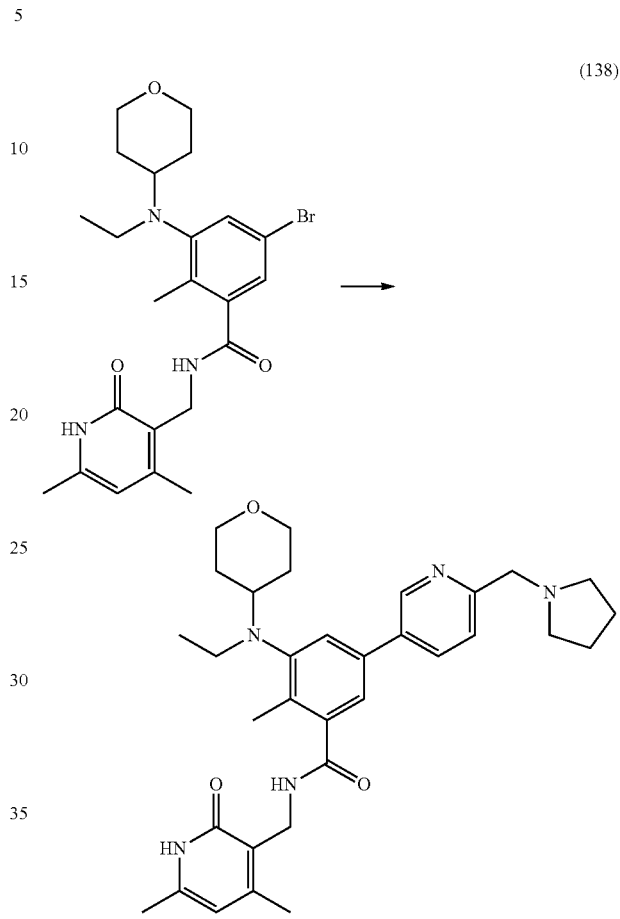

To a stirred solution of 5-bromo-N-[(4,6-dimethyl-2-oxo-1,2-dihydropyridin-3-yl)methyl]-3-[ethyl(oxan-4-yl)amino]-2-methylbenzamide (2.00 g, 4.20 mmol) and [5-(tetramethyl-1,3,2-dioxaborolan-2-yl)pyridin-2-yl]methanol (1.18 g, 5.04 mmol) in 1,4-dixoxane (40 mL) and H$_2$O (4 mL) was added Pd(PPh$_3$)$_4$ (485 mg, 0.420 mmol) and sodium carbonate (1.34 g, 12.6 mmol). The reaction mixture was stirred at 80° C. for 2 hours. Then, the reaction mixture was filtered through Celite pad. The filtrate was concentrated in vacuo, the resultant residue was purified by silica gel column chromatography (NH—SiO$_2$; heptane/ethylacetate=1/5 to ethyl acetate only) to give N-[(4,6-dimethyl-2-oxo-1,2-dihydropyridin-3-yl)methyl]-3-[ethyl(oxan-4-yl)amino]-5-[6-(hydroxymethyl)pyridin-3-yl]-2-methylbenzamide as a white solid (800 mg, 37%).

To a stirred solution of N-[(4,6-dimethyl-2-oxo-1,2-dihydropyridin-3-yl)methyl]-3-[ethyl(oxan-4-yl)amino]-5-[6-(hydroxymethyl)pyridin-3-yl]-2-methylbenzamide (200 mg, 0.396 mmol) in CH$_2$Cl$_2$ (4 mL) was added methanesulfonyl chloride (68.1 mg, 0.595 mmol) and Hunig's base (206 uL, 1.19 mmol). The reaction mixture was stirred at RT for 30 minutes. Then pyrrolidine (141 mg, 1.98 mmol) was added to the reaction mixture, and the resultant mixture was stirred at RT for 4 days. The mixture was quenched with water, and concentrated in vacuo. The residue was purified by silica gel column chromatography (NH—SiO$_2$; heptane/ethyl acetate=1/5 to ethyl acetate only) to give the titled compound as a white solid (21.0 mg, 9.5% yield). $^1$H-NMR (400 MHz, CDCl$_3$) δ ppm; 8.67 (d, J=2.0 Hz, 1H), 7.75 (dd, J=8.2, 2.0 Hz, 1H), 7.45 (d, J=8.2 Hz, 1H), 7.30 (d, J=2.0 Hz, 1H), 7.25 (d, J=2.0 Hz, 1H), 7.15 (t, J=5.7 Hz, 1H), 5.92 (s, 1H), 4.56 (d, J=5.7 Hz, 2H), 3.96 (m, 2H), 3.64 (s, 2H), 3.28-3.39 (m, 2H), 3.10 (q, J=7.0 Hz, 2H), 3.02 (m, 1H), 2.46 (m, 4H), 2.41 (s, 3H), 2.35 (s, 3H), 2.19 (s, 3H), 1.68-1.75 (m, 4H), 1.61 (m, 2H), 1.46 (m, 2H), 0.90 (t, J=7.0 Hz, 3H); MS (ESI) [M+H]$^+$ 558.6; HPLC 96.3% purity.

N-[(4,6-Dimethyl-2-oxo-1,2-dihydropyridin-3-yl)methyl]-3-[ethyl(oxan-4-yl)amino]-2-methyl-5-[6-(piperidin-1-ylmethyl)pyridin-3-yl]benzamide (139)

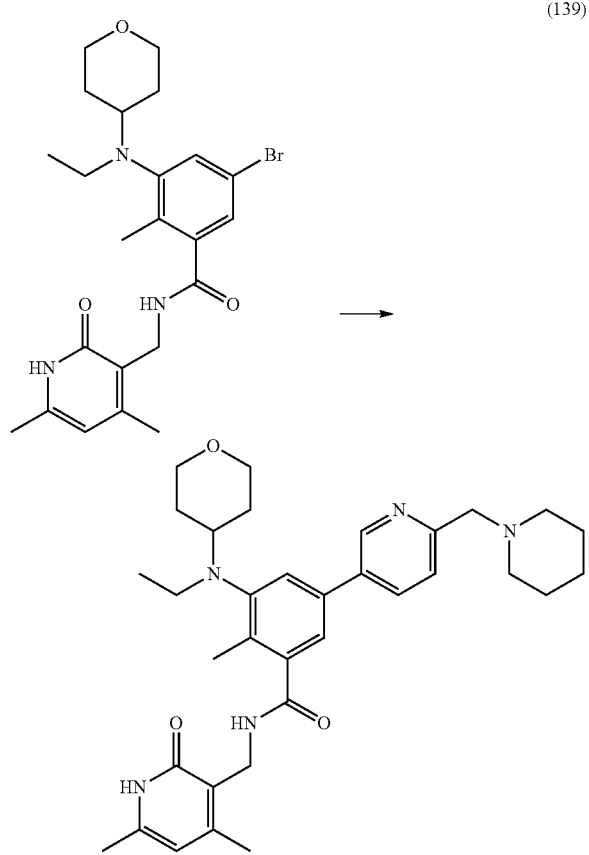

To a stirred solution of 5-bromo-N-[(4,6-dimethyl-2-oxo-1,2-dihydropyridin-3-yl)methyl]-3-[ethyl(oxan-4-yl)amino]-2-methylbenzamide (2.00 g, 4.20 mmol) and [5-(tetramethyl-1,3,2-dioxaborolan-2-yl)pyridin-2-yl]methanol (1.18 g, 5.04 mmol) in 1,4-dioxane (40 mL) and H$_2$O (4 mL) was added Pd(PPh$_3$)$_4$ (485 mg, 0.420 mmol) and sodium carbonate (1.34 g, 12.6 mmol). The reaction mixture was stirred at 80° C. for 2 hours. Then, the reaction mixture was filtered through Celite pad. The filtrate was concentrated in vacuo, the resultant residue was purified by silica gel column chromatography (NH—SiO$_2$; heptane/ethylacetate=1/5 to ethyl acetate only) to give N-[(4,6-dimethyl-2-oxo-1,2-dihydropyridin-3-yl)methyl]-3-[ethyl(oxan-4-yl)amino]-5-[6-(hydroxymethyl)pyridin-3-yl]-2-methylbenzamide as a white solid (800 mg, 37%).

To a stirred solution of N-[(4,6-dimethyl-2-oxo-1,2-dihydropyridin-3-yl)methyl]-3-[ethyl(oxan-4-yl)amino]-5-[6-(hydroxymethyl)pyridin-3-yl]-2-methylbenzamide (200 mg, 0.396 mmol) in CH$_2$Cl$_2$ (4 mL) was added methanesulfonyl chloride (54.4 mg, 0.475 mmol) and Hunig's base (206 uL, 1.19 mmol) The reaction mixture was stirred at RT for 30 minutes. Then piperidine (169 mg, 1.98 mmol) was added to the reaction mixture, and the resultant mixture was stirred at RT for 1 hour. The mixture was quenched with water, and concentrated in vacuo. The residue was purified by silica gel column chromatography (NH—SiO$_2$; heptane/ethyl acetate=1/5 to ethyl acetate/MeOH=20/1) to give the titled compound as a white solid (81.2 mg, 35.9% yield). $^1$H-NMR (400 MHz, CDCl$_3$) δ ppm; 8.64 (d, J=2.0 Hz, 1H), 7.73 (dd, J=8.2, 2.0 Hz, 1H), 7.42 (d, J=8.2 Hz, 1H), 7.28 (d, 0.1=2.0 Hz, 1H), 7.24 (d, J=2.0 Hz, 1H), 7.17-7.22 (m, 1H), 5.90 (s, 1H), 4.56 (d, J=8.0 Hz, 1H), 4.54 (d, J=8.0 Hz, 1H), 3.94 (m, 2H), 3.61 (s, 2H), 3.27-3.36 (m, 2H), 3.09 (q, J=7.0 Hz, 2H), 2.96-3.04 (m, 1H), 2.40 (m, 4H), 2.39 (s, 3H), 2.34 (s, 3H), 2.14 (s, 3H), 1.70 (m, 2H), 1.50-1.63 (m, 6H), 1.38-1.49 (m, 2H), 0.89 (t, J=7.0 Hz, 3H); MS (ESI) [M+H]$^+$ 572.5; HPLC 97.6% purity.

3-[Ethyl(oxan-4-yl)amino]-5-[6-(hydroxymethyl)pyridin-3-yl]-2-methyl-N-{[6-methyl-2-oxo-4-(2-propyl)-1,2-dihydropyridin-3-yl]methyl}benzamide

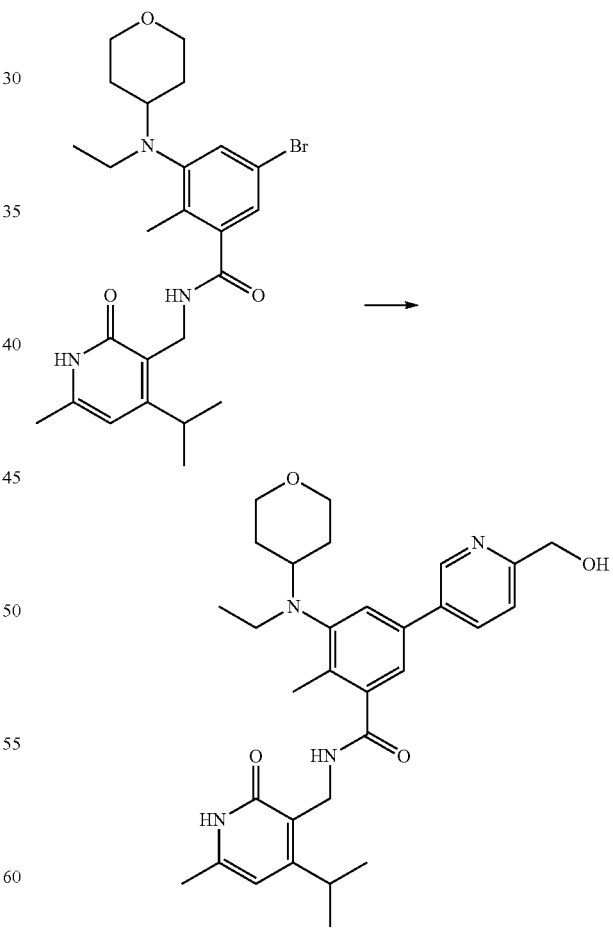

To a stirred solution of 5-bromo-3-[ethyl(oxan-4-yl)amino]-2-methyl-N-{[6-methyl-2-oxo-4-(2-propyl)-1,2-dihydropyridin-3-yl]methyl}benzamide (1.50 g, 2.97 mmol) and [5-(tetramethyl-1,3,2-dioxaborolan-2-yl)pyridin-2-yl]

methanol (1.89 g, 8.03 mmol) in 1,4-dioxane (20 mL) and water (5 mL) was added Pd(PPh$_3$)$_4$ (515 mg, 0.446 mmol) and sodium carbonate (1.14 g, 10.7 mmol). The reaction mixture was stirred at 80° C. for 2 hours. Then, [5-(tetramethyl-1,3,2-dioxaborolan-2-yl)pyridin-2-yl]methanol (800 mg, 3.40 mmol), Pd(PPh$_3$)$_4$ (200 mg, 0.173 mmol) and sodium carbonate (630 mg, 5.94 mmol) were added and stirred at 80° C. for 14 hours. After cooling to RT, ethyl acetate and water were added to the mixture. The aqueous layer was extracted with ethyl acetate. The combined organic layer was washed with water (twice) and brine. The organic layer was dried over MgSO$_4$ and filtered. The filtrate was concentrated in vacuo. The residue was purified by silica gel column chromatography (1; NH—SiO$_2$; ethyl acetate/MeOH=50/1 to 6/1, 2; SiO$_2$; ethyl acetate/MeOH=8/1 to 5/1) to give the titled compound as a white solid (457 mg, 29%). $^1$H-NMR (400 MHz, CDCl$_3$) δ ppm; 10.51 (br. s., 1H), 8.60 (s, 1H), 7.64-7.73 (m, 1H), 7.24-7.27 (m, 1H), 7.17-7.24 (m, 1H), 7.11-7.17 (m, 2H), 6.07 (s, 1H), 4.69 (br. s., 2H), 4.61 (d, J=6.2 Hz, 2H), 3.84-4.02 (m, 3H), 3.53-3.65 (m, 1H), 3.28-3.40 (m, 2H), 3.10 (q, J=7.0 Hz, 2H), 2.96-3.06 (m, 1H), 2.36 (s, 3H), 2.27 (s, 3H), 1.65-1.76 (m, 4H), 1.24 (d, J=7.0 Hz, 6H), 0.90 (t, J=7.0 Hz, 3H).

3-[Ethyl(oxan-4-yl)amino]-2-methyl-5-{6-[(4-methyl-1,4-diazepan-1-yl)methyl]pyridin-3-yl}-N-{[6-methyl-2-oxo-4-(2-propyl)-1,2-dihydropyridin-3-yl]methyl}benzamide (136)

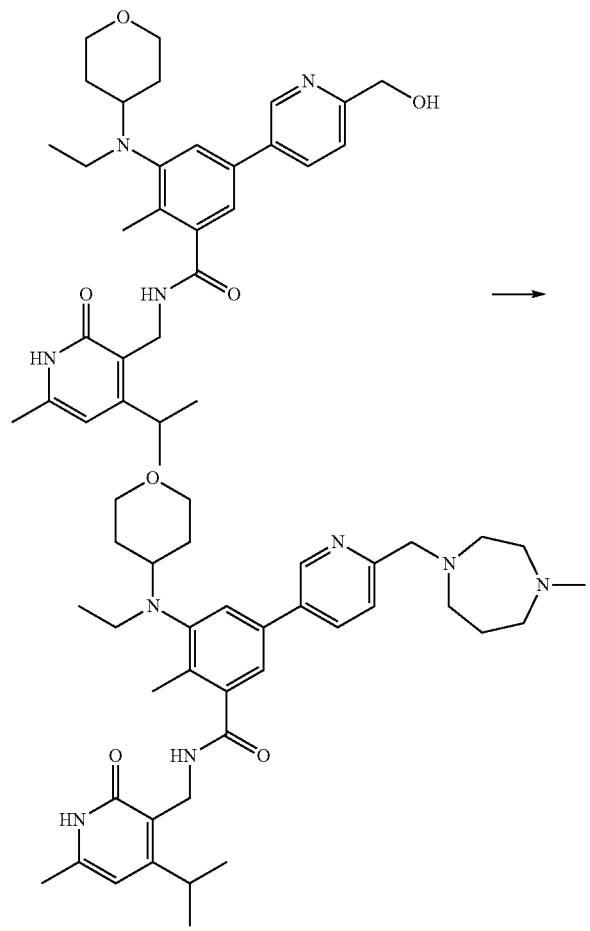

To a stirred solution of 3-[ethyl(oxan-4-yl)amino]-5-[6-(hydroxymethyl)pyridin-3-yl]-2-methyl-N-{[6-methyl-2-oxo-4-(2-propyl)-1,2-dihydropyridin-3-yl]methyl}benzamide (200 mg, 0.375 mmol) in CH$_2$Cl$_2$ (4 mL) was added methanesulfonyl chloride (51.6 mg, 0.451 mmol) and Hunig's base (195 uL, 1.13 mmol). The reaction mixture was stirred at RT for 1 hour. Then 1-methyl-homopiperazine (129 mg, 1.13 mmol) was added to the reaction mixture, and the resultant mixture was stirred at RT for 1 hour. The mixture was quenched with water, and concentrated in vacuo. The residue was purified by silica gel column chromatography (NH—SiO$_2$ ethyl acetate only to ethyl acetate/MeOH=15/1) to give the titled compound as a white solid (81.3 mg, 34.5% yield). $^1$H-NMR (400 MHz, CDCl$_3$) δ ppm; 8.65 (d, J=2.3 Hz, 1H), 7.76 (dd, J=8.2, 2.3 Hz, 1H), 7.50 (d, J=8.2 Hz, 1H), 7.29 (d, J=2.0 Hz, 1H), 7.23 (d, J=2.0 Hz, 1H), 7.12 (t, J=5.9 Hz, 1H), 6.03 (s, 1H), 4.61 (d, J=5.9 Hz, 2H), 3.95 (m, 2H), 3.81 (s, 2H), 3.54 (m, 1H), 3.27-3.37 (m, 2H), 3.10 (q, J=6.8 Hz, 2H), 3.01 (m, 1H), 2.76-2.84 (m, 4H), 2.60-2.71 (m, 4H), 2.37 (s, 3H), 2.33 (s, 3H), 2.22 (s, 3H), 1.84 (m, 2H), 1.67-1.74 (m, 4H), 1.21 (d, J=7.0 Hz, 6H), 0.85-0.90 (t, J=6.8 Hz, 3H); MS (ESI) [M+H]$^+$ 629.6; HPLC 91.7% purity.

3-[Ethyl(oxan-4-yl)amino]-5-(6-{[(3S)-3-hydroxypiperidin-1-yl]methyl}pyridin-3-yl)-2-methyl-N-{[6-methyl-2-oxo-4-(2-propyl)-1,2-dihydropyridin-3-yl]methyl}benzamide (141)

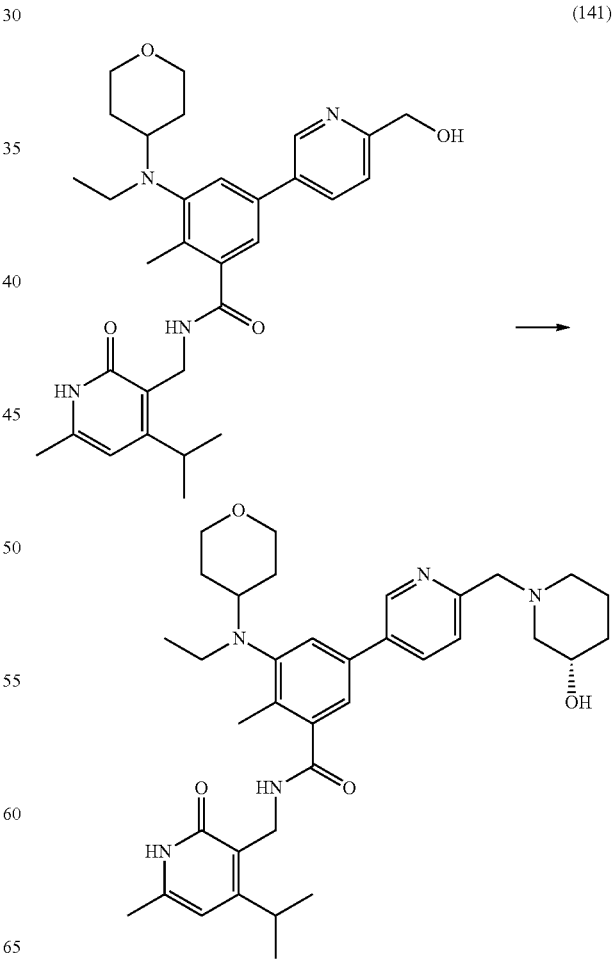

To a stirred solution of 3-[ethyl(oxan-4-yl)amino]-5-[6-(hydroxymethyl)pyridin-3-yl]-2-methyl-N-{[6-methyl-2-oxo-4-(2-propyl)-1,2-dihydropyridin-3-yl]methyl}benzamide (200 mg, 0.375 mmol) in CH$_2$Cl$_2$ (4 mL) was added methanesulfonyl chloride (51.6 mg, 0.451 mmol) and Hunig's base (195 uL, 1.13 mmol). The reaction mixture was stirred at RT for 1 hour. Then (S)-3-hydroxypiperidine HCl salt (258 mg, 1.88 mmol) was added to the reaction mixture, and the resultant mixture was stirred at RT for 1 hour. The mixture was quenched with water, and concentrated in vacuo. The residue was purified by silica gel column chromatography (NH—SiO$_2$; ethyl acetate/MeOH=20/1) to give the titled compound as a white solid (39.9 mg, 17.3% yield). $^1$H-NMR (400 MHz, CDCl$_3$) δ ppm; 8.63-8.66 (m, 1H), 7.74 (dd, J=8.2, 2.3 Hz, 1H), 7.40 (d, J=8.2 Hz, 1H), 7.28 (d, J=2.0 Hz, 1H), 7.22 (d, J=2.0 Hz, 1H), 7.17 (t, J=5.9 Hz, 1H), 6.02 (d, J=0.8 Hz, 1H), 4.61 (d, J=5.9 Hz, 2H), 3.91-3.98 (m, 2H), 3.82 (brs, 1H), 3.66 (s, 1H), 3.65 (s, 1H), 3.52 (m, 1H), 3.26-3.36 (m, 2H), 3.09 (q, J=7.0 Hz, 2H), 2.95-3.05 (m, 1H), 2.52 (m, 3H), 2.35-2.41 (m, 1H), 2.34 (s, 3H), 2.19 (s, 3H), 1.74-1.88 (m, 4H), 1.67-1.73 (m, 2H), 1.56 (m, 2H), 1.20 (d, J=7.0 Hz, 6H), 0.89 (t, J=7.0 Hz, 3H); MS (ESI) [M+H]$^+$ 616.6; HPLC 97.4% purity.

5-Bromo-2[(1-methylpiperidin-4-yl)oxy]pyridine

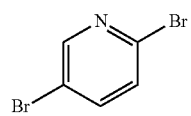

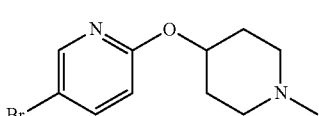

To a stirred solution of 4-hydroxy-1-methylpiperidine (175 mg, 1.52 mmol) in THF (8.0 mL) was added NaH (60%, 60.8 mg, 1.52 mmol). The reaction mixture was stirred for 10 min. 2,5-dibromopyridine (300 mg, 1.27 mmol) was added at 0° C. and stirred under reflux for 9.5 hours. After cooling to RT, ethyl acetate and water were added to the mixture. The organic layer was washed with water and brine. The organic layer was dried over MgSO$_4$ and filtered. The filtrate was concentrated in vacuo. The residue was purified by silica gel column chromatography (NH—SiO$_2$; Heptane/ethyl acetate=5/1 to 1/1) to give the titled compound as a colorless oil (309 mg, 90%). $^1$H-NMR (400 MHz, CDCl$_3$) δ ppm; 8.15 (d, J=2.6 Hz, 1H), 7.62 (dd, J=8.8, 2.6 Hz, 1H), 6.63 (d, J=8.8 Hz, 1H), 4.95-5.04 (m, 1H), 2.63-2.76 (m, 2H), 2.23-2.36 (m, 2H), 2.30 (s, 3H), 1.98-2.08 (m, 2H), 1.75-1.87 (m, 2H).

Methyl 3-[ethyl(oxan-4-yl)amino]-2-methyl-5-{6-[(1-methylpiperidin-4-yl)oxy]pyridin-3-yl}benzoate

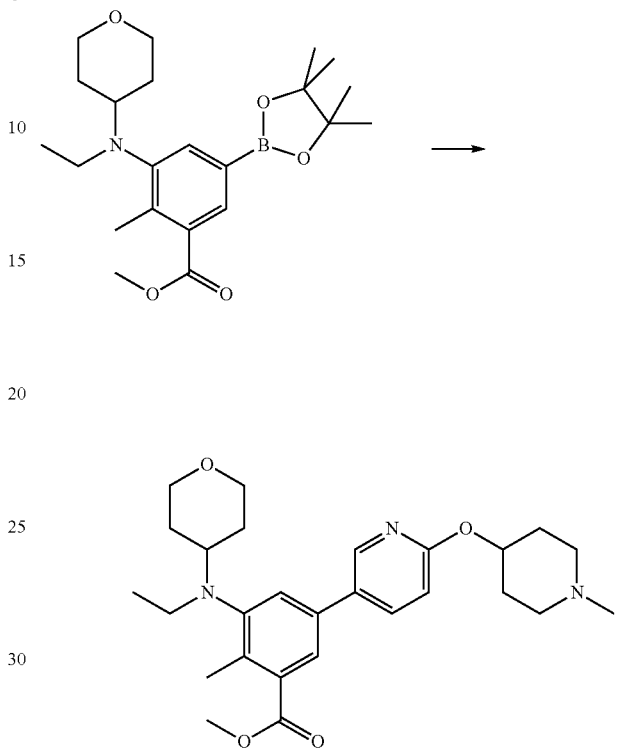

To a stirred solution of methyl 3-[ethyl(oxan-4-yl)amino]-2-methyl-5-(tetramethyl-1,3,2-dioxaborolan-2-yl)benzoate (110 mg, 0.273 mmol) and 5-bromo-2-[(1-methylpiperidin-4-yl)oxy]pyridine (96.1 mg, 0.355 mmol) in 1,4-dioxane (2.5 mL) and water (0.5 mL) was added Pd(PPh$_3$)$_4$ (47.3 mg, 0.0410 mmol) and sodium carbonate (104 mg, 0.982 mmol). The reaction mixture was stirred at 80° C. for 4 hours. After cooling to RT, ethyl acetate and water were added to the mixture. The mixture was filtered and partitioned. The aqueous layer was extracted with ethyl acetate. The combined organic layer was washed with water and brine. The organic layer was dried over MgSO$_4$ and filtered. The filtrate was concentrated in vacuo. The residue was purified by silica gel column chromatography (NH—SiO$_2$; heptane/ethyl acetate=3/1 to 1/1) to give the titled compound as a colorless oil (70.1 mg, 55%). $^1$H-NMR (400 MHz, CDCl$_3$) δ ppm; 8.33 (d, J=2.6 Hz, 1H), 7.77 (dd, J=8.6, 2.6 Hz, 1H), 7.73 (d, J=1.8 Hz, 1H), 7.41 (d, J=1.8 Hz, 1H), 6.79 (d, J=8.6 Hz, 1H), 5.05-5.15 (m, 1H), 3.92-4.02 (m, 2H), 3.92 (s, 3H), 3.29-3.38 (m, 2H), 3.11 (q, J=7.0 Hz, 2H), 2.97-3.06 (m, 1H), 2.69-2.79 (m, 2H), 2.53 (s, 3H), 2.32 (s, 3H), 2.24-2.37 (m, 2H), 2.03-2.14 (m, 2H), 1.80-1.93 (m, 2H), 1.63-1.77 (m, 4H), 0.90 (t, J=7.0 Hz, 3H).

N-[4,6-Dimethyl-2-oxo-1,2-dihydropyridin-3-yl)methyl]-3-[ethyl(oxan-4-yl)amino]-2-methyl-5-{6-[(1-methylpiperidin-4-yl)oxy]pyridin-3-yl}benzamide (133)

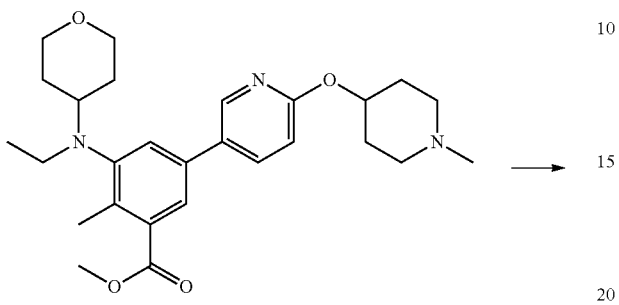

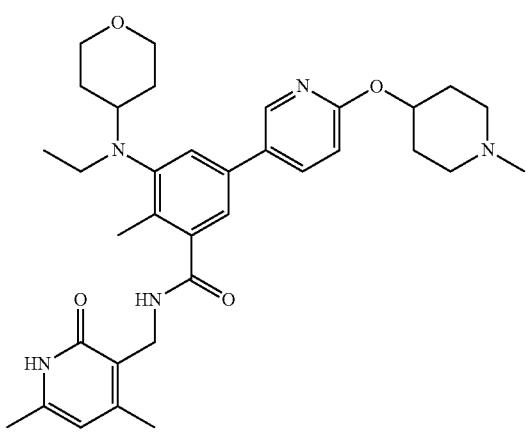

To a stirred solution of methyl 3-[ethyl(oxan-4-yl)amino]-2-methyl-5-{6-[(1-methylpiperidin-4-yl)oxy]pyridin-3-yl}benzoate (70.1 mg, 0.150 mmol) in ethanol (2 mL) was added aq. NaOH (5N, 150 uL). The reaction mixture was stirred at 90*C for 1 hour. After cooling to 0° C., the reaction mixture was neutralized with 5N—HCl. The mixture was concentrated in vacuo, and dried under vacuum pressure to give the crude product of 3-[ethyl(oxan-4-yl)amino]-2-methyl-5-{6-[(1-methylpiperidin-4-yl)oxy]pyridin-3-yl}benzoic acid.

To a stirred solution of the crude carboxylic acid and 3-(aminomethyl)-4,6-dimethyl-1,2-dihydropyridin-2-one HCl salt (42.4 mg, 0.225 mmol) in DMSO (2 mL) was added PYBOP (117 mg, 0.225 mmol) and Hunig's base (131 uL, 0.750 mmol). The reaction mixture was stirred at RT for 17 hours. The reaction mixture was quenched with water. The mixture was extracted with ethyl acetate (10 ml, twice), and the combined organic layer was washed with water (twice) and brine. The organic layer was dried over MgSO$_4$ and filtered. The filtrate was concentrated in vacuo. The residue was purified by silica gel column chromatography (NH—SiO$_2$ ethyl acetate/MeOH=50/1 to 10/1) to give the crude compound. The crude compound was suspended with ethyl acetate and heptane. The resultant precipitated solid was collected by filtration. The solid was dried under vacuum pressure to give the titled compound as a white solid (56.7 mg, 64%). $^1$H-NMR (400 MHz, CDCl$_3$) δ ppm; 10.23 (br. s., 1H), 8.27 (d, J=2.6 Hz, 1H), 7.70 (dd, J=8.4, 2.6 Hz, 1H), 7.25 (d, J=1.8 Hz, 1H), 7.20 (d, J=1.8 Hz, 1H), 7.10 (t, J=5.9 Hz, 1H), 6.75 (d, J=8.4 Hz, 1H), 5.91 (s, 1H), 5.03-5.12 (m, 1H), 4.55 (d, J=5.9 Hz, 2H), 3.92-3.99 (m, 2H), 3.27-3.37 (m, 2H), 3.09 (q, J=7.0 Hz, 2H), 2.95-3.05 (m, 1H), 2.68-2.79 (m, 2H), 2.41 (s, 3H), 2.33 (s, 3H), 2.32 (s, 3H), 2.26-2.36 (m, 2H), 2.19 (s, 3H), 2.03-2.12 (m, 2H), 1.80-1.91 (m, 2H), 1.62-1.76 (m, 4H), 0.89 (t, J=7.0 Hz, 3H); MS (ESI) [M+H]$^+$ 588.7; HPLC 97.0% purity.

1-Methylazetidin-3-ol

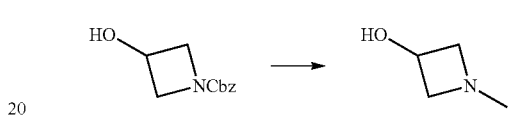

To a stirred solution of benzyl 3-hydroxyazetidine-1-carboxylate (134 mg, 0.646 mmol) in THF (5.0 mL) was added lithium aluminum hydride (75.0 mg, 0.968 mmol) at 0° C. and stirred under reflux for 2 hours. After cooling to 0° C., water (75 uL), 5N NaOH aq. (75 uL) and water (225 uL) were added to the mixture and stirred at r.t. for 30 min. The precipitated solid was removed by filtration. The filtrate was concentrated in vacuo. The residue was used for next step without further purification. (a colorless oil, 107 mg, quantitative yield). $^1$H-NMR (400 MHz, CDCl$_3$) δ ppm; 4.35-4.43 (m, 1H), 3.63-3.68 (m, 2H), 2.88-2.96 (m, 2H), 2.35 (s, 3H).

5-Bromo-2-[(1-methylazetidin-3-yl)oxy]pyridine

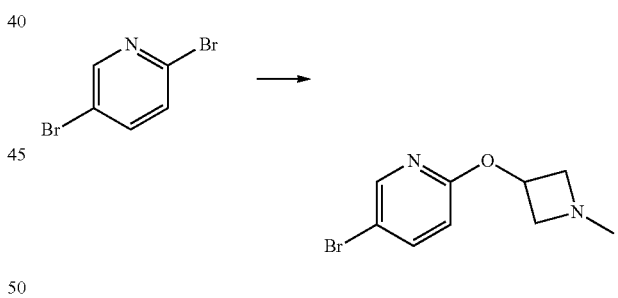

To a stirred solution of crude 1-methylazetidin-3-ol (107 mg, 1.23 mmol) in THF (5.0 mL) was added NaH (60%, 64.1 mg, 1.60 mmol). The reaction mixture was stirred for 15 min. 2,5-dibromopyridine (292 mg, 1.23 mmol) was added at 0° C. and the mixture was stirred under reflux for 17 hours. After cooling to rt, ethyl acetate and water were added to the mixture. The organic layer was washed with water and brine. The organic layer was dried over MgSO$_4$ and filtered. The filtrate was concentrated in vacuo. The residue was purified by silica gel column chromatography (NH—SiO$_2$; Heptane/ethyl acetate=6/1 to 2/1) to give the titled compound as a colorless oil (38.8 mg, 25% yield). $^1$H-NMR (400 MHz, CDCl$_3$) δ ppm; 8.14 (d, J=2.6 Hz, 1H), 7.64 (dd, J=8.8, 2.6 Hz, 1H), 6.66 (d, J=8.8 Hz, 1H), 5.12-5.20 (m, 1H), 3.71-3.87 (m, 2H), 3.02-3.17 (m, 2H), 2.40 (s, 3H).

235

Methyl 3-[ethyl(oxan-4-yl)amino]-2-methyl-5-{6-[(1-methylazetidin-3-yl)oxy]pyridin-3-yl}benzoate

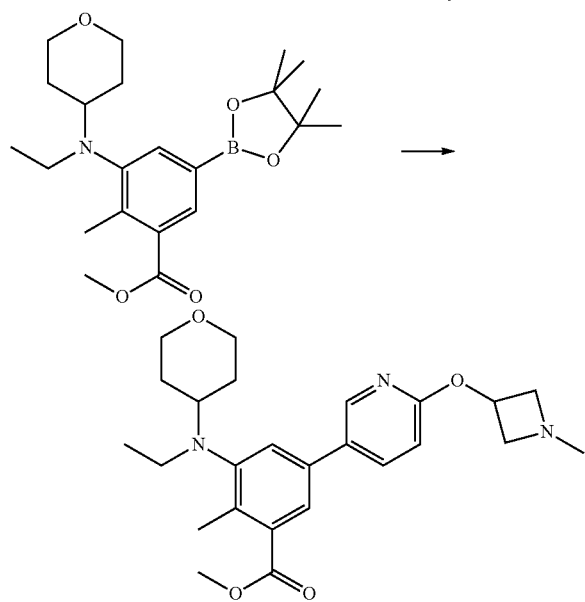

To a stirred solution of methyl 3-[ethyl(oxan-4-yl)amino]-2-methyl-5-(tetramethyl-1,3,2-dioxaborolan-2-yl)benzoate (77.2 mg, 0.192 mmol) and 5-bromo-2-[(1-methylazetidin-3-yl)oxy]pyridine (38.8 mg, 0.160 mmol) in 1,4-dioxane (2.0 mL) and water (0.5 mL) was added Pd(PPh$_3$)$_4$ (27.7 mg, 0.0240 mmol) and sodium carbonate (60.9 mg, 0.575 mmol). The reaction mixture was stirred at 80° C. for 1.5 hours. After cooling to RT, ethyl acetate and water were added to the mixture. The mixture was filtered and partitioned. The aqueous layer was extracted with ethyl acetate. The combined organic layer was washed with water and brine. The organic layer was dried over MgSO$_4$ and filtered. The filtrate was concentrated in vacuo. The residue was purified by silica gel column chromatography (NH—SiO$_2$; heptane/ethyl acetate=3/1 to 1/1) to give the titled compound as a colorless oil (33.1 mg, 47%). $^1$H-NMR (400 MHz, CDCl$_3$) δ ppm; 8.31 (dd, J=2.6, 0.7 Hz, 1H), 7.78 (dd, J=8.8, 2.6 Hz, 1H), 7.72 (d, J=2.2 Hz, 1H), 7.40 (d, J=1.8 Hz, 1H), 6.79-6.85 (m, 1H), 5.22-5.30 (m, 1H), 3.93-4.00 (m, 2H), 3.92 (s, 3H), 3.83-3.89 (m, 2H), 3.28-3.38 (m, 2H), 3.06-3.21 (m, 4H), 2.95-3.06 (m, 1H), 2.53 (s, 3H), 2.43 (s, 3H), 1.63-1.78 (m, 4H), 0.90 (t, J=7.1 Hz, 3H).

N-[(4,6-Dimethyl-2-oxo-1,2-dihydropyridin-3-yl)methyl]-3-[ethyl(oxan-4-yl)amino]-2-methyl-5-{6-[(1-methylazetidin-3-yl)oxy]pyridin-3-yl}benzamide (134)

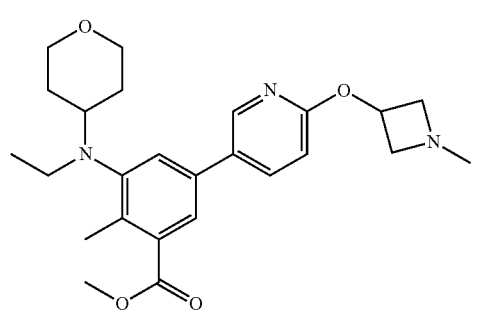

236

-continued

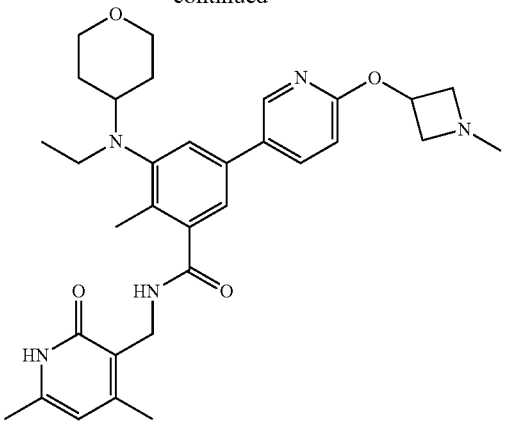

To a stirred solution of methyl 3-[ethyl(oxan-4-yl)amino]-2-methyl-5-{6-[(1-methylazetidin-3-yl)oxy]pyridin-3-yl}benzoate (33.1 mg, 0.0753 mmol) in methanol (600 uL) was added aq. NaOH (5N, 150 uL). The reaction mixture was stirred at 60*C for 1 hour. After cooling to RT, the reaction mixture was concentrated in vacuo, and dried under vacuum pressure to give the crude 3-[ethyl(oxan-4-yl)amino]-2-methyl-5-{6-[(1-methylazetidin-3-yl)oxy]pyridin-3-yl}benzoic acid sodium salt.

To a stirred solution of the crude carboxylic acid sodium salt and 3-(aminomethyl)-4,6-dimethyl-1,2-dihydropyridin-2-one HCl salt (21.3 mg, 0.113 mmol) in DMSO (300 uL) was added PYBOP (98.0 mg, 0.188 mmol) and Hunig's base (39.4 uL, 0.226 mmol). The reaction mixture was stirred at RT for 21 hours. The reaction mixture was quenched with water. The mixture was extracted with ethyl acetate (1 mL, twice), and the combined organic layer was concentrated in vacuo. The residue was purified by silica gel column chromatography (NH—SiO$_2$ ethylacetate/MeOH=10/1) to give the titled compound as a white solid (11.6 mg, 28%). $^1$H-NMR (400 MHz, CDCl$_3$) δ ppm; 8.25 (d, J=2.0 Hz, 1H), 7.71 (dd, J=8.8, 2.0 Hz, 1H), 7.25 (d, J=1.6 Hz, 1H), 7.20 (d, J=1.6 Hz, 1H), 7.18 (t, J=5.9 Hz, 1H), 6.76 (d, J=8.8 Hz, 1H), 5.93 (s, 1H), 5.17-5.28 (m, 1H), 4.56 (d, J=5.9 Hz, 2H), 3.95 (m, 2H), 3.79-3.87 (m, 2H), 3.27-3.37 (m, 2H), 3.05-3.18 (m, 4H), 2.94-3.04 (m, 1H), 2.39-2.44 (s x 2, 6H), 2.34 (s, 3H), 2.19 (s, 3H), 1.62-1.72 (m, 4H), 0.88 (t, J=7.0 Hz, 3H); MS (ESI) [M+H]$^+$ 560.6; HPLC 71.0% purity.

1-(5-Iodopyridin-2-yl)-4-methyl-1,4-diazepane

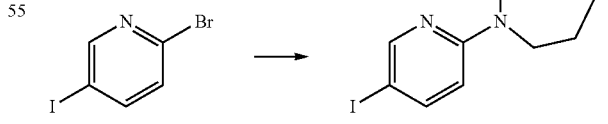

To a stirred solution of 2-bromo-5-iodopyridine (200 mg, 0.704 mmol) and 1-methyl homopiperazine (121 mg, 1.06 mmol) in NMP (3 mL) was added potassium carbonate (146 mg, 1.06 mmol). The reaction mixture was irradiated with Microwave at 150° C. for 2 hours. After completion of the reaction, ethyl acetate and water were added to the mixture. The aqueous layer was extracted with ethyl acetate, and the combined organic layer was washed with water (twice) and brine. The organic layer was dried over MgSO₄ and filtered. The filtrate was concentrated in vacuo. The residue was purified by silica gel column chromatography (NH—SiO₂; heptane/ethyl acetate=6/1 to 2/1) to give the titled compound as a white solid (187 mg, 83%). ¹H-NMR (400 MHz, CDCl₃) δ ppm; 8.23-8.28 (m, 1H), 7.60 (dd, J=9.0, 2.4 Hz, 1H), 6.33 (d, J=9.0 Hz, 1H), 3.74-3.81 (m, 2H), 3.55-3.63 (m, 2H), 2.63-2.70 (m, 2H), 2.51-2.59 (m, 2H), 2.37 (s, 3H), 1.96-2.04 (m, 2H).

Methyl 3-[ethyl(oxan-4-yl)amino]-2-methyl-5-[6-(4-methyl-1,4-diazepan-1-yl)pyridin-3-yl]benzoate

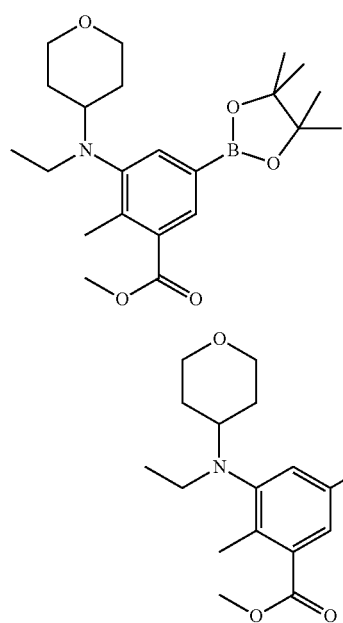

To a stirred solution of methyl 3-[ethyl(oxan-4-yl)amino]-2-methyl-5-(tetramethyl-1,3,2-dioxaborolan-2-yl)benzoate (180 mg, 0.446 mmol) and 1-(5-iodopyridin-2-yl)-4-methyl-1,4-diazepane (184 mg, 0.580 mmol) in 1,4-dioxane (4 mL) and water (1 mL) was added Pd(PPh₃)₄ (77.4 mg, 0.067 mmol) and sodium carbonate (170 mg, 1.61 mmol). The reaction mixture was stirred at 80° C. for 14.5 hours. After cooling to RT, ethyl acetate and water were added to the mixture. The aqueous layer was extracted with ethyl acetate. The combined organic layer was washed with water (twice) and brine. The organic layer was dried over MgSO₄ and filtered. The filtrate was concentrated in vacuo. The residue was purified by silica gel column chromatography (1; SiO₂; heptane/ethyl acetate=3/1 to 1/1, 2; SiO₂; heptane/ethyl acetate=1/1 to ethyl acetate/MeOH=8/1 to CHCl₃/MeOH=5/1) to give the titled compound as a colorless oil (25.5 mg, 12% yield). ¹H-NMR (400 MHz, CDCl₃) δ ppm; 8.38 (d, J=2.4 Hz, 1H), 7.72 (d, J=1.8 Hz, 1H), 7.68 (dd, J=8.8, 2.4 Hz, 1H), 7.41 (d, J=1.8 Hz, 1H), 6.56 (d, J=8.8 Hz, 1H), 3.86-4.01 (m, 4H), 3.92 (s, 3H), 3.64-3.68 (m, 2H), 3.29-3.38 (m, 2H), 3.10 (q, J=7.0 Hz, 2H), 2.96-3.06 (m, 1H), 2.75-2.84 (m, 2H), 2.60-2.70 (m, 2H), 2.51 (s, 3H), 2.43 (s, 3H), 2.05-2.17 (m, 2H), 1.61-1.80 (m, 4H), 0.90 ppm (t, J=7.0 Hz, 3H).

N-[(4,6-Dimethyl-2-oxo-1,2-dihydropyridin-3-yl)methyl]-3-[ethyl(oxan-4-yl)amino]-2-methyl-5-[6-(4-methyl-1,4-diazepan-1-yl)pyridin-3-yl]benzamide (137)

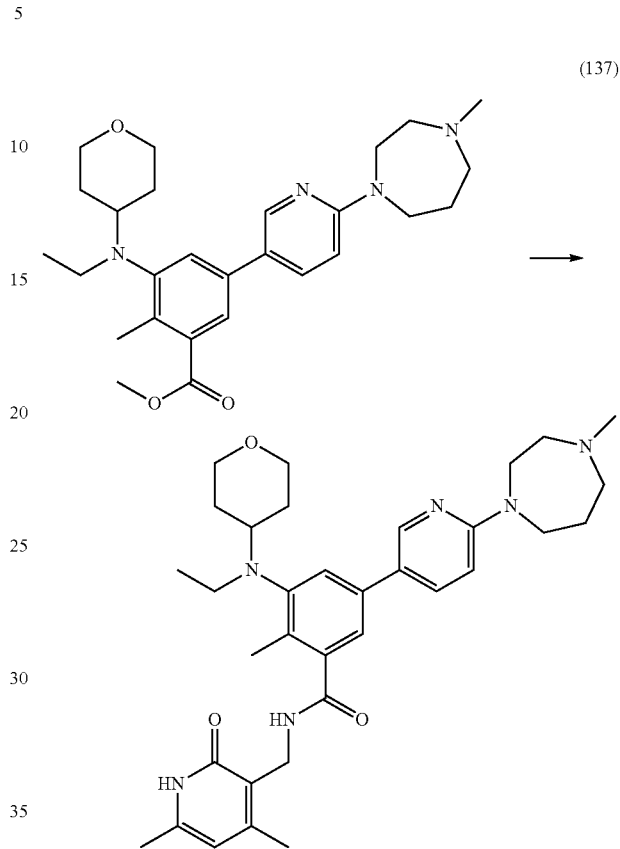

To a stirred solution of methyl 3-[ethyl(oxan-4-yl)amino]-2-methyl-5-[6-(4-methyl-1,4-diazepan-1-yl)pyridin-3-yl]benzoate (25.5 mg, 0.055 mmol) in ethanol (2 mL) was added aq. NaOH (5N, 44 uL). The reaction mixture was stirred at 90° C. for 1.5 hour. After cooling to 0° C. and neutralized with aq. 5N—HCl, the reaction mixture was concentrated in vacuo, and dried under vacuum pressure to give the crude 3-[ethyl(oxan-4-yl)amino]-2-methyl-5-[6-(4-methyl-1,4-diazepan-1-yl)pyridin-3-yl]benzoic acid sodium salt.

To a stirred solution of the crude carboxylic acid sodium salt and 3-(aminomethyl)-4,6-dimethyl-1,2-dihydropyridin-2-one HCl salt (13.4 mg, 0.071 mmol) in DMSO (2 mL) was added PYBOP (42.7 mg, 0.082 mmol) and Hunig's base (47.6 uL, 0.273 mmol). The reaction mixture was stirred at RT for 15 hours. The reaction mixture was quenched with water. The mixture was extracted with ethyl acetate (10 mL, twice), and the combined organic layer was washed with water (twice) and brine. The organic layer was dried over MgSO₄ and filtered. The filtrate was concentrated in vacuo. The residue was purified by silica gel column chromatography (NH—SiO₂ ethyl acetate/MeOH=50/1 to 10/1) to give the crude compound. The crude compound was suspended with ethyl acetate and heptane. The resultant precipitated solid was collected by filtration. The solid was dried under vacuum pressure to give the titled compound as a white solid (9.20 mg, 28%). ¹H-NMR (400 MHz, CDCl₃) δ ppm; 9.74 (br. s., 1H), 8.32 (d, J=2.6 Hz, 1H), 7.61 (dd, J=8.8, 2.6 Hz, 1H), 7.26 (br. s., 1H), 7.19 (d, J=1.8 Hz, 1H), 7.04-7.09 (m, 1H), 6.51 (d, J=8.8 Hz, 1H), 5.91 (s, 1H), 4.54 (d, J=5.9 Hz, 2H), 3.92-3.99 (m, 2H), 3.82-3.89 (m, 2H), 3.63-3.69 (m, 2H), 3.27-3.38 (m, 2H), 2.95-3.13 (m, 3H), 2.68-2.76 (m, 2H), 2.55-2.62 (m, 2H), 2.41 (s, 3H), 2.39 (s, 3H), 2.32 (s, 3H), 2.20 (s, 3H), 1.99-2.09 (m, 2H), 1.62-1.77 (m, 4H), 0.88 (t, J=7.0 Hz, 3H); MS (ESI) [M+H]$^+$ 587.7; HPLC 95.0% purity.

1-[(5-Bromopyridin-2-yl)methyl]piperidin-4-ol

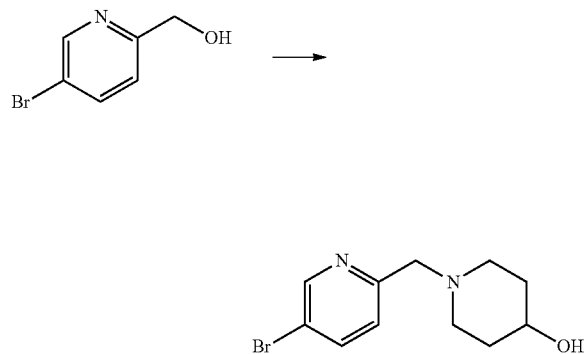

To a stirred solution of (4-bromophenyl)methanol (2.00 g, 10.6 mmol) in CH$_2$Cl$_2$ (40 mL) was added methanesulfonyl chloride (1.46 g, 12.8 mmol) and Hunig's base (5.54 mL, 31.8 mmol). The reaction mixture was stirred at RT for 1 hour. Then piperidin-4-ol (5.36 g, 53.0 mmol) was added to the reaction mixture, and the resultant mixture was stirred at RT for 16 hours. The mixture was quenched with water, and concentrated in vacuo. The residue was dissolved in ethyl acetate and water. The aqueous layer was extracted with ethyl acetate (100 mL, twice), and the combined organic layer was concentrated in vacuo. The residue was purified by silica gel column chromatography (NH—SiO$_2$; heptane/ethyl acetate=1/3) to give the titled compound as a brown oil (1.97 g, 69% yield). $^1$H-NMR (400 MHz, CDCl$_3$) δ ppm; 8.61 (d, J=2.3 Hz, 1H), 7.78 (dd, J=8.2, 2.3 Hz, 1H), 7.34 (d, J=8.2 Hz, 1H), 3.73 (m, 1H), 3.60 (s, 2H), 2.72-2.82 (m, 2H), 2.19-2.29 (m, 2H), 1.90 (m, 2H), 1.55-1.68 (m, 2H); MS (ESI) [M+H]$^+$ 271.1, 273.1.

Methyl 3-[ethyl(oxan-4-yl)amino]-5-{6-[(4-hydroxypiperidin-1-yl)methyl]pyridin-3-yl}-2-methyl-benzoate

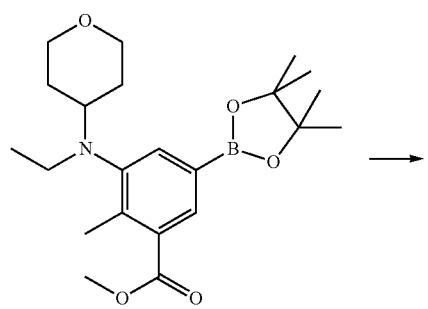

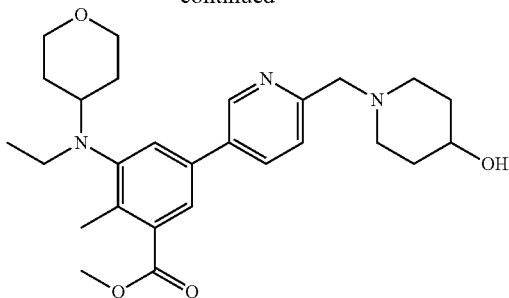

To a stirred solution of methyl 3-[ethyl(oxan-4-yl)amino]-2-methyl-5-(tetramethyl-1,3,2-dioxaborolan-2-yl)benzoate (480 mg, 1.19 mmol) and 1-[(5-bromopyridin-2-yl)methyl]piperidin-4-ol (484 mg, 1.79 mmol) in 1,4-dioxane (10 mL) and H$_2$O (2.5 mL) was added Pd(PPh$_3$)$_4$ (138 mg, 0.119 mmol) and sodium carbonate (378 mg, 3.57 mmol). The reaction mixture was stirred at 80° C. for 4 hours. Then, the reaction mixture was filtered through Celite pad. The filtrate was concentrated in vacuo, the resultant residue was purified by silica gel column chromatography (NH—SiO$_2$; ethylacetate only) to give the titled compound as a colorless oil (520 mg, 93%). $^1$H-NMR (400 MHz, CDCl$_3$) δ ppm; 8.76 (d, J=2.3 Hz, 1H), 7.84 (dd, J=8.4, 2.3 Hz, 1H), 7.69 (d, J=8.4 Hz, 1H), 7.49 (brs, 1H), 7.47 (brs, 1H), 3.98 (m, 2H), 3.94 (s, 3H), 3.74 (m, 1H), 3.72 (s, 2H), 3.36 (m, 2H), 3.14 (q, J=6.8 Hz, 2H), 2.99-3.09 (m, 1H), 2.73-2.87 (m, 2H), 2.56 (s, 3H), 2.20-2.34 (m, 2H), 1.94 (m, 2H), 1.64-1.80 (m, 6H), 0.93 (t, J=6.8 Hz, 3H); MS (ESI) [M+H]$^+$ 468.4.

3-[Ethyl(oxan-4-yl)amino]-5-{6-[(4-hydroxypiperidin-1-yl)methyl]pyridin-3-yl}-2-methyl-N-{[6-methyl-2-oxo-4-(2-propyl)-1,2-dihydropyridin-3-yl]methyl}benzamide (140)

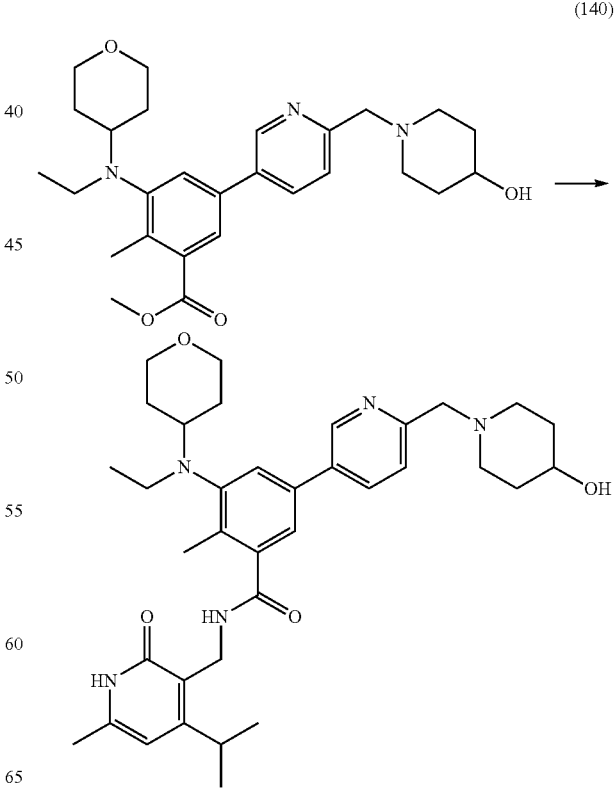

To a stirred solution of methyl 3-[ethyl(oxan-4-yl)amino]-5-{6-[(4-hydroxypiperidin-1-yl)methyl]pyridin-3-yl}-2-methylbenzoate (520 mg, 1.11 mmol) in methanol (10 mL) was added aq. NaOH (5 N, 1 mL). The reaction mixture was stirred at 60° C. for 1 hour. After cooling to rt, the reaction mixture was concentrated in vacuo, and dried under vacuum pressure to give the crude 3-[ethyl(oxan-4-yl)amino]-5-{6-[(4-hydroxypiperidin-1-yl)methyl]pyridin-3-yl}-2-methylbenzoic acid sodium salt.

To a stirred solution of the crude carboxylic acid sodium salt and 3-(aminomethyl)-6-methyl-4-(2-propyl)-1,2-dihydropyridin-2-one HCl salt (361 mg, 1.67 mmol) in DMSO (5 mL) was added PYBOP (145 mg, 2.78 mmol) and Hunig's base (580 uL, 3.33 mmol). The reaction mixture was stirred at RT for 20 hours. The reaction mixture was quenched with water. The mixture was extracted with ethyl acetate (10 mL, twice), and the combined organic layer was concentrated in vacuo. The residue was purified by silica gel column chromatography (NH—SiO$_2$ Ethyl acetate/MeOH=10/1) to give the titled compound as a white solid (250 mg, 37%). $^1$H-NMR (400 MHz, CDCl$_3$) δ ppm; 8.68 (d, J=2.0 Hz, 1H), 7.77 (dd, J=7.8, 2.0 Hz, 1H), 7.44 (d, J=7.8 Hz, 1H), 7.29 (d, J=2.0 Hz, 1H), 7.23 (d, J=2.0 Hz, 1H), 7.13 (t, J=5.9 Hz, 1H), 6.04 (s, 1H), 4.62 (d, J=5.9 Hz, 2H), 3.96 (m, 2H), 3.73 (m, 1H), 3.68 (s, 2H), 3.55 (m, 1H), 3.27-3.43 (m, 2H), 3.11 (q, J=7.0 Hz, 2H), 2.97-3.06 (m, 1H), 2.77-2.87 (m, 2H), 2.35 (s, 3H), 2.24 (s, 3H), 2.21-2.31 (m, 2H), 1.85-1.99 (m, 2H), 1.64-1.75 (m, 6H), 1.23 (s, 3H), 1.22 (s, 3H), 0.90 (t, J=7.0 Hz, 3H); MS (ESI) [M+H]$^+$ 616.7; HPLC 97.4% purity.

1-[(4-Bromo-2-fluorophenyl)methyl]piperidin-4-ol

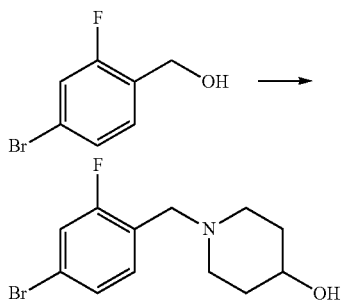

To a stirred solution of (4-bromo-2-fluorophenyl)methanol (2.00 g, 9.76 mmol) in CH$_2$Cl$_2$ (40 mL) was added methanesulfonyl chloride (1.34 g, 11.7 mmol) and Hunig's base (5.09 mL, 29.3 mmol). The reaction mixture was stirred at RT for 3 hours. Then piperidin-4-ol (4.94 g, 48.8 mmol) was added to the reaction mixture, and the resultant mixture was stirred at RT for 16 hours. The mixture was quenched with water, and concentrated in vacuo. The residue was dissolved in ethyl acetate and water. The aqueous layer was extracted with ethyl acetate (100 mL, twice), and the combined organic layer was concentrated in vacuo. The residue was purified by silica gel column chromatography (NH—SiO$_2$; heptane/ethyl acetate=1/2) to give the titled compound as a pale yellow solid (1.97 g, 70%). $^1$H-NMR (400 MHz, CDCl$_3$) δ ppm; 7.24-7.31 (m, 2H), 7.19-7.23 (m, 1H), 3.70 (m, 1H), 3.53 (m, 2H), 2.70-2.79 (m, 2H), 2.15-2.25 (m, 2H), 1.89 (m, 2H), 1.52-1.64 (m, 2H); MS (ESI) [M+H]$^+$ 288.1, 290.0.

Methyl 3-[ethyl(oxan-4-yl)amino]-5-{3-fluoro-4-[(4-hydroxypiperidin-1-yl)methyl]phenyl}-2-methylbenzoate

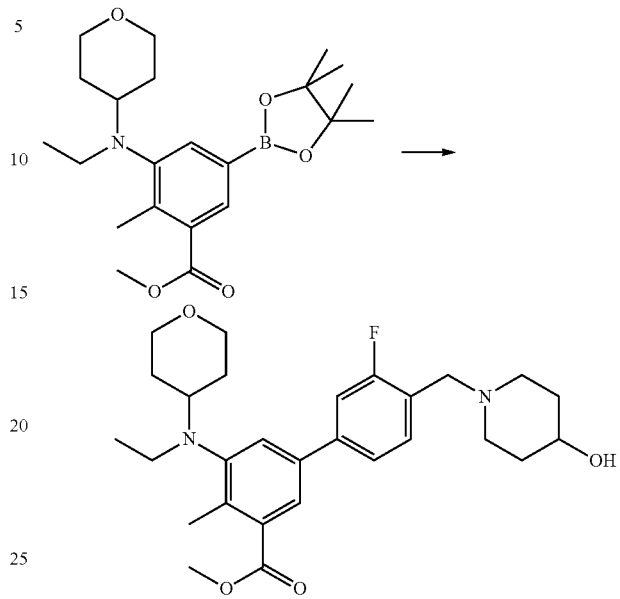

To a stirred solution of methyl 3-[ethyl(oxan-4-yl)amino]-2-methyl-5-(tetramethyl-1,3,2-dioxaborolan-2-yl)benzoate (430 mg, 1.07 mmol) and 1-[(4-bromo-2-fluorophenyl)methyl]piperidin-4-ol (461 mg, 1.60 mmol) in 1,4-dioxane (8 mL) and H$_2$O (2 mL) was added Pd(PPh$_3$)$_4$ (124 mg, 0.107 mmol) and sodium carbonate (340 mg, 3.21 mmol). The reaction mixture was stirred at 80° C. for 6 hours. Then, the reaction mixture was filtered through Celite pad. The filtrate was concentrated in vacuo, the resultant residue was purified by silica gel column chromatography (NH—SiO$_2$; ethyl acetate) to give the titled compound as a colorless oil (461 mg, 89%). $^1$H-NMR (400 MHz, CDCl$_3$) ppm; 7.42-7.48 (m, 2H), 7.28-7.37 (m, 2H), 7.19-7.24 (m, 1H), 3.98 (m, 2H), 3.93 (s, 3H), 3.71 (m, 1H), 3.63 (s, 2H), 3.29-3.40 (m, 2H), 3.13 (q, J=7.0 Hz, 2H), 2.97-3.07 (m, 1H), 2.71-2.86 (m, 2H), 2.55 (s, 3H), 2.15-2.29 (m, 2H), 1.92 (m, 4H), 1.65-1.80 (m, 4H), 0.92 (t, J=7.0 Hz, 3H); MS (ESI) [M+H]$^+$ 485.4.

N-[(4,6-Dimethyl-2-oxo-1,2-dihydropyridin-3-yl)methyl]-3-[ethyl(oxan-4-yl)amino]-5-{3-fluoro-4-[(4-hydroxypiperidin-1-yl)methyl]phenyl}-2-methylbenzamide (153)

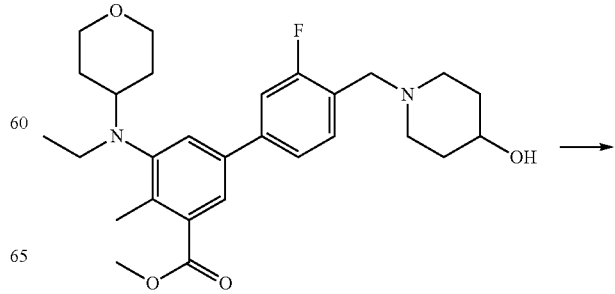

243

-continued

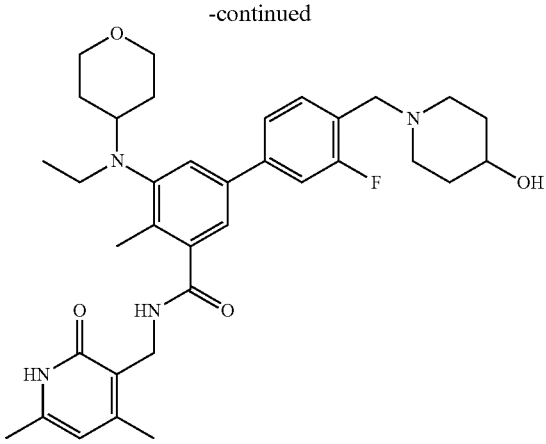

To a stirred solution of methyl 3-[ethyl(oxan-4-yl)amino]-5-{3-fluoro-4-[(4-hydroxypiperidin-1-yl)methyl]phenyl}-2-methylbenzoate (461 mg, 1.11 mmol) in methanol (10 mL) was added aq. NaOH (5 N, 1 mL). The reaction mixture was stirred at 60° C. for 1 hour. After cooling to rt, the reaction mixture was concentrated in vacuo, and dried under vacuum pressure to give the crude 3-[ethyl(oxan-4-yl)amino]-5-{3-fluoro-4-[(4-hydroxypiperidin-1-yl)methyl]phenyl}-2-methylbenzoic acid sodium salt.

To a stirred solution of the crude carboxylic acid sodium salt and 3-(aminomethyl)-4,6-dimethyl-1,2-dihydropyridin-2-one HCl salt (269 mg, 1.43 mmol) in DMSO (4 mL) was added PYBOP (1.24 mg, 2.38 mmol) and Hunig's base (497 uL, 2.85 mmol) The reaction mixture was stirred at RT for 20 hours. The reaction mixture was quenched with water. The mixture was extracted with ethyl acetate (10 mL, twice), and the combined organic layer was concentrated in vacuo. The residue was purified by silica gel column chromatography (NH—SiO$_2$ Ethyl acetate/MeOH=20/1) to give the titled compound as a white solid (208 mg, 36%). $^1$H-NMR (400 MHz, CDCl$_3$) δ ppm; 7.32-7.37 (m, 1H), 7.19-7.31 (m, 4H), 7.14 (dd, J=11.1, 1.8 Hz, 1H), 5.90 (s, 1H), 4.55 (d, J=5.9 Hz, 2H), 3.94 (m, 2H), 3.60-3.69 (m, 1H), 3.55 (s, 2H), 3.31 (m, 2H), 3.09 (q, J=7.0 Hz, 2H), 2.95-3.04 (m, 1H), 2.71-2.81 (m, 2H), 2.39 (s, 3H), 2.34 (s, 3H), 2.14-2.23 (m, 2H), 2.12 (s, 3H), 1.83 (m, 2H), 1.66-1.72 (m, 4H), 1.50-1.62 (m, 2H), 1.25 (t, J=7.0 Hz, 3H); MS (ESI) [M+H]$^+$ 605.6; HPLC 99.7% purity.

Azetidin-3-ol 2,2,2-trifluoroacetate

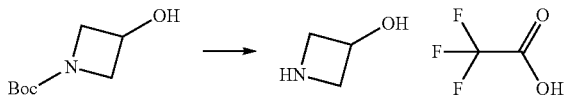

To a stirred solution of tert-butyl 3-hydroxyazetidine-1-carboxylate (3.44 g, 19.9 mmol) in DCM (10 mL) at rt was carefully added TFA (10 mL, 130 mmol). After a total of 1.5 h reaction, the solvents were removed in vacuo to give crude title compound (6.65 g, 35.5 mmol, 179% yield, contains residual TFA) as a light yellow oil. This was used for next step without further purification. $^1$H-NMR (400 MHz, DMSO-d$_6$) δ ppm: 8.6 (bs, 2H), 4.52 (m, 1H), 4.06 (m, 2H), 3.73 (m, 2H).

244

1-(5-Bromopyridin-2-yl)azetidin-3-ol

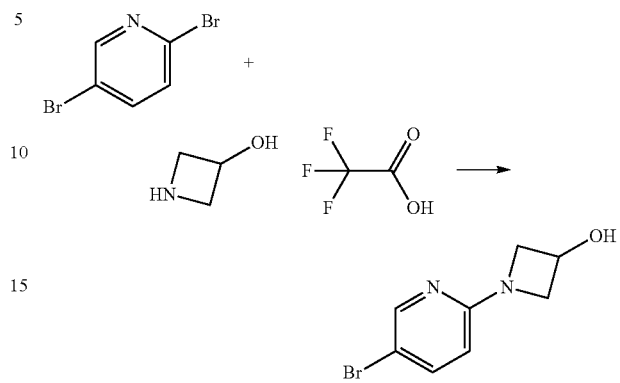

To crude azetidin-3-ol 2,2,2-trifluoroacetate (6.65 g, 19.9 mmol, containing an estimated 2.93 g of residual TFA) with magnetic stirrer was added triethylamine (6.77 mL, 48.5 mmol) portion wise over 5 min (carefully, exothermic) to give a biphasic mixture. Then acetonitrile (5 mL) was added (one layer formed) followed by 2,5-dibromopyridine (500 mg, 2.11 mmol). The reaction mixture was heated at 80° C. for 16 h. After cooling to room temperature, the reaction mixture was diluted with water (30 mL), extracted with EtOAc-Heptane (1:1, 5×30 mL). The combined extracts were washed with brine, dried over Na$_2$SO$_4$, filtered and concentrated in vacuo. Purification by silica gel column chromatography (30% to 100% EtOAc-Heptane) gave the titled compound (108 mg, 22% yield) as a colorless glassy film. $^1$H-NMR (400 MHz, C$_6$D$_6$) δ ppm: 8.25 (dd, J=2.4, 0.6 Hz, 1H), 7.12 (dd, J=8.8, 2.3 Hz, 1H), 5.54 (dd, J=8.8, 0.6 Hz, 1H), 4.06 (m, 1H), 3.77 (m, 2H), 3.43-3.67 (m, 2H); MS (ESI) [M+H]$^+$ 229.0.

2-Bromo-5-((1-methylpiperidin-4-yl)oxy)pyrazine

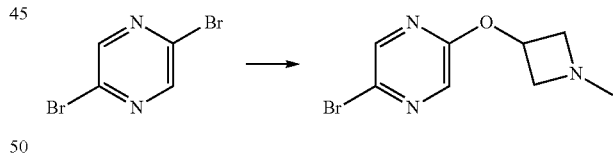

To a solution of hydrochloride salt of 1-methylazetidin-3-ol (442 mg, 3.57 mmol) in DMF (10 mL) was added NaH in mineral oil (60%, 286 mg, 7.15 mmol) at 0° C. and the resulting mixture was stirred for 0.5 h. Then dibromopyrazine (1.0 g, 4.20 mmol) was added portion wise. The reaction mixture was slowly warmed up to room temperature and stirred for 14 h. The reaction was quenched by addition of saturated aqueous solution of NH$_4$Cl and the mixture was extracted with EtOAc (3×40 mL). The combined org. phase was washed with brine, dried over Na$_2$SO$_4$, filtered and concentrated under vacuum. The crude mixture was purified by flash chromatography (SiO$_2$, 30% to 100% EtOAc:Heptane) to give the titled compound (230 mg, 26%). $^1$H-NMR (400 MHz): δ ppm 8.15 (d, J=1.2 Hz, 1H), 8.03 (d, J=1.2 Hz, 1H), 5.17 (ddd, J=11.2, 5.6, 5.6 Hz, 1H), 3.82-3.79 (m, 2H), 3.16-3.12 (m, 2H), 2.42 (s, 3H).

2-Bromo-5-((1-methylpiperidin-4-yl)oxy)pyrazine

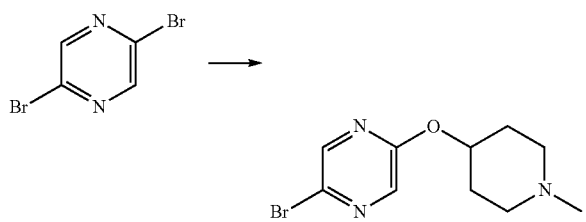

The titled compound was prepared (450 mg, 27% yield) in the same manner as described for 2-bromo-5((1-methylpiperidin-4-yl)oxy)pyrazine. ¹H-NMR (400 MHz): δ ppm 8.15 (d, J=1.2 Hz, 1H), 7.99 (d, J=1.6 Hz, 1H), 5.00 (dddd, J=8.0, 8.0, 4.0, 4.0, 1H), 2.79-2.66 (m, 2H), 2.35-2.26 (m, 2H), 2.32 (s, 3H), 2.08-2.02 (m, 2H), 1.90-1.81 (m, 2H).

5-Bromo-2-(methoxymethyl)pyridine

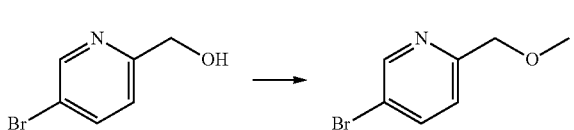

To a solution of (5-bromopyridin-2-yl)methanol (0.474 g, 2.52 mmol) in THF (30 mL, 366 mmol) and DMF (10 mL, 129 mmol) at 0° C. was added sodium hydride (60% in mineral oil, 0.202 g, 5.04 mmol) and the reaction mixture was stirred at room temperature for 1 h. After cooling the reaction mixture to 0° C., methyl iodide (0.158 mL, 2.52 mmol) was added. The reaction was stirred at room temperature for 2 h, and LCMS showed there was no more starting material was left. The reaction mixture was cooled to 0° C., quenched with MeOH and concentrated. The crude product was purified by silica gel chromatography using ethylacetate/heptane to give the titled compound (35.0 mg, 6.87% yield). ¹H-NMR (400 MHz): δ ppm 8.59 (d, J=2.4 Hz, 1H), 7.79 (dd, J=8.1, 2.4 Hz, 1H), 7.30 (d, J=7.9 Hz, 1H), 4.50 (s, 2H), 3.44 (s, 3H); MS (ESI) [M+H]⁺ 202.0.

1-Methyl-4-((5-(4,4,5,5-tetramethyl-1,3,2-dioxaborolan-2-yl)pyridin-2-yl)methyl)piperazine

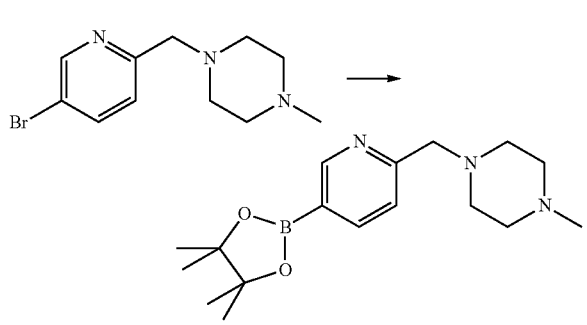

In a sealed tube was added 1((5-bromopyridin-2-yl)methyl)-4-methylpiperazine (500 mg, 1.85 mmol), bis(pinacolato)diboron (564 mg, 2.22 mmol), potassium acetate (272 mg, 2.78 mmol) and 1,4-dioxane (8 mL, 93.5 mmol). The mixture was degassed by bubbling through N₂ for 15 min. Then tricyclohexylphosphine (67.5 mg, 0.241=oft and tris(dibenzylideneacetone)dipalladium(0) (85.0 mg, 0.093 mmol) was added and degassed again for 15 min. The dark mixture was then sealed under N₂ and heated for 8 h at 80° C. MS (must use FlowInjection) showed desired mass of 318 (M+H) and no SM peak of 270/272. The reaction mixture was filtered through celite and washed with dioxane (10 mL) and then EtOAc (10 mL). The combined greenish dark yellow filtrate was concentrated and dried under vacuum overnight to give the product as a crude viscous yellow oil (1.33 g, 227% yield). HNMR is good for crude. The crude material was used directly without further purification. ¹H-NMR (400 MHz) δ ppm: 8.91 (s, 1H), 8.04 (d, J=7.6 Hz, 1H), 7.40 (d, J=7.6 Hz, 1H), 3.71 (s, 2H), 2.61 (bs, 8H), 2.36 (s, 3H), 1.36 (s, 12H); MS (ESI) [M+H]⁺ 318.3.

2-(Methoxymethyl)-5-(4,4,5,5-tetramethyl-1,3,2-dioxaborolan-2-yl)pyridine

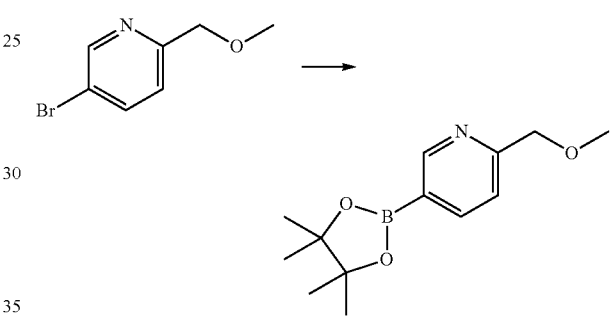

The titled compound was prepared (90.0 mg, 209% yield) in the same manner as described for 1-methyl-4-((5-(4,4,5,5-tetramethyl-1,3,2-dioxaborolan-2-yl)pyridin-2-yl)methyl)piperazine as a light yellow oil. The crude material was used directly without further purification. MS (ESI) [M+H]⁺ 250.3.

1-(5-(4,4,5,5-Tetramethyl-1,3,2-dioxaborolan-2-yl)pyridin-2-yl)azetidin-3-ol

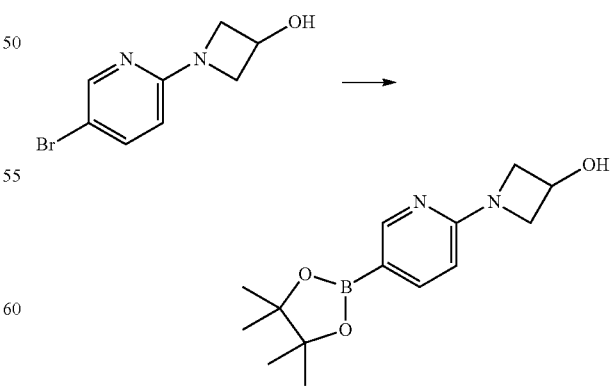

The titled compound was prepared (270 mg, 213% yield) in the same manner as described for 1-methyl-4-((5-(4,4,5,5-tetramethyl-1,3,2-dioxaborolan-2-yl)pyridin-2-yl)methyl)

piperazine as a light yellow semi-crystalline solid. The crude material was used directly without further purification. MS (ESI) [M+H]+ 277.3.

tert-Butyl 4-((5-(4,4,5,5-tetramethyl-1,3,2-dioxaborolan-2-yl)pyridin-2-yl)methyl)piperazine-1-carboxylate

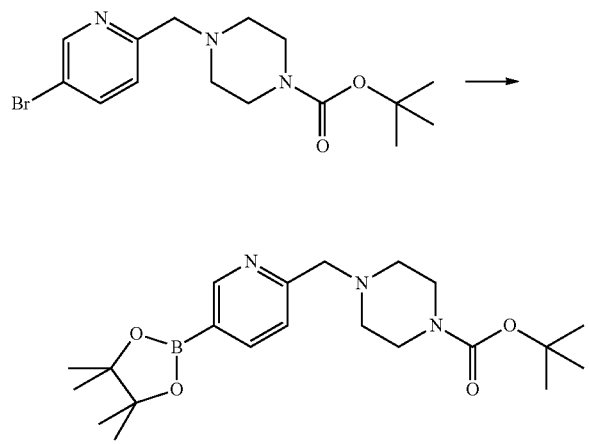

The titled compound was prepared (1.18 mg, 232% yield) in the same manner as described for 1-methyl-4-((5-(4,4,5,5-tetramethyl-1,3,2-dioxaborolan-2-yl)pyridin-2-yl)methyl) piperazine as crude oil. The crude material was used directly without further purification. MS (ESI) [M+11]+404.4.

1-(5-(4,4,5,5-Tetramethyl-1,3,2-dioxaborolan-2-yl) pyridin-2-yl)piperidin-4-ol

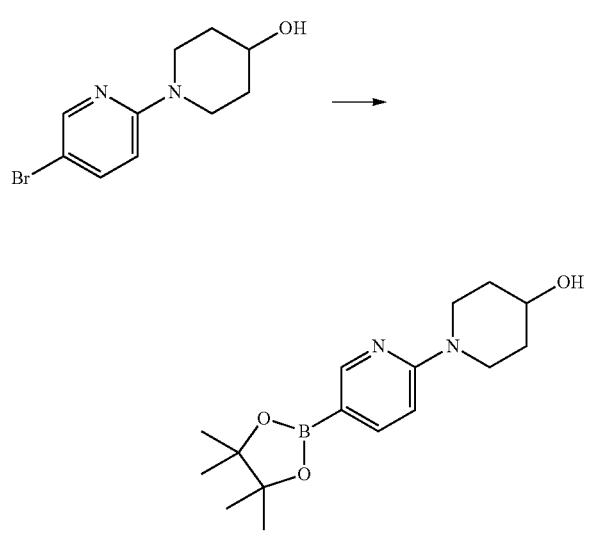

The titled compound was prepared (320 mg, 180% yield) in the same manner as described for 1-methyl-4-((5-(4,4,5,5-tetramethyl-1,3,2-dioxaborolan-2-yl)pyridin-2-yl)methyl) piperazine as a yellow-orange semi-crystalline solid. The crude material was used directly without further purification. MS (ESI) [M+H]+ 304.2.

2-(4-Methylpiperazin-1-yl)-5-(4,4,5,5-tetramethyl-1,3,2-dioxaborolan-2-yl)pyrazine

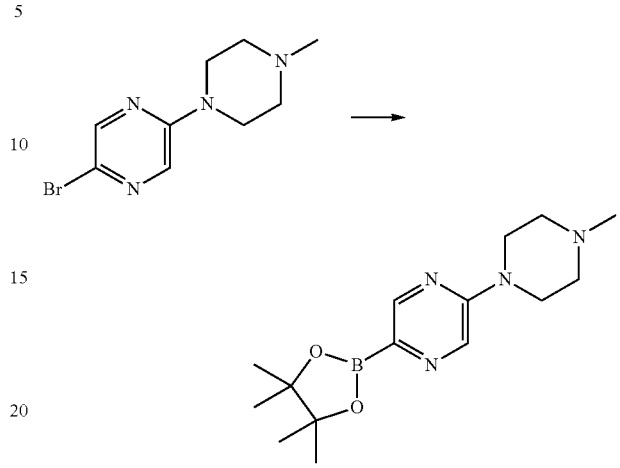

The titled compound was prepared (420 mg, 237% yield) in the same manner as described for 1-methyl-4-((5-(4,4,5,5-tetramethyl-1,3,2-dioxaborolan-2-yl)pyridin-2-yl)piperazine as a red oil. The crude material was used directly without further purification. MS (ESI) [M+H]+ 305.3.

2-((1-Methylazetidin-3-yl)oxy)-5-(4,4,5,5-tetramethyl-1,3,2-dioxaborolan-2-yl)pyrazine

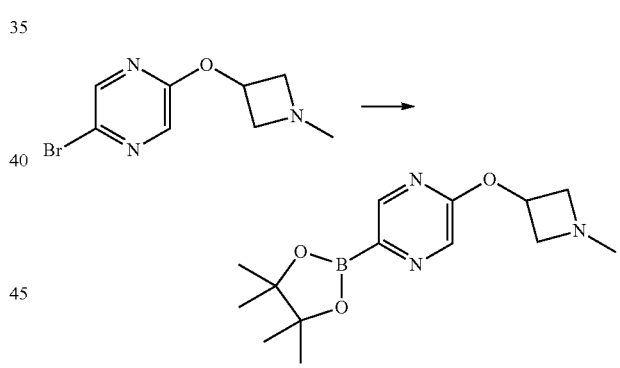

The titled compound was prepared (360 mg, 216% yield) in the same manner as described for 1-methyl-4-((5-(4,4,5,5-tetramethyl-1,3,2-dioxaborolan-2-yl)pyridin-2-yl)methyl) piperazine as a light yellow semi-crystalline solid. The crude material was used directly without further purification. MS (ESI) [M+H]+ 292.2.

2-((1-Methylpiperidin-4-yl)oxy)-5-(4,4,5,5-tetramethyl-1,3,2-dioxaborolan-2-yl)pyrazine

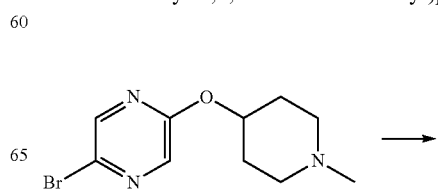

249

-continued

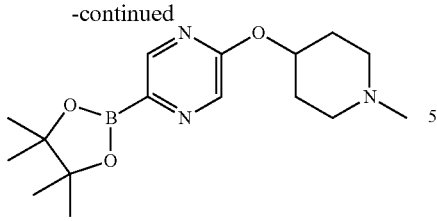

The titled compound was prepared (260 mg, 128% yield) in the same manner as described for 1-methyl-4-((5-(4,4,5,5-tetramethyl-1,3,2-dioxaborolan-2-yl)pyridin-2-yl)methyl)piperazine as a light yellow semi-crystalline solid. The crude material was used directly without further purification. MS (ESI) [M+H]$^+$ 320.2.

2-(4,4,5,5-Tetramethyl-1,3,2-dioxaborolan-2-yl)-5-(trifluoromethyl)pyrazine

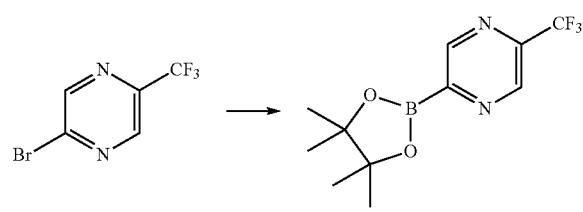 [SMILES: FC(F)(F)c1cnc(Br)cn1 ; CC1(C)OB(c2cnc(C(F)(F)F)cn2)OC1(C)C]

The titled compound was prepared (77.0 mg, 40% yield) in the same manner as described for 1-methyl-4-((5-(4,4,5,5-tetramethyl-1,3,2-dioxaborolan-2-yl)pyridin-2-yl)methyl)piperazine as a light dark oil. The crude material was used directly without further purification. MS (ESI) [M+H]$^+$ 275.1.

2,6-trans-Dimethylpiperidin-4-one

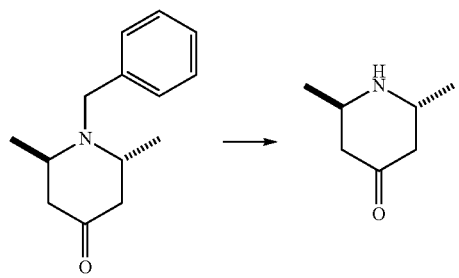

To a solution of 1-benzyl-2,6-trans-dimethylpiperidin-4-one (4.80 g, 22.1 mmol) in MeOH (100 mL) was added wet 10% Pd/C (1.0 g) under N2 atmosphere. The N$_2$ gas was displaced by H$_2$ gas and the mixture was stirred for 18 h at rt under hydrogen. The H$_2$ gas was replaced with N2 gas. The mixture was filtered through Celite, washed with MeOH and concentrated in vacuo. The crude material was used directly without further purification.

250 tert-Butyl 2,6-trans-dimethyl-4-oxopiperidine-1-carboxylate

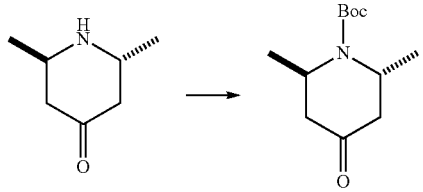

To a stirred solution of 2,6-trans-dimethylpiperidin-4-one (1.20 g, crude) and di-tert-butyl dicarbonate (10.3 g, 47.2 mmol) in DCM (15 mL) was added triethylamine (15.0 mL, 108 mmol). The reaction mixture was stirred at rt for 20 hours. The reaction mixture was concentrated in vacuo. The residue was purified by silica gel column chromatography (Heptane/EtOAc=3/1) to give the titled compound as white solid (1.40 g, 65% yield). $^1$H-NMR (400 MHz) δ ppm: 4.40 (m, 2H), 2.86 (dd, J=6.8, 18.0 Hz, 2H), 2.39 (dd, J=1.6, 17.6 Hz, 2H), 1.51 (s, 9H), 1.27 (d, J=6.4 Hz, 6H).

tert-Butyl 4-((5-bromo-3-(methoxycarbonyl)-2-methylphenyl)amino)-2,6-trans-dimethylpiperidine-1-carboxylate

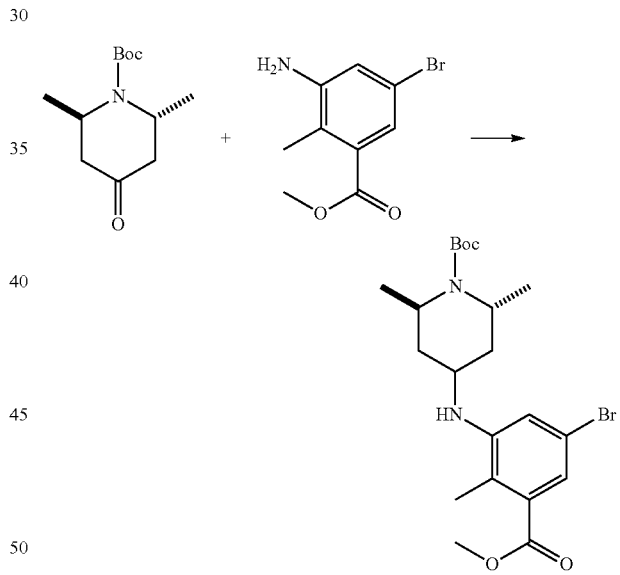

To a solution of methyl 3-amino-5-bromo-2-methylbenzoate (3.65 g, 15.0 mmol) and tert-butyl 2,6-trans-dimethyl-4-oxopiperidine-1-carboxylate (3.00 g, 13.2 mmol) in 1,2-dichloroethane (18 mL, 228 mmol) at rt was added acetic acid (6 mL, 105 mmol) and the mixture was stirred for 15 min. Then sodium triacetoxyborohydride (8.39 g, 40.0 mmol) was added and the mixture was stirred for overnight (17 h). TLC (20% E/H) showed Rf=0.35 for aniline, Rf=0.25 for ketone and Rf=0.45 for a new spot. And there is no SM ketone (limiting SM) left. The mixture was quenched by slow addition of sat. NaHCO$_3$ until the mixture was a pH about 8. The separated aq. phase was extracted with 3×EtOAc. The combined org. phase was dried (Na$_2$SO$_4$), filtered and concentrated to give a light yellow oil. The oil was purified by flash column chromatography (SiO₂, 15% EtOAc:Heptane) to give the titled compound as a semi-pure white solid (2.65 g, 41% yield). The crude material was used directly without further purification. This material was used directly without further purification. MS (ESI) [M+H]⁺ 455.3, 457.3.

tert-Butyl 4-((5-bromo-3-(methoxycarbonyl)-2-methylphenyl)(ethyl)amino)-2,6-trans-dimethylpiperidine-1-carboxylate

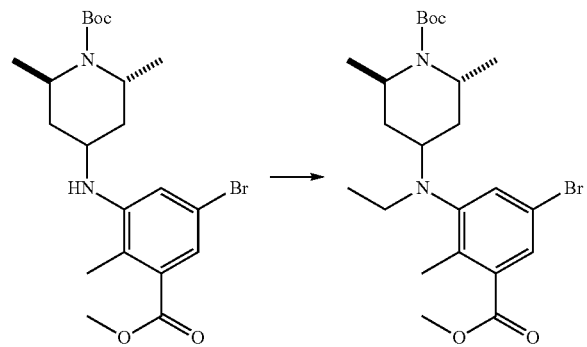 [SMILES: COC(=O)c1cc(Br)cc(NC2C[C@@H](C)N(C(=O)OC(C)(C)C)[C@H](C)C2)c1C ; CCN(c1cc(Br)cc(C(=O)OC)c1C)C1C[C@@H](C)N(C(=O)OC(C)(C)C)[C@H](C)C1]

To a solution of tert-butyl 4-((5-bromo-3-(methoxycarbonyl)-2-methylphenyl)amino)-2,6-trans-dimethylpiperidine-1-carboxylate (2.65 g, 5.81 mmol) and acetaldehyde (0.657 mL, 11.6 mmol) in 1,2-dichloroethane (15 mL, 190 mmol) at room temperature was added acetic acid (1.99 mL, 34.9 mmol) and the resulting mixture stirred for 10 min. Then sodium triacetoxyborohydride (3.70 g, 17.4 mmol) was added and stirred at room temperature for 3 h. The mixture was quenched by slow addition of saturated aqueous NaHCO₃ until the mixture was a pH 8. The aqueous phase was extracted with EtOAc. The combined organic phases were dried with Na₂SO₄, filtered and concentrated in vacuo to a light yellow oil. The oil was purified by flash column chromatography (SiO₂, 10% EtOAc:Heptane) to give the titled compound as a colorless oil (1.81 g, 64% yield). ¹H-NMR (400 MHz) δ ppm: 7.73 (d, J=2.1 Hz, 1H), 7.35 (d, J=2.1 Hz, 1H), 4.27 (m, 1H), 3.90 (s, 3H), 3.66 (m, 1H), 3.35 (m, 1H), 2.92-3.10 (m, 2H), 2.45 (s, 3H), 1.75-1.95 (m, 3H), 1.48 (m, 1H), 1.46 (s, 9H), 1.35 (d, J=6.7 Hz, 3H), 1.20 (d, J=6.7 Hz, 3H), 0.85 (t, J=7.0 Hz, 3H); MS (ESI) [M+H]⁺ 483.3, 485.4.

5-Bromo-3-((1-(tert-butoxycarbonyl)-2,6-trans-dimethylpiperidin-4-yl)(ethyl)amino)-2-methylbenzoic acid

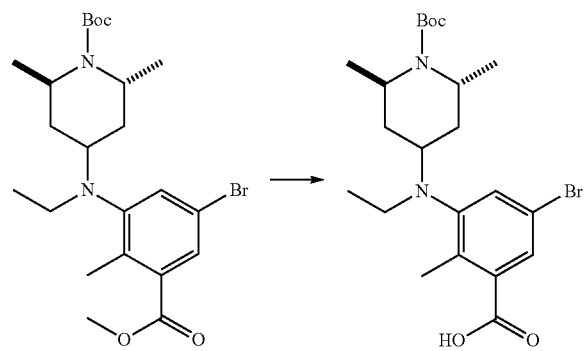 [SMILES: CCN(c1cc(Br)cc(C(=O)OC)c1C)C1C[C@@H](C)N(C(=O)OC(C)(C)C)[C@H](C)C1 ; CCN(c1cc(Br)cc(C(=O)O)c1C)C1C[C@@H](C)N(C(=O)OC(C)(C)C)[C@H](C)C1]

The titled compound was prepared (1.75 g, 100% yield) following the same procedure for the preparation of 3-[ethyl(1-methylpiperidin-4-yl)amino]-2-methyl-5-(trifluoromethyl)benzoic acid. ¹H-NMR (400 MHz) δ ppm: 7.87 (d, J=2.1 Hz, 1H), 7.37 (d, J=2.1 Hz, 1H), 4.25 (m, 1H), 3.64 (m, 1H), 3.33 (m, 1H), 2.90-3.10 (m, 2H), 2.49 (s, 3H), 1.71-1.92 (m, 3H), 1.47 (m, 1H), 1.44 (s, 9H), 1.33 (d, J=6.7 Hz, 3H), 1.17 (d, J=6.7 Hz, 3H), 0.84 (t, J=7.0 Hz, 3H); MS (ESI) [M+H]⁺ 469.3, 471.3.

tert-Butyl 4-((5-bromo-3-(((4,6-dimethyl-2-oxo-1,2-dihydropyridin-3-yl)methyl)carbamoyl)-2-methylphenyl)(ethyl)amino)-2,6-trans-dimethylpiperidine-1-carboxylate

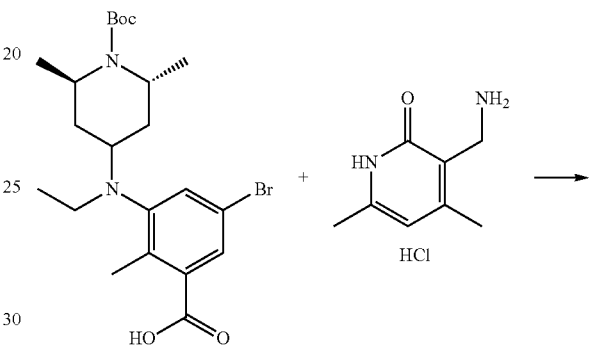

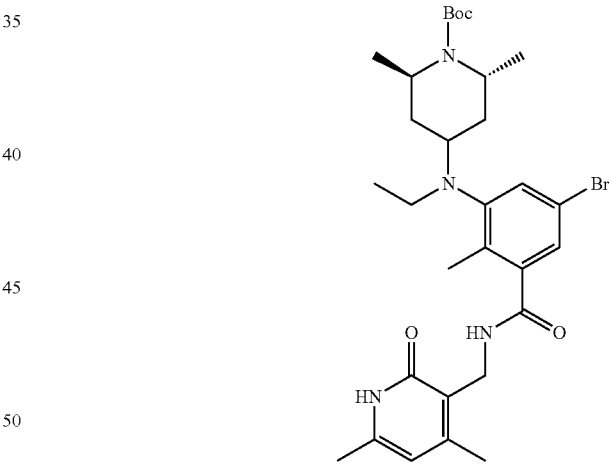

The titled compound was prepared (2.10 g, 93% yield) following the same procedure for the preparation of N-[(4,6-Dimethyl-2-oxo-1,2-dihydropyridin-3-yl)methyl]-3-[ethyl(1-methylpiperidin-4-yl)amino]-2-methyl-5-(trifluoromethyl)benzamide. ¹H-NMR (400 MHz) δ ppm: 7.18 (s, 2H), 5.95 (s, 1H), 4.50 (d, J=5.9 Hz, 2H), 4.25 (m, 1H), 3.60 (m, 1H), 3.31 (m, 1H), 2.98 (m, 2H), 2.37 (s, 3H), 2.23 (s, 6H), 1.82 (m, 2H), 1.74 (m, 1H), 1.44 (m, 1H), 1.43 (s, 9H), 1.31 (d, J=6.7 Hz, 3H), 1.15 (d, J=6.7 Hz, 3H), 0.81 (t, J=6.7 Hz, 3H); MS (ESI) [M+H]⁺ 603.5, 605. 5.

253 tert-Butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate

254 tert-Butyl 4-((3-(((4,6-dimethyl-2-oxo-1,2-dihydropyridin-3-yl)methyl)carbamoyl)-2-methyl-5-(6-(morpholinomethyl)pyridin-3-yl)phenyl)(ethyl)amino)-2,6-trans-dimethylpiperidine-1-carboxylate

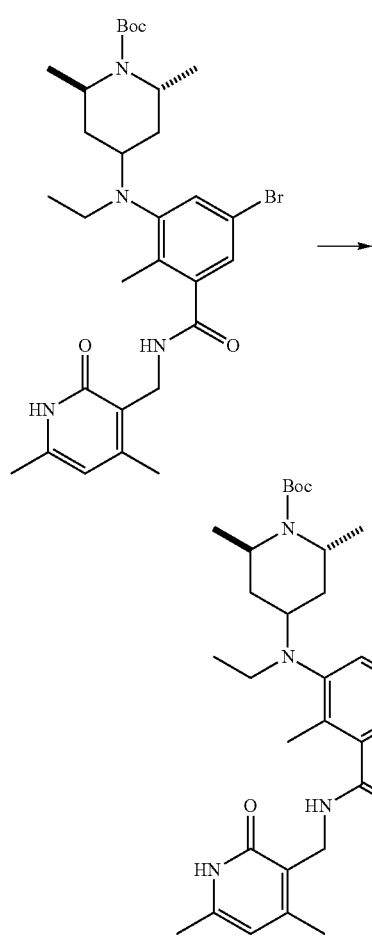

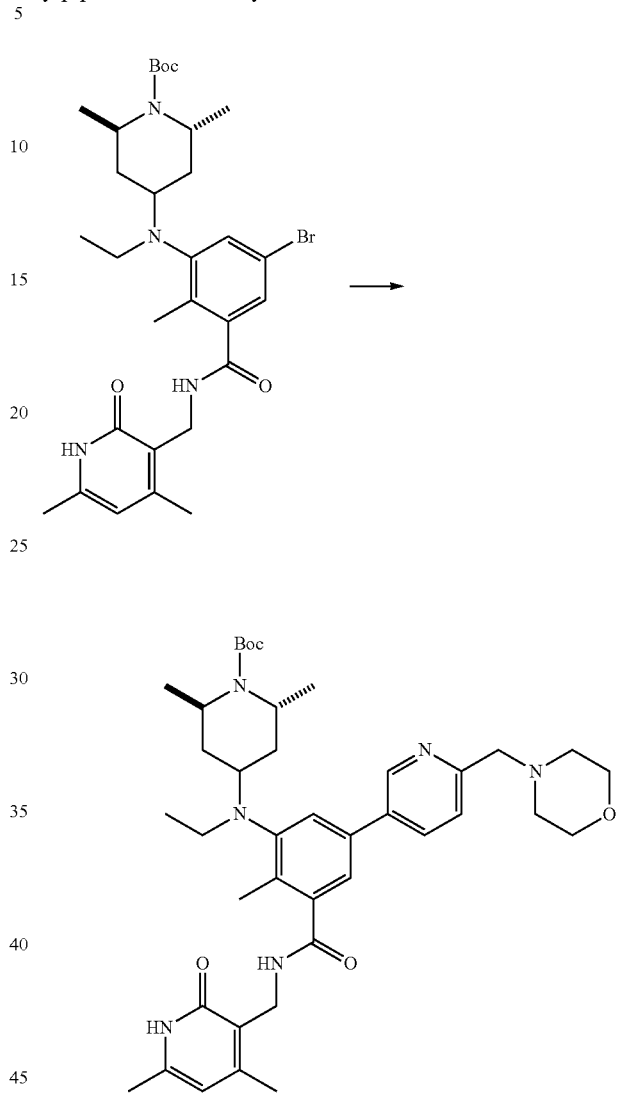

A solution of tert-butyl 4-((5-bromo-3-(((4,6-dimethyl-2-oxo-1,2-dihydropyridin-3-yl)methyl)carbamoyl)-2-methylphenyl)(ethyl)amino)-2,6-trans-dimethylpiperidine-1-carboxylate (100 mg, 0.166 mmol), 2-methoxy-5-(4,4,5,5-tetramethyl-1,3,2-dioxaborolan-2-yl)pyridine (58.4 mg, 0.249 mmol) and sodium carbonate (61.5 mg, 0.58 mmol) in 1,4-dioxane (1 mL, 11.7 mmol) and water (0.2 mL, 11.1 mmol) was degassed by bubbling $N_2$ for 15 min. Then Pd(Ph$_3$P)$_4$ (19.1 mg, 0.017 mmol) was added and degassed again for 10 min. The mixture was then sealed and heated at 100° C. for 4.5 h. MS showed reaction was done. The mixture was diluted with 5 mL water, extracted with 3×EtOAc, dried (Na$_2$SO$_4$), filtered and concentrated. The oil was purified by flash column chromatography (SiO$_2$, 10% to 100% EtOAc:Heptane) to give the titled compound (88 mg, 84% yield). $^1$H-NMR (400 MHz) δ ppm: 8.31 (d, J=2.4 Hz, 1H), 7.72 (dd, J=2.4, 8.5 Hz, 1H), 7.27 (s, 1H), 7.24 (bs, 1H), 6.80 (d, J=8.5 Hz, 1H), 5.94 (s, 1H), 4.56 (d, J=5.8 Hz, 2H), 4.29 (bs, 1H), 3.98 (s, 3H), 3.65 (m, 1H), 3.44 (m, 1H), 3.07 (m, 2H), 2.43 (s, 3H), 2.36 (s, 3H), 2.21 (s, 3H), 1.75-1.98 (m, 3H), 1.55 (m, 1H), 1.46 (s, 9H), 1.35 (d, J=6.4 Hz, 3H), 1.20 (d, J=6.7 Hz, 3H), 0.89 (bs, 3H); MS (ESI) [M+H]$^+$ 632.5.

The titled compound were obtained (116 mg, 100% yield) following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate. $^1$H-NMR (400 MHz, CD$_3$OD) δ ppm: 8.71 (d, J=2.0 Hz, 1H), 8.04 (dd, J=2.0, 8.3 Hz, 1H), 7.61 (d, J=7.8 Hz, 1H), 7.49 (d, J=1.5 Hz, 1H), 7.37 (d, J=2.0 Hz, 1H), 4.50 (s, 2H), 4.21 (m, 1H), 3.71 (m, 6H), 3.59 (m, 1H), 3.13 (m, 2H), 2.53 (m, 2H), 2.40 (s, 3H), 2.35 (s, 3H), 2.25 (s, 3H), 1.89 (m, 2H), 1.58 (m, 1H), 1.45 (s, 9H), 1.35 (d, J=6.9 Hz, 3H), 1.25 (d, J=7.2 Hz, 3H), 0.89 (t, d, J=6.9 Hz, 3H); MS (ESI) [M+H]$^+$ 701.6.

255 tert-Butyl 4-((5-(3-((1-(tert-butoxycarbonyl)-2,6-trans-dimethylpiperidin-4-yl)(ethyl)amino)-5-(((4,6-dimethyl-2-oxo-1,2-dihydropyridin-3-yl)methyl)carbamoyl)-4-methylphenyl)pyridin-2-yl)methyl)piperazine-1-carboxylate

256 tert-Butyl 4-((3-(((4,6-dimethyl-2-oxo-1,2-dihydropyridin-3-yl)methyl)carbamoyl)-2-methyl-5-(6-((4-methylpiperazin-1-yl)methyl)pyridin-3-yl)phenyl)(ethyl)amino)-2,6-trans-dimethylpiperidine-1-carboxylate

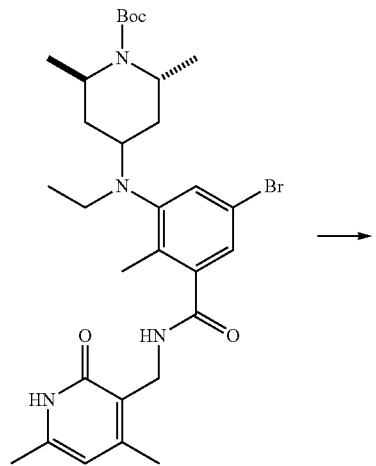

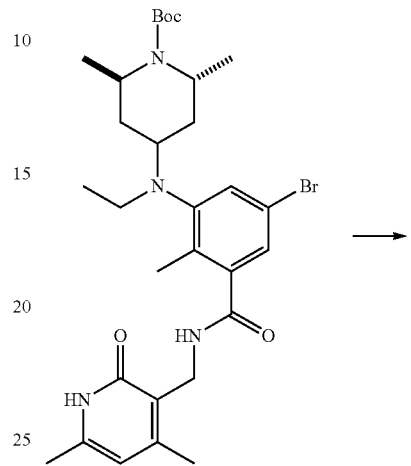

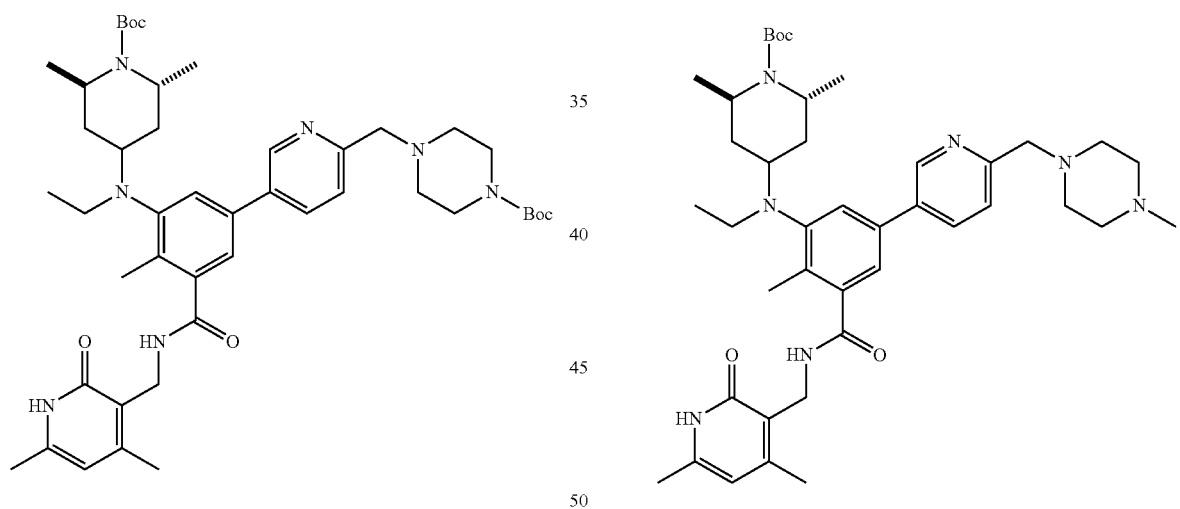

The titled compound was prepared (133 mg, 100% yield) as semi-pure compound following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate. MS (ESI) [M+H]$^+$ 800.8. The product was carried on to next step without further purification.

The titled compound was prepared (68.0 mg, 58% yield) as semi-pure compound following the similar procedure for the preparation of tert-butyl 4((3-(((4,6-dimethyl-2-oxo-1,2-dihydropyridin-3-yl)methyl)carbamoyl)-5-(6-methoxypyriclin-3-yl)-2-methylphenyl)(ethyl)amino)-2,6-trans-dimethylpiperidine-1-carboxylate. MS (ESI) [M+H]$^+$ 714.7. The product was carried on to next step without further purification.

257 tert-Butyl 4-((3-(((4,6-dimethyl-2-oxo-1,2-dihydropyridin-3-yl)methyl)carbamoyl)-2-methyl-5-(6-(4-methylpiperazin-1-yl)pyridin-3-yl)phenyl)(ethyl)amino)-2,6-trans-dimethylpiperidine-1-carboxylate

258

N-((4,6-Dimethyl-2-oxo-1,2-dihydropyridin-3-yl)methyl)-3-((2,6-trans-dimethylpiperidin-4-yl)(ethyl)amino)-5-(6-methoxypyridin-3-yl)-2-methylbenzamide

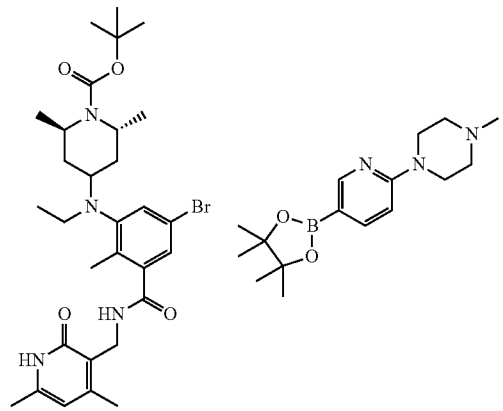

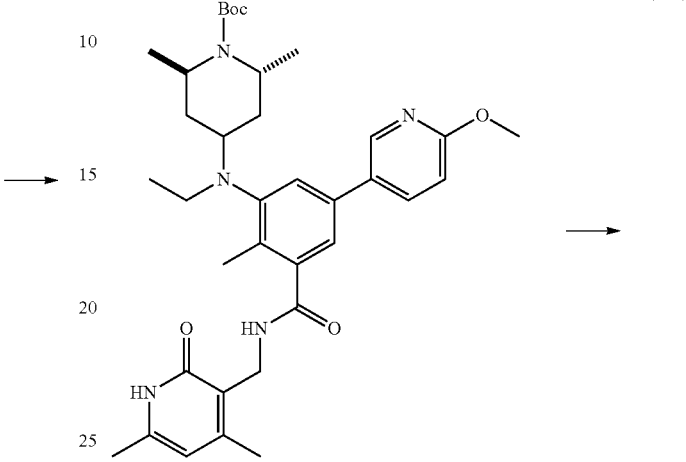

(120)

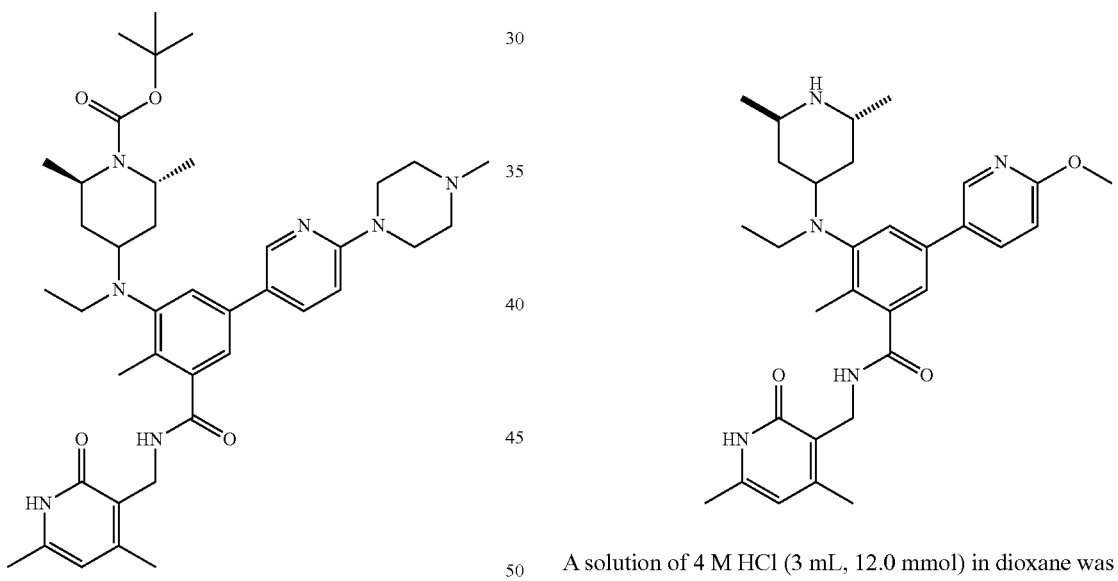

The titled compound were obtained (100 mg, 87% yield) following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate. $^1$H-NMR (500 MHz) δ ppm; 12.20 (br, s, 1H), 8.35 (d, J=2.4 Hz, 1H), 7.62 (dd, J=2.4, 8.8 Hz, 1H), 7.23 (d, J=2.0 Hz, 1H), 7.21 (d, J=1.5 Hz, 1H), 7.17 (t, J=5.9 Hz, 1H), 6.85 (d, J=8.8 Hz, 1H), 5.92 (s, 1H), 4.56 (d, J=5.9 Hz, 2H), 4.26 (m, 1H), 3.64 (m, 1H), 3.58 (t, J=4.9 Hz, 4H), 3.43 (m, 1H), 2.97-3.11 (m, 2H), 2.54 (t, J=4.9 Hz, 4H), 2.40 (s, 3H), 2.16 (s, 3H), 2.13 (s, 3H), 2.14 (s, 3H), 1.75-1.93 (m, 3H), 1.50 (m, 1H), 1.45 (s, 9H), 1.33 (d, J=6.8 Hz, 3H), 1.18 (d, J=6.8 Hz, 3H), 0.85 (t, J=7.3 Hz, 3H); MS (ESI) [M+H]$^+$ 700.7.

A solution of 4 M HCl (3 mL, 12.0 mmol) in dioxane was added to a solution of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate (88.0 mg, 0.139 mmol) in DCM (2 mL) at rt and an immediate white precipitate was observed. MS after 1 h showed reaction was done. TLC (50% E/H) showed no SM at Rf=0.3 and there is only a baseline. The mixture was concentrated and purified by reverse phase HPLC to give the titled compound (39.6 mg, 54% yield). $^1$H-NMR (400 MHz, CD$_3$OD) δ ppm; 8.30 (d, J=2.6 Hz, 1H), 7.88 (dd, J=2.3, 8.8 Hz, 1H), 7.39 (s, 1H), 7.26 (d, J=1.5 Hz, 1H), 6.84 (d, J=8.8 Hz, 1H), 6.08 (s, 1H), 4.45 (s, 2H), 3.90 (s, 3H), 3.55 (m, 1H), 3.26 (m, 1H), 3.17 (m, 3H), 2.36 (s, 3H), 2.28 (S, 3H), 2.21 (s, 3H), 1.93 (bd, J=12.3 Hz, 1H), 1.80 (m, 2H), 1.25 (m, 1H), 1.24 (d, J=7.0 Hz, 3H), 1.13 (d, J=6.1 Hz, 3H), 0.87 (t, J=7.0 Hz, 3H); MS (ESI) [M+H]$^+$ 532.4.

259
N-((4,6-Dimethyl-2-oxo-1,2-dihydropyridin-3-yl)methyl)-3-((2,6-trans-dimethylpiperidin-4-yl)(ethyl)amino)-2-methyl-5-(6-(morpholinomethyl)pyridin-3-yl)benzamide

260
N-((4,6-Dimethyl-2-oxo-1,2-dihydropyridin-3-yl)methyl)-3-((2,6-trans-dimethylpiperidin-4-yl)(ethyl)amino)-2-methyl-5-(6-(piperazin-1-ylmethyl)pyridin-3-yl)benzamide

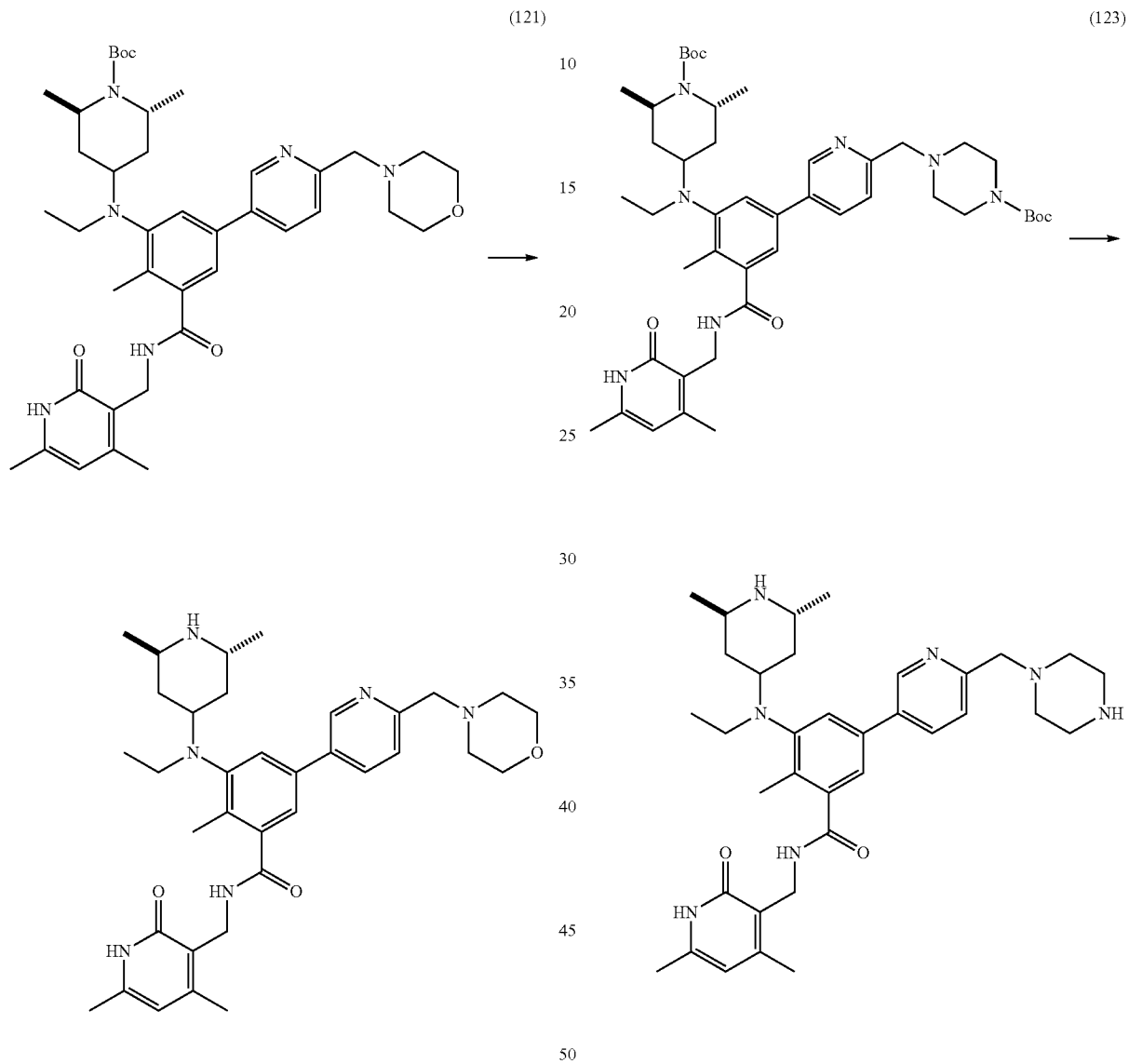

The titled compound was obtained (30.0 mg, 30% yield) following a similar procedure for the preparation of N-((4,6-dimethyl-2-oxo-1,2-dihydropyridin-3-yl)methyl)-3-((2,6-trans-dimethylpiperidin-4-yl)(ethyl)amino)-5-(6-methoxypyridin-3-yl)-2-methylbenzamide. $^1$H-NMR (400 MHz, CD$_3$OD) δ ppm; 8.67 (d, J=2.4 Hz, 1H), 8.01 (dd, J=2.4, 8.0 Hz, 1H), 7.57 (d, J=8.2 Hz, 1H), 7.46 (s, 1H), 7.33 (s, 1H), 6.08 (s, 1H), 4.46 (s, 2H), 3.67 (m, 6H), 3.55 (m, 1H), 3.31 (m, 1H), 3.14 (m, 3H), 2.49 (m, 4H), 2.36 (s, 3H), 2.30 (S, 3H), 2.21 (s, 3H), 1.90 (m Hz, 1H), 1.78 (m, 2H), 1.25 (m, 1H), 1.24 (d, J=7.0 Hz, 3H), 1.13 (d, J=6.1 Hz, 3H), 0.87 (t, J=7.0 Hz, 3H); MS (ESI) [M+H]$^+$ 601.6.

The titled compound was obtained (27.0 mg, 27% yield) following a similar procedure for the preparation of N-((4,6-dimethyl-2-oxo-1,2-dihydropyridin-3-yl)methyl)-3-((2,6-trans-dimethylpiperidin-4-yl)(ethyl)amino)-5-(6-methoxypyridin-3-yl)-2-methylbenzamide. $^1$H-NMR (400 MHz, CD$_3$OD) δ ppm; 8.67 (d, J=2.3 Hz, 1H), 8.01 (dd, J=2.3, 8.2 Hz, 1H), 7.58 (d, J=8.2 Hz, 1H), 7.45 (d, J=1.8 Hz, 1H), 7.32 (d, J=1.8 Hz, 1H), 6.08 (s, 1H), 4.46 (s, 2H), 3.66 (s, 2H), 3.47 (m, 1H), 3.25 (m, 2H), 3.13 (m, 2H), 3.05 (m, 1H), 2.84 (m, 4H), 2.49 (m, 4H), 2.36 (s, 3H), 2.30 (S, 3H), 2.21 (s, 3H), 1.95 (m Hz, 1H), 1.75 (m, 2H), 1.25 (m, 1H), 1.20 (d, J=7.0 Hz, 3H), 1.09 (d, J=6.1 Hz, 3H), 0.87 (t, J=6.7 Hz, 3H); MS (ESI) [M+H]$^+$ 600.6.

261

N-((4,6-Dimethyl-2-oxo-1,2-dihydropyridin-3-yl)methyl)-3-((2,6-trans-dimethylpiperidin-4-yl)(ethyl)amino)-2-methyl-5-(6-((4-methylpiperazin-1-yl)methyl)pyridin-3-yl)benzamide

262

N-((4,6-Dimethyl-2-oxo-1,2-dihydropyridin-3-yl)methyl)-3-((2,6-trans-dimethylpiperidin-4-yl)(ethyl)amino)-2-methyl-5-(6-(4-methylpiperazin-1-yl)pyridin-3-yl)benzamide

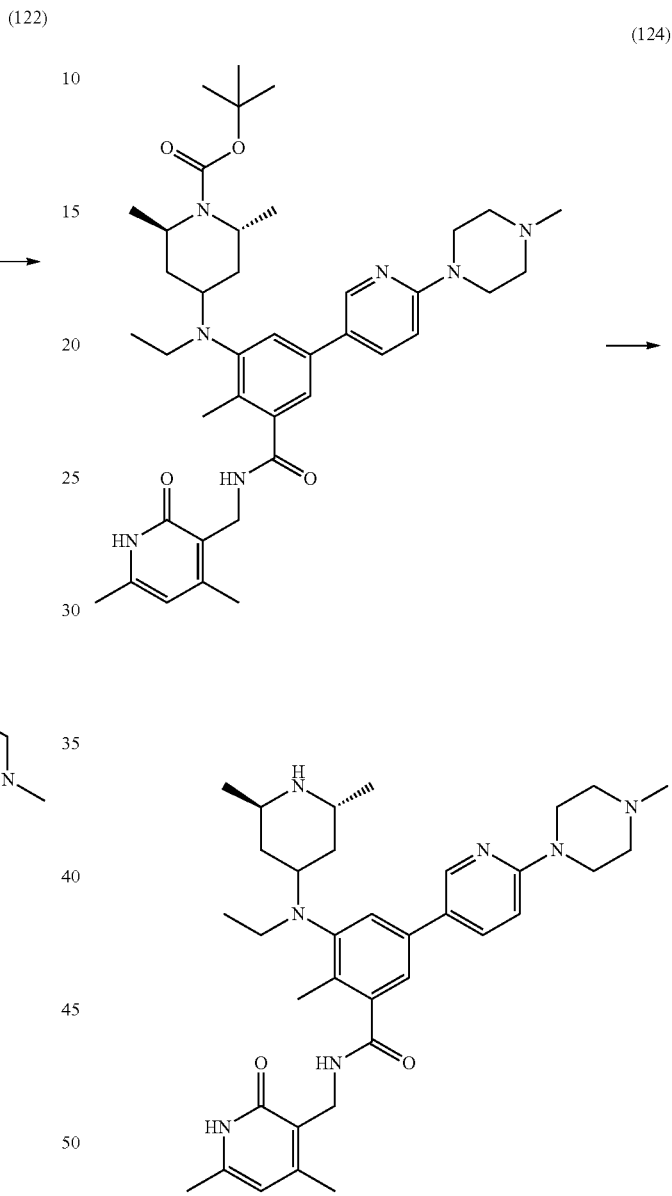

The titled compound was obtained (35.0 mg, 59% yield) following the similar procedure for the preparation of N-((4,6-dimethyl-2-oxo-1,2-dihydropyridin-3-yl)methyl)-3-((2,6-trans-dimethylpiperidin-4-yl)(ethyl)amino)-5-(6-methoxypyridin-3-yl)-2-methylbenzamide. $^1$H-NMR (400 MHz, CD$_3$OD) δ ppm; 8.66 (d, J=1.5 Hz, 1H), 8.00 (dd, J=2.1, 8.2 Hz, 1H), 7.55 (d, J=8.2 Hz, 1H), 7.44 (bs, 1H), 7.31 (bs, 1H), 6.08 (s, 1H), 4.46 (s, 2H), 3.68 (s, 2H), 3.45 (m, 1H), 3.30 (m, 2H), 3.14 (m, 2H), 2.98 (m, 1H), 2.50 (m, 7H), 2.36 (s, 3H), 2.29 (S, 3H), 2.25 (s, 3H), 2.21 (s, 3H), 1.85 (m, 1H), 1.75 (m, 2H), 1.25 (m, 1H), 1.19 (d, J=7.0 Hz, 3H), 1.05 (d, J=6.1 Hz, 3H), 0.86 (t, J=6.7 Hz, 3H); MS (ESI) [M+H]$^+$ 614.6.

The titled compound was obtained (106 mg, 54% yield) following the similar procedure for the preparation of N-((4,6-dimethyl-2-oxo-1,2-dihydropyridin-3-yl)methyl)-3-((2,6-trans-dimethylpiperidin-4-yl)(ethyl)amino)-5-(6-methoxypyridin-3-yl)-2-methylbenzamide. $^1$H-NMR (500 MHz, CD$_3$OD) δ ppm; 8.34 (d, J=2.5 Hz, 1H), 7.81 (J=2.5, 9.3 Hz, 1H), 7.40 (d, J=1.5 Hz, 1H), 7.26 (d, J=1.5 Hz, 1H), 6.90 (d, J=9.3 Hz, 1H), 6.12 (s, 1H), 4.50 (s, 2H), 3.60 (m, 4H), 3.49 (m, 1H), 3.26 (m, 1H), 3.15 (m, 2H), 3.06 (m, 1H), 2.57 (m, 4H), 2.40 (s, 3H), 2.36 (s, 3H), 2.31 (s, 3H), 2.24 (s, 3H), 1.90 (m, 1H), 1.78 (m, 2H), 1.28 (m, 1H), 1.23 (d, J=6.9 Hz, 3H), 1.12 (d, J=6.4 Hz, 3H), 0.90 (t, J=6.9 Hz, 3H); MS (ESI) [M+H]$^+$ 600.5.

263

3-((4-trans-Aminocyclohexyl)(ethyl)amino)-5-bromo-N-((4,6-dimethyl-2-oxo-1,2-dihydropyridin-3-yl)methyl)-2-methylbenzamide

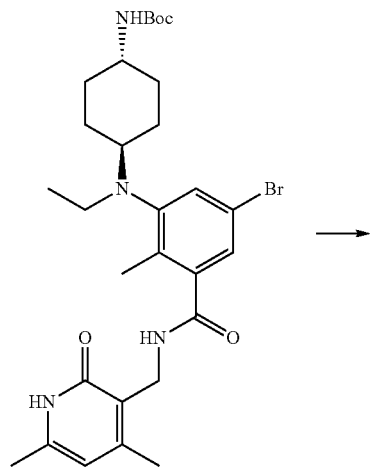

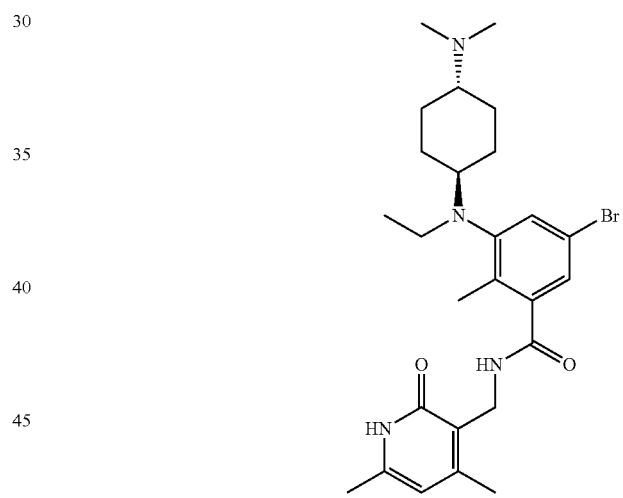

The titled compound was prepared following a similar procedures described for 3-((2,6-trans-dimethylpiperidin-4-yl)(ethyl)amino)-5-fluoro-N-((5-fluoro-1,4,6-trimethyl-2-oxo-1,2-dihydropyridin-3-yl)methyl)-2-methylbenzamide hydrochloride followed by silica gel chromatography purification (10% 7N NH$_3$/MeOH in DCM) (440 mg, 100%). $^1$H-NMR (500 MHz, CD$_3$OD) δ ppm 7.30 (d, J=2.0 Hz, 1H), 7.17 (d, J=2.0 Hz, 1H), 6.10 (s, 1H), 4.46 (s, 2H), 3.07 (q, J=7.0 Hz, 2H), 2.75-2.68 (m, 1H), 2.60-2.53 (m, 1H), 2.37 (s, 3H), 2.25 (s, 3H), 2.22 (s, 3H), 1.90-1.84 (m, 2H), 1.84-1.78 (m, 2H), 1.50-1.41 (m, 2H), 1.14-1.05 (m, 2H), 0.85 (t, J=7.0 Hz, 3H); MS (ESI) [M+H]$^+$ 489.3.

264

5-Bromo-N-(0,6-dimethyl-2-oxo-1,2-dihydropyridin-3-yl)methyl)-3-((4-trans-(dimethylamino)cyclohexyl)(ethyl)amino)-2-methylbenzamide

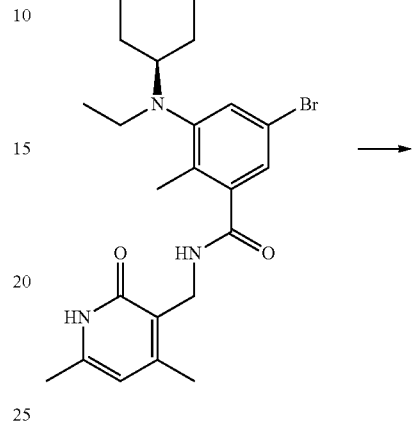

The titled compound was prepared following a similar procedures described for the preparation of methyl 3-[ethyl (1-methylpiperidin-4-yl)amino]-2-methyl-5-(trifluoromethyl)benzoate followed by silica gel chromatography purification (10% 7N NH$_3$/MeOH in DCM) (335 mg, 72%). $^1$H-NMR (500 MHz, CD$_3$OD) δ ppm 7.31 (d, J=2.0 Hz, 1a), 7.17 (D, J=2.0 Hz, 1H), 6.11 (s, 1H), 4.46 (s, 2H), 3.08 (q, J=7.0 Hz, 2H), 2.75-2.67 (m, 1H), 2.38 (s, 3H), 2.28 (s, 6H), 2.25 (s, 3H), 2.29-2.23 (m, 1H), 2.21 (s, 3H), 1.98-1.85 (m, 4H), 1.49-1.39 (m, 2H), 1.28-1.19 (m, 2H), 0.86 (t, J=7.0 Hz, 3H); MS (ESI) [M+H]$^+$ 519.4.

265

5-Bromo-3-(ethyl(tetrahydro-2H-pyran-4-yl)amino)-N-((4-isopropyl-6-methyl-2-oxo-1,2-dihydropyridin-3-yl)methyl)-2-methylbenzamide

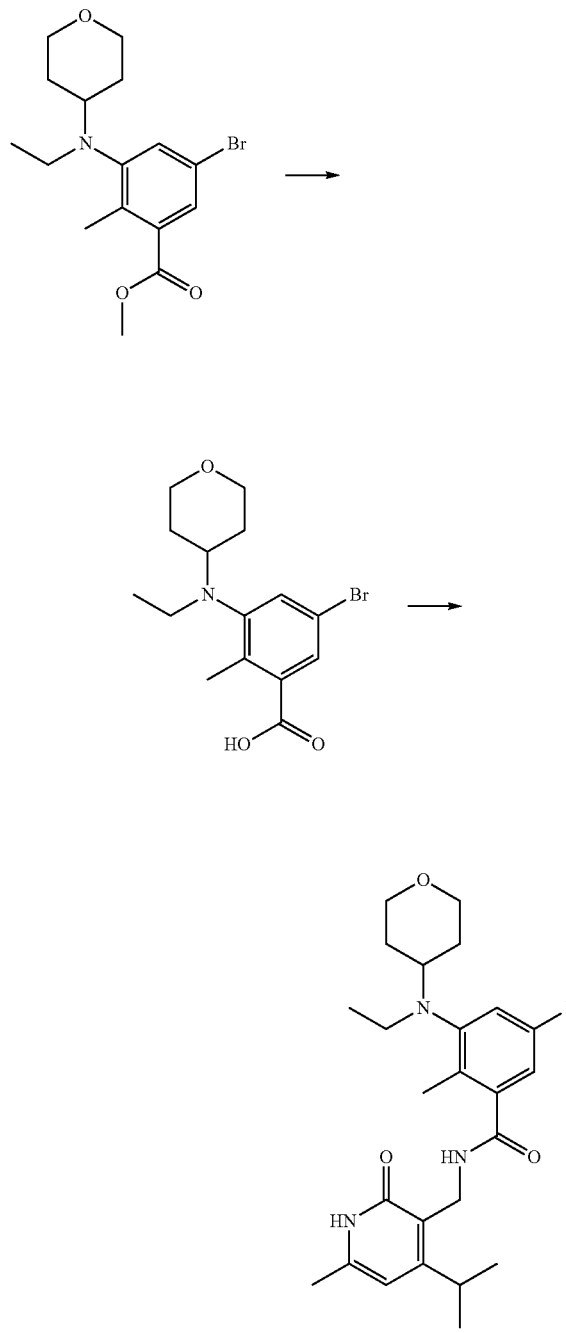

The titled compound was prepared (361 mg, 31% yield) following the same procedures for the preparation of 5-bromo-N-((4,6-dimethyl-2-oxo-1,2-dihydropyridin-3-yl)methyl)-3-(ethyl(tetrahydro-2H-pyran-4-yl)amino)-2-methylbenzamide. $^1$H-NMR (400 MHz) δ ppm; 13.8 (br, s, 1H), 7.20 (s, 1H), 7.08 (t, J=5.4 Hz, 1H), 5.09 (s, 1H), 4.60 (d, J=5.9 Hz, 2H), 3.96 (br, d, J=11.2 Hz, 2H), 3.52 (m. 1H), 3.32 (m, 2H), 3.06 (m, 2H), 2.96 (m, 1H), 2.30 (s, 3H), 2.27 (s, 3H), 1.64-1.72 (m, 4H), 1.22 (d, J=6.4 Hz, 6H), 0.88 (t, J=7.3 Hz, 3H)); MS (ESI) [M+H]$^+$ 504.4.

266

N-((4,6-Dimethyl-2-oxo-1,2-dihydropyridin-3-yl)methyl)-3-((4-trans-(dimethylamino)cyclohexyl)(ethyl)amino)-2-methyl-5-(6-(morpholinomethyl)pyridin-3-yl)benzamide (145)

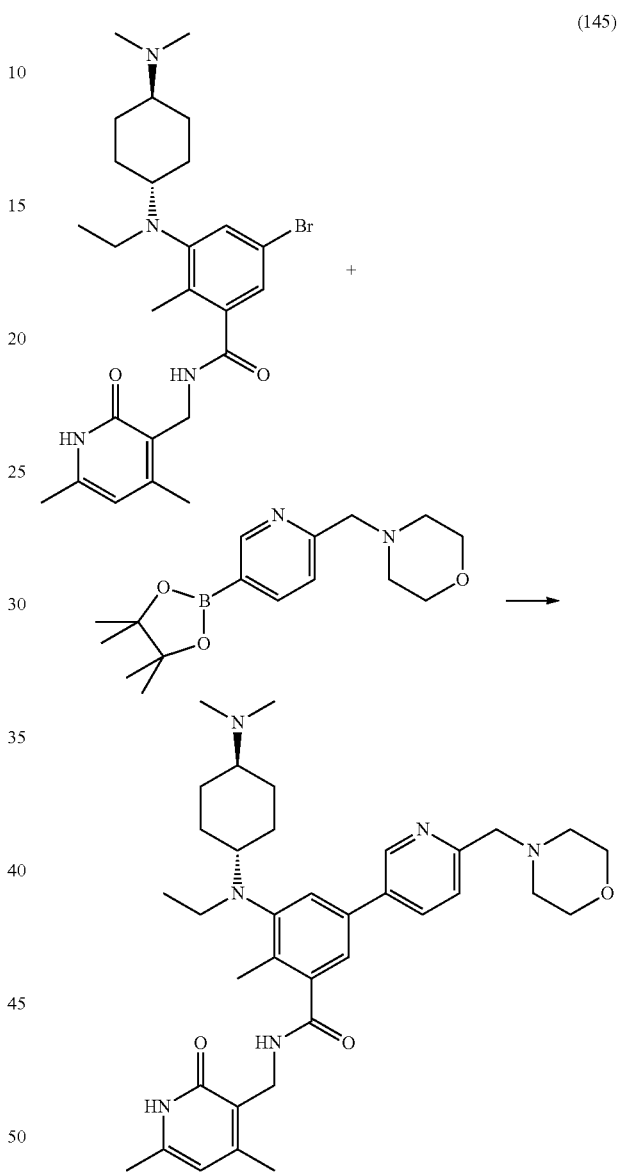

The titled compound was obtained (64.0 mg, 67% yield) as a light yellow solid following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate followed by reverse phase HPLC/MS purification. $^1$H-NMR (500 MHz, CD$_3$OD) δ ppm 8.68 (d, J=2.0 Hz, 1H), 8.03 (dd, J=8.0 Hz, J=2.0 Hz, 1H), 7.60 (d, J=8.0 Hz, 1H), 7.46 (d, J=2.0 Hz, 1H), 7.34 (d, J=2.0 Hz, 1H), 6.10 (s, 1H), 4.50 (s, 2H), 3.71 (m, 4H), 3.68 (s, 2H), 3.17 (q, J=7.0 Hz, 2H), 2.82-2.75 (m, 1H), 2.54-2.50 (m, 4H), 2.39 (s, 3H), 2.34 (s, 3H), 2.24 (s, 9H), 2.23-2.16 (m, 1H), 1.98-1.90 (m, 4H), 1.51-1.41 (m, 2H), 1.27-1.17 (m, 2H), 0.90 (t, J=7.0 HZ, 3H); MS (ESI) [M+H]$^+$ 615.6.

267

N-((4,6-Dimethyl-2-oxo-1,2-dihydropyridin-3-yl)methyl)-3-((4-trans-(dimethylamino)cyclohexyl)(ethyl)amino)-5-(6-(methoxymethyl)pyridin-3-yl)-2-methylbenzamide

268

N-((4,6-Dimethyl-2-oxo-1,2-dihydropyridin-3-yl)methyl)-3-((4-trans-(dimethylamino)cyclohexyl)(ethyl)amino)-5-(6-(3-hydroxyazetidin-1-yl)pyridin-3-yl)-2-methylbenzamide

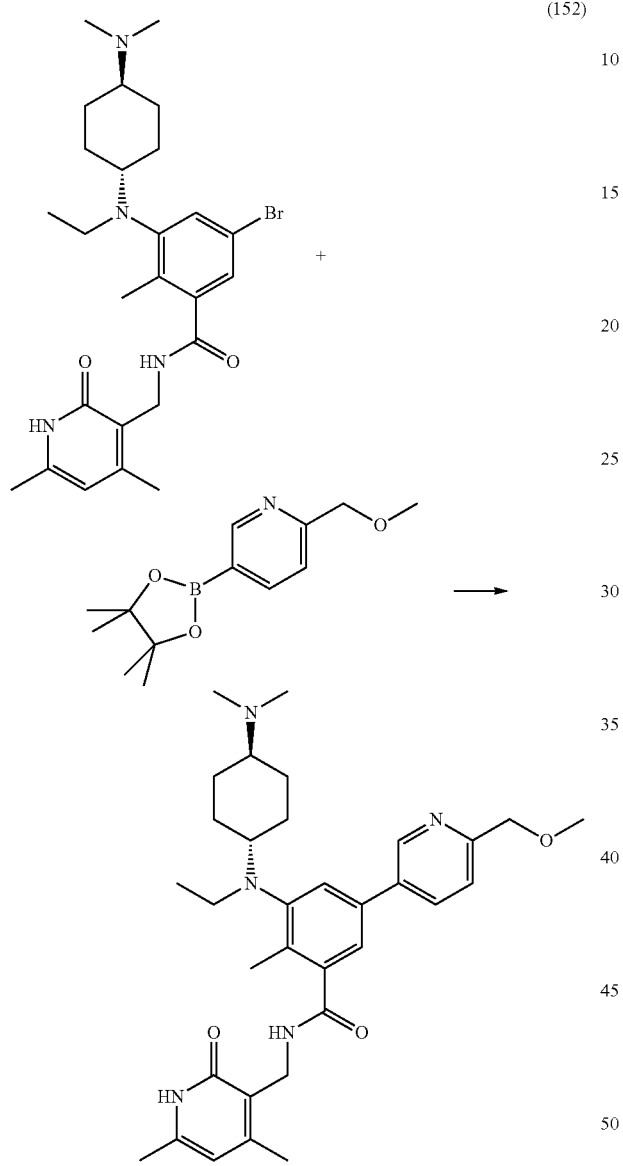

(152)

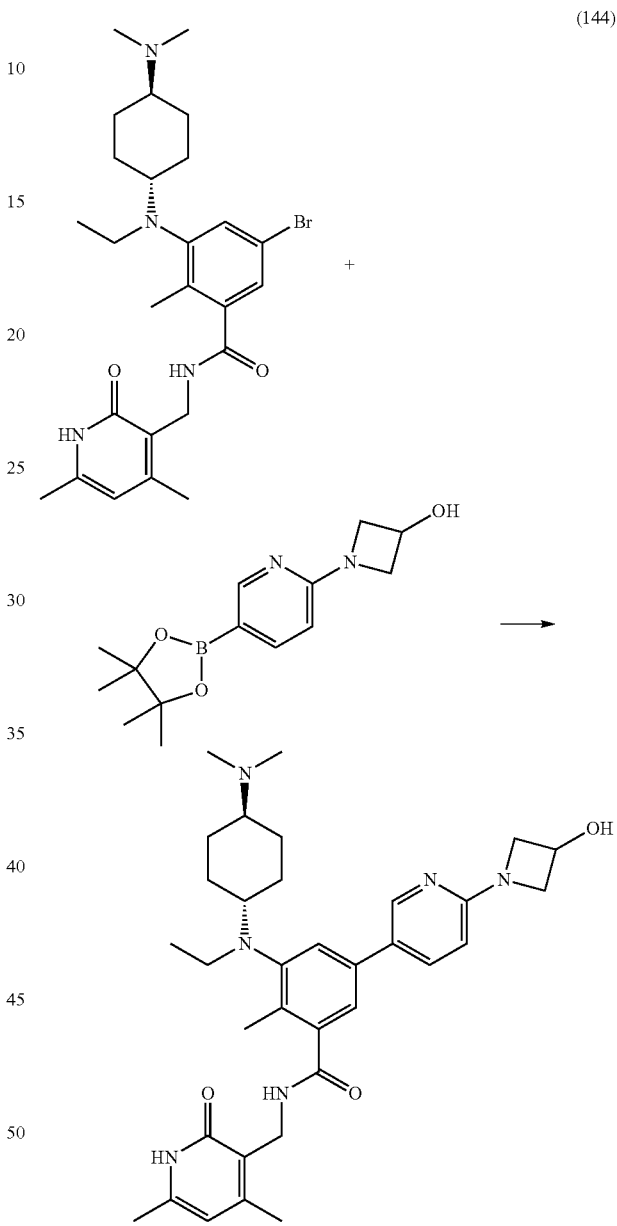

(144)

The titled compound was obtained (64.0 mg, 67% yield) as a light yellow solid following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate followed by reverse phase HPLC/MS purification. $^1$H-NMR (500 MHz, CD$_3$OD) δ ppm; 8.66 (d, J=2.2 Hz, 1H), 8.03 (dd, J=2.2 and 8.0 Hz, 1H), 7.54 (d, J=8.0 Hz, 1H), 7.43 (d, J=2.0 Hz, 1H), 7.30 (d, J=2.0 Hz, 1H), 6.08 (s, 1H), 4.55 (s, 2H), 4.45 (s, 2H), 3.44 (s, 3H), 3.14 (q, J=7.0 Hz, 2H), 2.75 (m, 1H), 2.36 (s, 3H), 2.29 (s, 9H), 2.21 (s, 3H), 2.19-2.25 (m, 1H), 1.93 (m, 4H), 1.45 (m, 2H), 1.23 (m, 2H), 0.86 (t, J=7.0 HZ, 3H); MS (ESI) [M+H]$^+$ 560.5.

The titled compound was obtained (31.0 mg, 27% yield) as a light yellow solid following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate followed by reverse phase HPLC/MS purification. $^1$H-NMR (400 MHz, CD$_3$OD) δ ppm: 8.20 (d, J=2.4 Hz, 1H), 7.77 (dd, J=8.5, 2.4 Hz, 1H), 7.33 (d, J=1.8 Hz, 1H), 7.20 (d, J=1.8 Hz, 1H), 6.48 (d, J=8.5 Hz, 1H), 6.10 (s, 1H), 4.70 (m, 1H), 4.48 (s, 2H), 4.28 (dd, J=9.4, 6.4 Hz, 2H), 3.82 (dd, J=9.4, 4.5 Hz, 2H), 3.14 (q, J=7.0 Hz, 2H), 2.75 (m, 1H). 2.38 (s, 3H), 2.29 (s, 3H), 2.24

(s, 6H), 2.23 (s, 3H), 2.17-2.26 (m, 1H), 1.93 (m, 4H), 1.44 (m, 2H), 1.21 (m, 2H), 0.88 (t, J=7.0 Hz, 3H); MS (ESI) [M+H]+ 587.6.

N-((4,6-Dimethyl-2-oxo-1,2-dihydropyridin-3-yl)methyl)-3-((4-trans-(dimethylamino)cyclohexyl)(ethyl)amino)-5-(6-(4-hydroxypiperidin-1-yl)pyridin-3-yl)-2-methylbenzamide

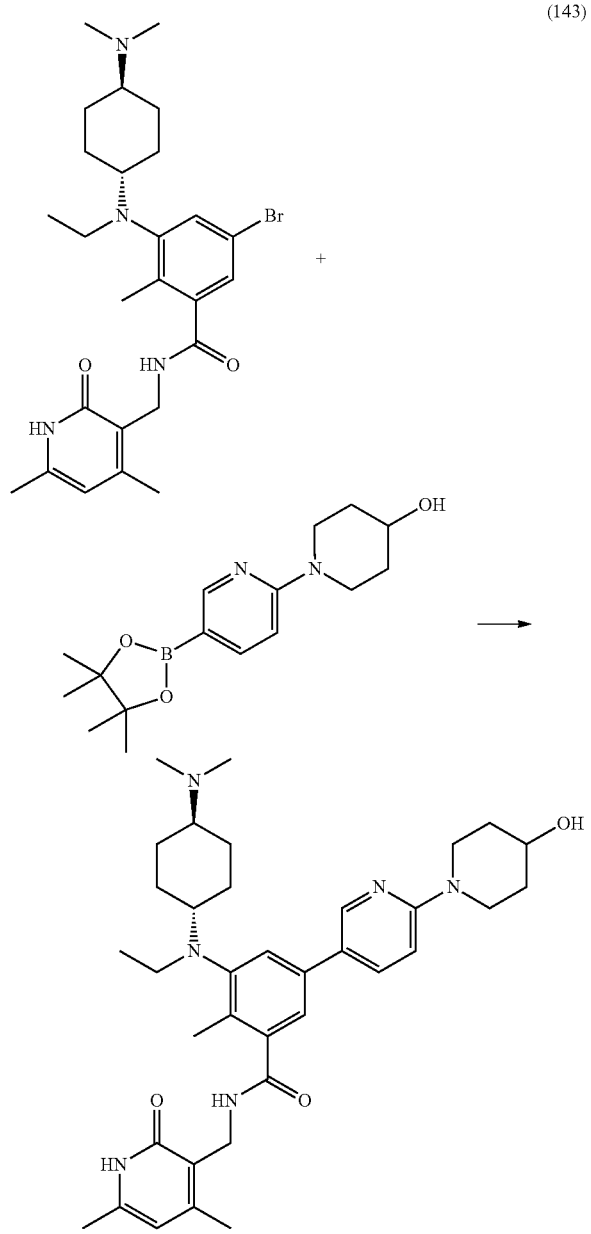

(143)

The titled compound was obtained (51.0 mg, 54% yield) as a white solid following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate followed by reverse phase HPLC/MS purification. ¹H-NMR (400 MHz, CD₃OD) δ ppm: 8.28 (d, J=2.6 Hz, 1H), 7.75 (dd, J=9.0, 2.6 Hz, 1H), 7.34 (d, J=1.8 Hz, 1H), 7.22 (d, J=1.8 Hz, 1H), 6.87 (d, J=8.8 Hz, 1H), 6.08 (s, 1H), 4.47 (s, 2H), 4.07 (dt, J=13.5, 4.1 Hz, 2H), 3.82 (m, 1H), 3.13 (m, 4H), 2.75 (m, 1H), 2.38 (s, 3H), 2.29 (s, 3H), 2.23 (s, 9H), 2.16-2.25 (m, 1H), 1.91 (m, 6H), 1.39-1.56 (m, 4H), 1.21 (m, 2H), 0.88 (t, J=6.9 Hz, 3H); MS (ESI) [M+H]+ 615.6.

N-((4,6-Dimethyl-2-oxo-1,2-dihydropyridin-3-yl)methyl)-3-((4-trans-(dimethylamino)cyclohexyl(ethyl)amino)-2-methyl-5-(5-(4-methylpiperazin-1-yl)pyrazin-2-yl)benzamide

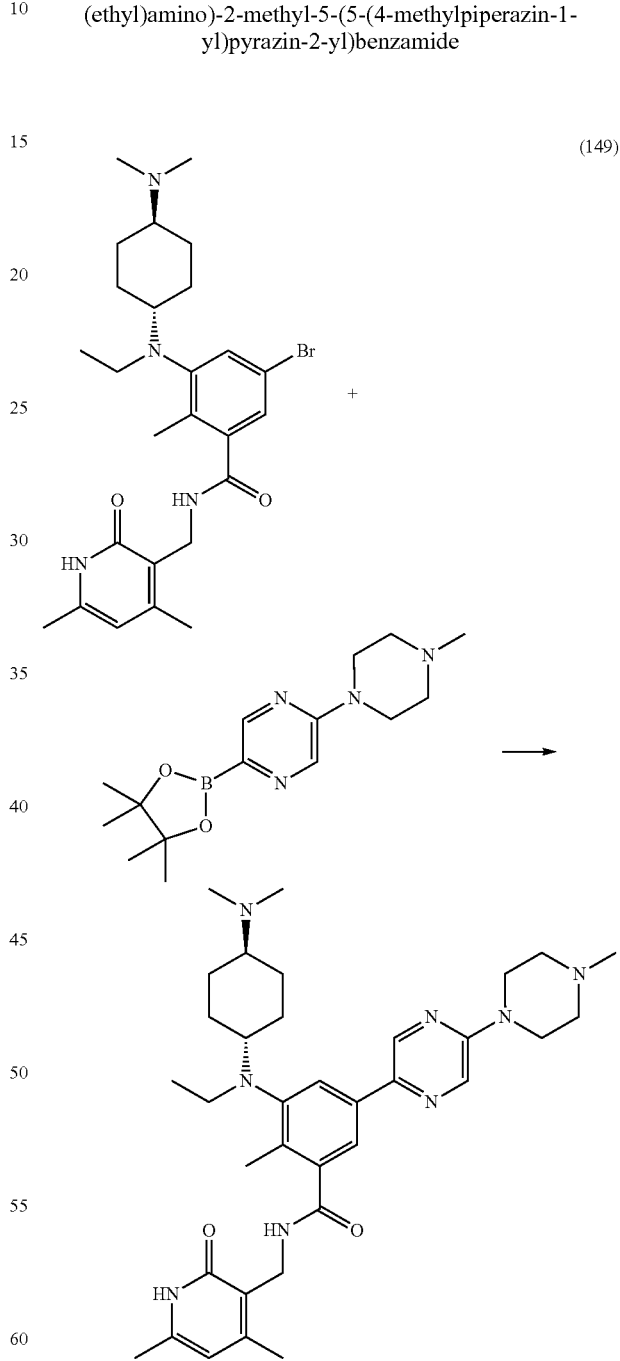

(149)

The titled compound was obtained (18.0 mg, 19% yield) as a light yellow glassy film material following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2, 6-trans-dimethylpiperidine-1-carboxylate followed by reverse phase HPLC/MS purification. $^1$H-NMR (400 MHz, CD$_3$OD) δ ppm: 8.54 (s, 1H), 8.24 (s, 1H), 7.77 (d, J=1.5 Hz 1H), 7.56 (d, J=1.2 Hz, 1H), 6.11 (s, 1H), 4.49 (s, 2H), 3.68 (m, 4H), 3.15 (q, J=6.9 Hz, 2H), 2.75 (m, 1H), 2.57 (m, 4H), 2.39 (s, 3H), 2.35 (s, 3H), 2.31 (s, 3H), 2.25 (s, 6H), 2.24 (s, 3H), 2.19-2.25 (m, 1H), 1.94 (m, 4H), 1.45 (m, 2H), 1.22 (m, 2H), 0.88 (t, J=6.9 Hz, 3H); MS (ESI) [M+H]$^+$ 615. 7.

N-((4,6-Dimethyl-2-oxo-1,2-dihydropyridin-3-yl)methyl)-3-((4-trans-(dimethylamino)cyclohexyl)(ethyl)amino)-5-(6-formylpyridin-3-yl)-2-methyl-benzamide

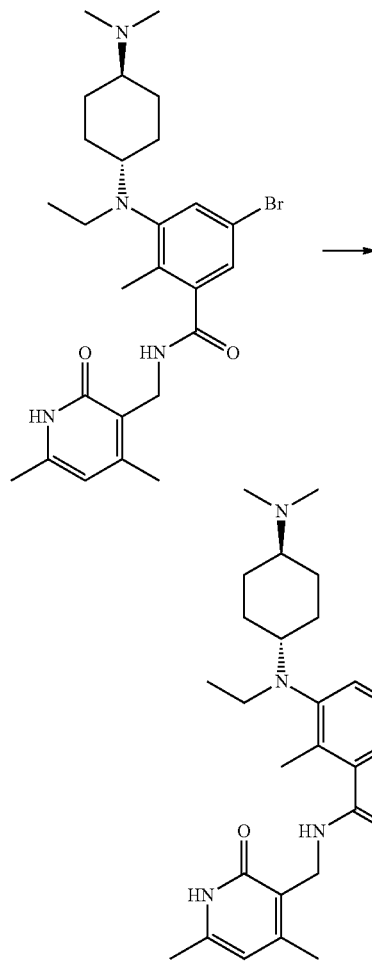

A microwave vial was charged with 5-bromo-N-((4,6-dimethyl-2-oxo-1,2-dihydropyridin-3-yl)methyl)-3-((4-trans-(dimethylamino)cyclohexyl)(ethyl)amino)-2-methyl-benzamide (286 mg, 0.553 mmol), 5-(4,4,5,5-tetramethyl-1,3,2-dioxaborolan-2-yl)picolinaldehyde (193 mg, 0.829 mmol), sodium carbonate (205 mg, 1.934 mmol), 1,4-dioxane (3340 μL, 39.0 mmol) and water (667 μL, 37.0 mmol). The suspension was bubbled with N2 for 5 min and Pd(Ph$_3$P)$_4$ (63.9 mg, 0.055 mmol) was added. The reaction mixture was bubbled with N$_2$ for additional 5 minutes, sealed and heated to 100° C. for 45 min under microwave condition. After cooling to room temperature the mixture was diluted with water (15 mL) and extracted with 10% MeOH/DCM (3×50 mL). The combined organic layers were dried (Na$_2$SO$_4$) and concentrated. The residue was purified by silica gel column chromatography (12 g column, 7N NH$_3$ in MeOH/DCM=5-20%) to give the titled compound as a semi-pure yellow solid (260 mg, 87% yield). MS (ESI) [M+H]$^+$ 544.4. This semi-pure product was used without further purification for next step.

N-((4,6-Dimethyl-2-oxo-1,2-dihydropyridin-3-yl)methyl)-3-((4-trans-(dimethylamino)cyclohexyl)(ethyl)amino)-2-methyl-5-(6-((4-methyl-1,4-diazepan-1-yl)methyl)pyridin-3-yl)benzamide (146)

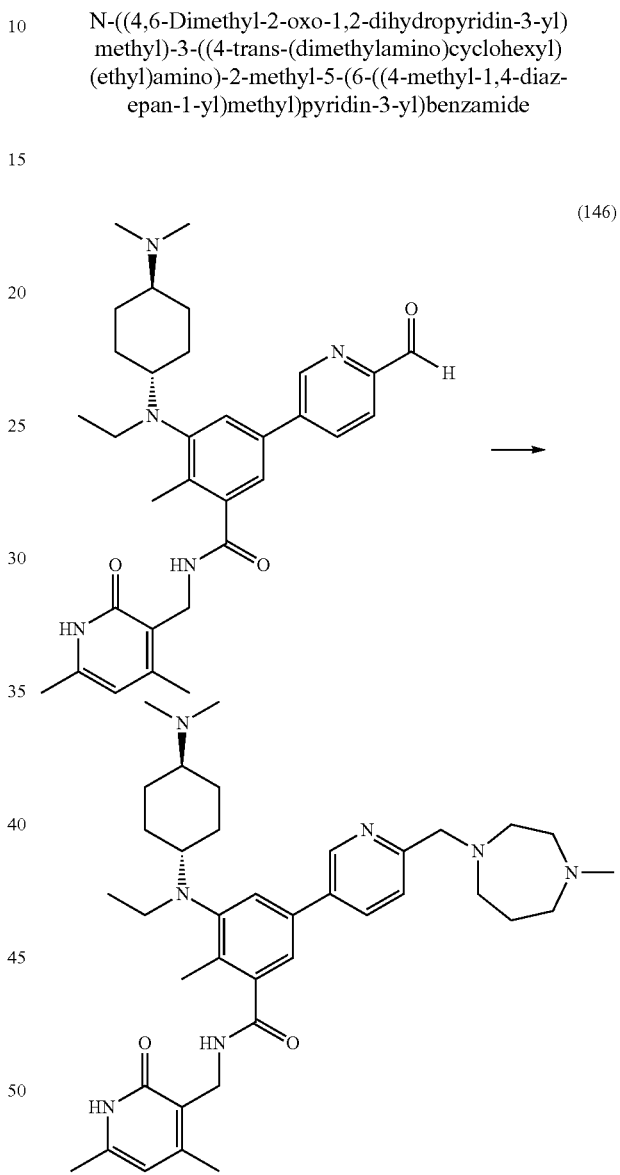

The titled compound was prepared (19.0 mg, 32% yield) following the same procedure described for N-((4,6-dimethyl-2-oxo-1,2-dihydropyridin-3-yl)methyl)-3-(ethyl(1-ethyl-2,6-trans-dimethylpiperidin-4-yl)amino)-5-fluoro-2-methylbenzamide. $^1$H-NMR (400 MHz, CD$_3$OD) δ ppm 8.64 (dd, J=2.42, 0.86 Hz, 1 H), 8.00 (dd, J=8.14, 2.35 Hz, 1 H), 7.60 (d, J=8.1 Hz, 1 H), 7.42 (d, J=2.02 Hz, 1 H), 7.29 (d, J=1.8 Hz, 1H), 6.08 (s, 1H), 4.46 (s, 2H), 3.80 (s, 2H), 3.14 (m, 2H), 2.78 (m, 7H), 2.72 (m, 2H), 2.38 (s, 3H), 2.36 (s, 3H), 2.36-2.29 (m, 2H), 2.29 (s, 9H), 2.21 (s, 3 H), 1.93 (m, 4H), 1.86 (m, 2H), 1.45 (m, 1H), 1.22 (m, 2H), 0.86 (t, J=7.7 Hz, 3H); MS (ESI) [M+H]$^+$ 642.6.

273

N-((4,6-Dimethyl-2-oxo-1,2-dihydropyridin-3-yl)methyl)-3-((4-trans-(dimethylamino)cyclohexyl)(ethyl)amino)-5-(6-(((S)-3-hydroxypiperidin-1-yl)methyl)pyridin-3-yl)-2-methylbenzamide

274

N-((4,6-Dimethyl-2-oxo-1,2-dihydropyridin-3-371)methyl)-3-((4-trans-(dimethylamino)cyclohexyl)(ethyl)amino)-5-(6-(((S)-3-hydroxypyrrolidin-1-yl)methyl)pyridin-3-yl)-2-methylbenzamide

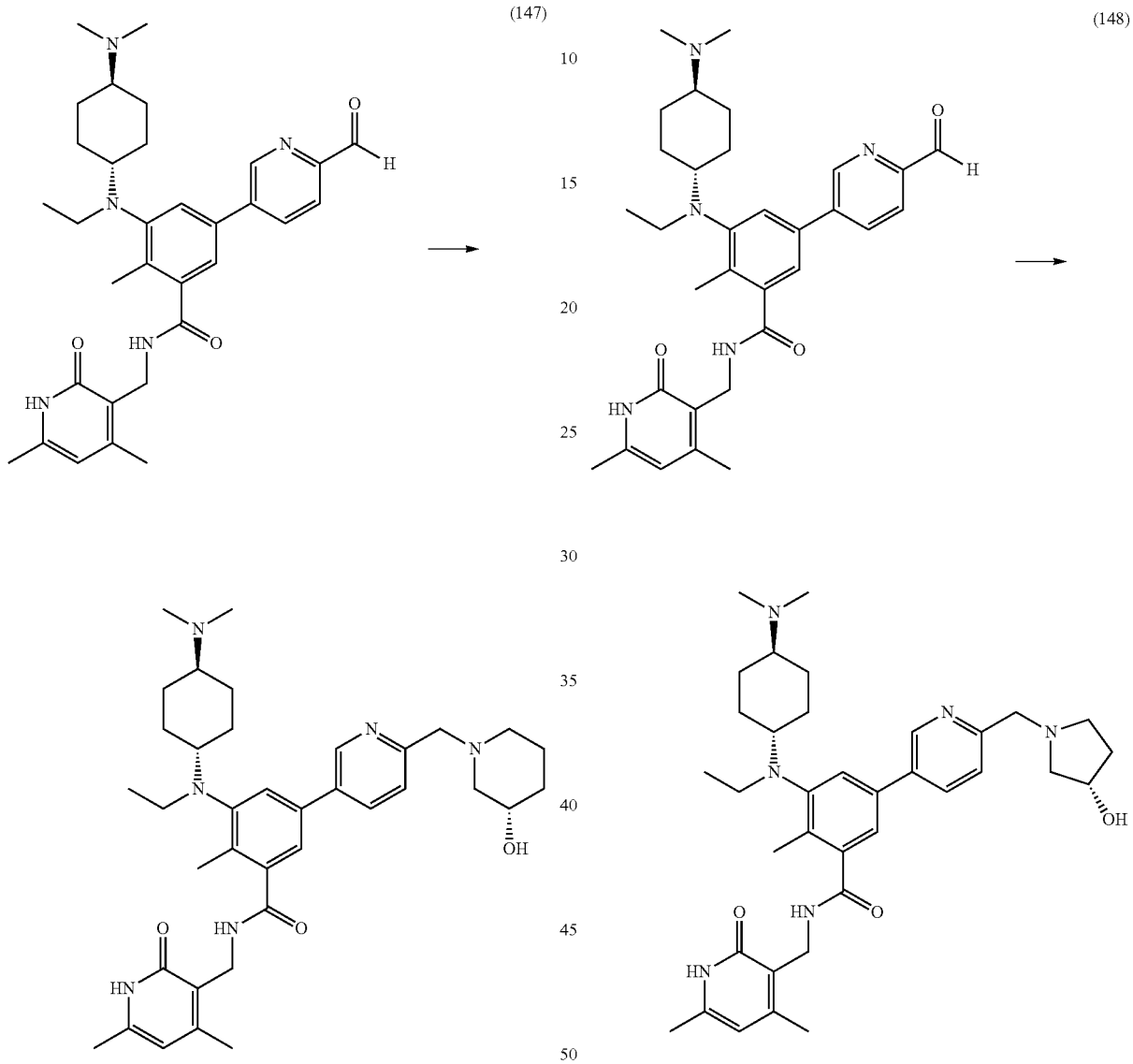

The titled compound was prepared (10.0 mg, 20% yield) as a white solid following the same procedure described for N-((4,6-dimethyl-2-oxo-1,2-dihydropyridin-3-yl)methyl)-3-(ethyl(1-ethyl-2,6-trans-dimethylpiperidin-4-yl)amino)-5-fluoro-2-methylbenzamide. $^1$H-NMR (400 MHz, CD$_3$OD) δ ppm; 8.65 (d, J=2.2 Hz, 1H), 8.00 (dd, J=1.3 Hz, 2.4 Hz, 1H), 7.56 (d, J=8.1 Hz, 1H), 7.42 (d, J=1.66 Hz, 1H), 7.30 (d, J=1.65 Hz, 1H), 6.08 (s, 1H), 4.46 (s, 2H), 3.67 (m, 3H), 3.14 (m, 2H), 2.78 (m, 2H), 2.36 (s, 3H), 2.32 (s, 6H), 2.29 (s, 3H), 2.25-2.40 (m, 1H), 2.21 (s, 3H), 2.14 (m, 1H), 1.93 (d, J=9.8 Hz, 4H), 1.75 (m, 1H), 1.44 (m, 4H), 1.21 (m, 5H), 0.86 (t, J=7.7 Hz, 3H); MS (ESI) [M+H]$^+$ 629.6.

The titled compound was prepared (7.00 mg, 15% yield) as a white solid following the same procedure described for N-((4,6-dimethyl-2-oxo-1,2-dihydropyridin-3-yl)methyl)-3-(ethyl(1-ethyl-2,6-trans-dimethylpiperidin-4-yl)amino)-5-fluoro-2-methylbenzamide $^1$H-NMR (400 MHz, CD$_3$OD) δ ppm; 8.65 (d, J=2.4 Hz, 1H), 8.00 (dd, J=1.4, 2.4 Hz, 1H), 7.56 (d, J=7.5 Hz, 1H), 7.42 (d, J=1.9 Hz, 1H), 7.29 (d, J=1.8 Hz, 1H), 6.08 (s, 1H), 4.45 (s, 2H), 4.32 (m, 1H), 3.78 (q, J=13.9, 8.25 Hz, 2H), 3.14 (q, J=7.0 Hz, 2H), 2.80 (m, 3H), 2.54 (m, 2H), 2.36 (s, 3H), 2.29 (s, 3H), 2.22 (s, 6H), 2.21 (s, 3H), 2.14 (m, 1H), 1.91 (m, 4H), 1.76 (m, 1H), 1.44 (m, 2H), 1.21 (m, 4H), 0.86 (t, J=7.1 Hz, 3H); MS (ESI) [M+H]$^+$ 615.6.

275

N-((4-isopropyl-6-methyl-2-oxo-1,2-dihydropyridin-3-yl)methyl)-3-((4-trans-(dimethylamino)cyclohexyl)(ethyl)amino)-5-(6-(((S)-3-hydroxypyrrolidin-1-yl)methyl)pyridin-3-yl)-2-methylbenzamide

276

N-((4,6-Dimethyl-2-oxo-1,2-dihydropyridin-3-yl)methyl)-3-((4-trans-(dimethylamino)cyclohexyl)(ethyl)amino)-5-(6-((3-hydroxyazetidin-1-yl)methyl)pyridin-3yl)-2-methylbenzamide

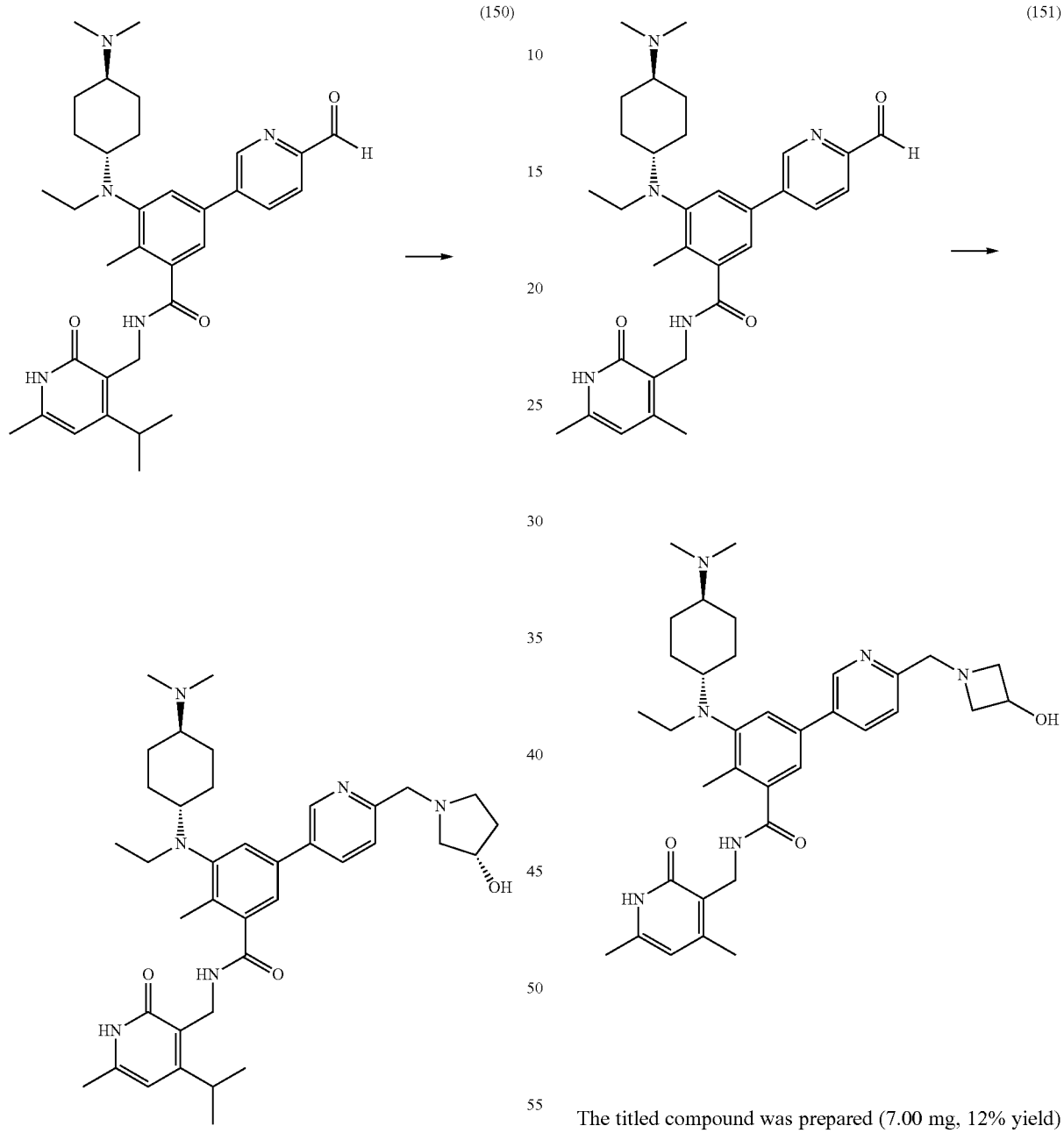

The titled compound was prepared following a procedure similar to that described for Compound 148 above.

The titled compound was prepared (7.00 mg, 12% yield) as a white solid following the same procedure described for N-((4,6-dimethyl-2-oxo-1,2-dihydropyridin-3-yl)methyl)-3-(ethyl(1-ethyl-2,6-trans-dimethylpiperidin-4-yl)amino)-5-fluoro-2-methylbenzamide. $^1$H-NMR (400 MHz, CD$_3$OD) δ ppm 8.66 (d, J=2 Hz, 1H) 7.99 (dd, J=2.6, 2.4 Hz, 1H) 7.44 (d, J=7.9 Hz, 1H), 7.42 (d, J=1.8 Hz, 1H), 7.29 (d, J=1.8 Hz, 1 H), 6.08 (s, 1H), 4.46 (s, 2H), 4.35 (m, 1 H), 3.79 (bs, 2H), 3.67 (m, 2H), 3.14 (m, 2H), 3.05 (m, 2H), 2.75 (m, 1H), 2.36 (s, 3H), 2.29 (s, 3H), 2.27 (s, 6H), 2.21 (s, 3H), 1.92 (m, 4H), 1.44 (m, 2H), 1.23 (m, 3H), 0.86 (t, J=7.0 Hz, 3H); MS (ESI) [M+H]$^+$ 601.6.

277

N-((4,6-Dimethyl-2-oxo-1,2-dihydropyridin-3-yl)methyl)-3-(ethyl(tetrahydro-2H-Pyran-4-yl)amino)-5-(5-methoxypyrazin-2-yl)-2-methylbenzamide

278

N-((4,6-Dimethyl-2-oxo-1,2-dihydropyridin-3-yl)methyl)-3-(ethyl(tetrahydro-2H-pyran-4-yl)amino)-2-methyl-5-(5-(trifluoromethyl)pyrazin-2-yl)benzamide

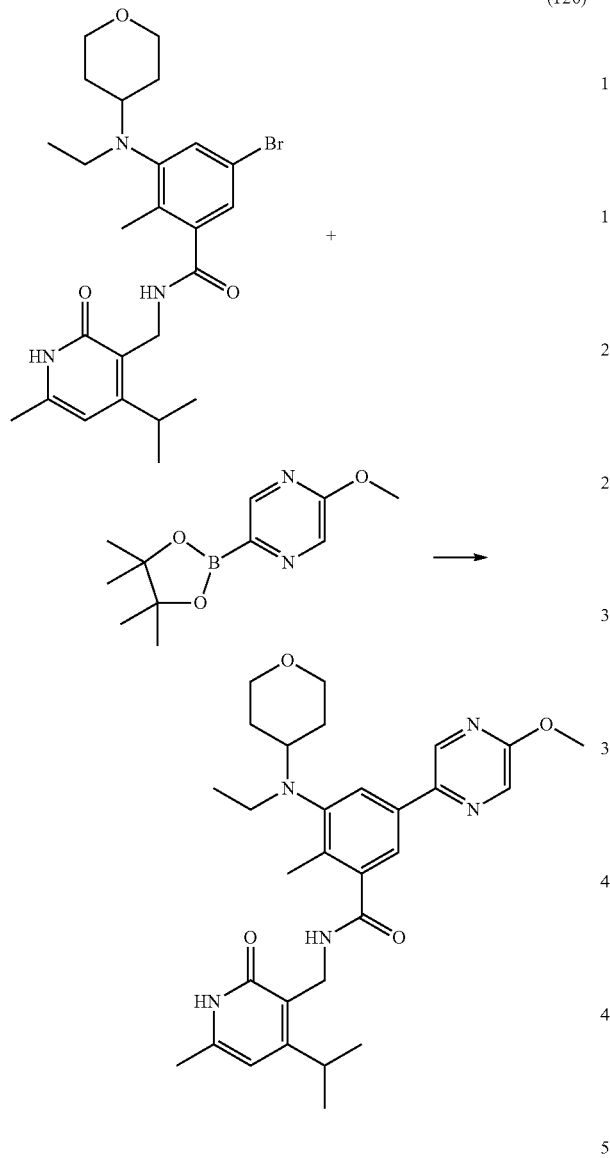

(126)

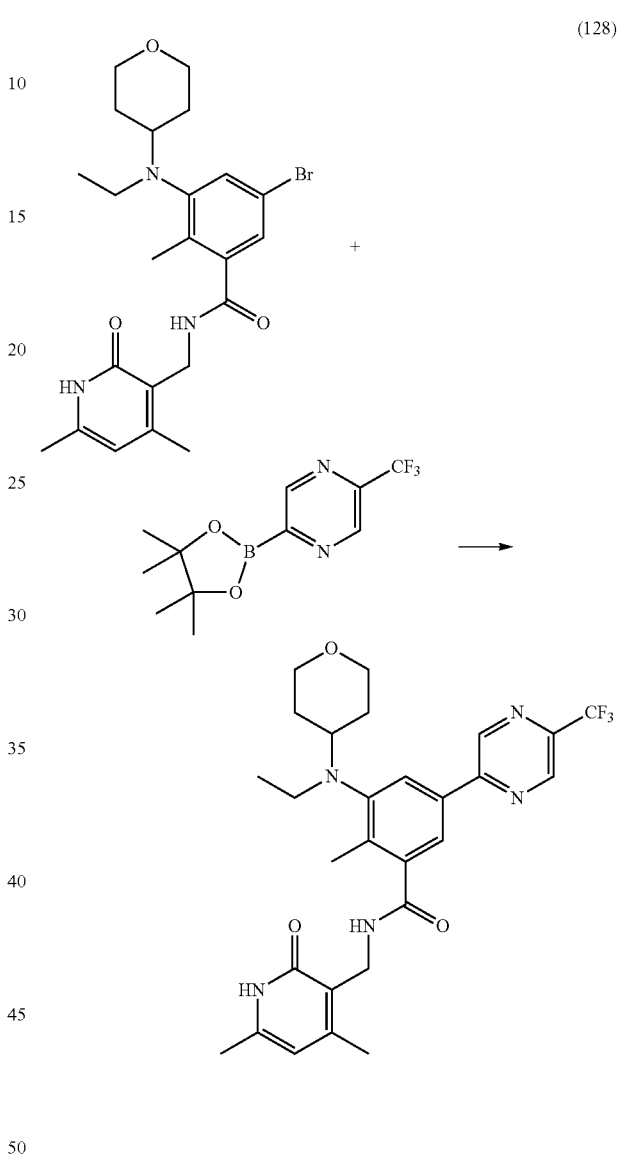

(128)

The titled compound was obtained (11.2 mg, 21% yield) following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate followed by reverse phase HPLC/MS purification. $^1$H-NMR (400 MHz, CD$_3$OD) δ ppm: 8.57 (J=1.2 Hz, 1H), 8.21 (J=1.2 Hz, 1H), 7.83 (d, J=1.8 Hz 1H), 7.61 (d, J=1.8 Hz, 1H), 6.21 (J=0.9 Hz, 1H), 4.52 (s, 2H), 3.97 (s, 3H), 3.88 (bd, J=11.6 Hz, 2H), 3.44 (m, 1H), 3.32 (m, 2H), 3.13 (q, J=7.0 Hz, 2H), 3.07 (m, 1H), 2.31 (s, 3H), 2.24 (s, 3H), 1.72 (m, 2H), 1.62 (m, 2H), 1.21 9d, J=6.7 Hz, 6H), 0.86 (t, J=7.0 Hz, 3H); MS (ESI) [M+H]$^+$ 534.4.

The titled compound was prepared (5.10 mg, 8.1% yield) following a similar procedure for the preparation of tert-butyl 4((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate followed by reverse phase HPLC/MS purification. $^1$H-NMR (400 MHz): δ ppm 10.30 (bs, 1H), 9.05 (d, J=1.2 Hz, 1H), 8.92 (d, J=0.8 Hz, 1H), 7.90 (d, J=2.0 Hz, 1H), 7.74 (d, J=1.6 Hz, 1H), 7.24 (t, J=6.0 Hz 1H), 5.95 (s, 1H), 4.57 (d, J=6.0 Hz, 2H), 3.97 (bd, J=7.9 Hz, 2H), 3.37-3.31 (m, 2H), 3.15 (q, J=7.0 Hz 2H), 3.06 (dddd, J=7.4, 7.4, 7.4, 7.4 Hz, 1H), 2.43 (s, 3H), 2.40 (s, 3H), 2.22 (s, 3H), 1.74-1.66 (m, 4H), 0.91 (t, J=7.0 Hz 3H); MS (ESI) [M+H]$^+$ 544.5.

279

N-((4,6-Dimethyl-2-oxo-1,2-dihydropyridin-3-yl)methyl)-3-(ethyl(tetrahydro-2H-pyran-4-yl)amino)-2-methyl-5-(5-((1-methylpiperidin-4-yl)oxy)pyrazin-2-yl)benzamide

280

N-((4,6-Dimethyl-2-oxo-1,2-dihydropyridin-3-yl)methyl)-3-(ethyl(tetrahydro-2H-pyran-4-yl)amino)-2-methyl-5-(5-((1-methylazetidin-3-yl)oxy)pyrazin-2-yl)benzamide

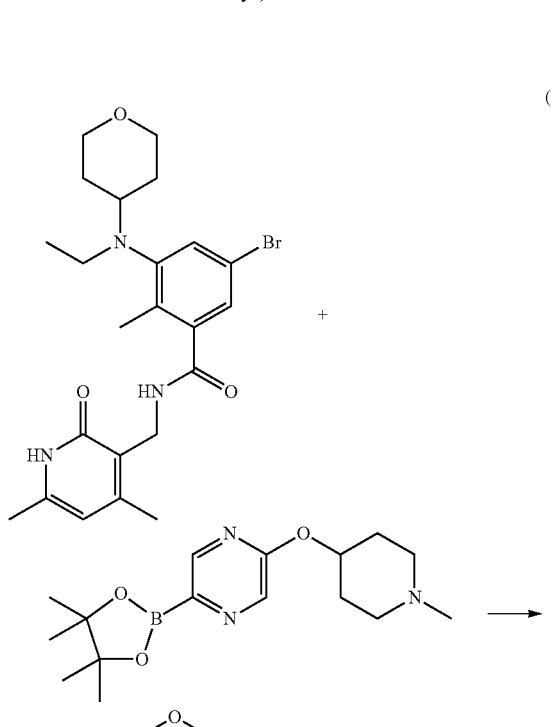

(132)

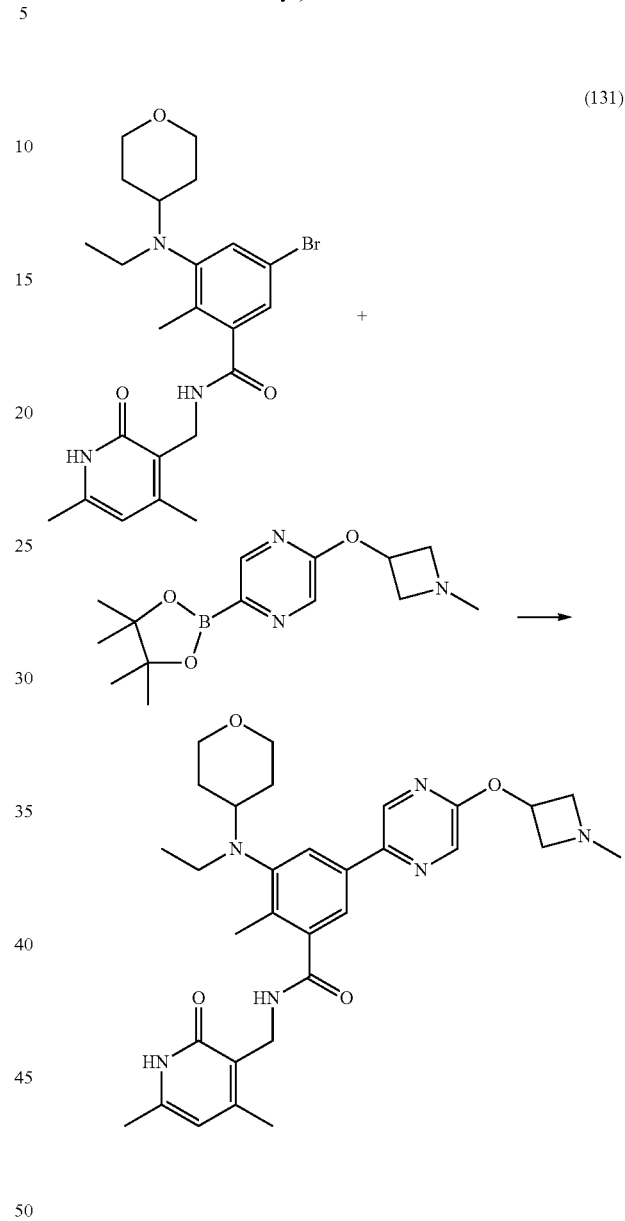

(131)

The titled compound was prepared (28.0 mg, 22% yield) following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methyl-phenyl)(ethyl)amino)-2,6-trans-dimethylpiperidine-1-carboxylate followed by reverse phase HPLC/MS purification. $^1$H-NMR (400 MHz): δ ppm 8.39 (d, J=1.2 Hz, 1 H), 8.17 (d, J=1.2 Hz, 1 H), 7.68 (d, J=1.2 Hz, 1 H), 7.58 (d, J=1.6 Hz, 1 H), 7.20 (t, J=5.6 Hz, 1 H), 5.91 (s, 1 H), 5.07-5.03 (m, 1 H), 4.56 (d, J=5.8 Hz, 2 H), 3.94 (br d, J=11.3 Hz, 2 H), 3.32 (ddd, J=11.1, 11.1, 2.8 Hz, 2 H), 3.11 (q, J=7.0 Hz 2 H), 3.04 (dddd, J=9.4, 9.4, 4.9, 4.9 Hz, 1 H), 2.76-2.69 (m, 2 H), 2.40 (s, 3 H), 2.36 (s, 3 H), 3.33-3.28 (m, 2 H), 2.32 (s, 3 H), 2.15 (s, 3 H), 2.09-2.05 (m, 4 H), 1.86 (dddd, J=12.5, 12.5, 3.7, 3.7 Hz, 2 H), 1.74-1.64 (m, 2 H), 0.88 (t, J=7.0 Hz, 3 H); MS (ESI) [M+H]$^+$ 589.6.

The titled compound was obtained (21.0 mg, 18% yield) following the same procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methyl-phenyl)(ethyl)amino)-2,6-trans-dimethylpiperidine-1-carboxylate followed by reverse phase HPLC/MS purification. $^1$H NMR (400 MHz): δ ppm 8.39 (d, J=1.2 Hz, 1H), 8.21 (d, J=1.6 Hz, 1H), 7.69 (d, J=2.0 Hz, 1H), 7.59 (d, J=1.6 Hz, 1H), 7.22 (t, J=6.0 Hz 1H), 5.91 (s, 1H), 5.21 (dddd, J=5.9, 5.9, 5.9, 5.9 Hz, 1H), 4.56 (d, J=5.8 Hz, 2H), 3.94 (bd, J=11.3 Hz, 2H), 3.83-3.80 (m, 2H), 3.32 (ddd, J=11.1, 11.1, 3.2 Hz, 2H), 3.17-3.09 (m, 4H), 3.06 (dddd, J=10.1, 10.1, 5.0, 5.0 Hz, 1H) 2.41 (s, 3 H), 2.40 (s, 3H), 2.36 (s, 3H), 2.15 (s, 3H), 1.74-1.64 (m, 4H), 0.88 (t, J=7.0 Hz, 3H); MS (ESI) [M+H]$^+$ 561.5.

281

N-((4,6-Dimethyl-2-oxo-1,2-dihydropyridin-3-yl)methyl)-3-(ethyl(tetrahydro-2H-pyran-4-yl)amino)-5-(5-isopropoxypyrazin-2-yl)-2-methylbenzatnide

282

Methyl 3-{[trans-4-(dimethylamino)cyclohexyl](ethyl)amino}-2-methyl-5-[3-(morpholin-4-yl)-1-propyn-1-yl]benzoate

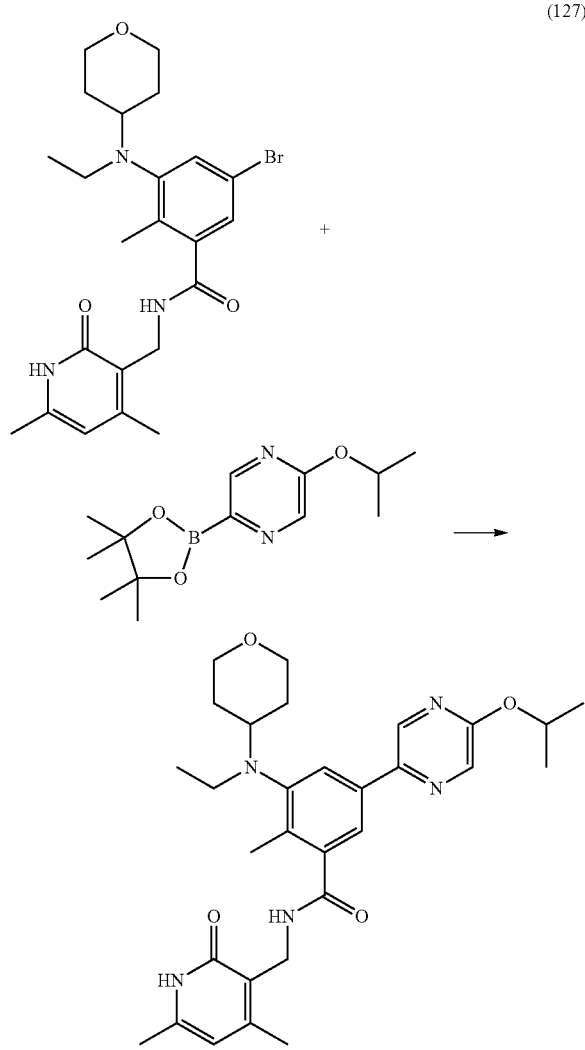

(127)

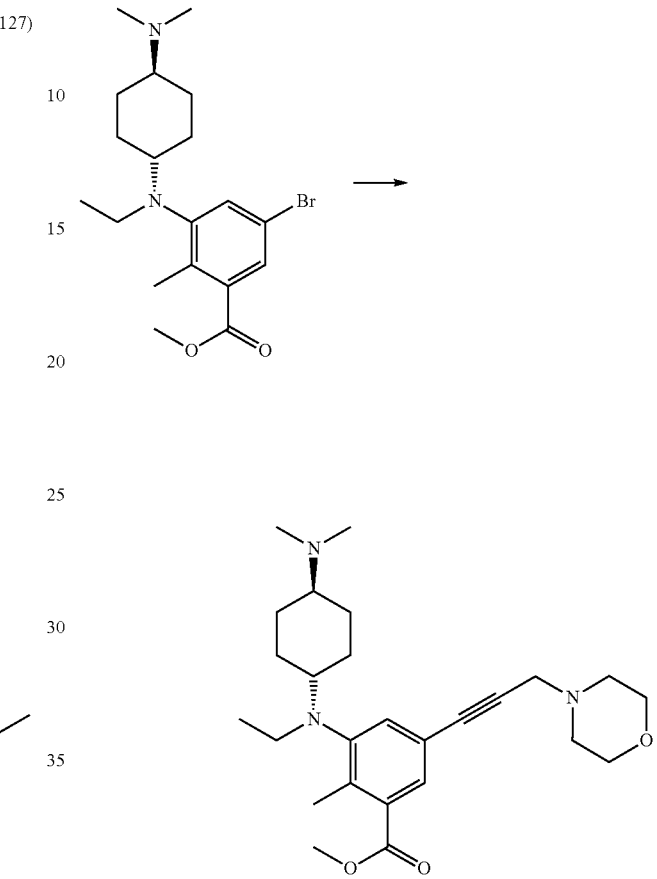

The titled compound was obtained (23.0 mg, 34% yield) following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate followed by reverse phase HPLC/MS purification. $^1$H-NMR (400 MHz): δ ppm 8.40 (d, J=1.2 Hz, 1H), 8.12 (d, J=1.2 Hz, 1H), 7.69 (d, J=2.0 Hz, 1H), 7.59 (d, J=2.0 Hz, 1H), 7.24 (t, J=6.0 Hz 1H), 5.91 (s, 1H), 5.27 (septet, J=6.4 Hz, 1H), 4.56 (d, J=5.6 Hz, 2H), 3.94 (br d, J=11.2 Hz, 2H), 3.32 (ddd, J=11.2, 11.2, 2.8 Hz, 2H), 3.12 (q, J=7.2 Hz, 2H), 3.32 (dddd, J=9.9, 9.9, 4.8, 4.8 Hz, 1H), 2.40 (s, 3H), 2.36 (s, 3H), 2.14 (s, 3H), 1.73-1.66 (m, 4H), 1.38 (s, 3H), 1.37 (s, 3H), 0.89 (t, J=7.0 Hz, 3H); MS (ESI) [M+H]$^+$ 534.5.

To a stirred solution of methyl 5-bromo-3-{[trans-4-(dimethylamino)cyclohexyl](ethyl)amino}-2-methylbenzoate (80 mg, 0.201 mmol) and 4-(1-propyn-3-yl)morpholine (0.051 ml, 0.4 mmol) in DMF (4 mL) was added Pd(PPh$_3$)$_4$ (23.0 mg, 0.0199 mmol), CuI (7.60 mg, 0.0399 mmol), and triethylamine (0.056 mL, 0.399 mmol). The reaction mixture was stirred at 80° C. for 1.5 hours. The mixture was cooled to rt, diluted with EtOAc and water, and filtered through celite pad. The filtrate was partitioned. The organic layer was washed with water and brine, dried over Na$_2$SO$_4$, filtered, and concentrated. The residue was purified by silica gel column chromatography (NH—SiO$_2$; EtOAc/heptane=1/3-1/1 to EtOAc only) to give the titled compound as a crude product (73.2 mg, ~76% purity, 64%). $^1$H-NMR (400 MHz, CDCl$_3$) δ ppm; 7.68 (br-s, 1H), 7.29 (br-s, 1H), 3.89 (s, 3H), 3.77-3.80 (m, 4H), 3.50 (s, 2H), 3.03 (q, J=6.8 Hz, 2H), 2.60-2.67 (m, 5H), 2.47 (s, 3H), 2.26 (s, 6H), 2.13-2.20 (m, 1H), 1.85-1.91 (m, 4H), 1.17-1.36 (m, 4H), 0.84 (t, J=6.8 Hz, 3H); MS (ESI) [M+H]$^+$ 442.4.

N-[(4,6-Dimethyl-2-oxo-1,2-dihydropyridin-3-yl)methyl]-3-{[trans-4-(dimethylamino)cyclohexyl](ethyl)amino}-2-methyl-5-[3-(morpholin-4-yl)prop-1-yn-1-yl]benzamide (111)

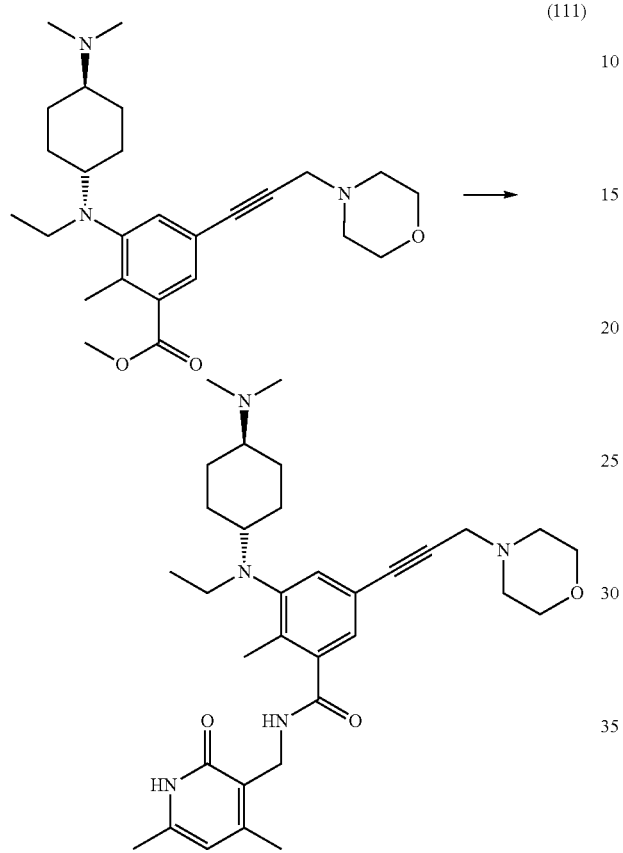

To a stirred solution of methyl 3-{[trans-4-(dimethylamino)cyclohexyl](ethyl)aminol}-2-methyl-5-[3-(morpholin-4-yl)-1-propyn-1-yl]benzoate (56.2 mg, 0.127 mmol) in ethanol (1.5 mL) was added aq. NaOH (5 N, 0.051 mL). The reaction mixture was stirred at 70° C. for 1.5 hours. After cooling to rt, the reaction mixture was concentrated in vacuo, azeotroped with toluene (twice), and dried in vacuo.

To a stirred solution of the crude 3-{[trans-4-(dimethylamino)cyclohexyl](ethyl)amino}-2-methyl-5-[3-(morpholin-4-yl)-1-propyn-1-yl]benzoic acid and 3-(aminomethyl)-4,6-dimethyl-1,2-dihydropyridin-2-one HCl salt (31.1 mg, 0.165 mmol) in DMSO (2 mL) was added PYBOP (100 mg, 0.191 mmol) and Hunig's base (0.066 mL, 0.381 mmol). The reaction mixture was stirred at RT for 14 h. The reaction mixture was quenched with water, diluted with CHCl₃, and partitioned. The organic layer was washed with water and brine, dried over Na₂SO₄, filtered, and concentrated. The residue was purified by silica gel column chromatography (NH—SiO₂; EtOAc to EtOAc/MeOH=10/1-5/1). The mixture was triturated with EtOAc-hexane to give the titled compound (34.7 mg, 49%). The compound was purified again by PTLC (NH—SiO₂; EtOAc/MeOH=10/1 4 developments) and triturated with EtOAc-hexane to give the compound with higher purity as a white solid. ¹H-NMR (400 MHz, DMSO-d₆) δ ppm; 7.15 (s, 1H), 7.13 (s, 1H), 7.03 (t, J=6.4 Hz, 1H), 5.92 (s, 1H), 4.51 (d, J=6.4 Hz, 2H), 3.73-3.86 (m, 4H), 3.48 (s, 2H), 3.01 (q, J=7.2 Hz, 2H), 2.62-2.66 (m, 5H), 2.40 (s, 3H), 2.29 (s, 3H), 2.25 (s, 6H), 2.23 (s, 3H), 2.11-2.19 (m, 1H), 1.82-1.87 (m, 4H), 1.12-1.42 (m, 4H), 0.83 (t, J=7.2 Hz, 3H); MS (ESI) [M+H]⁺ 562.6; HPLC 95.4% purity.

1-Methyl-4-(1-propyn-3-yl)-1,4-diazepane

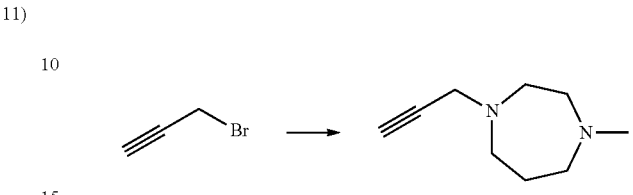

To a stirred solution of 3-bromo-1-propyne (ca. 9.2 M, 865 uL, 7.96 mmol) in acetone (8 mL) was added cesium carbonate (2.85 g, 8.76 mmol) and 1-methyl-homopiperazine (1.00 g, 8.76 mmol). The reaction mixture was stirred at RT for 18 hours. Then the reaction mixture was filtered, and the filtrate was concentrated in vacuo to give the titled compound as a brown oil (887 mg, 61%). ¹HNMR (400 MHz, CDCl₃) δ ppm; 3.38 (s, 1H), 3.37 (s, 1H), 2.76-2.84 (m, 4H), 2.63-2.70 (m, 4H), 2.37 (s, 3H), 1.85 (s, 1H), 1.79-1.89 (m, 2H).

Methyl 3-{[trans-4-(dimethylamino)cyclohexyl](ethyl)amino}-2-methyl-5-[3-(4-methyl-1,4-diazepan-1-yl)-1-propyn-1-yl]benzoate

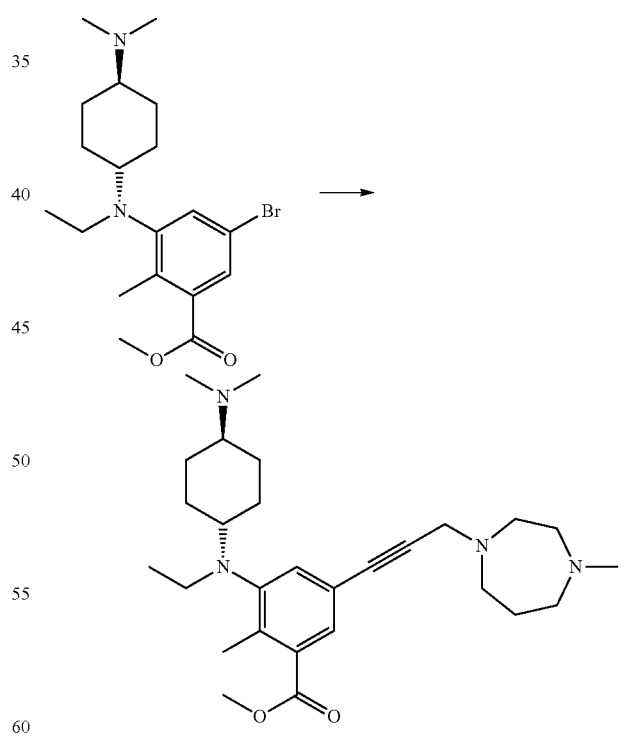

To a stirred solution of methyl 5-bromo-3-{[trans-4-(dimethylamino)cyclohexyl](ethyl)amino}-2-methylbenzoate (295 mg, 0.742 mmol) and 1-methyl-4-(1-propyn-4-yl)-1,4-diazepane (338 mg, 2.23 mmol) in DMF (7.4 mL) was added Pd(PPh₃)₄ (171 mg, 0.148 mmol), CuI (28 mg, 0.148 mmol), and triethylamine (0.31 mL, 2.23 mmol). The reaction mixture was stirred at 80° C. for 2 hours. The mixture was cooled to rt, diluted with EtOAc and water, and filtered through Celite pad. The filtrate was partitioned. The organic layer was washed with water and brine, dried over Na₂SO₄, filtered, and concentrated. The residue was purified by silica gel column chromatography (NH—SiO₂; EtOAc/heptane=1/2-1/1 to EtOAc only) to give the titled compound as a crude product (120 mg, 72% purity, 35%). ¹H-NMR (400 MHz, CDCl₃) δ ppm; 7.29-7.33 (m, 2H), 3.89 (s, 3H), 3.58 (s, 2H), 3.03 (q, J=7.2 Hz, 2H), 2.85-2.90 (m, 4H), 2.62-2.71 (m, 5H), 2.47 (s, 3H), 2.38 (s, 3H), 2.25 (s, 6H), 2.13-2.20 (m, 1H), 1.84-1.90 (m, 6H), 1.13-1.40 (m, 4H), 0.84 (t, J=7.2 Hz, 3H); MS (ESI) [M+H]⁺ 469.5.

N-[(4,6-Dimethyl-2-oxo-1,2-dihydropyridin-3-yl)methyl]-3-{[trans-4-(dimethylamino)cyclohexyl](ethyl)amino}-2-methyl-5-[3-(4-methyl-1,4-diazepan-1-yl)-1-propyn-1-yl]benzamide (112)

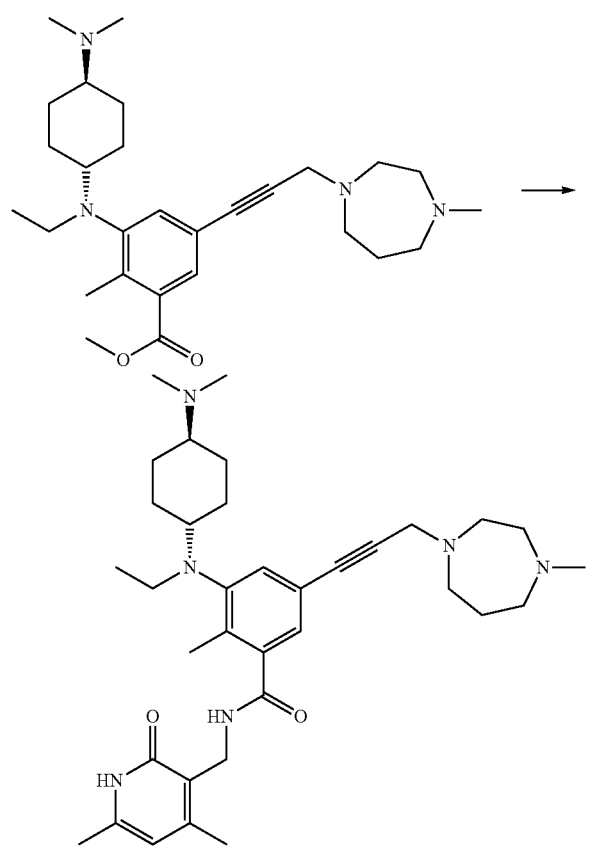

To a stirred solution of methyl 3-{[trans-4-(dimethylamino)cyclohexyl](ethyl)amino}-2-methyl-5-[3-(4-methyl-1,4-diazepan-1-yl)-1-propyn-1-yl]benzoate (120 mg, 0.256 mmol) in ethanol (4 mL) was added aq. NaOH (5N, 0.150 mL). The reaction mixture was stirred at 70° C. for 2 hours. After cooling to rt, the reaction mixture was neutralized with 2N—HCl (0.25 mL), concentrated in vacuo, azeotroped with toluene (twice), and dried in vacuo.

To a stirred solution of the crude 3-{[trans-4-(dimethylamino)cyclohexyl]ethyl)amino}-2-methyl-5-[3-(4-methyl-1,4-diazepan-1-yl)-1-propyn-1-yl]benzoic acid and 3-(aminomethyl)-4,6-dimethyl-1,2-dihydropyridin-2-one HCl salt (63.0 mg, 0.333 mmol) in DMF (4 mL) was added PYBOP (200 mg, 0.384 mmol) and Hunig's base (0.179 mL, 1.02 mmol). The reaction mixture was stirred at RT for 14 h. The mixture was directly evaporated. The residue was purified by silica gel column chromatography (NH—SiO₂; EtOAc to EtOAc/MeOH=10/1-5/1) to give the titled compound (101 mg, 67%). The compound was purified again by PTLC (NH—SiO₂; EtOAc/MeOH=10/1 4 developments) and triturated with TBME-hexane to give the compound with higher purity as a white solid. 1H-NMR (400 MHz, DMSO-d6) δ ppm; 7.13-7.16 (m, 1H), 7.13 (s, 1H), 7.12 (s, 1H), 5.92 (s, 1H), 4.50 (d, J=6.0 Hz, 2H), 3.55 (s, 2H), 3.01 (q, J=7.2 Hz, 2H), 2.84-2.90 (m, 4H), 2.69-2.73 (m, 4H), 2.59-2.65 (m, 1H), 2.39 (s, 3H), 2.37 (s, 3H), 2.30 (s, 3H), 2.24 (s, 6H), 2.22 (s, 3H), 2.12-2.17 (m, 1H), 1.84-1.89 (m, 6H), 1.13-1.40 (m, 4H), 0.83 (t, J=7.2 Hz, 3H); MS (ESI) [M+H]⁺ 589.6; HPLC 93.5% purity.

3-((tert-Butyldiphenylsilyl)oxy)-1-(prop-2-yn-1-yl)azetidine

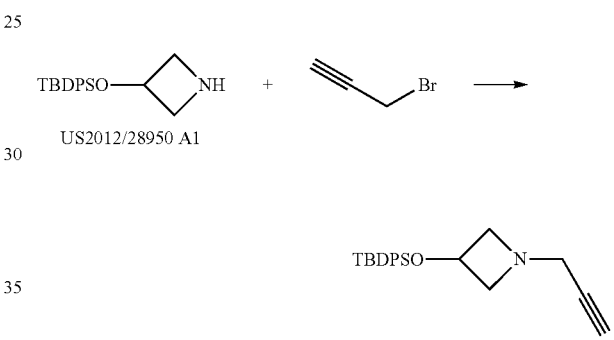

US2012/28950 A1

To a stirred solution of 3-((tert-butyldiphenylsilyl)oxy)azetidine (935 mg, 3.00 mmol) and Hunig base (786 mL, 4.50 mmol) in DCM (10 mL) at -78° C. was added propargyl bromide (267 mL, 3.00 mmol) slowly. After 5 min, the reaction was warmed up to 23° C. slowly and stirred for 1 h. The reaction was quenched with sat. aq. NaHCO₃ and water, the aq. phase was extracted with DCM, the combined organic extracts was dried over Na₂SO₄, filtered and concentrated in vacuo. The residue was purified by silica gel column chromatography (heptane/EtOAc=3/1) to give the titled compound as colorless oil (588 mg, 49% yield). ¹H-NMR (400 MHz) δ ppm: 7.63 (m, 4H), 7.40 (m, 6H), 4.42 (dddd, J=5.6 Hz, 1H), 3.45 (ddd, J=2.4, 6.0, 6.0 Hz, 2H), 3.28 (d, J=2.4 Hz, 2H), 3.19 (ddd, J=2.0, 6.0, 6.0 Hz, 2H), 2.27 (t, J=2.4 Hz, 1H), 1.06 (s, 9H).

Methyl 5-(3-(3-((tert-butyldiphenylsilyl)oxy)azetidin-1-yl)prop-1-yn-1-yl)-3-((4-trans-(dimethylamino)cyclohexyl)(ethyl)amino)-2-methylbenzoate

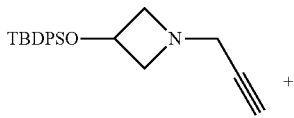

+

287

-continued

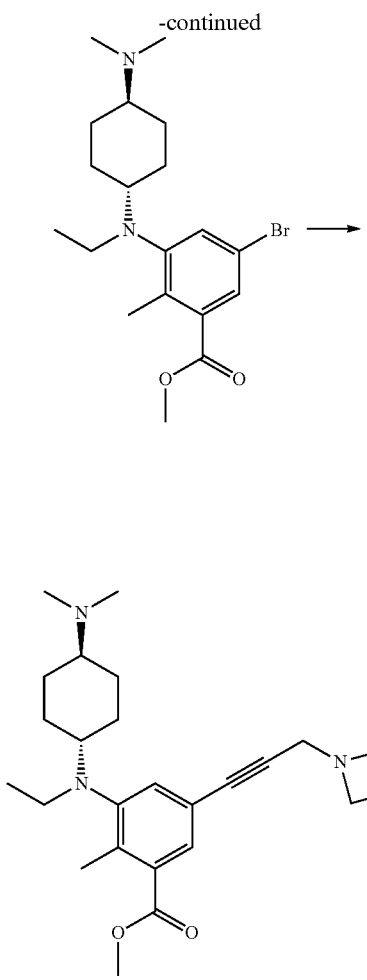

The solution of 3-((tert-butyldiphenylsilyl)oxy)-1-(prop-2-yn-1-yl)azetidine (584 mg, 1.67 mmol), methyl 5-bromo-3-((4-trans-(dimethylamino)cyclohexyl)(ethyl)amino)-2-methylbenzoate (604 mg, 1.52 mmol) and triethylamine (2.10 mL, 15.2 mmol) in DMF (15 mL) was bubbled through $N_2$ for 10 min. Then CuI (28.9 mg, 152 mmol) and Pd(PPh$_3$)$_4$ (88.0 mg, 0.076 mmol) were added and $N_2$ was bubbled through for another 10 min. The reaction mixture was heated at 100° C. for 6 h and then cooled down to rt. The reaction was quenched with sat. aq. NaHCO$_3$ and water and the separated aq. phase was extracted with TBME. The combined organic extracts were dried over Na$_2$SO$_4$, filtered and concentrated. The residue was purified by silica gel column chromatography (10% 7 N NH$_3$ in MeOH/DCM) to give the titled compound as pale brown foam (709 mg, 70% yield). $^1$H-NMR (400 MHz) δ ppm: 7.58 (m, 5H), 7.39 (m, 7H), 4.40 (dddd, J=6.0 Hz, 1H), 3.83 (s, 3H), 3.49 (s, 2H), 3.42 (m, 2H), 3.36 (m, 2H), 3.05 (ddd, J=6.8 Hz, 2H), 2.65 (m, 1H), 2.44 (s, 3H), 2.25 (s, 6H), 2.23 (m, 1H), 1.89 (br. d. J=9.6 Hz, 4H), 1.37 (m, 2H), 1.19 (m, 2H), 0.99 (s, 9H), 0.82 (t, J=6.8 Hz, 3H); MS (ESI) [M+H]$^+$ 666.6.

288

3-((4-trans-(Dimethylamino)cyclohexyl)(ethyl)amino)-5-(3-(3-hydroxyazetidin-1-yl)prop-1-yn-1-yl)-2-methylbenzoic acid

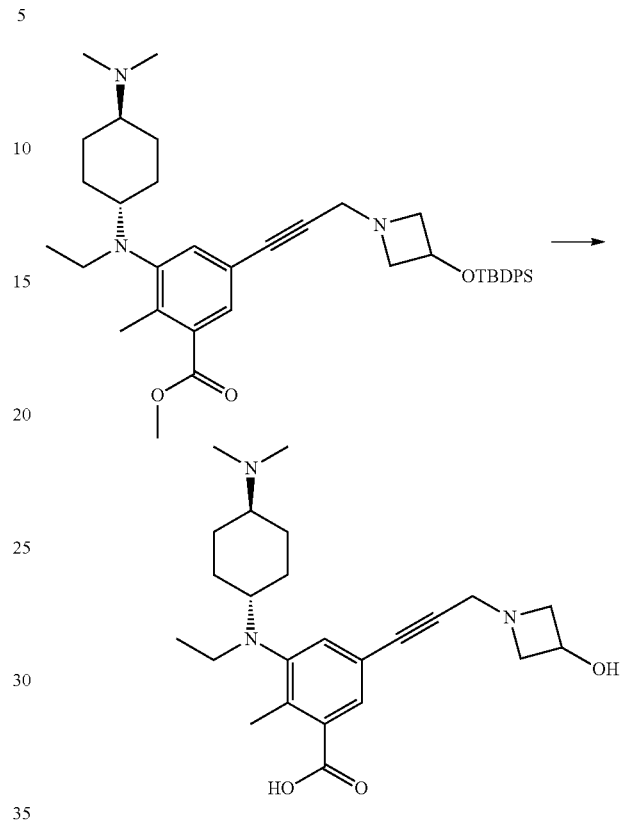

To the solution of methyl 5-(3-(3-((tert-butyldiphenylsilyl)oxy)azetidin-1-yl)prop-1-yn-1yl)-3-((4-trans-(dimethylamino)cyclohexyl)(ethyl)amino)-2-methylbenzoate (696 mg, 1.05 mmol) in EtOH (10 mL) was added 1.0 N NaOH aq. solution (3.2 mL, 3.20 mmol). The reaction mixture was heated at 60° C. for 6 h. After cooling to 23° C., 1.0 N aq. HCl (3.3 mL, 3.30 mmol) was added. The mixture was concentrated in vacuo to give the titled compound as crude products. MS (ESI) [M+H]$^+$ 414.4.

3-((4-trans-(Dimethylamino)cyclohexyl)(ethyl)amino)-5-(3-(3-hydroxyazetidin-1-yl)prop-1-yn-1-yl)-N-((4-isopropyl-6-methyl-2-oxo-1,2-dihydropyridin-3-yl)methyl)-2-methylbenzamide (110)

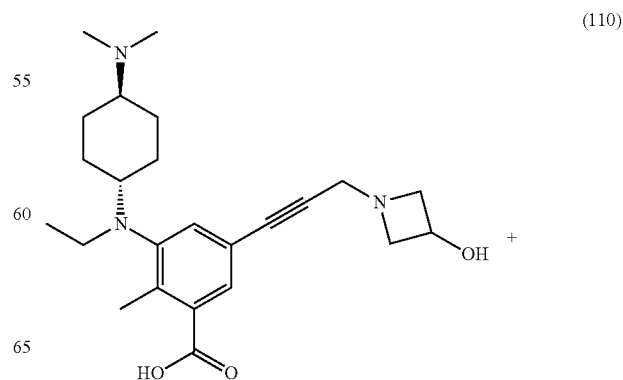

+

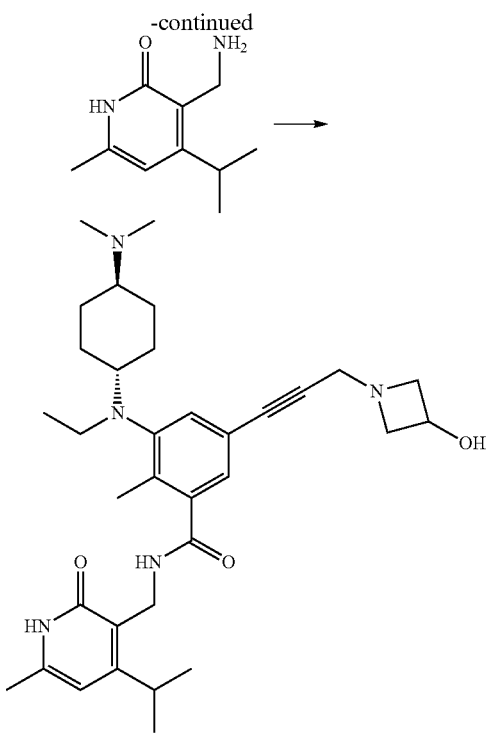

To a stirred solution of 3-((4-trans-(dimethylamino)cyclohexyl)(ethyl)amino)-5-(3-(3-hydroxyazetidin-1-yl)prop-1-yn-1-yl)-2-methylbenzoic acid (crude, 432 mg, 1.05 mmol) and 3-(aminomethyl)-4-isopropyl-6-methylpyridin-2(1H)-one (162 mg, 0.90 mmol) in DMSO (5 mL) was added EDC (258 mg, 1.45 mmol) and HOBT (206 mg, 1.35 mmol). The reaction mixture was stirred at 23° C. for 20 h. A fraction of the mixture was purified by HPLC to give the titled compound as white solid (16.7 mg). $^1$H-NMR (400 MHz) δ ppm: 7.25 (d, J=1.6 Hz, 1H), 7.10 (d, J=1.2 Hz, 1H), 6.24 (s, 1H), 4.51 (s, 2H), 4.36 (dddd, J=6.4 Hz, 1H), 3.64 (dd, J=2.0, 6.4 Hz, 2H), 3.52 (s, 2H), 3.44 (m, 1H), 3.17 (dd, J=2.0, 6.4 Hz, 2H), 3.08 (ddd, J=6.8 Hz, 2H), 2.69 (m, 1H), 2.28 (s, 6H), 2.26 (s, 6H), 2.23 (m, 1H), 1.92 (m, 4H), 1.43 (m, 2H), 1.23 (d, J=6.8 Hz, 6H), 1.24 (m, 2H), 0.84 (t, J=6.8 Hz, 3H). $^{13}$C-NMR (400 MHz) δ ppm: 172.26, 166.06, 163.28, 151.26, 145.72, 140.51, 135.90, 129.27, 126.36, 121.68, 121.28, 105.95, 85.86, 84.79, 64.88, 63.19, 63.00, 62.30, 47.16, 42.07, 41.74, 35.86, 31.08, 29.63, 28.45, 23.03, 19.01, 15.55, 13.78; MS (ESI) [M+H]$^+$ 576.6.

1-(Prop-2-yn-1-yl)piperidine

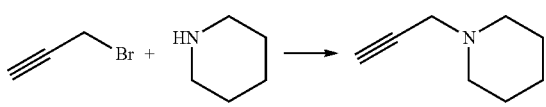

To a stirred solution of piperidine (388 mg, 4.56 mmol) in acetone (10 mL) was added Cs$_2$CO$_3$ (1490 mg, 4.56 mmol) followed by drop wise addition of 3-bromoprop-1-yne (542 mg, 4.56 mmol). After stirring over weekend at r.t., the reaction mixture was filtered and the filtrate was evaporated to dryness. The residue was partitioned between ethyl ether and aqueous NaHCO$_3$ solution. The separated organic layer was dried and evaporated to give the titled compound (389 mg, 69% yield) as an orange-brown oil. $^1$H-NMR (400 MHz) δ ppm; 3.27 (d, J=2.5 Hz, 2H), 2.45-2.53 (m, 4H), 2.22 (t, J=2.6 Hz, 1H), 1.58-1.64 (m, 4H), 1.39-1.45 (m, 2H).

1-(Prop-2-yn-1-yl)pyrrolidine

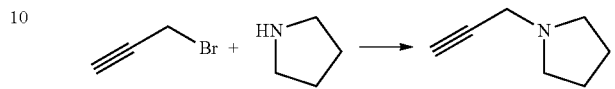

The titled compound was prepared (423 mg, 61%) following the same procedure described for 1-(prop-2-yn-1-yl)piperidine. $^1$H-NMR (400 MHz) δ ppm; 3.39 (d, J=2.6 Hz, 2H), 2.58-2.62 (m, 4H), 2.19 (t, J=4.1 Hz, 1H), 1.77-1.80 (m, 4H).

(S)-1-(Prop-2-yn-1-yl)piperidin-3-ol

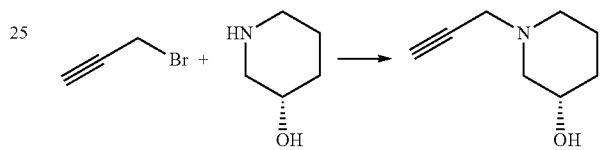

The titled compound was prepared (138 mg, 46%) following the same procedure described for 1-(prop-2-yn-1-yl)piperidine. $^1$H-NMR (400 MHz) δ ppm; 3.78-3.83 (m, 1H), 3.28 (t, J=2.6 Hz, 2H), 2.68 (bd, J=10 Hz, 1H), 2.38-2.49 (m, 3H), 2.24 (t, J=2.5 Hz, 1H), 1.42-1.83 (m, 4H).

3,5-cis-Dimethyl-1-(prop-2-yn-1-yl)piperazine

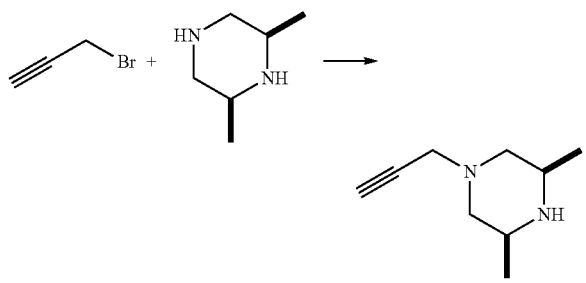

A solution of 2,6-cis-dimethylpiperazine (1920 mg, 16.8 mmol) in DCM (10 mL) was added to a solution of 3-bromoprop-1-yne (500 mg, 4.20 mmol) in DCM (10 mL) at −78° C. and the mixture was stirred for 30 min and then warmed to rt. MS showed reaction was completed shown by strong desired peak of 153 (M+H) and excess SM peak of 115 (M+H). TLC (10% 7N NH$_3$ in MeOH/DCM) showed Rf=0.6 for new spot and Rf=0.4 for SM amine. The mixture was concentrated and chromatography (50 g column, 10% MeOH/DCM and then 5% 7N NH$_3$ in MeOH/DCM) purification gave the titled compound (0.550 g, 86% yield). $^1$H-NMR (400 MHz) ppm; 4.84 (bs, 1H), 3.31 (d, J=2.4 Hz, 2H), 2.98 (m, 2H), 2.79 (dd d, J=2.1, 11.3 Hz, 2H), 2.26 (t, J=2.4 Hz, 1H), 1.89 (dd, J=10.4, 10.7 Hz 2H), 1.10 (d, J=6.4 Hz, 6H); MS (ESI) [M+H]$^+$ 153.1.

1-(tert-Butyldiphenylsilyl)-2,6-cis-dimethyl-4-(prop-2-yn-1-yl)piperazine

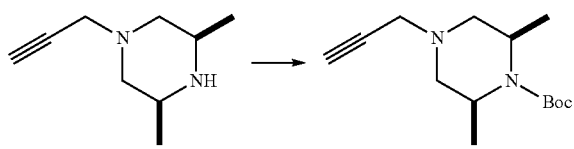 [SMILES: C#CCN1C[C@@H](C)N[C@@H](C)C1 ; C#CCN1C[C@@H](C)N(C(=O)OC(C)(C)C)[C@@H](C)C1]

The titled compound was prepared (138 mg, 46%) following the same procedure described for tert-butyl 4-(ethyl (5-fluoro-3-(methoxycarbonyl)-2-methylphenyl)amino)-2,6-trans-dimethylpiperidine-1-carboxylate. $^1$H-NMR (400 MHz): δ ppm 4.16 (bs, 2H), 3.33 (m, 2H), 2.62 (m, 2H), 2.43 (m, 2H), 2.25 (bs, 1H), 1.52 (s, 9H), 1.37 (s, J=6.7 Hz, 3H); MS (ESI) [M+H]$^+$ 253.2.

N-((4,6-Dimethyl-2-oxo-1,2-dihydropyridin-3-yl) methyl)-3-((4-trans-(dimethylamino)cyclohexyl) (ethyl)amino)-5-(3-((S)-3-hydroxypiperidin-1-yl) prop-1-yn-1-yl)-2-methylbenzamide The titled compound was prepared (27.0 mg, 43% yield) in the same procedure as described for the preparation of 3-((4-trans-(dimethylamino)cyclohexyl)(ethyl)amino)-5-(3-(3-hydroxyazetidin-1-yl)prop-1-yn-1-yl)-N-((4-isopropyl-6-methyl-2-oxo-1,2-dihydropyridin-3-yl)methyl)-2-methylbenzamide in three step sequences. The titled compound was purified by reverse phase HPLC/MS. $^1$H-NMR (400 MHz, CD$_3$OD) δ ppm 7.19 (d, J=1.2 Hz, 1H), 7.05 (d, J=1.6 Hz, 1H), 6.07 (s, 1H), 4.42 (s, 2H), 3.63-3.70 (m, 1H), 3.48 (d, J=1.8 Hz, 2H), 3.04 (q, J=7.0 Hz, 2H), 2.96-3.01 (m, 1H), 2.75-2.78 (m, 1H), 2.62-2.68 (m, 1H), 2.34 (s, 3H), 2.22 (s, 3H), 2.22 (s, 6H), 2.21 (s, 3H), 2.08-2.22 (m, 3H), 1.72-1.90 (m, 6H), 1.13-1.59 (m, 6H), 0.80 (t, J=7.1 Hz, 3H). MS (ESI) [M+H]$^+$ 576.8.

N-((4,6-Dimethyl-2-oxo-1,2-dihydropyridin-3-yl) methyl)-3-((4-trans-(dimethylamino)cyclohexyl) (ethyl)amino)-5-(3-(3-hydroxyazetidin-1-yl)prop-1-yn-1-yl)-2-methylbenzamide (108)

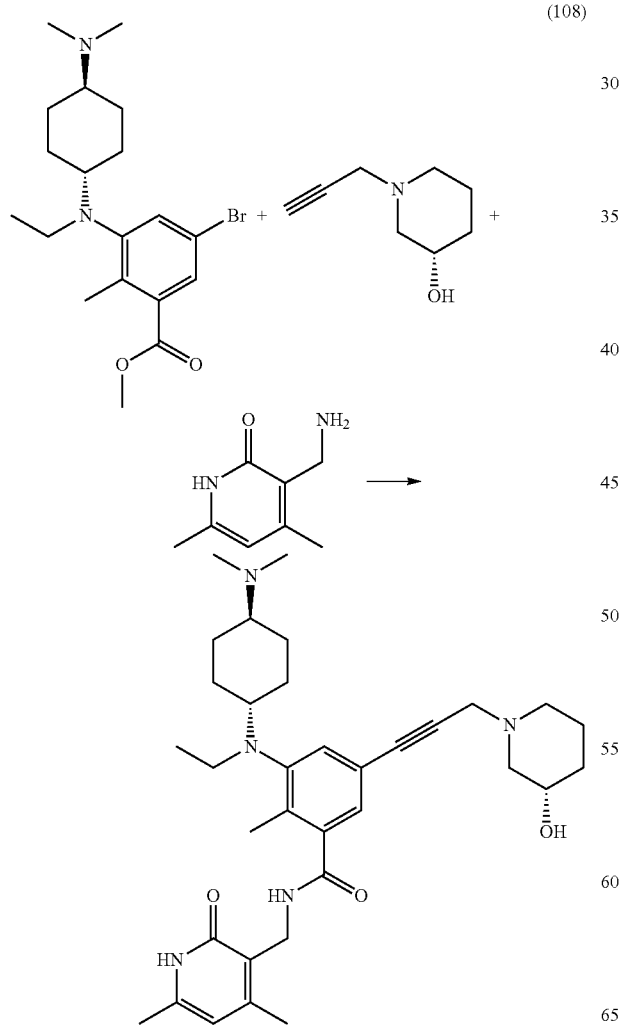

(109)

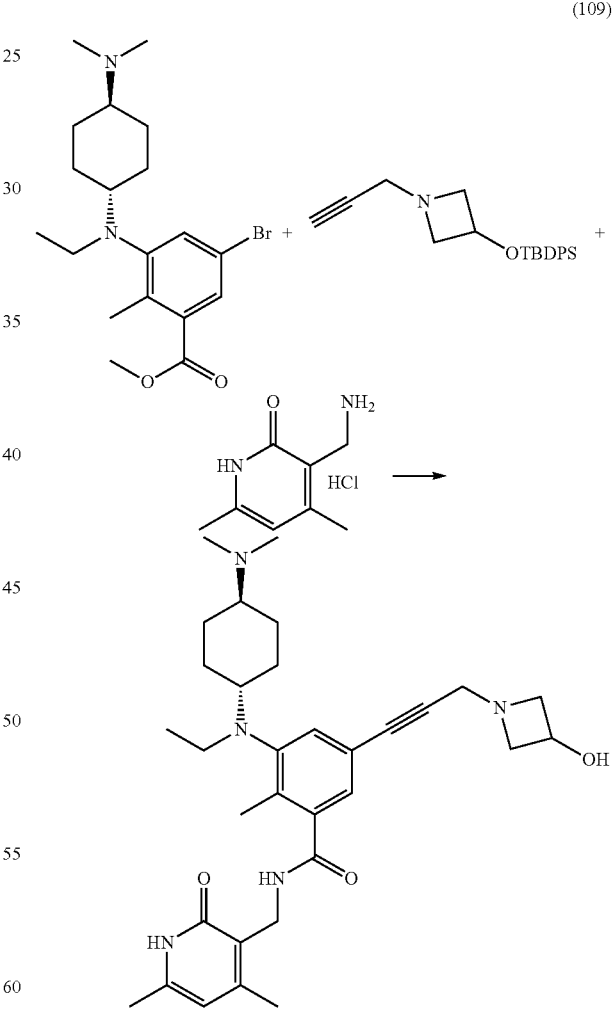

The titled compound were prepared (64.0 mg, 41% yield) in a similar manner as described for the preparation of 3-(((4-trans-(dimethylamino)cyclohexyl)(ethyl)amino)-5-(3-(3-hydroxyazetidin-1-yl)prop-1-yn-1-yl)-N-((4-isopropyl-6-methyl-2-oxo-1,2-dihydropyridin-3-yl)methyl)-2- methylbenzamide in three step sequences. The titled compound was purified by reverse phase HPLC/MS. ¹H-NMR (400 MHz, CD₃OD) δ ppm 7.22 (d, J=1.3 Hz, 1H), 7.08 (d, J=1.6 Hz, 1H), 6.07 (s, 1H), 4.42 (s, 2H), 4.32 (m, 1H), 3.58-3.62 (m, 2H), 3.48 (s, 2H), 3.12-3.16 (m, 2H), 3.04 (q, J=7.0 Hz, 2H), 2.60-2.69 (m, 1H), 2.34 (s, 3H), 2.23 (s, 3H), 2.22 (s, 6H), 2.21 (s, 3H), 2.13-2.20 (m, 1H), 1.84-1.90 (m, 4H), 1.34-1.44 (m, 2H), 1.10-1.22 (m, 2H), 0.80 (t, J=6.8 Hz, 3H). MS (ESI) [M+H]⁺ 548.7.

N-((4,6-Dimethyl-2-oxo-1,2-dihydropyridin-3-yl)methyl)-3-(ethyl(tetrahydro-2H-pyran-4-yl)amino)-2-methyl-5-(3-(piperidin-1-yl)prop-1-yn-1-yl)benzamide

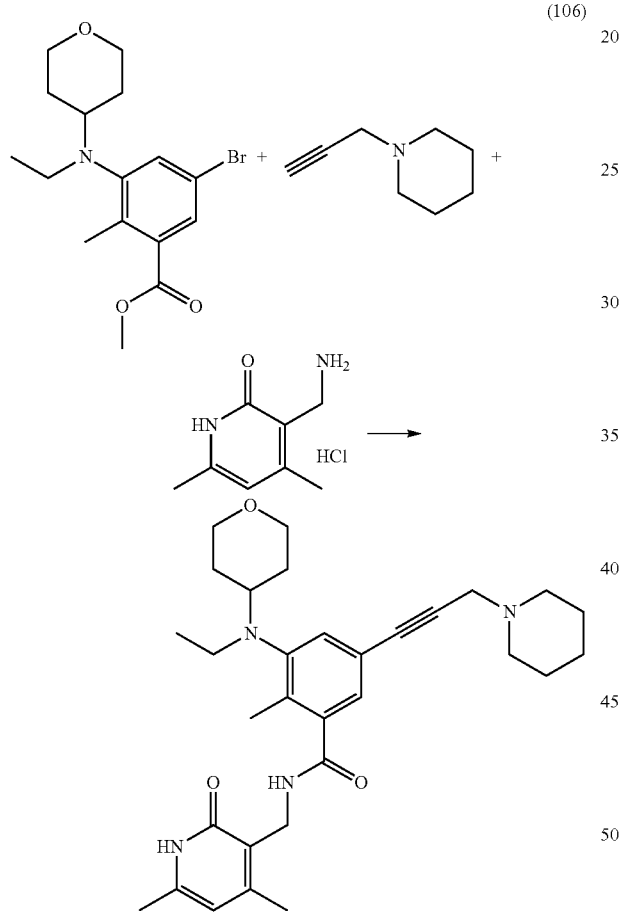

(106)

The titled compound were prepared (33.0 mg, 50% yield) in a similar manner as described for the preparation of 3-((4-trans-(dimethylamino)cyclohexyl)(ethyl)amino)-5-(3-(3-hydroxyazetidin-1-yl)prop-1-yn-1-yl)-N-((4-isopropyl-6-methyl-2-oxo-1,2-dihydropyridin-3-yl)methyl)-2-methyl-benzamide in three step sequences. The titled compound was purified by reverse phase HPLC/MS. ¹H-NMR (400 MHz, CD₃OD): δ ppm 7.26 (d, J=1.6 Hz, 1H), 7.10 (d, J=1.6 Hz, 1H), 6.10 (s, 1H), 4.45 (s, 2H), 3.90 (m, 2H), 3.46 (s, 2H), 3.35 (m, 2H), 3.10-2.98 (m, 3H), 2.60 (bs, 4H), 2.37 (s, 3H), 2.27 (s, 3H), 2.24 (s, 3H), 1.65 (m, 8H), 1.48 (bs, 2H), 0.84 (t, J=7.0 Hz, 3H); MS (ESI) [M+H]⁺ 519.4.

N-((4,6-Dimethyl-2-oxo-1,2-dihydropyridin-3-yl)methyl)-3-(ethyl(tetrahydro-2H-pyran-4-yl)amino)-2-methyl-5-(3-(pyrrolidin-1-yl)prop-1-yn-1-yl)benzamide

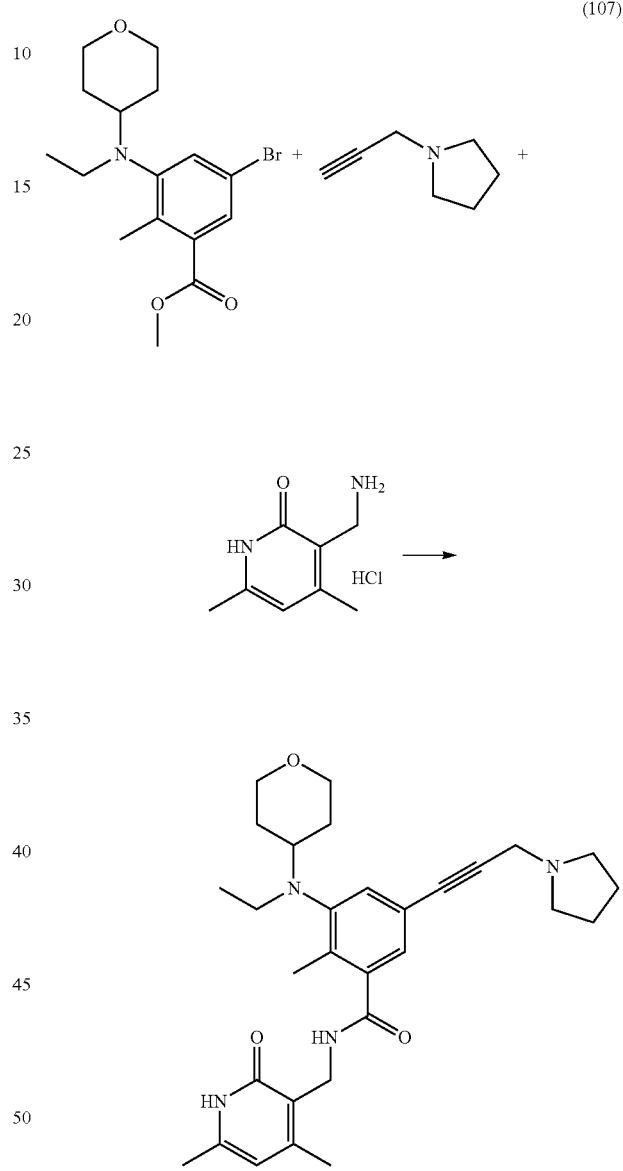

(107)

The titled compound were prepared (30.0 mg, 23% yield) in a similar manner as described for the preparation of 3-((4-trans-(dimethylamino)cyclohexyl)(ethyl)amino)-5-(3-(3-hydroxyazetidin-1-yl)prop-1-yn-1-yl)-N-((4-isopropyl-6-methyl-2-oxo-1,2-dihydropyridin-3-yl)methyl)-2-methyl-benzamide in three step sequences. The titled compound was purified by reverse phase HPLC/MS. ¹H-NMR (400 MHz, CD₃OD): δ ppm 7.25 (d, J=1.5 Hz, 1H), 7.10 (d, J=1.6 Hz, 1H), 6.10 (s, 1H), 4.44 (s, 2H), 3.90 (m, 2H), 3.60 (s, 2H), 3.34 (m, 2H), 3.10-2.98 (m, 3H), 2.71 (bs, 4H), 2.36 (s, 3H), 2.27 (s, 3H), 2.23 (s, 3H), 1.85 (m, 4H), 1.70-1.55 (m, 4H), 0.83 (t, J=6.8 Hz, 3H); MS (ESI) [M+H]⁺ 505.5.

295

5-(3-(4-(tert-Butyldiphenylsilyl)-3,5-cis-dimethyl-piperazin-1-yl)prop-1-yn-1-yl)-3-(ethyl(tetrahydro-2H-pyran-4-yl)amino)-N-((4-isopropyl-6-methyl-2-oxo-1,2-dihydropyridin-3-yl)methyl)-2-methylbenzamide

296

5-(3-(cis-3,5-Dimethylpiperazin-1-yl)prop-1-yn-1-yl)-3-(ethyl(tetrahydro-2H-pyran-4-yl)amino)-N-((4-isopropyl-6-methyl-2-oxo-1,2-dihydropyridin-3-yl)methyl)-2-methylbenzamide

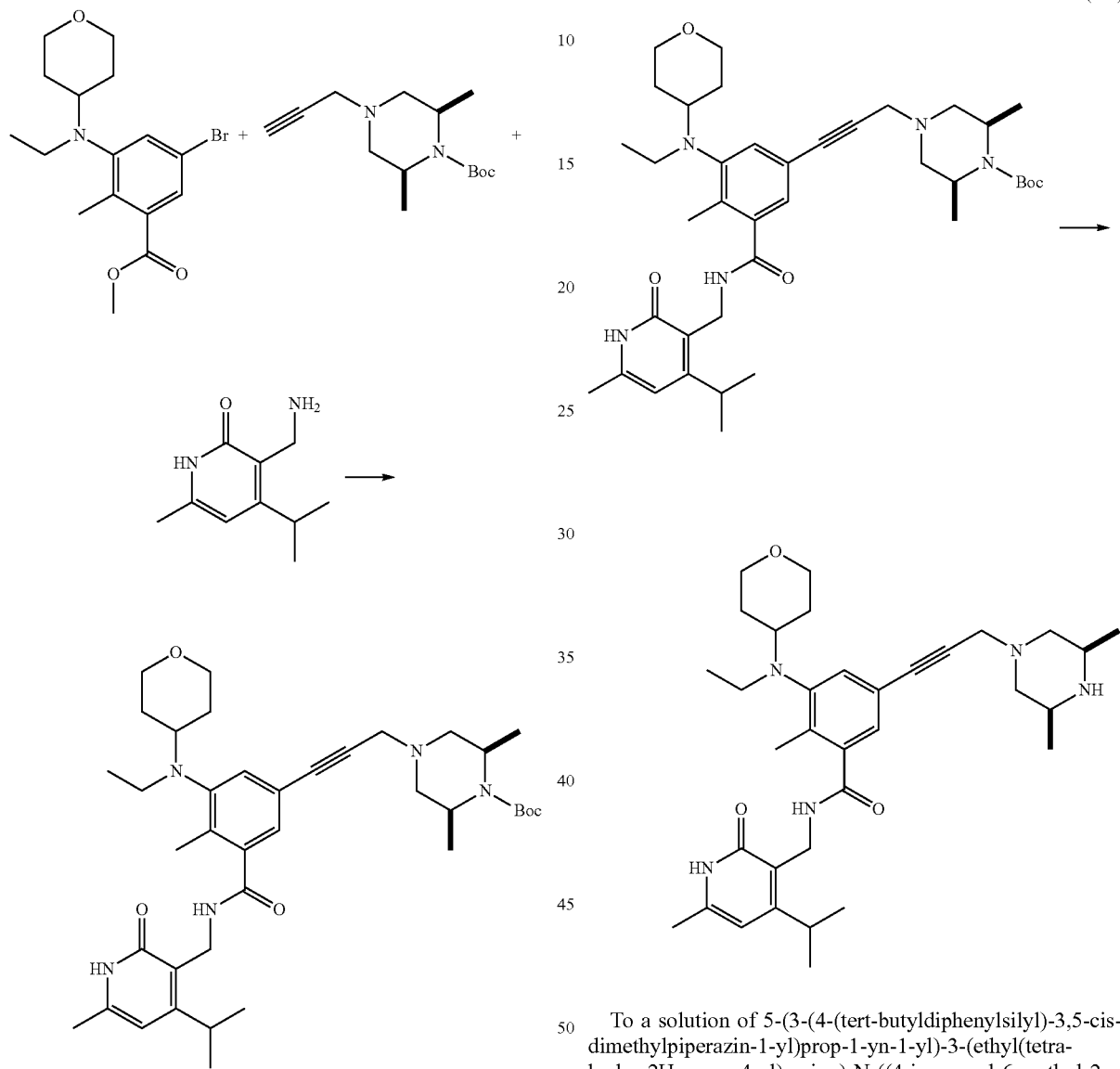

(101)

The titled compound were prepared (40.0 mg, 15% yield) in a similar manner as described for the preparation of 3-((4-trans-(dimethylamino)cyclohexyl)(ethyl)amino)-5-(3-(3-hydroxyazetidin-1-yl)prop-1-yn-1-yl)-N-((4-isopropyl-6-methyl-2-oxo-1,2-dihydropyridin-3-yl)methyl)-2-methylbenzamide in three step sequences. The titled compound was purified by reverse phase HPLC/MS. $^1$H-NMR (400 MHz, CD$_3$OD): δ ppm 7.25 (d, J=1.7 Hz, 1H), 7.09 (d, J=1.4 Hz, 1H), 6.23 (d, J=0.9 Hz, 1H), 4.50 (s, 2H), 4.09 (m 2H), 3.90 (m, 2H), 3.53 (s, 2H), 3.43 (m, 1H), 3.36 (m, 2H), 3.08 (t, J=6.9 Hz, 2H), 3.01 (m, 1H), 2.74 (m, 2H), 2.38 (dd, J=11.5, 4.1 Hz, 2H), 2.28 (s, 3H), 2.27 (s, 3H), 1.7-1.58 (m, 4H), 1.47 (s, 9H), 1.31 (d, J=6.7 Hz, 6H), 1.23 (d, J=6.9 Hz, 6H), 0.84 (t, J=6.9 Hz, 3H); MS (ESI) [M+H]$^+$ 676.7.

To a solution of 5-(3-(4-(tert-butyldiphenylsilyl)-3,5-cis-dimethylpiperazin-1-yl)prop-1-yn-1-yl)-3-(ethyl(tetrahydro-2H-pyran-4-yl)amino)-N-((4-isopropyl-6-methyl-2-oxo-1,2-dihydropyridin-3-yl)methyl)-2-methylbenzamide (40 mg, 0.059 mmol) in DCM (381 μL, 5.918 mmol) was added 4 M HCl in 1,4-dioxane (1480 μL, 5.918 mmol) at rt. The reaction was stirred at room temperature for 2 h. The reaction mixture was then concentrated and the residue was purified by reverse phase HPLC/MS to give the titled compound (33 mg, 97% yield). $^1$H-NMR (400 MHz, CD$_3$OD): δ ppm 7.27 (d, J=1.5 Hz, 1H), 7.11 (d, J=1.6 Hz, 1H), 6.23 (d, J=0.6 Hz, 1H), 4.50 (s, 2H), 3.91 (m, 2H), 3.52 (s, 2H), 3.44 (q, J=7.0 Hz, 1H), 3.34 (m, 2H), 3.07 (q, J=6.9 Hz, 2H), 3.01 (m, 1H), 2.98 (m, 2H), 2.86 (m, 2H), 2.28 (s, 3H), 2.27 (s, 3H), 1.95 (t, J=10.8 Hz, 2H), 1.70 (m, 2H), 1.60 (qd, J=12.7, 4.2 Hz, 2H), 1.23 (d, J=6.6 Hz, 6H), 1.09 (d, J=6.4 Hz, 6H), 0.84 (t, J=7.0 Hz, 3H); MS (ESI) [M+H]$^+$ 576.5.

tert-Butyl 4-((3-(ethyl(tetrahydro-2H-pyran-4-yl) amino)-5-(methoxycarbonyl)-4-methylphenyl)ethynyl)piperidine-1-carboxylate

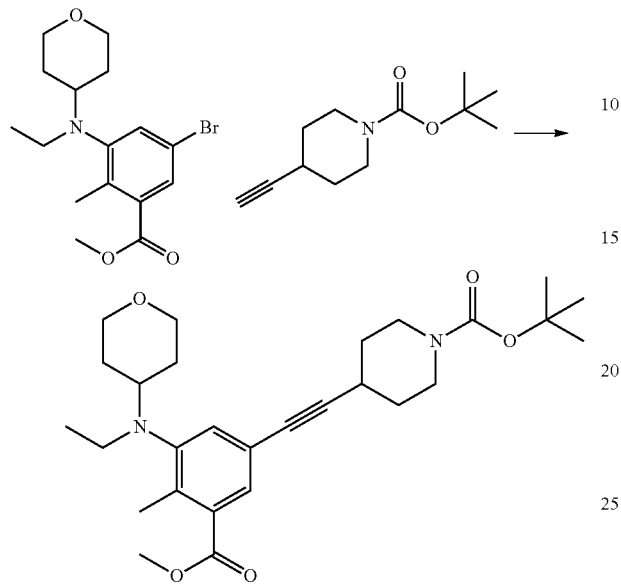

To a solution of methyl 5-bromo-3-(ethyl(tetrahydro-2H-pyran-4-yl)amino)-2-methylbenzoate (1.80 g, 5.05 mmol) and tert-butyl 4-ethynylpiperidine-1-carboxylate (1.80 g, 8.59 mmol) in DMF (40 ml) was added triethylamine (2.82 ml, 20.2 mmol) and Copper(I) iodide (0.096 g, 0.505 mmol). The reaction mixture was degassed by bubbling nitrogen for 15 min. Then tetrakis(triphenylphosphine)palladium(0) (0.292 g, 0.253 mmol) was introduced and degassed for additional 10 min by bubbling nitrogen. The reaction mixture was heated at 80° C. for 6 h. The reaction was quenched with sat. NaHCO3, extracted with TBME (3×40 mL), dried over Na2SO4, filtered and concentrated. The residue was purified by chromatography (0% to 40% AcOEt/Heptane) to give the titled compound (2.40 g, 98% yield). $^1$H-NMR (500 MHz) δ ppm; 7.65 (s, 1H), 7.28 (s, 1H), 3.97 (brd, J=11.3 Hz, 2H), 3.90 (s, 3H), 3.76 (m, 2H), 3.34 (dt, J=2.0, 11.7 Hz, 2H), 3.24 (ddd, J=3.4, 8.8, 12.2 Hz, 2H), 3.08 (brs, 2H), 2.98 (brs, 1H), 2.80 (dddd, J=3.9, 3.9, 3.9, 3.9 Hz, 1H), 2.52 (s, 3H), 1.87 (m, 2H), 1.60-1.74 (m, 6H), 1.48 (s, 9H), 0.89 (t, J=6.8 Hz, 3H)); MS (ESI) [M+H]$^+$ 485.4.

5-((1-(tert-Butoxycarbonyl)piperidin-4-yl)ethynyl)-3-(ethyl(tetrahydro-2H-pyran-4-yl)amino)-2-methylbenzoic acid

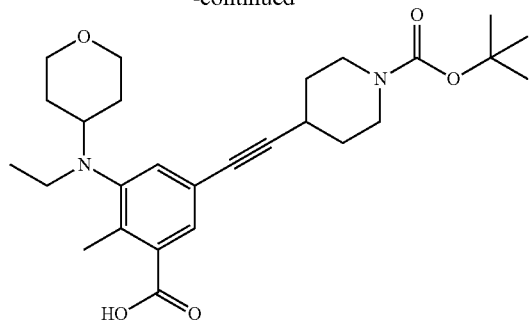

To a solution of tert-butyl 4-((3-(ethyl(tetrahydro-2H-pyran-4-yl)amino)-5-(methoxycarbonyl)-4-methylphenyl) ethynyl)piperidine-1-carboxylate (2.4 g, 4.95 mmol) in ethanol (20.0 mL) was added a solution of sodium hydroxide (0.565 g, 14.1 mmol) in water (3.0 ml) at rt. The reaction mixture was heated at 60° C. for 6 h. The reaction was quenched with 1 M HCl (5 mL) and then excess citric acid solution to adjust to the pH to 5. The mixture was concentrated to remove EtOH and the remaining aqueous phase was extracted with AcOEt (2×40 mL). The organic layers were combined, dried over Na$_2$SO$_4$, filtered and concentrated. The residue was purified by chromatography (10%-100% AcOEt/Heptane) to give the titled compound (2.30 g, 99% yield). $^1$H-NMR (500 MHz) δ ppm; 7.82 (s, 1H), 7.35 (s, 1H), 3.98 (brd, J=11.3 Hz, 2H), 3.77 (m, 2H), 3.35 (dt, J=1.5, 11.3 Hz, 2H), 3.25 (ddd, J=3.4, 8.3, 12.2 Hz, 2H), 3.11 (brs, 2H), 3.00 (brs, 1H), 2.81 (dddd, J=3.9, 3.9, 3.9, 3.9 Hz, 1H), 2.60 (s, 3H), 1.88 (m, 2H), 1.60-1.78 (m, 6H), 1.48 (s, 9H), 0.90 (t, J=6.8 Hz, 3H); MS (ESI) [M+H]$^+$ 471.4.

tert-Butyl 4-((3-(((4,6-dimethyl-2-oxo-1,2-dihydropyridin-3-yl)methyl)carbamoyl)-5-(ethyl(tetrahydro-2H-pyran-4-yl)amino)-4-methylphenyl)ethynyl)piperidine-1-carboxylate

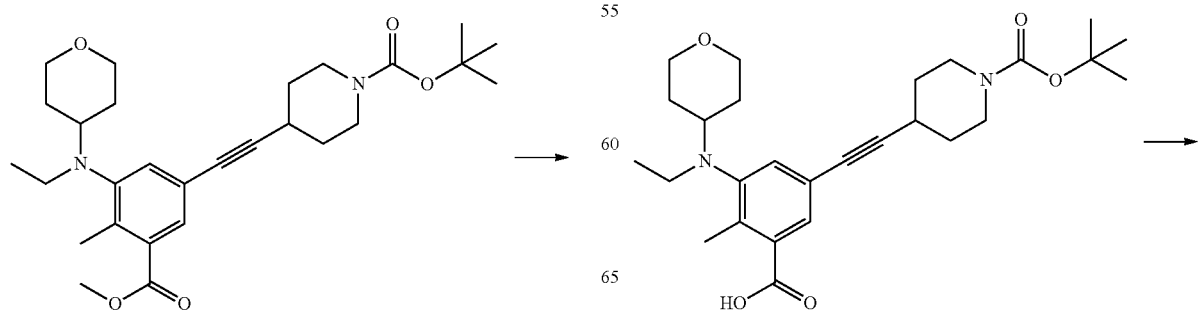

299
-continued

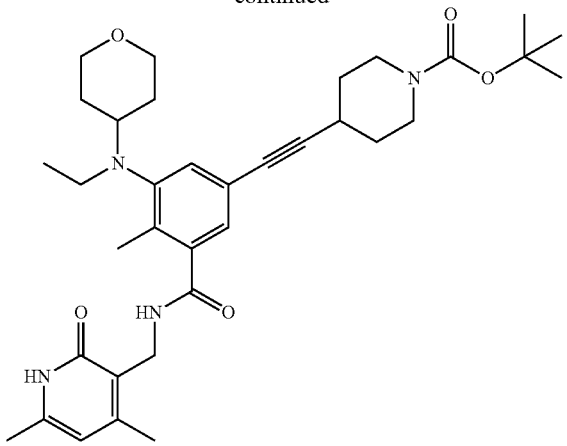

To a solution of 5-(((1-(tert-butoxycarbonyl)piperidin-4-yl)ethynyl)-3-(ethyl(tetrahydro-2H-pyran-4-yl)amino)-2-methylbenzoic acid (1.06 g, 2.25 mmol) in DMSO (5.8 mL) at it was added triethylamine (0.90 mL, 6.44 mmol) and (4,6-dimethyl-2-oxo-1,2-dihydropyridin-3-yl)methanaminium chloride (0.405 g, 2.15 mmol). The clear solution become heterogenous. Then HOBT (0.493 g, 3.22 mmol) and EDC (0.617 g, 3.22 mmol) were added and the resulting reaction mixture was stirred at rt overnight. The reaction was quenched with water (80 mL) and the slurry was stirred for 1 h at rt. The slurry was filtrated and the cake was washed with water (2×20 mL). The collected solid was dried under vacuum to give the titled compound (1.27 g, 98% yield). $^1$H-NMR (500 MHz, CD$_3$OD) δ ppm; 7.22 (s, 1H), 7.08 (d, J=1.0 Hz 1H), 6.11 (s, 1H), 4.45 (s, 2H), 3.92 (brd, J=10.8 Hz, 2H), 3.78 (dd, J=4.4, 5.4 Hz, 1H), 3.75 (dd, J=4.4, 5.4 Hz, 1H), 3.36 (t, J=11.7 Hz, 2H), 3.21 (br t, J=8.3 Hz, 2H), 3.07 (q, J=7.3 Hz, 2H), 3.01 (dddd, J=3.9, 3.9, 11.3, 11.3 Hz, 1H), 2.84 (dddd, J=3.4, 3.4. 3.9, 3.9 Hz, 1H), 2.38 (s, 3H), 2.28 (s, 3H), 2.25 (s, 3H), 1.88 (m, 2H), 1.70 ((brd, J=12.2 Hz, 2H), 1.60 (m, 4H), 1.47 (s, 9H), 0.87 (t, J=7.3 Hz, 3H); MS (ESI) [M+H]$^+$ 605.6.

tert-Butyl 4-((3-(ethyl(tetrahydro-2H-pyran-4-yl)amino)-5-(((4-isopropyl-6-methyl-2-oxo-1,2-dihydropyridin-3-yl)methyl)carbamoyl)-4-methylphenyl)ethynyl)piperidine-1-carboxylate

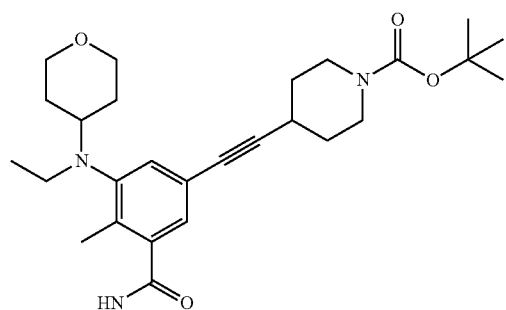

300
-continued

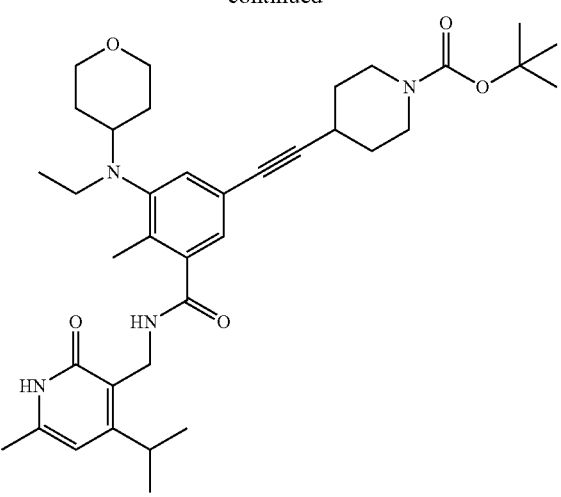

The titled compound were prepared (491 mg, 34% yield) in a similar manner as described for the preparation of 34(4-trans-(dimethylamino)cyclohexyl)(ethyl)amino)-5-(3-(3-hydroxyazetidin-1-yl)prop-1-yn-1-yl)-N-((4-isopropyl-6-methyl-2-oxo-1,2-dihydropyridin-3-yl)methyl)-2-methyl-benzamide. $^1$H-NMR (500 MHz, CD$_3$OD) δ ppm; 8.22 (t, J=4.9 Hz 1H), 7.22 (s, 1H), 7.06 (d, J=1.0 Hz 1H), 6.24 (s, 1H), 4.52 (d, J=4.4 Hz, 2H), 3.92 (br, d, J=10.8 Hz, 2H), 3.75 (m, 2H), 3.45 (m, 1H), 3.34 (t, J=11.7 Hz, 2H), 3.20 (br, d, J=10.3 Hz, 2H), 3.07 (q, J=7.3 Hz, 2H), 3.01 (m, 1H), 2.83 (m, 1H), 2.28 (s, 6H), 1.87 (m, 2H), 1.70 ((br, d, J=11.3 Hz, 2H), 1.60 (m, 4H), 1.47 (s, 9H), 1.24 (d, J=6.9 Hz, 6H), 0.85 (t, J=6.9 Hz, 3H); MS (ESI) [M+H]$^+$ 633.7.

3-(Ethyl(tetrahydro-2H-pyran-4-yl)amino)-N-((4-isopropyl-6-methyl-2-oxo-1,2-dihydropyridin-3-yl)methyl)-2-methyl-5-(piperidin-4-ylethynyl)benzamide

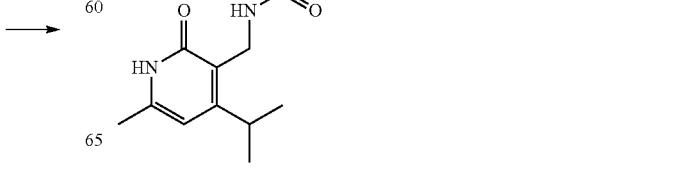

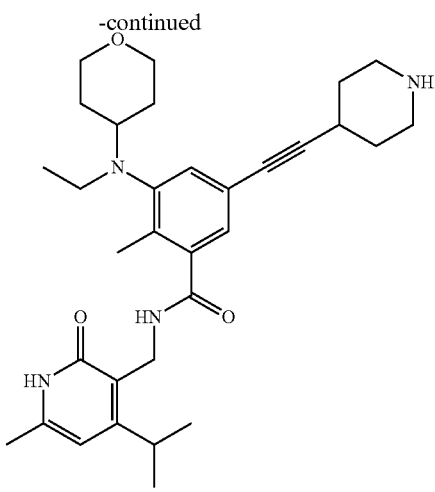
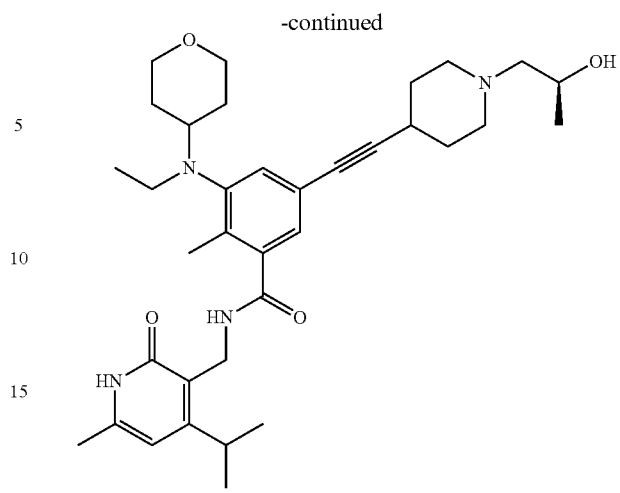

To a solution of tert-butyl 4-((3-(ethyl(tetrahydro-2H-pyran-4-yl)amino)-5-(((4-isopropyl-6-methyl-2-oxo-1,2-dihydropyridin-3-yl)methyl)carbamoyl)-4-methylphenyl)ethynyl)piperidine-1-carboxylate (212 mg, 0.335 mmol) in DCM (2 mL) at rt was added 4 M HCl in 1,4-dioxane (3 mL, 12.0 mmol) and the reaction mixture became cloudy. After stirring for 30 min, TLC (10% MeOH/DCM) showed reaction was done, Rf=0.5 for SM and Rf=0.3 for new spot. The mixture was concentrated, redissolved in DCM and washed with sat. Na$_2$SO$_4$. The aq. phase was extracted with 4×DCM until no more product was detected by TLC. The combined org. phase was dried (Na$_2$SO$_4$), filtered and concentrated to give the titled compound as a brownish solid (257 mg, 144% yield). Assume 100% yield of 178 mg and go next step reaction without further purification. HNMR and MS showed it is desired with some minor impurities. $^1$H-NMR (400 MHz, CD$_3$OD) δ ppm; 7.18 (d, J=1.5 Hz 1H), 7.03 (d, J=1.5 Hz, 1H), 6.20 (s, 1H), 4.47 (s, 2H), 3.88 (m, 2H), 3.45 (m, 1H), 3.31 (m, 2H), 2.93-3.15 (m, 5H), 2.79 (m, 3H), 2.24 (s, 6H), 1.98 (m, 3H), 1.40-1.75 (m, 6H), 1.19 (d, J=6.7 Hz, 6H), 0.81 (t, J=7.0 Hz, 3H); MS (ESI) [M+H]$^+$ 533.5.

(S)-3-(Ethyl(tetrahydro-2H-pyran-4-yl)amino)-5-((1-(2-hydroxypropyl)piperidin-4-yl)ethynyl)-N-((4-isopropyl-6-methyl-2-oxo-1,2-dihydropyridin-3-yl)methyl)-2-methylbenzamide To 3-(ethyl(tetrahydro-2H-pyran-4-yl)amino)-N-((4-isopropyl-6-methyl-2-oxo-1,2-dihydro pyridin-3-yl)methyl)-2-methyl-5-(piperidin-4-ylethynyl)benzamide (80 mg) in methanol (4.1 mL) was added (S)-2-methyloxirane (24 uL) in a sealed tube. The reaction mixture was heated at 65° C. for 3 hrs. The reaction mixture was concentrated in vacuo and the residue was purified by HPLC to give the titled compound (33.0 mg, 50% yield). $^1$H-NMR (500 MHz, CD$_3$OD) δ ppm; 7.21 (s, 1H), 7.06 (d, J=1.0 Hz, 1H), 6.24 (s, 2H), 4.50 (s, 2H), 3.94 (m, 1H), 3.92 (br, d, J=10.8 Hz, 2H), 3.46 (m, 1H), 3.35 (t, J=11.7 Hz, 2H), 3.07 (q, J=6.8 Hz, 2H), 3.01 (m, 1H), 2.90 (m, 1H), 2.84 (m, 1H), 2.64 (m, 1H), 2.3-2.42 (m, 3H), 2.28 (s, 6H), 1.94 (m, 2H), 1.67-1.80 (m, 4H), 1.60 (dq, J=4.4, 11.7 Hz, 2H), 1.24 (d, J=6.3 Hz, 6H), 1.15 (d, J=6.4 Hz, 3H), 0.85 (t, J=7.3 Hz, 3H); MS (ESI) [M+H]$^+$ 591.5.

(R)-3-(Ethyl(tetrahydro-2H-pyran-4-yl)amino)-5-((1-(2-hydroxypropyl)piperidin-4-yl)ethynyl)-N-((4-isopropyl-6-methyl-2-oxo-1,2-dihydropyridin-3-yl)methyl)-2-methylbenzamide

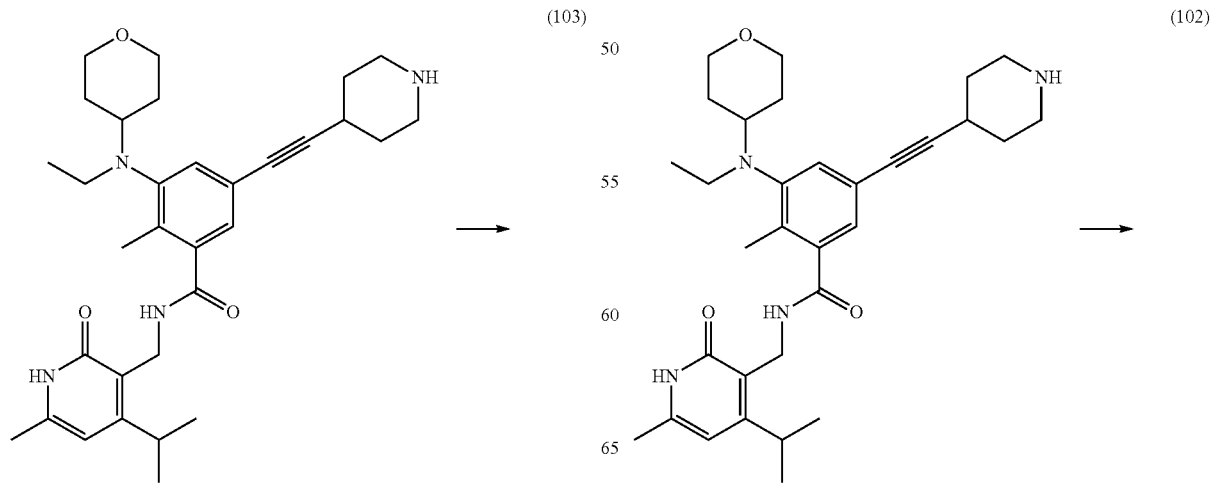

303
-continued

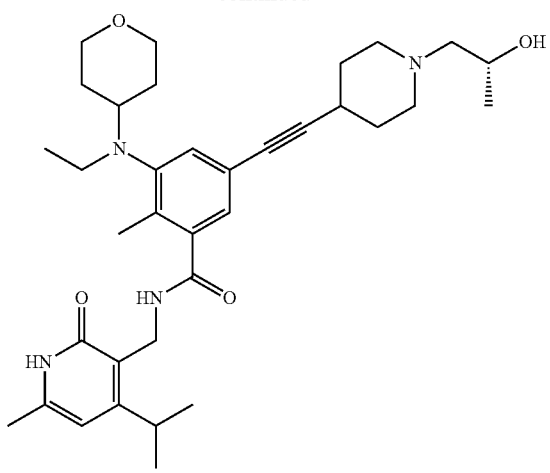

To 3-(ethyl(tetrahydro-2H-pyran-4-yl)amino)-N-((4-isopropyl-6-methyl-2-oxo-1,2-dihydro pyridin-3-yl)methyl)-2-methyl-5-(piperidin-4-ylethynyl)benzamide (80.0 mg) in methanol (4.1 mL) was added (R)-2-methyloxirane (24 μL) in a sealed tube. The reaction mixture was heated at 65° C. for 3 hrs. The reaction mixture was concentrated in vacuo and the residue was purified by HPLC to give the titled compound (33.0 mg, 50% yield). $^1$H-NMR (500 MHz, CD$_3$OD) δ ppm; 7.21 (d, J=1.0 Hz, 1H), 7.06 (d, J=1.0 Hz, 1H), 6.24 (s, 1H), 4.50 (s, 2H), 3.94 (m, 1H), 3.92 (br, d, J=10.8 Hz, 2H), 3.46 (m, 1H), 3.35 (t, J=11.7 Hz, 2H), 3.07 (q, J=6.8 Hz, 2H), 3.01 (m, 1H), 2.88 (m, 1H), 2.82 (m, 1H), 2.62 (m, 1H), 2.3-2.42 (m, 3H), 2.28 (s, 6H), 1.94 (m, 2H), 1.67-1.80 (m, 4H), 1.60 (dq, J=4.4, 11.7 Hz, 2H), 1.24 (d, J=6.9 Hz, 6H), 1.14 (d, J=5.9 Hz, 3H), 0.85 (t, J=6.9 Hz, 3H); MS (ESI) [M+H]$^+$ 591.6.

N-((4,6-Dimethyl-2-oxo-1,2-dihydropyridin-3-yl)methyl)-3-(ethyl(tetrahydro-2H-pyran-4-yl)amino)-2-methyl-5-(piperidin-4-ylethynyl)benzamide 304
-continued

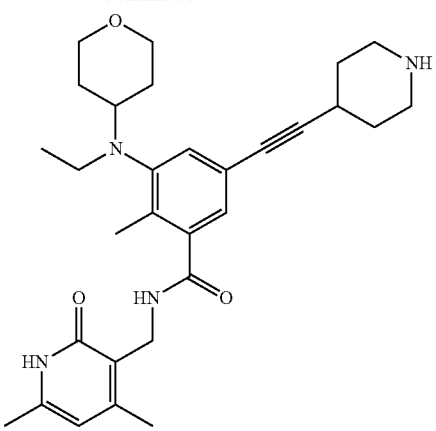

To a solution of tert-butyl 4-((3-(((4,6-dimethyl-2-oxo-1,2-dihydropyridin-3-yl)methyl)carbamoyl)-5-(ethyl(tetrahydro-2H-pyran-4-yl)amino)-4-methylphenyl)ethynyl)piperidine-1-carboxylate (250 mg, 0.413 mmol) in DCM (3 mL) was added 4M HCl in 1,4-dioxane (3 mL, 12.0 mmol) at 20° C. The mixture was stirred at 20° C. for 1 h. LCMS indicated that the reaction was completed. The reaction mixture was directly concentrated and the residue was dissolved in DCM and then neutralized with sat. NaHCO$_3$/brine. The organic layer was dried (Na$_2$SO$_4$) and filtered. And the filtrate was concentrated. The residue was used for alkylation without further purification (209 mg, 100%). $^1$H-NMR (500 MHz, CD$_3$OD) δ ppm 7.21 (bs, 1H), 7.07 (bs, 1H), 6.11 (s, 1H), 4.46 (s, 2H), 3.95-3.89 (m, 2H), 3.39-3.34 (m, 2H), 3.08 (q, J=7.0 Hz, 2H), 3.06-2.98 (m, 3H), 2.79-2.72 (m, 1H), 2.72-2.65 (m, 2H), 2.38 (s, 3H), 2.28 (s, 3H), 2.25 (s, 3H), 1.94-1.88 (m, 2H), 1.73-1.68 (m, 2H), 1.68-1.56 (m, 4H), 0.85 (t, J=7.0 Hz, 3H); MS (ESI) [M+H]$^+$ 505.5.

N-((4,6-Dimethyl-2-oxo-1,2-dihydropyridin-3-yl)methyl)-3-(ethyl(tetrahydro-2H-pyran-4-yl)amino)-2-methyl-5-((1-methylpiperidin-4-yl)ethynyl)benzamide

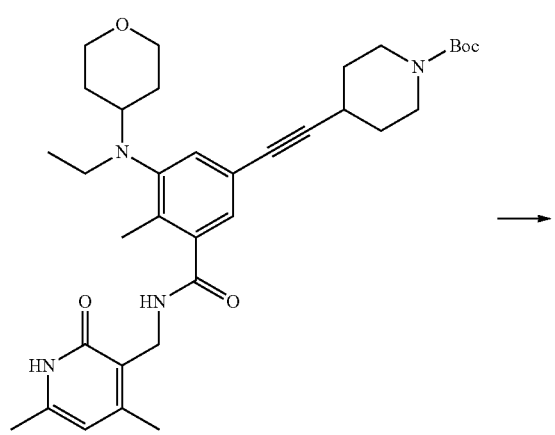

(105)

305

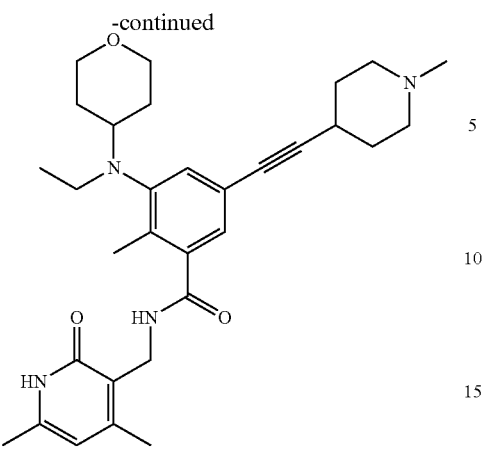

To a solution of N-((4,6-dimethyl-2-oxo-1,2-dihydropyridin-3-yl)methyl)-3-(ethyl(tetrahydro-2H-pyran-4-yl)amino)-2-methyl-5-(piperidin-4-ylethynyl)benzamide (100 mg, 0.198 mmol) in methanol (5 mL) was added 35% formaldehyde in H$_2$O (0.155 mL, 1.98 mmol) at 0° C. After stirring at 0° C. for 10 min, sodium cyanoborohydride (24.9 mg, 0.396 mmol) was added. The resulting mixture was stirred at 0° C. for 1 h. LCMS indicated that the reaction was completed. The reaction was quenched with sat. NaHCO$_3$/brine and extracted with EtAOc/Heptane. The organic layer was dried (Na$_2$SO$_4$), filtered and concentrated. The residue was purified by chromatography (10 g column, MeOH/DCM=1:9, and then MeOH/7 M NH$_3$ in MeOH/DCM=1:1:8) to afford the titled compound (96.0 mg, 93%). $^1$H-NMR (500 MHz, CD$_3$OD) δ ppm 7.22 (bs, 1H), 7.08 (bs, 1H), 6.10 (s, 1H), 4.46 (s, 2H), 3.94-3.87 (m, 2H), 3.35-3.30 (m, 2H), 3.07 (q, J=7.0 Hz, 2H), 3.04-2.97 (m, 1H), 2.79-2.71 (m, 2H), 2.67-2.58 (m, 1H), 2.38 (s, 3H), 2.28 (s, 3H), 2.28 (s, 3H), 2.25 (s, 3H), 2.28-2.21 (m, 2H), 1.97-1.91 (m, 2H), 1.78-1.67 (m, 4H), 1.64-1.54 (m, 2H), 0.85 (t, J=7.0 Hz, 3H); MS (ESI) [M+H]$^+$ 519.4.

N-((4,6-Dimethyl-2-oxo-1,2-dihydropyridin-3-yl)methyl)-3-(ethyl(tetrahydro-2H-pyran-4-yl)amino)-5-((1-ethylpiperidin-4-yl)ethynyl)-2-methylbenzamide (104)

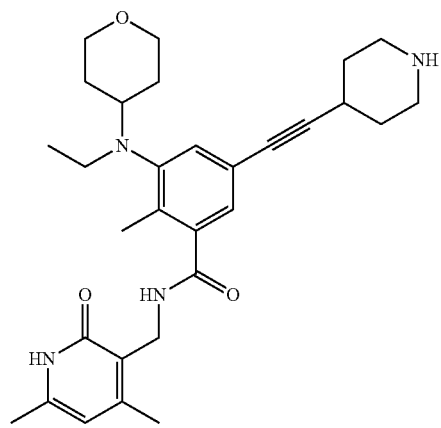

306

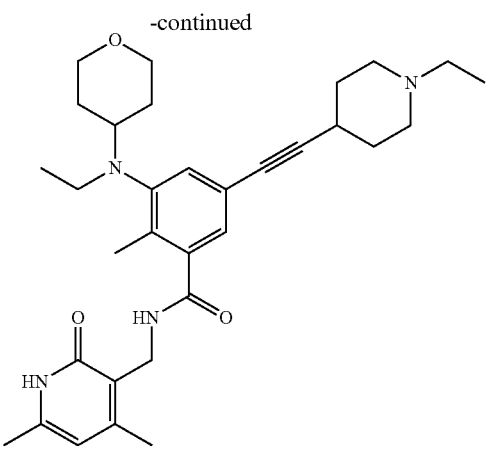

To a pear flask with N-((4,6-Dimethyl-2-oxo-1,2-dihydropyridin-3-yl)methyl)-3-(ethyl(tetrahydro-2H-pyran-4-yl)amino)-2-methyl-5-(piperidin-4-ylethynyl)benzamide (100 mg, 0.198 mmol) in methanol (5 mL, 124 mmol) was added acetaldehyde (0.112 mL, 1.98 mmol) at 0° C. After stirring at 0° C. for 10 min, sodium cyanobororhydride (24.9 mg, 0.396 mmol) was added. The mixture was stirred at 0° C. for 1 h. MS indicated that the reaction was completed. The reaction was quenched with sat. NaHCO$_3$/brine and extracted with EtAOc/Hept. The organic layer was dried (Na$_2$SO$_4$), filtered and concentrated. The residue was purified chromatography (10.0 g column, MeOH/DCM=1:9, then MeOH/7 M NH$_3$ in MeOH/DCM=1:1:8) to afford the titled compound (90.0 mg, 85%). $^1$H-NMR (500 MHz, CD$_3$OD) δ ppm 7.21 (s, 1H), 7.07 (s, 1H), 6.11 (s, 1H), 4.46 (s, 2H), 3.95-3.88 (m, 2H), 3.37-3.33 (m, 2H), 3.07 (q, J=7.0 Hz, 2H), 3.05-2.98 (m, 1H), 2.87-2.78 (m, 2H), 2.69-2.61 (m, 1H), 2.45 (q, J=7.0 Hz, 2H), 2.38 (s, 3H), 2.28 (s, 3H), 2.25 (s, 3H), 2.28-2.20 (m, 2H), 1.99-1.93 (m, 2H), 1.79-1.67 (m, 4H), 1.64-1.55 (m, 2H), 1.11 (t, J=7.0 Hz, 3H), 0.85 (t, J=7.0 Hz, 3H); MS (ESI) [M+H]$^+$ 533. 5.

tert-Butyl 4-((5-bromo-3-(methoxycarbonyl)-2-methylphenyl)amino)piperidine-1-carboxylate

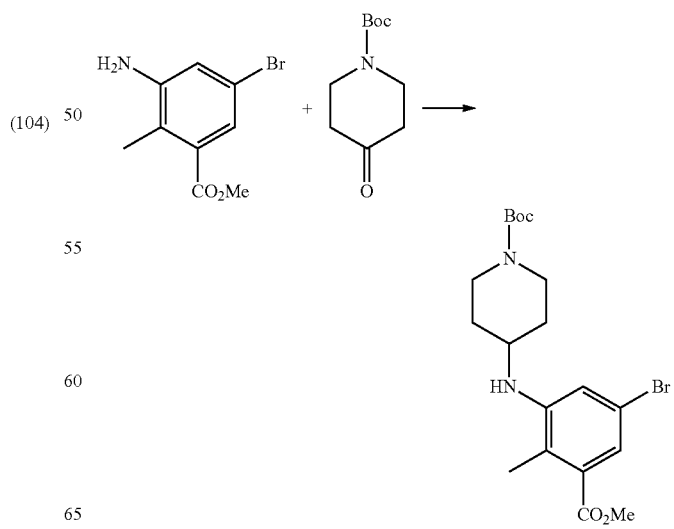

307

The titled compound were prepared (1.75, 68% yield) in a similar manner as described for the preparation of tert-butyl 4-((3-(methoxycarbonyl)-2-methyl-5-(trifluoromethyl)phenyl)amino)piperidine-1-carboxylate. ¹H-NMR (500 MHz) δ ppm 7.25 (s, 1H), 6.85 (s, 1H), 4.05 (br, 2H), 3.88 (s, 3H), 3.49-3.41 (m, 1H), 2.98 (t, J=10 Hz, 2H), 2.23 (s, 3H), 2.09-2.02 (m, 2H), 1.48 (s, 9H), 1.44-1.34 (m, 2H); MS (ESI) [M+H]⁺ 427.2, 429.2.

tert-Butyl 4-((5-bromo-3-(methoxycarbonyl)-2-methylphenyl)(ethyl)amino)piperidine-1-carboxylate

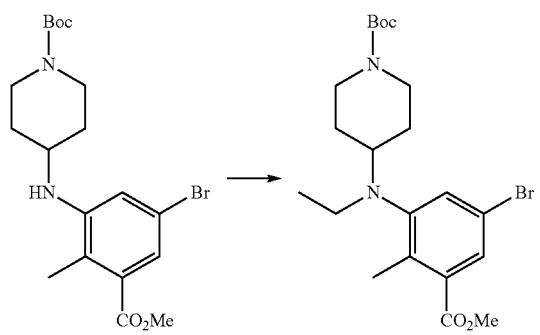 [SMILES: COC(=O)c1cc(Br)cc(NC2CCN(C(=O)OC(C)(C)C)CC2)c1C ; CCN(c1cc(Br)cc(C(=O)OC)c1C)C1CCN(C(=O)OC(C)(C)C)CC1]

The titled compound were prepared (1.28 g, 87% yield) in a similar manner as described for the preparation of tert-butyl 4-(ethyl(3-(methoxycarbonyl)-2-methyl-5-(trifluoromethyl)phenyl)amino)piperidine-1-carboxylate. ¹H-NMR (500 MHz) δ ppm 7.71 (d, J 2.0 Hz, 1H), 7.36 (d, J=2.0 Hz, 1H), 4.05 (br, 2H), 3.90 (s, 3H), 3.04 (q, J=6.5 Hz, 2H), 2.90-2.84 (m, 1H), 2.70 (t, J=12.5 Hz, 2H), 2.45 (s, 3H), 1.78-1.70 (m, 2H), 1.55-1.47 (m, 2H), 1.46 (s, 9H), 0.89 (t, J=6.5 Hz, 3H) MS (ESI) [M+H]⁺ 455.3, 457.3.

5-Bromo-3-((1-(tert-butoxycarbonyl)piperidin-4-yl)(ethyl)amino)-2-methylbenzoic acid

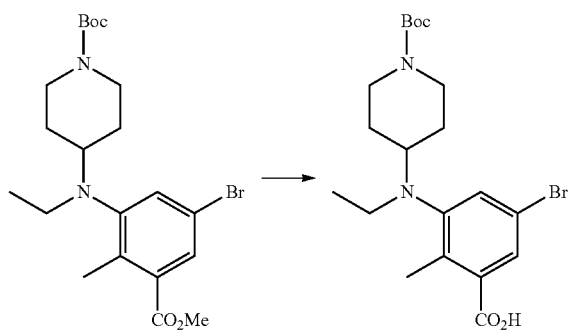 [SMILES: CCN(c1cc(Br)cc(C(=O)OC)c1C)C1CCN(C(=O)OC(C)(C)C)CC1 ; CCN(c1cc(Br)cc(C(=O)O)c1C)C1CCN(C(=O)OC(C)(C)C)CC1]

The titled compound were prepared (1.07 g, 100% yield) in a similar manner as described for the preparation of 3-[ethyl(1-methylpiperidin-4-yl)amino]-2-methyl-5-(trifluoromethyl)benzoic acid. ¹H-NMR (500 MHz) δ ppm 7.81 (d, J=2.0 Hz, 1H), 7.36 (d, J=2.0 Hz, 1H), 4.03 (m, 2H), 3.02 (q, J=7.0 Hz, 2H), 2.89-2.83 (m, 1H), 2.73-2.66 (m, 2H), 2.47 (s, 3H), 1.77-1.70 (m, 2H), 1.53-1.45 (m, 2H), 1.43 (s, 9H), 0.85 (t, J=7.0 Hz, 3H); MS (ESI) [M+H]⁺ 441.3, 443.3.

308 tert-Butyl-4-((5-bromo-3-(((4,6-dimethyl-2-oxo-1,2-dihydropyridin-3-yl)methyl)carbamoyl)-2-methylphenyl)(ethyl)amino)piperidine-1-carboxylate

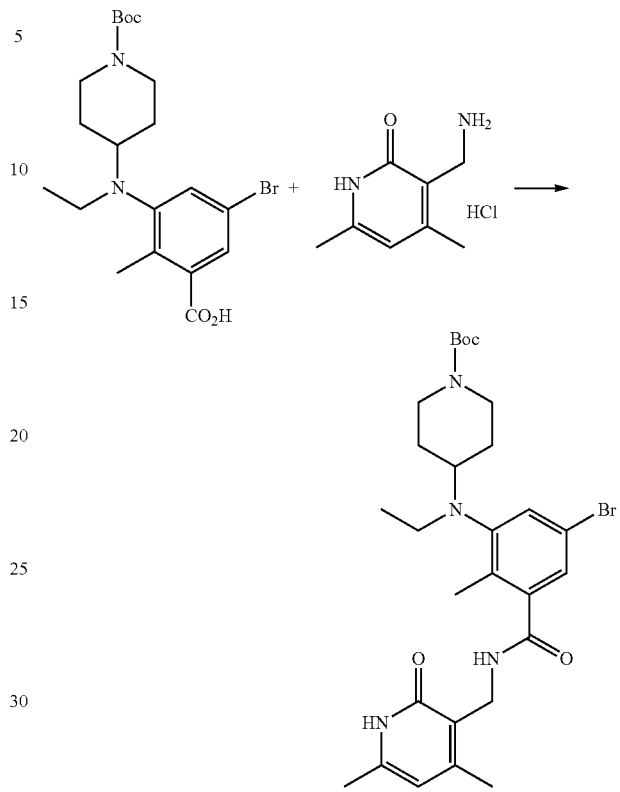

The titled compound was prepared (1.10 g, 77% yield) following the same procedure for the preparation of N-[(4,6-dimethyl-2-oxo-1,2-dihydropyridin-3-yl)methyl]-3-[ethyl(1-methylpiperidin-4-yl)amino]-2-methyl-5-(trifluoromethyl)benzamide. ¹H-NMR (500 MHz) δ ppm 7.36 (d, J=2.0 Hz, 1H), 7.21 (d, J=2.0 Hz, 1H), 6.11 (s, 1H), 4.46 (s, 2H), 4.04-3.98 (m, 2H), 3.07 (q, J=7.0 Hz, 2H), 3.01-2.94 (m, 1H), 2.80-2.70 (m, 2H), 2.38 (s, 3H), 2.25 (s, 3H), 2.23 (s, 3H), 1.78-1.72 (m, 2H), 1.52-1.46 (m, 2H, 1.45 (s, 9H), 0.86 (t, J=7.0 Hz, 3H); MS (ESI) [M+H]⁺ 575.4, 7.4.

5-Bromo-N-((4,6-dimethyl-2-oxo-1,2-dihydropyridin-3-yl)methyl)-3-(ethyl(piperidin-4-yl)amino)-2-methylbenzamide

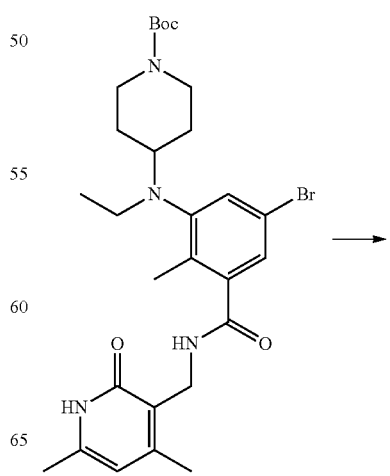

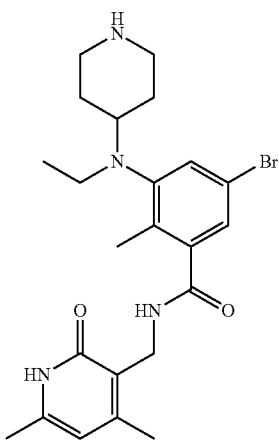

The titled compound was prepared (413 mg, 100% yield) following a similar procedure for the preparation of 3-((2,6-trans-dimethylpiperidin-4-yl)(ethyl)amino)-5-fluoro-N-((5-fluoro-1,4,6-trimethyl-2-oxo-1,2-dihydropyridin-3-yl)methyl)-2-methylbenzamide hydrochloride followed by silica gel chromatography purification (10% 7N NH$_3$ in MeOH/DCM). $^1$H-NMR (500 MHz, CD$_3$OD) δ ppm 7.33 (d, J=2.0 Hz, 1H), 7.19 (d, J=2.0 Hz, 1H), 6.10 (s, 1H), 4.45 (s, 2H), 3.09 (q, J=7.5 Hz, 2H), 3.05-2.99 (m, 2H), 2.90-2.83 (m, 1H), 2.52-2.45 (m, 2H), 2.37 (s, 3H), 2.25 (s, 3H), 2.24 (s, 3H), 1.78-1.72 (m, 2H), 1.58-1.49 (m, 2H), 0.86 (t, J=7.5 Hz, 3H); MS (ESI) [M+H]$^+$ 475.3, 477.4.

5-Bromo-N-((4,6-dimethyl-2-oxo-1,2-dihydropyridin-3-yl)methyl)-3-(ethyl(1-methylpiperidin-4-yl)amino)-2-methylbenzamide

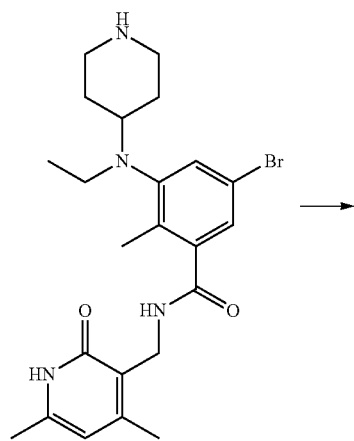

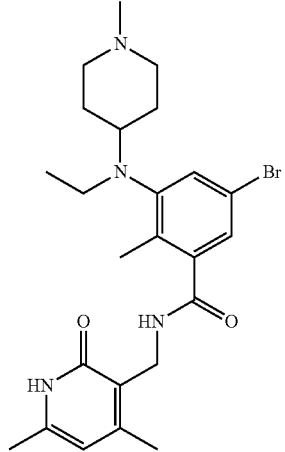

The titled compound was prepared (400 mg, 84% yield) following a similar procedure for the preparation of methyl 3-[ethyl(1-methylpiperidin-4-yl)amino]-2-methyl-5-(trifluoromethyl)benzoate. $^1$H-NMR (500 MHz, CD$_3$OD) δ ppm 7.35 (d, J=2.0 Hz, 1H), 7.20 (d, J=2.0 Hz, 1H), 6.12 (s, 1H), 4.46 (s, 2H), 3.08 (q, J=7.0 Hz, 2H), 2.90-2.84 (m, 2H), 2.85-2.79 (m, 1H), 2.37 (s, 3H), 2.26 (s, 3H), 2.25 (s, 3H), 2.23 (s, 3H), 2.08-2.01 (m, 2H), 1.80-1.74 (m, 2H), 1.71-1.62 (m, 2H), 0.86 (t, J=7.0 Hz, 3H); MS (ESI) [M+H]$^+$ 489.3, 491.4.

N-((4,6-Dimethyl-2-oxo-1,2-dihydropyridin-3-yl)methyl)-3-(ethyl(1-methylpiperidin-4-yl)amino)-2-methyl-5-(6-(4-methylpiperazin-1-yl)pyridin-3-yl)benzamide (125)

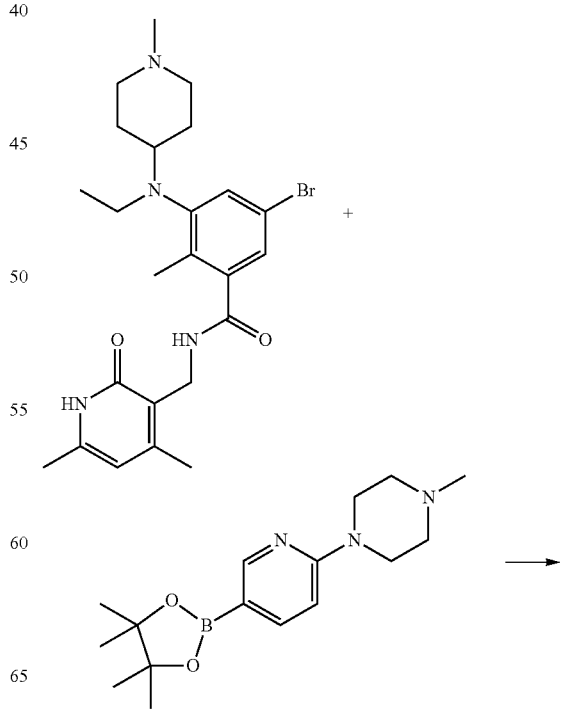

311
-continued

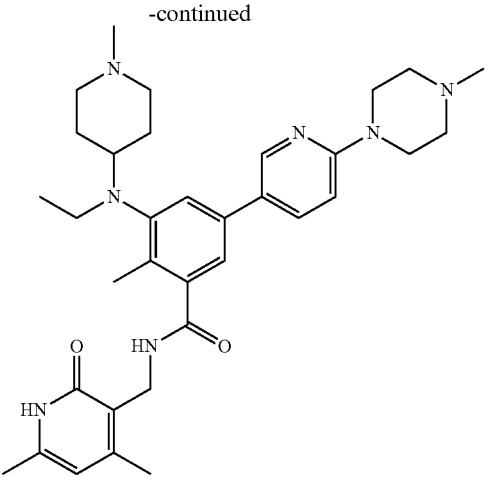

The titled compound were obtained (34.0 mg, 28% yield) following a similar procedure for the preparation of tert-butyl 4-((3-(((4,6-dimethyl-2-oxo-1,2-dihydropyridin-3-yl)methyl)carbamoyl)-5-(6-methoxypyridin-3-yl)-2-methylphenyl)(ethyl)amino)-2,6-trans-dimethylpiperidine-1-carboxylate. $^1$H-NMR (500 MHz, CD$_3$OD) δ ppm 8.33 (d, J=2.5 Hz, 1H), 7.81 (dd, J=8.8, 2.5 Hz, 1H), 7.40 (d, J=2.0 Hz, 1H), 7.26 (d, J=2.0 Hz, 1H), 6.90 (d, J=8.8 Hz, 1H), 6.12 (s, 1H), 4.50 (s, 2H), 3.62-3.57 (m, 4H), 3.15 (q, J=7.0 Hz, 2H), 2.94-2.89 (m, 1H), 2.892.84 (m, 2H), 2.60-2.56 (m, 4H), 2.40 (s, 3H), 2.36 (s, 3H), 2.31 (s, 3H), 2.26 (s, 3H), 2.25 (s, 3H), 2.10-2.03 (m, 2H), 1.86-1.80 (m, 2H), 1.75-1.66 (m, 2H), 0.90 (t, J=7.0 Hz, 3H); MS (ESI) [M+H]$^+$ 586.6.

Compounds 157-163 were synthesized by the methods similar to those described above. The analytical data for Compounds 157-163 are provided below.

Compound 157: LCMS: 545.5 (M+1)$^+$; TFA-salt: $^1$H NMR (DMSO-d$_6$, 400 MHz) δ 11.48 (brs, 1H), 8.96 (brs, 1H), 8.17 (s, 1H), 7.38-7.08 (m, 1H), 6.96 (s, 1H), 5.87 (s, 2H), 4.35 (s, 2H), 3.82 (d, 2H, J=10.4 Hz), 3.51 (t, 2H, J=10.4 Hz), 3.41-3.29 (m, 1H), 3.27-3.06 (m, 4H), 3.05-2.89 (m, 3H), 2.88-2.76 (m, 1H), 2.19 (s, 6H), 2.11 (s, 3H), 1.96 (m, 2H), 1.72 (q, 1H, J=12 Hz), 1.65-1.41 (m, 4H), 0.93 (brs, 2H), 0.85-0.73 (m, 5H).

Compound 158: LCMS: 559.6 (M+1)$^+$; TFA-salt: NMR (DMSO-d$_6$, 400 MHz) δ 11.47 (brs, 1H), 9.36 (m, 1H), 8.17 (brs, 1H), 7.23-7.07 (m, 1H), 6.97 (s, 1H), 5.87 (s, 1H), 4.24 (m, 2H), 3.84 (d, 2H, J=12.0 Hz), 3.61 (q, 1H, J=8.0 Hz), 3.40-3.18 (m, 4H), 3.10-2.88 (m, 3H), 2.87-2.21 (m, 2H), 2.25-2.09 (m, 14H), 1.93 (m, 2H), 1.79-1.49 (m, 7H), 0.78 (t, 3H, J=6.8 Hz).

Compound 159: LCMS: 561.5 (M+1)$^+$; TFA-salt: $^1$H NMR (DMSO-d$_6$, 400 MHz) δ 11.48 (brs, 1H), 10.41 (brs, 1H), 8.17 (s, 1H), 7.25-7.05 (m, 2H), 6.97 (s, 1H), 5.87 (s, 1H), 4.73 (d, 4H, J=6.4 Hz), 4.35 (s, 1H), 4.25 (d, 2H, J=5.2 Hz), 3.82 (d, 2H, J=10.4 Hz), 3.47-3.30 (m, 2H), 3.20 (t, 2H, J=10.4 Hz), 3.13-2.78 (m, 6H), 2.19 (s, 6H), 2.11 (s, 3H), 2.03 (m, 2H), 1.78 (q, 1H, J=12 Hz), 1.68-1.40 (m, 4H), 0.78 (t, 3H, J=6.8 Hz).

Compound 160: LCMS: 588.7 (M+1)$^+$; $^1$H NMR (DMSO-d$_6$, 400 MHz) δ 11.45 (brs, 1H), 8.15 (m, 1H), 7.09 (s, 1H), 6.92 (s, 1H), 5.85 (s, 1H), 4.24 (d, 2H, J=4.8 Hz), 3.92-3.83 (m, 1H), 3.70-3.62 (m, 1H), 3.38 (q, 1H, J=7.2 Hz), 3.35-3.20 (m, 1H), 3.17-30.6 (m, 1H), 3.00 (q, 2H, J=7.2), 2.93-2.84 (m, 1H), 2.18 (d, 2H, J=6.8 Hz), 2.22-207 (m, 15H), 1.99 (s, 3H), 1.90-1.70 (m, 6H), 1.64-1.42 (m, 2H), 1.34 (q, 2H, J=12.0 Hz), 1.17-1.05 (m, 2H), 0.76 (t, 3H, J=6.8 Hz).

Compound 161: LCMS: 628.6 (M+1)$^+$; $^1$H NMR (DMSO-d$_6$, 400 MHz) δ 11.46 (brs, 1H), 8.16 (t, 1H, 4.8 Hz), 7.08 (s, 1H), 6.9 (s, 1H), 5.85 (s, 1H), 4.24 (d, 2H, J=4.8 Hz), 3.16 (q, 2H, J=10.4 Hz), 2.99 (q, 2H, 6.8 Hz), 2.89-2.70 (m, 2H), 2.68-2.53 (m, 4H), 2.48-2.45 (m, 1H), 2.20-2.03 (m, 15H), 1.89-1.70 (m, 6H), 1.65-1.54 (m, 2H), 1.40-1.36 (m, 2H), 1.11 (q, 2H, J=11.2 Hz), 0.76 (t, 3H, J=6.8 Hz).

Compound 162: LCMS: 574.5 (M+1)$^+$; TFA-salt: $^1$H NMR (DMSO-d$_6$, 400 MHz) δ 11.48 (brs, 1H), 10.4-9.90 (m, 1H), 8.16 (s, 1H), 7.16 (s, 1H), 7.01 (s, 1H), 5.87 (s, 2H), 4.43 (brs, 2H), 4.25 (d, 2H, J=4.4 Hz), 4.25-3.97 (m, 4H), 3.82 (d, 2H, J=8.0 Hz), 3.23 (t, 2H, J=11.2 Hz), 3.20-2.95 (m, 4H), (2.95-2.73 (m, 4H), 2.19 (s, 6H), 2.11-1.99 (m, 5H), 1.80 (brs, 2H), 1.65-1.40 (m, 4H), 0.78 (t, 3H, J=6.8 Hz).

Compound 163: LCMS: 535.5 (M+1)$^+$; TFA-salt: $^1$H NMR (DMSO-d$_6$, 400 MHz) δ 8.32 (s, 2H), 7.95 (t, 1H, J=4.4 Hz), 7.11 (s, 1H), 6.93 (s, 1H), 6.09 (s, 1H), 4.19 (d, 2H, J=4.4 Hz), 3.83 (brs, 2H), 3.80 (s, 3H), 3.23 (t, 2H, J=10.8 Hz), 2.99 (q, 2H, 1=7.2 Hz), 2.97-2.89 (m, 1H), 2.68-2.52 (m, 2H), 2.22-2.15 (m, 9H), 2.13-2.03 (m, 2H), 1.88-1.68 (m, 2H), 1.65-1.54 (m, 4H), 1.53-1.42 (m, 2H), 0.77 (t, 3H, 1=6.8 Hz).

Example 2

Bioassay Protocol and General Methods

Protocol for Wild-Type and Mutant PRC2 Enzyme Assays

General Materials. S-adenosylmethionine (SAM), S-adenosylhomocyteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol. 384-well streptavidin Flashplates were purchased from PerkinElmer.

Substrates. Peptides representative of human histone H3 residues 21-44 containing either an unmodified lysine 27 (H3K27me0) or dimethylated lysine 27 (H3K27me2) were synthesized with a C-terminal G(K-biotin) linker-affinity tag motif and a C-terminal amide cap by 21$^{st}$ Century Biochemicals. The peptides were high-performance liquid chromatography (HPLC) purified to greater than 95% purity and confirmed by liquid chromatography mass spectrometry (LC-MS). The sequences are listed below.

(SEQ ID NO: 1)
H3K27me0: ATKAARKSAPATGGVKKPHRYRPGGK(biotin)-amide (SEQ ID NO: 2)
H3K27me2: ATKAARK(me2)SAPATGGVKKPHRYRPGGK(biotin)-amide Chicken erythrocyte oligonucleosomes were purified from chicken blood according to established procedures.

Recombinant PRC2 Complexes. Human PRC2 complexes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates. The assays were all performed in a buffer consisting of 20 mM bicine (pH=7.6), 0.5 mM DTT, 0.005% BSG and 0.002% Tween20, prepared on the day of use. Compounds in 100% DMSO (1 were spotted into polypropylene 384-well V-bottom plates (Greiner) using a Platemate 2×3 outfitted with a 384-channel pipet head (Thermo). DMSO (1 μL) was added to columns 11, 12, 23, 24, rows A H for the maximum signal control, and SAH, a known product and inhibitor of PRC2 (1 μL) was added to columns 11,12, 23, 24, rows I-P for the minimum signal control. A cocktail (40 μL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 μL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 2, below. The assays were stopped by the addition of non-radioactive SAM (10 μL) to a final concentration of 600 μM, which dilutes the $^3$H-SAM to a level where its incorporation into the peptide substrate is no longer detectable. 50 μL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 2

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate. The assays were performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 uL) was added to columns 11, 12, 23, 24, rows A H for the maximum signal control, and SAH, a known product and inhibitor of PRC2 (1 up was added to columns 11,12, 23, 24, rows I-P for the minimum signal control. A cocktail (40 RP containing the wild-type PRC2 enzyme and chicken erythrocyte oligonucleosome was added by Multidrop Combi (Thermo). The compounds were allowed to incubate with PRC2 for 30 mM at 25° C., then a cocktail (10 μL) containing a mixture of non-radioactive and $^3$H-SAM was added to initiate the reaction (final volume=51 μL). The final concentrations were as follows: wild-type PRC2 enzyme was 4 nM, non-radioactive SAM was 430 nM, $^3$H-SAM was 120 nM, chicken erythrocyte olignonucleosome was 120 nM, SAH in the minimum signal control wells was 1 mM and the DMSO concentration was 1%. The assay was stopped by the addition of non-radioactive SAM (10 μL) to a final concentration of 600 μM, which dilutes the $^3$H-SAM to a level where its incorporation into the chicken erythrocyte olignonucleosome substrate is no longer detectable. 50 μL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^3$H-labeled chicken erythrocyte oligonucleosome bound to the Flashplate surface, measured as disintegrations per minute (dpm) or alternatively, referred to as counts per minute (cpm).

% Inhibition Calculation $$\% \ inh = 100 - \left(\frac{dpm_{cmpd} - dpm_{min}}{dpm_{max} - dpm_{min}}\right) \times 100$$

Where dpm=disintegrations per minute, cmpd=signal in assay well, and mM and max are the respective minimum and maximum signal controls.

Four-parameter $IC_{50}$ fit $$Y = Bottom + \frac{(Top - Bottom)}{1 + \left(\frac{X}{IC_{50}}\right)^{Hill\ Coefficient}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

$IC_{50}$ values for the PRC2 enzyme assays on peptide substrates (e.g., EZH2 wild type and Y641F) are presented in Tables 3A and 3B below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, N.Y., USA. Extraction Buffer and Neutralization Buffer (5λ) were purchased from Active Motif, Carlsbad, Calif., USA. Rabbit anti-Histone H3 antibody was purchased from Abcam, Cambridge, Mass., USA. Rabbit anti-H3K27me3 and HRP-conjugated anti-rabbit-IgG were purchased from Cell Signaling Technology, Danvers, Mass., USA. TMB "Super Sensitive" substrate was sourced from BioFX Laboratories, Owings Mills, Md., USA. IgG-free Bovine Serum Albumin was purchased from Jackson ImmunoResearch, West Grove, Pa., USA. PBS with Tween (10×PBST) was purchased from KPL, Gaithersburg, Md., USA. Sulfuric Acid was purchased from Ricca Chemical, Arlington, Tex., USA. Immulon ELISA plates were purchased from Thermo, Rochester, N.Y., USA. V-bottom cell culture plates were purchased from Corning Inc., Corning, N.Y., USA. V-bottom polypropylene plates were purchased from Greiner Bio-One, Monroe, N.C., USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$ on a plate shaker.

WSU-DLCL2 cells were seeded in assay medium at a concentration of 50,000 cells per mL to a 96-well V-bottom cell culture plate with 200 µL, per well. Compound (1 µL) from 96 well source plates was added directly to V-bottom cell plate. Plates were incubated on a titer-plate shaker at 37° C., 5% $CO_2$ for 96 hours. After four days of incubation, plates were spun at 241×g for five minutes and medium was aspirated gently from each well of cell plate without disturbing cell pellet. Pellet was resuspended in 200 nL DPBS and plates were spun again at 241×g for five minutes. The supernatant was aspirated and cold (4° C.) Extraction buffer (100 µL) was added per well. Plates were incubated at 4° C. on orbital shaker for two hours. Plates were spun at 3427×g x 10 minutes. Supernatant (80 µL per well) was transferred to its respective well in 96 well V-bottom polypropylene plate. Neutralization Buffer 5× (20 µL per well) was added to V-bottom polypropylene plate containing supernatant. V-bottom polypropylene plates containing crude histone preparation (CHP) were incubated on orbital shaker×five minutes. Crude Histone Preparations were added (2 µL per well) to each respective well into duplicate 96 well ELISA plates containing 100 µL Coating Buffer (1×PBS+BSA 0.05% w/v). Plates were sealed and incubated overnight at 4° C. The following day, plates were washed three times with 300 µL per well 1×PBST. Wells were blocked for two hours with 300 µL per well ELISA Diluent ((PBS (1×) BSA (2% w/v) and Tween20 (0.05% v/v)). Plates were washed three times with 1×PBST. For the Histone H3 detection plate, 100 µL per well were added of anti-Histone-H3 antibody (Abram, ab1791) diluted 1:10,000 in ELISA Diluent. For H3K27 trimethylation detection plate, 100 µL per well were added of anti-H3K27me3 diluted 1:2000 in ELISA diluent. Plates were incubated for 90 minutes at room temperature. Plates were washed three times with 300 µL 1×PBST per well. For Histone H3 detection, 100 µL of HRP-conjugated anti-rabbit IgG antibody diluted to 1:6000 in ELISA diluent was added per well. For H3K27me3 detection, 100 µL of HRP conjugated anti-rabbit IgG antibody diluted to 1:4000 in ELISA diluent was added per well. Plates were incubated at room temperature for 90 minutes. Plates were washed four times with 1×PBST 300 µL per well. TMB substrate 100 µL was added per well. Histone H3 plates were incubated for five minutes at room temperature. H3K27me3 plates were incubated for 10 minutes at room temperature. The reaction was stopped with sulfuric acid 1N (100 µL per well). Absorbance for each plate was read at 450 nm.

First, the ratio for each well was determined by:

$$\left(\frac{\text{H3K27me3 OD450 value}}{\text{Histone H3 OD450 value}}\right)$$

Each plate included eight control wells of DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 µM. Percent inhibition was determined and $IC_{50}$ curves were generated using duplicate wells per concentration of compound. $IC_{50}$ values for this assay are presented in Tables 3A and 3B below.

$$\text{Percent Inhibition} = 100 - \left(\left(\frac{\text{(Individual Test Sample Ratio)} - \text{(Background Avg Ration)}}{\text{(Minimum Inhibition Ratio)} - \text{(Background Average Ration)}}\right) * 100\right)$$

Cell Proliferation Analysis

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

WSU-DLCL2 suspension cells were maintained in growth medium (RPMI 1640 supplemented with 10% v/v heat inactivated fetal bovine serum and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$.

For the assessment of the effect of compounds on the proliferation of the WSU-DLCL2 cell line, exponentially growing cells were plated in 384-well white opaque plates at a density of 1250 cell/ml in a final volume of 50 µl of assay medium. A compound source plate was prepared by performing triplicate nine-point 3-fold serial dilutions in DMSO, beginning at 10 mM (final top concentration of compound in the assay was 20 µM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity>90% for 6 days. Cell viability was measured by quantization of ATP present in the cell cultures, adding 35 µl of Cell Titer Glo® reagent to the cell plates. Luminescence was read in the SpectraMax M5. The concentration inhibiting cell viability by 50% was determined using a 4-parametric fit of the normalized dose response curves. $IC_{50}$ values for this assay are also presented in Tables 3A and 3B below. The mass spectral data for these compounds are also listed in Tables 3A and 3B below.

TABLE 3A

| Compound# | EZH2 IC$_{50}$ peptide v2 (μM) | WSU Prolif. IC$_{50}$ (μM) | H3K27Me3 ELISA IC$_{50}$ (μM) | MS (free form) |
|---|---|---|---|---|
| 1 | <0.005 | 0.0230 | 0.077 | 588.37 |
| 3 | 0.0113 | 0.1858 | 0.278 | 574.35 |
| 4 | 0.0089 | 23.575 | 21.835 | 575.35 |
| 5 | 0.0131 | — | — | 589.36 |
| 6 | 0.01537 | — | 0.0575 | 632.8 |
| 6b | <0.005 | — | 0.0339 | 604.8 |
| 2 | 0.01498 | 0.38533 | 0.11043 | 605.81 |
| 7 | 0.02096 | 0.6514 | 0.45845 | 618.85 |
| 8 | 0.00882 | 0.10959 | 0.29186 | 564.76 |
| 9 | 0.0053 | 1.30749 | 0.51541 | 500.65 |
| 10 | 0.00736 | 0.30657 | 0.4687 | 482.66 |
| 11 | 0.00627 | — | 0.67305 | 512.68 |
| 12 | 0.02902 | — | 0.30784 | 556.74 |
| 13 | — | — | >50.0 uM | 611.82 |
| 14 | — | — | 17.08469 | 625.84 |
| 15 | 0.00486 | 0.34641 | 0.33988 | 573.77 |
| 16 | 0.00596 | 0.67511 | 0.28656 | 589.77 |
| 17 | 0.01288 | 0.50666 | 0.40245 | 590.76 |
| 18 | 0.00859 | — | 0.55322 | 574.76 |
| 19 | 0.00981 | — | — | 588.78 |
| 20 | <0.005 | — | — | 590.76 |
| 21 | 0.01011 | 1.39074 | 0.84001 | 574.76 |
| 22 | 0.02825 | — | 1.03851 | 560.73 |
| 23 | <0.005 | — | 0.40058 | 562.75 |
| 24 | <0.005 | — | — | 661.88 |
| 25 | 0.0089 | 2.21876 | 0.64998 | 566.77 |
| 26 | <0.005 | 0.138 | 0.087 | 657.89 |
| 157 | <0.005 | — | 0.140 | 544.727 |
| 158 | <0.005 | — | 0.215 | 558.754 |
| 159 | <0.005 | — | 0.262 | 560.727 |
| 160 | 0.014 | — | 0.094 | 587.795 |
| 161 | <0.005 | — | 0.034 | 627.783 |
| 162 | 0.012 | — | — | 573.769 |
| 163 | <0.005 | — | 0.043 | 534.69 |
| 105 | 0.0084 | 0.325 | 0.150 | 518.69 |

TABLE 3B

| Compound# | ELISA H3K27me3 IC50 (uM) | WSU proliferation IC50 (uM) | WT EZH2 IC50 (uM) | MS (free form) |
|---|---|---|---|---|
| 138 | 0.28837 | 0.17765 | <0.01 | 557.3366 |
| 139 | 0.09578 | 0.02487 | <0.01 | 571.3522 |
| 141 | 0.34934 | 0.12309 | <0.01 | 615.3785 |
| 130 | 0.2175 | 0.21755 | <0.01 | 504.2737 |
| 129 | 0.35416 | 0.25424 | <0.01 | 546.3206 |
| 154 | 0.52946 | 0.39402 | <0.01 | 576.3112 |
| 156 | 0.68433 | 0.88954 | <0.01 | 588.3312 |
| 135 | 0.192 | 0.17591 | <0.01 | 600.3788 |
| 115 | >25.0 uM | >20.0 uM | 0.49679 | 474.2806 |
| 113 | >25.0 uM | >20.0 uM | 1.22291 | 456.2901 |
| 116 | >25.0 uM | 13.17177 | 0.13186 | 470.3057 |
| 117 | 8.95891 | >20.0 uM | 0.35005 | 470.3057 |
| 124 | 0.16568 | 0.15789 | <0.01 | 599.3948 |
| 118 | 11.73835 | 3.94855 | 0.0363 | 456.2901 |
| 120 | 1.42887 | 1.37881 | <0.01 | 531.3209 |
| 123 | >25.0 uM | 7.90155 | <0.01 | 599.3948 |
| 121 | 13.93552 | 3.8273 | <0.01 | 600.3788 |
| 122 | >25.0 uM | 7.55766 | <0.01 | 613.4104 |
| 119 | 11.2514 | 3.38069 | 0.01853 | 470.3057 |
| 125 | 0.29127 | 0.15475 | <0.01 | 585.3791 |
| 126 | 2.03218 | 0.90644 | <0.01 | 533.3002 |
| 146 | 0.16112 | 0.21694 | <0.01 | 641.4417 |
| 128 | 1.55449 | 0.9747 | <0.01 | 543.2457 |
| 127 | 0.52523 | 0.71702 | <0.01 | 533.3002 |
| 150 | 0.37722 | 0.36055 | <0.01 | 642.4257 |
| 145 | 0.08424 | 0.18514 | <0.01 | 614.3944 |
| 147 | 0.07432 | 0.11609 | <0.01 | 628.4101 |
| 148 | 0.5036 | 0.24287 | <0.01 | 614.3944 |
| 151 | 0.61791 | 0.68226 | <0.01 | 600.3788 |
| 131 | 0.30571 | 0.19355 | <0.01 | 560.3111 |
| 152 | 0.06 | 0.412 | 0.018 | 559.3522 |
| 143 | 0.018 | 0.276 | <0.01 | 614.3944 |
| 144 | 0.092 | 1.539 | <0.01 | 586.3631 |
| 149 | 0.02 | 0.316 | <0.01 | 614.4057 |
| 132 | 0.177 | 0.526 | 0.02 | 588.3424 |
| 106 | 0.044 | 0.188 | <0.01 | 518.3257 |
| 107 | 0.028 | 0.0262 | 0.011 | 504.31 |
| 108 | 0.042 | 0.438 | <0.01 | 575.3835 |
| 101 | 0.126 | 0.536 | <0.01 | 575.3835 |
| 105 | 0.058 | 0.325 | <0.01 | 518.3257 |
| 104 | 0.066 | 0.549 | <0.01 | 532.3413 |
| 102 | 0.256 | 0.614 | 0.01 | 590.3832 |
| 103 | 0.232 | 0.745 | <0.01 | 590.3832 |
| 109 | 0.244 | 1.064 | <0.01 | 547.3522 |
| 110 | 2.007 | 2.452 | <0.01 | 575.3835 |
| 142 | 0.699 | 1.996 | | 627.3032 |
| 136 | 0.259 | 0.566 | | 628.4101 |
| 137 | 0.056 | 0.505 | | 586.3631 |
| 155 | | | | 560.2999 |
| 111 | 0.014 | 0.201 | <0.005 | 561.3679 |
| 112 | 0.179 | 0.798 | | 588.4152 |
| 140 | | 0.716 | | 615.3785 |
| 153 | | 0.476 | | 604.3425 |
| 133 | | 0.503 | | 587.3472 |
| 134 | | | | 559.3159 |

Example 3

Derivation of the Lowest Cytotoxic Concentration (LCC)

It is well established that cellular proliferation proceeds through cell division that results in a doubling of the number of cells after division, relative to the number of cells prior to division. Under a fixed set of environmental conditions (e.g., pH, ionic strength, temperature, cell density, medium content of proteins and growth factors, and the like) cells will proliferate by consecutive doubling (i.e., division) according to the following equation, provided that sufficient nutrients and other required factors are available.

$$N_t = N_0 \times 2^{\frac{t}{t_D}} \quad (A.1)$$

where $N_t$ is the cell number at a time point (t) after initiation of the observation period, $N_0$ is the cell number at the initiation of the observation period, t is the time after initiation of the observation period and $t_D$ is the time interval required for cell doubling, also referred to as the doubling time. Equation A.1 can be converted into the more convenient form of an exponential equation in base e, taking advantage of the equality, $0.693 = \ln(2)$.

$$N_t = N_0 e^{\frac{0.693 t}{t_D}} \quad (A.2)$$

The rate constant for cell proliferation ($k_p$) is inversely related to the doubling time as follows.

$$k_p = \frac{0.693}{t_D} \quad (A.3)$$

Combining equation A.2 and A.3 yields, $$N_t = N_0 e^{k_p t} \tag{A.4}$$

Thus, according to equation A.4 cell number is expected to increase exponentially with time during the early period of cell growth referred to as log-phase growth. Exponential equations like equation A.4 can be linearized by taking the natural logarithm of each side.

$$\ln(N_t) = \ln(N_0) + k_p t \tag{A.5}$$

Thus a plot of $\ln(N_t)$ as a function of time is expected to yield an ascending straight line with slope equal to $k_p$ and y-intercept equal to $\ln(N_0)$.

Changes in environmental conditions can result in a change in the rate of cellular proliferation that is quantifiable as changes in the proliferation rate constant $k_p$. Among conditions that may result in a change in proliferation rate is the introduction to the system of an antiproliferative compound at the initiation of the observation period (i.e., at t=0). When an antiproliferative compound has an immediate impact on cell proliferation, one expects that plots of $\ln(N_t)$ as a function of time will continue to be linear at all compound concentrations, with diminishing values of $k_p$ at increasing concentrations of compound.

Depending on the mechanistic basis of antiproliferative action, some compounds may not immediately effect a change in proliferation rate. Instead, there may be a period of latency before the impact of the compound is realized. In such cases a plot of $\ln(N_t)$ as a function of time will appear biphasic, and a time point at which the impact of the compound begins can be identified as the breakpoint between phases. Regardless of whether a compound's impact on proliferation is immediate or begins after a latency period, the rate constant for proliferation at each compound concentration is best defined by the slope of the $\ln(N_t)$ vs. time curve from the time point at which compound impact begins to the end of the observation period of the experiment.

A compound applied to growing cells may affect the observed proliferation in one of two general ways: by inhibiting further cell division (cytostasis) or by cell killing (cytotoxicity). If a compound is cytostatic, increasing concentration of compound will reduce the value of $k_p$ until there is no further cell division. At this point, the rate of cell growth, and therefore the value of $k_p$, will be zero. If, on the other hand, the compound is cytotoxic, then the value of $k_p$ will be composed of two rate constants: a rate constant for continued cell growth in the presence of the compound ($k_g$) and a rate constant for cell killing by the compound ($k_d$). The overall rate constant for proliferation at a fixed concentration of compound will thus be the difference between the absolute values of these opposing rate constants.

$$k_p = |k_g| - |k_d| \tag{A.6}$$

At compound concentrations for which the rate of cell growth exceeds that of cell killing, the value of $k_p$ will have a positive value (i.e., $k_p > 0$). At compound concentrations for which the rate of cell growth is less than that for cell killing, the value of $k_p$ will have a negative value (i.e., $k_p < 0$) and the cell number will decrease with time, indicative of robust cytotoxicity. When $k_g$ exactly matches $k_d$ then the overall proliferation rate constant, $k_p$, will have a value of zero. We can thus define the lowest cytotoxic concentration (LCC) as that concentration of compound that results in a value of $k_p$ equal to zero, because any concentration greater than this will result in clearly observable cytotoxicity. Nota bene: at concentrations below the LCC there is likely to be cell killing occurring, but at a rate that is less than that of residual cell proliferation. The treatment here is not intended to define the biological details of compound action. Rather, the goal here is to merely define a practical parameter with which to objectively quantify the concentration of compound at which the rate of cell killing exceeds new cell growth. Indeed, the LCC represents a breakpoint or critical concentration above which frank cytotoxicity is observed, rather than a cytotoxic concentration per se. In this regard, the LCC can be viewed similar to other physical breakpoint metrics, such as the critical micelle concentration (CMC) used to define the concentration of lipid, detergent or other surfactant species above which all molecules incorporate into micellar structures.

Traditionally, the impact of antiproliferative compounds on cell growth has been most commonly quantified by the $IC_{50}$ value, which is defined as that concentration of compound that reduces the rate of cell proliferation to one half that observed in the absence of compound (i.e., for the vehicle or solvent control sample). The $IC_{50}$, however, does not allow the investigator to differentiate between cytostatic and cytotoxic compounds. The LCC, in contrast, readily allows one to make such a differentiation and to further quantify the concentration at which the transition to robust cytotoxic behavior occurs.

If one limits the observation time window to between the start of impact and the end of the experiment, then the data will generally fit well to a linear equation when plotted as $\ln(N_t)$ as a function of time (vide supra). From fits of this type, the value of $k_p$ can be determined at each concentration of compound tested. A replot of the value of $k_p$ as a function of compound concentration ([I]) will have the form of a descending isotherm, with a maximum value at [I]=0 of $k_{max}$ (defined by the vehicle or solvent control sample) and a minimum value at infinite compound concentration of $k_{min}$.

$$k_p = \frac{(k_{max} - k_{min})}{1 + \frac{[I]}{I_{mid}}} + k_{min} \tag{A.7}$$

where $I_{mid}$ is the concentration of compound yielding a value of $k_p$ that is midway between the values of $k_{max}$ and $k_{min}$ (note that the value of $I_{mid}$ is not the same as the $IC_{50}$, except in the case of a complete and purely cytostatic compound). Thus, fitting the replot data to equation A.7 provides estimates of $k_{max}$, $k_{min}$, and $I_{mid}$. If a compound is cytostatic (as defined here), the value of $k_{min}$ cannot be less than zero. For cytotoxic compounds, $k_{min}$ will be less than zero and the absolute value of $k_{min}$ will relate directly to the effectiveness of the compound in killing cells.

The fitted values derived from equation A.7 can also be used to determine the value of the LCC. By definition, when [I]=LCC, $k_p$=0. Thus, under these conditions equation A.7 becomes.

$$0 = \frac{(k_{max} - k_{min})}{1 + \frac{LCC}{I_{mid}}} + k_{min} \tag{A.8}$$

Algebraic rearrangement of equation A.8 yields an equation for the LCC.

$$LCC = I_{mid}\left[\left(\frac{k_{max} - k_{min}}{-k_{min}}\right) - 1\right] \quad (A.9)$$

This analysis is simple to implement with nonlinear curve fitting software and may be applied during cellular assays of compound activity throughout the drug discovery and development process. In this manner, the LCC may provide a valuable metric for the assessment of compound SAR (structure-activity relationship).

Example 4

In vivo Assays

Mice

Female Fox Chase SCID® Mice (CB17/Icr-Prkdc$_{scid}$/IcrIcoCrl, Charles River Laboratories) or athymic nude mice (Crl:NU(Ncr)-Foxn1$_{nu}$, Charles River Laboratories) are 8 weeks old and had a body-weight (BW) range of 16.0-21.1 g on D1 of the study. The animals are fed ad libitum water (reverse osmosis 1 ppm Cl) and NIH 31 Modified and Irradiated Lab Diet® consisting of 18.0% crude protein, 5.0% crude fat, and 5.0% crude fiber. The mice are housed on irradiated Enrich-o'cobs™ bedding in static microisolators on a 12-hour light cycle at 20-22° C. (68-72° F.) and 40-60% humidity. All procedures comply with the recommendations of the *Guide for Care and Use of Laboratory Animals* with respect to restraint, husbandry, surgical procedures, feed and fluid regulation, and veterinary care.

Tumor Cell Culture

Human lymphoma cell lines line are obtained from different sources (ATCC, DSMZ), e.g., WSU-DLCL2 obtained from DSMZ. The cell lines are maintained at Piedmont as suspension cultures in RPMI-1640 medium containing 100 units/mL penicillin G sodium salt, 100 g/mL streptomycin, and 25 g/mL gentamicin. The medium is supplemented with 10% fetal bovine serum and 2 mM glutamine. The cells are cultured in tissue culture flasks in a humidified incubator at 37° C., in an atmosphere of 5% $CO_2$ and 95% air.

In Vivo Tumor Implantation

Human lymphoma cell lines, e.g., WSU-DLCL2 cells, are harvested during mid-log phase growth, and re-suspended in PBS with 50% Matrigel™ (BD Biosciences). Each mouse receives $1 \times 10^7$ cells (0.2 mL cell suspension) subcutaneously in the right flank. Tumors are calipered in two dimensions to monitor growth as the mean volume approached the desired 80-120 mm³ range. Tumor size, in mm³, is calculated from:

$$\text{Tumor volume} = \frac{w^2 \times l}{2}$$

where w=width and l=length, in mm, of the tumor. Tumor weight can be estimated with the assumption that 1 mg is equivalent to 1 mm$_3$ of tumor volume. After 10-30 days mice with 108-126 mm³ tumors are sorted into treatment groups with mean tumor volumes of 117-119 mm³.

Test Articles

Test compounds are stored at room temperature and protected from light. On each treatment day, fresh compound formulations are prepared by suspending the powders in 0.5% sodium carboxymethylcellulose (NaCMC) and 0.1% Tween® 80 in deionized water. Compound 141 (free base) is dissolved in sterile saline and the pH is adjusted to 4.5 with HCl fresh every day. The vehicles, 0.5% NaCMC and 0.1% Tween® 80 in deionized water or sterile saline pH 4.5, are used to treat the control groups at the same schedules. Formulations are stored away from light at 4° C. prior to administration. Unless otherwise specified, compounds referred to and tested in this experiment are in their specific salt forms mentioned in this paragraph.

Treatment Plan

Mice are treated at compound doses ranging from 12.5-600 mg/kg and at TID (three time a day every 8 h), BID (2 times a day every 12 h) or QD (once a day) schedules for various amounts of days by oral gavage or injections via the intraperitoneal route. Each dose is delivered in a volume of 0.2 mL/20 g mouse (10 mL/kg), and adjusted for the last recorded weight of individual animals. The maximal treatment length is 28 days.

Median Tumor Volume (MTV) and Tumor Growth Inhibition (TGI) Analysis

Treatment efficacy is determined on the last treatment day. MTV(n), the median tumor volume for the number of animals, n, evaluable on the last day, is determined for each group. Percent tumor growth inhibition (% TGI) can be defined several ways. First, the difference between the MTV(n) of the designated control group and the MTV(n) of the drug-treated group is expressed as a percentage of the MTV(n) of the control group:

$$\% \ TGI = \left(\frac{MTV(n)_{control} - MTV(n)_{treated}}{MTV(n)_{control}}\right) \times 100$$

Another way of calculating % TGI is taking the change of the tumor size from day 1 to day n into account with n being the last treatment day.

$$\% \ TGI = \left(\frac{\Delta MTV_{control} - \Delta MTV_{treated}}{\Delta MTV_{control}}\right) \times 100$$

$$\Delta MTV_{control} = MTV(n)_{control} - MTV(1)_{control}$$

$$\Delta MTV_{treated} = MTV(n)_{treated} - MTV(1)_{treated}$$

Toxicity

Animals are weighed daily on Days 1-5, and then twice weekly until the completion of the study. The mice are examined frequently for overt signs of any adverse, treatment related side effects, which are documented. Acceptable toxicity for the maximum tolerated dose (MTD) is defined as a group mean BW loss of less than 20% during the test, and not more than 10% mortality due to TR deaths. A death is to be classified as TR if it is attributable to treatment side effects as evidenced by clinical signs and/or necropsy, or due to unknown causes during the dosing period. A death is to be classified as NTR if there is evidence that the death is unrelated to treatment side effects. NTR deaths during the dosing interval would typically be categorized as NTRa (due to an accident or human error) or NTRm (due to necropsy-confirmed tumor dissemination by invasion and/or metastasis). Orally treated animals that die from unknown causes during the dosing period may be classified as NTRu when group performance does not support a TR classification and necropsy, to rule out a dosing error, is not feasible.

Sampling

On days 7 or 28 during the studies mice are sampled in a pre-specified fashion to assess target inhibition in tumors. Tumors are harvested from specified mice under RNAse free conditions and bisected. Frozen tumor tissue from each animal is snap frozen in liquid $N_2$ and pulverized with a mortar and pestle.

Statistical and Graphical Analyses

All statistical and graphical analyses are performed with Prism 3.03 (GraphPad) for Windows. To test statistical significance between the control and treated groups over the whole treatment time course a repeated measures ANOVA test followed by Dunnets multiple comparison post test or a 2 way ANOVA test are employed. Prism reports results as non-significant (ns) at P>0.05, significant (symbolized by "*") at 0.01<P<0.05, very significant ("") at 0.001<P<0.01 and extremely significant ("*") at P<0.001.

Histone Extraction

For isolation of histones, 60-90 mg tumor tissue is homogenized in 1.5 ml nuclear extraction buffer (10 mM Tris-HCl, 10 mM $MgCl_2$, 25 mM KCl, 1% Triton X-100, 8.6% Sucrose, plus a Roche protease inhibitor tablet 1836145) and incubated on ice for 5 minutes. Nuclei are collected by centrifugation at 600 g for 5 minutes at 4° C. and washed once in PBS. Supernatant is removed and histones extracted for one hour, with vortexing every 15 minutes, with 0.4 N cold sulfuric acid. Extracts are clarified by centrifugation at 10,000 g for 10 minutes at 4° C. and transferred to a fresh microcentrifuge tube containing 10× volume of ice cold acetone. Histones are precipitated at −20° C. for 2 hours-overnight, pelleted by centrifugation at 10,000 g for 10 minutes, and resuspended in water.

ELISA

Histones are prepared in equivalent concentrations in coating buffer (PBS+0.05% BSA) yielding 0.5 ng/ul of sample, and 100 ul of sample or standard is added in duplicate to 2 96-well ELISA plates (Thermo Labsystems, Immulon 4HBX #3885). The plates are sealed and incubated overnight at 4° C. The following day, plates are washed 3× with 300 ul/well PBST (PBS+0.05% Tween 20; 10×PBST, KPL #51-14-02) on a Bio Tek plate washer. Plates are blocked with 300 ul/well of diluent (PBS+2% BSA+0.05% Tween 20), incubated at RT for 2 hours, and washed 3× with PBST. All antibodies are diluted in diluent. 100 ul/well of anti-H3K27me3 (CST #9733, 50% glycerol stock 1:1,000) or anti-total H3 (Abeam ab1791, 50% glycerol 1:10,000) is added to each plate. Plates are incubated for 90 min at RT and washed 3× with PBST. 100 ul/well of anti-Rb-IgG-HRP (Cell Signaling Technology, 7074) is added 1:2,000 to the H3K27Me3 plate and 1:6,000 to the H3 plate and incubated for 90 min at RT. Plates are washed 4× with PBST. For detection, 100 ul/well of TMB substrate (BioFx Laboratories, #TMBS) is added and plates incubated in the dark at RT for 5 min. Reaction is stopped with 100 ul/well 1N $H_2SO_4$. Absorbance at 450 nm is read on SpectaMax M5 Microplate reader.

7 Day PD Study

In order to test whether a compound can modulate the H3K27me3 histone mark in tumors in vivo, WSU-DLCL2 xenograft tumor bearing mice are treated with the compound at either 200 mg/kg BID or 400 mg/kg QD or vehicle (BID schedule) for 7 days. There are 4 animals per group. Animals are euthanized 3 h after the last dose and tumor is preserved in a frozen state as described above. Following histone extraction the samples are applied to ELISA assays using antibodies directed against the trimethylated state of histone H3K27 (H3K27me3) or total histone H3. Based on these data the ratio of globally methylated to total H3K27 is calculated. The mean global methylation ratios for all groups as measured by ELISA indicate target inhibition range compared to vehicle.

28 Day Efficacy Study in WSU-DLCL2 Xenograft Model

In order to test whether a compound could induce a tumor growth inhibition in vivo WSU-DLCL2 xenograft tumor bearing mice are treated with the compound at 12.5, 25 or 50 mg/kg QD for 28 days via intraperitoneal injection. Tumor volume and body weights are determined twice a week. A parallel cohort of mice (n=4 per group) is treated at the same doses for 7 days, and mice are euthanized on day 7, 3 h after the last dose for tumor sampling and assessment of target inhibition. The result of the ELISA measuring global methylation of H3K27me3 normalized to total H3 is determined.

Efficacy Study with Increasing Doses in WSU-DLCL2 Xenograft Model

In order to test whether a compound could induce an anti-tumor effect in vivo, WSU-DLCL2 xenograft tumor bearing mice are treated with a compound at, e.g., 37.5, 75 or 150 mg/kg TID for 28 days. There are 12 mice per group for the efficacy arm of the experiment. A parallel cohort is dosed for 7 days at the same doses and schedules for assessment of target inhibition after 7 days (n=6 per group). The tumor growth over the treatment course of 28 days for vehicle and compound treated groups is measured.

Histones are extracted from tumors collected after 7 days of dosing (parallel PD cohort) and at the end of the study on day 28 for the efficacy cohort (3 h after the last dose for both cohorts). The H3K27me3 methyl mark is assessed for modulation with treatment in a dose dependent matter.

Efficacy Study at Different Dose Schedules

To assess whether a compound would lead to tumor growth inhibition at other dosing schedules but TID a WSU-DLCL2 xenograft efficacy study is performed where TID, BID and QD schedules are compared side by side. There are 12 animals per group, and mice are treated for 28 days. The tumor growth over the treatment course of 28 days for vehicle and compound treated groups is measured.

On day 28 mice are euthanized and tumors are collected 3 h after the last dose for assessment of target inhibition.

Example 5

Anti-cancer Effect on the KARPAS-422 Human Diffused Large B-Cell Lymphoma Mouse Xenograft Model A test compound is analyzed for its anti-cancer activity in KARPAS-422 mouse xenograft model, which is a human diffused large B-Cell lymphoma xenograft model. 45 female of CAnN.Cg-Foxn1nu/CrlCrlj mice (Charles River Laboratories Japan) with KARPAS-422 tumors whose mean tumor volume (TV) reached approximately 150 $mm^3$ are selected based on their TVs, and are randomly divided into five groups. The oral administration of compound (e.g., 80.5, 161, 322, and 644 mg/kg) or vehicle is started on day 1. Compound is given once daily on day 1 and day 29 and twice daily everyday from day 2 to day 28. The administration volume (0.1 mL/10 g body weight) is calculated from the body weight before administration. The TV and body weight are measured twice a week. The design for this experiment is shown in Table 4.

TABLE 4

Dosing Scheme

| Group | No. of Animals | Treatment (twice a day) | Route and Schedule |
|---|---|---|---|
| 1 | 9 | Vehicle (0.5% Methyl Cellulose, 0.1% Tween-80) | PO; BID × 28 days |

TABLE 4-continued

Dosing Scheme

| Group | No. of Animals | Treatment (twice a day) | Route and Schedule |
|---|---|---|---|
| 2 | 9 | 80.5 mg/kg Compound | PO; BID × 28 days |
| 3 | 9 | 161 mg/kg Compound | PO; BID × 28 days |
| 4 | 9 | 322 mg/kg Compound | PO; BID × 28 days |
| 5 | 9 | 644 mg/kg Compound | PO; bid × 28 days |

TV is calculated from caliper measurements by the formula for the volume of a prolate ellipsoid $(L \times W^2)/2$ where L and W are the respective orthogonal length and width measurements (mm).

Data are expressed as the mean±standard deviation (SD). The differences in TV between the vehicle-treated and compound-treated groups are analyzed by a repeated measures analysis of variance (ANOVA) followed by the Dunnett-type multiple comparison test. A value of $P<0.05$ (two sided) is considered statistically significant. Statistical analyses are performed using the Prism 5 software package version 5.04 (GraphPad Software, Inc., Calif., USA).

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula III:

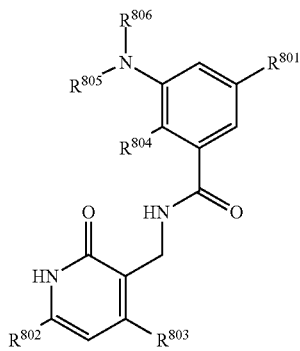
(III)

or a pharmaceutically acceptable salt thereof; wherein
- $R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl;
- each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;
- each of $R^{804}$ and $R^{805}$, independently is $C_{1-4}$ alkyl; and
- $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl, provided that the compound is not

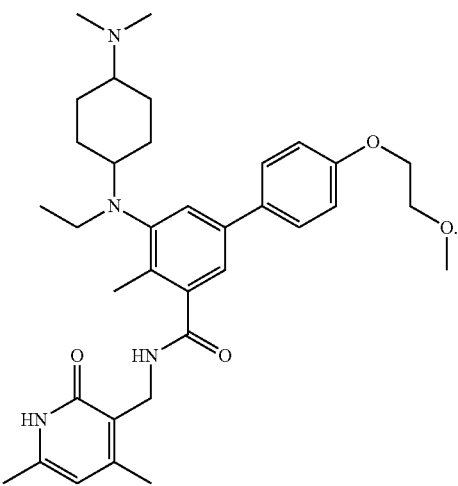

2. The compound of claim 1, wherein $Q_x$ is a bond or methyl linker, and $T_x$ is tetrahydropyranyl, piperidinyl substituted by 1, 2, or 3 $C_{1-4}$ alkyl groups, or cyclohexyl substituted by N($C_{1-4}$ alkyl)$_2$ wherein one or both of the $C_{1-4}$ alkyl is optionally substituted with $C_{1-6}$ alkoxy.

3. The compound of claim 1, wherein (i) $R^{806}$ is cyclohexyl substituted by N($C_{1-4}$ alkyl)$_2$; or (ii) $R^{806}$ is

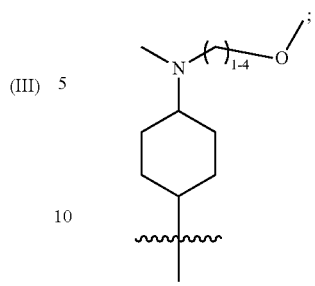

or (iii) $R^{801}$ is phenyl or 5- or 6-membered heteroaryl substituted with O—$C_{1-6}$ alkyl-$R_x$; or (iv) $R^{802}$ is methyl or isopropyl and $R^{803}$ is methyl or methoxyl; or (v) $R^{804}$ is methyl.

4. The compound of claim 1, wherein the compound is of Formula IVa or IVb:

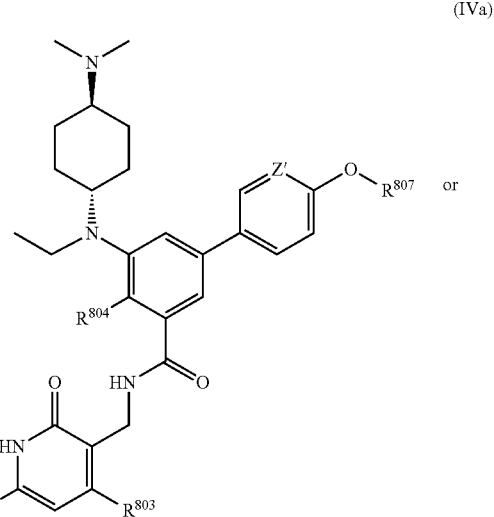
(IVa)

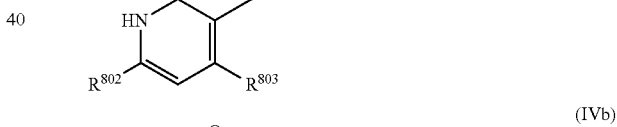
or

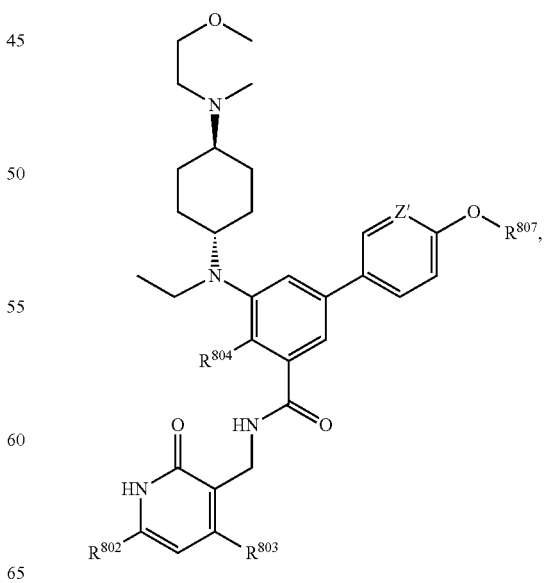
(IVb)

wherein Z' is CH or N, and $R^{807}$ is $C_{2-3}$ alkyl-$R_x$.

5. The compound of claim 4, wherein $R^{807}$ is —CH$_2$CH$_2$OH, —CH$_2$CH$_2$OCH$_3$, or —CH$_2$CH$_2$OCH$_2$CH$_2$OCH$_3$.

6. A compound of Formula II:

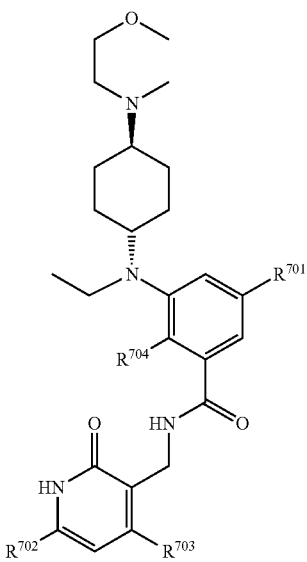

(II)

or a pharmaceutically acceptable salt thereof; wherein
$R^{701}$ is H, F, OR$^{707}$, NHR$^{707}$, —(C≡C)—(CH$_2$)$_{n7}$—R$^{708}$, phenyl, 5- or 6-membered heteroaryl, C$_{3-8}$ cycloalkyl, or 4-7 membered heterocycloalkyl containing 1-3 heteroatoms, wherein the phenyl, 5- or 6-membered heteroaryl, C$_{3-8}$ cycloalkyl or 4-7 membered heterocycloalkyl each independently is optionally substituted with one or more groups selected from halo, C$_{1-3}$ alkyl, OH, O—C$_{1-6}$ alkyl, NH—C$_{1-6}$ alkyl, and, C$_{1-3}$ alkyl substituted with C$_{3-8}$ cycloalkyl or 4-7 membered heterocycloalkyl containing 1-3 heteroatoms, wherein each of the O—C$_{1-6}$ alkyl and NH—C$_{1-6}$ alkyl is optionally substituted with hydroxyl, O—C$_{1-3}$ alkyl or NH—C$_{1-3}$ alkyl, each of the O—C$_{1-3}$ alkyl and NH—C$_{1-3}$ alkyl being optionally further substituted with O—C$_{1-3}$ alkyl or NH—C$_{1-3}$ alkyl;

each of $R^{702}$ and $R^{703}$, independently is H, halo, C$_{1-4}$ alkyl, C$_{1-6}$ alkoxyl or C$_6$-C$_{10}$ aryloxy, each optionally substituted with one or more halo;

$R^{704}$ is C$_{1-4}$ alkyl;

$R^{707}$ is C$_{1-4}$ alkyl optionally substituted with one or more groups selected from hydroxyl, C$_{1-4}$ alkoxy, amino, mono- or di-C$_{1-4}$ alkylamino, C$_{3-8}$ cycloalkyl, and 4-7 membered heterocycloalkyl containing 1-3 heteroatoms, wherein the C$_{3-8}$ cycloalkyl or 4-7 membered heterocycloalkyl each independently is further optionally substituted with C$_{1-3}$ alkyl;

$R^{708}$ is C$_{1-4}$ alkyl optionally substituted with one or more groups selected from OH, halo, and C$_{1-4}$ alkoxy, 4-7 membered heterocycloalkyl containing 1-3 heteroatoms, or O—C$_{1-6}$ alkyl, wherein the 4-7 membered heterocycloalkyl can be optionally further substituted with OH or C$_{1-6}$ alkyl; and $n_7$ is 0, 1 or 2.

7. The compound of claim 6, wherein (i) $R^{702}$ is methyl or isopropyl and $R^{703}$ is methyl or methoxyl; or (ii) $R^{704}$ is methyl; or (iii) $R^{701}$ is OR$^{707}$ and $R^{707}$ is C$_{1-3}$ alkyl optionally substituted with OCH$_3$ or morpholino; or (iv) $R^{701}$ is H or F; or (v) $R^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —OCH$_2$CH$_2$OCH$_3$; or (vi) $R^{708}$ is morpholine, piperidine, piperazine, pyrrolidine, diazepane, or azetidine, each of which is optionally substituted with OH or C$_{1-6}$ alkyl; or (vii) $R^{708}$ is morpholine; or (viii) $R^{708}$ is piperazine substituted with C$_{1-6}$ alkyl; or (ix) $R^{708}$ is methyl, t-butyl or C(CH$_3$)$_2$OH.

8. A compound of Formula VI or VII:

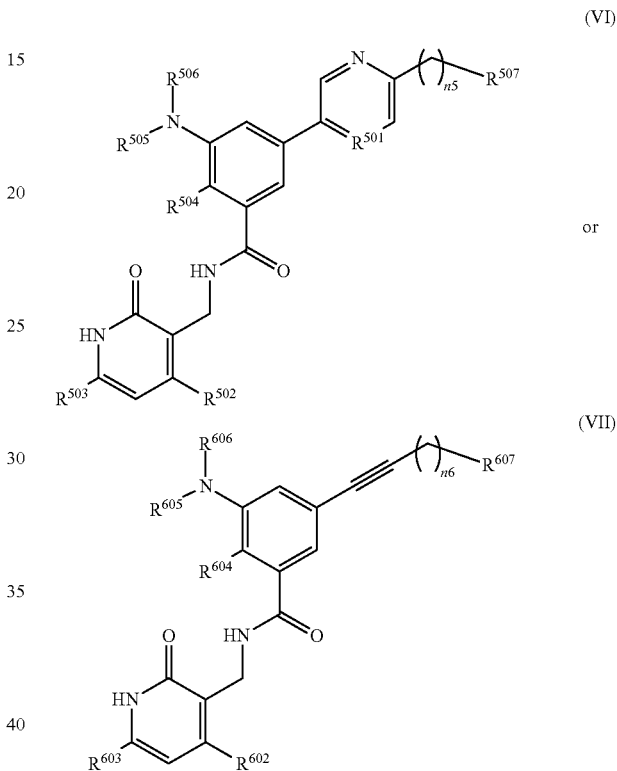

or a pharmaceutically acceptable salt thereof;
wherein
$n_5$ is 0, 1, or 2;
$n_6$ is 1 or 2;
$R^{501}$ is C(H) or N;
$R^{502}$, $R^{503}$, $R^{504}$ and $R^{505}$ are, independently for each occurrence, C$_{1-4}$ alkyl;
$R^{506}$ is cyclohexyl substituted by N(C$_{1-4}$ alkyl)$_2$ or piperidine substituted by 1, 2, or 3 C$_{1-4}$ alkyl groups;
when $R^{501}$ is C(H), $R^{507}$ is morpholine; piperidine; diazepane; pyrrolidine; azetidine; O—C$_{1-6}$ alkyl; or O-heterocycle, wherein the heterocycle is a 4-7 membered heterocycle containing an oxygen or nitrogen, or both, and wherein the nitrogen can optionally be substituted with C$_{1-3}$ alkyl; wherein the piperidine, diazepane, pyrrolidine or azetidine groups can be optionally further substituted with OH, C$_{1-6}$ alkyl, or O—C$_{1-3}$ alkyl;
or when $R^{501}$ is C(H), $R^{507}$ can be piperazine optionally further substituted with C$_{1-6}$ alkyl, provided that $R^{506}$ is piperidine substituted by 1, 2, or 3 C$_{1-4}$ alkyl groups;
when $R^{501}$ is N, $R^{507}$ is morpholine; piperidine; piperazine; diazepane; pyrrolidine; azetidine; O—C$_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, piperazine, diazepane, pyrrolidine or azetidine groups can be optionally further substituted with OH, $C_{1-6}$ alkyl, or O—$C_{1-3}$ alkyl;

$R^{602}$, $R^{603}$, $R^{604}$ and $R^{605}$ are, independently for each occurrence, $C_{1-4}$ alkyl;

$R^{606}$ is cyclohexyl substituted by $N(C_{1-4}$ alkyl$)_2$ or piperidine substituted by 1, 2, or 3 $C_{1-4}$ alkyl groups; and $R^{607}$ is morpholine, piperidine, piperazine, pyrrolidine, diazepane, azetidine or O—$C_{1-6}$ alkyl, wherein the piperidine, diazepane or azetidine groups can be optionally further substituted with OH or $C_{1-6}$ alkyl.

9. The compound of claim 8, wherein the compound is of Formula (VI), wherein (i) $R^{501}$ is C(H), and $R^{507}$ is piperidine; diazepane; pyrrolidine; azetidine; O—$C_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, diazepane, pyrrolidine or azetidine groups can be optionally further substituted with OH, $C_{1-6}$ alkyl, or O—$C_{1-3}$ alkyl; or (ii) $R^{501}$ is C(H) and $R^{507}$ is piperidine, diazepane, pyrrolidine, azetidine or O—$C_{1-6}$ alkyl, wherein the piperidine, diazepane, pyrrolidine or azetidine groups can be optionally further substituted with OH or $C_{1-6}$ alkyl; or (iii) $R^{501}$ is C(H), $R^{507}$ is piperazine optionally further substituted with $C_{1-6}$ alkyl, and $R^{506}$ is piperidine substituted by 1, 2, or 3 $C_{1-4}$ alkyl groups; or (iv) $R^{501}$ is N, and $R^{507}$ is morpholine, piperidine, piperazine, diazepane, pyrrolidine, azetidine or O—$C_{1-6}$ alkyl, wherein the piperidine, piperazine, diazepane, pyrrolidine or azetidine groups can be optionally further substituted with OH or $C_{1-6}$ alkyl.

10. The compound of claim 8, wherein the compound is of Formula (VI), wherein (i) $R^{502}$ is methyl or isopropyl, and $R^{503}$ is methyl; or (ii) $R^{502}$ is methyl or isopropyl, and $R^{503}$ is methyl; or (iii) $R^{504}$ is methyl; or (iv) $R^{505}$ is ethyl; or (v) $R^{506}$ is

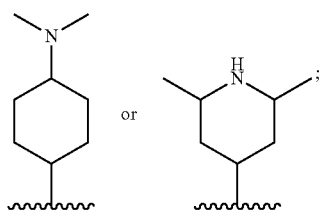

or (vi) $R^{506}$ is

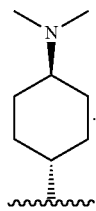

11. The compound of claim 8, wherein the compound is of Formula (VI), wherein (i) when $R^{501}$ is C(H), $R^{507}$ is piperidine or diazepane, which are substituted with OH or $C_{1-6}$ alkyl, or when $R^{501}$ is N, $R^{507}$ is piperidine, piperazine, or diazepane, which are optionally further substituted with OH or $C_{1-6}$ alkyl; or (ii) when $R^{501}$ is C(H), $R^{507}$ is piperidine substituted with $C_{1-6}$ alkyl, or when $R^{501}$ is N, $R^{507}$ is piperidine substituted with OH or piperazine substituted with $C_{1-6}$ alkyl; or (iii) when $R^{501}$ is N, $R^{507}$ is unsubstituted piperazine; or (iv) when $R^{501}$ is C(H) or N, $R^{507}$ is O—$C_{1-6}$ alkyl or O-heterocycle, and $n_5$ is 1; or (v) when $R^{501}$ is C(H), $R^{507}$ is unsubstituted piperazine and $R^{506}$ is piperidine substituted by 1, 2, or 3 $C_{1-4}$ alkyl groups; or (vi) $n_5$ is 0 or 1.

12. The compound of claim 8, being of Formula VII:

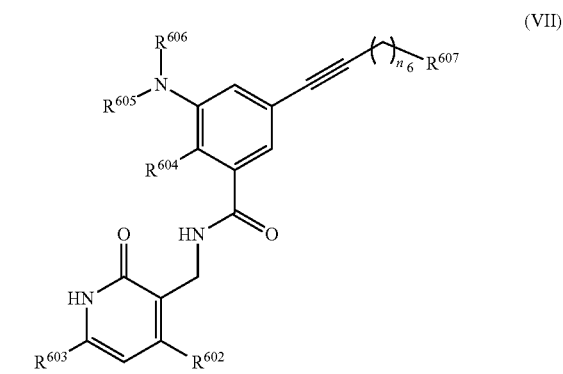

or a pharmaceutically acceptable salt thereof.

13. The compound of claim 12, wherein (i) $R^{602}$ is methyl or isopropyl and $R^{603}$ is methyl; or (ii) $R^{604}$ is methyl and $R^{605}$ is ethyl; or (iii) $R^{607}$ is piperidine or diazepane, each of which is substituted with OH or $C_{1-6}$ alkyl; or (iv) $R^{607}$ is piperidine substituted with OH; or (v) $R^{606}$ is

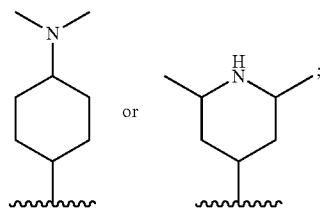

or (vi) $R^{606}$ is

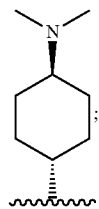

or (vii) $n_6$ is 2.

14. A pharmaceutical composition comprising a compound of claim 8 or a pharmaceutically acceptable salt thereof and a pharmaceutically acceptable carrier.

15. A method of treating a cancer selected from lymphoma, leukemia, melanoma, myelodysplastic syndromes, malignant rhabdoid tumor, or INI1-deficient tumor, the method comprising administering to a subject in need thereof a therapeutically effective amount of a compound of claim 8 or a pharmaceutically acceptable salt thereof.

16. The method of claim 15, wherein the cancer is diffuse large B-cell lymphoma (DLBCL), non-Hodgkin's lymphoma (NHL), follicular lymphoma, chronic myelogenous leukemia (CML), acute myeloid leukemia, acute lymphocytic leukemia, or mixed lineage leukemia.

17. The method of claim 15, wherein the cancer is INI1-deficient tumor.

18. The method of claim 15, wherein the cancer is lymphoma.

19. The method of claim 15, wherein the cancer is leukemia.

20. The method of claim 15, wherein the cancer is melanoma.

21. The method of claim 15, wherein the cancer is myelodysplastic syndromes.

22. The method of claim 15, wherein the cancer is malignant rhabdoid tumor.

23. The method of claim 16, wherein the cancer is diffuse large B-cell lymphoma (DLBCL).

24. The method of claim 16, wherein the cancer is non-Hodgkin's lymphoma (NHL).

25. The method of claim 16, wherein the cancer is follicular lymphoma.

26. The method of claim 16, wherein the cancer is chronic myelogenous leukemia (CML).

27. The method of claim 16, wherein the cancer is acute myeloid leukemia.

28. The method of claim 16, wherein the cancer is acute lymphocytic leukemia.

29. The method of claim 16, wherein the cancer is mixed lineage leukemia.

30. The method of claim 17, wherein the cancer is follicular lymphoma.

31. The method of claim 17, wherein the cancer is malignant rhabdoid tumor.

* * * * *